(12) United States Patent
Mantoulidis et al.

(10) Patent No.: US 8,653,087 B2
(45) Date of Patent: Feb. 18, 2014

(54) PYRIDO [5, 4-D] PYRIMIDINES AS CELL PROLIFERATION INHIBITORS

(75) Inventors: Andreas Mantoulidis, Vienna (AT); Georg Dahmann, Attenweiler (DE); Peter Ettmayer, Vienna (AT); Christian Klein, Vienna (AT); Steffen Steurer, Vienna (AT); Irene Waizenegger, Vienna (AT); Stephan Karl Zahn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 31 days.

(21) Appl. No.: 13/062,058

(22) PCT Filed: Sep. 8, 2009

(86) PCT No.: PCT/EP2009/061656
§ 371 (c)(1), (2), (4) Date: Apr. 13, 2011

(87) PCT Pub. No.: WO2010/026262
PCT Pub. Date: Mar. 11, 2010

(65) Prior Publication Data
US 2012/0094975 A1 Apr. 19, 2012

(30) Foreign Application Priority Data
Sep. 8, 2008 (EP) .................................... 08163897

(51) Int. Cl.
*A01N 43/90* (2006.01)
*A61K 31/519* (2006.01)
*C07D 487/00* (2006.01)

(52) U.S. Cl.
USPC ....................................... 514/262.1; 544/262

(58) Field of Classification Search
None
See application file for complete search history.

(56) References Cited

U.S. PATENT DOCUMENTS

| | | | |
|---|---|---|---|
| 5,707,989 A | 1/1998 | Himmelsbach et al. | |
| 5,821,240 A | 10/1998 | Himmelsbach et al. | |
| 5,977,102 A | 11/1999 | Himmelsbach et al. | |
| 7,166,628 B2 | 1/2007 | Cogan et al. | |
| 7,214,802 B2 | 5/2007 | Cogan et al. | |
| 7,485,657 B2 | 2/2009 | Cogan et al. | |
| 7,511,042 B2 | 3/2009 | Cogan et al. | |
| 7,514,458 B2 | 4/2009 | Cogan et al. | |
| 7,531,560 B2 | 5/2009 | Cogan et al. | |
| 7,569,568 B2 | 8/2009 | Cogan et al. | |
| 7,858,804 B2 | 12/2010 | Frutos et al. | |
| 8,198,308 B2 | 6/2012 | Steurer et al. | |
| 2004/0102492 A1 | 5/2004 | Cogan et al. | |
| 2005/0153972 A1 | 7/2005 | Cogan et al. | |
| 2005/0256113 A1 | 11/2005 | Cogan et al. | |
| 2006/0079519 A1 | 4/2006 | Cogan et al. | |
| 2006/0100204 A1 | 5/2006 | Cogan et al. | |
| 2007/0032492 A1 | 2/2007 | Cogan et al. | |
| 2007/0142371 A1 | 6/2007 | Cogan et al. | |
| 2008/0182837 A1 | 7/2008 | Steurer et al. | |
| 2009/0127815 A1 | 5/2009 | Tani et al. | |
| 2010/0240657 A1 | 9/2010 | Sapountzis et al. | |
| 2011/0183952 A1 | 7/2011 | Sapountzis et al. | |
| 2011/0312939 A1 | 12/2011 | Steurer et al. | |
| 2012/0046270 A1 | 2/2012 | Ettmayer et al. | |
| 2012/0094975 A1 | 4/2012 | Mantoulidis et al. | |

FOREIGN PATENT DOCUMENTS

| | | |
|---|---|---|
| CA | 2248316 | 9/1997 |
| CA | 2248720 | 9/1997 |
| EP | 0837063 A1 | 4/1998 |
| EP | 1029853 A1 | 8/2000 |
| WO | 9519774 A1 | 7/1995 |
| WO | 9607657 A1 | 3/1996 |
| WO | 9640142 A1 | 12/1996 |
| WO | 9732880 A1 | 9/1997 |
| WO | 9732882 A1 | 9/1997 |
| WO | 9802434 A1 | 1/1998 |
| WO | 9802437 A1 | 1/1998 |
| WO | 0044728 A1 | 8/2000 |
| WO | 2004050642 A1 | 6/2004 |
| WO | 2005023761 A2 | 3/2005 |
| WO | 2005056535 A1 | 6/2005 |
| WO | 2005090333 A1 | 9/2005 |

(Continued)

OTHER PUBLICATIONS

International Search Report, Form PCT/ISA/210, for corresponding PCT/EP2009/061656; date of mailing: Oct. 15, 2009.

(Continued)

*Primary Examiner* — Jeffrey Murray
(74) *Attorney, Agent, or Firm* — Michael P. Morris; Mary-Ellen M. Devlin

(57) ABSTRACT

The present invention encompasses compounds of general formula (1) wherein the groups $R^1$ to $R^4$, $X^1$, $X^2$, $X^3$, $L^1$ and $L^2$ are defined as in claim 1, which are suitable for the treatment of diseases characterized by excessive or anomalous cell proliferation, and the use thereof in such a treatment.

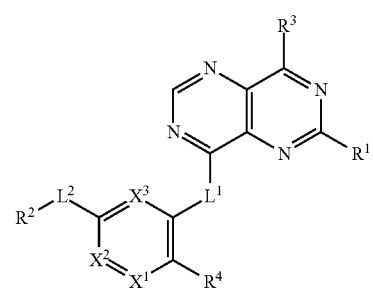

(1)

13 Claims, No Drawings

(56) References Cited

FOREIGN PATENT DOCUMENTS

| WO | 2005115991 A1 | 12/2005 |
|---|---|---|
| WO | 2007056016 A2 | 5/2007 |
| WO | 2007075896 A2 | 7/2007 |
| WO | 2008003770 A1 | 1/2008 |
| WO | 2008021388 A1 | 2/2008 |
| WO | 2008089034 A2 | 7/2008 |
| WO | 2008127591 A2 | 10/2008 |
| WO | 2009003998 A2 | 1/2009 |
| WO | 2009003999 A2 | 1/2009 |
| WO | 2009012283 A1 | 1/2009 |
| WO | 2010026262 A1 | 3/2010 |
| WO | 2010034838 A2 | 4/2010 |
| WO | 2010042337 A1 | 4/2010 |
| WO | 2010094695 A1 | 8/2010 |
| WO | 2011117381 A1 | 9/2011 |
| WO | 2011117382 A1 | 9/2011 |
| WO | 2012085127 A1 | 6/2012 |
| WO | 2012101238 A1 | 8/2012 |
| WO | 2012104388 A1 | 8/2012 |

OTHER PUBLICATIONS

Rewcastle, Gordon, W., et al; Tyrosine Kinase Inhibitors. 14. Structure-Activity Relationshipsfor Methyl-amino-Substituted Derivatives of 4-[(3-Bromophenyl)amino]-6-(methylamino)-pyrido[3,4-d]pyrimidine (PD 158780), a Potent and Specific Inhibitor of the Tyrosine Kinase Activity of Receptors for the EGF Family of Growth Factors; Journal of Medicinal Chemistry (1998) vol. 41 pp. 742-751.

Rewcastle, Gordon., et al; Tyrosine Kinase Inhibitors. 10. Isomeric 4-[(3-Bromophenyl)Amino]Pyrido[d]-Pyrimidines Are Potent ATP Binding Site Inhibitors of the Tyrosine Kinase Function of the Epidermal Growth Factor Receptor; Journal of Medicinal Chemistry (1996) vol. 39 pp. 1823-1835.

PYRIDO [5, 4-D] PYRIMIDINES AS CELL PROLIFERATION INHIBITORS

The present invention relates to new compounds of general formula (1)

(1)

wherein the groups $R^1$ to $R^4$, $X^1$, $X^2$, $X^3$, $L^1$ and $L^2$ have the meanings given in the claims and specification and the tautomers, racemates, enantiomers, diastereomers and mixtures thereof and the salts of all these forms and their use as medicaments.

BACKGROUND TO THE INVENTION

Pyrimido[5,4-d]pyrimidines for inhibiting tyrosinekinases, which are involved in signal transduction, are described in WO 96/07657, WO 97/32880 and WO 97/32882.

The aim of the present invention is to discover new active substances which can be used for the prevention and/or treatment of diseases characterised by excessive or abnormal cell proliferation.

DETAILED DESCRIPTION OF THE INVENTION

It has now been found that, surprisingly, compounds of general formula (1), wherein the groups $R^1$ to $R^4$, $X^1$, $X^2$, $X^3$, $L^1$ and $L^2$ have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (1)

(1)

wherein
$R^1$ denotes hydrogen or a group optionally substituted by one or more identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl, or
a suitable substituent, selected from among —$OR^c$, —$SR^c$, —$NR^cR^c$, —$NR^cNR^cR^c$ and —$S(O)R^c$;
$R^2$ denotes a group optionally substituted by one or more identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;
$R^3$ is selected from among hydrogen, $C_{1-4}$alkyl, halogen, —OH, —O($C_{1-4}$alkyl), —$NH_2$, —NH($C_{1-4}$alkyl) and —N($C_{1-4}$alkyl)$_2$;
$R^4$ is selected from among hydrogen, —CN, —$NO_2$, —$NH_2$, —NH($C_{1-4}$alkyl), —N($C_{1-4}$alkyl)$_2$, $C_{1-4}$alkyl, $C_{1-4}$haloalkyl, $C_{1-4}$alkoxy, $C_{1-5}$cycloalkyl and halogen;
$X^1$, $X^2$ and $X^3$ are each selected independently of one another from among nitrogen and $CR^{4*}$,
wherein at most two of the atoms $X^1$, $X^2$ and $X^3$ may be nitrogen atoms and $R^{4*}$ are each selected independently of one another from among hydrogen, —CN, —$NO_2$, —$NH_2$, —NH($C_{1-4}$alkyl), —N($C_{1-4}$alkyl)$_2$, $C_{1-4}$alkyl, $C_{1-4}$haloalkyl, $C_{1-4}$alkoxy, $C_{1-5}$cycloalkyl and halogen;
$L^1$ is selected from among —$CH_2$—, —NH—, —NMe-, —O— and —S—;
$L^2$ is selected from among —C(O)NH—, —C(O)N($C_{1-4}$alkyl)-, —NHC(O)—, —N($C_{1-4}$alkyl)C(O)—, —$CH_2$—NHC(O)—, —C(O)—, —C(S)NH—, —NHC(S)—, —$NHCH_2$—, —$CH_2NH$—, —$S(O)_2NH$—, —$NHS(O)_2$, —NHC(O)NH—, —OC(O)NH— and —NHC(O)O—;
each $R^b$ is a suitable substituent and is selected independently of one another from among —$OR^c$, —$SR^c$, —$NR^cR^c$, —$ONR^cR^c$, —$N(OR^c)R^c$, —$NR^gNR^cR^c$, halogen, —CN, —$NO_2$, —$N_3$, —$C(O)R^c$, —$C(O)OR^c$, —$C(O)NR^cR^c$, —$C(O)NR^gNR^cR^c$, —$C(O)NR^gOR^c$, —$C(NR^g)R^c$, —N=$CR^cR^c$, —$C(NR^g)OR^c$, —$C(NR^g)NR^cR^c$, —$C(NR^g)NR^gNR^cR^c$, —$C(NOR^g)R^c$, —$C(NOR^g)NR^cR^c$, —$C(NNR^gR^g)R^c$, —$OS(O)R^c$, —$OS(O)OR^c$, —$OS(O)NR^cR^c$, —$OS(O)_2R^c$, —$OS(O)_2OR^c$, —$OS(O)_2NR^cR^c$, —$OC(O)R^c$, —$OC(O)OR^c$, —$OC(O)NR^cR^c$, —$OC(NR^g)R^c$, —$OC(NR^g)NR^cR^c$, —$ONR^gC(O)R^c$, —$S(O)R^c$, —$S(O)OR^c$, —$S(O)NR^cR^c$, —$S(O)_2R^c$, —$S(O)_2OR^c$, —$S(O)_2NR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —N=$CR^cNR^cR^c$, —$NR^gC(NR^g)OR^c$, —$NR^gC(NR^g)NR^cR^c$, —$NR^gC(NOR^g)R^c$, —$NR^gS(O)R^c$, —$NR^gS(O)OR^c$, —$NR^gS(O)_2R^c$, —$NR^gS(O)_2OR^c$, —$NR^gS(O)_2NR^cR^c$, —$NR^gNR^gC(O)R^c$, —$NR^gNR^gC(O)NR^cR^c$, —$NR^gNR^gC(NR^g)R^c$ and —N($OR^g$)C(O)$R^c$ and the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems;
each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$halo alkyl, $C_{3-10}$cycloalkyl, $C_{6-10}$aryl, 5-12 membered heteroaryl and 3-14 membered heterocycloalkyl;
each $R^d$ is a suitable substituent and is selected independently of one another from among —$OR^e$, —$SR^e$, —$NR^eR^e$, —$ONR^eR^e$, —$N(OR^e)R^e$, —$N(R^g)NR^eR^e$, halogen, —CN, —NO, —$NO_2$, —$N_3$, —$C(O)R^e$, —$C(O)OR^e$, —$C(O)NR^eR^e$, —$C(O)NR^gNR^eR^e$, —$C(O)NR^gOR^e$, —$C(NR^g)R^e$, —N=$CR^eR^e$, —$C(NR^g)OR^e$, —$C(NR^g)NR^eR^e$, —$C(NR^g)NR^gNR^eR^e$, —$C(NOR^g)R^e$, —$C(NOR^g)NR^eR^e$, —$C(NNR^gR^g)R^e$, —$OS(O)R^e$, —$OS(O)OR^e$, —$OS(O)NR^eR^e$, —$OS(O)_2R^e$, —$OS(O)_2OR^e$, —$OS(O)_2NR^eR^e$, —$OC(O)R^e$, —$OC(O)OR^e$, —$OC(O)NR^eR^e$, —$OC(NR^g)R^e$, —$OC(NR^g)NR^eR^e$, —$ONR^gC(O)R^e$, —$S(O)R^e$, —$S(O)OR^e$, —$S(O)NR^eR^e$, —$S(O)_2R^e$, —$S(O)_2OR^e$, —$S(O)_2NR^eR^e$, —$NR^gC(O)R^e$, —$NR^gC(O)OR^e$, —$NR^gC(O)NR^eR^e$, —$NR^gC(O)$ NR$^g$NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$ and —N(OR$^g$)C(O)R$^e$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$halo alkyl, C$_{3-10}$cycloalkyl, C$_{6-10}$aryl, 5-12 membered heteroaryl and 3-14 membered heterocycloalkyl;

each R$^f$ is a suitable substituent and is selected independently of one another from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO$_2$, —N$_3$, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N=CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —NR$^h$C(O)R$^g$, —NR$^h$C(O)OR$^g$, —NR$^h$C(O)NR$^g$R$^g$, —NR$^h$C(O)NR$^h$NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^h$ is selected independently of one another from among hydrogen, C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

while the compounds (1) may optionally also be present in the form of their tautomers, racemates, enantiomers, diastereomers and mixtures thereof, or also as pharmacologically acceptable salts of all the above-mentioned forms.

In one aspect (A1) the invention relates to compounds (1), wherein
R$^3$ denotes hydrogen.

In another aspect (A2) the invention relates to compounds (1), wherein
R$^3$ denotes —NH$_2$ or —NHMe.

In another aspect (B1) the invention relates to compounds (1), wherein
R$^1$ denotes hydrogen.

In another aspect (A1B1) the invention relates to compounds (1), wherein R$^1$ and R$^3$ denote hydrogen.

In another aspect (B2) the invention relates to compounds (1), wherein
R$^1$ is a group optionally substituted by one or more identical or different R$^b$ and/or R$^c$, selected from among 5-12 membered heteroaryl and 3-14 membered heterocycloalkyl, and R$^b$ and R$^c$ are as hereinbefore defined.

In another aspect (B3) the invention relates to compounds (1), wherein
R$^1$ is a 3-7 membered, monocyclic and nitrogen-containing heterocycloalkyl or 6-10 membered, bicyclic and nitrogen-containing heterocycloalkyl optionally substituted by one or more identical or different R$^b$ and/or R$^c$,
R$^1$ is bound to the pyrimido[5,4-d]pyrimidine structure through a nitrogen atom, and R$^b$ and R$^c$ are as hereinbefore defined.

In another aspect (B4) the invention relates to compounds (1), wherein
R$^1$ is a group optionally substituted by one or more identical or different R$^b$ and/or R$^c$, selected from among piperidyl, perhydro-1,4-diazepinyl, piperazinyl, octahydro-pyrrolo[1,2-c]pyrazinyl, 2,5-diazabicyclo[2,2,1]heptyl, octahydro-pyrido[1,2-c]pyrazinyl, perhydro-1,4-oxazepinyl, morpholinyl, pyrrolidinyl, perhydroazepinyl, thiomorpholinyl, thiazolidinyl and azetidinyl,
R$^1$ is bound to the pyrimido[5,4-d]pyrimidine structure via a nitrogen atom, and R$^b$ and R$^c$ are as hereinbefore defined.

In another aspect (B5) the invention relates to compounds (1), wherein
R$^1$ is a 2-methyl-2,7-diazaspiro[4.4]nonyl optionally substituted by one or more identical or different R$^b$ and/or R$^c$, which binds to the pyrimido[5,4-d]pyrimidine structure via a nitrogen atom,
and R$^b$ and R$^c$ are as hereinbefore defined.

In another aspect (B6) the invention relates to compounds (1) with one of the structural aspects B2 to B5,
wherein R$^1$ is heterocycloalkyl which is bound to the pyrimido[5,4-d]pyrimidine structure via a nitrogen atom and is optionally substituted by one or more substituents, each independently selected from among R$^{b1}$ and R$^{c1}$;

each R$^{b1}$ is selected independently of one another from among —OR$^{c1}$, —NR$^{c1}$R$^{c1}$, halogen, —C(O)R$^{c1}$ and =O, while the latter substituent may only be a substituent in non-aromatic ring systems, each R$^{c1}$ independently of one another denotes hydrogen or a group optionally substituted by one or more identical or different R$^{d1}$ and/or R$^{e1}$, selected from among C$_{1-6}$alkyl, phenyl, C$_{3-10}$cycloalkyl, 5-12 membered heteroaryl and 3-14 membered heterocycloalkyl, each R$^{d1}$ is selected independently of one another from among —OR$^{e1}$ and —NR$^{e1}$R$^{e1}$, each R$^{e1}$ independently of one another denotes hydrogen or a group optionally substituted by one or more identical or different C$_{1-6}$alkyl, selected from among
C$_{1-6}$alkyl, C$_{3-10}$cycloalkyl, 5-12 membered heteroaryl and 3-14 membered heterocycloalkyl.

In another aspect (B7) the invention relates to compounds (1), wherein
R$^1$ is selected from among

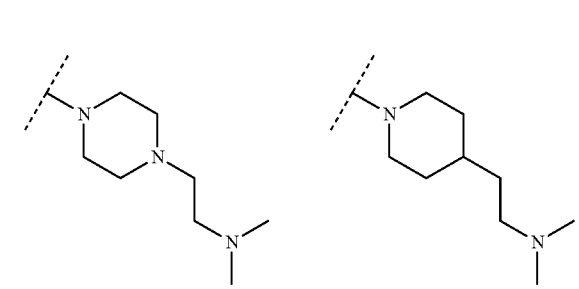

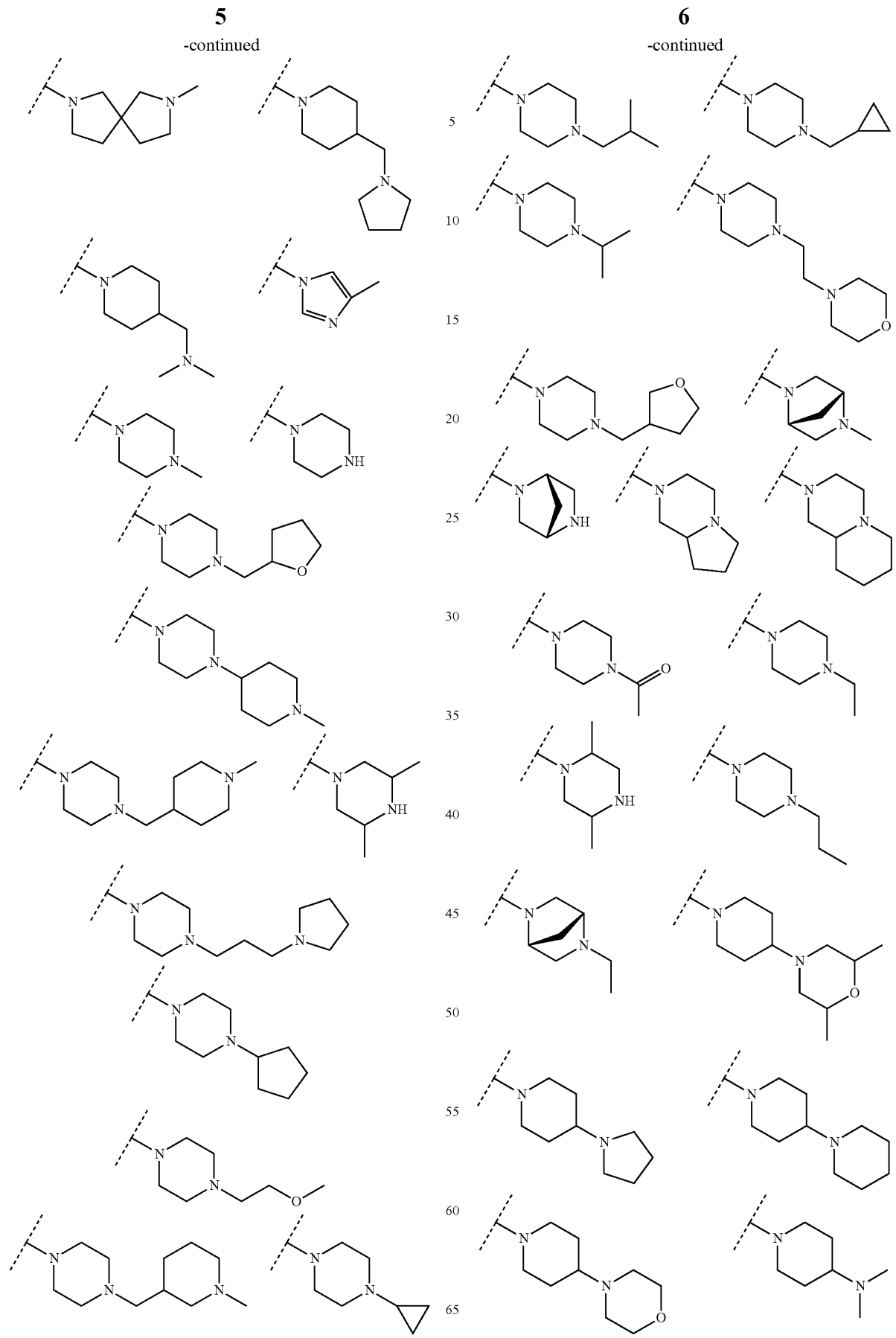

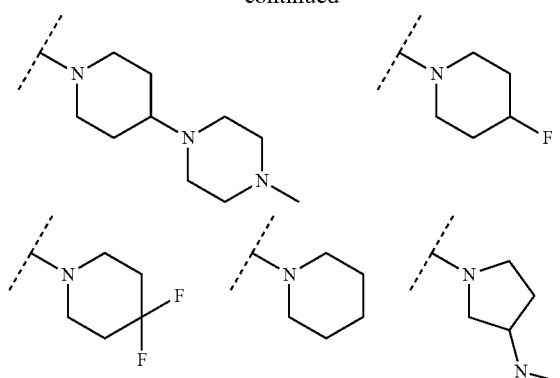
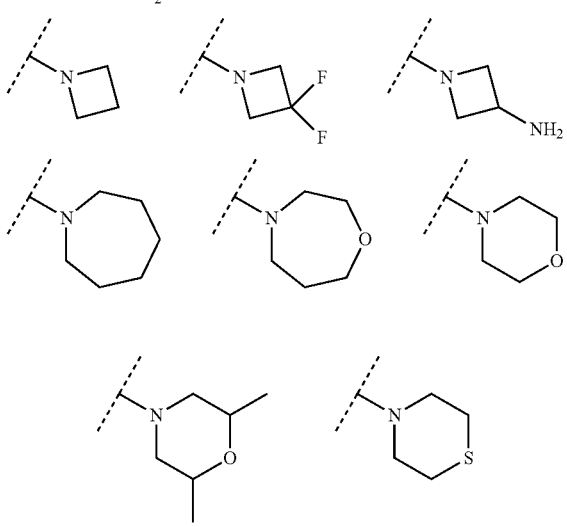
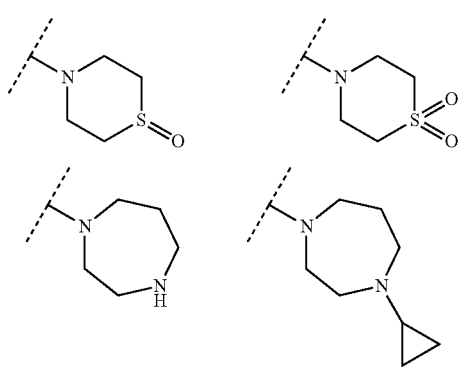
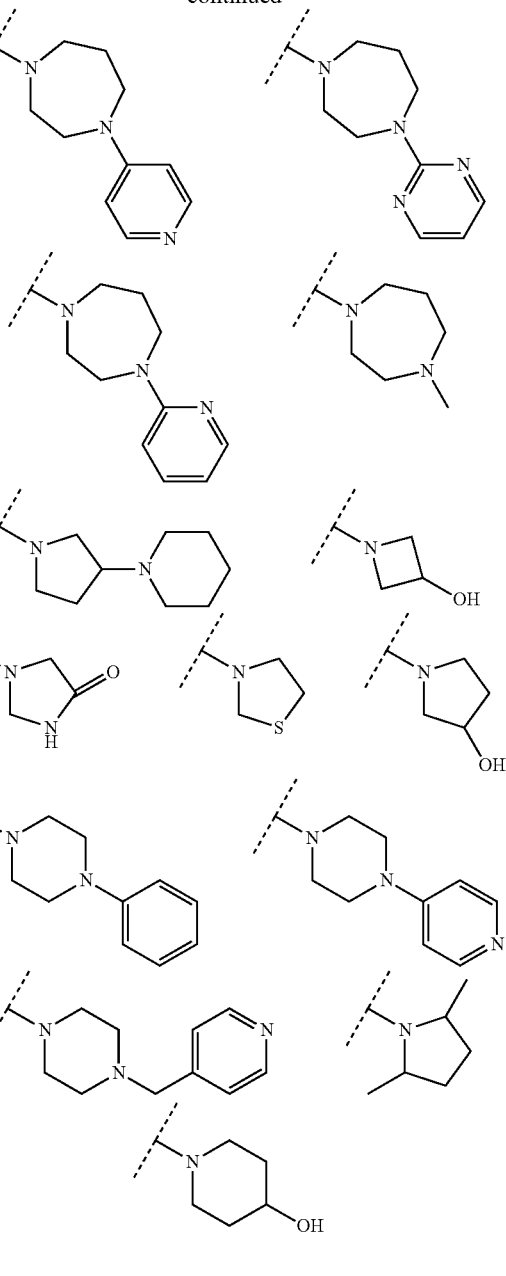

In another aspect (B8) the invention relates to compounds (1), wherein
$R^1$ denotes $-NR^{c2}R^{c3}$ and
$R^{c2}$ and $R^{c3}$ are each defined as $R^c$ defined hereinbefore.

In another aspect (B9) the invention relates to compounds (1), wherein
$R^1$ denotes $-NR^{c2}R^{c3}$ and
$R^{c2}$ is selected from among hydrogen, $C_{1-6}$alkyl, $C_{3-6}$cycloalkyl, phenyl, 5-6 membered heteroaryl and 3-7 membered heterocycloalkyl,
$R^{c3}$ is a group optionally substituted by one or more identical or different $R^{d3}$ and/or $R^{e3}$, selected from among $C_{1-6}$alkyl, $C_{1-6}$haloalkyl, $C_{3-10}$cycloalkyl and 3-14 membered heterocycloalkyl,
each $R^{d3}$ is selected independently of one another from among halogen, $-NR^{e3}R^{e3}$ and $-OR^{e3}$,
each $R^{e3}$ independently of one another denotes hydrogen or a group optionally substituted by one or more identical or different $R^{f3}$ and/or $R^{g3}$, selected from among $C_{1-6}$alkyl, $C_{6-10}$aryl, 5-12 membered heteroaryl and 3-14 membered heterocycloalkyl, each $R^{f3}$ denotes —$OR^{g3}$ and each $R^{g3}$ are each selected independently of one another from among hydrogen and $C_{1-6}$alkyl.

In another aspect (B10) the invention relates to compounds (1) with one of the structural aspects B8 or B9, wherein $R^{c2}$ denotes hydrogen.

In another aspect (B11) the invention relates to compounds (1), wherein $R^1$ is selected from among

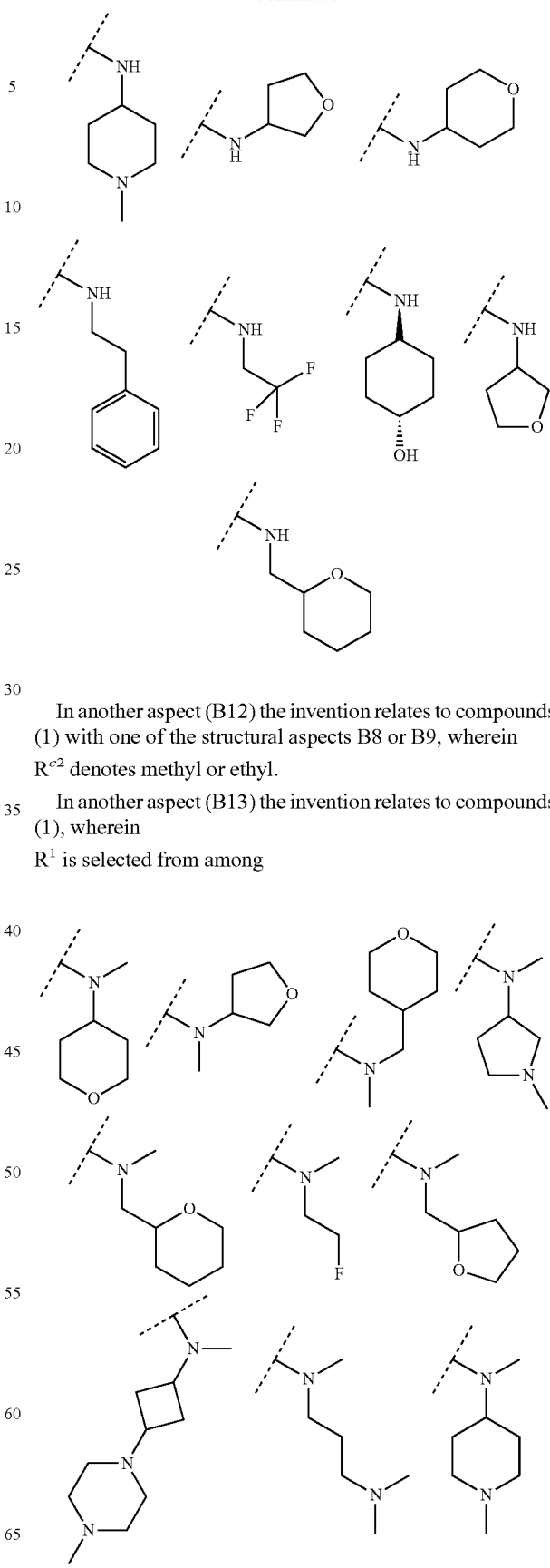

In another aspect (B12) the invention relates to compounds (1) with one of the structural aspects B8 or B9, wherein $R^{c2}$ denotes methyl or ethyl.

In another aspect (B13) the invention relates to compounds (1), wherein $R^1$ is selected from among

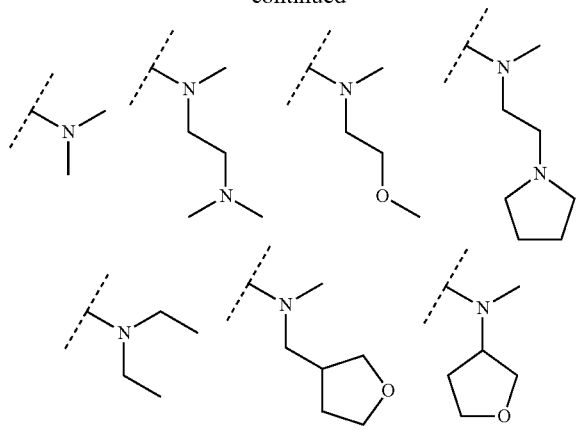

In another aspect (C1) the invention relates to compounds (1), wherein
$R^4$ denotes fluorine, bromine, chlorine or methyl.

In another aspect (D1) the invention relates to compounds (1), wherein
$X^1$ denotes $CR^{4*-1}$, $X^2$ denotes $CR^{4*-2}$ and $X^3$ denotes $CR^{4*-3}$ and
$R^{4*-1}$, $R^{4*-2}$ and $R^{4*-3}$ are each selected from among hydrogen, fluorine, chlorine and methyl and at least two of the groups $R^{4*-1}$, $R^{4*-2}$ and $R^{4*-3}$ denote hydrogen.

In another aspect (D2) the invention relates to compounds (1), wherein
$X^1$, $X^2$ and $X^3$ each denote CH.

In another aspect (D3) the invention relates to compounds (1), wherein
$X^1$ denotes nitrogen, $X^2$ denotes $CR^{4*-2}$ and $X^3$ denotes $CR^{4*-3}$ and $R^{4*-2}$ and $R^{4*-3}$ are each selected from among hydrogen, fluorine, bromine, chlorine and methyl and at least one of the groups $R^{4*-2}$ and $R^{4*-3}$ denotes hydrogen.

In another aspect (D4) the invention relates to compounds (1), wherein
$X^1$ denotes nitrogen, $X^2$ denotes CH and $X^3$ denotes CH.

In another aspect (E1) the invention relates to compounds (1), wherein
$L^1$ denotes —NH— or —NMe-.

In another aspect (F1) the invention relates to compounds (1), wherein
$R^2$ is a group optionally substituted by one or more identical or different $R^b$ and/or $R^c$, selected from among $C_{6-10}$aryl and 5-12 membered heteroaryl,
and $R^b$ and $R^c$ are as hereinbefore defined.

In another aspect (F2) the invention relates to compounds (1), wherein
$R^2$ is a group optionally substituted by one or more identical or different $R^b$ and/or $R^c$, selected from among phenyl and 5-6 membered heteroaryl, and $R^b$ and $R^c$ are as hereinbefore defined.

In another aspect (F3) the invention relates to compounds (1), wherein
$R^2$ is a 5-6 membered heteroaryl optionally substituted by one or more identical or different $R^b$ and/or $R^c$
and $R^b$ and $R^c$ are as hereinbefore defined.

In another aspect (F4) the invention relates to compounds (1),
wherein $R^2$ is a heteroaryl which is selected from among furyl, thienyl, pyrrolyl, oxazolyl, thiazolyl, triazolyl, isoxazolyl, isothiazolyl, pyrazolyl, imidazolyl, oxadiazolyl, thiadiazolyl, pyridyl and pyrimidyl, and is optionally substituted by one or two substituents, each independently selected from among $C_{3-7}$cycloalkyl, phenyl, 4-7 membered heterocycloalkyl, methyl, ethyl, n-propyl, isopropyl, n-butyl, 1-methylpropyl, isobutyl, sec.-butyl, tert.-butyl, n-pentyl, 1-methylbutyl, 1-ethylpropyl, isopentyl, neopentyl, trifluoromethyl, difluoromethyl, fluoromethyl, tert.-butoxy, trifluoromethoxy,

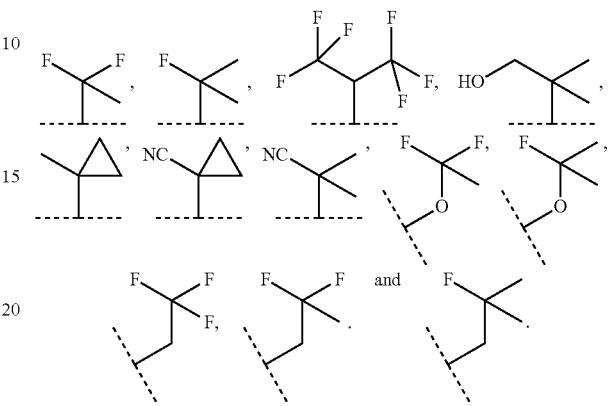

In another aspect (F5) the invention relates to compounds (1), wherein
$R^2$ is a phenyl optionally substituted by one or more identical or different $R^b$ and/or $R^c$, and $R^b$ and $R^c$ are as hereinbefore defined.

In another aspect (F6) the invention relates to compounds (1), wherein
$R^2$ denotes a phenyl

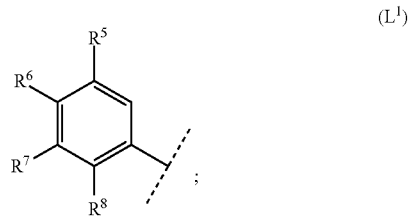

(L$^1$)

$R^5$ is selected from among hydrogen, $C_{1-6}$alkyl, —O$C_{1-6}$alkyl, $C_{1-6}$haloalkyl, —O$C_{1-6}$haloalkyl, $C_{3-7}$cycloalkyl and 3-7 membered heterocycloalkyl, all the above-mentioned groups optionally being substituted by $C_{1-6}$alkyl, —CN or —OH;

$R^6$ is selected from among hydrogen, $C_{1-6}$alkyl, —O$C_{1-6}$alkyl, $C_{1-6}$haloalkyl, —O$C_{1-6}$haloalkyl, —CN, —OH, halogen, —NH$C_{1-6}$alkyl and —N($C_{1-6}$alkyl)$_2$, the latter two optionally being substituted in the alkyl moiety by a substituent —N($C_{1-6}$alkyl)$_2$;

$R^7$ is selected from among hydrogen, —O$C_{1-6}$alkyl, halogen, —NHS(O)$_2C_{1-6}$alkyl, —S(O)$_2$NH$_2$, —S(O)$_2$NH$C_{1-6}$alkyl, —S(O)$_2$N($C_{1-6}$alkyl)$_2$,

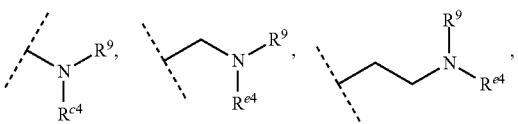

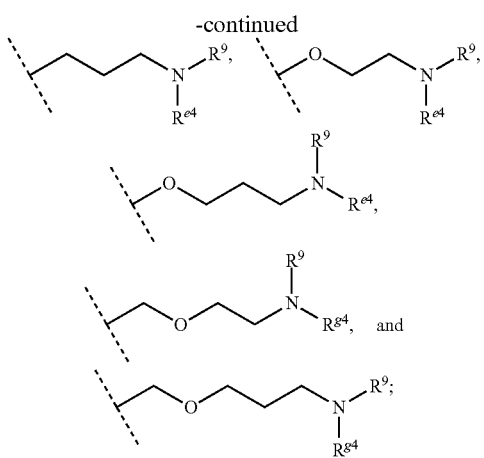

R⁹ is selected from among hydrogen and C₁₋₆alkyl;
R^{e4} is hydrogen or a group optionally substituted by one or more identical or different R^{d4} and/or R^{e4}, selected from among C₁₋₆alkyl and 3-14 membered heterocycloalkyl;
each R^{d4} is a suitable substituent and is selected independently of one another from among —OR^{e4}, —NR^{e4}R^{e4} and halogen;
each R^{e4} independently of one another denotes hydrogen or a group optionally substituted by one or more identical or different R^{f4} and/or R^{g4}, selected from among C₁₋₆alkyl, C₁₋₆haloalkyl, C₃₋₁₀cycloalkyl, C₆₋₁₀aryl, 5-12 membered heteroaryl and 3-14 membered heterocycloalkyl;
each R^{f4} is a suitable substituent and is selected independently of one another from among —OR^{g4}, —NR^{g4}R^{g4} and halogen as well as the bivalent substituent =O, which may only be a substituent in non-aromatic ring systems;
each R^{g4} independently of one another denotes hydrogen or a group optionally substituted by one or more identical or different R^{h4}, selected from among C₁₋₆alkyl, C₃₋₁₀cycloalkyl, 5-12 membered heteroaryl and 3-14 membered heterocycloalkyl;
each R^{h4} is selected independently of one another from among C₁₋₆alkyl and the bivalent substituent =O, which may only be a substituent in non-aromatic ring systems;
or
the group —NR^{g}R^{e4} denotes a nitrogen-containing, 3-14 membered heterocycloalkyl or 5-12 membered heteroaryl, optionally substituted by one or more identical or different group(s) selected from among R^{d4} and R^{e4};
the group —NR^{g}R^{e4} denotes a nitrogen-containing, 3-14 membered heterocycloalkyl or 5-12 membered heteroaryl, optionally substituted by one or more identical or different group(s) selected from among R^{f4} and R^{g4};
the group —NR^{g}R^{g4} denotes a nitrogen-containing 3-14 membered heterocycloalkyl or 5-12 membered heteroaryl, optionally substituted by one or more identical or different group(s) R^{h4}; and
R⁸ is selected from among hydrogen, C₁₋₆alkyl, —OC₁₋₆alkyl, —CN, halogen, 5-12 membered heteroaryl and 3-14 membered heterocycloalkyl.

In another aspect (F7) the invention relates to compounds (1) with structural aspect F6, wherein at least one of the groups R⁵ to R⁸ is not hydrogen.

In another aspect (F8) the invention relates to compounds (1) with structural aspect F6, wherein
R⁵ is selected from among

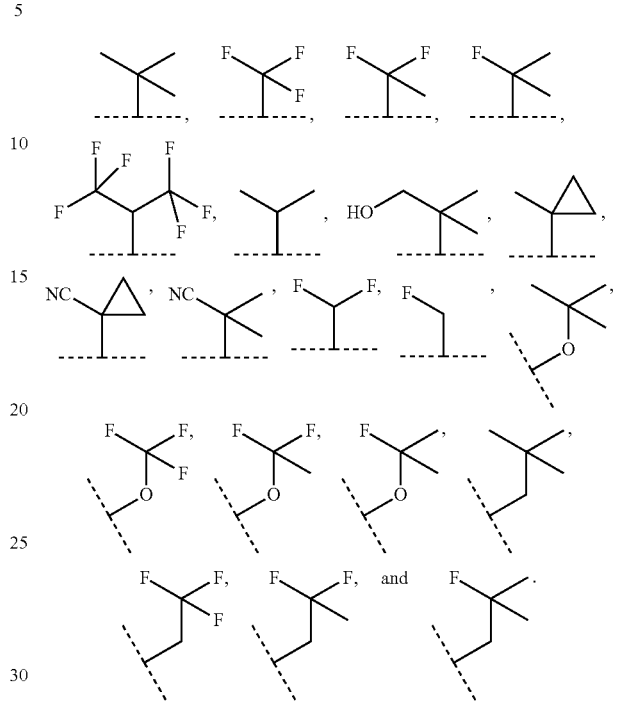

In another aspect (F9) the invention relates to compounds (1), wherein
R² is selected from among

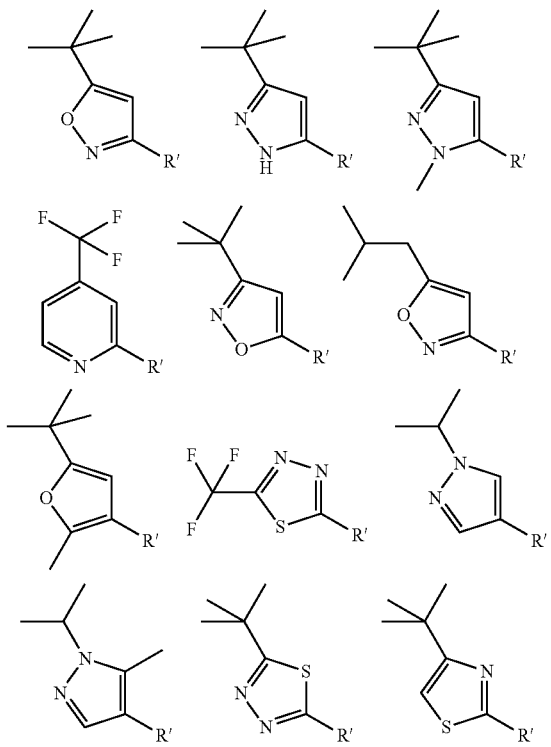

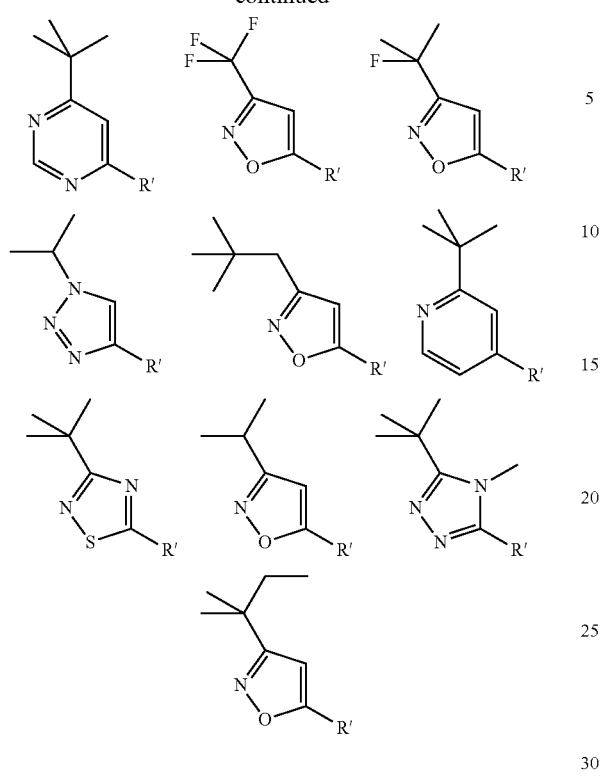
and R' denotes the binding site to the linker unit $L^2$.
In another aspect (F10) the invention relates to compounds (1), wherein
$R^2$ is selected from among
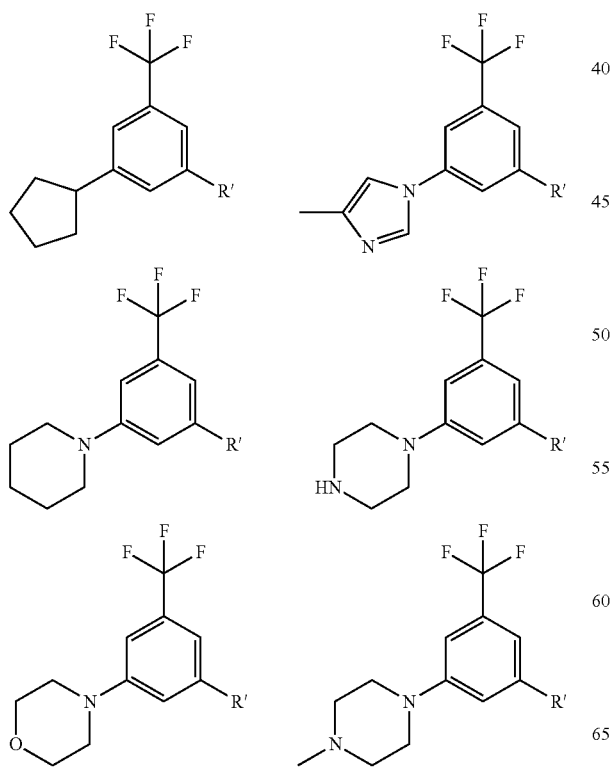
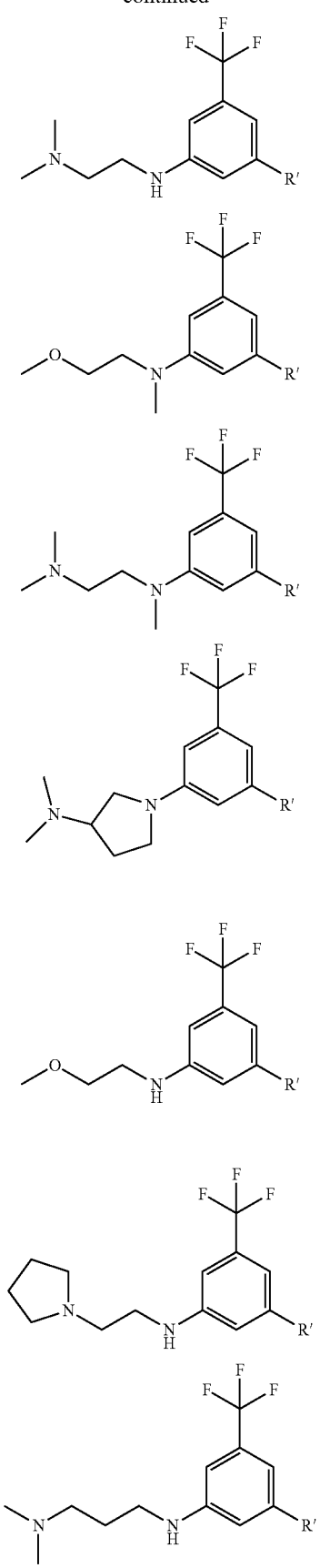

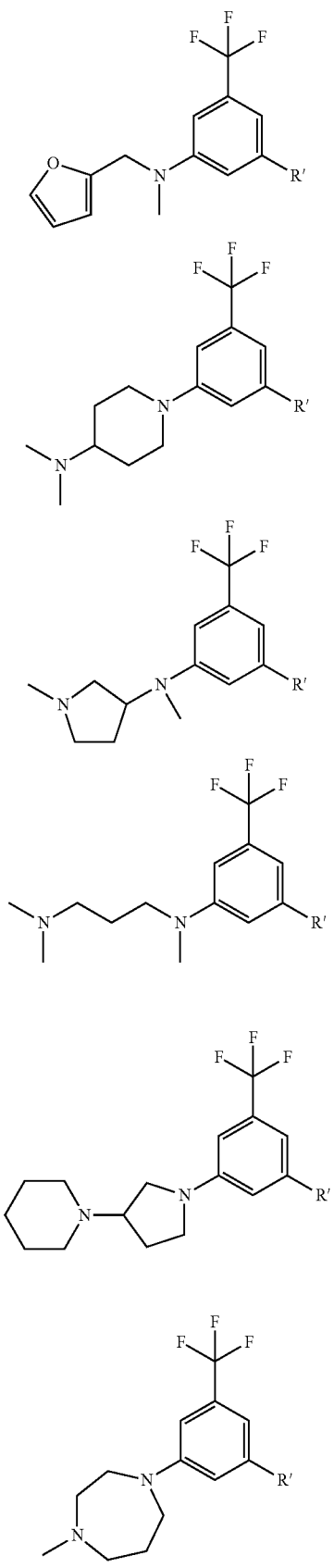
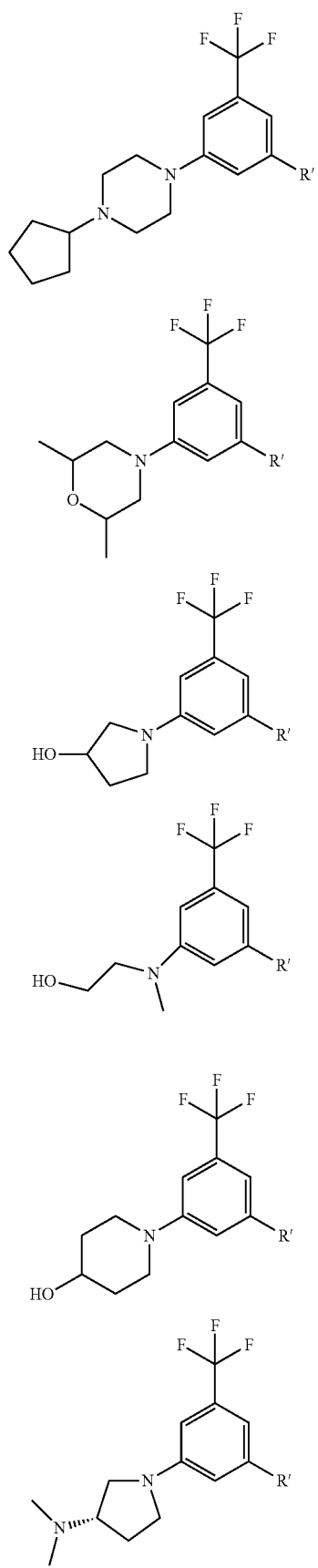

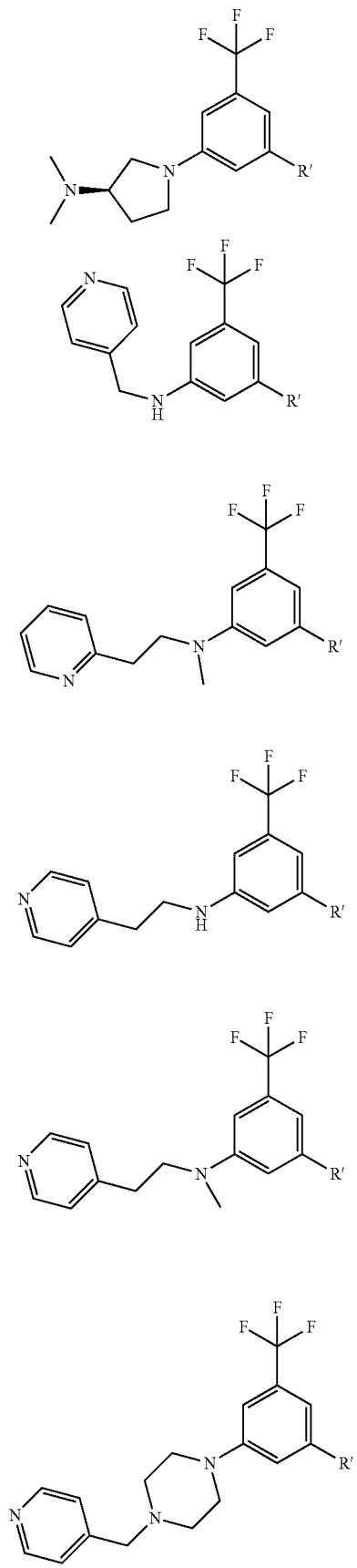
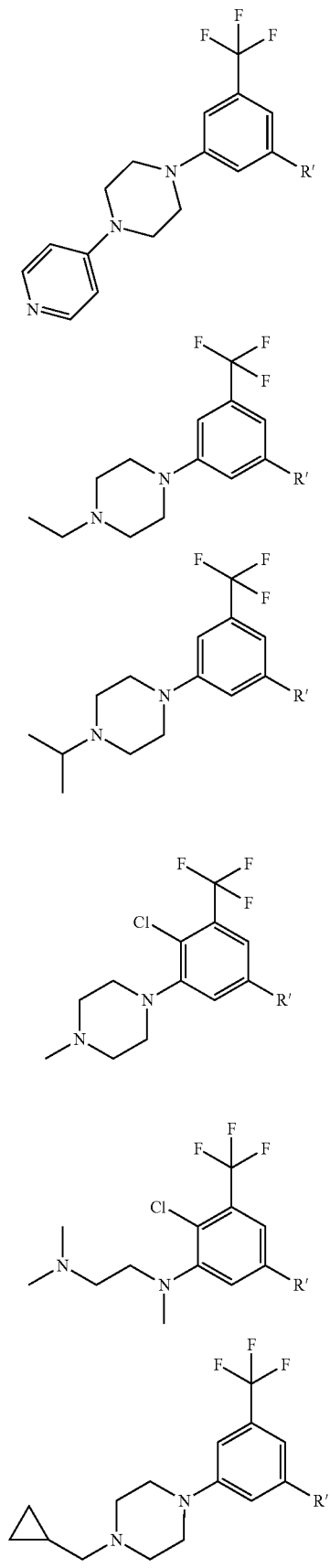

-continued
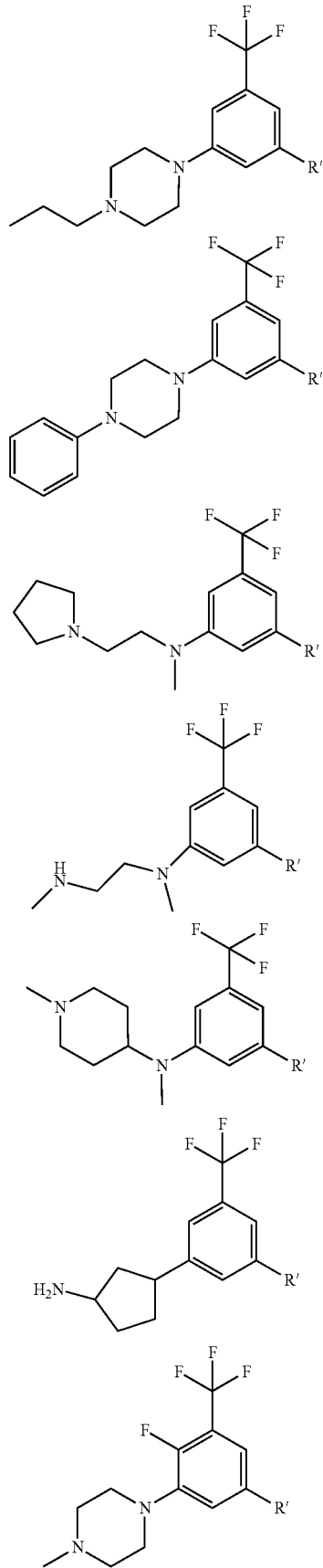
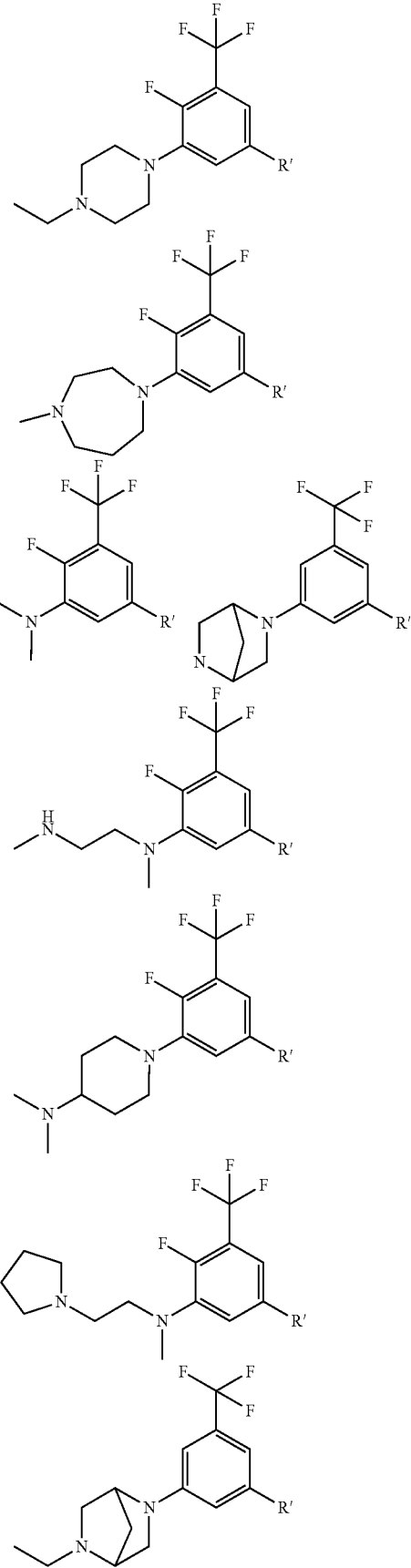

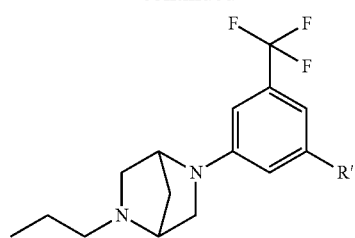
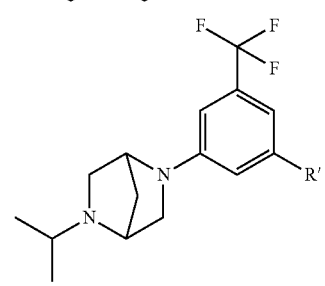
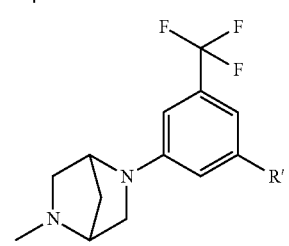
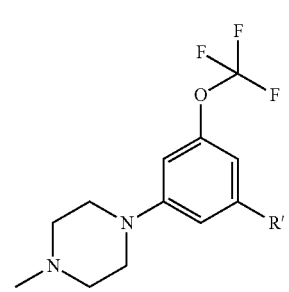
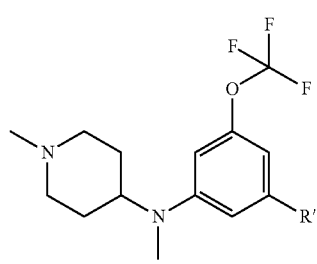
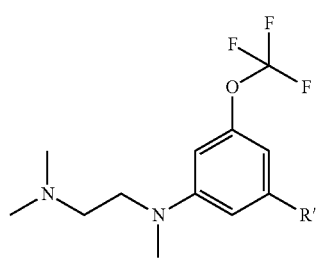
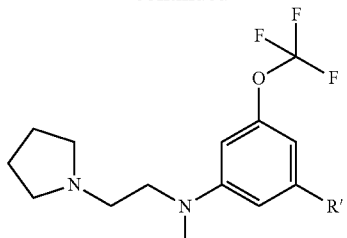
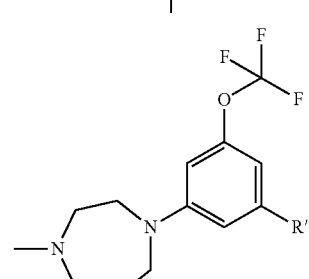
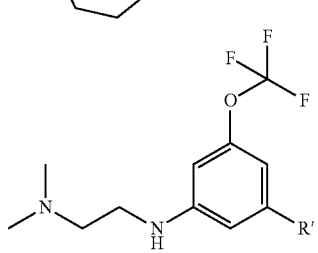
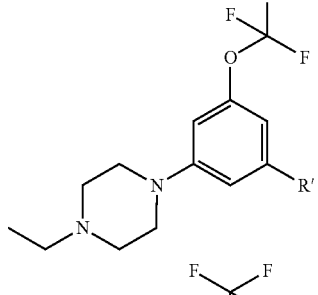
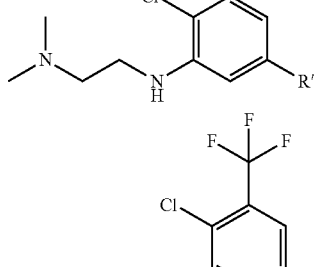
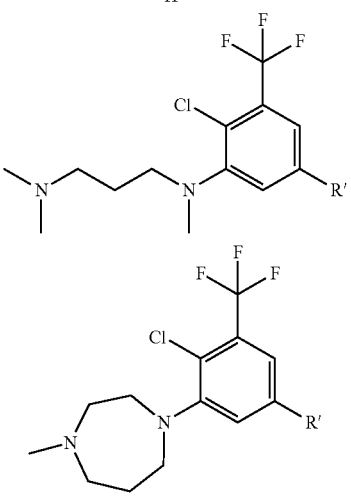

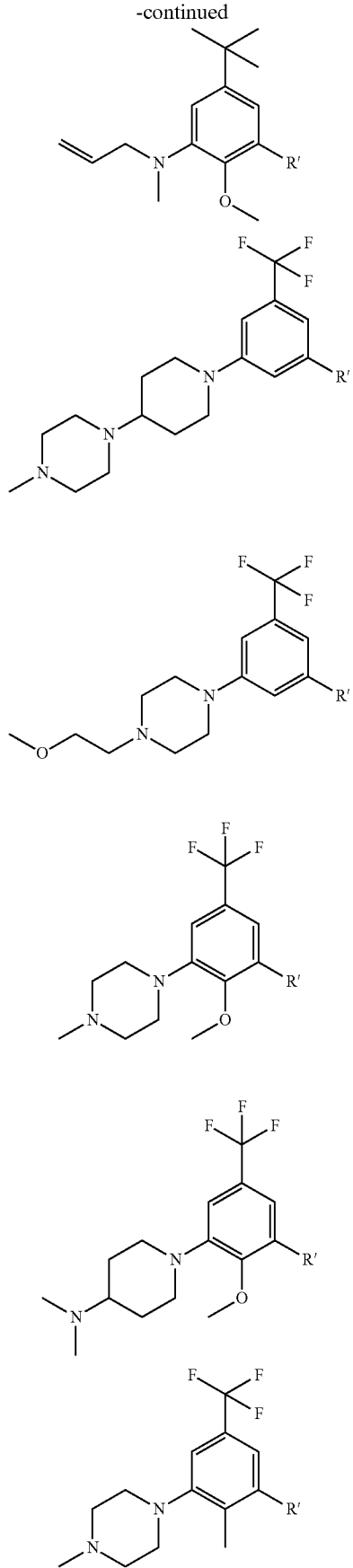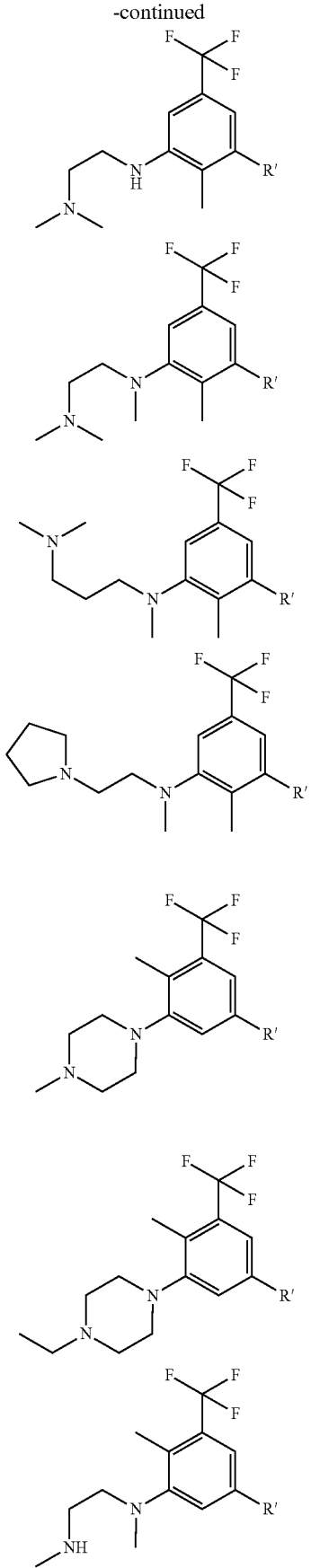

27
-continued
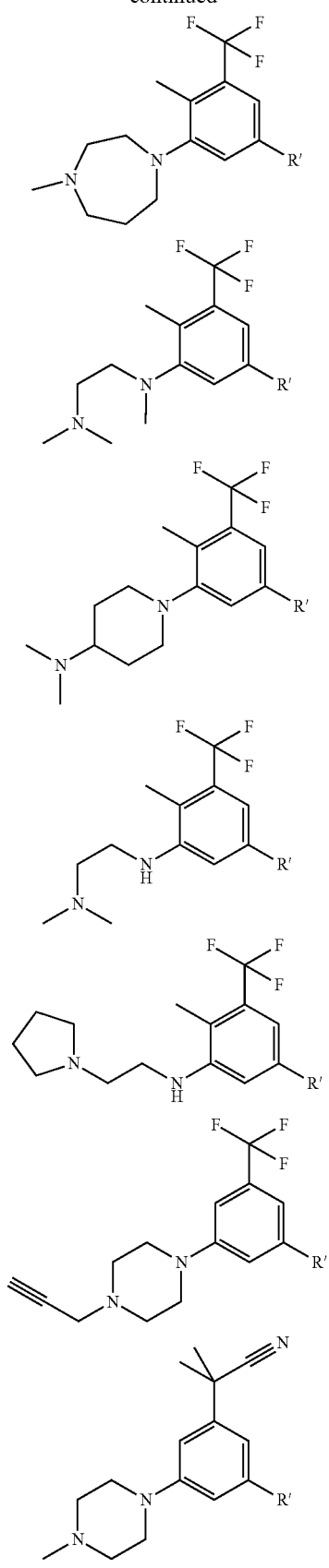
28
-continued
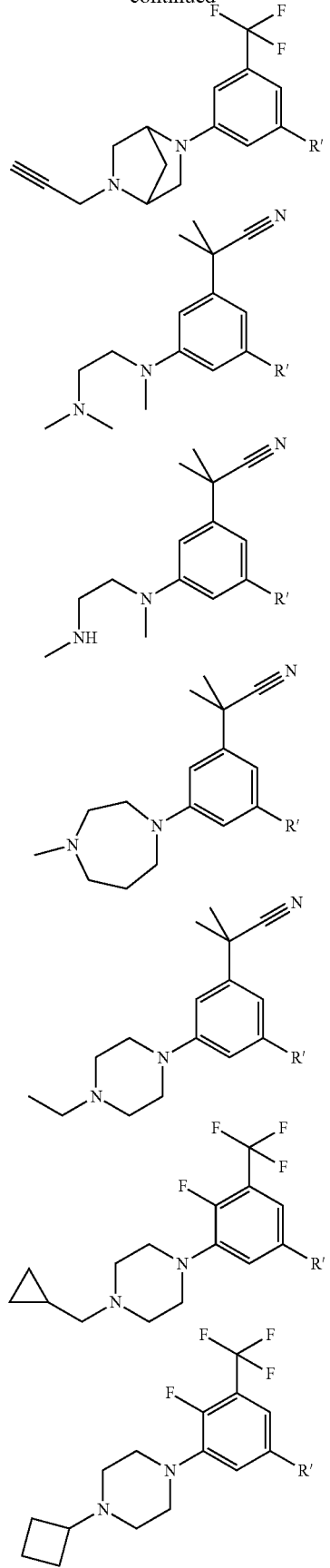

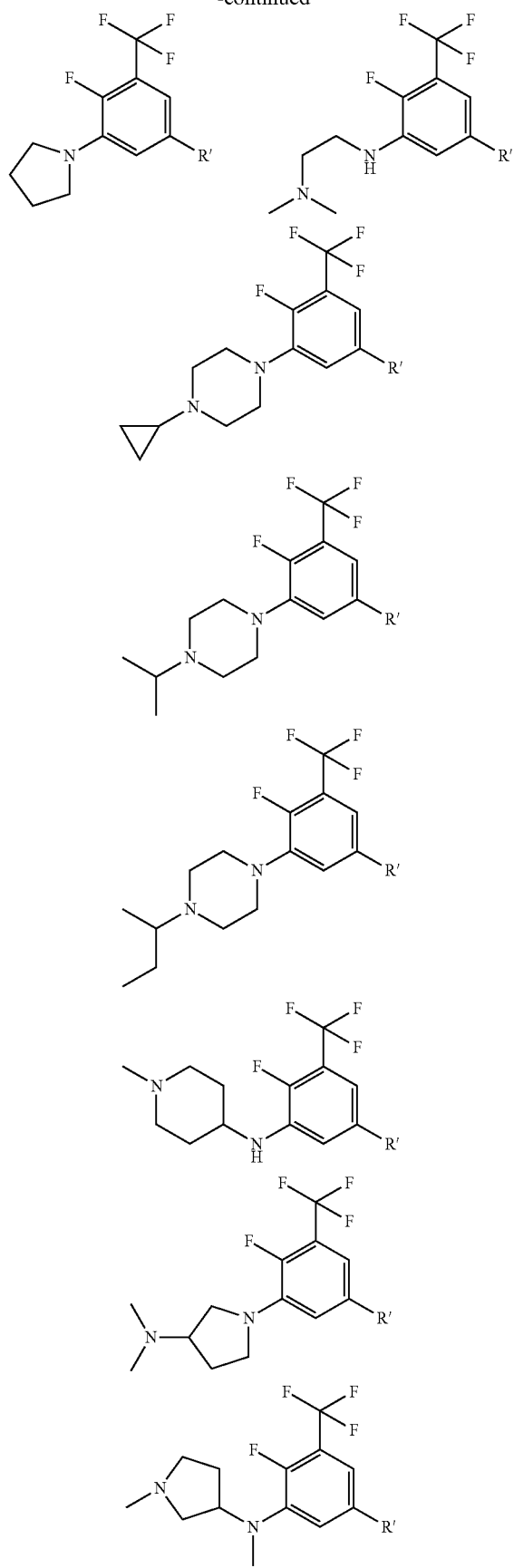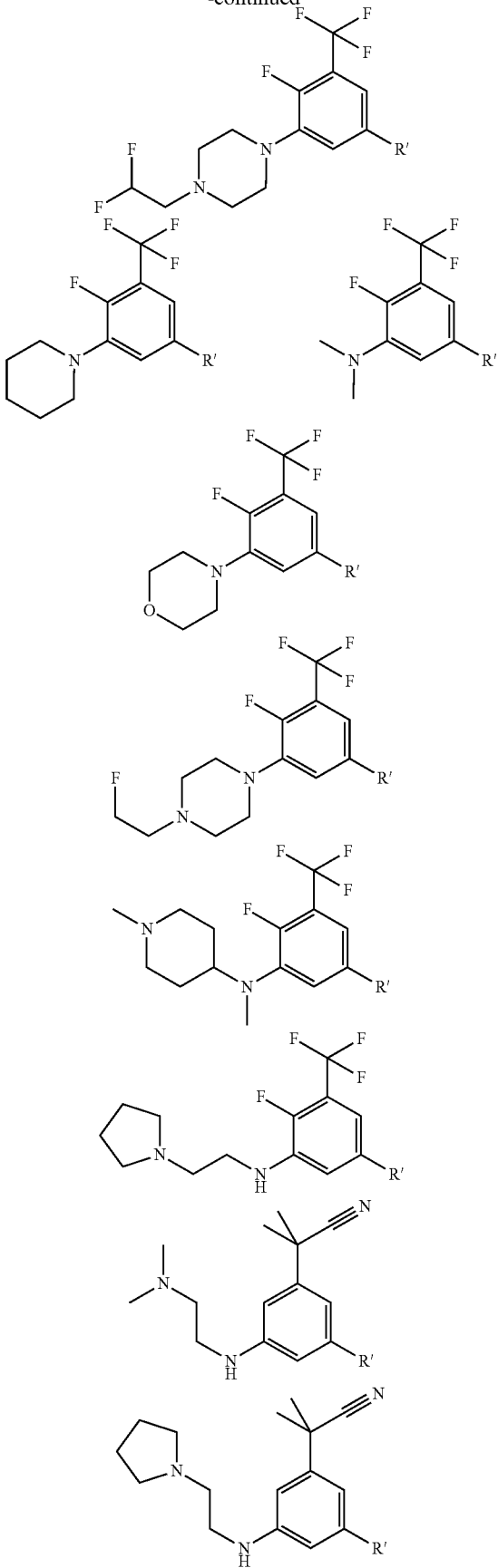

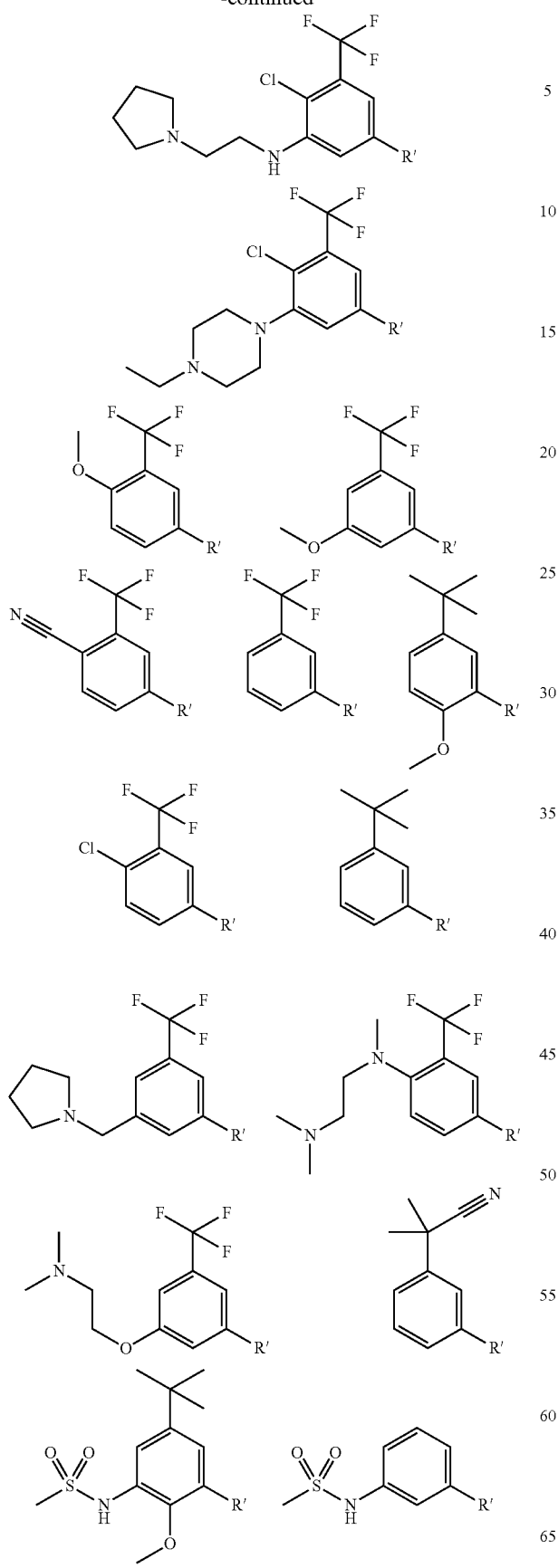
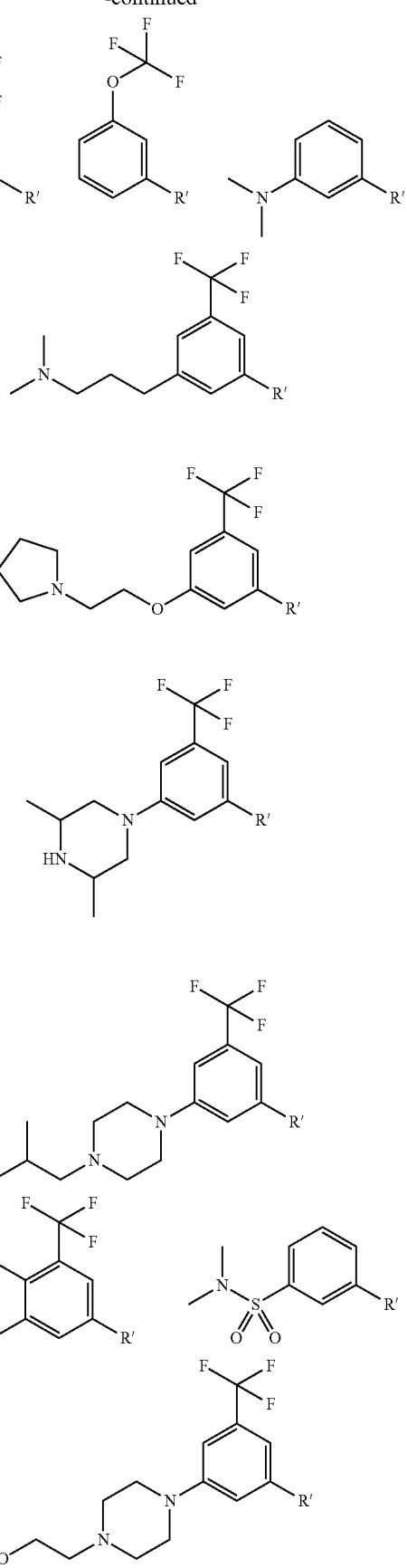

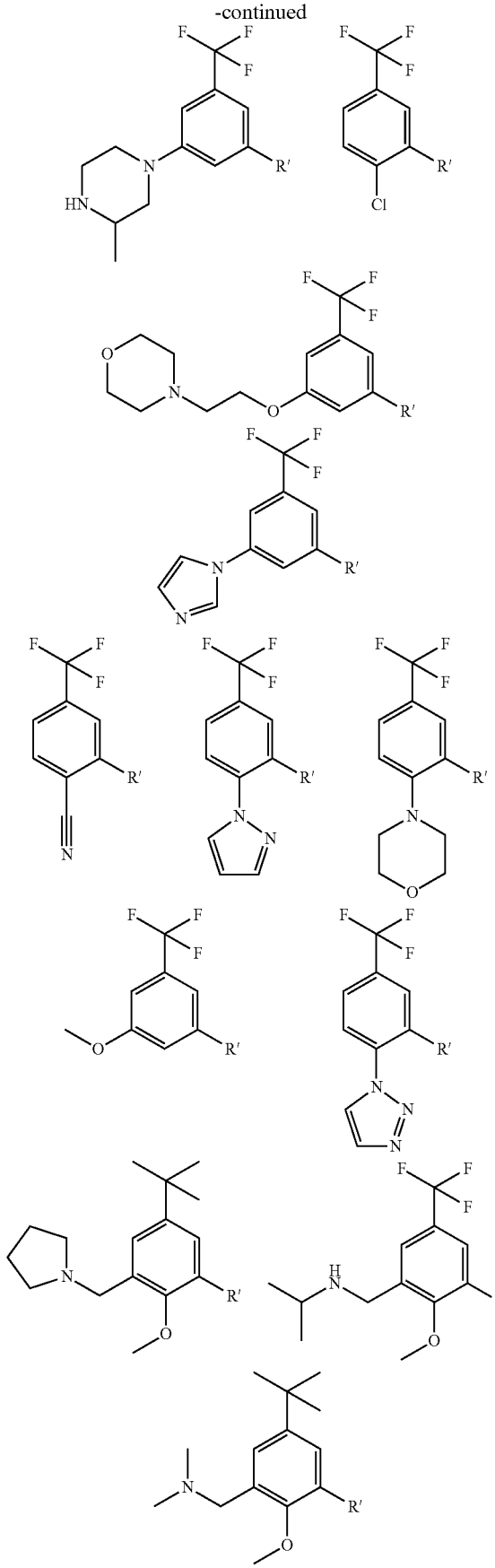
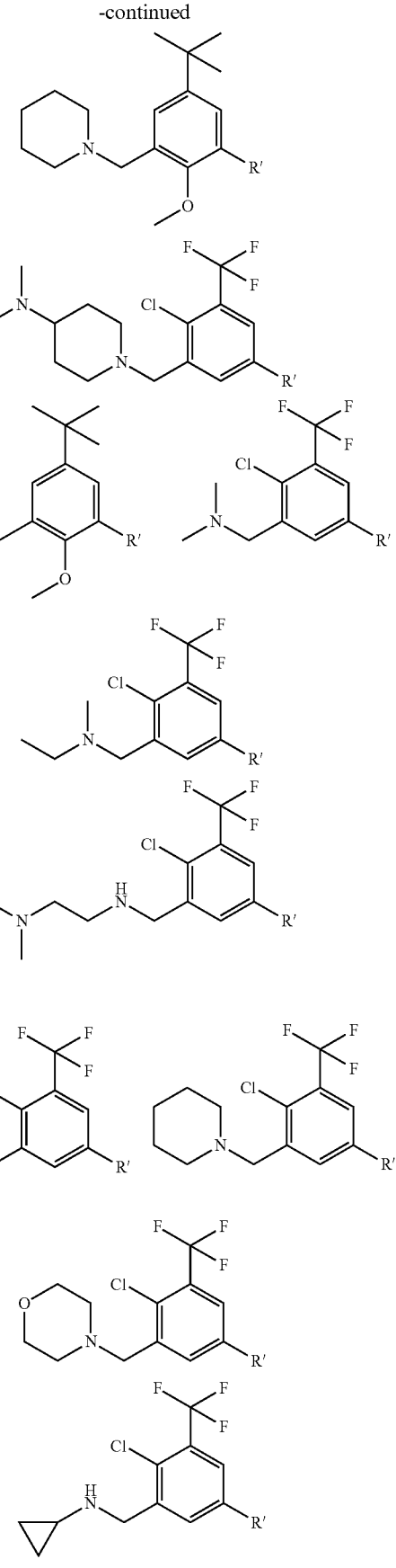

-continued
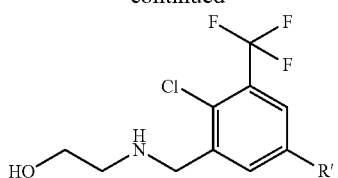
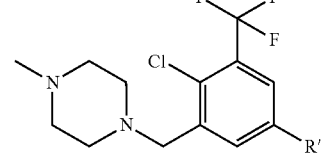
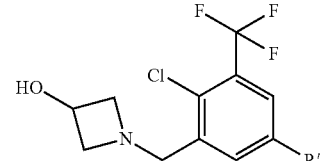
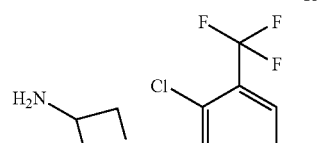
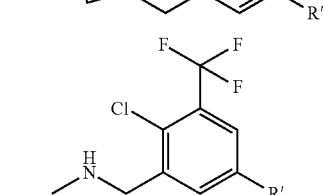
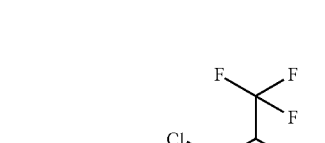
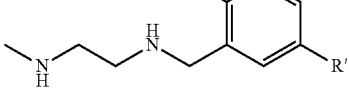
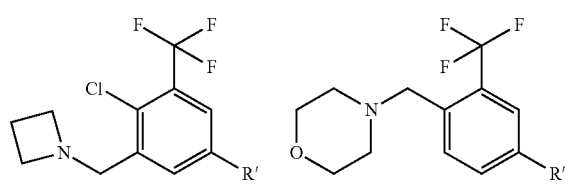
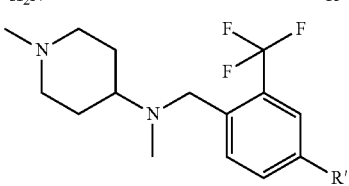
-continued
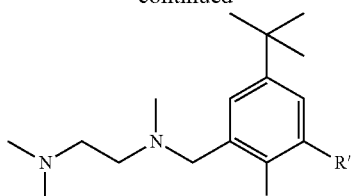
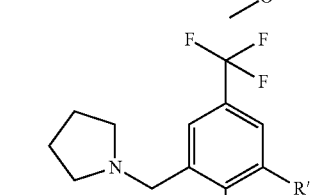
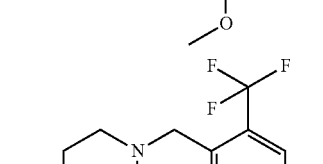
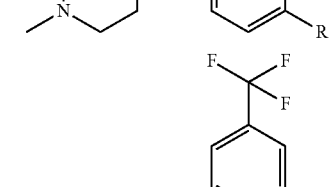
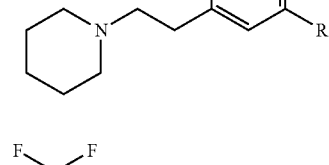
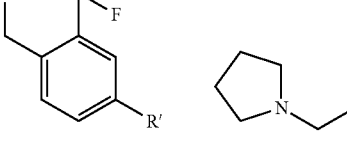
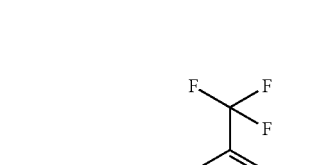
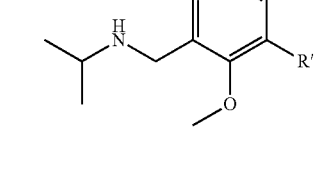
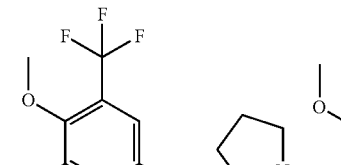

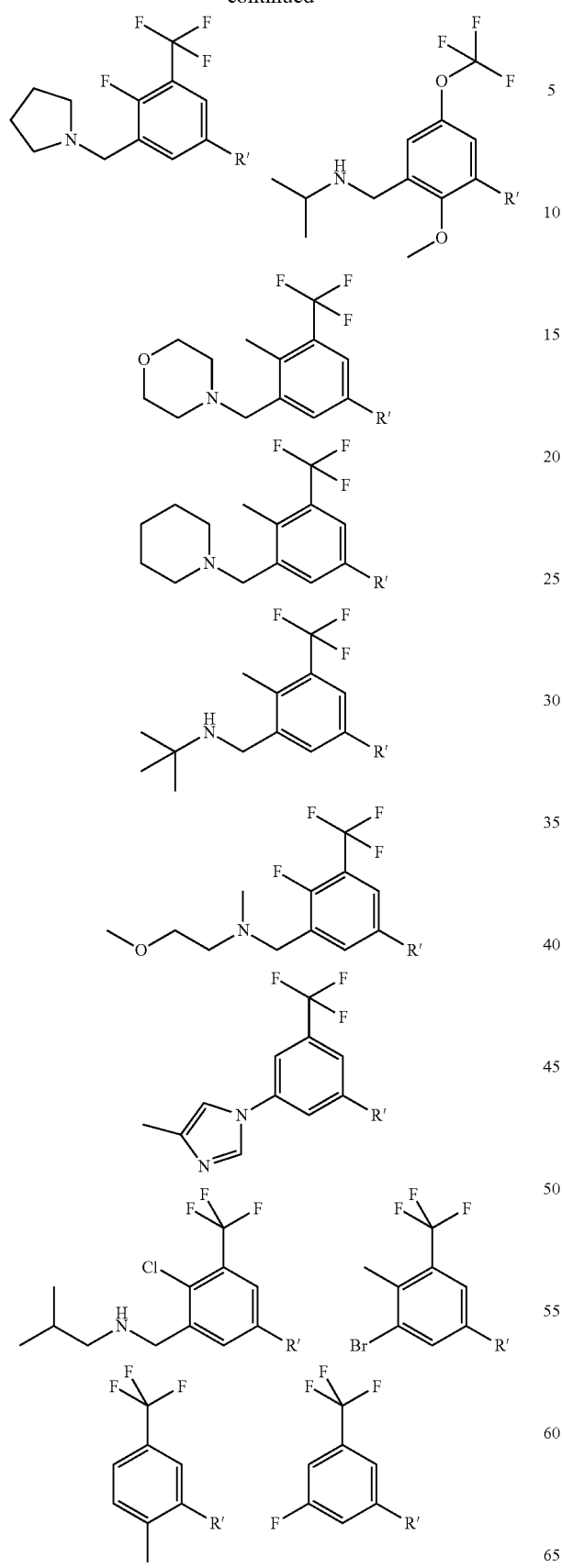
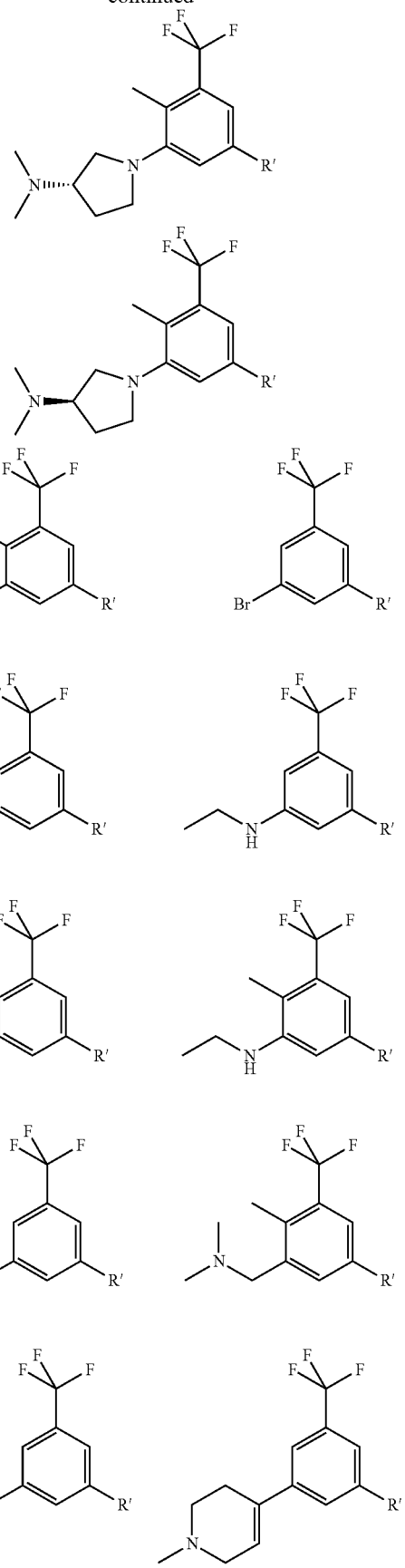

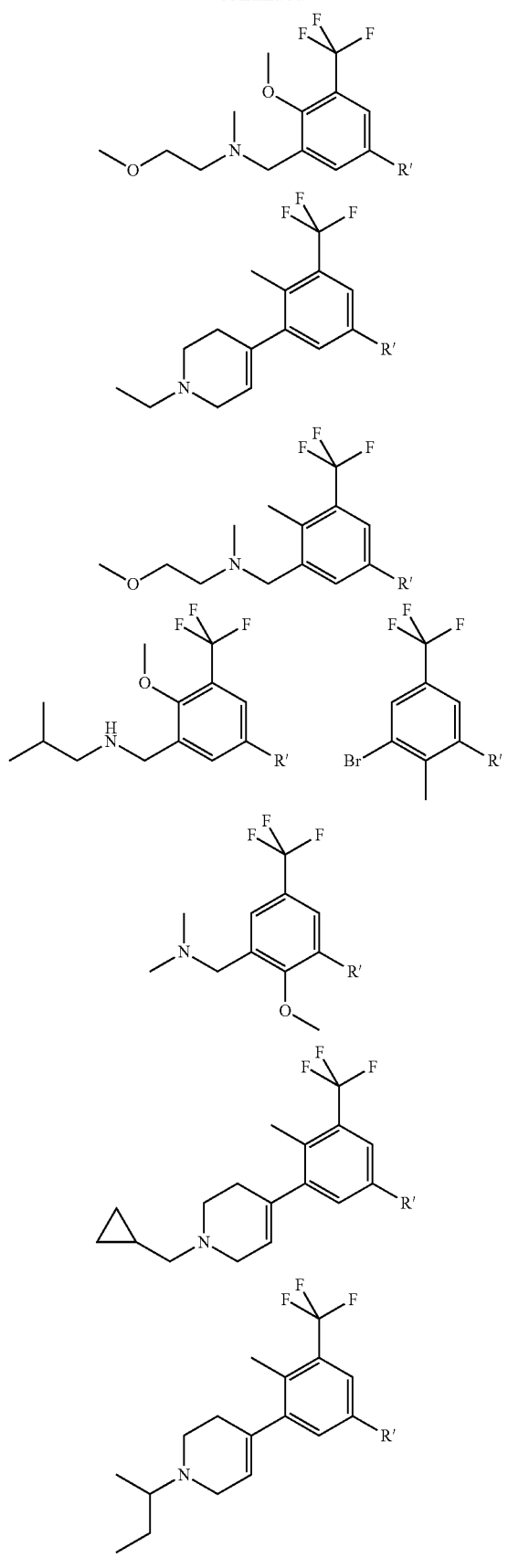
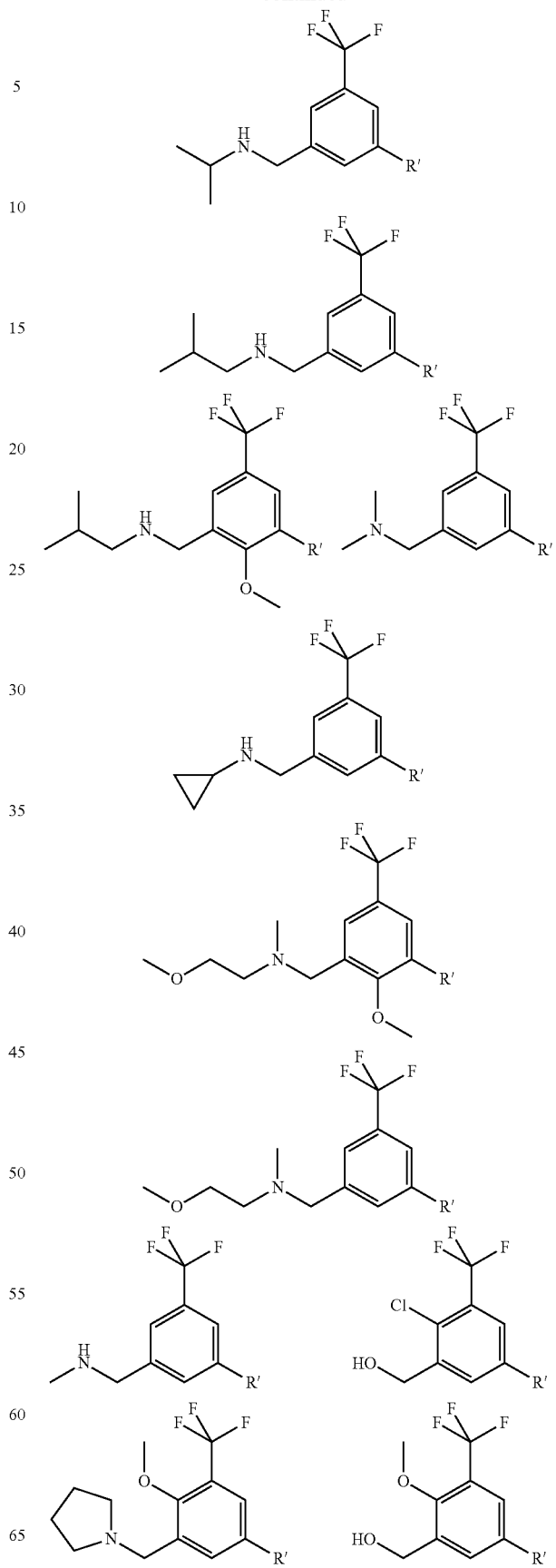

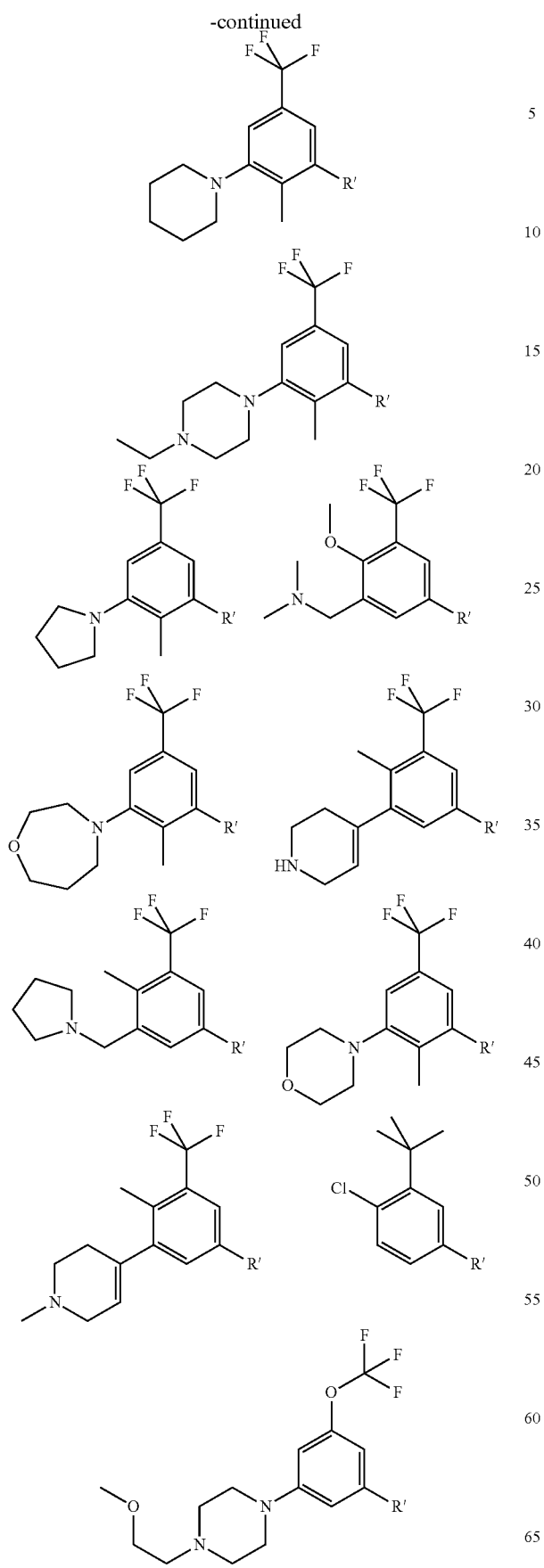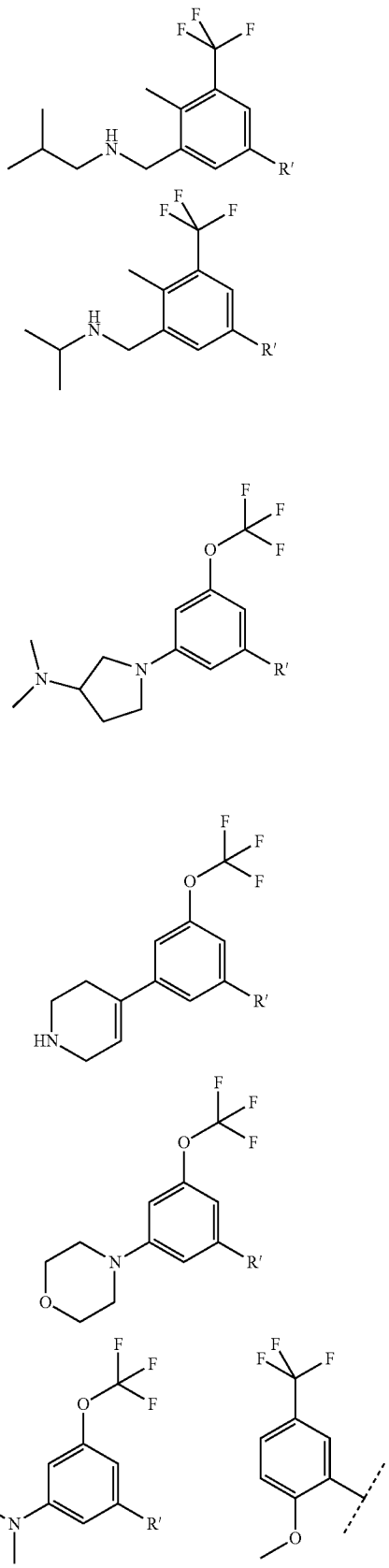
and R' denotes the binding site to the linker unit $L^2$.

In another aspect (F11) the invention relates to compounds (1), wherein
$R^2$ is selected from among

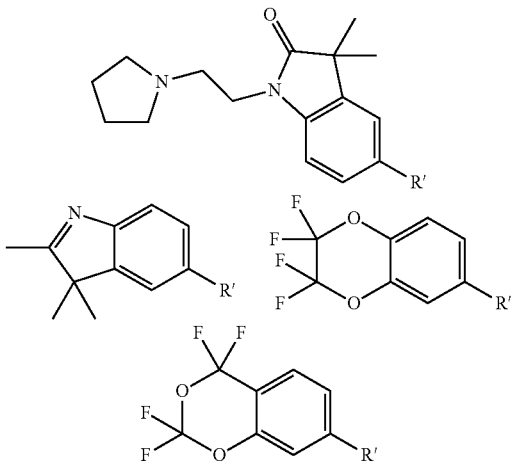

and R' denotes the binding site to the linker unit $L^2$.

In another aspect (G1) the invention relates to compounds (1), wherein
$L^2$ denotes $(R^2)$—NHC(O)—.

In another aspect (G2) the invention relates to compounds (1), wherein
$L^2$ denotes $(R^2)$—C(O)NH—.

All the above-mentioned structural aspects A to G relating to different molecular parts of the compounds (1) according to the invention may be permutated with one another as desired to form combinations ABCDEFG, so as to obtain preferred compounds (1). Each combination ABCDEFG represents and defines individual embodiments or generic partial amounts of compounds according to the invention. Every individual embodiment or partial amount defined by this combination is expressly included and is an object of the invention.

In another aspect the invention relates to compounds—or the pharmacologically acceptable salts thereof—of general formula (1) as medicaments.

In another aspect the invention relates to pharmaceutical preparations, containing as active substance one or more compounds of general formula (1) or the pharmacologically acceptable salts thereof, optionally in combination with conventional excipients and/or carriers.

In another aspect the invention relates to compounds of general formula (1) for use in the treatment and/or prevention of cancer, infections, inflammations and autoimmune diseases.

In another aspect the invention relates to compounds of general formula (1) for use in the treatment and/or prevention of cancer.

In another aspect the invention relates to a pharmaceutical preparation comprising a compound of general formula (1), while the compounds (1) may optionally also be in the form of the tautomers, racemates, enantiomers, diastereomers and mixtures thereof or as the respective pharmacologically acceptable salts of all the above-mentioned forms, and at least one other cytostatic or cytotoxic active substance different from formula (1).

DEFINITIONS

As used herein, the following definitions apply, unless stated otherwise:

The use of the prefix $C_{x-y}$, where x and y in each case denote a natural number (x<y), indicates that the chain or cyclic structure or combination of chain and cyclic structure referred to and mentioned in direction connection may consist in total of a maximum of y and a minimum of x carbon atoms.

The information as to the number of members in groups containing one or more hetero-atom(s) (heteroalkyl, heteroaryl, heteroarylalkyl, heterocycloalkyl, heterocycloalkylalkyl) refers to the total atomic number of all the ring members or chain members or the total of all the ring and chain members.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms. Examples of individual sub-groups are listed below:

Straight-Chain (Unbranched) or Branched, Saturated Hydrocarbon Chains:
methyl; ethyl; n-propyl; isopropyl (1-methylethyl); n-butyl; 1-methylpropyl; isobutyl (2-methylpropyl); sec.-butyl (1-methylpropyl); tert.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:
vinyl(ethenyl); prop-1-enyl; allyl(prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:
ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

From alkyl as hereinbefore defined and its subgroups the term alkylene can also be derived. Alkylene unlike alkyl is bivalent and requires two bonding partners. Formally the second valency is produced by removing a hydrogen atom from an alkyl. Corresponding groups are for example —CH$_3$ and —CH$_2$, —CH$_2$CH$_3$ and —CH$_2$CH$_2$ or >CHCH$_3$ etc. For all the subgroups of alkyl there are correspondences for alkylene.

By heteroatoms are meant oxygen, nitrogen and sulphur atoms.

By the term heteroalkyl are meant groups which are derived from the alkyl as hereinbefore defined in its widest sense by replacing, in the hydrocarbon chains, one or more of the groups —CH$_3$ independently of one another by the groups —OH, —SH or —NH$_2$, one or more of the groups —CH$_2$— independently of one another by the groups —O—, —S— or —NH—, one or more of the groups >CH— by the group >N—, one or more of the groups =CH— by the group =N—, one or more of the groups =CH$_2$ by the group =NH or one or more of the groups ≡CH by the group ≡N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom. The following are listed by way of example:
dimethylaminomethyl; dimethylaminoethyl (1-dimethylaminoethyl; 2-dimethyl-amino-ethyl); dimethylaminopropyl (1-dimethylaminopropyl, 2-dimethylaminopropyl, 3-dimethylaminopropyl); diethylaminomethyl; diethylaminoethyl (1-diethylamino ethyl, 2-diethylamino ethyl); diethylaminopropyl (1-diethylaminopropyl, 2-diethylaminopropyl, 3-diethylaminopropyl); diisopropylaminoethyl (1-diisopropylaminoethyl, 2-diisopropyl-aminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

From heteroalkyl as hereinbefore defined and its subgroups the term heteroalkylene can also be derived. Heteroalkylene unlike heteroalkyl is bivalent and requires two bonding partners. Formally the second valency is produced by removing a hydrogen atom from a heteroalkyl. Corresponding groups are for example —CH$_2$NH$_2$ and —CH$_2$NH— or >CHNH$_2$, —NHCH$_3$ and >NCH$_3$ or —NHCH$_2$—, —CH$_2$OCH$_3$ and —CH$_2$OCH$_2$— or >CHOCH$_3$ etc. For all the subgroups of heteroalkyl there are correspondences for heteroalkylene.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms. Typical examples are listed below:
—CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C≡C—CF$_3$; —CHFCH$_2$CH$_3$; —CHFCH$_2$CF$_3$ etc.

From haloalkyl as hereinbefore defined and its subgroups the term haloalkylene can also be derived. Haloalkylene unlike haloalkyl is bivalent and requires two bonding partners.

Formally the second valency is produced by removing a hydrogen atom from a haloalkyl. Corresponding groups are for example —CH$_2$F and —CHF—, —CHFCH$_2$F and —CHFCHF— or >CFCH$_2$F etc. For all the subgroups of haloalkyl there are correspondences for haloalkylene.

Halogen encompasses fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system. The following individual sub-groups are listed by way of example:
Monocyclic Hydrocarbon Rings, Saturated:
cyclopropyl; cyclobutyl; cyclopentyl; cyclohexyl; cycloheptyl etc.
Monocyclic hydrocarbon rings, unsaturated:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.
Bicyclic Hydrocarbon Rings (Saturated and Unsaturated):
bicyclo[2.2.0]hexyl; bicyclo[3.2.0]heptyl; bicyclo[3.2.1]octyl; bicyclo[2.2.2]octyl; bicyclo[4.3.0]nonyl(octahydroindenyl); bicyclo[4.4.0]decyl(decahydronaphthalene); bicyclo[2.2.1]heptyl(norbornyl); (bicyclo[2.2.1]hepta-2,5-dienyl(norborna-2,5-dienyl); bicyclo[2.2.1]hept-2-enyl (norbornenyl); bicyclo[4.1.0]heptyl(norcaranyl); bicyclo-[3.1.1]heptyl(pinanyl) etc.
Spirohydrocarbon Rings (Saturated and Unsaturated):
spiro[2.5]octyl, spiro[3.3]heptyl, spiro[4.5]dec-2-ene, etc.

If the free valency of a cycloalkyl is saturated off, an alicyclic ring is obtained.

From cycloalkyl as hereinbefore defined and its subgroups the term cycloalkylene can also be derived. Cycloalkylene unlike cycloalkyl is bivalent and requires two bonding partners. Formally the second valency is produced by removing a hydrogen atom from a cycloalkyl. Corresponding groups are for example cyclohexyl and

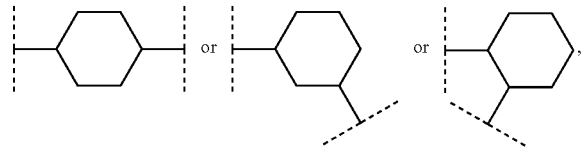

cyclopentenyl and

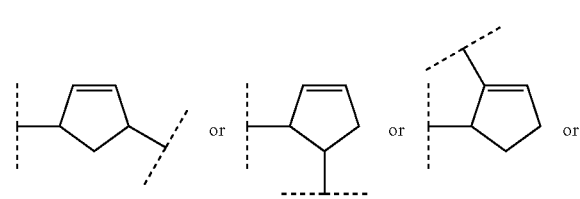

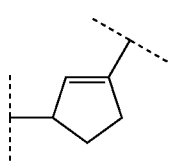

etc.

For all the subgroups of cycloalkyl there are correspondences for cycloalkylene.

Cycloalkylalkyl refers to the combination of the alkyl in question, as hereinbefore defined, with cycloalkyl, both in their widest sense. Alternatively cycloalkylalkyl may also be regarded as a combination of cycloalkyl with alkylene. Formally, cycloalkylalkyl is obtained by first linking an alkyl as substituent directly with the molecule and then substituting with a cycloalkyl. The linking of alkyl and cycloalkyl may be carried out in both groups using carbon atoms that are suitable for this purpose. The respective subgroups of alkyl (alkylene) and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system. Typical examples are listed below:

phenyl, naphthyl, indanyl (2,3-dihydroindenyl), 1,2,3,4-tetrahydronaphthyl; fluorenyl, etc.

If the free valency of an aryl is saturated off, an aromatic group is obtained.

From aryl as hereinbefore defined the term arylene can also be derived. Arylene unlike aryl is bivalent and requires two bonding partners. Formally the second valency is produced by removing a hydrogen atom from an aryl. Corresponding groups are for example phenyl and

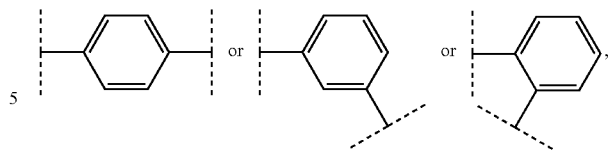

naphthyl and

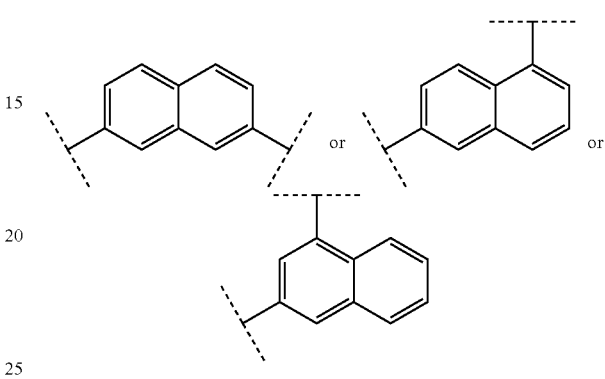

etc. For all the subgroups of aryl there are correspondences for arylene.

Arylalkyl denotes the combination of the groups alkyl and aryl as hereinbefore defined, in each case in their broadest sense. Alternatively arylalkyl may also be regarded as a combination of aryl with alkylene. Formally, arylalkyl is obtained by first linking an alkyl as substituent directly to the molecule and substituting it with an aryl group. The alkyl and aryl may be linked in both groups via any carbon atoms suitable for this purpose. The respective sub-groups of alkyl (alkylene) and aryl are also included in the combination of the two groups. Typical examples are listed below:

benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. The prerequisite for the presence of heteroaryl is a heteroatom and an aromatic system, although it need not necessarily be a heteroaromatic system. Thus 2,3-dihydro-1H-indol-6-yl

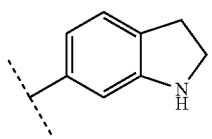

may according to the definition be a heteroaryl.

If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen. Typical examples are listed below.

Monocyclic Heteroaryls:

furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls indolyl; isoindolyl; benzofuryl; benzothienyl; benzoxazolyl; benzothiazolyl; benzisoxazolyl; dihydroindolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; coumarinyl; isocoumarinyl; chromonyl; chromanonyl; tetrahydroquinolinyl; dihydroquinolinyl; dihydroquinolinonyl; dihydroisoquinolinonyl; dihydrocoumarinyl; dihydroisocoumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzothiopyranyl-5-oxide and benzothiopyranyl-S,S-dioxide etc.

If the free valency of a heteroaryl is saturated off, a heteroaromatic group is obtained.

From heteroaryl as hereinbefore defined the term heteroarylene can also be derived. Heteroarylene unlike heteroaryl is bivalent and requires two bonding partners. Formally the second valency is produced by removing a hydrogen atom from a heteroaryl.

Corresponding groups are for example pyrrolyl and

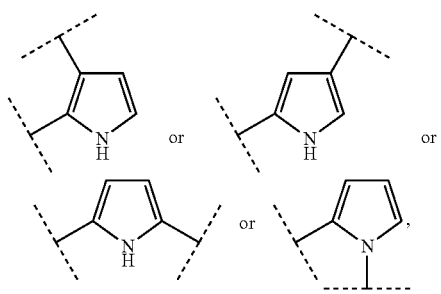

2,3-dihydro-1H-indolyl and

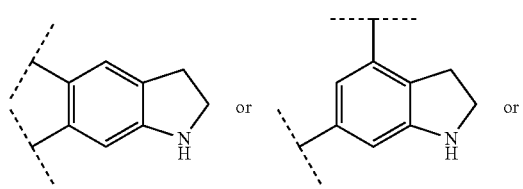

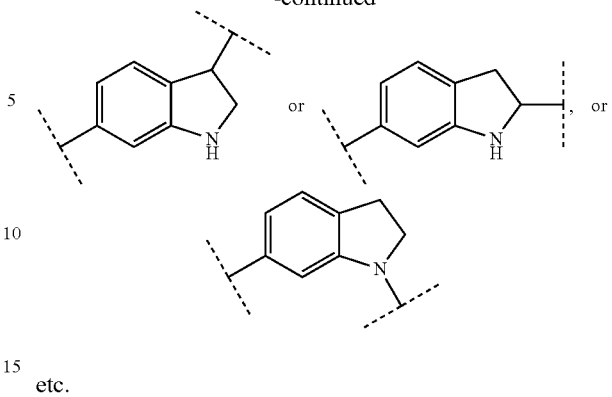

etc.

For all the subgroups of heteroaryl there are correspondences for heteroarylene.

Heteroarylalkyl denotes the combination of the alkyl in question as hereinbefore defined with heteroaryl, both in their broadest sense. Alternatively heteroarylalkyl may also be regarded as a combination of heteroaryl with alkylene. Formally heteroarylalkyl is obtained by first linking an alkyl as substituent directly with the molecule and then substituting it with a heteroaryl. The linking of the alkyl and heteroaryl may be achieved on the alkyl side via any carbon atoms suitable for this purpose and on the heteroaryl side via any carbon or nitrogen atoms suitable for this purpose. The respective subgroups of alkyl (alkylene) and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system. Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-5-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydropyrimidinyl; dihydrofuryl; dihydropyranyl; tetrahydrothienyl-5-oxide; tetrahydrothienyl-S,S-dioxide; homothiomorpholinyl-5-oxide; 2,3-dihydroazet; 2H-pyrrolyl; 4H-pyranyl; 1,4-dihydropyridinyl etc.

Bicyclic Heterorings (Saturated and Unsaturated):
8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl etc.

Spiro-Heterorings (Saturated and Unsaturated):
1,4-dioxa-spiro[4.5]decyl; 1-oxa-3.8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

If the free valency of a heterocycloalkyl is saturated off, then a heterocyclic ring is obtained.

From heterocycloalkyl as hereinbefore defined the term heterocycloalkylene can also be derived. Heterocycloalkylene unlike heterocycloalkyl is bivalent and requires two bonding partners. Formally the second valency is produced by removing a hydrogen atom from a heterocycloalkyl. Corresponding groups are for example piperidinyl and

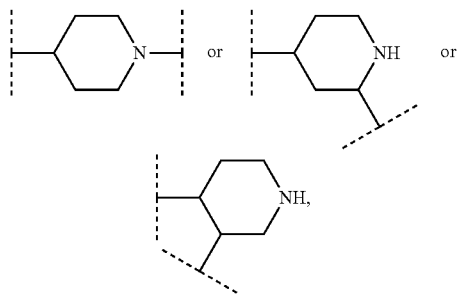

2,3-dihydro-1H-pyrrolyl and

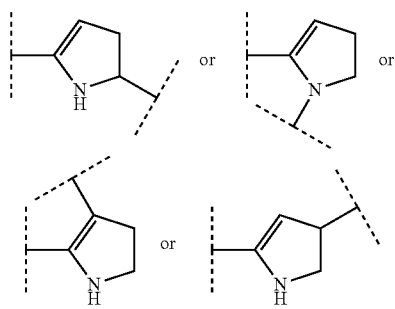

etc. For all the subgroups of heterocycloalkyl there are correspondences for heterocycloalkylene.

Heterocycloalkylalkyl denotes the combination of the alkyl in question as hereinbefore defined with heterocycloalkyl, both in their broadest sense. Alternatively heterocycloalkylalkyl may also be regarded as a combination of heterocycloalkyl with alkylene. Formally heterocycloalkyl is obtained by first linking an alkyl as substituent directly with the molecule and then substituting it with a heterocycloalkyl. The linking of the alkyl and heterocycloalkyl may be achieved on the alkyl side via any carbon atoms suitable for this purpose and on the heterocycloalkyl side via any carbon or nitrogen atoms suitable for this purpose. The respective sub-groups of alkyl and heterocycloalkyl are also included in the combination of the two groups.

By is substituted is meant that a hydrogen atom that is bound directly to the atom under consideration is replaced by another atom or another group of atoms (substituent). Depending on the starting conditions (number of hydrogen atoms) mono- or polysubstitution may take place at an atom.

Bivalent substituents such as for example =S, =NR, =NOR, =NNRR, =NN(R)C(O)NRR, =N$_2$ or the like may only be substituents at carbon atoms, while the bivalent substituent =O may also be a substituent of sulphur. Generally speaking, substitution by a bivalent substituent may only take place at ring systems and requires exchange for two geminal hydrogen atoms, i.e. hydrogen atoms that are bound to the same carbon atom saturated before the substitution. Substitution by a bivalent substituent is therefore only possible at the group —CH$_2$— or sulphur atoms of a ring system.

In addition to this, the term "suitable substituent" denotes a substituent which on the one hand is suitable on account of its valency and on the other hand leads to a system with chemical stability.

The following are some abbreviated notations and their structural correspondences:

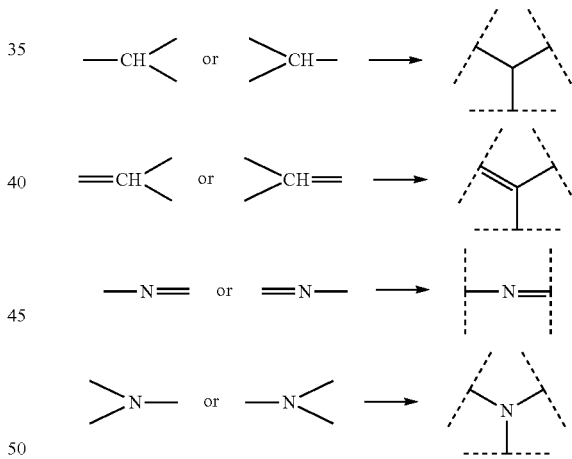

If for example in the sequence A-B—C the member B were to correspond to the structural detail —N=, this is to be understood as both A=N—C and

A-N=C

If for example in the sequence

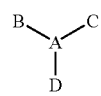

the member A were to correspond to the structural detail >C= this is to be understood as being

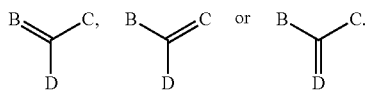

In a diagram such as for example

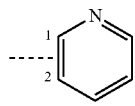

the dotted line indicates that the ring system may be attached to the molecule via the carbon 1 or 2, i.e. is equivalent to the following diagram

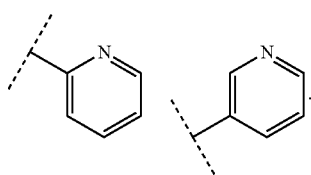

For bivalent groups where the valency with which they bind which adjacent group is critical, the corresponding binding partners are given in brackets, wherever it is necessary for clarification, as in the following formulae:

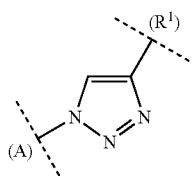

or $(R^2)$—C(O)NH— or $(R^2)$—NHC(O)—;

Groups or substituents are frequently selected from among alternative groups/substituents with a corresponding group designation (e.g. $R^a$, $R^b$ etc). If a group of this kind is used repeatedly to define a compound according to the invention in different parts of the molecule, it should always be borne in mind that the respective uses are to be regarded as being totally independent of one another.

List of Abbreviations

| | |
|---|---|
| Ac | acetyl |
| ATP | adenosine triphosphate |
| Bn | benzyl |
| Boc | tert.-butyloxycarbonyl |
| Bu | butyl |
| c | concentration |
| chex | cyclohexane |
| d | day(s) |
| TLC | thin layer chromatography |
| DCM | dichloromethane |
| DEA | diethylamine |
| DIPEA | N-ethyl-N,N-diisopropylamine (HÜNIG base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| EDTA | ethylenediaminetetraacetic acid |
| EE | ethyl acetate |
| EGTA | ethyleneglycoltetraacetic acid |
| eq | equivalent(s) |
| ESI | electron spray ionization |
| Et | ethyl |
| $Et_2O$ | diethyl ether |
| EtOH | ethanol |
| h | hour |
| HATU | O-(7-azabenzotriazol-1-yl)-N,N,N',N'-tetramethyl-uronium hexafluorophosphate |
| hex | hexyl |
| HPLC | high performance liquid chromatography |
| Hünig base | N-ethyl-N,N-diisopropylamine |
| i | iso |
| cat. | catalyst, catalytically |
| conc. | concentrated |
| LC | liquid chromatography |
| sln. | solution |
| mCPBA | meta-chloroperbenzoic acid |
| Me | methyl |
| MeOH | methanol |
| min | minutes |
| MPLC | medium pressure liquid chromatography |
| MS | mass spectrometry |
| NMP | N-methylpyrrolidone |
| NP | normal phase |
| n.a. | not available |
| PBS | phosphate-buffered saline |
| Ph | phenyl |
| PMSF | benzylsulphonic acid fluoride |
| Pr | propyl |
| Py | pyridine |
| rac | racemic |
| red. | reduction |
| $R_f$(Rf) | retention factor |
| RP | reversed phase |
| RT | room temperature |
| $S_N$ | nucleophilic substitution |
| TBAF | tetrabutylammonium fluoride |
| TBME | tert-butylmethylether |
| TBTU | O-(benzotriazol-1-yl)-N,N,N',N'-tetramethyl-uronium tetrafluoroborate |
| TEA | triethylamine |
| temp. | temperature |
| tert. | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | para-toluenesulphonic acid |
| UV | ultraviolet |

Features and advantages of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

Microwave reactions are carried out in an initiator/reactor made by Biotage or in an Explorer made by CEM in sealed containers (preferably 2, 5 or 20 mL), preferably with stirring.

Chromatography

For preparative medium pressure chromatography (MPLC, normal phase) silica gel made by Millipore (name: Granula Silica Si-60A 35-70 μm) or C-18 RP-silica gel (RP-phase) made by Macherey Nagel (name: Polygoprep 100-50 C18) is used. Automated normal phase chromatography is also carried out on a CombiFlash Companion XL apparatus in combination with a CombiFlash Foxy 200 fraction collector made by Isco.

For this, commercially obtainable RediSepRf (120 g silica gel) one-way columns are used. The thin layer chromatography is carried out on ready-made silica gel 60 TLC plates on glass (with fluorescence indicator F-254) made by Merck.

The preparative high pressure chromatography (HPLC) of the example compounds according to the invention is carried out with columns made by Waters (names: XTerra Prep. MS C18, 5 μm, 30×100 mm or XTerra Prep. MS C18, 5 μm, 50×100 mm OBD or Symmetrie C18, 5 μm, 19×100 mm or Sunfire C18 OBD, 19×100 mm, 5 μm or Sunfire Prep C 10 μm OBD 50×150 mm or X-Bridge Prep C18 5 μm OBD 19×50 mm), Agilent (name: Zorbax SB-C8 5 μm PrepHT 21.2×50 mm) and Phenomenex (names: Gemini C18 5 μm AXIA 21.2×50 mm or Gemini C18 10 μm 50×150 mm). Different gradients of $H_2O$/acetonitrile or $H_2O$/MeOH are used to elute the compounds, while 0.1% HCOOH is added to the water.

The preparative high pressure chromatography (HPLC) on normal phase of the example compounds according to the invention is carried out with columns made by Macherey & Nagel (name: Nucleosil, 50-7, 40×250 mm) and VDSoptilab (name: Kromasil 100 $NH_2$, 10 μM, 50×250 mm). Different gradients of DCM/MeOH are used to elute the compounds, while 0.1% $NH_3$ is added to the MeOH.

The analytical HPLC (reaction control) of intermediate compounds is carried out using columns made by Agilent (names: Zorbax SB-C8, 5 μm, 21.2×50 mm or Zorbax SB-C8 3.5 μm 2.1×50 mm) and Phenomenex (name: Gemini C18 3 μm 2×30 mm). The analytical equipment is also equipped with a mass detector in each case.

HPLC-Mass Spectroscopy/UV-Spectrometry

The retention times/MS-ESI⁺ for characterising the example compounds according to the invention are produced using different HPLC-MS apparatus (high performance liquid chromatography with mass detector). Compounds that elute at the injection peak are given the retention time $t_{Ret}$=0.00.

Details of the methods:
HPLC-MS Method 1
HPLC: Agilent 1100 Series
MS: Agilent LC/MSD SL
Column: Waters, Xterra MS C18, 2.5 μm, 2.1×30 mm, Part. No. 186000592
Eluant: A: $H_2O$ with 0.1% HCOOH; B: acetonitrile (HPLC grade)
Detection: MS: Positive and negative mode
Mass range: 120-900 m/z
Flow 1.10 mL/min
Column temp.: 40° C.
Gradient: 0.00 min: 5% eluant B
　0.00-2.50 min: 5%→95% eluant B
　2.50-2.80 min: 95% eluant B
　2.81-3.10 min: 95%→5% eluant B
HPLC-MS method 2
HPLC: HP 1100
MS: Waters ZQ2000
Column: Waters, Sunfire C18, 3.5 μm, 4.6×50 mm
Eluant: A: $H_2O$ with 0.1% TFA; B: acetonitrile with 0.1% TFA (in each case HPLC grade)
Detection: MS: positive mode
Mass range: 120-820 m/z
Flow 1.5 mL/min
Column temp.: 40° C.
Gradient: 0.00 min: 5% eluant B
　0.00-2.00 min: 5%→100% eluant B
　2.00-2.50 min: 100% eluant B
　2.50-2.60 min: 100%→5% eluant B
HPLC-MS-Method 3
HPLC: HP 1100
MS: Waters ZQ2000
Column: Supelco, Ascentis C18, 2.7 μm, 4.6×50 mm
Eluant: A: $H_2O$ with 0.1% TFA; B: acetonitrile with 0.1% TFA (in each case HPLC grade)
Detection: MS: Positive mode
Mass range: 120-820 m/z
Flow 1.5 mL/min
Column temp.: 40° C.
Gradient: 0.00 min: 5% eluant B
　0.00-2.00 min: 5%→100% eluant B
　2.00-2.50 min: 100% eluant B
　2.50-2.60 min: 100%→5% eluant B The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Reaction scheme A

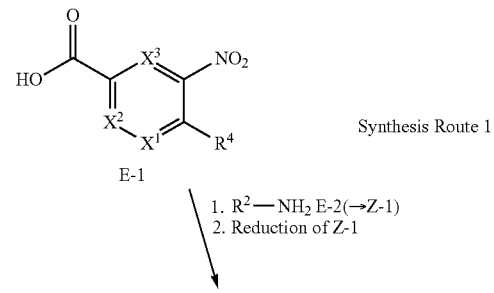

Synthesis Route 1

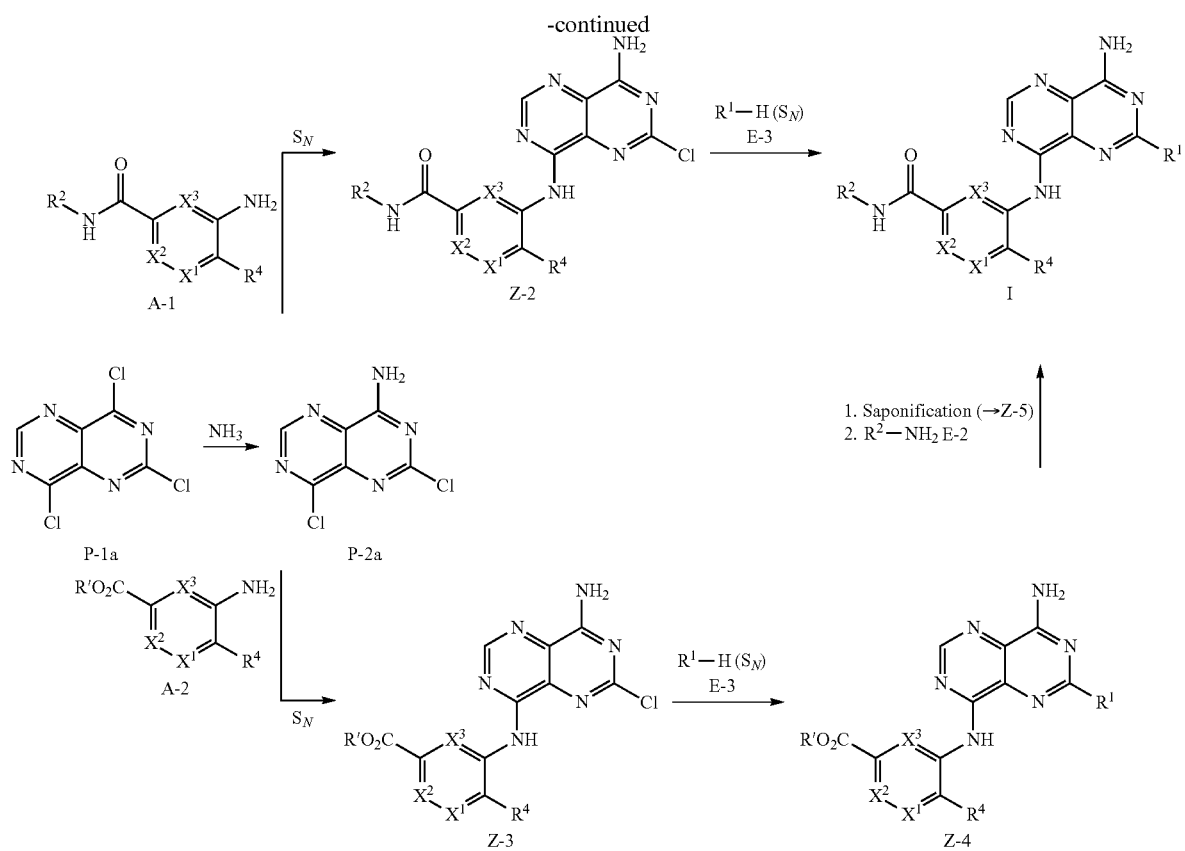

Synthesis Route 2

(R' = common carboxyl protecting group e.g. $C_{1-6}$Alkyl, Benzyl)

Example Compounds of Type I:

Trisubstituted pyrimidopyrimidines I may be obtained for example by two alternative methods according to Reaction scheme A (synthesis route 1 or 2).

Starting from 2,4,8-trichloro-pyrimido[5,4-d]pyrimidine P-1a the chlorine atoms are successively substituted. In the first step the substitution is carried out using ammonia in the 4-position. In the second step the 8-position of the intermediate products P-2a is substituted by the aniline components A-1 or A-2, preferably under basically catalysed conditions at elevated temperature.

If A-1 is used the complete left-hand molecular part of the end compounds I is thereby introduced into the intermediate compound Z-2, so that finally there only remains the substitution in the 2-position by components $R^1$—H (E-3), which are preferably primary and secondary (also cyclic) amines and alcohols (in the form of the alkoxides). The components A-1 are obtained by amide coupling of the nitrocarboxylic acids E-1 with amines E-2 to form the intermediate product Z-1 and subsequent reduction of the nitro group. To carry out the amide coupling common coupling reagents as used in peptide chemistry (e.g. HATU or TBTU), are optionally used or the nitro acids E-1 are activated in some other way, e.g. as acid halides (e.g. with thionyl chloride, oxalyl chloride, GHOSEZ reagent).

By contrast, by using A-2 first of all only the central phenyl or heteroaryl ring and a protected linker fragment (carboxylate) of the later linker $L^2$ (e.g. amide) is incorporated, before the group $R^1$ is introduced analogously. Therefore in this case additional reaction steps (saponification, activation, amidation) are needed to obtain compounds I. The amide coupling is carried out as described hereinbefore for the nitro acids E-1.

Alternatively to P-1a other educts P-1 are possible which allow successive and selective substitution, i.e. have other leaving groups.

Both the group $R^1$ and the group $R^2$ of compounds I according to the invention may be modified in other reaction steps (not shown), to obtain other compounds I according to the invention. These reaction steps may be reactions of substitution, alkylation, acylation or addition.

a) Method for Synthesising P-1a:

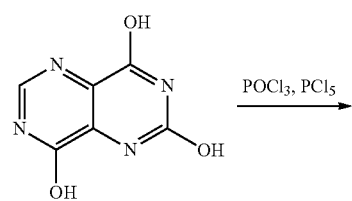

-continued

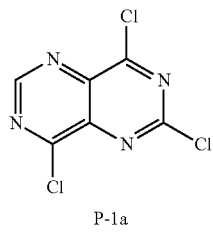

P-1a 2,4,8-trihydroxy-pyrimido[5,4-d]pyrimidine (40 g, 222 mmol), potassium chloride (1.68 g, 22.53 mmol) and phosphorus pentachloride (152 g, 730 mmol) are placed in phosphorus oxychloride (240 mL). The reaction mixture is refluxed for 5 h. After cooling the mixture is evaporated down, the residue is triturated several times with petroleum ether and decanted off. The precipitate remaining is mixed with ice water, suction filtered, dissolved in DCM, dried on sodium sulphate and filtered off. The mother liquor is mixed with activated charcoal and heated. The activated charcoal is suction filtered, the filtrate is filtered through silica gel, washed with DCM, evaporated down using the rotary evaporator and 2,4,8-trichloro-pyrimido[5,4-d]pyrimidine P-1a (HPLC-MS: MS (M+H)$^+$=234/236/238/240) is obtained. P-1a is used further without any further purification (purity approx. 95%).

b) Method for Synthesising P-2a:

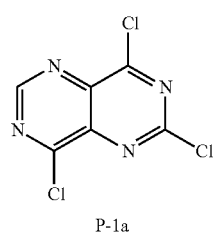

P-1a

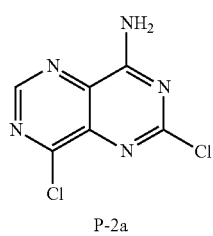

P-2a

P-1a (95%; 4.0 g, 16.14 mmol) is placed in THF (350 mL) and TEA (2.26 mL, 16.14 mmol). The reaction mixture is cooled to approx. −65° C. with a bath of acetone and dry ice. Then ammonia (0.5 M in dioxane; 41.96 mL, 20.98 mmol) is slowly added dropwise. The reaction mixture is stirred further and slowly heated to RT. After 16 h the reaction mixture is evaporated down, the residue is taken up in 300 mL EE and extracted with 1×200 mL and 2×100 mL water. The organic phase is dried on MgSO$_4$, filtered and evaporated down using the rotary evaporator. The intermediate product P-2a (HPLC-MS: t$_{Ret.}$=0.92 min; MS (M+H)$^+$=216/218) is further reacted directly.

c) Method for Synthesising A-1a:

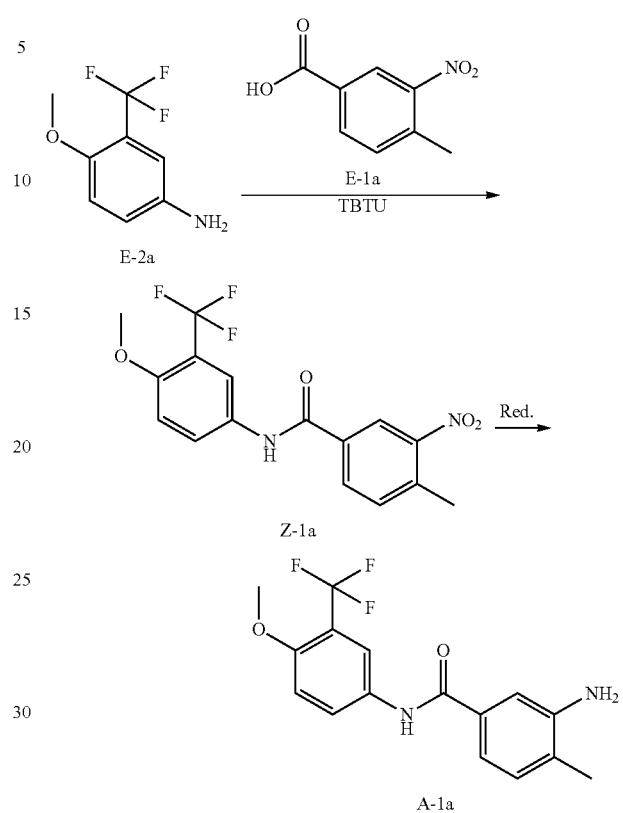

4-methyl-3-nitrobenzoic acid E-1a (2.0 g, 11 mmol) is taken up in DCM (40 mL) and mixed with TEA (5.1 mL, 27.6 mmol) and TBTU (3.9 g, 12.2 mmol). After 10 min 4-methoxy-3-trifluoromethylaniline E-2a (2.11 g, 11 mmol) is added and the mixture is stirred for another 2 h at RT. The precipitate formed is filtered off, washed repeatedly with water, dried and Z-1a (MS (M+H)$^+$=355) is obtained.

The aromatic nitro compound Z-1a (3.5 g, 9.9 mmol) is taken up in EtOH (30 mL), mixed with an ammonium chloride solution (264 mg, 4.94 mmol in 20 mL H$_2$O) and heated to 70° C. At this temperature iron powder (5.52 g, 99 mmol) is added batchwise and the mixture is stirred for a further 4 h at 70° C. After cooling it is filtered through silica gel, washed with DCM/MeOH, the filtrate obtained is dried using the rotary evaporator and A-1a is obtained.

d) Method for Synthesising A-1b:

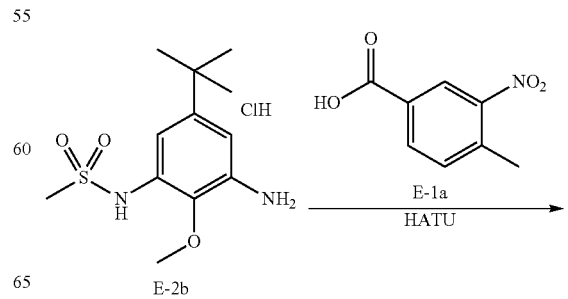

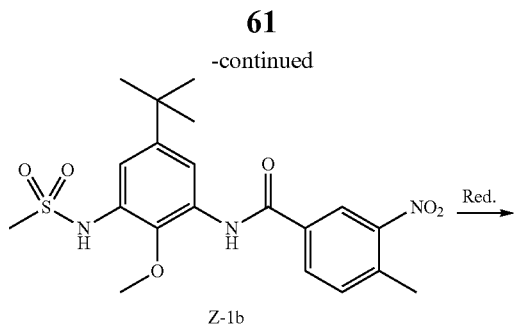

Z-1b

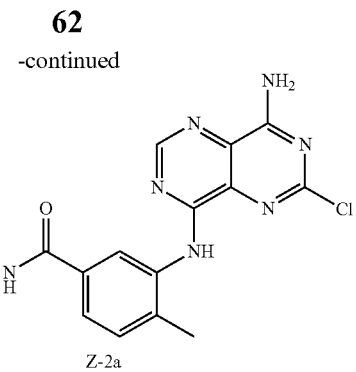

Z-2a

P-2a (200 mg, 0.93 mmol), aniline A-1a (300 mg, 0.93 mmol) and TEA (155 μL, 1.53 mmol) are placed in DMF (3 mL). The reaction mixture is stirred overnight at 65° C. The reaction mixture is combined with 20 mL water and stirred for 15 min. The precipitate formed is filtered off, washed with diethyl ether, taken up in toluene, evaporated down and Z-2a is obtained.

f) Method for Synthesising Z-2b:

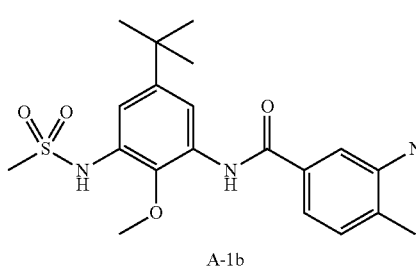

A-1b

E-1a (2.0 g, 11.04 mmol) is taken up in DCM (40 mL) and mixed with TEA (5.1 mL, 27.6 mmol) and HATU (6.3 g, 16.6 mmol). After 10 min aniline E-2b (3.41 g, 11.04 mmol) is added and the mixture is stirred for another 2 h at RT. For working up it is diluted with water and the phases are separated. The organic phase is extracted 1× with saturated NH$_4$Cl solution, 1× with saturated NaHCO$_3$ solution and 1× with saturated NaCl solution, dried on MgSO$_4$, filtered, evaporated down using the rotary evaporator and Z-1b is obtained.

The aromatic nitro compound Z-1b (3.5 g, 8.04 mmol) is taken up in EtOH (30 mL), combined with an ammonium chloride solution (215 mg, 4.02 mmol in 20 mL H$_2$O) and heated to 70° C. At this temperature iron powder (4.49 g, 80.4 mmol) is added batchwise and the mixture is stirred for a further 5 h at 70° C. After cooling it is filtered through silica gel, washed with DCM/MeOH (9:1), the filtrate obtained is dried using the rotary evaporator and A-1b is obtained.

Analogously to the method for synthesising A-1a and A-1b further anilines A-1 may be obtained from the corresponding educts E-1 and E-2.

e) Method for Synthesising Z-2a:

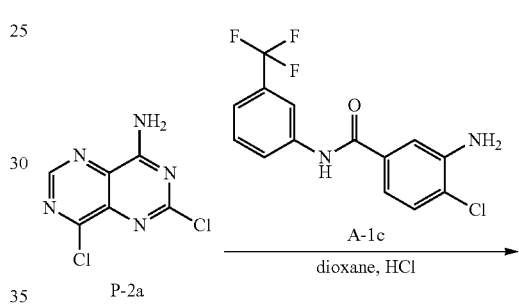

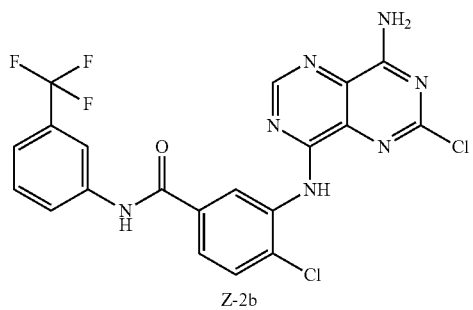

Z-2b

P-2a (200 mg, 0.93 mmol) and aniline A-1c (291 mg, 0.93 mmol) are taken up in dioxane (3 mL). Hydrogen chloride (1M in Et$_2$O, 5 μL, 0.102 mmol) is added. The reaction mixture is stirred for 25 min at 65° C. in the microwave reactor. The precipitate formed is filtered off, washed with water, taken up in toluene, evaporated down and Z-2b is obtained.

Analogously to the methods for synthesising Z-2a and Z-2b further intermediate compounds Z-2 are obtained by reacting components A-1 with P-2a.

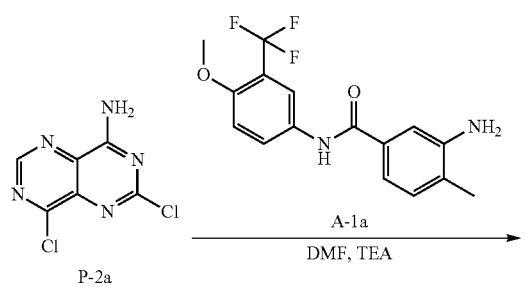

g) Method for Synthesising Example Compound I-1:

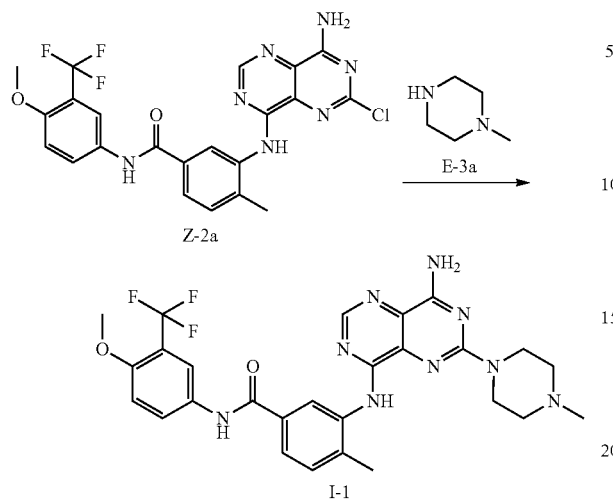

i) Method for Synthesising Z-4-a:

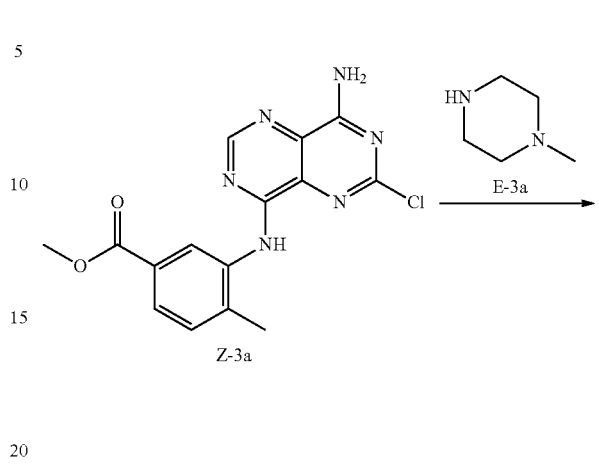

Z-2a (50 mg, 0.1 mmol) and N-methylpiperazine E-3a (40 mg, 0.4 mmol) are taken up in 0.5 mL DMSO and DIPEA (180 µL, 1.4 mmol) is added. The reaction mixture is stirred for 25 min at 120° C. in the microwave reactor. The reaction mixture is filtered and purified by preparative HPLC. The product-containing fractions of I-1 (HPLC-MS: $t_{Ret.}$=2.17 min; MS (M+H)$^+$=568) are freeze-dried.

h) Method for Synthesising Z-3a:

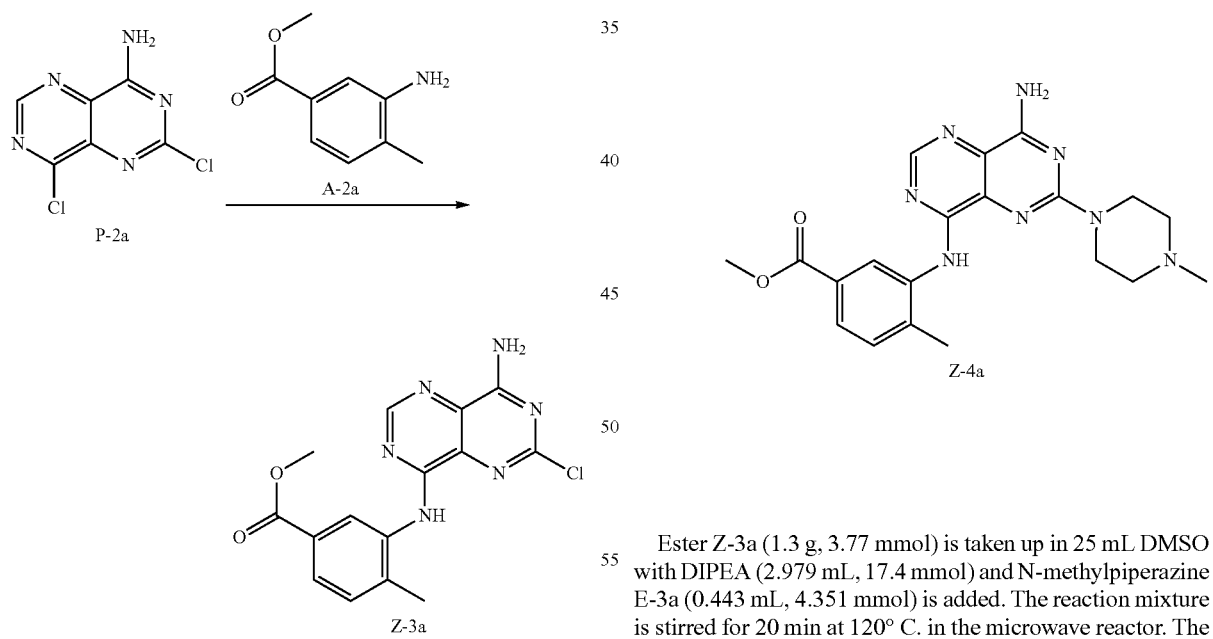

P-2a (1.439 g, 6.6 mmol) and aniline A-2a (1.0 g, 6.05 mmol) are placed in THF (5 mL). The reaction mixture is stirred overnight at RT. The precipitate formed is filtered off, dried and Z-3a is obtained.

Analogously to the method for synthesising Z-3a further intermediate compounds Z-3 are obtained by reacting components A-2 with P-2a.

Ester Z-3a (1.3 g, 3.77 mmol) is taken up in 25 mL DMSO with DIPEA (2.979 mL, 17.4 mmol) and N-methylpiperazine E-3a (0.443 mL, 4.351 mmol) is added. The reaction mixture is stirred for 20 min at 120° C. in the microwave reactor. The reaction mixture is mixed with water, the precipitate formed is filtered off, taken up in toluene, evaporated down 2× azeotropically and Z-4a is obtained.

Analogously to the method for synthesising Z-4-a further intermediate compounds Z-4 are obtained by reacting intermediate compounds Z-3 with components E-3.

j) Method for Synthesising Example Compound I-2:

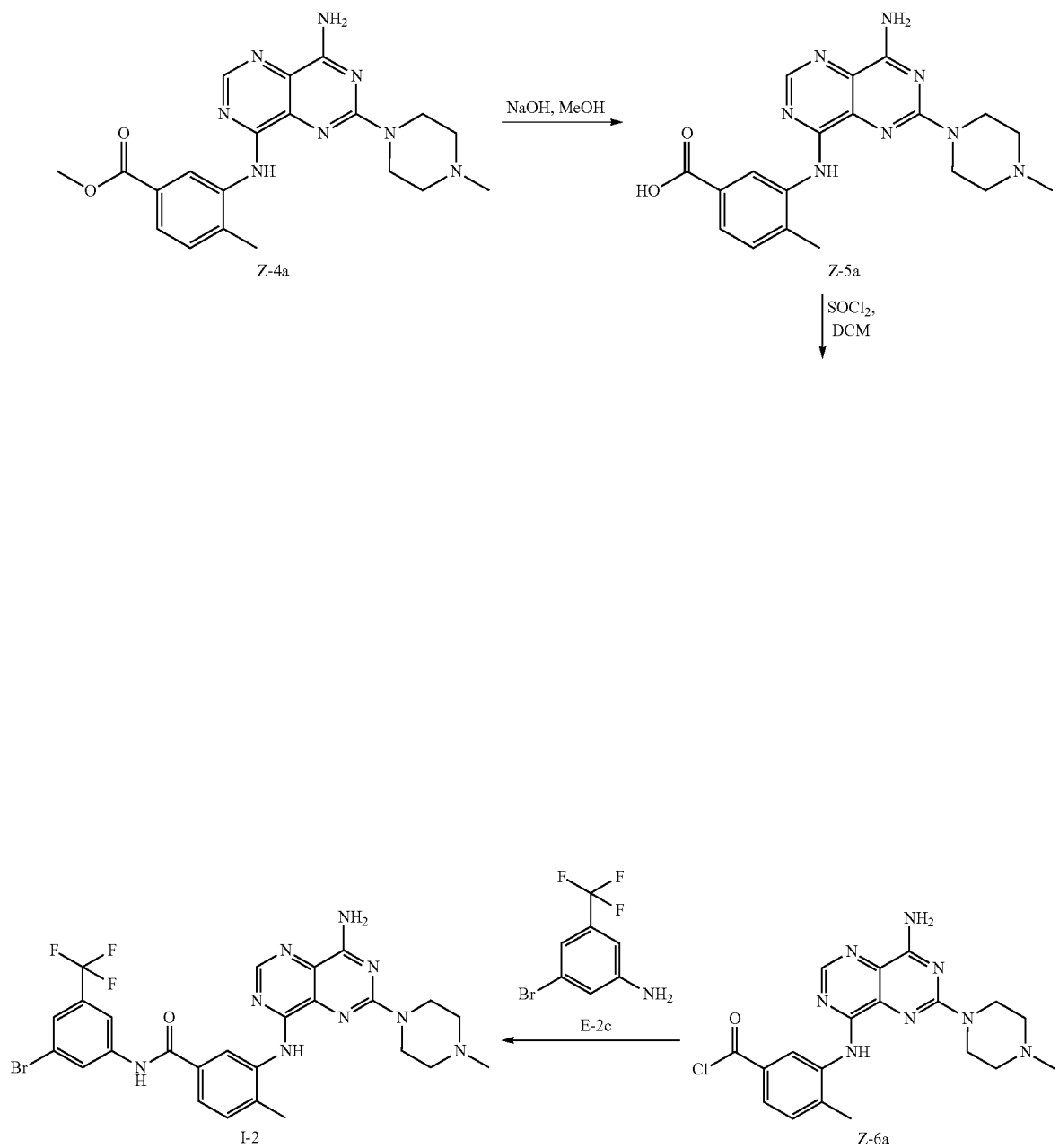

Methylester Z-4-a (1.216 g, 2.98 mmol) is placed in MeOH (30 mL) and mixed at RT with an aqueous NaOH solution (5.0 mol/L, 12.146 mL, 60.73 mmol). Then the mixture is stirred overnight at 50° C. For working up the pH is adjusted to neutral by the addition of an HCl solution. The reaction mixture is extracted 2× with water/EE (1:1), the organic phases are dried on MgSO$_4$, filtered, evaporated down and Z-5a is obtained.

Benzoic acid Z-5a (100 mg, 0.25 mmol) is taken up in DCM (5 mL) and mixed under argon with thionyl chloride (300 µL, 2.38 mmol). The reaction mixture is stirred for 1 h at RT. Then the mixture is evaporated down, dried azeotropically with dry toluene and Z-6a is obtained.

Acid chloride Z-6a (100 mg, 0.24 mmol) is taken up in DCM (3 mL) and mixed with 3-bromo-5-trifluoromethyl-phenylamine E-2c (58 mg, 0.24 mmol) and pyridine (100 µL). The reaction mixture is stirred for 2 h at RT. For working up the mixture is evaporated down, taken up in DMSO, filtered and purified by preparative HPLC. The product-containing fractions of I-2 (HPLC-MS: $t_{Ret.}$=2.44 min; MS (M+H)$^+$ =616/618) are freeze-dried.

Analogously to methods a) to g) (synthesis route 1) or a), b) and h) to j) (synthesis route 2) besides I-1 and I-2 the following compounds I-3 to I-88 according to the invention are also prepared (Table 1).

TABLE 1
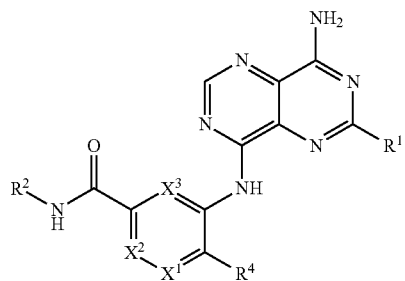
Example Compounds I-1 to I-88
| # | Structure | $t_{Ret.}$ (HPLC) [min] | MS $(M + H)^+$ |
|---|---|---|---|
| I-1 | 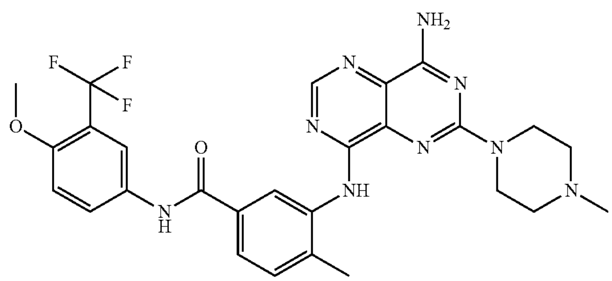 [SMILES: COc1ccc(NC(=O)c2ccc(C)c(Nc3ncnc4c(N)nc(N5CCN(C)CC5)nc34)c2)cc1C(F)(F)F] | 2.17 | 568 |
| I-2 | 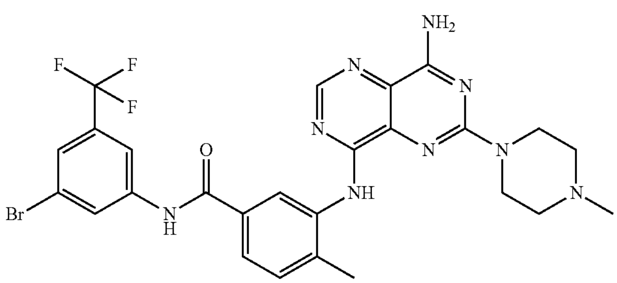 [SMILES: Cc1ccc(C(=O)Nc2cc(Br)cc(C(F)(F)F)c2)cc1Nc1ncnc2c(N)nc(N3CCN(C)CC3)nc12] | 2.44 | 616/618 |
| I-3 | 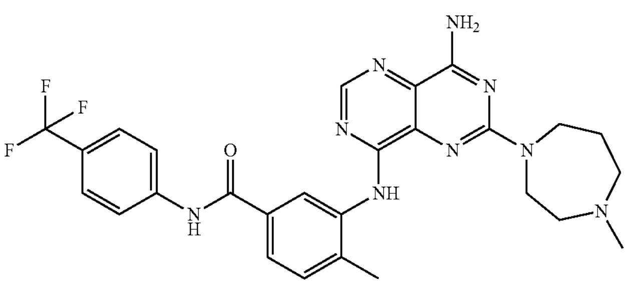 [SMILES: Cc1ccc(C(=O)Nc2ccc(C(F)(F)F)cc2)cc1Nc1ncnc2c(N)nc(N3CCCN(C)CC3)nc12] | 1.70 | 552 |
| I-4 | 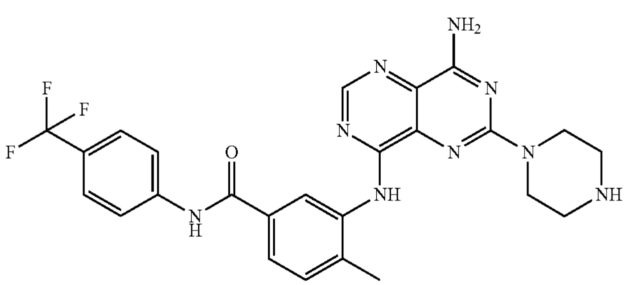 [SMILES: Cc1ccc(C(=O)Nc2ccc(C(F)(F)F)cc2)cc1Nc1ncnc2c(N)nc(N3CCNCC3)nc12] | 1.68 | 524 |

TABLE 1-continued
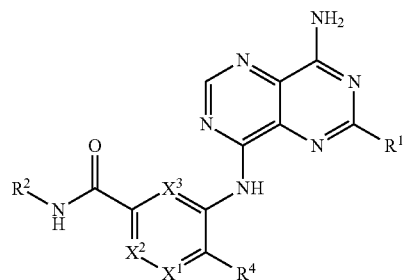
Example Compounds I-1 to I-88
| # | Structure | $t_{Ret.}$ (HPLC) [min] | MS $(M + H)^+$ |
|---|---|---|---|
| I-5 | 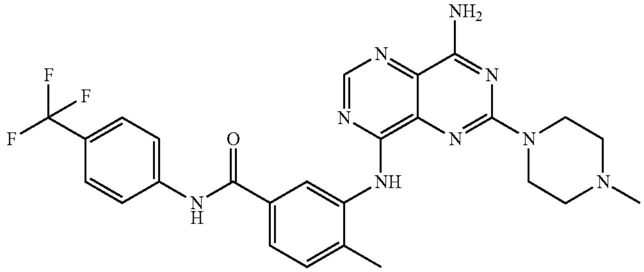 [SMILES: Cc1ccc(C(=O)Nc2ccc(C(F)(F)F)cc2)cc1Nc1ncnc2c(N)nc(N3CCN(C)CC3)nc12] | 1.67 | 538 |
| I-6 | 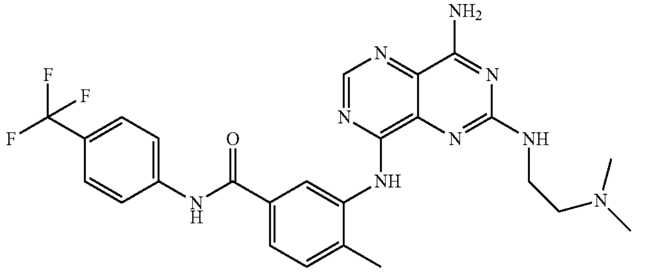 [SMILES: Cc1ccc(C(=O)Nc2ccc(C(F)(F)F)cc2)cc1Nc1ncnc2c(N)nc(NCCN(C)C)nc12] | 1.67 | 526 |
| I-7 | 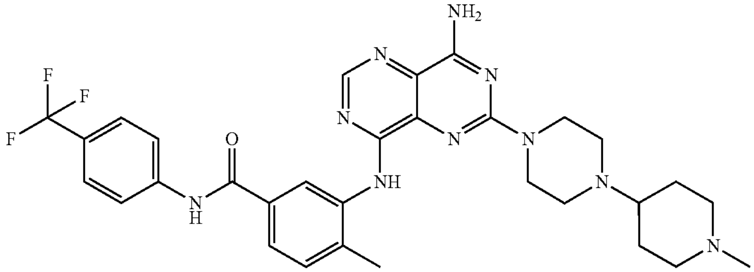 [SMILES: Cc1ccc(C(=O)Nc2ccc(C(F)(F)F)cc2)cc1Nc1ncnc2c(N)nc(N3CCN(C4CCN(C)CC4)CC3)nc12] | 1.47 | 621 |
| I-8 | 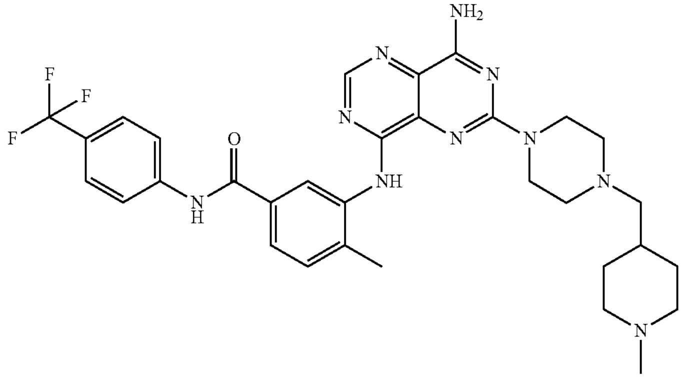 [SMILES: Cc1ccc(C(=O)Nc2ccc(C(F)(F)F)cc2)cc1Nc1ncnc2c(N)nc(N3CCN(CC4CCN(C)CC4)CC3)nc12] | 1.51 | 635 |

TABLE 1-continued
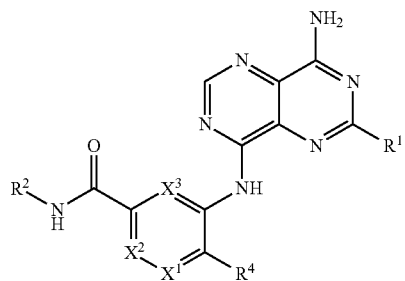
Example Compounds I-1 to I-88
| # | Structure | $t_{Ret.}$ (HPLC) [min] | MS $(M + H)^+$ |
|---|---|---|---|
| I-9 | 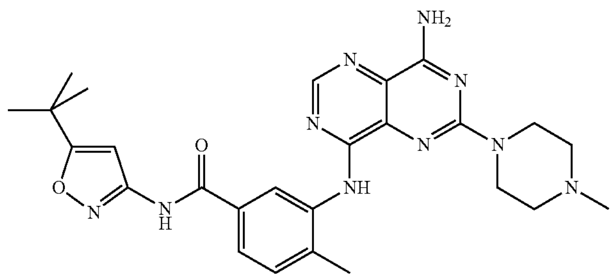 [SMILES: Cc1ccc(C(=O)Nc2cc(C(C)(C)C)on2)cc1Nc1ncnc2c(N)nc(N3CCN(C)CC3)nc12] | 2.14 | 517 |
| I-10 | 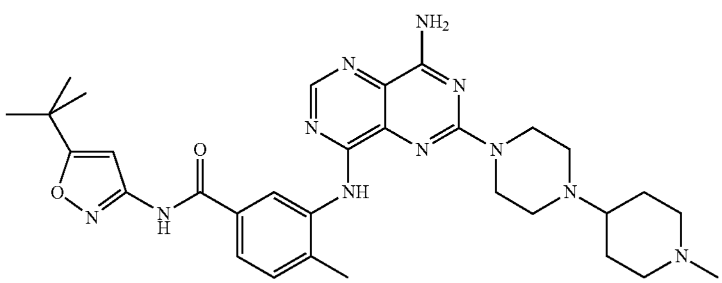 [SMILES: Cc1ccc(C(=O)Nc2cc(C(C)(C)C)on2)cc1Nc1ncnc2c(N)nc(N3CCN(C4CCN(C)CC4)CC3)nc12] | 2.16 | 600 |
| I-11 | 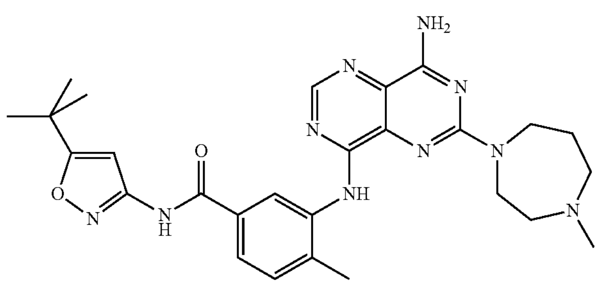 [SMILES: Cc1ccc(C(=O)Nc2cc(C(C)(C)C)on2)cc1Nc1ncnc2c(N)nc(N3CCCN(C)CC3)nc12] | 2.22 | 531 |
| I-12 | 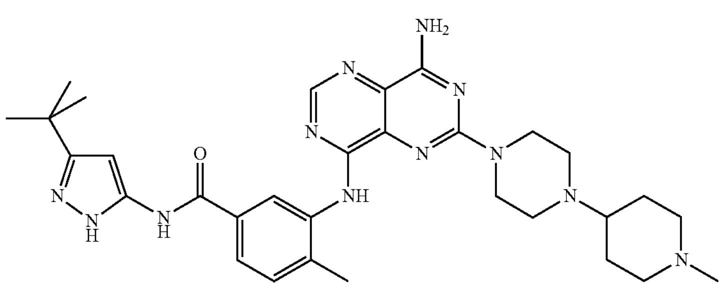 [SMILES: Cc1ccc(C(=O)Nc2cc(C(C)(C)C)n[nH]2)cc1Nc1ncnc2c(N)nc(N3CCN(C4CCN(C)CC4)CC3)nc12] | 1.94 | 599 |

TABLE 1-continued

Example Compounds I-1 to I-88
| # | Structure | t$_{Ret.}$ (HPLC) [min] | MS (M + H)$^+$ |
|---|---|---|---|
| I-13 | 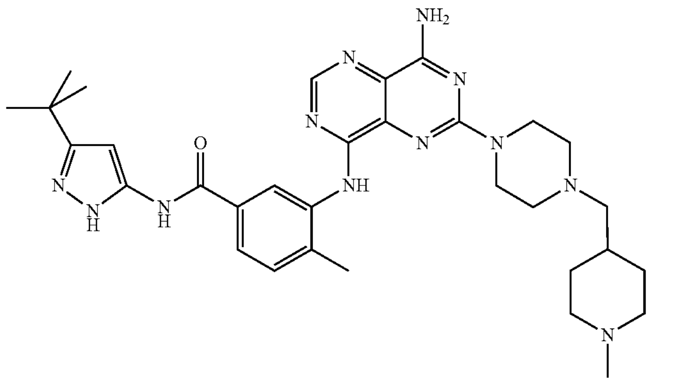 [SMILES: Cc1ccc(C(=O)Nc2cc(C(C)(C)C)n[nH]2)cc1Nc1ncnc2c(N)nc(N3CCN(CC4CCN(C)CC4)CC3)nc12] | 1.88 | 613 |
| I-14 | 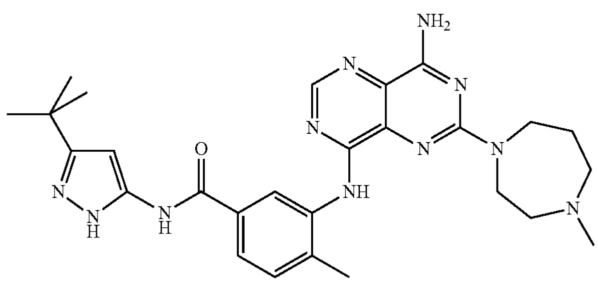 [SMILES: Cc1ccc(C(=O)Nc2cc(C(C)(C)C)n[nH]2)cc1Nc1ncnc2c(N)nc(N3CCCN(C)CC3)nc12] | 1.98 | 530 |
| I-15 | 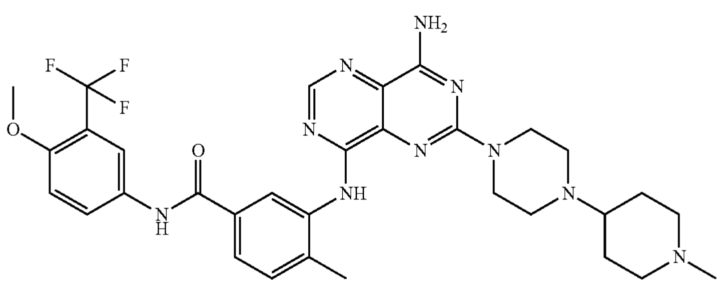 [SMILES: COc1ccc(NC(=O)c2ccc(C)c(Nc3ncnc4c(N)nc(N5CCN(C6CCN(C)CC6)CC5)nc34)c2)cc1C(F)(F)F] | 2.18 | 651 |

TABLE 1-continued
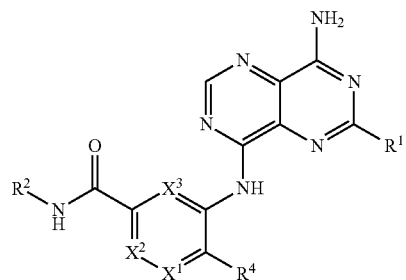
Example Compounds I-1 to I-88
| # | Structure | $t_{Ret.}$ (HPLC) [min] | MS $(M + H)^+$ |
|---|---|---|---|
| I-16 | 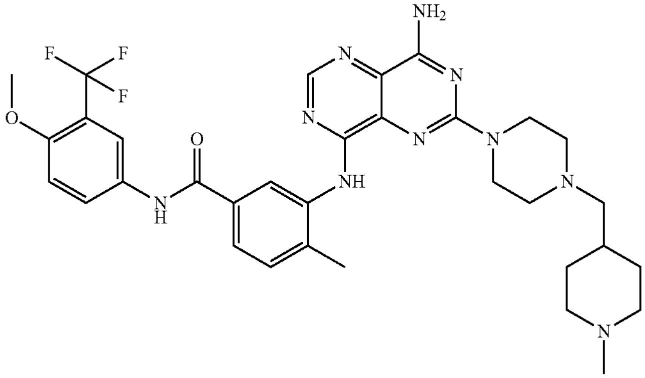 [SMILES: COc1ccc(NC(=O)c2ccc(C)c(Nc3ncnc4c(N)nc(N5CCN(CC6CCN(C)CC6)CC5)nc34)c2)cc1C(F)(F)F] | 2.36 | 665 |
| I-17 | 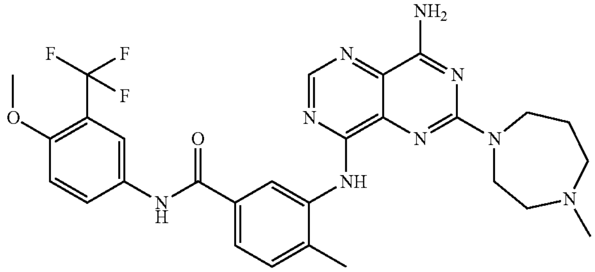 [SMILES: COc1ccc(NC(=O)c2ccc(C)c(Nc3ncnc4c(N)nc(N5CCCN(C)CC5)nc34)c2)cc1C(F)(F)F] | 2.23 | 582 |
| I-18 | 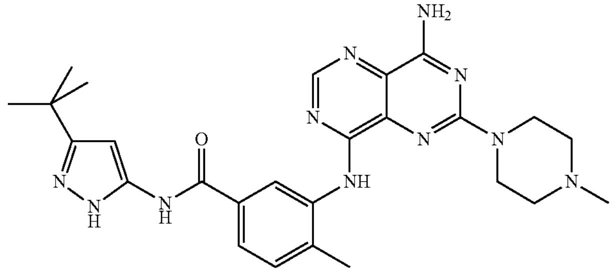 [SMILES: Cc1ccc(C(=O)Nc2cc(C(C)(C)C)n[nH]2)cc1Nc1ncnc2c(N)nc(N3CCN(C)CC3)nc12] | 1.91 | 516 |
| I-19 | 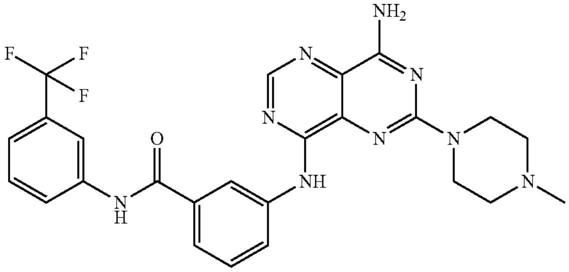 [SMILES: CN1CCN(c2nc(N)c3ncnc(Nc4cccc(C(=O)Nc5cccc(C(F)(F)F)c5)c4)c3n2)CC1] | 2.11 | 524 |

TABLE 1-continued
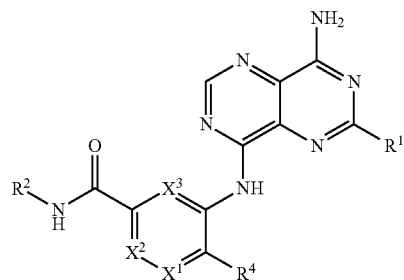
Example Compounds I-1 to I-88
| # | Structure | $t_{Ret.}$ (HPLC) [min] | MS (M + H)⁺ |
|---|---|---|---|
| I-20 | 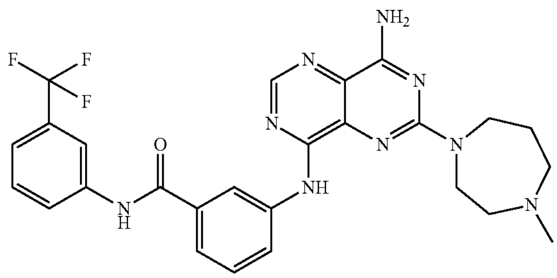 [SMILES: CN1CCCN(c2nc(N)c3ncnc(Nc4cccc(C(=O)Nc5cccc(C(F)(F)F)c5)c4)c3n2)CC1] | 2.23 | 538 |
| I-21 | 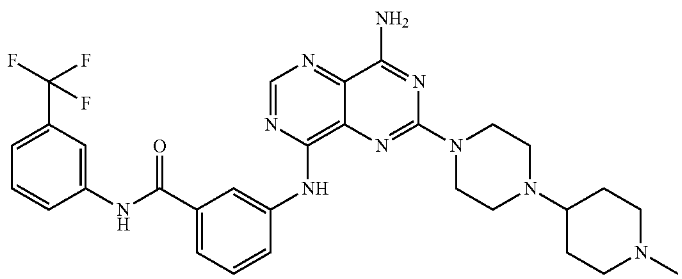 [SMILES: CN1CCC(N2CCN(c3nc(N)c4ncnc(Nc5cccc(C(=O)Nc6cccc(C(F)(F)F)c6)c5)c4n3)CC2)CC1] | 2.27 | 607 |
| I-22 | 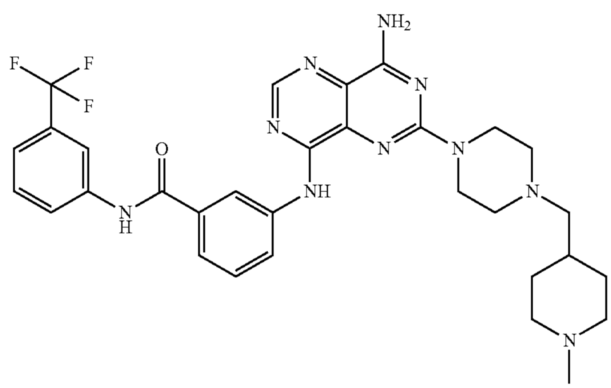 [SMILES: CN1CCC(CN2CCN(c3nc(N)c4ncnc(Nc5cccc(C(=O)Nc6cccc(C(F)(F)F)c6)c5)c4n3)CC2)CC1] | 2.29 | 621 |
| I-23 | 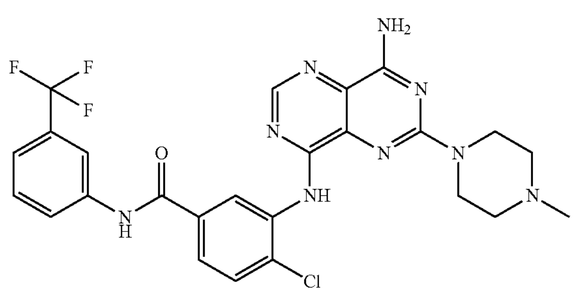 [SMILES: CN1CCN(c2nc(N)c3ncnc(Nc4cc(C(=O)Nc5cccc(C(F)(F)F)c5)ccc4Cl)c3n2)CC1] | 2.31 | 558 |

TABLE 1-continued
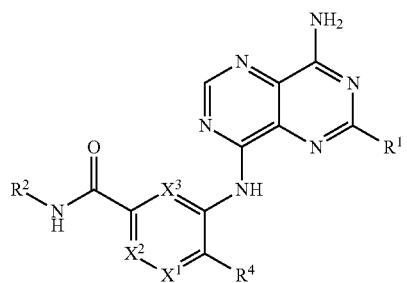
Example Compounds I-1 to I-88
| # | Structure | $t_{Ret.}$ (HPLC) [min] | MS (M + H)⁺ |
|---|---|---|---|
| I-24 | 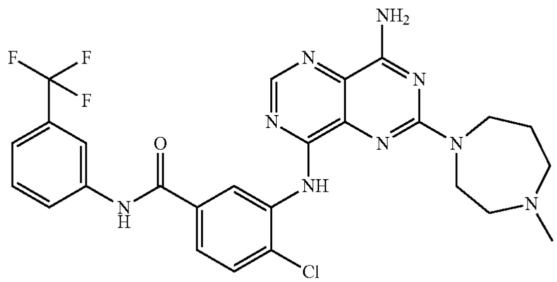 [SMILES: CN1CCCN(c2nc(N)c3ncnc(Nc4cc(C(=O)Nc5cccc(C(F)(F)F)c5)ccc4Cl)c3n2)CC1] | 2.38 | 572 |
| I-25 | 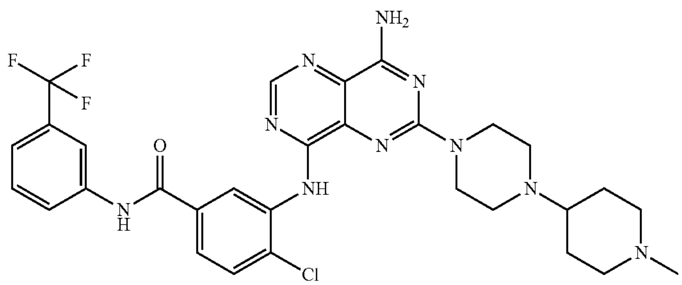 [SMILES: CN1CCC(N2CCN(c3nc(N)c4ncnc(Nc5cc(C(=O)Nc6cccc(C(F)(F)F)c6)ccc5Cl)c4n3)CC2)CC1] | 2.44 | 641 |
| I-26 | 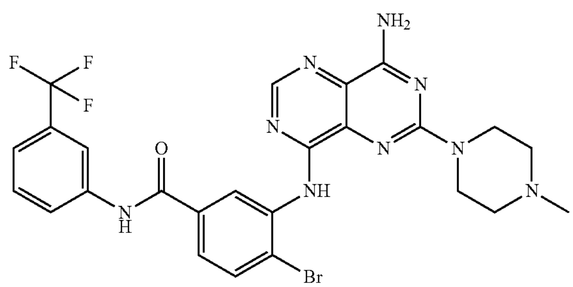 | 2.41 | 602/604 |
| I-27 | 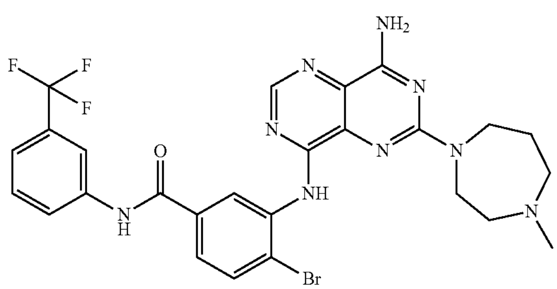 [SMILES: CN1CCCN(c2nc(N)c3ncnc(Nc4cc(C(=O)Nc5cccc(C(F)(F)F)c5)ccc4Br)c3n2)CC1] | 2.51 | 616/618 |

TABLE 1-continued
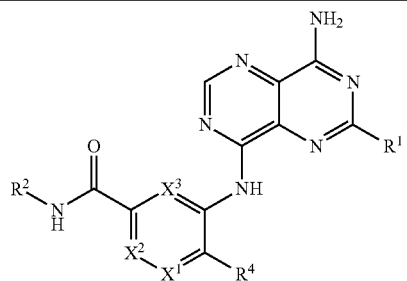
Example Compounds I-1 to I-88
| # | Structure | $t_{Ret.}$ (HPLC) [min] | MS $(M + H)^+$ |
|---|---|---|---|
| I-28 | 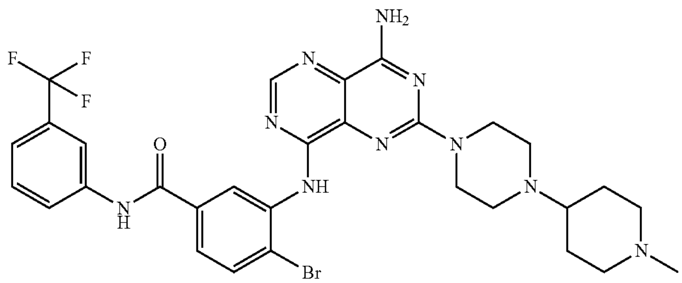 | 2.44 | 685/687 |
| I-29 | 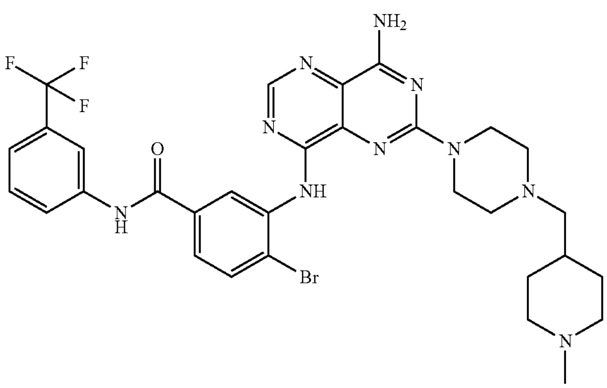 | 2.75 | 699/701 |
| I-30 | 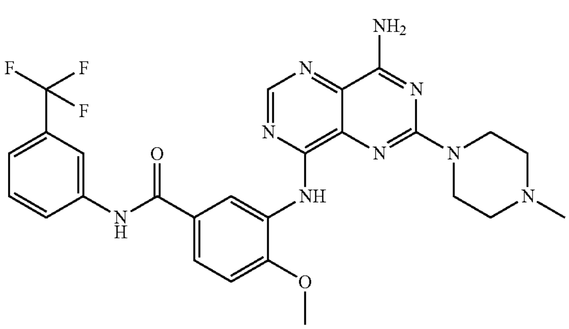 [SMILES: COc1ccc(C(=O)Nc2cccc(C(F)(F)F)c2)cc1Nc1ncnc2c(N)nc(N3CCN(C)CC3)nc12] | 2.28 | 554 |

TABLE 1-continued
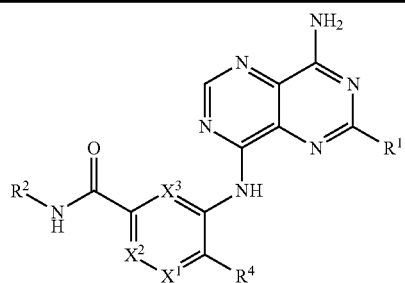
Example Compounds I-1 to I-88
| # | Structure | t_{Ret.} (HPLC) [min] | MS (M + H)+ |
|---|---|---|---|
| I-31 | 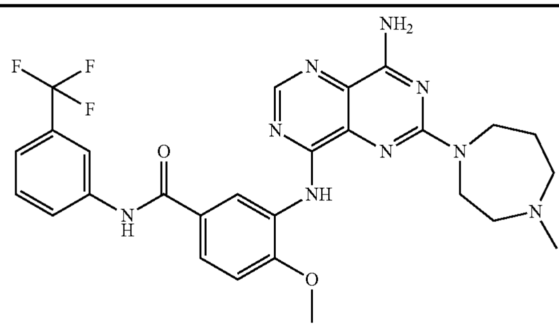 | 2.31 | 568 |
| I-32 | 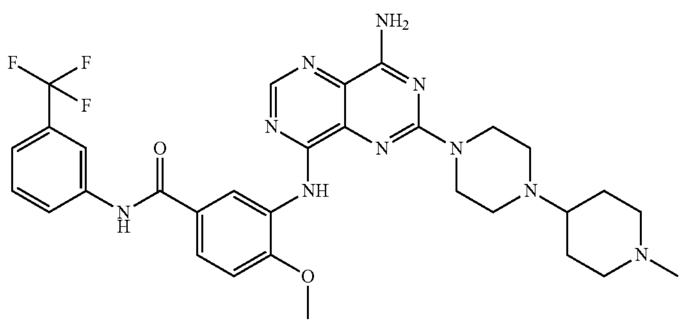 [SMILES: COc1ccc(C(=O)Nc2cccc(C(F)(F)F)c2)cc1Nc1ncnc2c(N)nc(N3CCN(C4CCN(C)CC4)CC3)nc12] | 2.35 | 637 |
| I-33 | 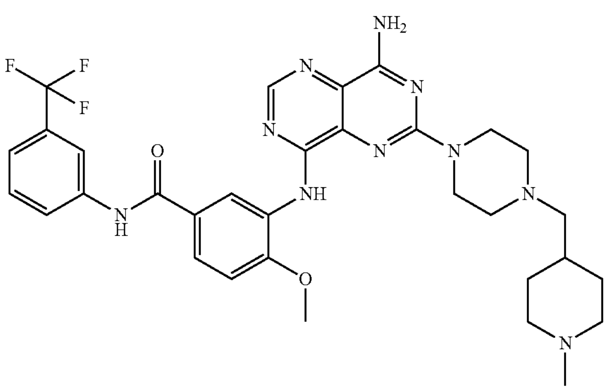 | 2.45 | 651 |

US 8,653,087 B2

TABLE 1-continued

Example Compounds I-1 to I-88

| # | Structure | t_Ret. (HPLC) [min] | MS (M + H)+ |
|---|---|---|---|
| I-34 | 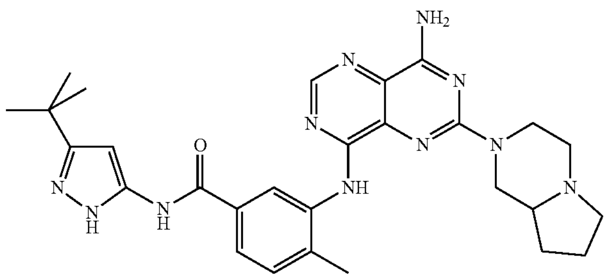 [SMILES: Cc1ccc(C(=O)Nc2cc(C(C)(C)C)n[nH]2)cc1Nc1ncnc2c(N)nc(N3CCN4CCCC4C3)nc12] | 2.04 | 542 |
| I-35 | 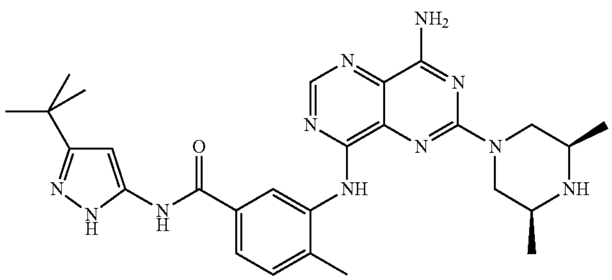 [SMILES: Cc1ccc(C(=O)Nc2cc(C(C)(C)C)n[nH]2)cc1Nc1ncnc2c(N)nc(N3C[C@@H](C)N[C@@H](C)C3)nc12] | 1.93 | 530 |
| I-36 | 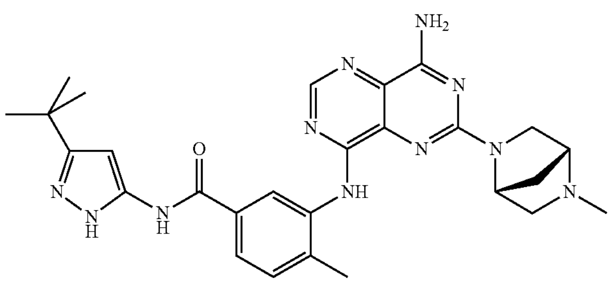 [SMILES: Cc1ccc(C(=O)Nc2cc(C(C)(C)C)n[nH]2)cc1Nc1ncnc2c(N)nc(N3C[C@H]4C[C@@H]3CN4C)nc12] | 1.89 | 528 |
| I-37 | 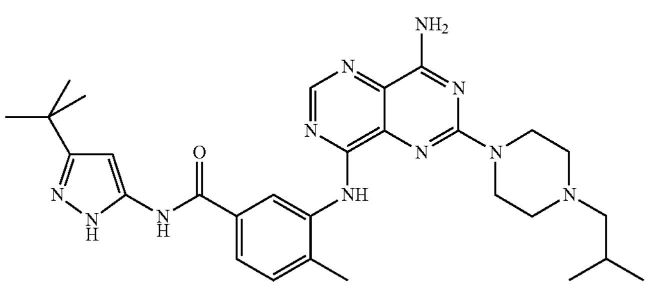 [SMILES: Cc1ccc(C(=O)Nc2cc(C(C)(C)C)n[nH]2)cc1Nc1ncnc2c(N)nc(N3CCN(CC(C)C)CC3)nc12] | 2.38 | 558 |

TABLE 1-continued
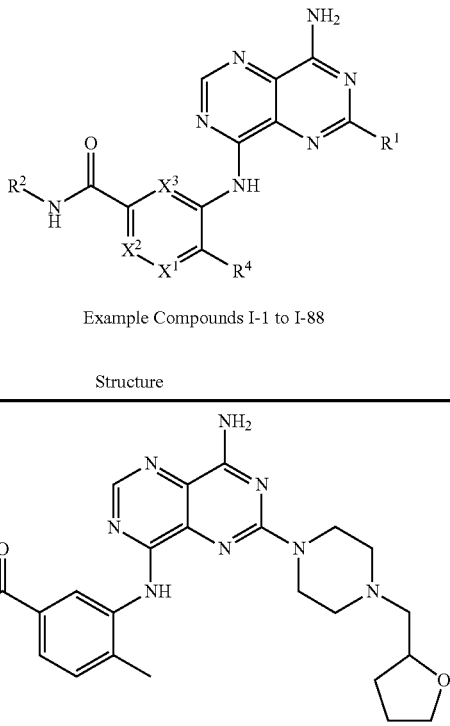
Example Compounds I-1 to I-88
| # | Structure | t_Ret. (HPLC) [min] | MS (M + H)+ |
|---|---|---|---|
| I-38 | 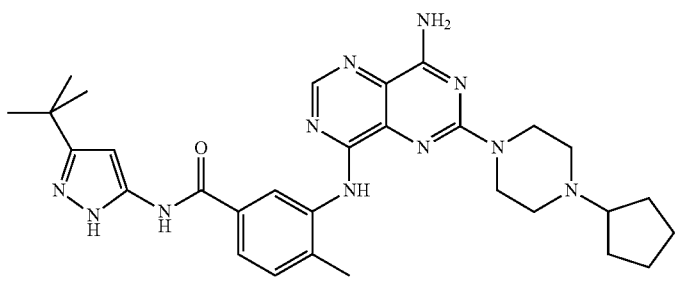 [SMILES: Cc1ccc(C(=O)Nc2cc(C(C)(C)C)n[nH]2)cc1Nc1ncnc2c(N)nc(N3CCN(C4CCCC4)CC3)nc12] | 2.06 | 586 |
| I-39 | 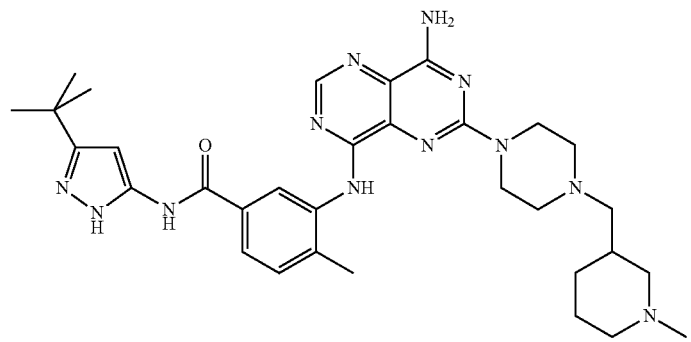 [SMILES: Cc1ccc(C(=O)Nc2cc(C(C)(C)C)n[nH]2)cc1Nc1ncnc2c(N)nc(N3CCN(CC4CCCN(C)C4)CC3)nc12] | 2.23 | 570 |
| I-40 | 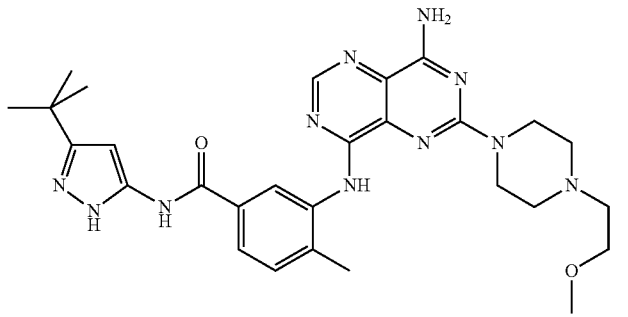 | 2.10 | 613 |
| I-41 | 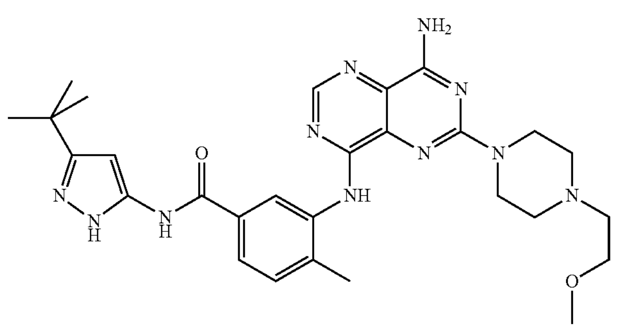 [SMILES: COCCN1CCN(c2nc(N)c3ncnc(Nc4cc(C(=O)Nc5cc(C(C)(C)C)n[nH]5)ccc4C)c3n2)CC1] | 1.98 | 560 |

TABLE 1-continued

Example Compounds I-1 to I-88

| # | Structure | t_Ret. (HPLC) [min] | MS (M + H)+ |
|---|---|---|---|
| I-42 | 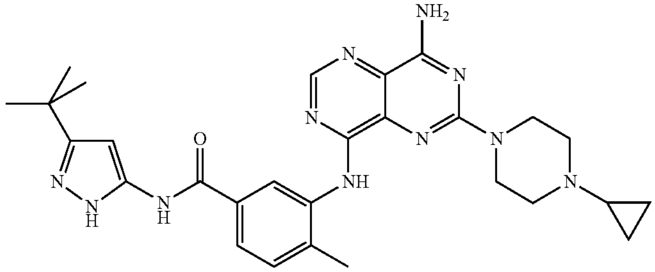 [SMILES: Cc1ccc(C(=O)Nc2cc(C(C)(C)C)n[nH]2)cc1Nc1ncnc2c(N)nc(N3CCN(C4CC4)CC3)nc12] | 2.16 | 542 |
| I-43 | 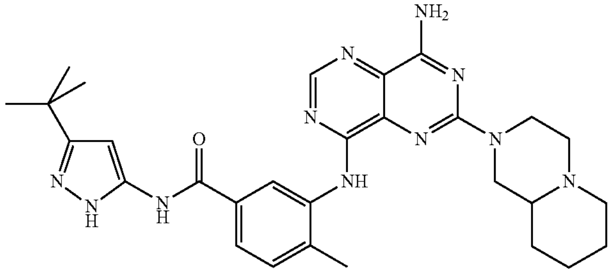 [SMILES: Cc1ccc(C(=O)Nc2cc(C(C)(C)C)n[nH]2)cc1Nc1ncnc2c(N)nc(N3CCN4CCCCC4C3)nc12] | 2.12 | 556 |
| I-44 | 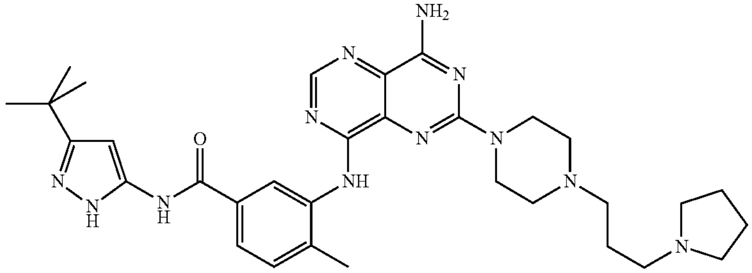 [SMILES: Cc1ccc(C(=O)Nc2cc(C(C)(C)C)n[nH]2)cc1Nc1ncnc2c(N)nc(N3CCN(CCCN4CCCC4)CC3)nc12] | 2.26 | 613 |
| I-45 | 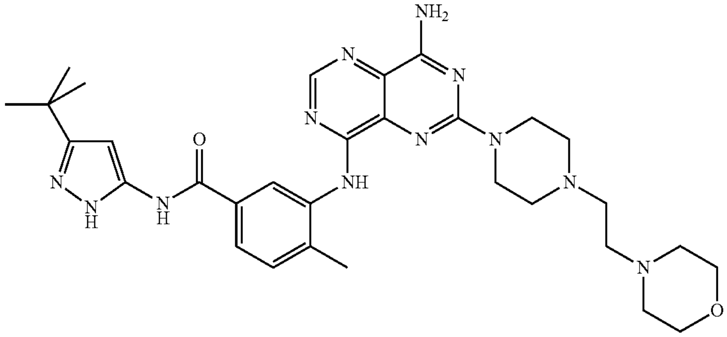 [SMILES: Cc1ccc(C(=O)Nc2cc(C(C)(C)C)n[nH]2)cc1Nc1ncnc2c(N)nc(N3CCN(CCN4CCOCC4)CC3)nc12] | 2.15 | 615 |

TABLE 1-continued

Example Compounds I-1 to I-88

| # | Structure | t_Ret. (HPLC) [min] | MS (M + H)+ |
|---|---|---|---|
| I-46 | 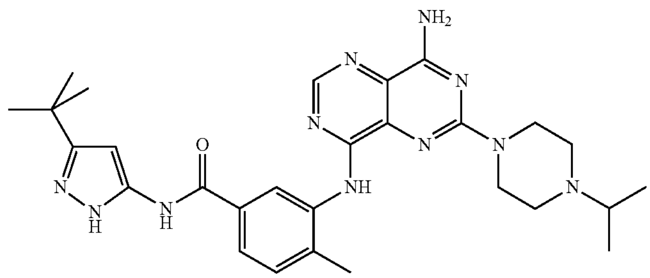 [SMILES: Cc1ccc(C(=O)Nc2cc(C(C)(C)C)n[nH]2)cc1Nc1ncnc2c(N)nc(N3CCN(C(C)C)CC3)nc12] | 2.46 | 544 |
| I-47 | 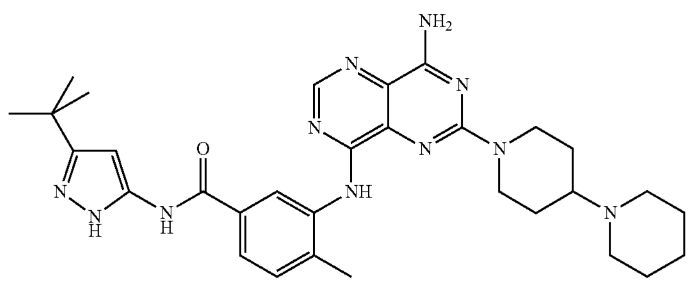 [SMILES: Cc1ccc(C(=O)Nc2cc(C(C)(C)C)n[nH]2)cc1Nc1ncnc2c(N)nc(N3CCC(N4CCCCC4)CC3)nc12] | 2.51 | 584 |
| I-48 | 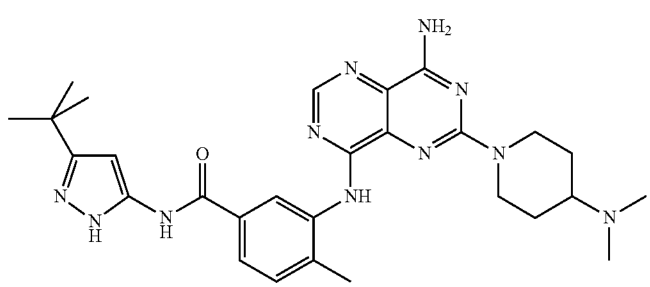 [SMILES: Cc1ccc(C(=O)Nc2cc(C(C)(C)C)n[nH]2)cc1Nc1ncnc2c(N)nc(N3CCC(N(C)C)CC3)nc12] | 2.30 | 544 |
| I-49 | 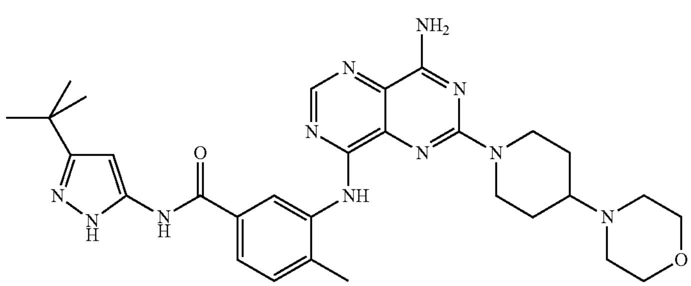 [SMILES: Cc1ccc(C(=O)Nc2cc(C(C)(C)C)n[nH]2)cc1Nc1ncnc2c(N)nc(N3CCC(N4CCOCC4)CC3)nc12] | 2.29 | 586 |

TABLE 1-continued

Example Compounds I-1 to I-88

| # | Structure | $t_{Ret.}$ (HPLC) [min] | MS $(M + H)^+$ |
|---|---|---|---|
| I-50 | 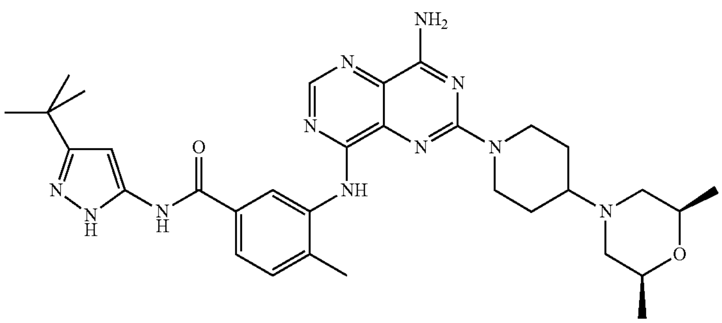 [SMILES: Cc1ccc(C(=O)Nc2cc(C(C)(C)C)n[nH]2)cc1Nc1ncnc2c(N)nc(N3CCC(N4C[C@@H](C)O[C@@H](C)C4)CC3)nc12] | 2.48 | 614 |
| I-51 | 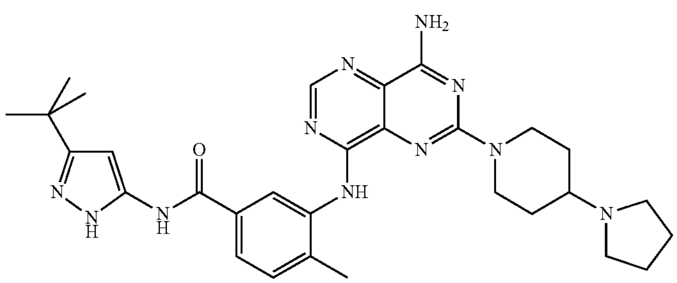 [SMILES: Cc1ccc(C(=O)Nc2cc(C(C)(C)C)n[nH]2)cc1Nc1ncnc2c(N)nc(N3CCC(N4CCCC4)CC3)nc12] | 2.42 | 570 |
| I-52 | 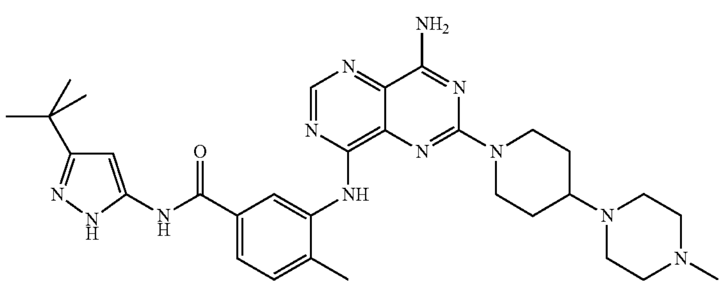 [SMILES: Cc1ccc(C(=O)Nc2cc(C(C)(C)C)n[nH]2)cc1Nc1ncnc2c(N)nc(N3CCC(N4CCN(C)CC4)CC3)nc12] | 2.18 | 599 |
| I-53 | 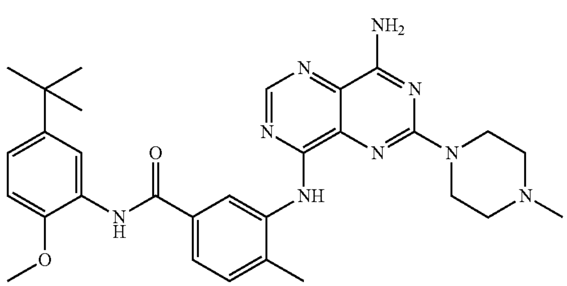 [SMILES: COc1ccc(C(C)(C)C)cc1NC(=O)c1ccc(C)c(Nc2ncnc3c(N)nc(N4CCN(C)CC4)nc23)c1] | 2.48 | 556 |

TABLE 1-continued

Example Compounds I-1 to I-88

| # | Structure | $t_{Ret.}$ (HPLC) [min] | MS $(M + H)^+$ |
|---|---|---|---|
| I-54 | 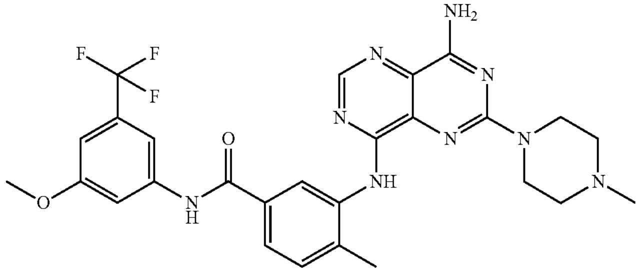 | 2.28 | 568 |
| I-55 | 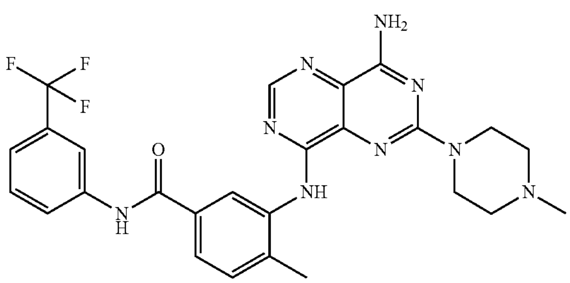 [SMILES: Cc1ccc(C(=O)Nc2cccc(C(F)(F)F)c2)cc1Nc1ncnc2c(N)nc(N3CCN(C)CC3)nc12] | 1.67 | 538 |
| I-56 | 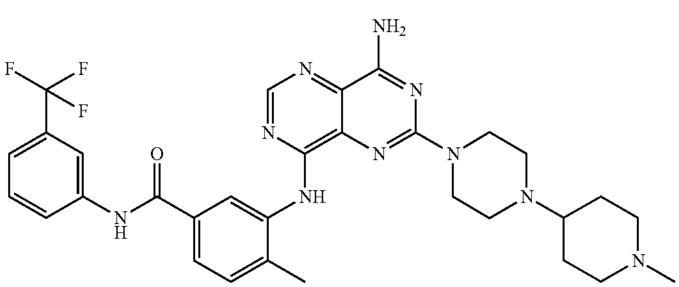 [SMILES: Cc1ccc(C(=O)Nc2cccc(C(F)(F)F)c2)cc1Nc1ncnc2c(N)nc(N3CCN(C4CCN(C)CC4)CC3)nc12] | 1.45 | 621 |
| I-57 | 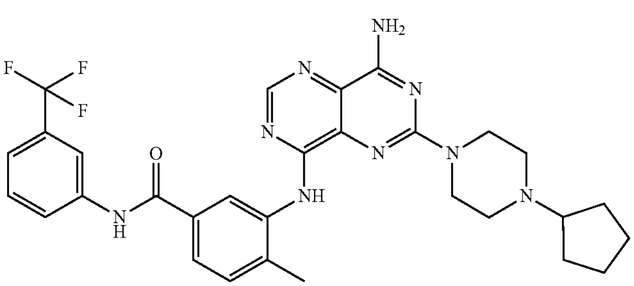 [SMILES: Cc1ccc(C(=O)Nc2cccc(C(F)(F)F)c2)cc1Nc1ncnc2c(N)nc(N3CCN(C4CCCC4)CC3)nc12] | 1.76 | 592 |

TABLE 1-continued
Example Compounds I-1 to I-88
| # | Structure | $t_{Ret.}$ (HPLC) [min] | MS $(M + H)^+$ |
|---|---|---|---|
| I-58 | 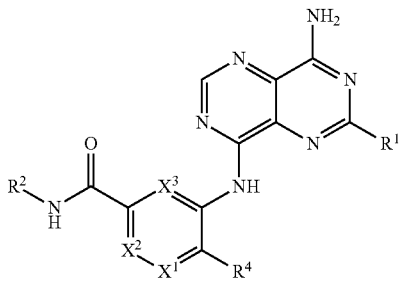 | 1.73 | 578 |
| I-59 | 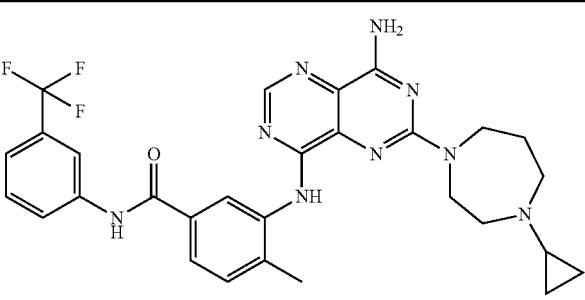 | 1.69 | 538 |
| I-60 | 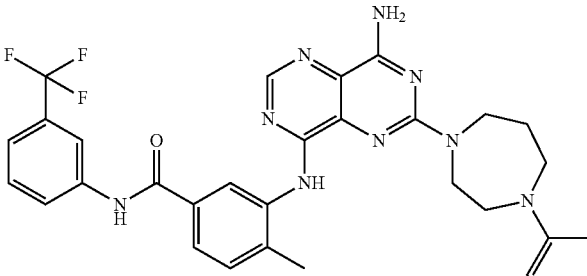 | 1.46 | 615 |

TABLE 1-continued
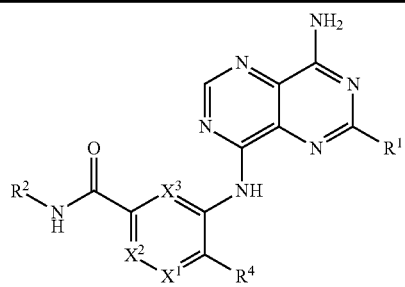
Example Compounds I-1 to I-88
| # | Structure | $t_{Ret.}$ (HPLC) [min] | MS $(M + H)^+$ |
|---|---|---|---|
| I-61 | 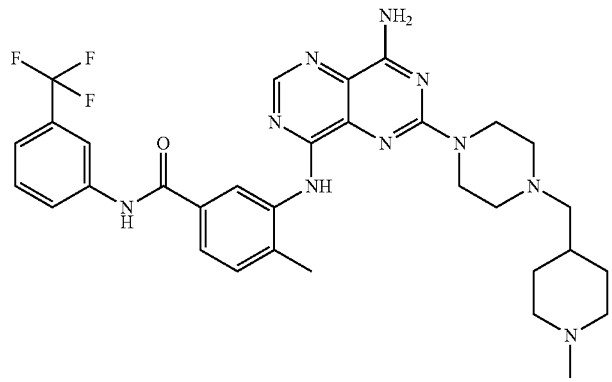 [SMILES: Cc1ccc(C(=O)Nc2cccc(C(F)(F)F)c2)cc1Nc1ncnc2c(N)nc(N3CCN(CC4CCN(C)CC4)CC3)nc12] | 0.0 | 635 |
| I-62 | 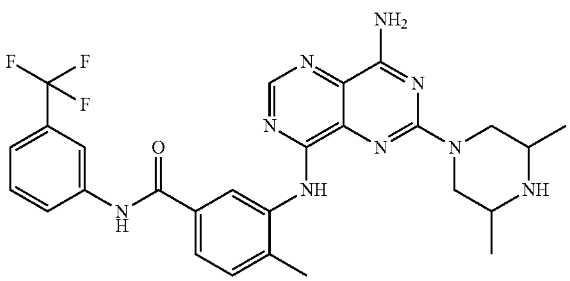 [SMILES: Cc1ccc(C(=O)Nc2cccc(C(F)(F)F)c2)cc1Nc1ncnc2c(N)nc(N3CC(C)NC(C)C3)nc12] | 1.70 | 552 |
| I-63 | 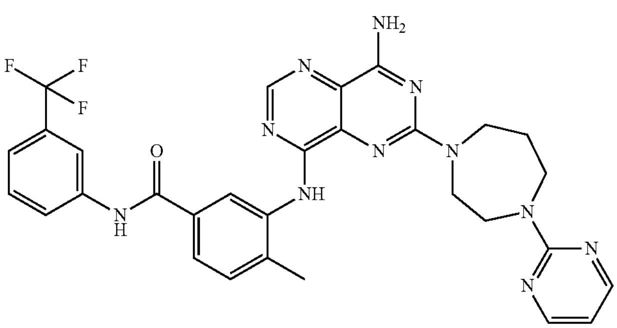 [SMILES: Cc1ccc(C(=O)Nc2cccc(C(F)(F)F)c2)cc1Nc1ncnc2c(N)nc(N3CCCN(c4ncccn4)CC3)nc12] | 2.47 | 616 |
| I-64 | 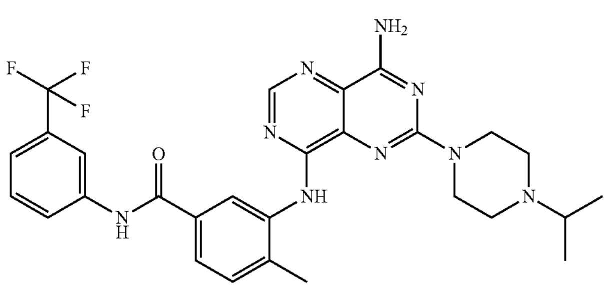 [SMILES: Cc1ccc(C(=O)Nc2cccc(C(F)(F)F)c2)cc1Nc1ncnc2c(N)nc(N3CCN(C(C)C)CC3)nc12] | 1.71 | 566 |

TABLE 1-continued

Example Compounds I-1 to I-88

| # | Structure | $t_{Ret.}$ (HPLC) [min] | MS $(M + H)^+$ |
|---|---|---|---|
| I-65 | 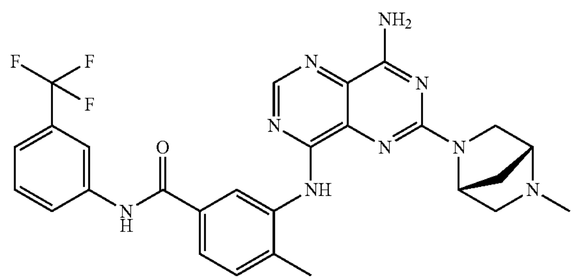 [SMILES: Cc1ccc(C(=O)Nc2cccc(C(F)(F)F)c2)cc1Nc1ncnc2c(N)nc(N3C[C@H]4C[C@@H]3CN4C)nc12] | 1.66 | 550 |
| I-66 | 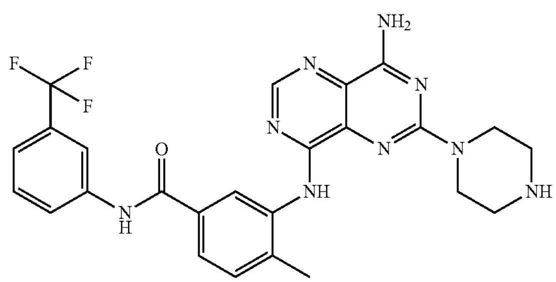 [SMILES: Cc1ccc(C(=O)Nc2cccc(C(F)(F)F)c2)cc1Nc1ncnc2c(N)nc(N3CCNCC3)nc12] | 1.66 | 524 |
| I-67 | 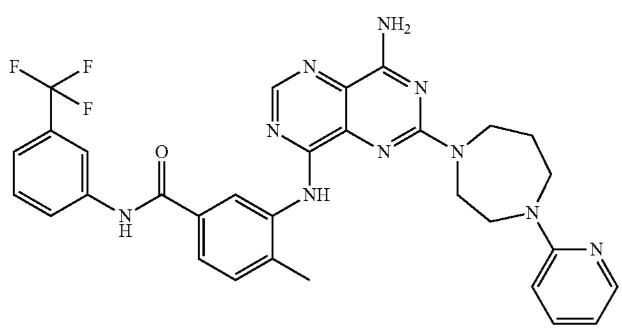 [SMILES: Cc1ccc(C(=O)Nc2cccc(C(F)(F)F)c2)cc1Nc1ncnc2c(N)nc(N3CCCN(c4ccccn4)CC3)nc12] | 1.82 | 615 |
| I-68 | 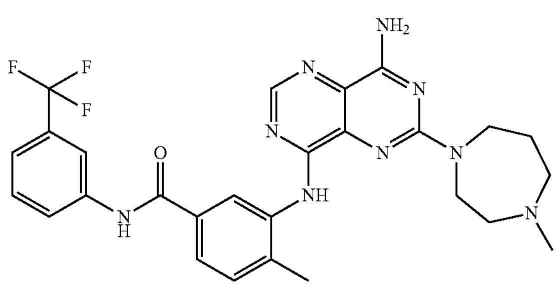 [SMILES: Cc1ccc(C(=O)Nc2cccc(C(F)(F)F)c2)cc1Nc1ncnc2c(N)nc(N3CCCN(C)CC3)nc12] | 1.70 | 552 |

TABLE 1-continued

Example Compounds I-1 to I-88

| # | Structure | t<sub>Ret.</sub> (HPLC) [min] | MS (M + H)⁺ |
|---|---|---|---|
| I-69 | 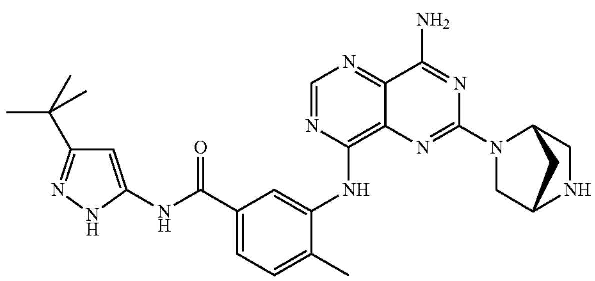 [SMILES: Cc1ccc(C(=O)Nc2cc(C(C)(C)C)n[nH]2)cc1Nc1ncnc2c(N)nc(N3C[C@@H]4C[C@H]3CN4)nc12] | 1.78 | 514 |
| I-70 | 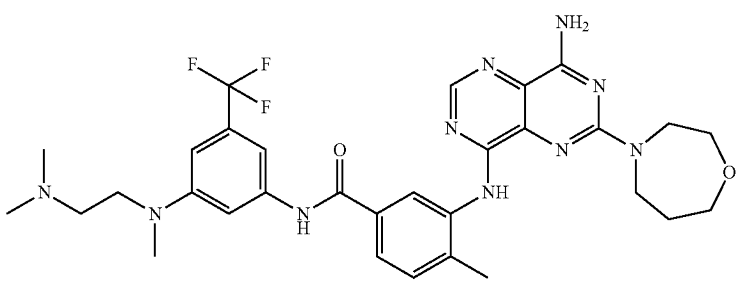 [SMILES: Cc1ccc(C(=O)Nc2cc(N(C)CCN(C)C)cc(C(F)(F)F)c2)cc1Nc1ncnc2c(N)nc(N3CCCOCC3)nc12] | 2.38 | 639 |
| I-71 | 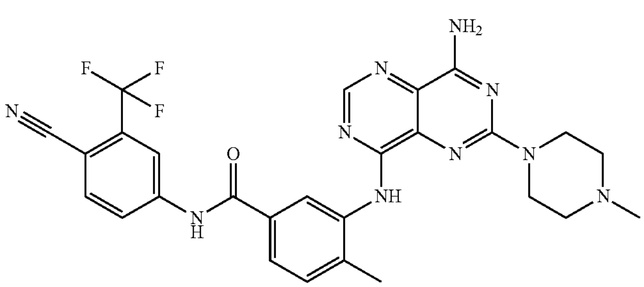 [SMILES: Cc1ccc(C(=O)Nc2ccc(C#N)c(C(F)(F)F)c2)cc1Nc1ncnc2c(N)nc(N3CCN(C)CC3)nc12] | 2.23 | 563 |
| I-72 | 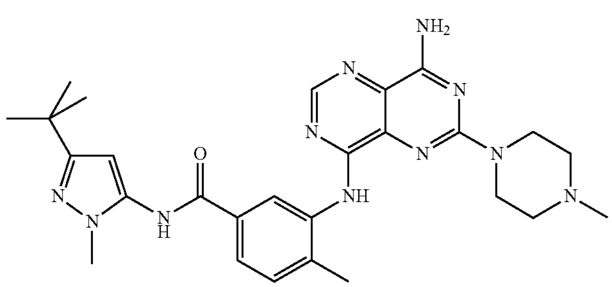 [SMILES: Cc1ccc(C(=O)Nc2cc(C(C)(C)C)nn2C)cc1Nc1ncnc2c(N)nc(N3CCN(C)CC3)nc12] | 1.98 | 530 |

TABLE 1-continued
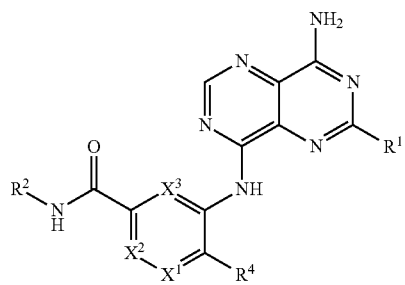
Example Compounds I-1 to I-88
| # | Structure | $t_{Ret.}$ (HPLC) [min] | MS $(M + H)^+$ |
|---|---|---|---|
| I-73 | 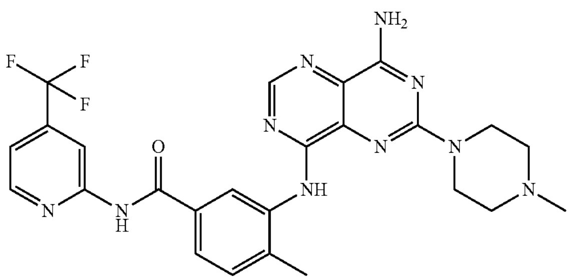 [SMILES: Cc1ccc(C(=O)Nc2cc(C(F)(F)F)ccn2)cc1Nc1ncnc2c(N)nc(N3CCN(C)CC3)nc12] | 2.17 | 539 |
| I-74 | 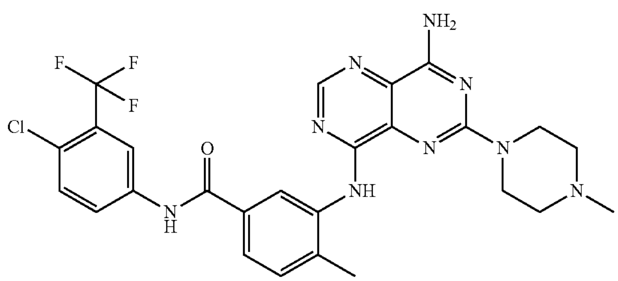 [SMILES: Cc1ccc(C(=O)Nc2ccc(Cl)c(C(F)(F)F)c2)cc1Nc1ncnc2c(N)nc(N3CCN(C)CC3)nc12] | 2.36 | 572 |
| I-75 | 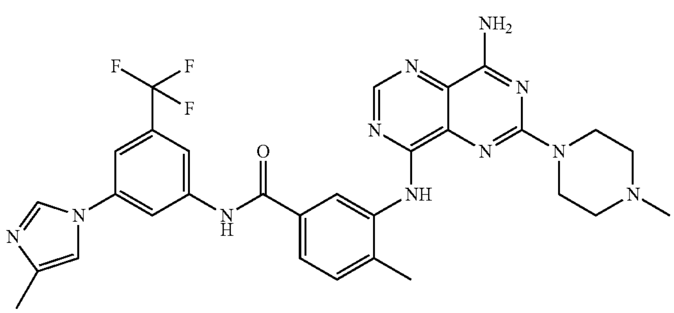 [SMILES: Cc1cn(-c2cc(NC(=O)c3ccc(C)c(Nc4ncnc5c(N)nc(N6CCN(C)CC6)nc45)c3)cc(C(F)(F)F)c2)cn1] | 2.15 | 618 |
| I-76 | 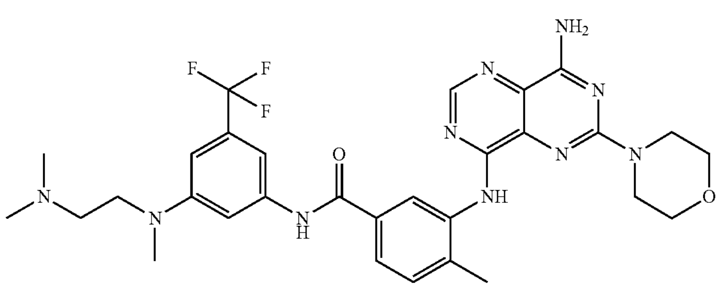 [SMILES: Cc1ccc(C(=O)Nc2cc(N(C)CCN(C)C)cc(C(F)(F)F)c2)cc1Nc1ncnc2c(N)nc(N3CCOCC3)nc12] | 2.32 | 625 |

TABLE 1-continued

Example Compounds I-1 to I-88

| # | Structure | t<sub>Ret.</sub> (HPLC) [min] | MS (M + H)⁺ |
|---|---|---|---|
| I-77 | 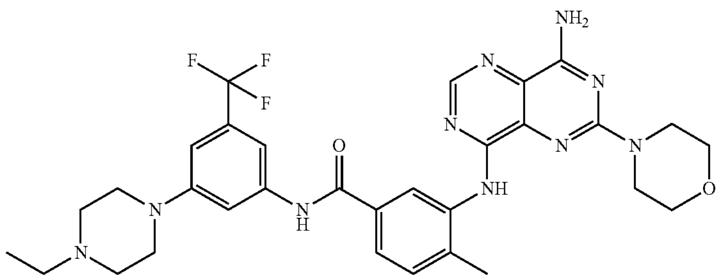 [SMILES: CCN1CCN(c2cc(NC(=O)c3ccc(C)c(Nc4ncnc5c(N)nc(N6CCOCC6)nc45)c3)cc(C(F)(F)F)c2)CC1] | 2.32 | 637 |
| I-78 | 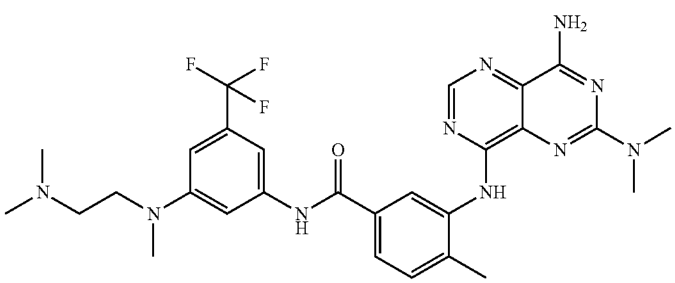 | 2.43 | 583 |
| I-79 | 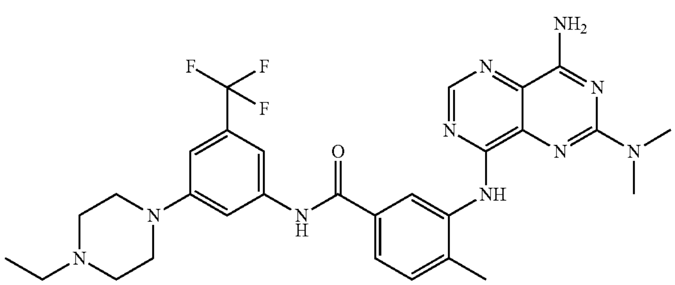 [SMILES: CCN1CCN(c2cc(NC(=O)c3ccc(C)c(Nc4ncnc5c(N)nc(N(C)C)nc45)c3)cc(C(F)(F)F)c2)CC1] | 2.44 | 595 |
| I-80 | 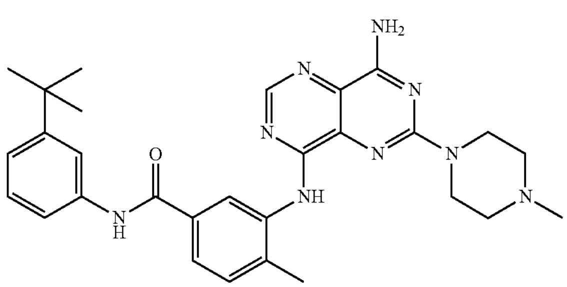 [SMILES: Cc1ccc(C(=O)Nc2cccc(C(C)(C)C)c2)cc1Nc1ncnc2c(N)nc(N3CCN(C)CC3)nc12] | 2.31 | 526 |

TABLE 1-continued

Example Compounds I-1 to I-88

| # | Structure | $t_{Ret.}$ (HPLC) [min] | MS $(M + H)^+$ |
|---|---|---|---|
| I-81 | 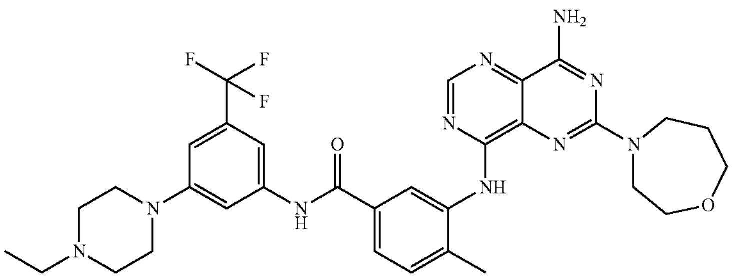 [SMILES: CCN1CCN(c2cc(NC(=O)c3ccc(C)c(Nc4ncnc5c(N)nc(N6CCCOCC6)nc45)c3)cc(C(F)(F)F)c2)CC1] | 2.39 | 652 |
| I-82 | 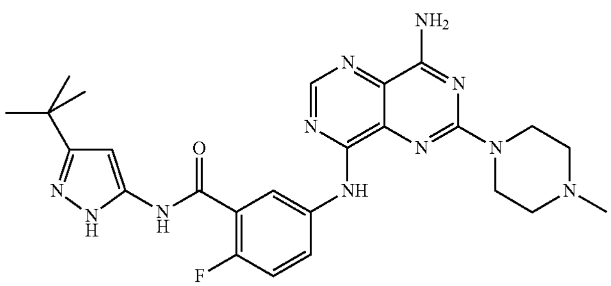 [SMILES: CN1CCN(c2nc(N)c3ncnc(Nc4ccc(F)c(C(=O)Nc5cc(C(C)(C)C)n[nH]5)c4)c3n2)CC1] | 2.23 | 520 |
| I-83 | 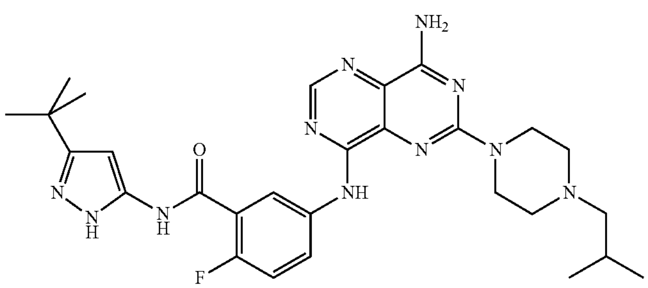 [SMILES: CC(C)CN1CCN(c2nc(N)c3ncnc(Nc4ccc(F)c(C(=O)Nc5cc(C(C)(C)C)n[nH]5)c4)c3n2)CC1] | 2.66 | 562 |
| I-84 | 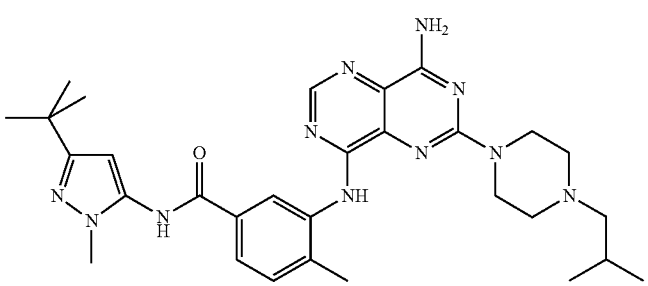 [SMILES: Cc1ccc(C(=O)Nc2cc(C(C)(C)C)nn2C)cc1Nc1ncnc2c(N)nc(N3CCN(CC(C)C)CC3)nc12] | 2.47 | 572 |

TABLE 1-continued

Example Compounds I-1 to I-88

| # | Structure | $t_{Ret.}$ (HPLC) [min] | MS $(M + H)^+$ |
|---|---|---|---|
| I-85 | 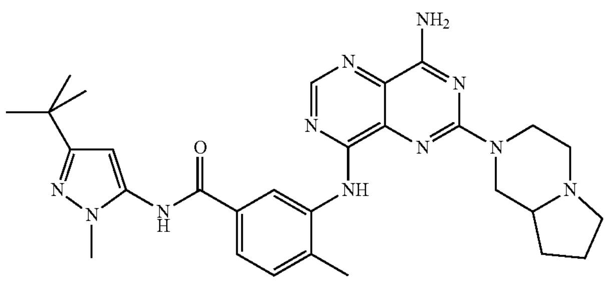 [SMILES: Cc1ccc(C(=O)Nc2cc(C(C)(C)C)nn2C)cc1Nc1ncnc2c(N)nc(N3CCN4CCCC4C3)nc12] | 2.11 | 556 |
| I-86 | 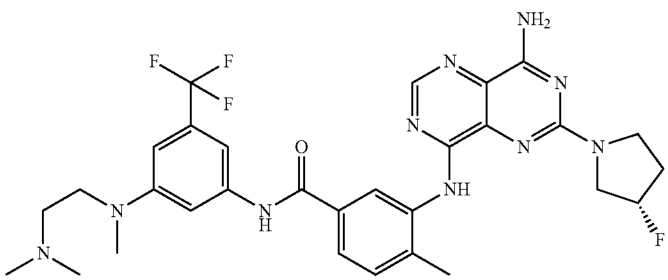 [SMILES: Cc1ccc(C(=O)Nc2cc(N(C)CCN(C)C)cc(C(F)(F)F)c2)cc1Nc1ncnc2c(N)nc(N3CC[C@H](F)C3)nc12] | 2.42 | 627 |
| I-87 | 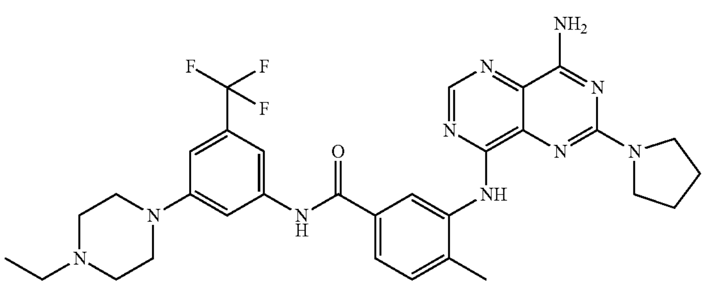 [SMILES: CCN1CCN(c2cc(NC(=O)c3ccc(C)c(Nc4ncnc5c(N)nc(N6CCCC6)nc45)c3)cc(C(F)(F)F)c2)CC1] | 2.56 | 621 |
| I-88 | 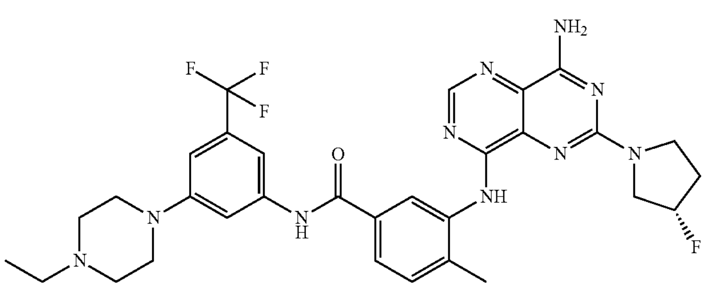 [SMILES: CCN1CCN(c2cc(NC(=O)c3ccc(C)c(Nc4ncnc5c(N)nc(N6CC[C@H](F)C6)nc45)c3)cc(C(F)(F)F)c2)CC1] | 2.42 | 639 |

Reaction scheme B

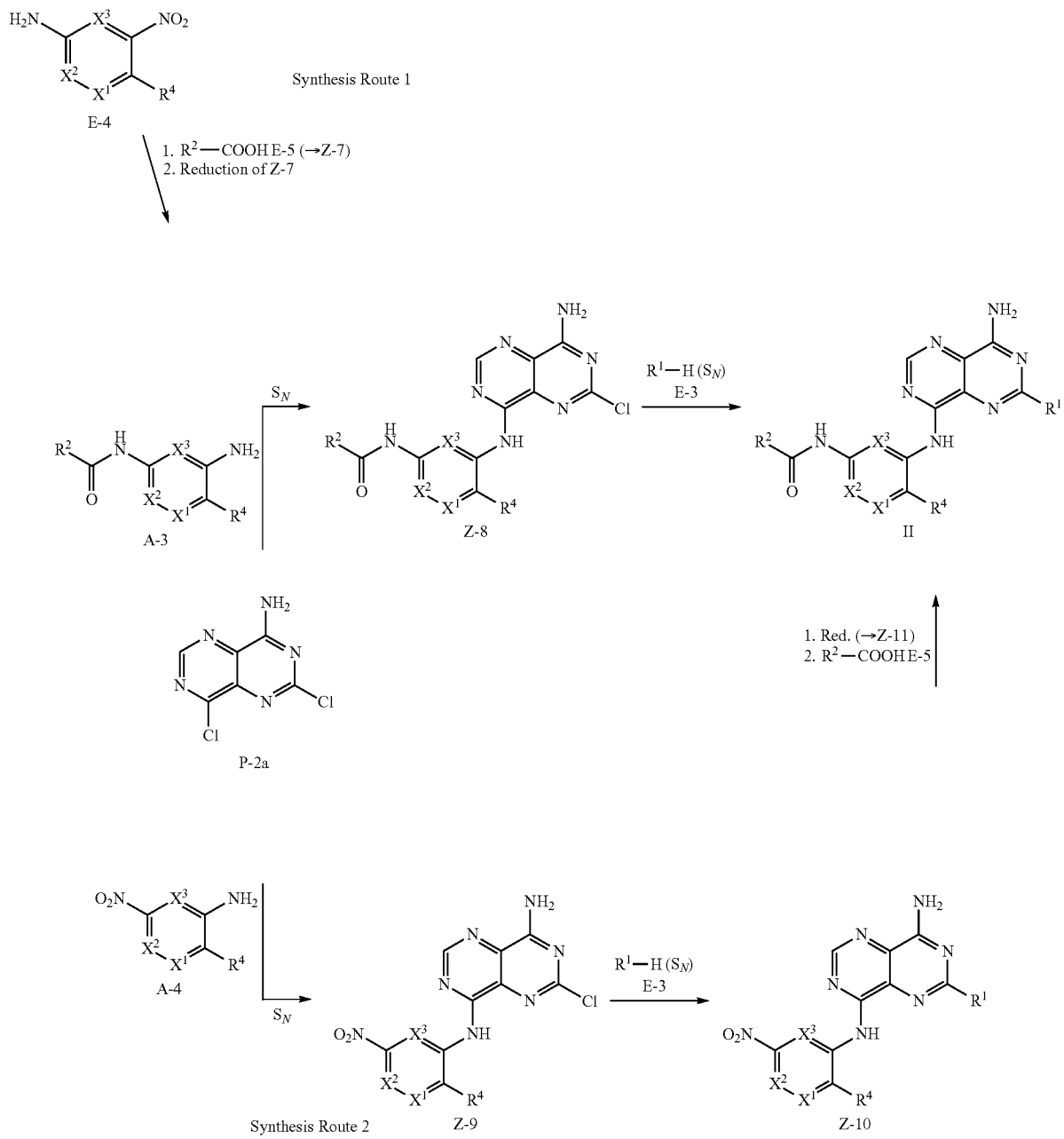

Example Compounds of Type II:

Example compounds II differ from those of type I by an inverted amide bond between the central (hetero-)aromatic six-membered ring and the group $R^2$ (Reaction scheme B). These compounds are obtained analogously to the compounds I in terms of the method used, except that the reactivities are inverted accordingly in the educt components E-4 and E-5 or A-4 (compared with E-1 and E-2 or A-2).

For compounds of type II for example the following two synthesis routes are possible: Starting from P-2a the 8-position is substituted by the aniline components A-3 or A-4. With regard to the use of A-3 reference is made to the remarks relating to Reaction scheme A (synthesis route 1 via intermediate compound Z-2). The components A-3 are obtained by amide coupling of the nitroanilines E-4 with carboxylic acids E-5 to obtain intermediate product Z-7 and subsequent reduction of the nitro group.

When A-4 is used first of all only the central phenyl or heteroaryl ring and the precursor of a linker fragment (nitro→amino) of the later linker $L^2$ is incorporated before the group $R^1$ is introduced analogously. In this case additional reaction steps are necessary (reduction, activation, amidation) in order to obtain compounds II.

Both the group $R^1$ and the group $R^2$ of compounds II according to the invention may be modified in other reaction steps (not shown), to obtain further compounds II according to the invention. These reaction steps may be reactions of substitution, alkylation, acylation or addition.

a) Method for Synthesising A-3a:

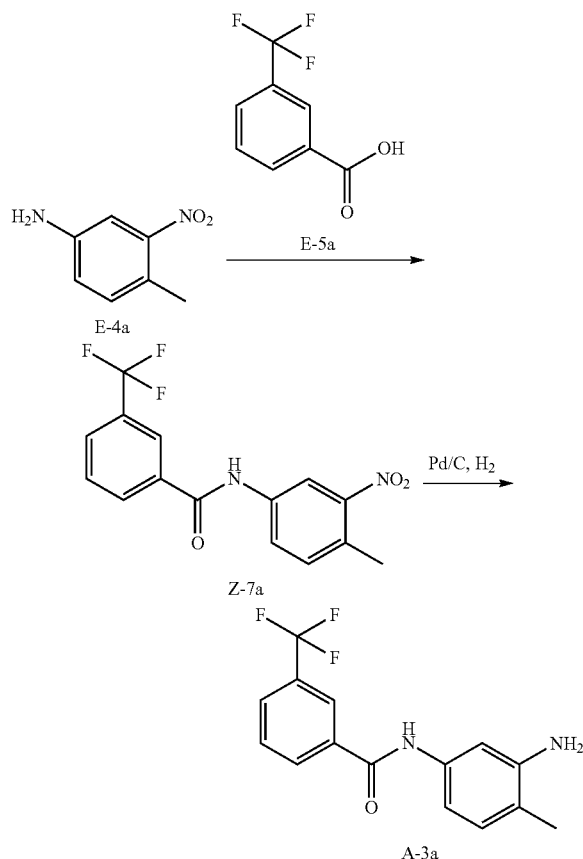

3-trifluoromethylbenzoic acid E-5a (10.03 g, 51.7 mmol) is taken up in 150 mL toluene. a solution of oxalyl chloride (7.6 mL, 57.58 mmol) in 100 mL toluene is added dropwise. DMF (4 mL) is added and the reaction mixture is stirred for 2 h at 90° C. Then it is evaporated down, the residue is taken up in 100 mL DCM and cooled with an ice bath. 4-Methyl-3-nitroaniline E-4-a (8.91 g, 56.8 mmol) and TEA (8.7 mL, 62.14 mmol) are added, the ice bath is removed and the reaction mixture is stirred overnight at RT. For working up it is filtered, washed with DCM and the filtrate is evaporated down. The residue is mixed with 0.5 M NaOH solution (20 mL), the precipitate formed is filtered off and washed with water. The solid is suspended in 20 mL 0.5 M HCl solution and 10 mL EE, stirred for 15 min at RT and filtered off. The solid is suspended in 30 mL TBME, stirred for 10 min in the ultrasound bath, filtered off, dried and Z-7a (HPLC-MS: $t_{Ret.}$=2.30 min; MS (M+H)$^+$=325) is obtained.

The aromatic nitro compound Z-7a (4.4 g, 13.57 mmol) is taken up in THF (85 mL) and MeOH (15 mL). Pd/C (200 mg) is carefully added. The reaction vessel is filled with 7 bar H$_2$, the reaction mixture is stirred overnight at RT, filtered through Celite, washed with THF, the filtrate obtained is dried using the rotary evaporator and A-3a (HPLC-MS: $t_{Ret.}$=1.73 min; MS (M+H)$^+$=295) is obtained.

Analogously to the method for synthesising A-3a further anilines A-3 were obtained from the corresponding educts E-4 and E-5.

b) Method for Synthesising Z-8a:

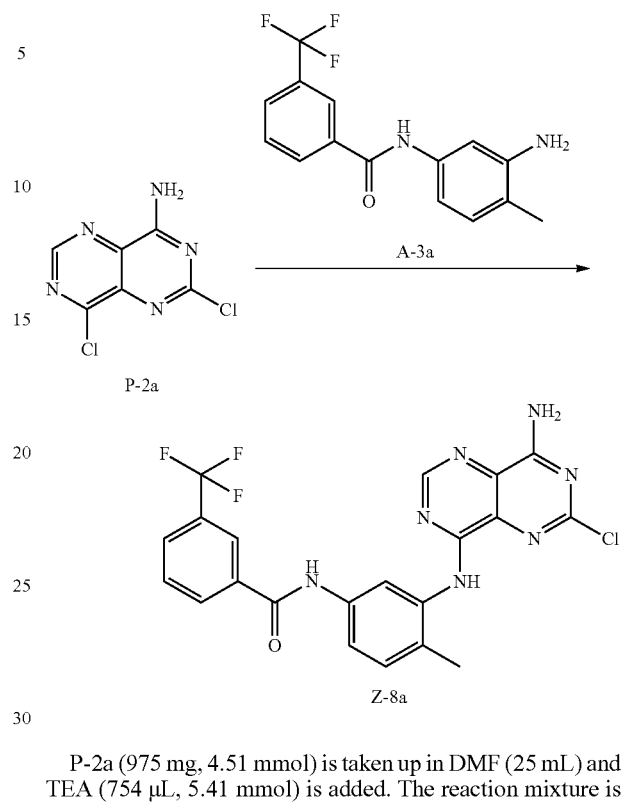

P-2a (975 mg, 4.51 mmol) is taken up in DMF (25 mL) and TEA (754 µL, 5.41 mmol) is added. The reaction mixture is combined with aniline A-3a (1.327 g, 4.51 mmol) and stirred overnight at RT. For working up 100 mL ice water are added, the precipitate formed is filtered off and Z-8a is obtained.

Analogously to the method for synthesising Z-8a further intermediate compounds Z-8 are obtained by reacting components A-3 with P-2a.

c) Method for Synthesising Example Compound II-1:

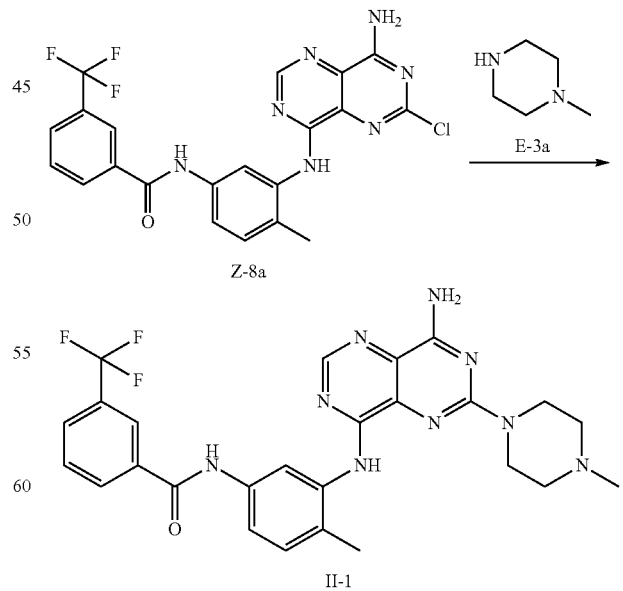

Z-8a (50 mg, 0.11 mmol) is taken up in DMSO (900 µL), mixed with N-methylpiperazine E-3a (32 mg, 0.32 mmol)

and stirred for 15 min at 150° C. in the microwave reactor. The reaction mixture is purified by preparative HPLC. The product-containing fractions of II-1 (HPLC-MS: $t_{Ret.}$=1.59 min; MS (M+H)$^+$=538) are freeze-dried.

Analogously to methods a) to c) (synthesis route 1) or synthesis route 2 described, in addition to II-1 the following compounds II-2 to II-19 according to the invention are also prepared (Table 2).

TABLE 2

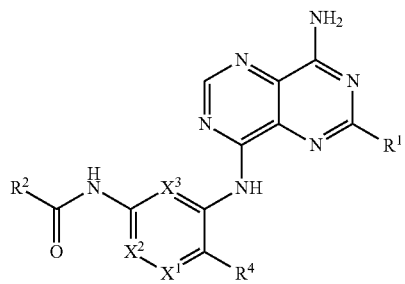

Example Compounds II-1 to II-19

| # | Structure | $t_{Ret.}$ (HPLC) [min] | MS (M + H)$^+$ |
|---|---|---|---|
| II-1 | 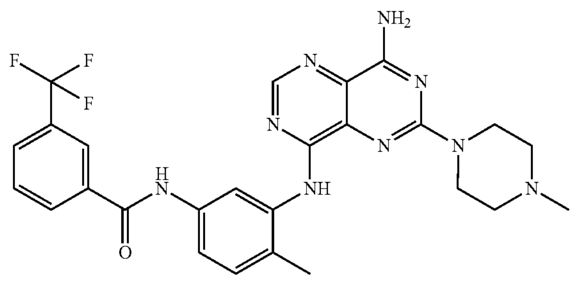 [SMILES: Cc1ccc(NC(=O)c2cccc(C(F)(F)F)c2)cc1Nc1ncnc2c(N)nc(N3CCN(C)CC3)nc12] | 1.59 | 538 |
| II-2 | 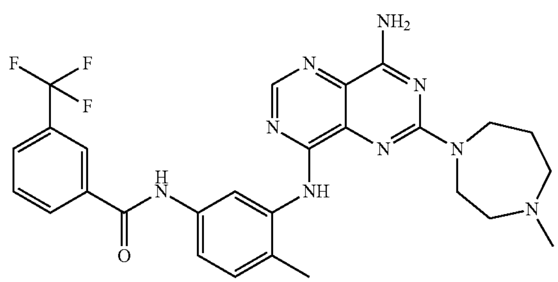 [SMILES: Cc1ccc(NC(=O)c2cccc(C(F)(F)F)c2)cc1Nc1ncnc2c(N)nc(N3CCCN(C)CC3)nc12] | 1.63 | 552 |
| II-3 | 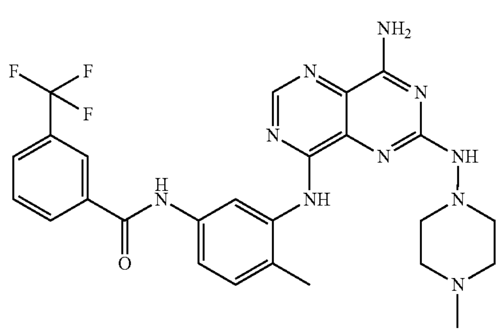 [SMILES: Cc1ccc(NC(=O)c2cccc(C(F)(F)F)c2)cc1Nc1ncnc2c(N)nc(NN3CCN(C)CC3)nc12] | 1.73 | 553 |

TABLE 2-continued
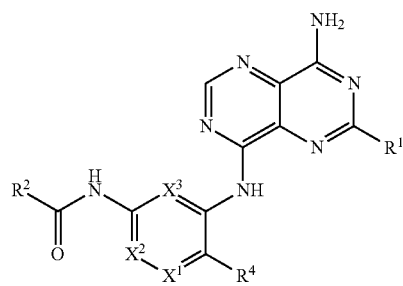
Example Compounds II-1 to II-19
| # | Structure | $t_{Ret.}$ (HPLC) [min] | MS $(M + H)^+$ |
|---|---|---|---|
| II-4 | 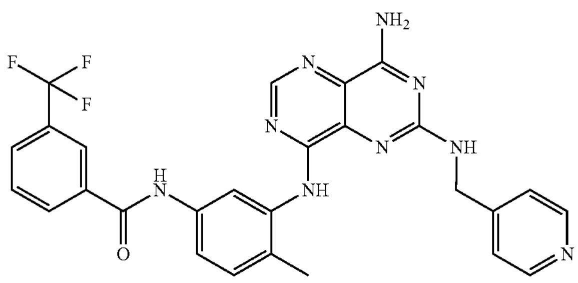 [SMILES: Cc1ccc(NC(=O)c2cccc(C(F)(F)F)c2)cc1Nc1ncnc2c(N)nc(NCc3ccncc3)nc12] | 1.66 | 546 |
| II-5 | 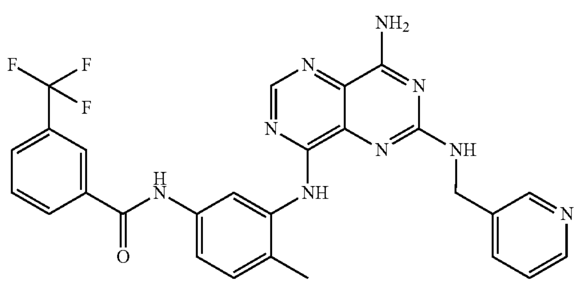 [SMILES: Cc1ccc(NC(=O)c2cccc(C(F)(F)F)c2)cc1Nc1ncnc2c(N)nc(NCc3cccnc3)nc12] | 1.80 | 546 |
| II-6 | 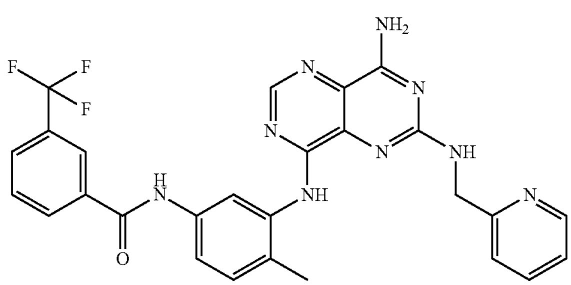 [SMILES: Cc1ccc(NC(=O)c2cccc(C(F)(F)F)c2)cc1Nc1ncnc2c(N)nc(NCc3ccccn3)nc12] | 1.80 | 546 |
| II-7 | 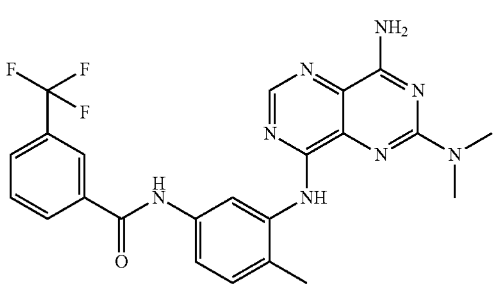 [SMILES: Cc1ccc(NC(=O)c2cccc(C(F)(F)F)c2)cc1Nc1ncnc2c(N)nc(N(C)C)nc12] | 2.29 | 483 |

TABLE 2-continued
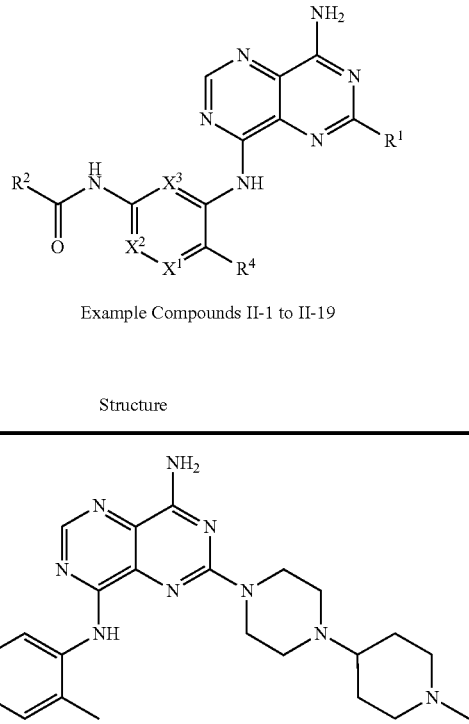
Example Compounds II-1 to II-19
| # | Structure | $t_{Ret.}$ (HPLC) [min] | MS $(M + H)^+$ |
|---|---|---|---|
| II-8 | 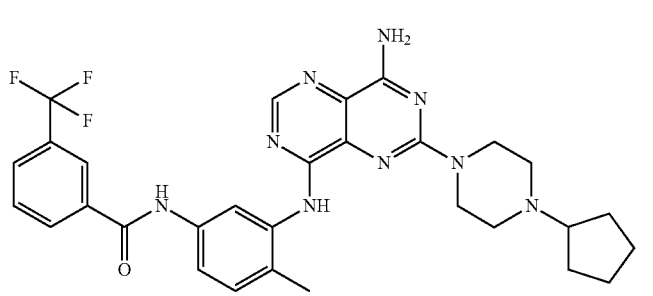 [SMILES: Cc1ccc(NC(=O)c2cccc(C(F)(F)F)c2)cc1Nc1ncnc2c(N)nc(N3CCN(C4CCCC4)CC3)nc12] | 1.42 | 621 |
| II-9 | 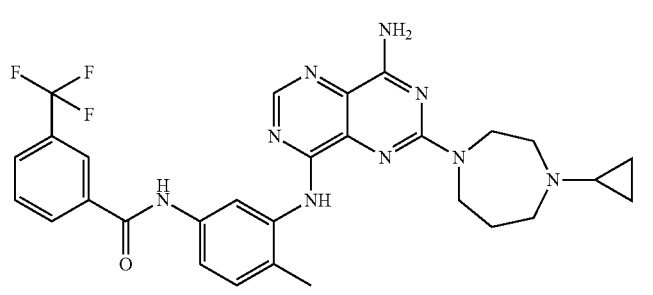 [SMILES: Cc1ccc(NC(=O)c2cccc(C(F)(F)F)c2)cc1Nc1ncnc2c(N)nc(N3CCCN(C4CC4)CC3)nc12] | 1.75 | 592 |
| II-10 | 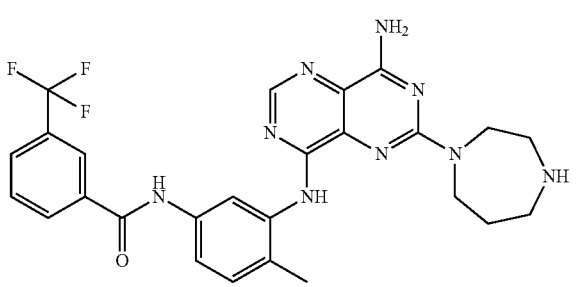 | 1.69 | 578 |
| II-11 | 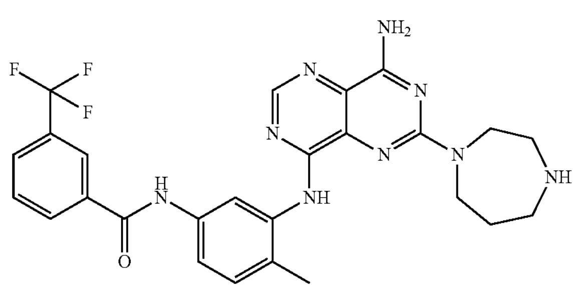 [SMILES: Cc1ccc(NC(=O)c2cccc(C(F)(F)F)c2)cc1Nc1ncnc2c(N)nc(N3CCCNCC3)nc12] | 1.64 | 538 |

US 8,653,087 B2
TABLE 2-continued
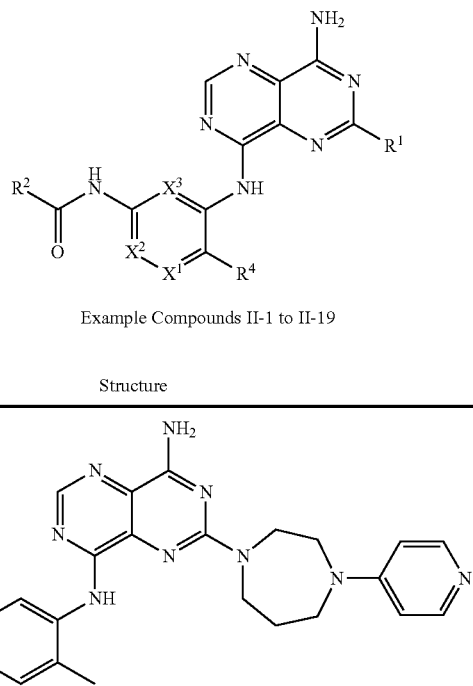
Example Compounds II-1 to II-19
| # | Structure | t$_{Ret.}$ (HPLC) [min] | MS (M + H)+ |
|---|---|---|---|
| II-12 | 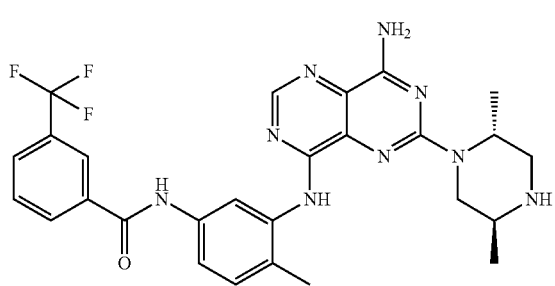 [SMILES: Cc1ccc(NC(=O)c2cccc(C(F)(F)F)c2)cc1Nc1ncnc2c(N)nc(N3C[C@H](C)NC[C@H]3C)nc12] | 1.74 | 615 |
| II-13 | 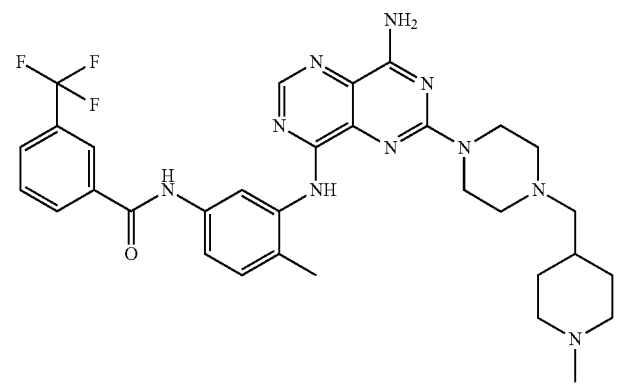 [SMILES: Cc1ccc(NC(=O)c2cccc(C(F)(F)F)c2)cc1Nc1ncnc2c(N)nc(N3CCN(CC4CCN(C)CC4)CC3)nc12] | 1.68 | 552 |
| II-14 | 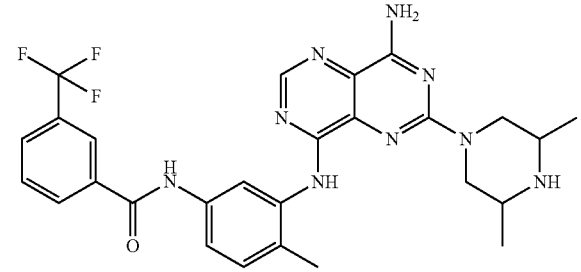 | 0.0 | 635 |
| II-15 | 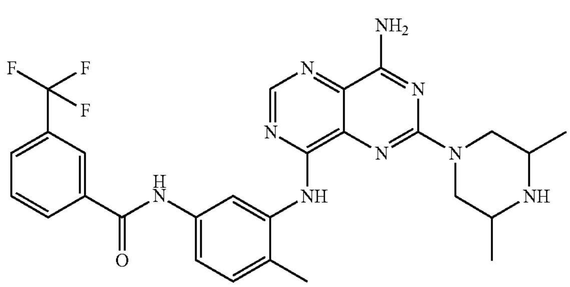 [SMILES: Cc1ccc(NC(=O)c2cccc(C(F)(F)F)c2)cc1Nc1ncnc2c(N)nc(N3CC(C)NC(C)C3)nc12] | 1.64 | 552 |

TABLE 2-continued
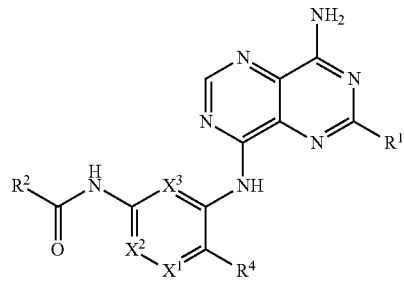
Example Compounds II-1 to II-19
| # | Structure | t$_{Ret.}$ (HPLC) [min] | MS (M + H)$^+$ |
|---|---|---|---|
| II-16 | 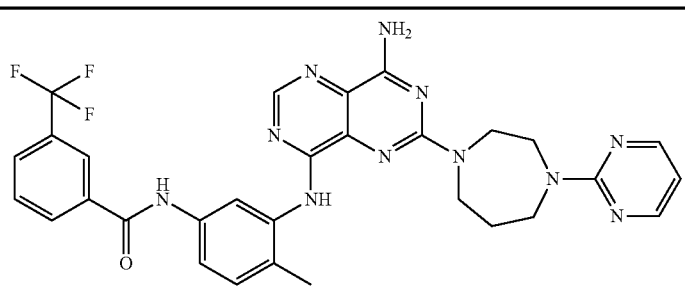 | 2.40 | 616 |
| II-17 | 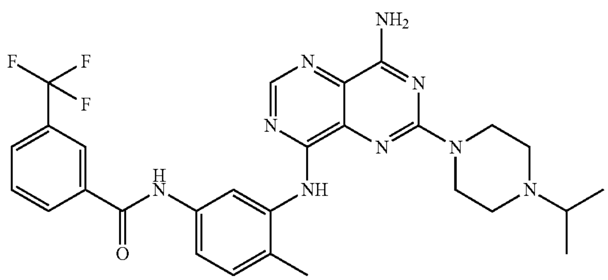 [SMILES: Cc1ccc(NC(=O)c2cccc(C(F)(F)F)c2)cc1Nc1ncnc2c(N)nc(N3CCN(C(C)C)CC3)nc12] | 1.68 | 566 |
| II-18 | 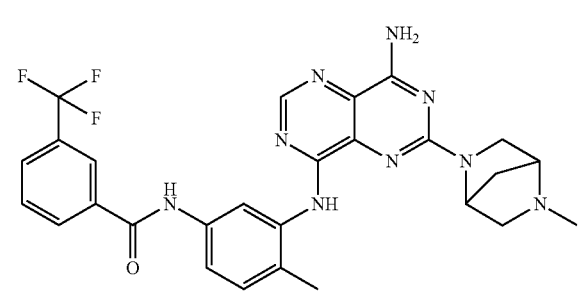 [SMILES: Cc1ccc(NC(=O)c2cccc(C(F)(F)F)c2)cc1Nc1ncnc2c(N)nc(N3CC4CC3CN4C)nc12] | 1.61 | 550 |
| II-19 | 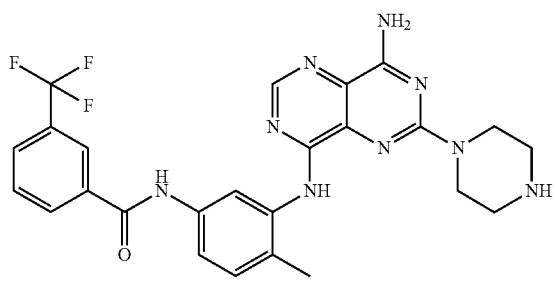 [SMILES: Cc1ccc(NC(=O)c2cccc(C(F)(F)F)c2)cc1Nc1ncnc2c(N)nc(N3CCNCC3)nc12] | 1.62 | 524 |

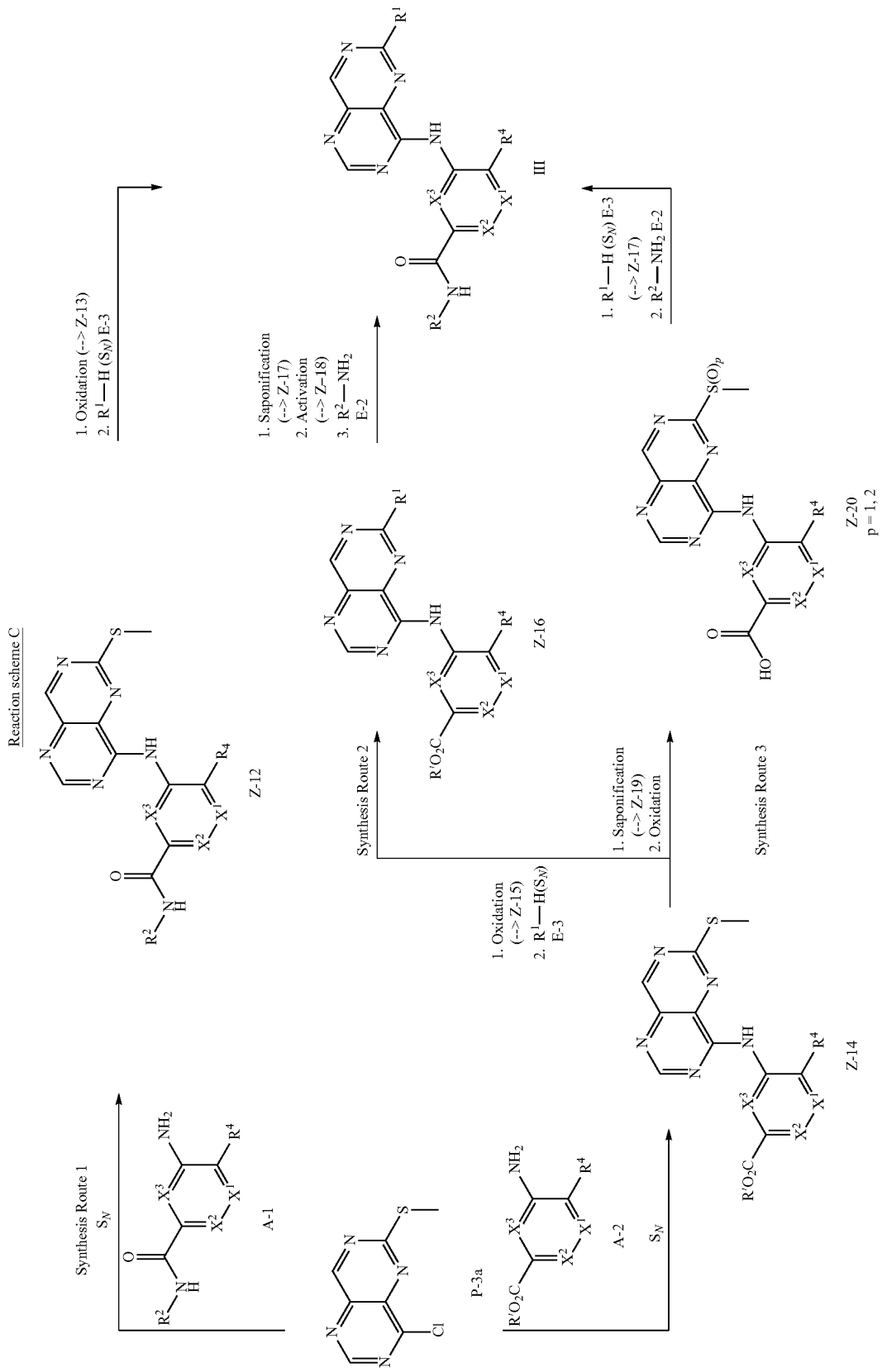

Example Compounds of Type III:

2,8-disubstituted pyrimidopyrimidines III may also be obtained for example by the following methods (Reaction scheme C, synthesis routes 1-3).

Starting from 8-chloro-2-methylsulphanyl-pyrimido[5,4-d]pyrimidine P-3a the 8-position is substituted by the aniline components A-1 or A-2, preferably under basically catalysed conditions at elevated temperature.

If A-1 is used (synthesis route 1) the complete left-hand molecular part of the end compounds III is thereby introduced into the intermediate compound Z-12, so that finally there only remains the substitution in the 2-position by components $R^1$—H (E-3), which are preferably primary and secondary (also cyclic) amines or alcohols (in the form of the alkoxides). For this, however, first the methylsulphanyl group has to be activated in the 2-position by oxidation to form the corresponding sulphoxide/sulphone for the substitution (for the synthesis of the components A-1 cf. the remarks made under Reaction scheme A). In this reaction, a mixture of the sulphoxide and sulphone is usually obtained, which is further reacted as one.

By contrast, by using A-2 (synthesis routes 2 and 3) first of all only the central phenyl or heteroaryl ring and a protected linker fragment (carboxylate) of the later linker $L^2$ (e.g. amide) is incorporated, before the group $R^1$ is introduced. With the intermediate compound Z-14 there are the alternative possibilities of either oxidising/activating the methylsulphanyl group, then substituting it with a component E-3 and lastly, after saponification, introducing the group $R^2$ (through the component E-2) (synthesis route 2) or first of all carrying out saponification and oxidation and then carrying out the nucleo-philic substitution by E-3 followed by the amide coupling of E-2 (synthesis route 3).

Alternatively to P-3a other educts P-3 are possible which allow successive and selective substitution, i.e. have other leaving groups.

Both the group $R^1$ and the group $R^2$ of compounds III according to the invention may be modified in other reaction steps (not shown), to obtain other compounds III according to the invention. These reaction steps may be reactions of substitution, alkylation, acylation or addition.

a) Method for Synthesising P-3a:

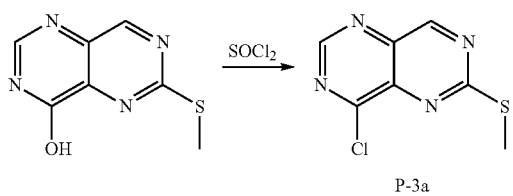

P-3a 8-hydroxy-2-methylsulphanyl-pyrimido[5,4-d]pyrimidine (16.5 g, 85 mmol) is placed in acetonitrile (125 mL), combined with DMF (400 μL) and heated to 30° C. At this temperature the thionyl chloride (16 mL, 215 mmol) is added dropwise. The reaction mixture is stirred for 4.5 h at 95° C. After cooling it is evaporated down, the residue is taken up in DCM and filtered through silica gel. The filtrate is washed with a saturated NaHCO$_3$ solution, dried on Na$_2$SO$_4$, filtered off, the solvent removed and P-3a (HPLC-MS: $t_{Ret.}$=1.64 min; MS (M+H)$^+$=213/215) is obtained.

b) Method for Synthesising Z-12a:

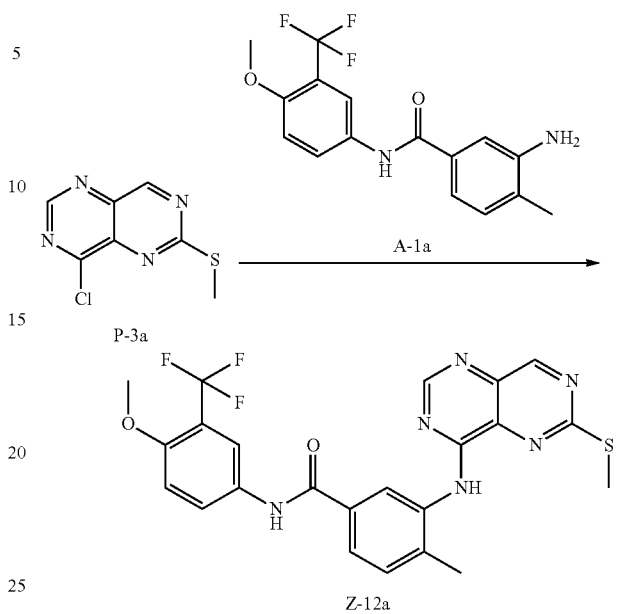

Z-12a

Aniline A-1a (453 mg, 1.4 mmol) and 8-chloro-2-methylsulphanyl-pyrimido[5,4-d]pyrimidine P-3a (270 mg, 1.27 mmol) are placed in dioxane (3 mL) and DIPEA (352 μL, 1.9 mmol) and refluxed overnight. For working up the reaction mixture is evaporated down, the residue is suspended in MeOH, the precipitate formed is filtered off, dried and Z-12a (HPLC-MS: $t_{Ret.}$=1.99 min; MS (M+H)$^+$=501) is obtained.

c) Method for Synthesising Z-12b:

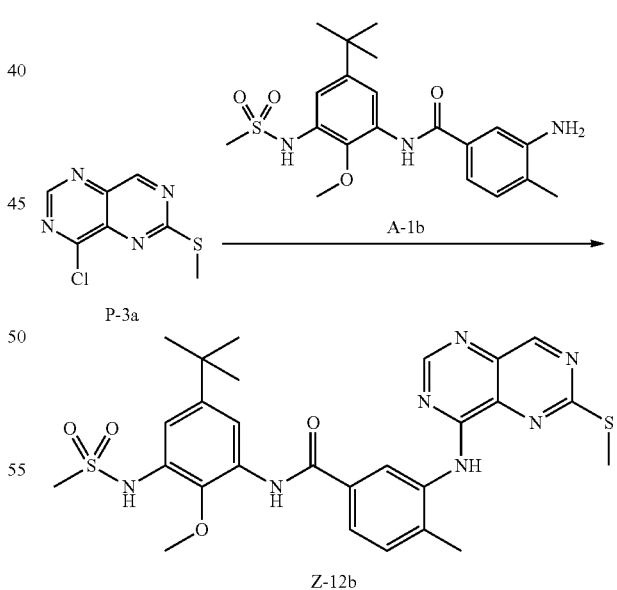

Z-12b

Aniline A-1b (3.3 g, 8.14 mmol) and 8-chloro-2-methylsulphanyl-pyrimido[5,4-d]pyrimidine P-3a (1.73 g, 8.14 mmol) are placed in acetic acid (20 mL) and stirred overnight at 50° C. For working up the reaction mixture is evaporated down, the residue is suspended in isopropanol/water (1:1), the precipitate formed is filtered off, dried and Z-12b is obtained.

Analogously to the methods for synthesising Z-12a and Z-12b further intermediate compounds Z-12 are obtained by reacting components A-1 with P-3a.

d) Method for Synthesising Example Compound III-1:

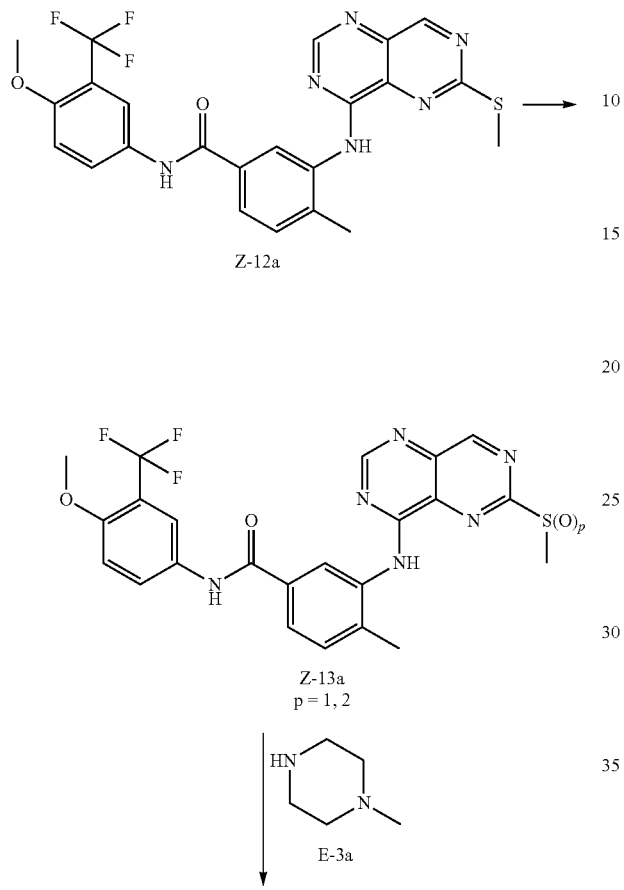

Z-12a (310 mg, 0.62 mmol) is taken up in DCM (5 mL). Then at RT mCPBA (70%, 183 mg, 0.74 mmol) is added and the reaction mixture is stirred for 1 h at RT. The precipitate formed is filtered off, washed with DCM, dried and Z-13a is obtained. Sulphoxide/sulphone Z-13a (90 mg, 0.174 mmol) and N-methylpiperazine E-3a (31 µL, 0.28 mmol) are placed in dioxane (0.5 mL). TEA (51 µL, 0.35 mmol) is added dropwise. The reaction mixture is stirred for 2 h at 60° C. For working up the mixture is evaporated down, the residue is suspended in isopropanol/water and filtered off. The solid is washed with water, dissolved in acetonitrile/water/2 M HCl solution, freeze-dried and III-1 (HPLC-MS: $t_{Ret.}$=2.18 min; MS (M+H)$^+$=553) is obtained.

e) Method for Synthesising Z-14a:

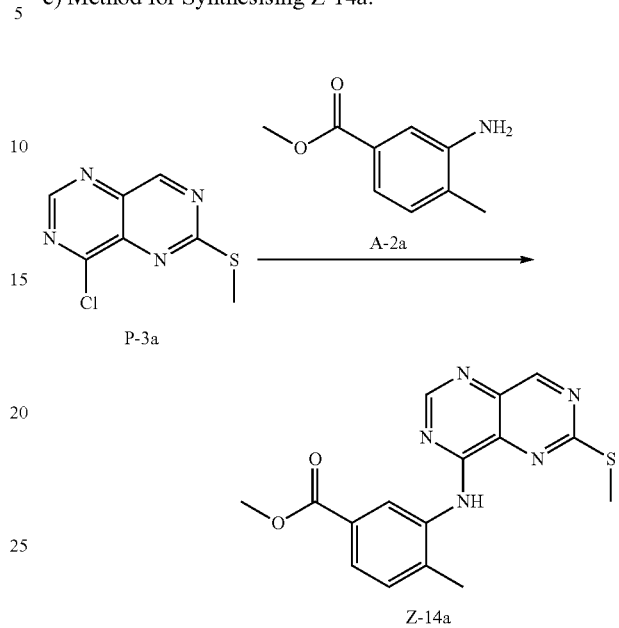

Methyl 3-amino-4-methylbenzoate A-2a (4.04 g, 24.45 mmol) and 8-chloro-2-methylsulphanyl-pyrimido[5,4-c/]pyrimidine P-3a (80%, 5.0 g, 18.81 mmol) are placed in dioxane (8 mL) and DIPEA (4.525 mL, 24.45 mmol) and refluxed overnight with stirring. For working up the reaction mixture is evaporated down, the residue is suspended in MeOH, the precipitate formed is filtered off, dried and Z-14a (HPLC-MS: $t_{Ret.}$=2.01 min; MS (M+H)$^+$=342) is obtained.

Analogously to the method for synthesising Z-14a further intermediate compounds Z-14 are obtained by reacting components A-2 with P-3a.

f) Method for Synthesising Z-16a:

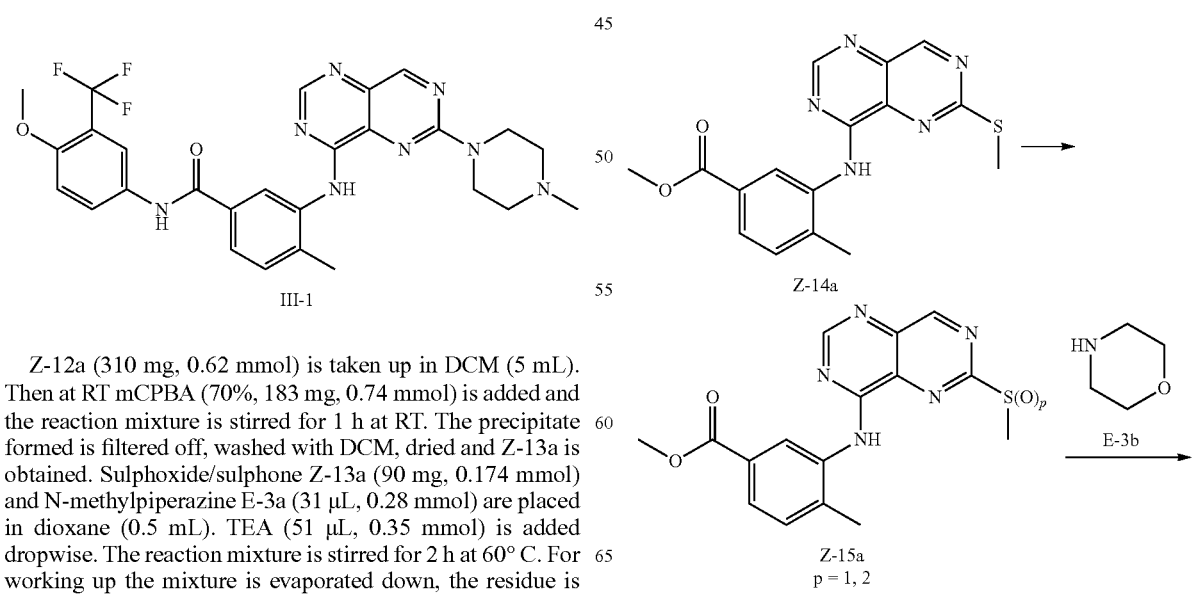

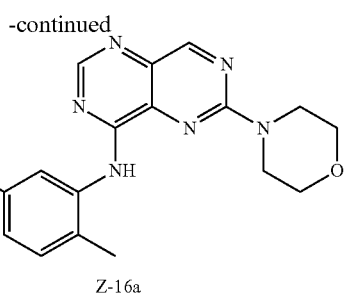

Z-16a

Z-14a (5.5 g, 16.1 mmol) is taken up in DCM (40 mL), combined at RT with mCPBA (70%, 3.61 g, 16.1 mmol) and stirred for 1 h. The precipitate formed is filtered off, washed with DCM, dried and Z-15a (HPLC-MS: $t_{Ret.}$=1.45 min; MS (M+H(+Na))$^+$=358(380)) is obtained.

Sulphoxide/sulphone Z-15a (1.0 g, 2.8 mmol) and morpholine E-3b (704 µL, 7.28 mmol) are placed in dioxane (30 mL). TEA (815 µL, 5.6 mmol) is added dropwise to this suspension and then it is heated to 60° C. for 2 h. For working up the mixture is evaporated down, the residue is suspended with iPrOH/water, filtered, dried and Z-16a (HPLC-MS: $t_{Ret.}$=1.94 min; MS (M+H)$^+$=381) is obtained.

g) Method for Synthesising Z-16b:

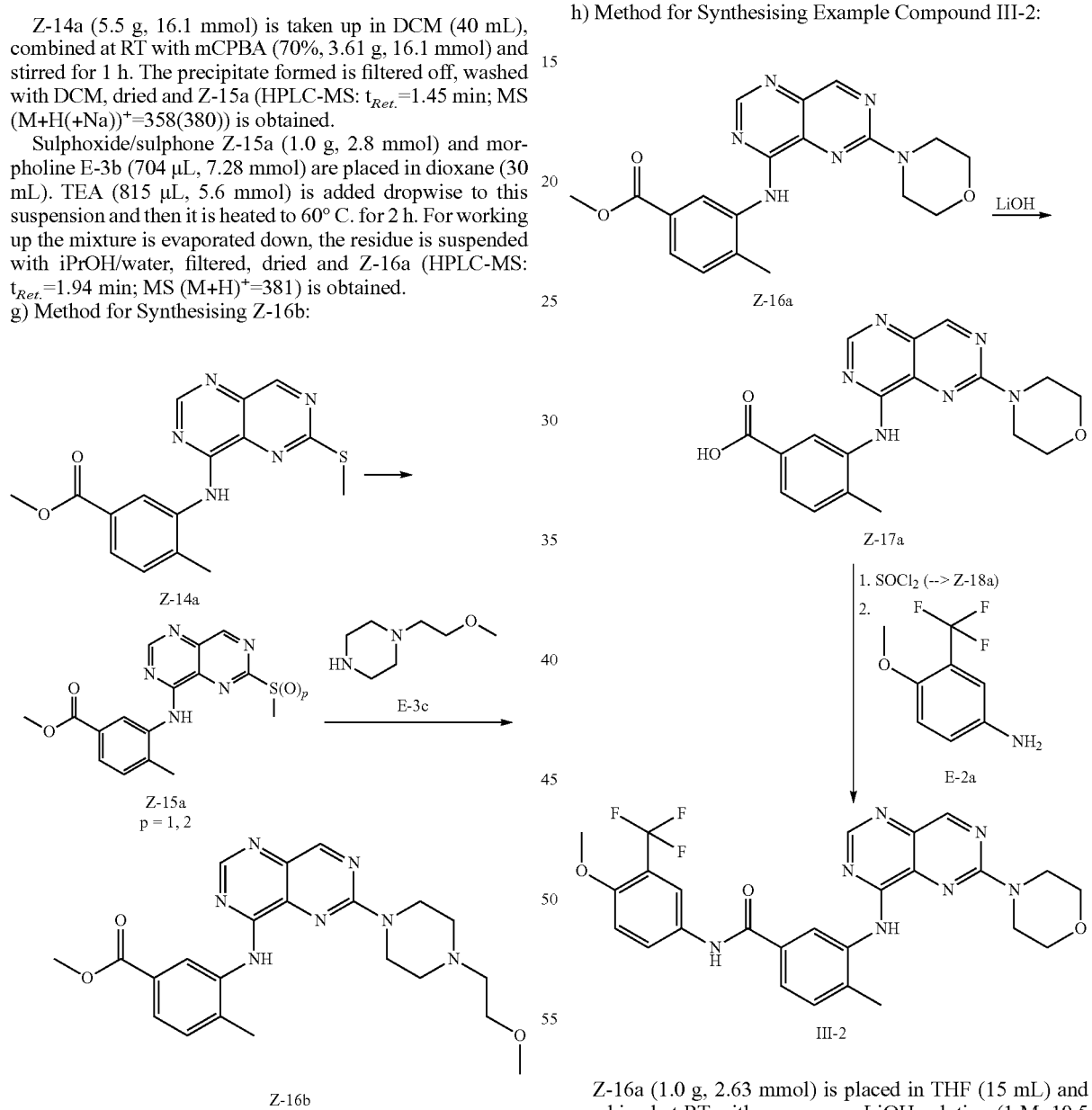

Z-14a

Z-15a
p = 1, 2

E-3c

Z-16b

Z-14a (5.5 g, 16.1 mmol) is taken up in DCM (40 mL), combined at RT with mCPBA (70%, 3.61 g, 16.1 mmol) and stirred for 1 h. The precipitate formed is filtered off, washed with DCM, dried and Z-15a (HPLC-MS: $t_{Ret.}$=1.45 min; MS (M+H(+Na))$^+$=358(380)) is obtained.

Sulphoxide/sulphone Z-15a (3.0 g, 8.4 mmol) and 1-(2-methoxyethyl)-piperazine E-3c (2.5 mL, 16.8 mmol) are placed in dioxane (25 mL). TEA (3 mL, 23 mmol) is added dropwise to this suspension and then the mixture is heated to 60° C. for 2 h. For working up the mixture is evaporated down, the residue is suspended with iPrOH/water, filtered, dried and Z-16b (HPLC-MS: $t_{Ret.}$=1.95 min; MS (M+H)$^+$=438) is obtained.

Analogously to the methods for synthesising Z-16a and Z-16b other intermediate compounds Z-16 are obtained by oxidising components Z-14 and reacting with amines E-3. Further intermediate compounds Z-16 are obtained by reacting with alcohols E-3 (in the form of their alkoxides), e.g. with sodium methoxide.

h) Method for Synthesising Example Compound III-2:

Z-16a

Z-17a

1. SOCl$_2$ (--> Z-18a)
2.

E-2a

III-2

Z-16a (1.0 g, 2.63 mmol) is placed in THF (15 mL) and combined at RT with an aqueous LiOH solution (1 M, 10.5 mL). Then the mixture is refluxed for 2 h with stirring. For working up the pH is adjusted to 5.5 by the addition of a 1N HCl solution. After evaporation in vacuo the precipitate formed is filtered off, washed with water, dried and Z-17a (HPLC-MS: $t_{Ret.}$=1.31 min; MS (M+H)$^+$=367) is obtained.

Benzoic acid Z-17a (1.1 g, 3.0 mmol) is suspended in thionyl chloride and stirred for 1 h at 60° C. The reaction mixture is evaporated down and dried azeotropically with dry toluene. The acid chloride Z-18a (400 mg, 1.04 mmol) is then taken up in a little NMP (1.2 mL) and combined with 4-methoxy-3-trifluoromethyl-phenylamine E-2a (188 mg, 1.55 mmol) and DIPEA (300 μL, 1.75 mmol). For working up water is added, the precipitate obtained is filtered off, dried and Example compound III-2 (HPLC-MS: $t_{Ret.}$=2.20 min; MS (M+H)$^+$=540) is obtained.

i) Method for Synthesising Z-17b:

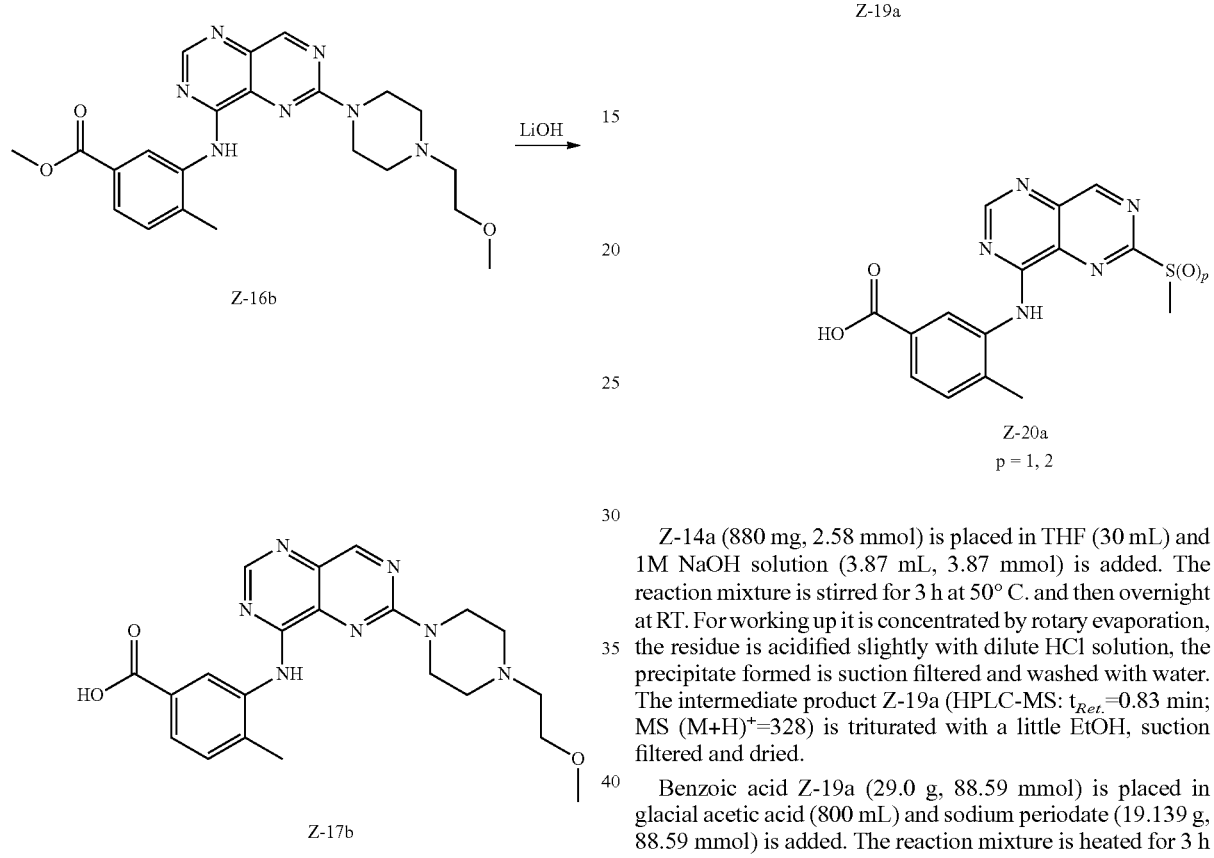

Z-16b (3.42 g, 7.81 mmol) is placed in THF (25 mL) and combined at RT with an aqueous LiOH solution (1.3 g, 31.4 mmol in 10 mL). Then the mixture is refluxed for 2 h with stirring. For working up the pH is adjusted to 5.5 by the addition of a 1N HCl solution. After evaporation in vacuo the precipitate formed is filtered off, washed with 5 mL water, dried and Z-17b (HPLC-MS: $t_{Ret.}$=1.05 min; MS (M+H)$^+$=424) is obtained.

j) Method for Synthesising Z-20a:

Z-14a (880 mg, 2.58 mmol) is placed in THF (30 mL) and 1M NaOH solution (3.87 mL, 3.87 mmol) is added. The reaction mixture is stirred for 3 h at 50° C. and then overnight at RT. For working up it is concentrated by rotary evaporation, the residue is acidified slightly with dilute HCl solution, the precipitate formed is suction filtered and washed with water. The intermediate product Z-19a (HPLC-MS: $t_{Ret.}$=0.83 min; MS (M+H)$^+$=328) is triturated with a little EtOH, suction filtered and dried.

Benzoic acid Z-19a (29.0 g, 88.59 mmol) is placed in glacial acetic acid (800 mL) and sodium periodate (19.139 g, 88.59 mmol) is added. The reaction mixture is heated for 3 h to 80° C. After cooling it is mixed with aqueous $Na_2S_2O_5$ solution (15 mL; 10%) and largely concentrated by rotary evaporation. The residue is mixed with water, the precipitate formed is suction filtered, washed with water, dried in the vacuum dryer at 70° C. and Z-20a (HPLC-MS: $t_{Ret.}$=1.81 min; MS (M+H)$^+$=360) is obtained.

Analogously to the method for synthesising Z-20a further intermediate compounds Z-20 are obtained by saponification of components Z-14 and oxidation.

k) Method for Synthesising Example Compound III-3:

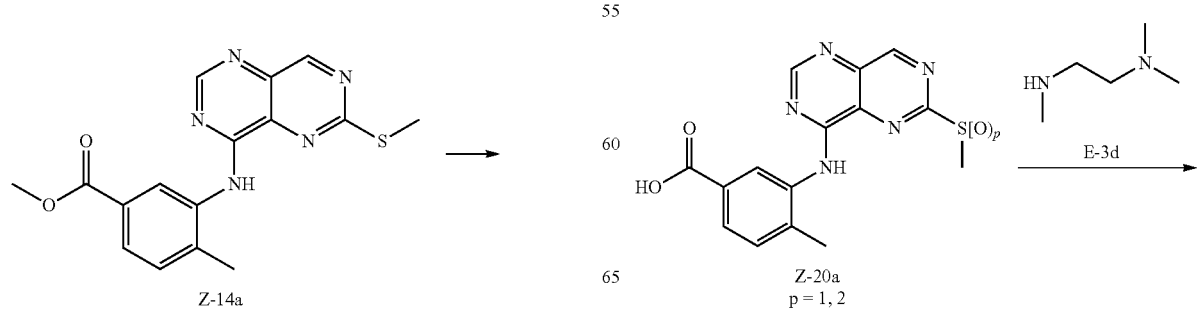

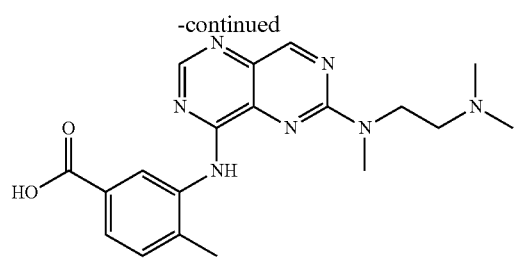

Z-17a

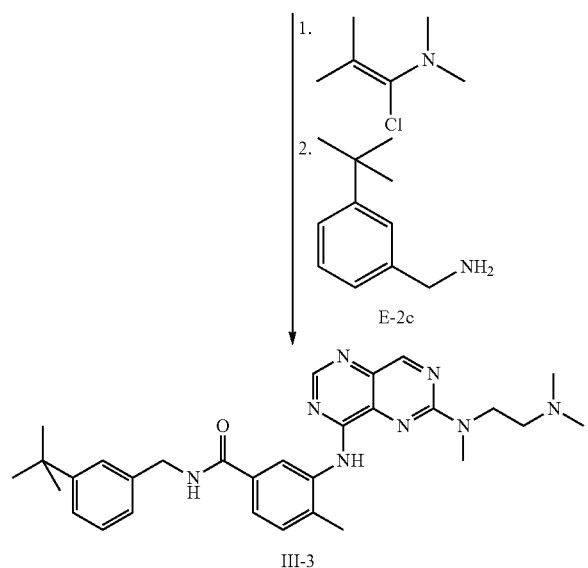

Sulphoxide/sulphone Z-20a (2.0 g, 5.57 mmol), amine E-3d (1.137 g, 11.13 mmol) and DIPEA (1.94 mL, 11.03 mmol) are taken up in DMF (30 mL) and stirred overnight at RT. The solvent is spun off, the residue is mixed with a little water. The precipitate formed is suction filtered, washed with a little cold water, dried and Z-17a (HPLC-MS: $t_{Ret.}$=1.47 min; MS (M+H)$^+$=382) is obtained.

Benzoic acid Z-17a (50 mg, 0.13 mmol) is suspended in DCM (5 mL). 1-Chloro-N,N,2-trimethylpropenylamine (41 mg, 0.30 mmol) is added and the reaction mixture is stirred for 3 h at RT. Then it is concentrated by rotary evaporation and the residue is suspended in dioxane/acetonitrile (3 mL, 1:1). Benzylamine E-2c (100 mg, 0.50 mmol) and DIPEA (65 mg, 0.50 mmol) are added and the reaction mixture is stirred overnight at RT. For working up the mixture is concentrated by rotary evaporation, the residue is taken up in DMF and the reaction mixture is purified by RP-LC/MS. The product-containing fractions of III-3 (HPLC-MS: $t_{Ret.}$=1.91 min; MS (M+H)$^+$=525) are freeze-dried.

Analogously to the methods a) to d) (synthesis route 1) or a), e) to h) (synthesis route 2) as well as a), d), i) and k) (synthesis route 3), besides III-1, III-2 and III-3 the following compounds III-4 to III-608 according to the invention are also prepared (Table 3).

TABLE 3

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-1 | 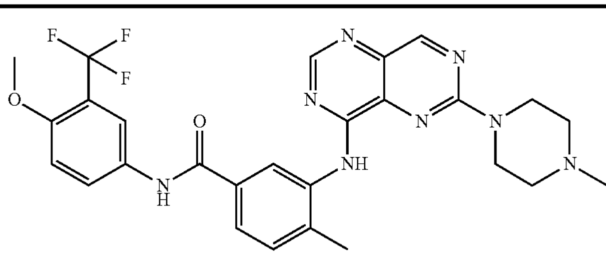 | 2.18 | 553 |

TABLE 3-continued
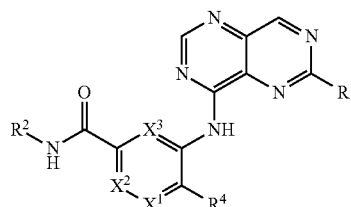
Example Compounds III-1 to III-579 and III-592 to III-608
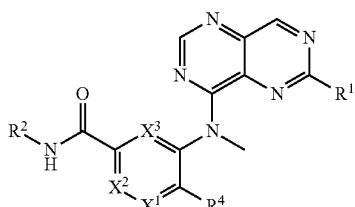
Example Compounds III-580 to III-587
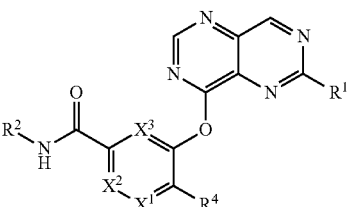
Example Compounds III-588 to III-591
| # | Structure | t$_{Ret.}$ (HPLC) [min] | MS (M + H)$^+$ |
|---|---|---|---|
| III-2 | 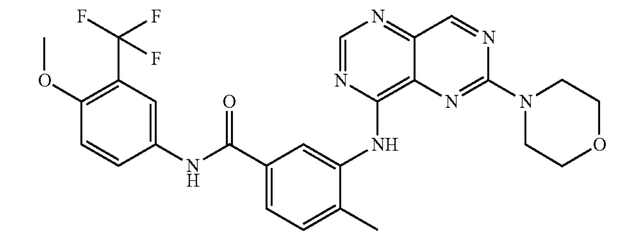 | 2.21 | 540 |
| III-3 | 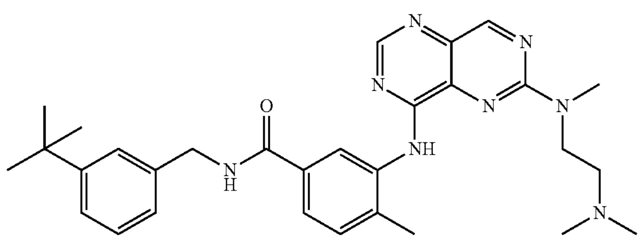 [SMILES: Cc1ccc(C(=O)NCc2cccc(C(C)(C)C)c2)cc1Nc1ncnc2cnc(N(C)CCN(C)C)nc12] | 1.91 | 527 |
| III-4 | 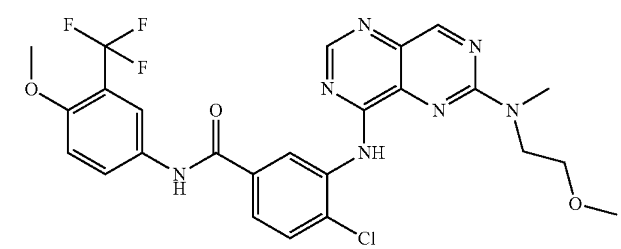 [SMILES: COCCN(C)c1ncc2ncnc(Nc3cc(C(=O)Nc4ccc(OC)c(C(F)(F)F)c4)ccc3Cl)c2n1] | 2.27 | 562 |
| III-5 | 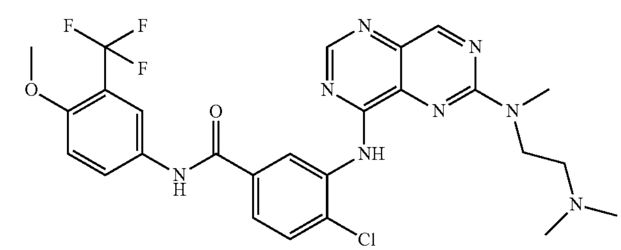 [SMILES: COc1ccc(NC(=O)c2ccc(Cl)c(Nc3ncnc4cnc(N(C)CCN(C)C)nc34)c2)cc1C(F)(F)F] | 1.74 | 575 |
| III-6 | 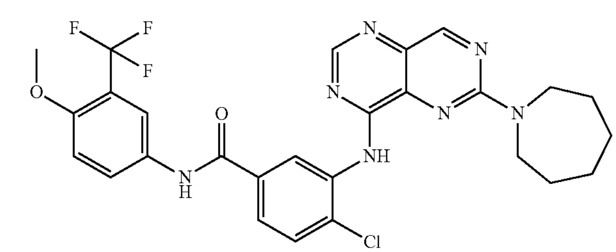 [SMILES: COc1ccc(NC(=O)c2ccc(Cl)c(Nc3ncnc4cnc(N5CCCCCC5)nc34)c2)cc1C(F)(F)F] | 2.56 | 572 |

TABLE 3-continued
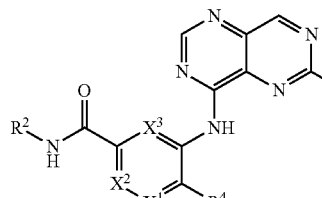
Example Compounds III-1 to III-579 and III-592 to III-608
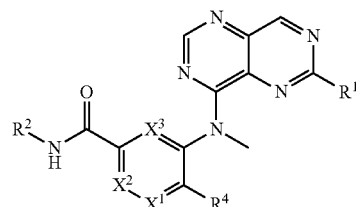
Example Compounds III-580 to III-587
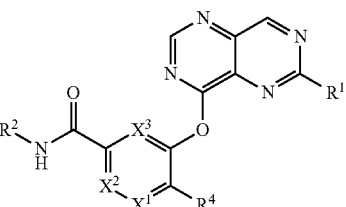
Example Compounds III-588 to III-591
| # | Structure | t_Ret. (HPLC) [min] | MS (M + H)+ |
|---|---|---|---|
| III-7 | 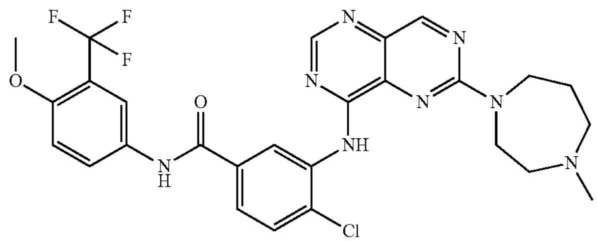 [SMILES: COc1ccc(NC(=O)c2ccc(Cl)c(Nc3ncnc4cnc(N5CCCN(C)CC5)nc34)c2)cc1C(F)(F)F] | 1.73 | 587 |
| III-8 | 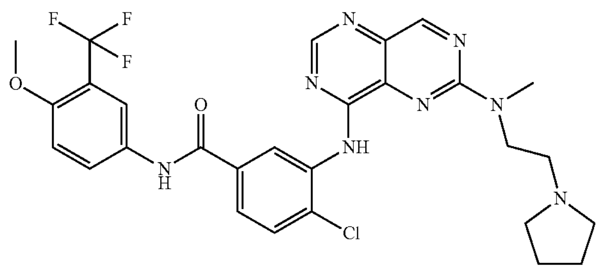 [SMILES: COc1ccc(NC(=O)c2ccc(Cl)c(Nc3ncnc4cnc(N(C)CCN5CCCC5)nc34)c2)cc1C(F)(F)F] | 1.75 | 601 |
| III-9 | 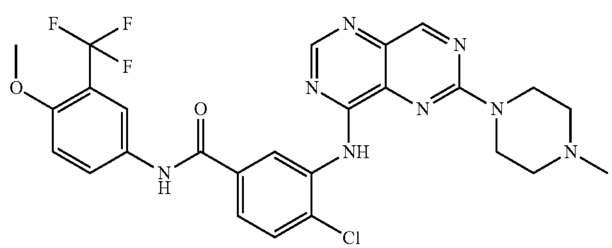 [SMILES: COc1ccc(NC(=O)c2ccc(Cl)c(Nc3ncnc4cnc(N5CCN(C)CC5)nc34)c2)cc1C(F)(F)F] | 1.73 | 573 |
| III-10 | 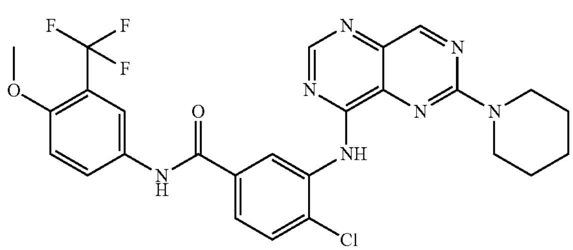 [SMILES: COc1ccc(NC(=O)c2ccc(Cl)c(Nc3ncnc4cnc(N5CCCCC5)nc34)c2)cc1C(F)(F)F] | 2.46 | 558 |
| III-11 | 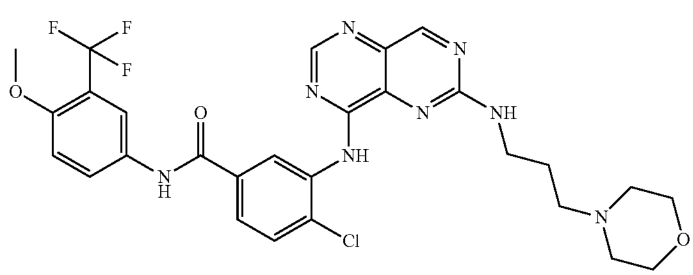 [SMILES: COc1ccc(NC(=O)c2ccc(Cl)c(Nc3ncnc4cnc(NCCCN5CCOCC5)nc34)c2)cc1C(F)(F)F] | 1.72 | 617 |

TABLE 3-continued
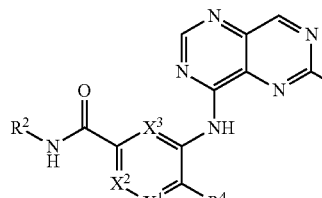
Example Compounds III-1 to III-579 and III-592 to III-608
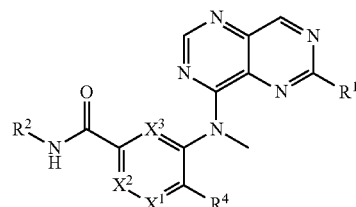
Example Compounds III-580 to III-587
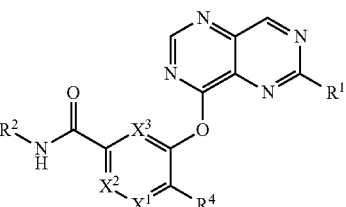
Example Compounds III-588 to III-591
| # | Structure | $t_{Ret.}$ (HPLC) [min] | MS (M + H)+ |
|---|---|---|---|
| III-12 | 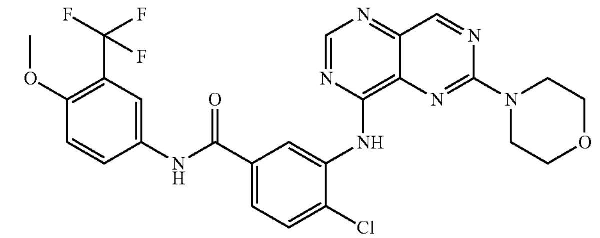 [SMILES: COc1ccc(NC(=O)c2ccc(Cl)c(Nc3ncnc4cnc(N5CCOCC5)nc34)c2)cc1C(F)(F)F] | 2.26 | 560 |
| III-13 | 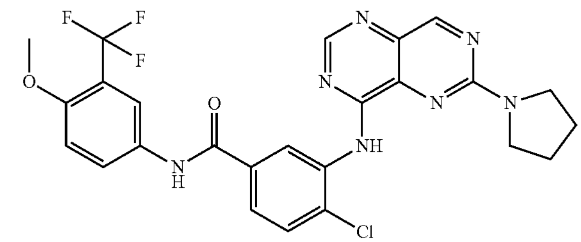 [SMILES: COc1ccc(NC(=O)c2ccc(Cl)c(Nc3ncnc4cnc(N5CCCC5)nc34)c2)cc1C(F)(F)F] | 2.41 | 544 |
| III-14 | 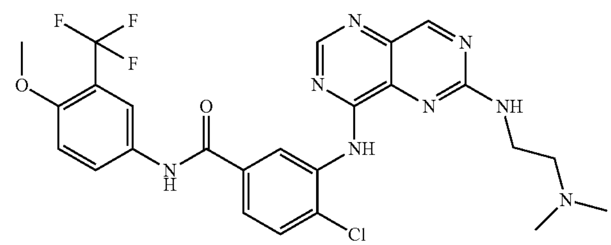 [SMILES: COc1ccc(NC(=O)c2ccc(Cl)c(Nc3ncnc4cnc(NCCN(C)C)nc34)c2)cc1C(F)(F)F] | 1.69 | 561 |
| III-15 | 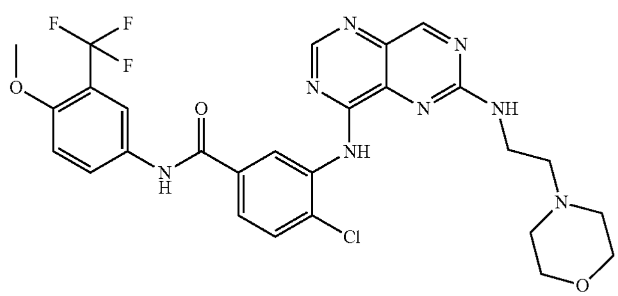 [SMILES: COc1ccc(NC(=O)c2ccc(Cl)c(Nc3ncnc4cnc(NCCN5CCOCC5)nc34)c2)cc1C(F)(F)F] | 1.73 | 603 |
| III-16 | 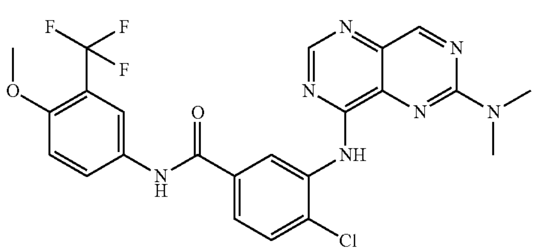 [SMILES: COc1ccc(NC(=O)c2ccc(Cl)c(Nc3ncnc4cnc(N(C)C)nc34)c2)cc1C(F)(F)F] | 2.27 | 518 |

TABLE 3-continued
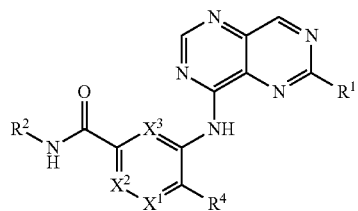
Example Compounds III-1 to III-579 and III-592 to III-608
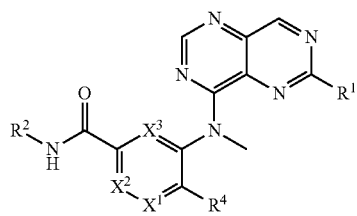
Example Compounds III-580 to III-587
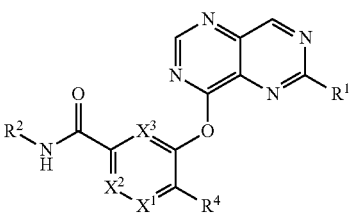
Example Compounds III-588 to III-591
| # | Structure | $t_{Ret.}$ (HPLC) [min] | MS (M + H)$^+$ |
|---|-----------|---|---|
| III-17 | 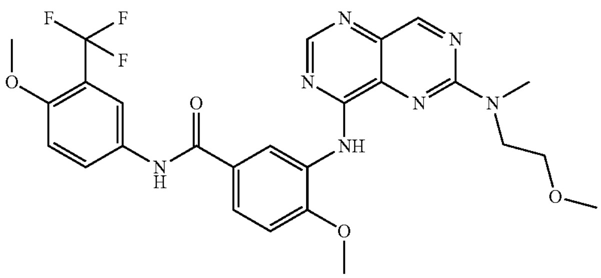 [SMILES: COCCN(C)c1ncc2ncnc(Nc3cc(C(=O)Nc4ccc(OC)c(C(F)(F)F)c4)ccc3OC)c2n1] | 2.08 | 558 |
| III-18 | 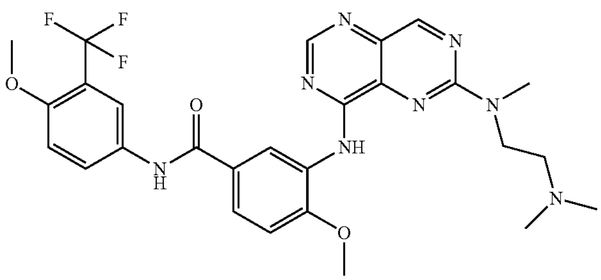 [SMILES: COc1ccc(C(=O)Nc2ccc(OC)c(C(F)(F)F)c2)cc1Nc1ncnc2cnc(N(C)CCN(C)C)nc12] | 1.65 | 571 |
| III-19 | 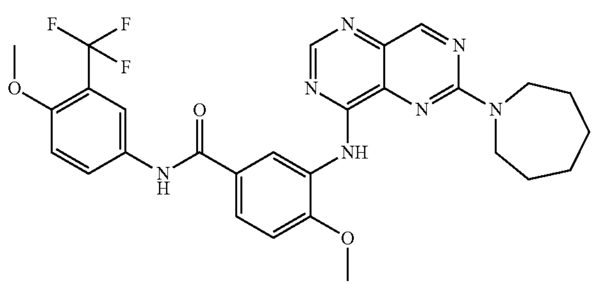 [SMILES: COc1ccc(C(=O)Nc2ccc(OC)c(C(F)(F)F)c2)cc1Nc1ncnc2cnc(N3CCCCCC3)nc12] | 2.33 | 568 |
| III-20 | 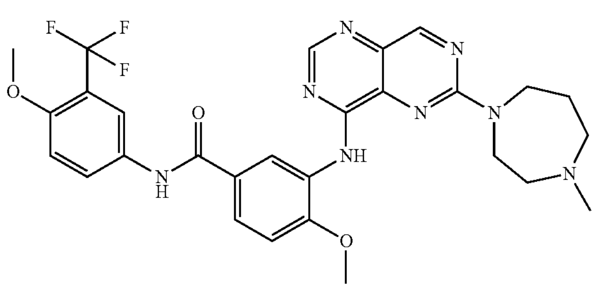 [SMILES: COc1ccc(C(=O)Nc2ccc(OC)c(C(F)(F)F)c2)cc1Nc1ncnc2cnc(N3CCCN(C)CC3)nc12] | 1.64 | 583 |

TABLE 3-continued
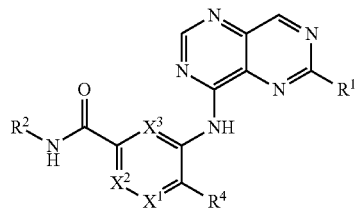
Example Compounds III-1 to III-579 and III-592 to III-608
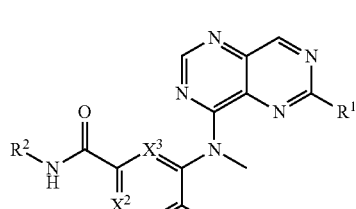
Example Compounds III-580 to III-587
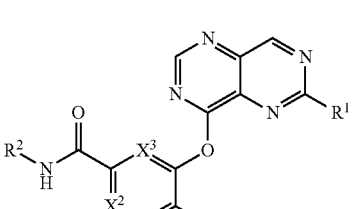
Example Compounds III-588 to III-591
| # | Structure | t$_{Ret.}$ (HPLC) [min] | MS (M + H)$^+$ |
|---|---|---|---|
| III-21 | 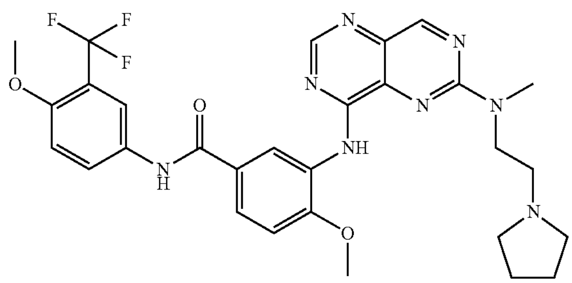 [SMILES: COc1ccc(C(=O)Nc2ccc(OC)c(C(F)(F)F)c2)cc1Nc1ncnc2cnc(N(C)CCN3CCCC3)nc12] | 1.77 | 597 |
| III-22 | 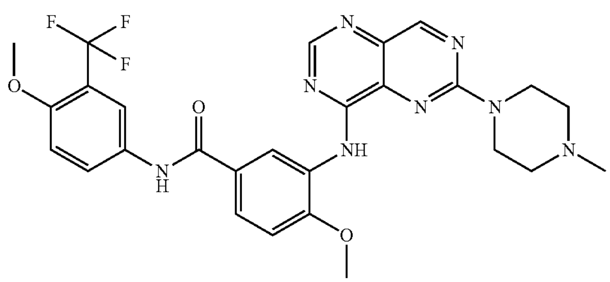 [SMILES: COc1ccc(C(=O)Nc2ccc(OC)c(C(F)(F)F)c2)cc1Nc1ncnc2cnc(N3CCN(C)CC3)nc12] | 1.64 | 569 |
| III-23 | 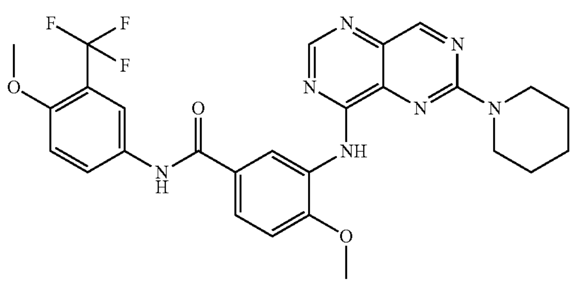 [SMILES: COc1ccc(C(=O)Nc2ccc(OC)c(C(F)(F)F)c2)cc1Nc1ncnc2cnc(N3CCCCC3)nc12] | 2.35 | 554 |
| III-24 | 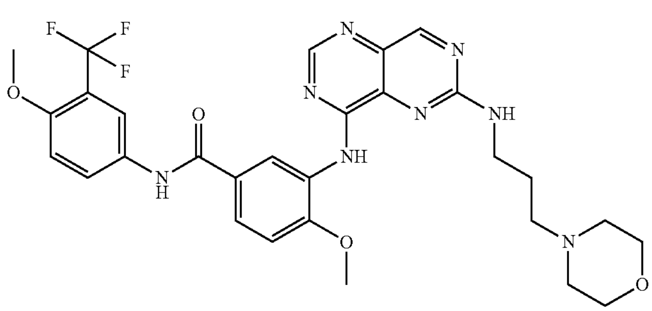 [SMILES: COc1ccc(C(=O)Nc2ccc(OC)c(C(F)(F)F)c2)cc1Nc1ncnc2cnc(NCCCN3CCOCC3)nc12] | 1.63 | 613 |

TABLE 3-continued

Example Compounds III-1 to III-579
and III-592 to III-608

Example Compounds III-580 to III-587
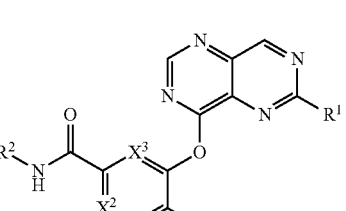
Example Compounds III-588 to III-591
| # | Structure | $t_{Ret.}$ (HPLC) [min] | MS (M + H)$^+$ |
|---|---|---|---|
| III-25 | 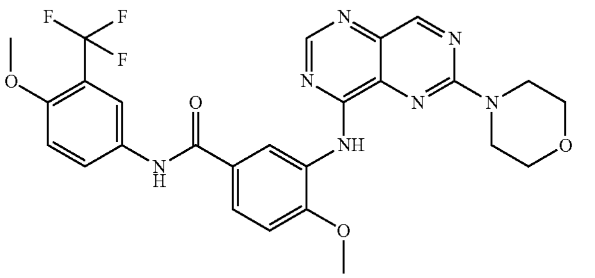 [SMILES: COc1ccc(C(=O)Nc2ccc(OC)c(C(F)(F)F)c2)cc1Nc1ncnc2cnc(N3CCOCC3)nc12] | 2.29 | 556 |
| III-26 | 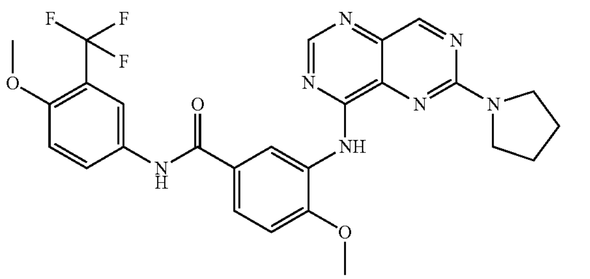 [SMILES: COc1ccc(C(=O)Nc2ccc(OC)c(C(F)(F)F)c2)cc1Nc1ncnc2cnc(N3CCCC3)nc12] | 2.09 | 540 |
| III-27 | 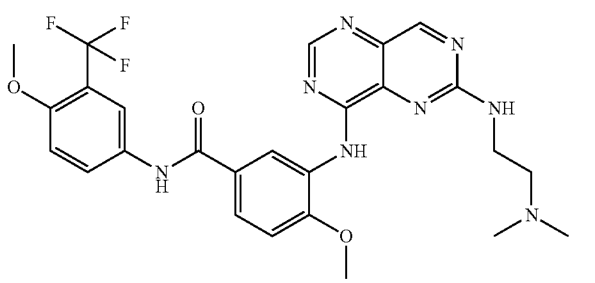 [SMILES: COc1ccc(C(=O)Nc2ccc(OC)c(C(F)(F)F)c2)cc1Nc1ncnc2cnc(NCCN(C)C)nc12] | 2.34 | 557 |
| III-28 | 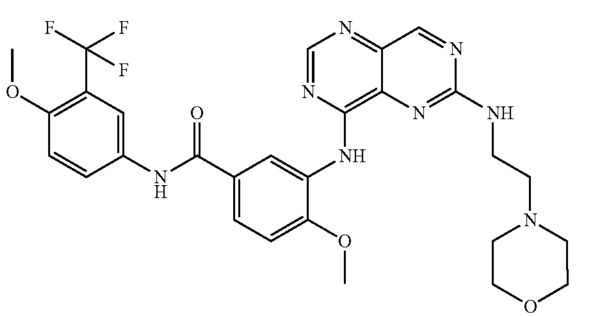 [SMILES: COc1ccc(C(=O)Nc2ccc(OC)c(C(F)(F)F)c2)cc1Nc1ncnc2cnc(NCCN3CCOCC3)nc12] | 1.63 | 599 |

TABLE 3-continued
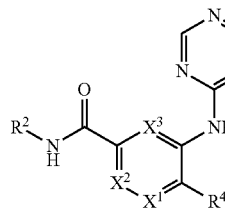
Example Compounds III-1 to III-579
and III-592 to III-608
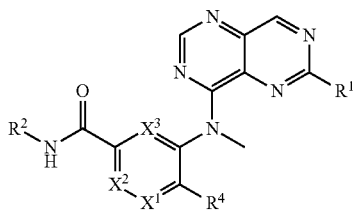
Example Compounds III-580 to III-587
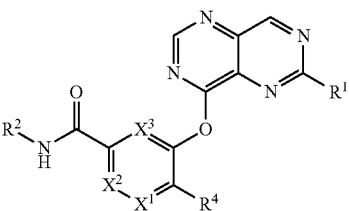
Example Compounds III-588 to III-591
| # | Structure | t$_{Ret.}$ (HPLC) [min] | MS (M + H)$^+$ |
|---|---|---|---|
| III-29 | 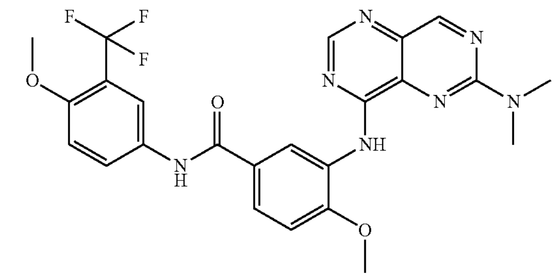 [SMILES: COc1ccc(C(=O)Nc2ccc(OC)c(C(F)(F)F)c2)cc1Nc1ncnc2cnc(N(C)C)nc12] | 2.74 | 514 |
| III-30 | 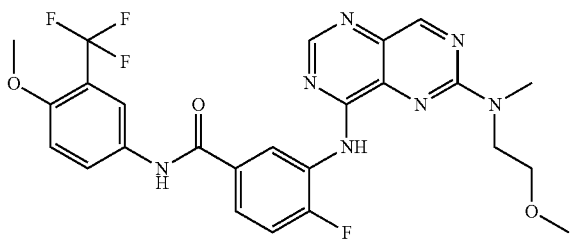 [SMILES: COCCN(C)c1ncc2ncnc(Nc3cc(C(=O)Nc4ccc(OC)c(C(F)(F)F)c4)ccc3F)c2n1] | 2.07 | 546 |
| III-31 | 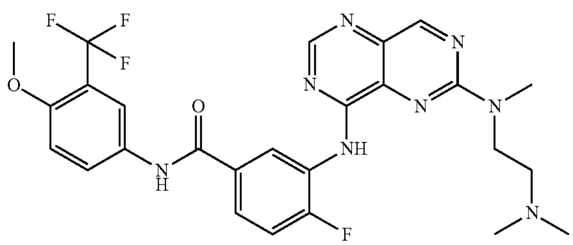 [SMILES: COc1ccc(NC(=O)c2ccc(F)c(Nc3ncnc4cnc(N(C)CCN(C)C)nc34)c2)cc1C(F)(F)F] | 2.32 | 559 |
| III-32 | 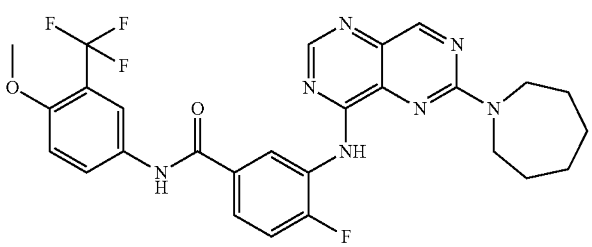 [SMILES: COc1ccc(NC(=O)c2ccc(F)c(Nc3ncnc4cnc(N5CCCCCC5)nc34)c2)cc1C(F)(F)F] | 2.32 | 556 |
| III-33 | 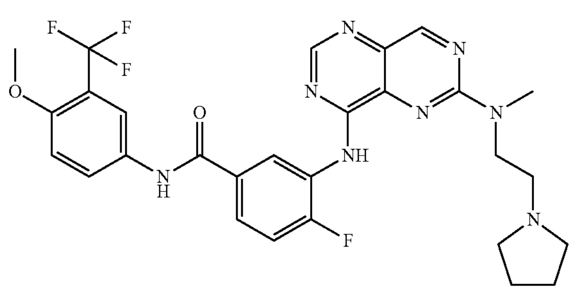 [SMILES: COc1ccc(NC(=O)c2ccc(F)c(Nc3ncnc4cnc(N(C)CCN5CCCC5)nc34)c2)cc1C(F)(F)F] | 2.33 | 585 |

TABLE 3-continued
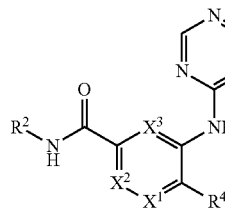
Example Compounds III-1 to III-579 and III-592 to III-608
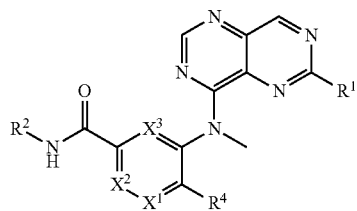
Example Compounds III-580 to III-587
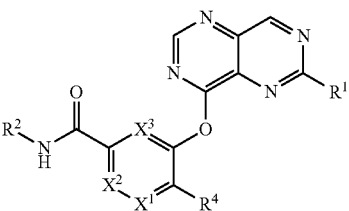
Example Compounds III-588 to III-591
| # | Structure | $t_{Ret.}$ (HPLC) [min] | MS (M + H)$^+$ |
|---|---|---|---|
| III-34 | 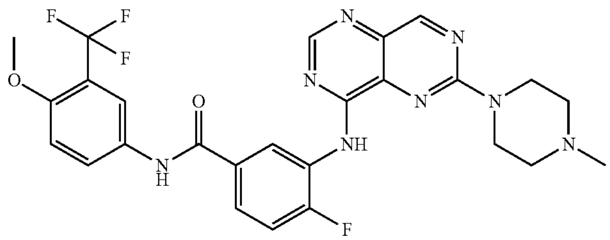 | 1.65 | 557 |
| III-35 | 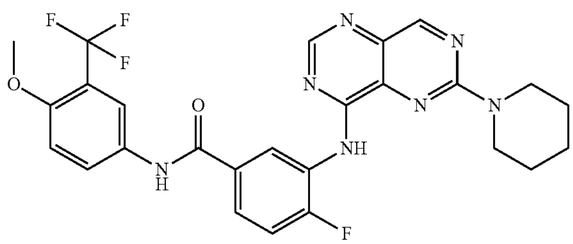 | 2.82 | 542 |
| III-36 | 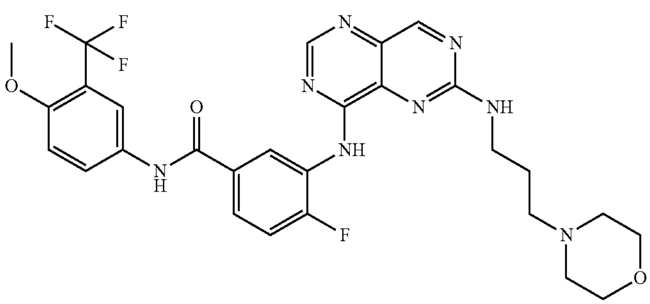 [SMILES: COc1ccc(NC(=O)c2ccc(F)c(Nc3ncnc4cnc(NCCCN5CCOCC5)nc34)c2)cc1C(F)(F)F] | 1.64 | 601 |
| III-37 | 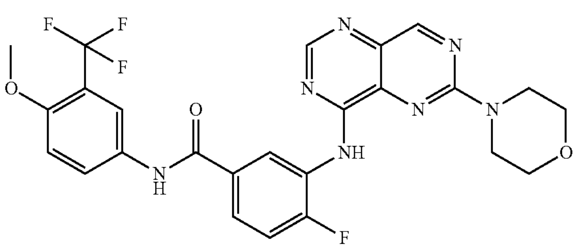 [SMILES: COc1ccc(NC(=O)c2ccc(F)c(Nc3ncnc4cnc(N5CCOCC5)nc34)c2)cc1C(F)(F)F] | 2.69 | 544 |
| III-38 | 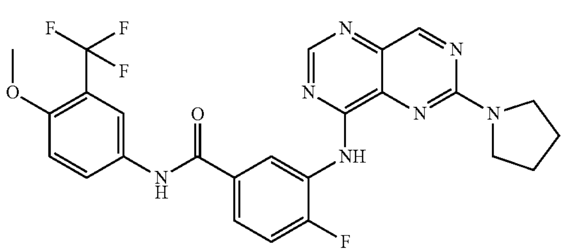 [SMILES: COc1ccc(NC(=O)c2ccc(F)c(Nc3ncnc4cnc(N5CCCC5)nc34)c2)cc1C(F)(F)F] | 2.16 | 528 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-39 | 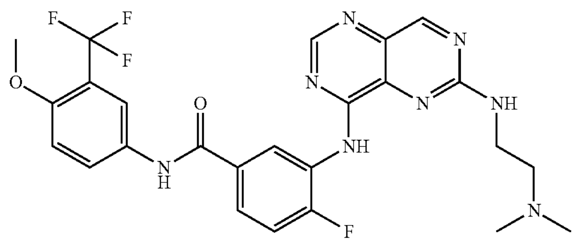 [SMILES: COc1ccc(NC(=O)c2ccc(F)c(Nc3ncnc4cnc(NCCN(C)C)nc34)c2)cc1C(F)(F)F] | 2.27 | 545 |
| III-40 | 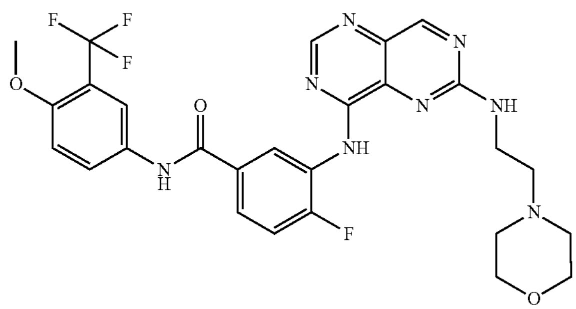 [SMILES: COc1ccc(NC(=O)c2ccc(F)c(Nc3ncnc4cnc(NCCN5CCOCC5)nc34)c2)cc1C(F)(F)F] | 1.64 | 587 |
| III-41 | 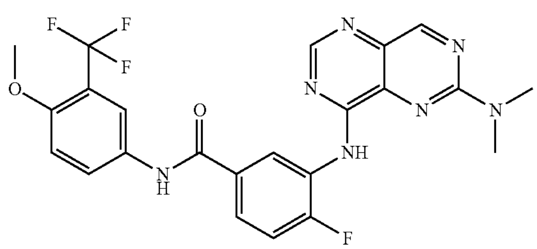 [SMILES: COc1ccc(NC(=O)c2ccc(F)c(Nc3ncnc4cnc(N(C)C)nc34)c2)cc1C(F)(F)F] | 2.80 | 502 |
| III-42 | 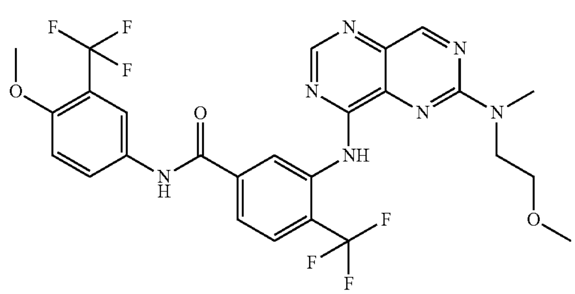 [SMILES: COCCN(C)c1ncc2ncnc(Nc3cc(C(=O)Nc4ccc(OC)c(C(F)(F)F)c4)ccc3C(F)(F)F)c2n1] | 2.29 | 596 |

TABLE 3-continued
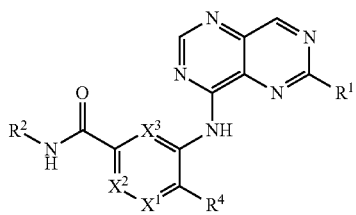
Example Compounds III-1 to III-579 and III-592 to III-608
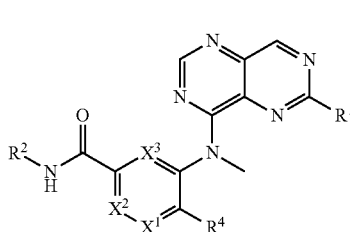
Example Compounds III-580 to III-587
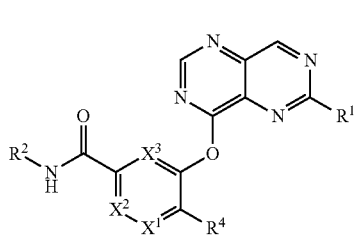
Example Compounds III-588 to III-591
| # | Structure | $t_{Ret.}$ (HPLC) [min] | MS (M + H)$^+$ |
|---|---|---|---|
| III-43 | 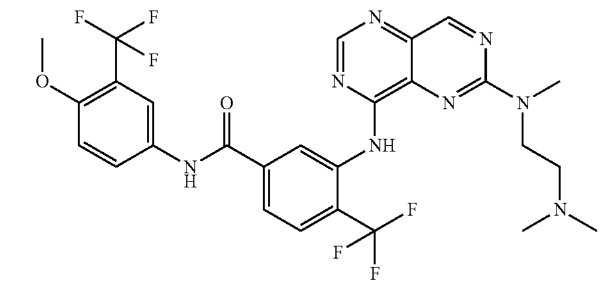 [SMILES: COc1ccc(NC(=O)c2ccc(C(F)(F)F)c(Nc3ncnc4cnc(N(C)CCN(C)C)nc34)c2)cc1C(F)(F)F] | 2.41 | 609 |
| III-44 | 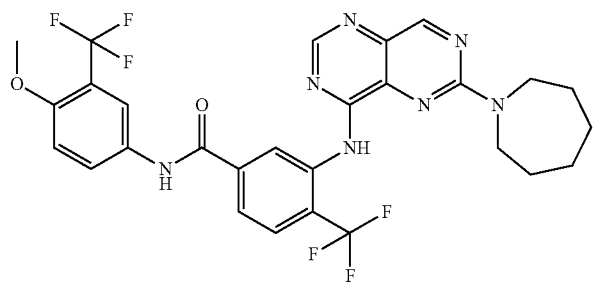 [SMILES: COc1ccc(NC(=O)c2ccc(C(F)(F)F)c(Nc3ncnc4cnc(N5CCCCCC5)nc34)c2)cc1C(F)(F)F] | 2.57 | 606 |
| III-45 | 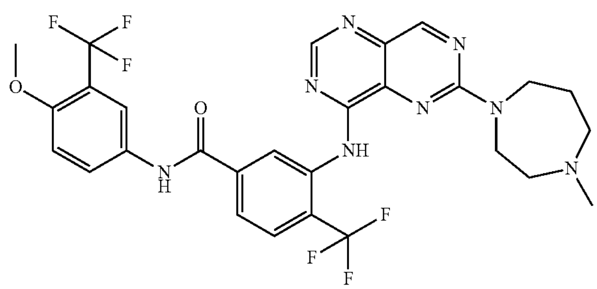 [SMILES: COc1ccc(NC(=O)c2ccc(C(F)(F)F)c(Nc3ncnc4cnc(N5CCCN(C)CC5)nc34)c2)cc1C(F)(F)F] | 2.41 | 621 |
| III-46 | 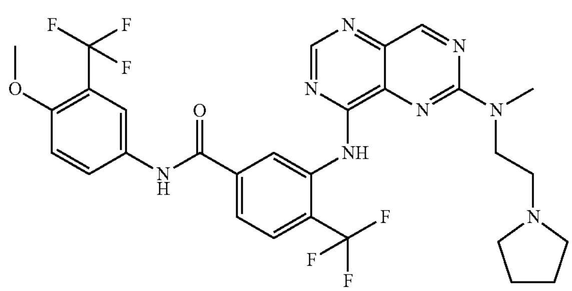 [SMILES: COc1ccc(NC(=O)c2ccc(C(F)(F)F)c(Nc3ncnc4cnc(N(C)CCN5CCCC5)nc34)c2)cc1C(F)(F)F] | 1.78 | 635 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-47 | 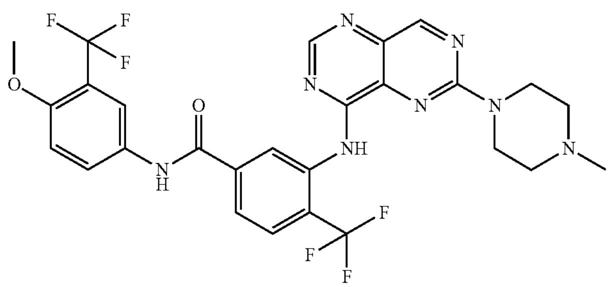 [SMILES: COc1ccc(NC(=O)c2ccc(C(F)(F)F)c(Nc3ncnc4cnc(N5CCN(C)CC5)nc34)c2)cc1C(F)(F)F] | 2.44 | 607 |
| III-48 | 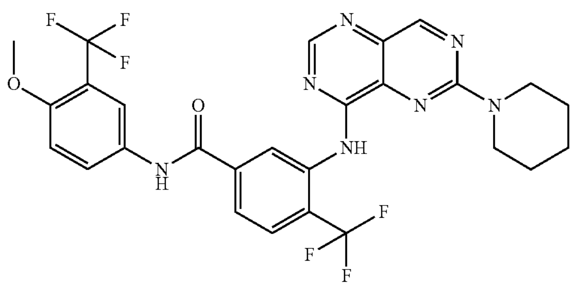 [SMILES: COc1ccc(NC(=O)c2ccc(C(F)(F)F)c(Nc3ncnc4cnc(N5CCCCC5)nc34)c2)cc1C(F)(F)F] | 2.72 | 592 |
| III-49 | 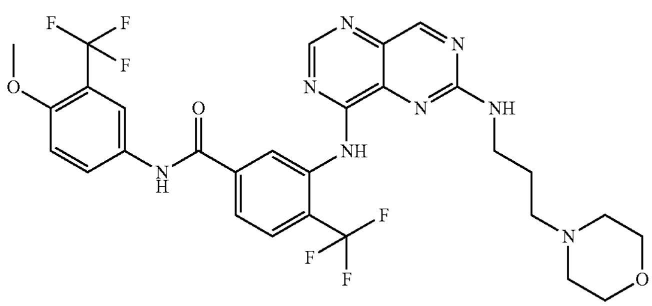 [SMILES: COc1ccc(NC(=O)c2ccc(C(F)(F)F)c(Nc3ncnc4cnc(NCCCN5CCOCC5)nc34)c2)cc1C(F)(F)F] | 2.40 | 651 |
| III-50 | 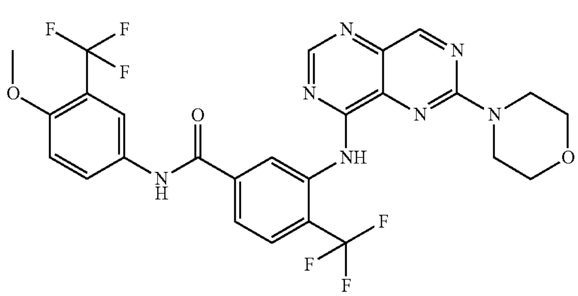 [SMILES: COc1ccc(NC(=O)c2ccc(C(F)(F)F)c(Nc3ncnc4cnc(N5CCOCC5)nc34)c2)cc1C(F)(F)F] | 2.24 | 594 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-51 | 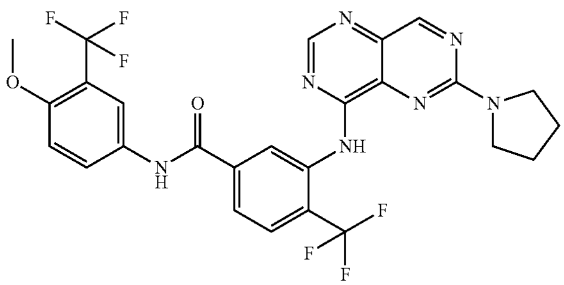 [SMILES: COc1ccc(NC(=O)c2ccc(C(F)(F)F)c(Nc3ncnc4cnc(N5CCCC5)nc34)c2)cc1C(F)(F)F] | 2.38 | 578 |
| III-52 | 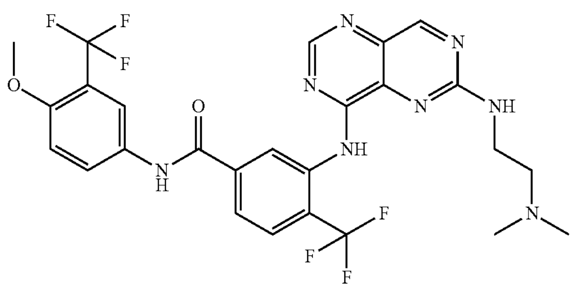 [SMILES: COc1ccc(NC(=O)c2ccc(C(F)(F)F)c(Nc3ncnc4cnc(NCCN(C)C)nc34)c2)cc1C(F)(F)F] | 1.70 | 595 |
| III-53 | 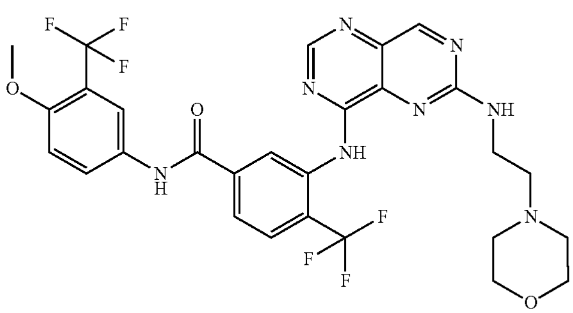 [SMILES: COc1ccc(NC(=O)c2ccc(C(F)(F)F)c(Nc3ncnc4cnc(NCCN5CCOCC5)nc34)c2)cc1C(F)(F)F] | 2.46 | 637 |
| III-54 | 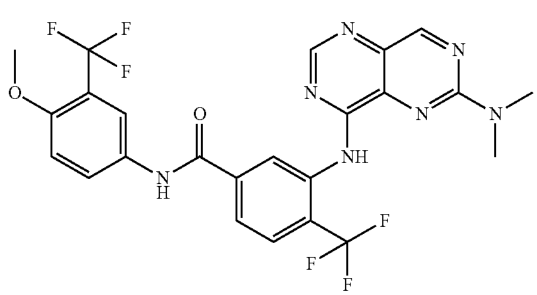 [SMILES: COc1ccc(NC(=O)c2ccc(C(F)(F)F)c(Nc3ncnc4cnc(N(C)C)nc34)c2)cc1C(F)(F)F] | 2.30 | 552 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-55 | 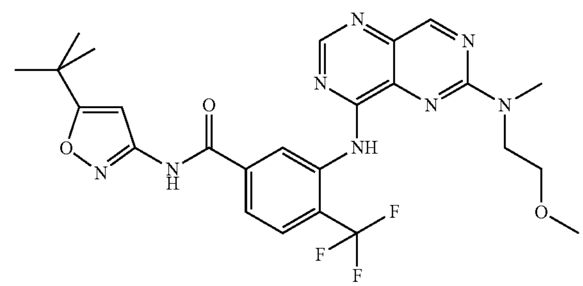 [SMILES: COCCN(C)c1ncc2ncnc(Nc3cc(C(=O)Nc4cc(C(C)(C)C)on4)ccc3C(F)(F)F)c2n1] | 2.29 | 545 |
| III-56 | 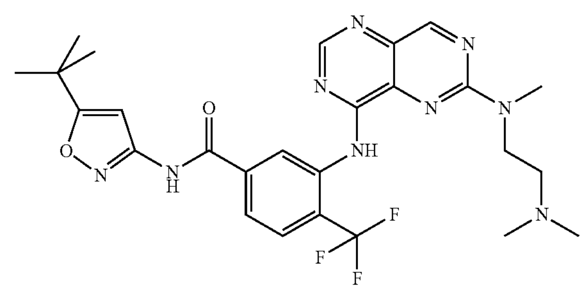 [SMILES: CN(C)CCN(C)c1ncc2ncnc(Nc3cc(C(=O)Nc4cc(C(C)(C)C)on4)ccc3C(F)(F)F)c2n1] | 1.73 | 558 |
| III-57 | 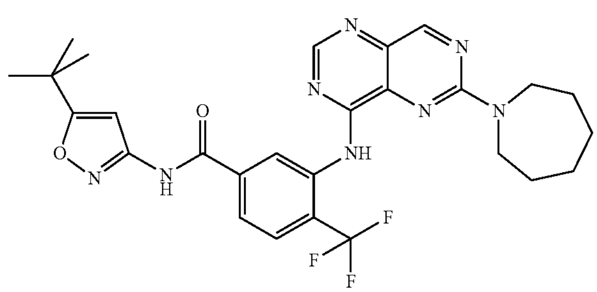 [SMILES: CC(C)(C)c1cc(NC(=O)c2ccc(C(F)(F)F)c(Nc3ncnc4cnc(N5CCCCCC5)nc34)c2)no1] | 2.61 | 555 |
| III-58 | 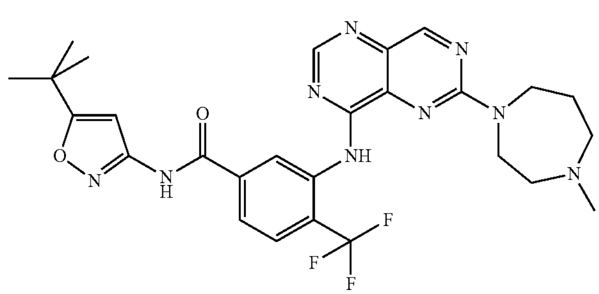 [SMILES: CN1CCCN(c2ncc3ncnc(Nc4cc(C(=O)Nc5cc(C(C)(C)C)on5)ccc4C(F)(F)F)c3n2)CC1] | 1.72 | 570 |

TABLE 3-continued
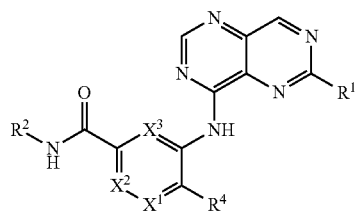
Example Compounds III-1 to III-579 and III-592 to III-608
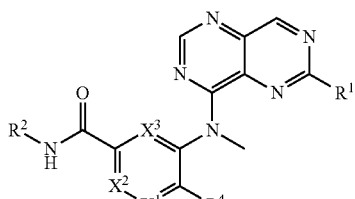
Example Compounds III-580 to III-587
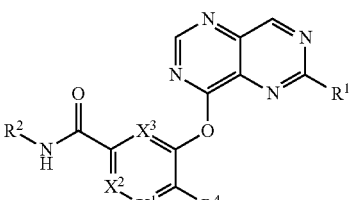
Example Compounds III-588 to III-591
| # | Structure | $t_{Ret.}$ (HPLC) [min] | MS (M + H)$^+$ |
|---|---|---|---|
| III-59 | 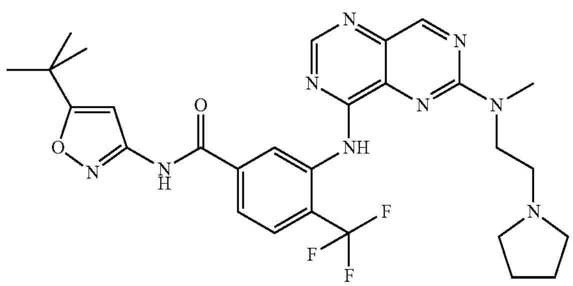 [SMILES: CN(CCN1CCCC1)c1ncc2ncnc(Nc3cc(C(=O)Nc4cc(C(C)(C)C)on4)ccc3C(F)(F)F)c2n1] | 2.56 | 584 |
| III-60 | 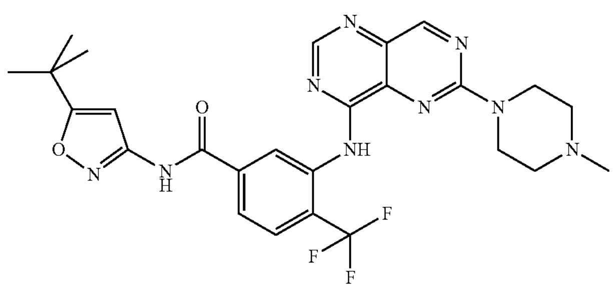 [SMILES: CN1CCN(c2ncc3ncnc(Nc4cc(C(=O)Nc5cc(C(C)(C)C)on5)ccc4C(F)(F)F)c3n2)CC1] | 1.70 | 556 |
| III-61 | 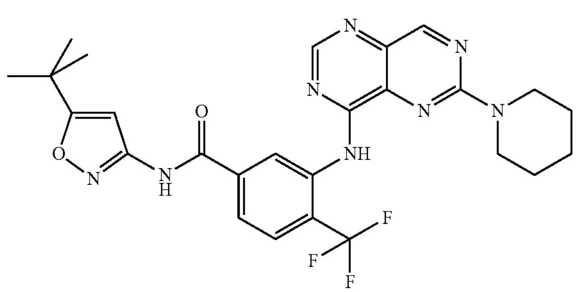 [SMILES: CC(C)(C)c1cc(NC(=O)c2ccc(C(F)(F)F)c(Nc3ncnc4cnc(N5CCCCC5)nc34)c2)no1] | 2.51 | 541 |
| III-62 | 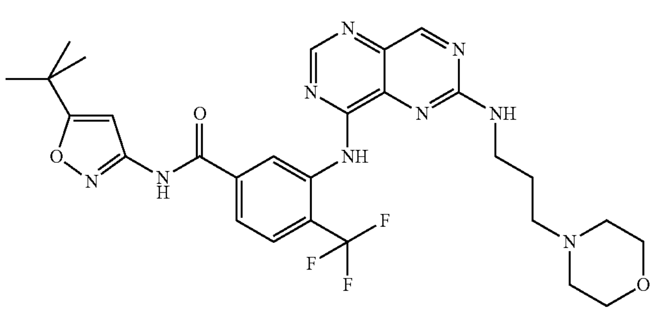 [SMILES: CC(C)(C)c1cc(NC(=O)c2ccc(C(F)(F)F)c(Nc3ncnc4cnc(NCCCN5CCOCC5)nc34)c2)no1] | 1.70 | 600 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-63 | 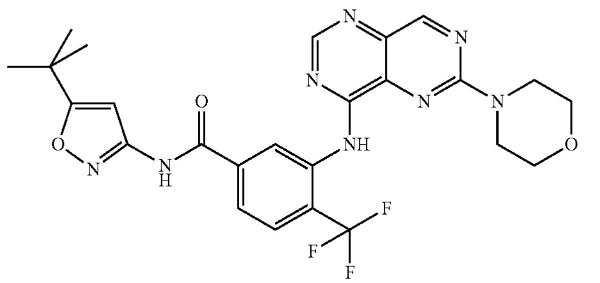 [SMILES: CC(C)(C)c1cc(NC(=O)c2ccc(C(F)(F)F)c(Nc3ncnc4cnc(N5CCOCC5)nc34)c2)no1] | 2.26 | 543 |
| III-64 | 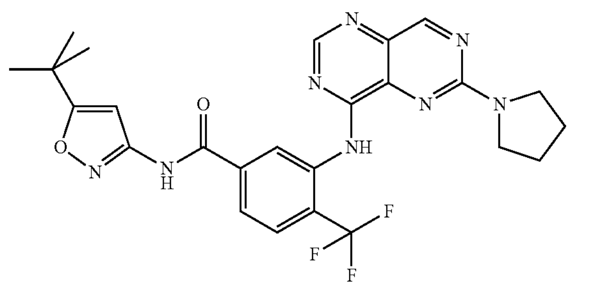 [SMILES: CC(C)(C)c1cc(NC(=O)c2ccc(C(F)(F)F)c(Nc3ncnc4cnc(N5CCCC5)nc34)c2)no1] | 2.43 | 527 |
| III-65 | 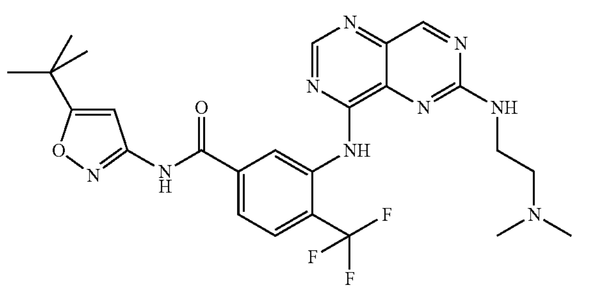 [SMILES: CN(C)CCNc1ncc2ncnc(Nc3cc(C(=O)Nc4cc(C(C)(C)C)on4)ccc3C(F)(F)F)c2n1] | 2.53 | 544 |
| III-66 | 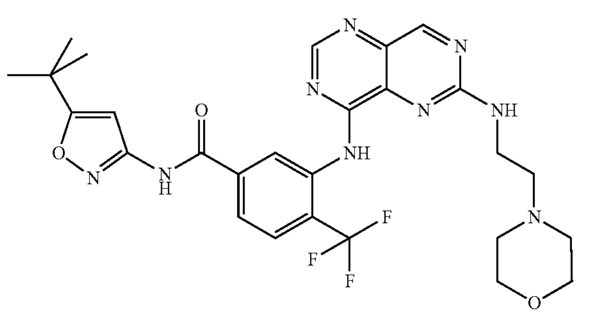 [SMILES: CC(C)(C)c1cc(NC(=O)c2ccc(C(F)(F)F)c(Nc3ncnc4cnc(NCCN5CCOCC5)nc34)c2)no1] | 1.69 | 586 |

TABLE 3-continued
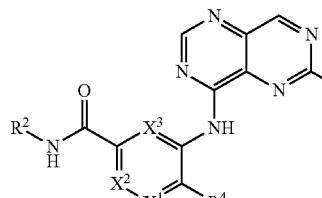
Example Compounds III-1 to III-579 and III-592 to III-608
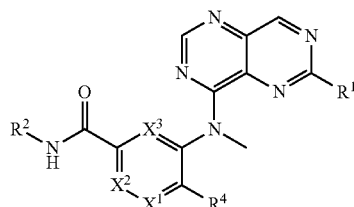
Example Compounds III-580 to III-587
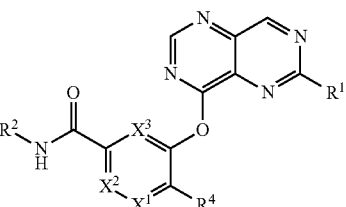
Example Compounds III-588 to III-591
| # | Structure | t_Ret. (HPLC) [min] | MS (M + H)+ |
|---|---|---|---|
| III-67 | 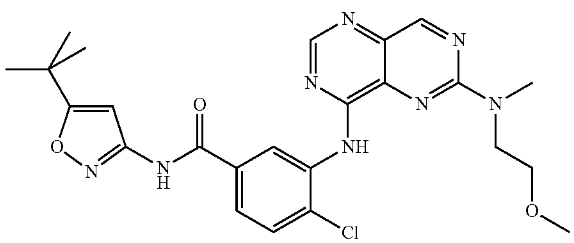 [SMILES: COCCN(C)c1ncc2ncnc(Nc3cc(C(=O)Nc4cc(C(C)(C)C)on4)ccc3Cl)c2n1] | 2.57 | 511 |
| III-68 | 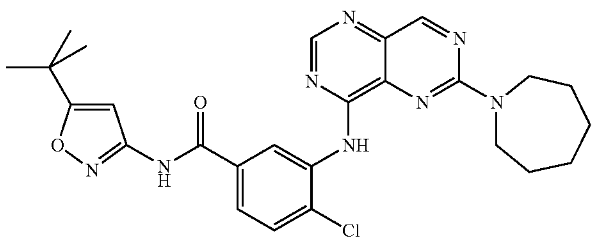 [SMILES: CC(C)(C)c1cc(NC(=O)c2ccc(Cl)c(Nc3ncnc4cnc(N5CCCCCC5)nc34)c2)no1] | 2.92 | 521 |
| III-69 | 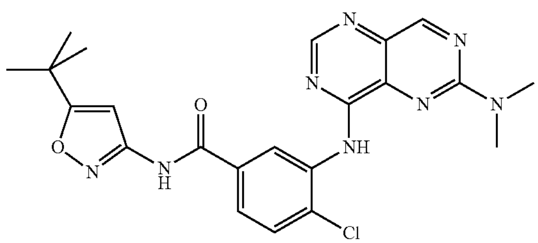 [SMILES: CN(C)c1ncc2ncnc(Nc3cc(C(=O)Nc4cc(C(C)(C)C)on4)ccc3Cl)c2n1] | 2.59 | 467 |
| III-70 | 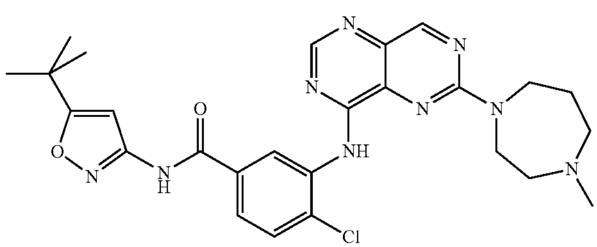 | 1.57 | 536 |
| III-71 | 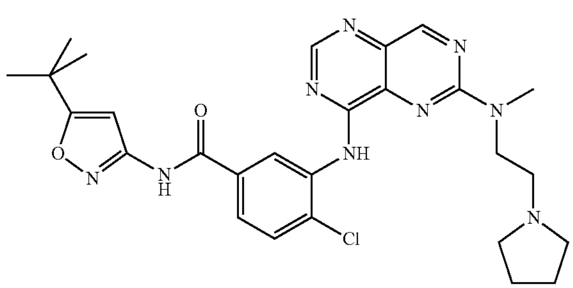 | 1.62 | 550 |

TABLE 3-continued
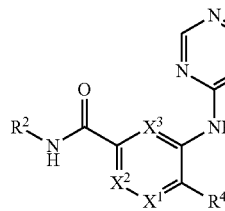
Example Compounds III-1 to III-579 and III-592 to III-608
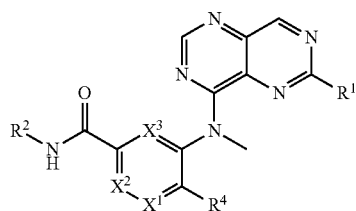
Example Compounds III-580 to III-587
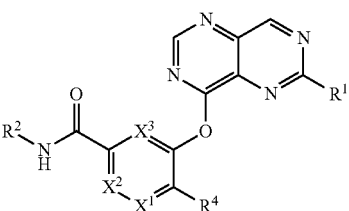
Example Compounds III-588 to III-591
| # | Structure | t$_{Ret.}$ (HPLC) [min] | MS (M + H)$^+$ |
|---|---|---|---|
| III-72 | 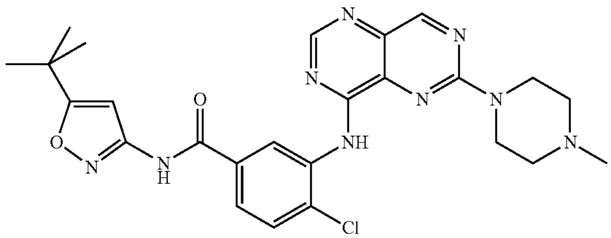 [SMILES: CN1CCN(c2ncc3ncnc(Nc4cc(C(=O)Nc5cc(C(C)(C)C)on5)ccc4Cl)c3n2)CC1] | 1.53 | 522 |
| III-73 | 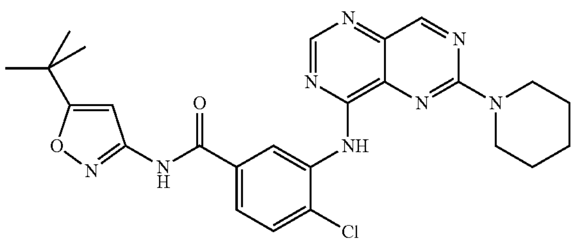 [SMILES: CC(C)(C)c1cc(NC(=O)c2ccc(Cl)c(Nc3ncnc4cnc(N5CCCCC5)nc34)c2)no1] | 2.25 | 507 |
| III-74 | 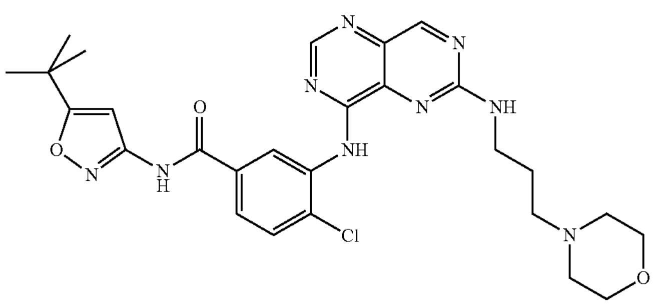 [SMILES: CC(C)(C)c1cc(NC(=O)c2ccc(Cl)c(Nc3ncnc4cnc(NCCCN5CCOCC5)nc34)c2)no1] | 1.54 | 566 |
| III-75 | 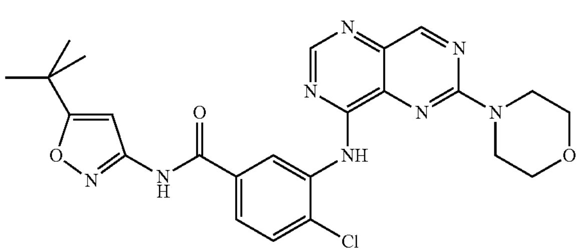 [SMILES: CC(C)(C)c1cc(NC(=O)c2ccc(Cl)c(Nc3ncnc4cnc(N5CCOCC5)nc34)c2)no1] | 1.99 | 509 |
| III-76 | 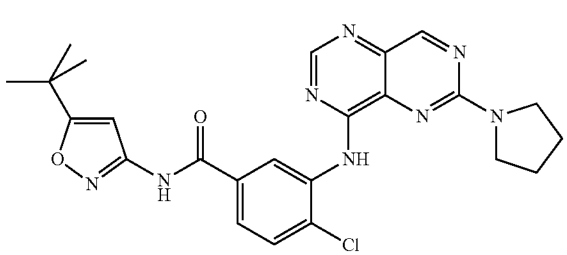 [SMILES: CC(C)(C)c1cc(NC(=O)c2ccc(Cl)c(Nc3ncnc4cnc(N5CCCC5)nc34)c2)no1] | 1.99 | 493 |

TABLE 3-continued
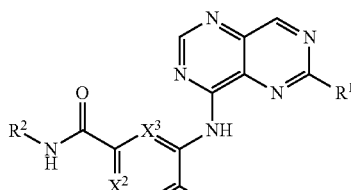
Example Compounds III-1 to III-579 and III-592 to III-608
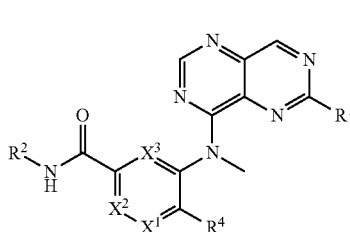
Example Compounds III-580 to III-587
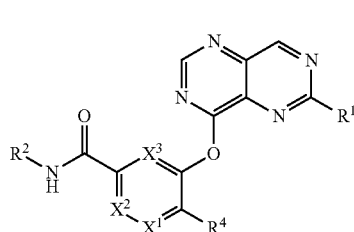
Example Compounds III-588 to III-591
| # | Structure | $t_{Ret.}$ (HPLC) [min] | MS (M + H)$^+$ |
|---|---|---|---|
| III-77 | 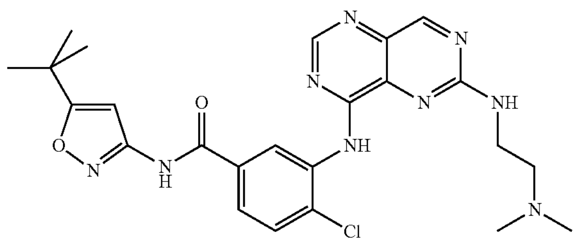 | 1.52 | 510 |
| III-78 | 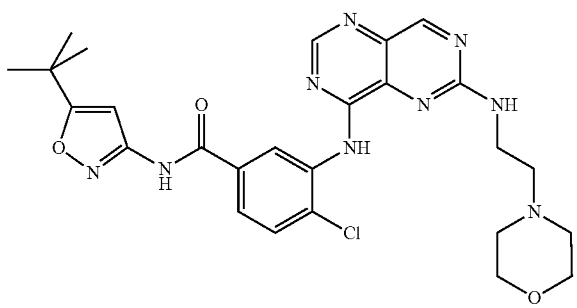 | 1.53 | 552 |
| III-79 | 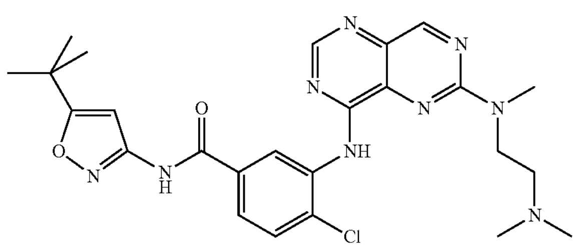 [SMILES: CN(C)CCN(C)c1ncc2ncnc(Nc3cc(C(=O)Nc4cc(C(C)(C)C)on4)ccc3Cl)c2n1] | 1.94 | 524 |
| III-80 | 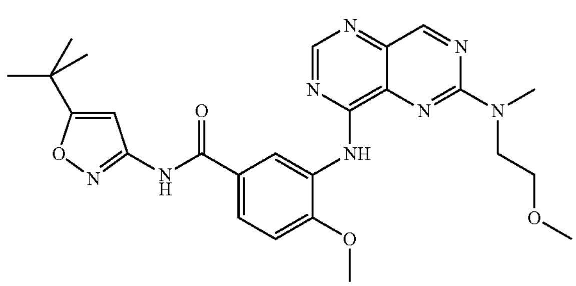 [SMILES: COCCN(C)c1ncc2ncnc(Nc3cc(C(=O)Nc4cc(C(C)(C)C)on4)ccc3OC)c2n1] | 1.81 | 507 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)⁺ |
|---|---|---|---|
| III-81 | | 1.80 | 505 |
| III-82 | | 1.89 | 489 |
| III-83 | | 1.82 | 463 |
| III-84 | | 2.37 | 495 |
| III-85 | | 2.66 | 505 |

TABLE 3-continued
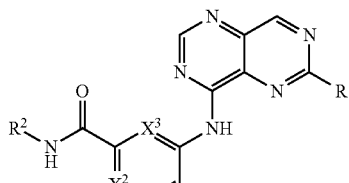
Example Compounds III-1 to III-579 and III-592 to III-608
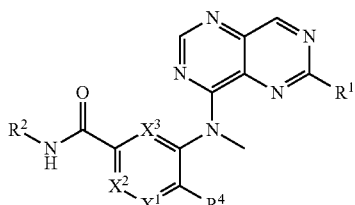
Example Compounds III-580 to III-587
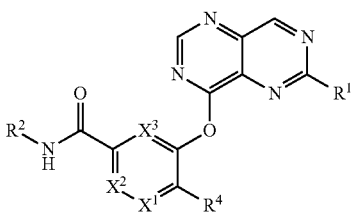
Example Compounds III-588 to III-591
| # | Structure | t_Ret. (HPLC) [min] | MS (M + H)+ |
|---|---|---|---|
| III-86 | 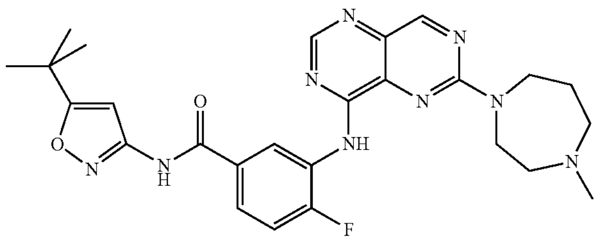 [SMILES: CN1CCCN(c2ncc3ncnc(Nc4cc(C(=O)Nc5cc(C(C)(C)C)on5)ccc4F)c3n2)CC1] | 1.84 | 520 |
| III-87 | 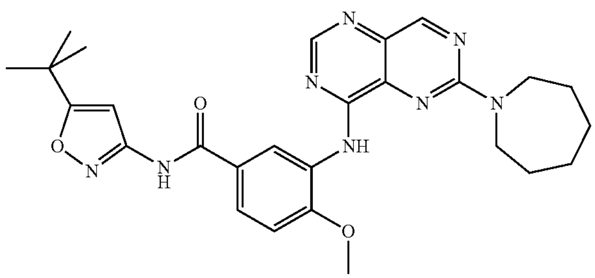 [SMILES: COc1ccc(C(=O)Nc2cc(C(C)(C)C)on2)cc1Nc1ncnc2cnc(N3CCCCCC3)nc12] | 2.08 | 517 |
| III-88 | 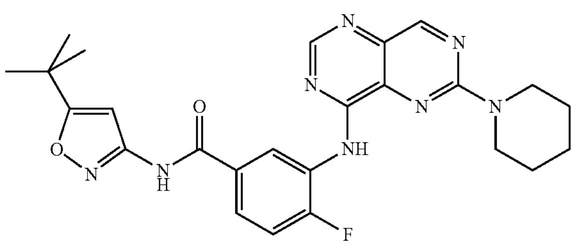 [SMILES: CC(C)(C)c1cc(NC(=O)c2ccc(F)c(Nc3ncnc4cnc(N5CCCCC5)nc34)c2)no1] | 2.50 | 491 |
| III-89 | 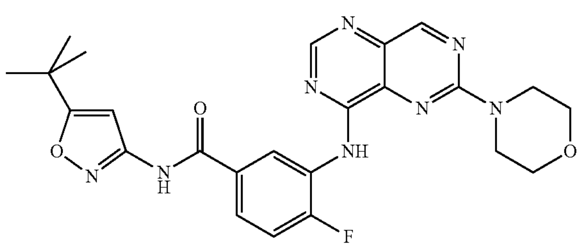 [SMILES: CC(C)(C)c1cc(NC(=O)c2ccc(F)c(Nc3ncnc4cnc(N5CCOCC5)nc34)c2)no1] | 2.32 | 493 |
| III-90 | 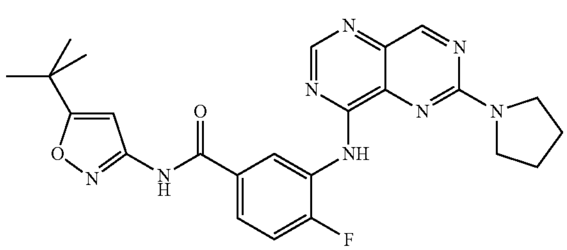 [SMILES: CC(C)(C)c1cc(NC(=O)c2ccc(F)c(Nc3ncnc4cnc(N5CCCC5)nc34)c2)no1] | 2.43 | 477 |

TABLE 3-continued
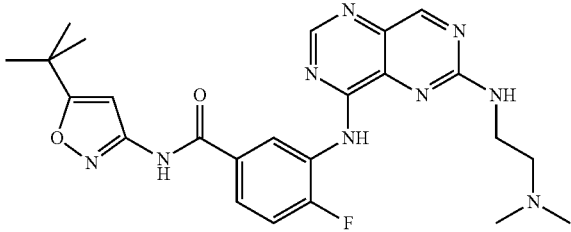 [SMILES: CN(C)CCNc1ncc2ncnc(Nc3cc(C(=O)Nc4cc(C(C)(C)C)on4)ccc3F)c2n1]
Example Compounds III-1 to III-579 and III-592 to III-608
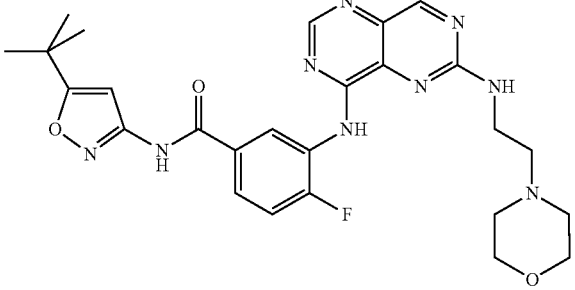
Example Compounds III-580 to III-587
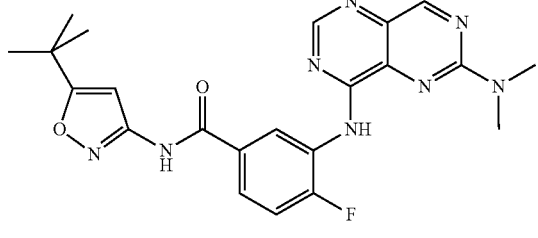
Example Compounds III-588 to III-591
| # | Structure | t<sub>Ret.</sub> (HPLC) [min] | MS (M + H)<sup>+</sup> |
|---|---|---|---|
| III-91 | 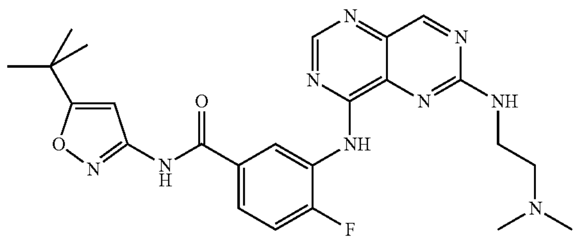 | 1.78 | 494 |
| III-92 | 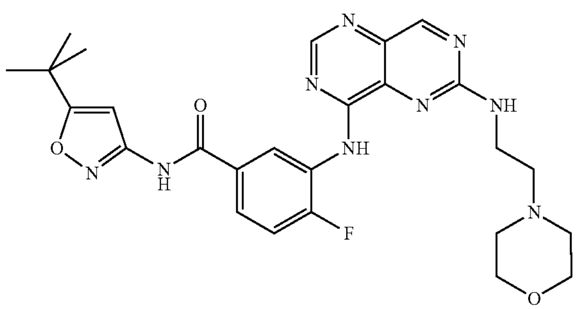 [SMILES: CC(C)(C)c1cc(NC(=O)c2ccc(F)c(Nc3ncnc4cnc(NCCN5CCOCC5)nc34)c2)no1] | 1.79 | 536 |
| III-93 | 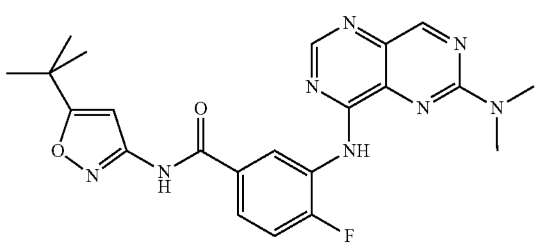 [SMILES: CN(C)c1ncc2ncnc(Nc3cc(C(=O)Nc4cc(C(C)(C)C)on4)ccc3F)c2n1] | 2.36 | 451 |
| III-94 | 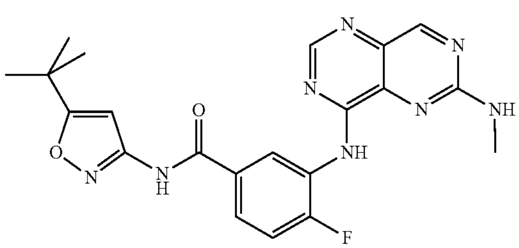 [SMILES: CNc1ncc2ncnc(Nc3cc(C(=O)Nc4cc(C(C)(C)C)on4)ccc3F)c2n1] | 2.15 | 437 |
| III-95 | 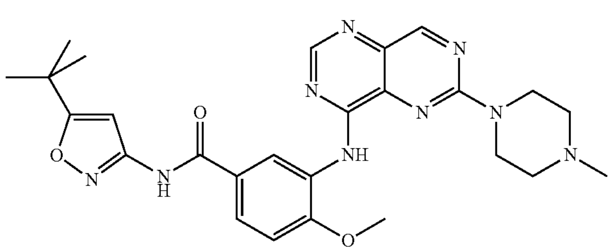 [SMILES: COc1ccc(C(=O)Nc2cc(C(C)(C)C)on2)cc1Nc1ncnc2cnc(N3CCN(C)CC3)nc12] | 2.38 | 518 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)⁺ |
|---|---|---|---|
| III-96 | | 2.46 | 532 |
| III-97 | | 1.54 | 546 |
| III-98 | | 1.53 | 298 (M + 2H)²⁺ |
| III-99 | | 1.63 | 305 (M + 2H)²⁺ |
| III-100 | | 1.55 | 282 (M + 2H)²⁺ |

TABLE 3-continued
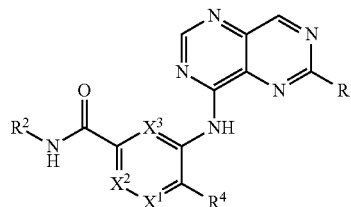 Example Compounds III-1 to III-579 and III-592 to III-608
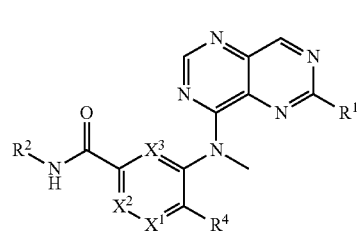 Example Compounds III-580 to III-587
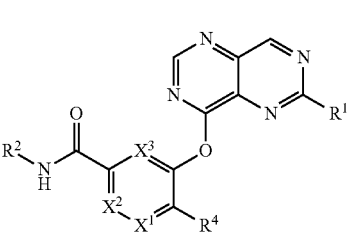 Example Compounds III-588 to III-591
| # | Structure | $t_{Ret.}$ (HPLC) [min] | MS (M + H)+ |
|---|---|---|---|
| III-101 | 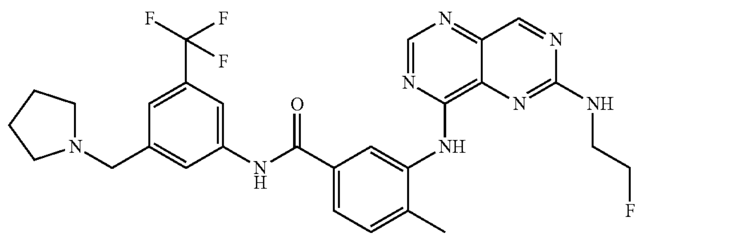 [SMILES: Cc1ccc(C(=O)Nc2cc(CN3CCCC3)cc(C(F)(F)F)c2)cc1Nc1ncnc2cnc(NCCF)nc12] | 1.48 | 285 (M + 2H)$^{2+}$ |
| III-102 | 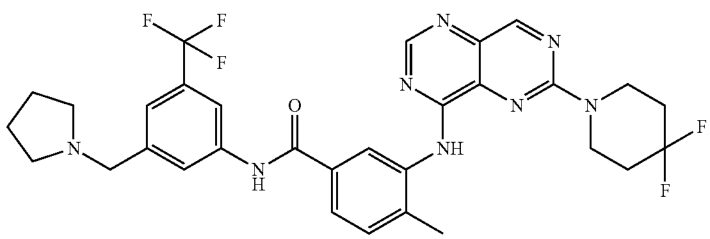 [SMILES: Cc1ccc(C(=O)Nc2cc(CN3CCCC3)cc(C(F)(F)F)c2)cc1Nc1ncnc2cnc(N3CCC(F)(F)CC3)nc12] | 1.67 | 314 (M + 2H)$^{2+}$ |
| III-103 | 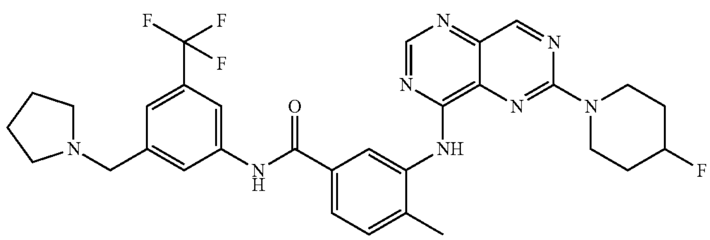 [SMILES: Cc1ccc(C(=O)Nc2cc(CN3CCCC3)cc(C(F)(F)F)c2)cc1Nc1ncnc2cnc(N3CCC(F)CC3)nc12] | 1.62 | 305 (M + 2H)$^{2+}$ |
| III-104 | 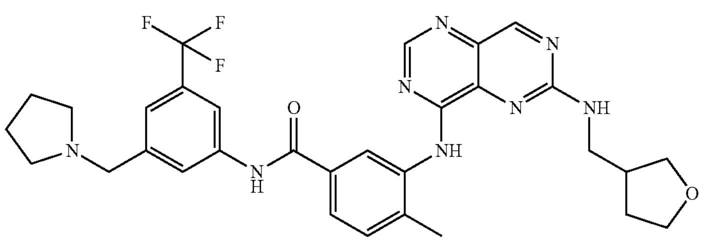 [SMILES: Cc1ccc(C(=O)Nc2cc(CN3CCCC3)cc(C(F)(F)F)c2)cc1Nc1ncnc2cnc(NCC3CCOC3)nc12] | 1.47 | 304 (M + 2H)$^{2+}$ |
| III-105 | 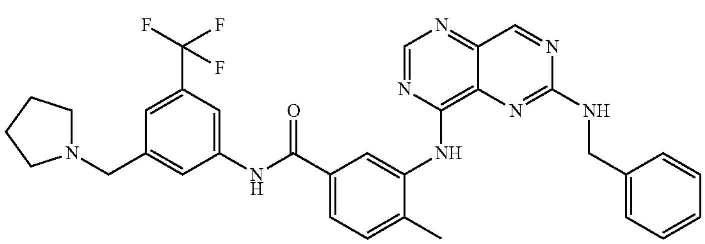 [SMILES: Cc1ccc(C(=O)Nc2cc(CN3CCCC3)cc(C(F)(F)F)c2)cc1Nc1ncnc2cnc(NCc3ccccc3)nc12] | 1.65 | 307 (M + 2H)$^{2+}$ |

TABLE 3-continued
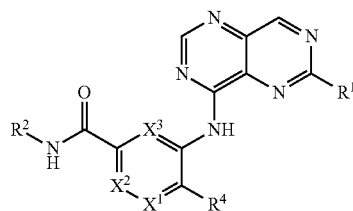
Example Compounds III-1 to III-579 and III-592 to III-608
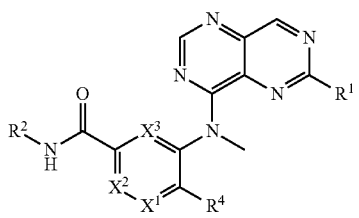
Example Compounds III-580 to III-587
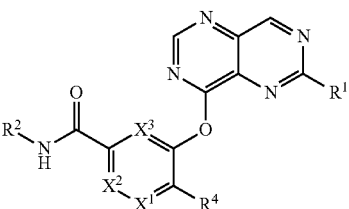
Example Compounds III-588 to III-591
| # | Structure | $t_{Ret.}$ (HPLC) [min] | MS $(M+H)^+$ |
|---|---|---|---|
| III-106 | 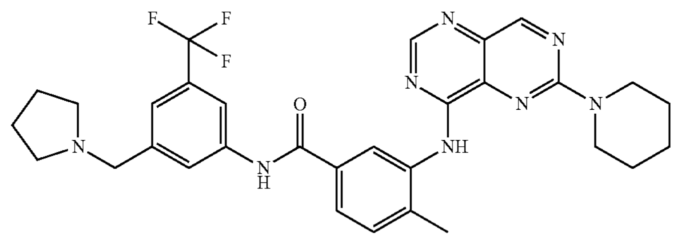 [SMILES: Cc1ccc(C(=O)Nc2cc(CN3CCCC3)cc(C(F)(F)F)c2)cc1Nc1ncnc2cnc(N3CCCCC3)nc12] | 1.68 | 296 $(M+2H)^{2+}$ |
| III-107 | 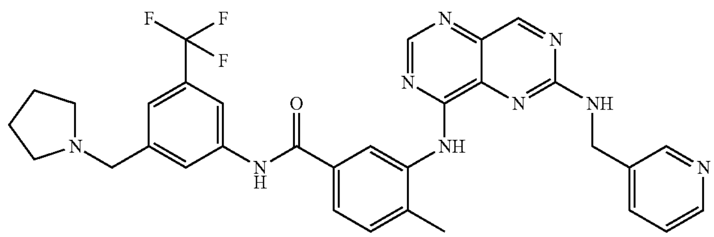 [SMILES: Cc1ccc(C(=O)Nc2cc(CN3CCCC3)cc(C(F)(F)F)c2)cc1Nc1ncnc2cnc(NCc3cccnc3)nc12] | 1.31 | 307 $(M+2H)^{2+}$ |
| III-108 | 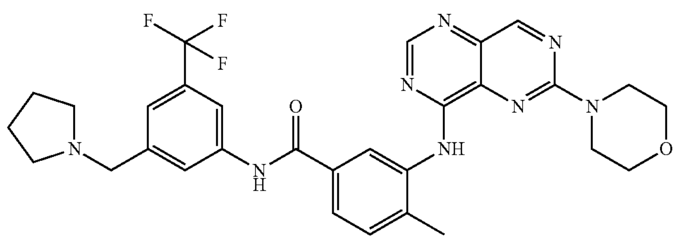 [SMILES: Cc1ccc(C(=O)Nc2cc(CN3CCCC3)cc(C(F)(F)F)c2)cc1Nc1ncnc2cnc(N3CCOCC3)nc12] | 1.52 | 297 $(M+2H)^{2+}$ |
| III-109 | 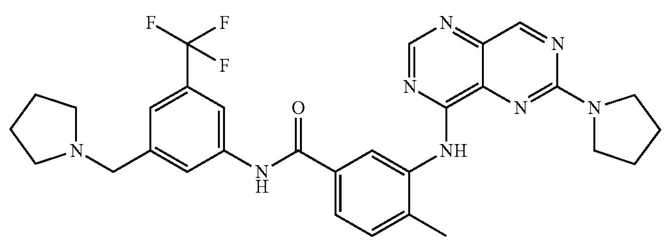 [SMILES: Cc1ccc(C(=O)Nc2cc(CN3CCCC3)cc(C(F)(F)F)c2)cc1Nc1ncnc2cnc(N3CCCC3)nc12] | 1.59 | 289 $(M+2H)^{2+}$ |
| III-110 | 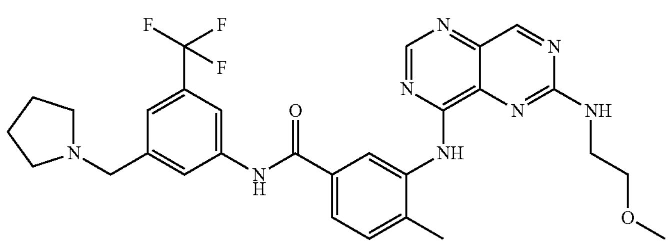 [SMILES: COCCNc1ncc2ncnc(Nc3cc(C(=O)Nc4cc(CN5CCCC5)cc(C(F)(F)F)c4)ccc3C)c2n1] | 1.46 | 291 $(M+2H)^{2+}$ |

TABLE 3-continued
| | | |
|---|---|---|
| 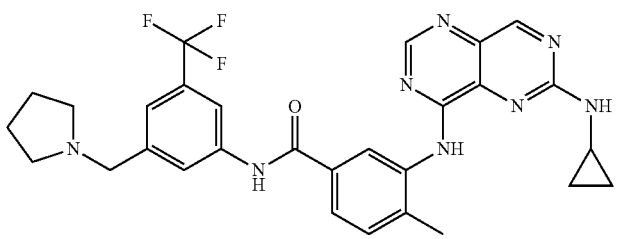 | 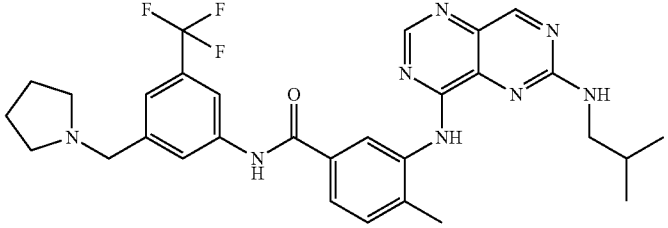 | 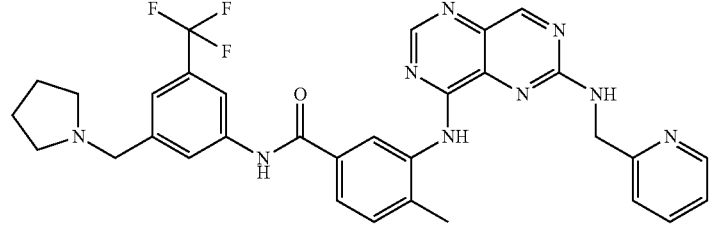 |
| Example Compounds III-1 to III-579 and III-592 to III-608 | Example Compounds III-580 to III-587 | Example Compounds III-588 to III-591 |
| # | Structure | $t_{Ret.}$ (HPLC) [min] | MS (M + H)$^+$ |
|---|---|---|---|
| III-111 | 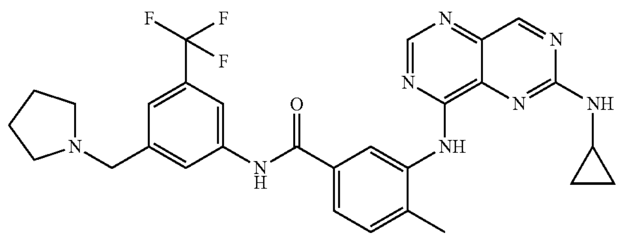 [SMILES: Cc1ccc(C(=O)Nc2cc(CN3CCCC3)cc(C(F)(F)F)c2)cc1Nc1ncnc2cnc(NC3CC3)nc12] | 1.54 | 282 (M + 2H)$^{2+}$ |
| III-112 | 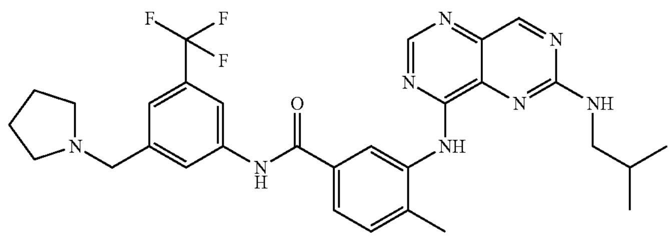 [SMILES: Cc1ccc(C(=O)Nc2cc(CN3CCCC3)cc(C(F)(F)F)c2)cc1Nc1ncnc2cnc(NCC(C)C)nc12] | 1.64 | 290 (M + 2H)$^{2+}$ |
| III-113 | 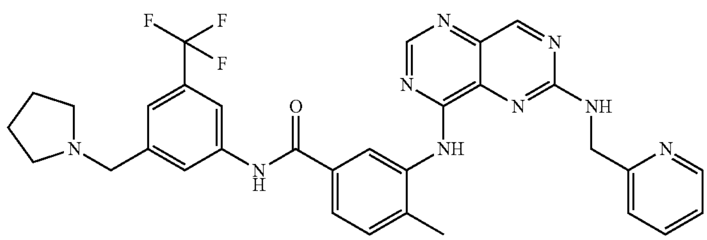 [SMILES: Cc1ccc(C(=O)Nc2cc(CN3CCCC3)cc(C(F)(F)F)c2)cc1Nc1ncnc2cnc(NCc3ccccn3)nc12] | 1.32 | 307 (M + 2H)$^{2+}$ |
| III-114 | 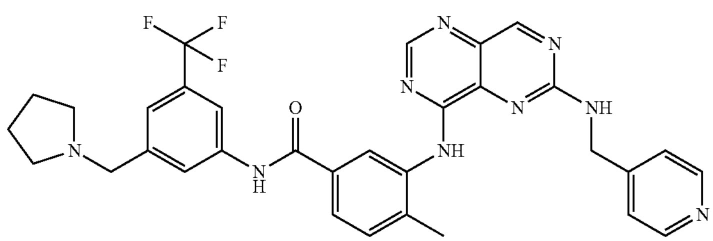 [SMILES: Cc1ccc(C(=O)Nc2cc(CN3CCCC3)cc(C(F)(F)F)c2)cc1Nc1ncnc2cnc(NCc3ccncc3)nc12] | 1.31 | |
| III-115 | 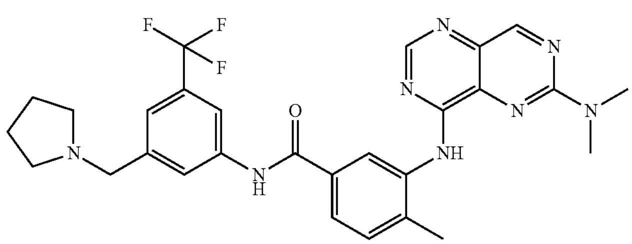 [SMILES: Cc1ccc(C(=O)Nc2cc(CN3CCCC3)cc(C(F)(F)F)c2)cc1Nc1ncnc2cnc(N(C)C)nc12] | 1.54 | 276 (M + 2H)$^{2+}$ |
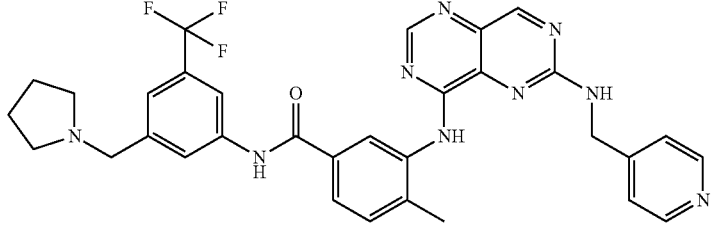
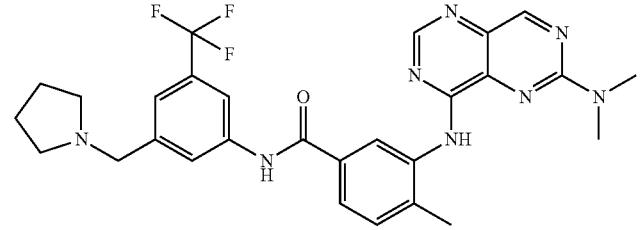

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-116 | 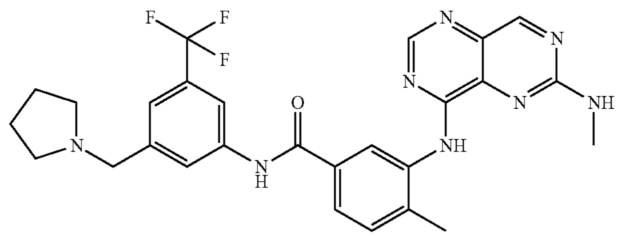 [SMILES: CNc1ncc2ncnc(Nc3cc(C(=O)Nc4cc(CN5CCCC5)cc(C(F)(F)F)c4)ccc3C)c2n1] | 1.44 | 269 (M + 2H)$^{2+}$ |
| III-117 | 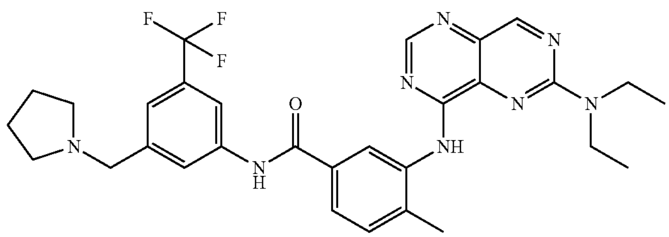 [SMILES: CCN(CC)c1ncc2ncnc(Nc3cc(C(=O)Nc4cc(CN5CCCC5)cc(C(F)(F)F)c4)ccc3C)c2n1] | 1.67 | 290 (M + 2H)$^{2+}$ |
| III-118 | 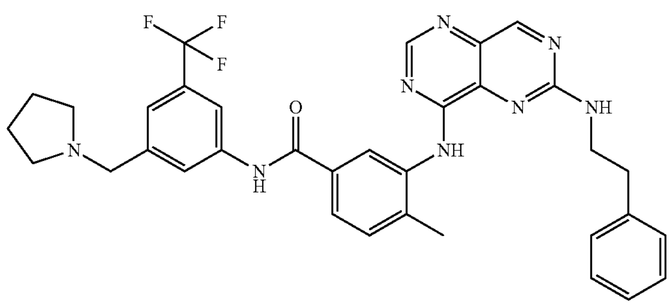 [SMILES: Cc1ccc(C(=O)Nc2cc(CN3CCCC3)cc(C(F)(F)F)c2)cc1Nc1ncnc2cnc(NCCc3ccccc3)nc12] | 1.70 | 314 (M + 2H)$^{2+}$ |
| III-119 | 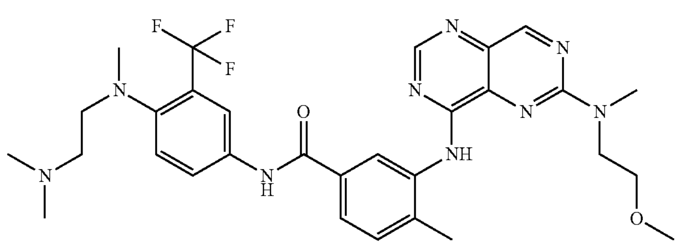 | 1.51 | 306 (M + 2H)$^{2+}$ |
| III-120 | 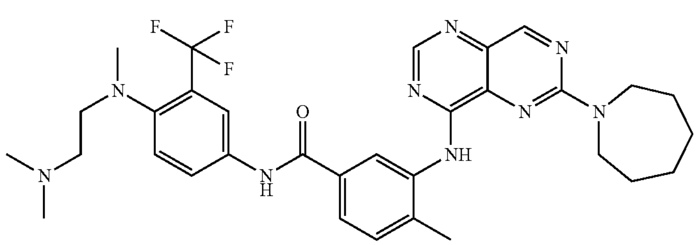 [SMILES: Cc1ccc(C(=O)Nc2ccc(N(C)CCN(C)C)c(C(F)(F)F)c2)cc1Nc1ncnc2cnc(N3CCCCCC3)nc12] | 1.72 | 311 (M + 2H)$^{2+}$ |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)⁺ |
|---|-----------|---|---|
| III-121 | 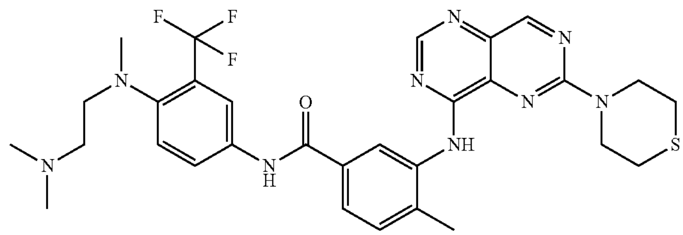 [SMILES: Cc1ccc(C(=O)Nc2ccc(N(C)CCN(C)C)c(C(F)(F)F)c2)cc1Nc1ncnc2cnc(N3CCSCC3)nc12] | 1.62 | 313 (M + 2H)²⁺ |
| III-122 | 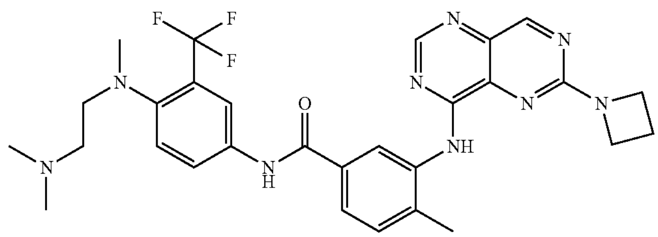 [SMILES: Cc1ccc(C(=O)Nc2ccc(N(C)CCN(C)C)c(C(F)(F)F)c2)cc1Nc1ncnc2cnc(N3CCC3)nc12] | 1.50 | 290 (M + 2H)²⁺ |
| III-123 | 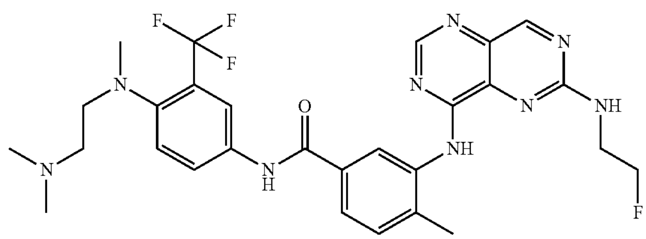 [SMILES: Cc1ccc(C(=O)Nc2ccc(N(C)CCN(C)C)c(C(F)(F)F)c2)cc1Nc1ncnc2cnc(NCCF)nc12] | 1.45 | 293 (M + 2H)²⁺ |
| III-124 | 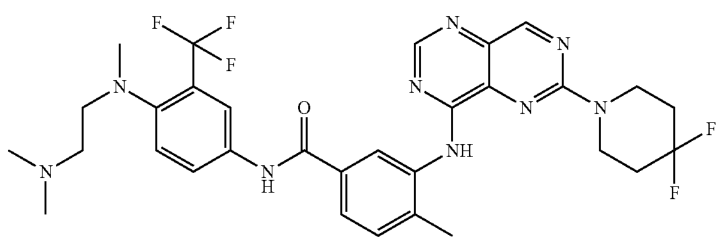 [SMILES: Cc1ccc(C(=O)Nc2ccc(N(C)CCN(C)C)c(C(F)(F)F)c2)cc1Nc1ncnc2cnc(N3CCC(F)(F)CC3)nc12] | 1.67 | 322 (M + 2H)²⁺ |
| III-125 | 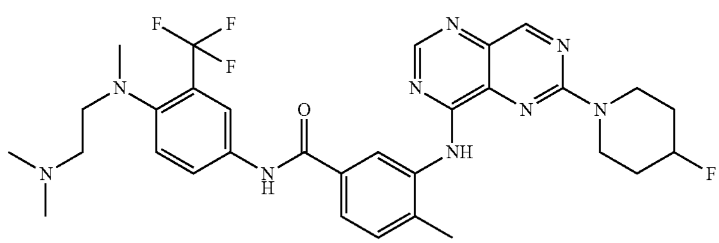 [SMILES: Cc1ccc(C(=O)Nc2ccc(N(C)CCN(C)C)c(C(F)(F)F)c2)cc1Nc1ncnc2cnc(N3CCC(F)CC3)nc12] | 1.60 | 313 (M + 2H)²⁺ |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-126 | 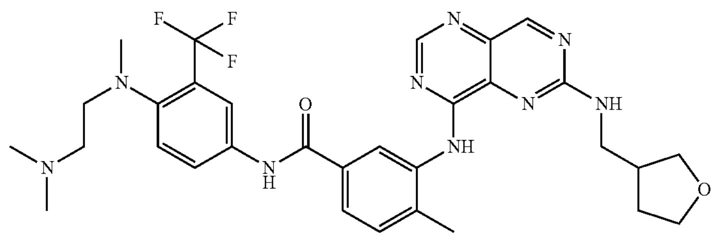 [SMILES: Cc1ccc(C(=O)Nc2ccc(N(C)CCN(C)C)c(C(F)(F)F)c2)cc1Nc1ncnc2cnc(NCC3CCOC3)nc12] | 1.44 | 312 (M + 2H)²⁺ |
| III-127 | 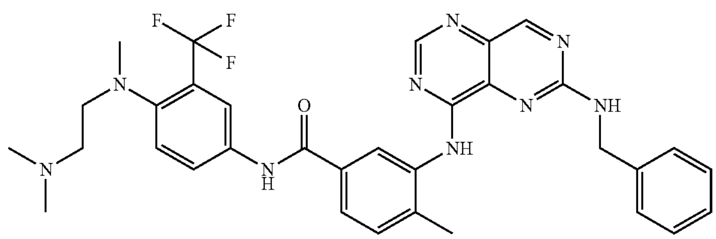 [SMILES: Cc1ccc(C(=O)Nc2ccc(N(C)CCN(C)C)c(C(F)(F)F)c2)cc1Nc1ncnc2cnc(NCc3ccccc3)nc12] | 1.64 | 315 (M + 2H)²⁺ |
| III-128 | 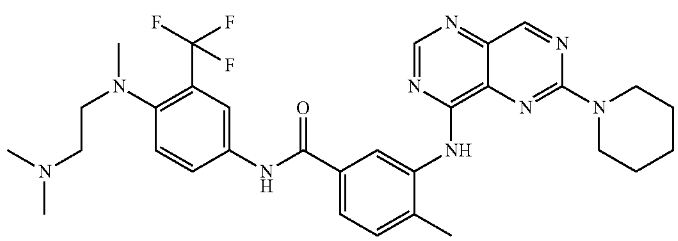 [SMILES: Cc1ccc(C(=O)Nc2ccc(N(C)CCN(C)C)c(C(F)(F)F)c2)cc1Nc1ncnc2cnc(N3CCCCC3)nc12] | 1.67 | 304 (M + 2H)²⁺ |
| III-129 | 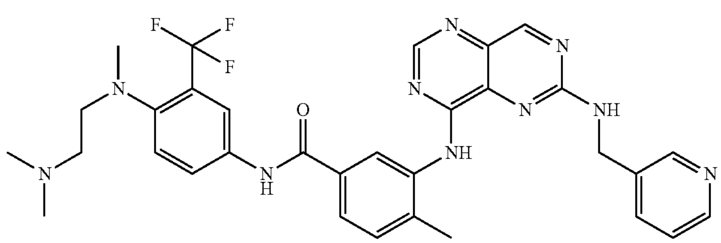 [SMILES: Cc1ccc(C(=O)Nc2ccc(N(C)CCN(C)C)c(C(F)(F)F)c2)cc1Nc1ncnc2cnc(NCc3cccnc3)nc12] | 1.28 | 316 (M + 2H)²⁺ |
| III-130 | 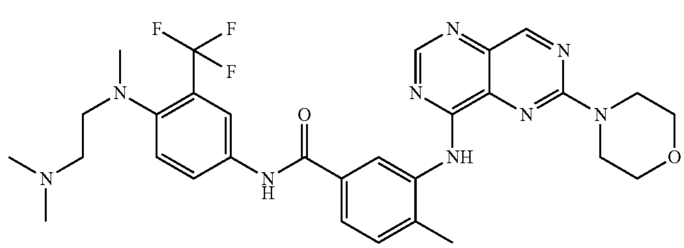 [SMILES: Cc1ccc(C(=O)Nc2ccc(N(C)CCN(C)C)c(C(F)(F)F)c2)cc1Nc1ncnc2cnc(N3CCOCC3)nc12] | 1.95 | 610 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-131 | 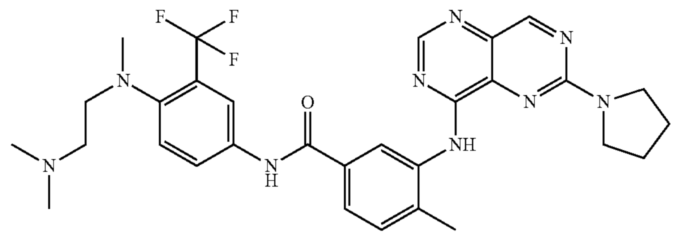 [SMILES: Cc1ccc(C(=O)Nc2ccc(N(C)CCN(C)C)c(C(F)(F)F)c2)cc1Nc1ncnc2cnc(N3CCCC3)nc12] | 1.59 | 297 (M + 2H)2+ |
| III-132 | 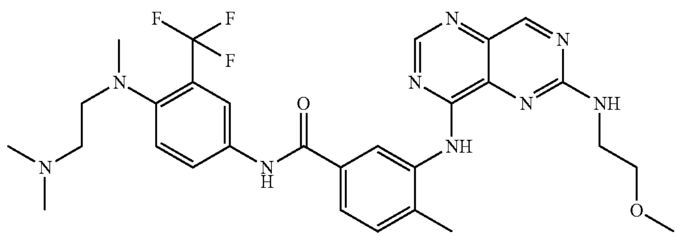 | 1.43 | 299 (M + 2H)2+ |
| III-133 | 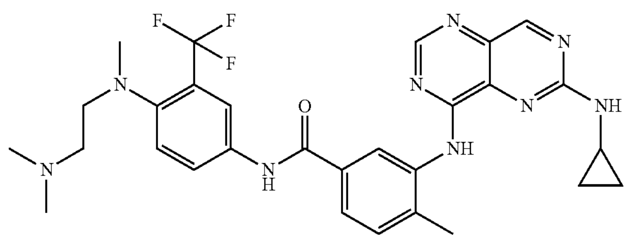 [SMILES: Cc1ccc(C(=O)Nc2ccc(N(C)CCN(C)C)c(C(F)(F)F)c2)cc1Nc1ncnc2cnc(NC3CC3)nc12] | 1.51 | 290 (M + 2H)2+ |
| III-134 | 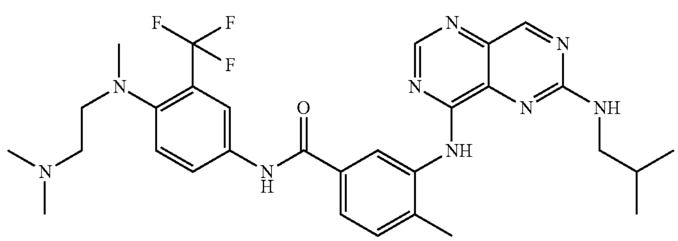 [SMILES: Cc1ccc(C(=O)Nc2ccc(N(C)CCN(C)C)c(C(F)(F)F)c2)cc1Nc1ncnc2cnc(NCC(C)C)nc12] | 1.63 | 298 (M + 2H)2+ |
| III-135 | 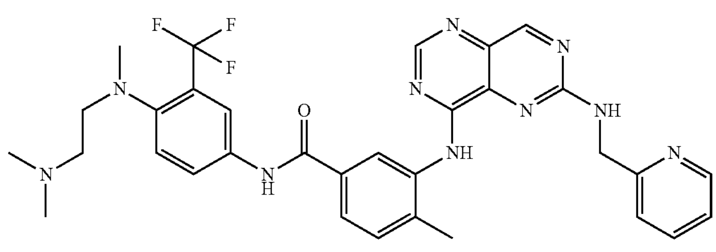 [SMILES: Cc1ccc(C(=O)Nc2ccc(N(C)CCN(C)C)c(C(F)(F)F)c2)cc1Nc1ncnc2cnc(NCc3ccccn3)nc12] | 1.29 | 316 (M + 2H)2+ |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-136 | 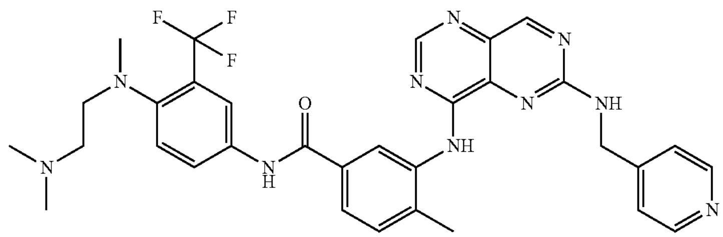 [SMILES: Cc1ccc(C(=O)Nc2ccc(N(C)CCN(C)C)c(C(F)(F)F)c2)cc1Nc1ncnc2cnc(NCc3ccncc3)nc12] | 1.27 | 316 (M + 2H)$^{2+}$ |
| III-137 | 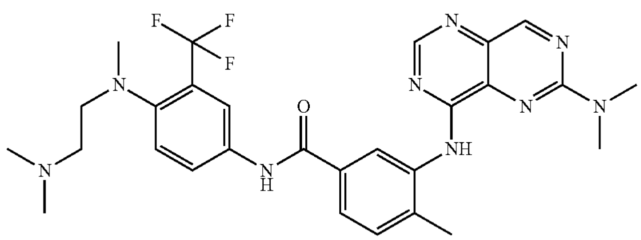 | 1.50 | 284 (M + 2H)$^{2+}$ |
| III-138 | 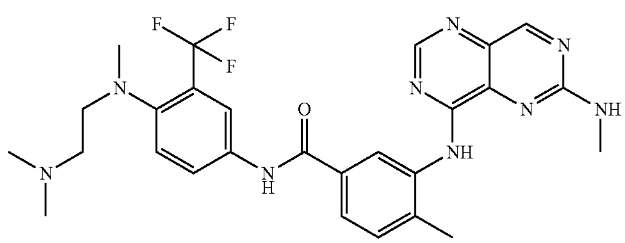 | 1.41 | 277 (M + 2H)$^{2+}$ |
| III-139 | 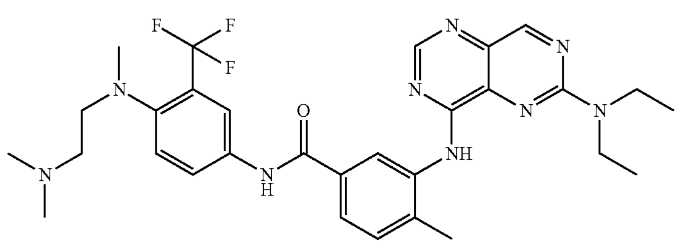 [SMILES: CCN(CC)c1ncc2ncnc(Nc3cc(C(=O)Nc4ccc(N(C)CCN(C)C)c(C(F)(F)F)c4)ccc3C)c2n1] | 1.65 | 298 (M + 2H)$^{2+}$ |
| III-140 | 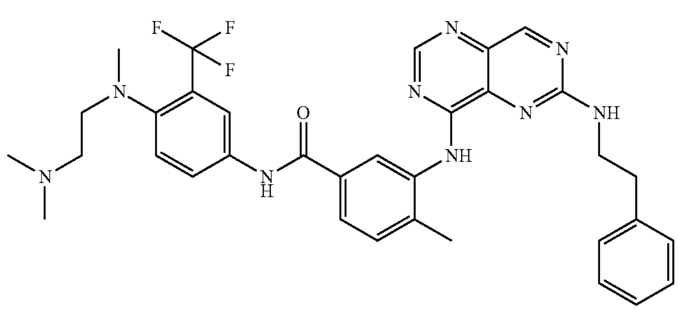 [SMILES: Cc1ccc(C(=O)Nc2ccc(N(C)CCN(C)C)c(C(F)(F)F)c2)cc1Nc1ncnc2cnc(NCCc3ccccc3)nc12] | 1.67 | 322 (M + 2H)$^{2+}$ |

TABLE 3-continued
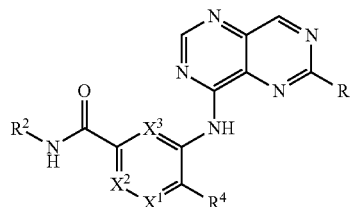  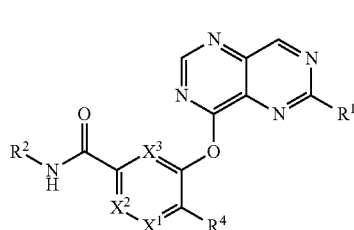
Example Compounds III-1 to III-579 and III-592 to III-608 | Example Compounds III-580 to III-587 | Example Compounds III-588 to III-591
| # | Structure | t$_{Ret.}$ (HPLC) [min] | MS (M + H)$^+$ |
|---|---|---|---|
| III-141 | 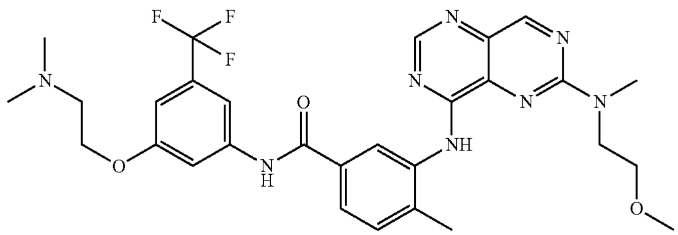 | 1.53 | 300 (M + 2H)$^{2+}$ |
| III-142 | 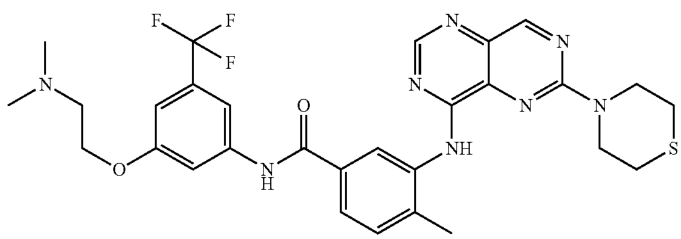 [SMILES: Cc1ccc(C(=O)Nc2cc(OCCN(C)C)cc(C(F)(F)F)c2)cc1Nc1ncnc2cnc(N3CCSCC3)nc12] | 1.62 | |
| III-143 | 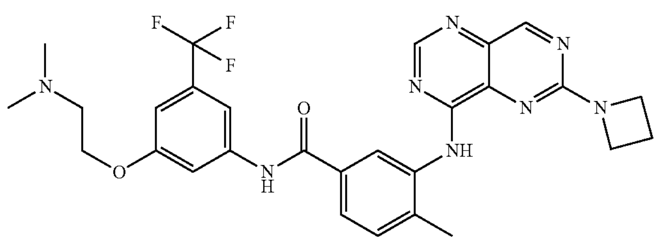 [SMILES: Cc1ccc(C(=O)Nc2cc(OCCN(C)C)cc(C(F)(F)F)c2)cc1Nc1ncnc2cnc(N3CCC3)nc12] | 1.53 | |
| III-144 | 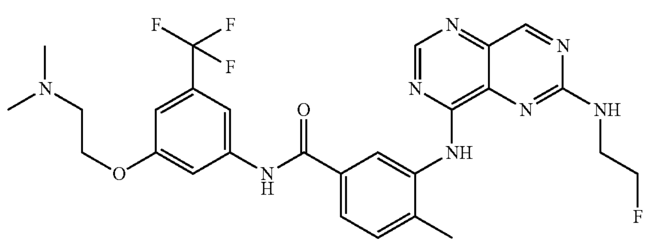 [SMILES: Cc1ccc(C(=O)Nc2cc(OCCN(C)C)cc(C(F)(F)F)c2)cc1Nc1ncnc2cnc(NCCF)nc12] | 1.47 | 287 (M + 2H)$^{2+}$ |
| III-145 | 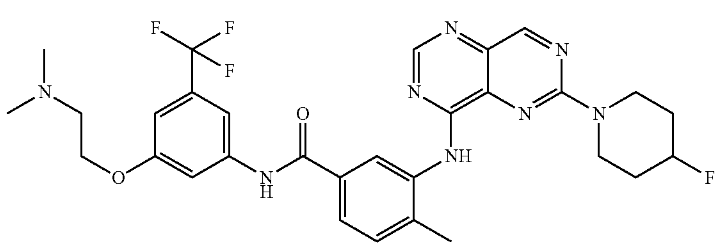 [SMILES: Cc1ccc(C(=O)Nc2cc(OCCN(C)C)cc(C(F)(F)F)c2)cc1Nc1ncnc2cnc(N3CCC(F)CC3)nc12] | 1.61 | 307 (M + 2H)$^{2+}$ |

TABLE 3-continued
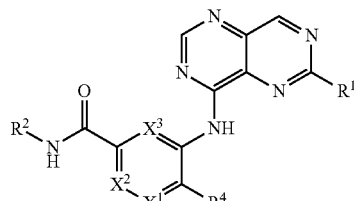
Example Compounds III-1 to III-579 and III-592 to III-608
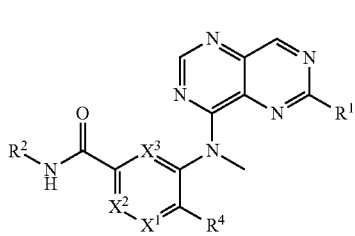
Example Compounds III-580 to III-587
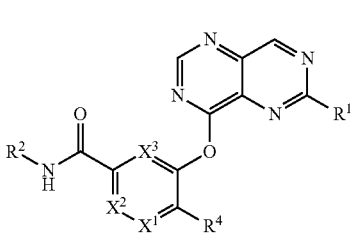
Example Compounds III-588 to III-591
| # | Structure | $t_{Ret.}$ (HPLC) [min] | MS (M + H)$^+$ |
|---|---|---|---|
| III-146 | 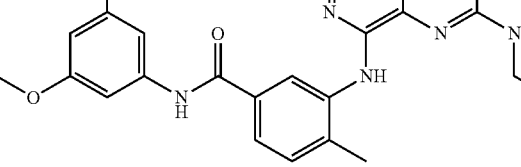 | 1.47 | 306 (M + 2H)$^{2+}$ |
| III-147 | 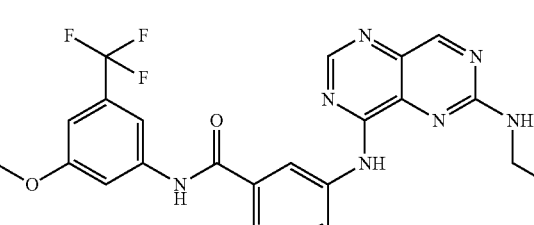 | 1.64 | 309 (M + 2H)$^{2+}$ |
| III-148 | 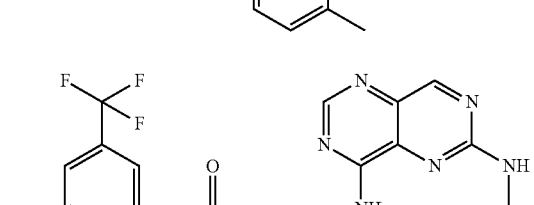 | 1.31 | 309 (M + 2H)$^{2+}$ |
| III-149 | 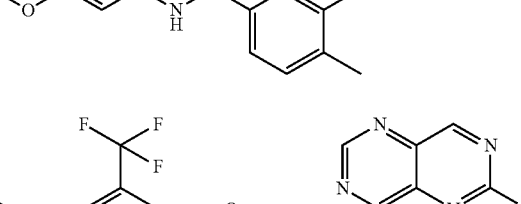 | 1.50 | 299 (M + 2H)$^{2+}$ |
| III-150 | 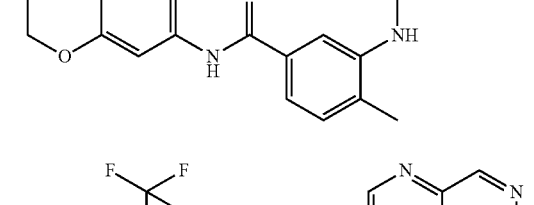 | 1.59 | 291 (M + 2H)$^{2+}$ |

TABLE 3-continued
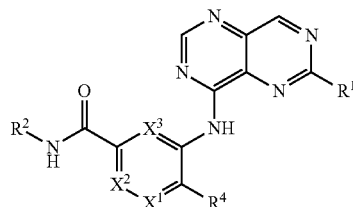
Example Compounds III-1 to III-579 and III-592 to III-608
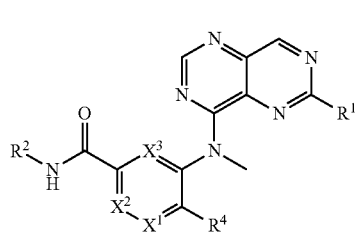
Example Compounds III-580 to III-587
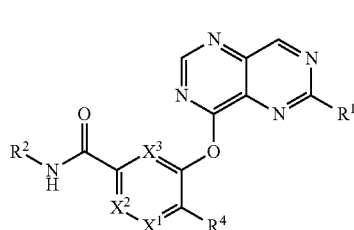
Example Compounds III-588 to III-591
| # | Structure | $t_{Ret.}$ (HPLC) [min] | MS (M + H)⁺ |
|---|---|---|---|
| III-151 | 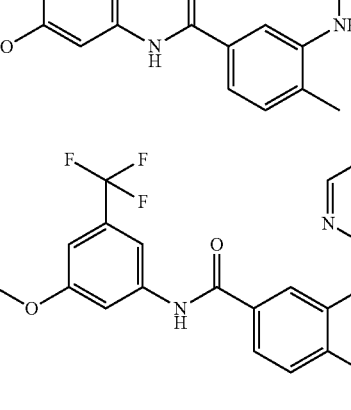 | 1.46 | 293 (M + 2H)²⁺ |
| III-152 | 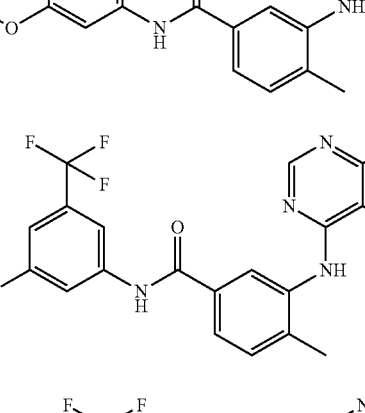 | 1.53 | |
| III-153 | 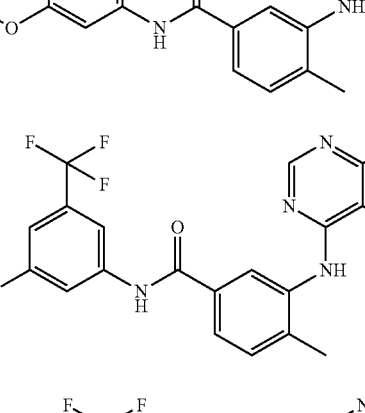 | 1.63 | 292 (M + 2H)²⁺ |
| III-154 | 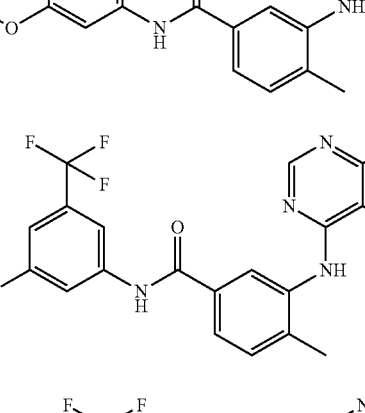 | 1.32 | 309 (M + 2H)²⁺ |
| III-155 | 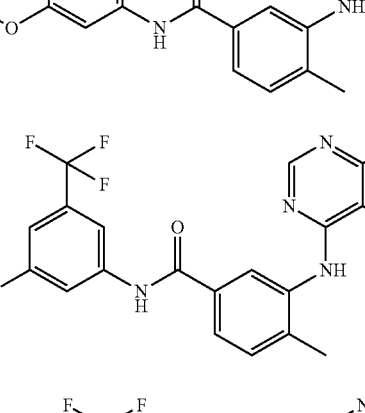 | 1.52 | 278 (M + 2H)²⁺ |

TABLE 3-continued
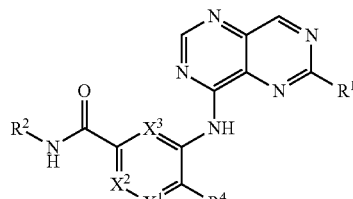
Example Compounds III-1 to III-579 and III-592 to III-608
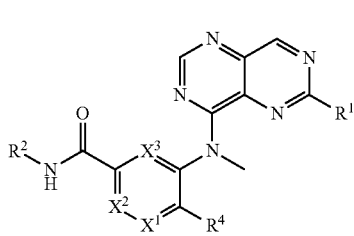
Example Compounds III-580 to III-587
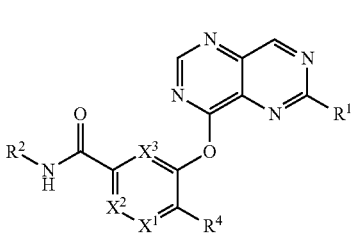
Example Compounds III-588 to III-591
| # | Structure | $t_{Ret.}$ (HPLC) [min] | MS (M + H)⁺ |
|---|---|---|---|
| III-156 | 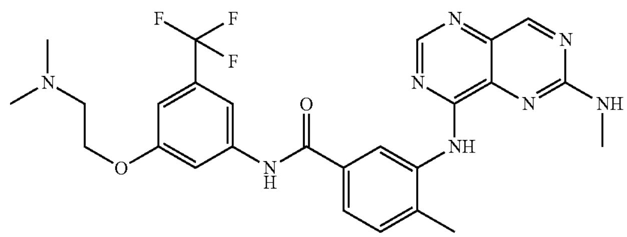 | 1.44 | |
| III-157 | 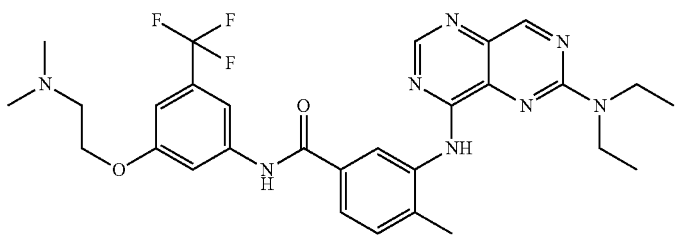 [SMILES: CCN(CC)c1ncc2ncnc(Nc3cc(C(=O)Nc4cc(OCCN(C)C)cc(C(F)(F)F)c4)ccc3C)c2n1] | 1.67 | 292 (M + 2H)²⁺ |
| III-158 | 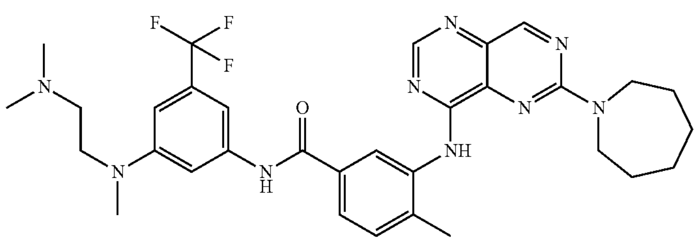 [SMILES: Cc1ccc(C(=O)Nc2cc(N(C)CCN(C)C)cc(C(F)(F)F)c2)cc1Nc1ncnc2cnc(N3CCCCCC3)nc12] | 1.76 | 311 (M + 2H)²⁺ |
| III-159 | 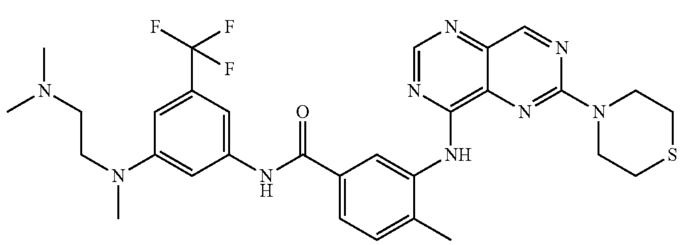 [SMILES: Cc1ccc(C(=O)Nc2cc(N(C)CCN(C)C)cc(C(F)(F)F)c2)cc1Nc1ncnc2cnc(N3CCSCC3)nc12] | 1.65 | 313 (M + 2H)²⁺ |
| III-160 | 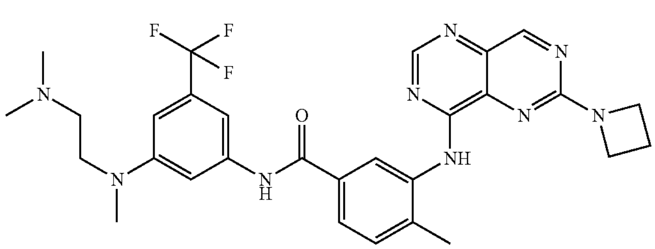 [SMILES: Cc1ccc(C(=O)Nc2cc(N(C)CCN(C)C)cc(C(F)(F)F)c2)cc1Nc1ncnc2cnc(N3CCC3)nc12] | 1.55 | 290 (M + 2H)²⁺ |

TABLE 3-continued
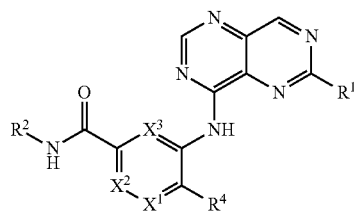
Example Compounds III-1 to III-579 and III-592 to III-608
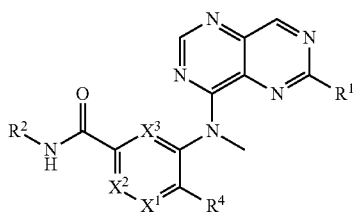
Example Compounds III-580 to III-587
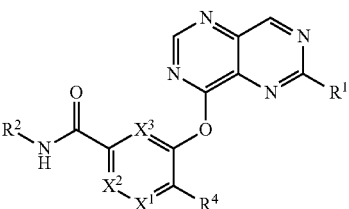
Example Compounds III-588 to III-591
| # | Structure | $t_{Ret.}$ (HPLC) [min] | MS (M + H)$^+$ |
|---|---|---|---|
| III-161 | 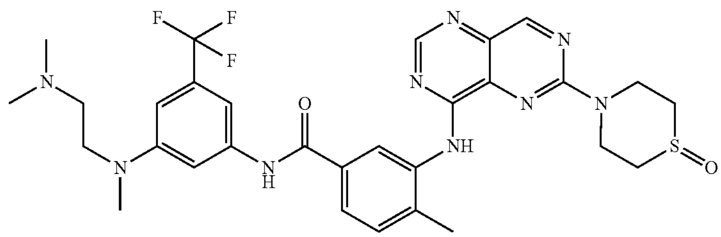 [SMILES: Cc1ccc(C(=O)Nc2cc(N(C)CCN(C)C)cc(C(F)(F)F)c2)cc1Nc1ncnc2cnc(N3CCS(=O)CC3)nc12] | 1.41 | 321 (M + 2H)$^{2+}$ |
| III-162 | 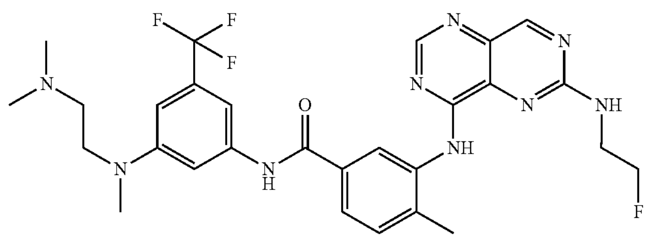 [SMILES: Cc1ccc(C(=O)Nc2cc(N(C)CCN(C)C)cc(C(F)(F)F)c2)cc1Nc1ncnc2cnc(NCCF)nc12] | 1.51 | 293 (M + 2H)$^{2+}$ |
| III-163 | 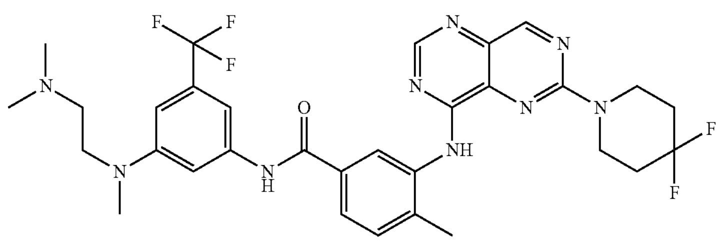 [SMILES: Cc1ccc(C(=O)Nc2cc(N(C)CCN(C)C)cc(C(F)(F)F)c2)cc1Nc1ncnc2cnc(N3CCC(F)(F)CC3)nc12] | 1.70 | 322 (M + 2H)$^{2+}$ |
| III-164 | 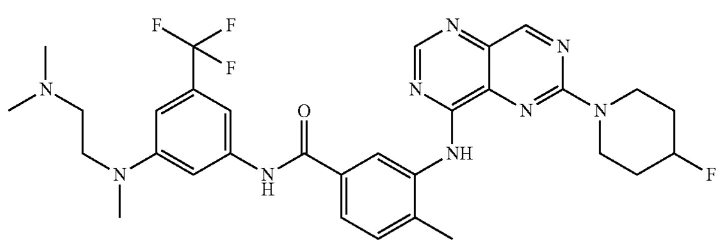 [SMILES: Cc1ccc(C(=O)Nc2cc(N(C)CCN(C)C)cc(C(F)(F)F)c2)cc1Nc1ncnc2cnc(N3CCC(F)CC3)nc12] | 1.64 | 313 (M + 2H)$^{2+}$ |
| III-165 | 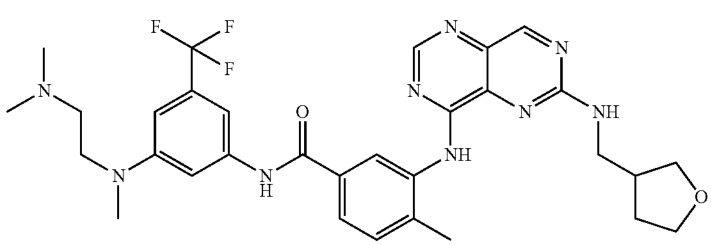 [SMILES: Cc1ccc(C(=O)Nc2cc(N(C)CCN(C)C)cc(C(F)(F)F)c2)cc1Nc1ncnc2cnc(NCC3CCOC3)nc12] | 1.50 | 312 (M + 2H)$^{2+}$ |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-166 | 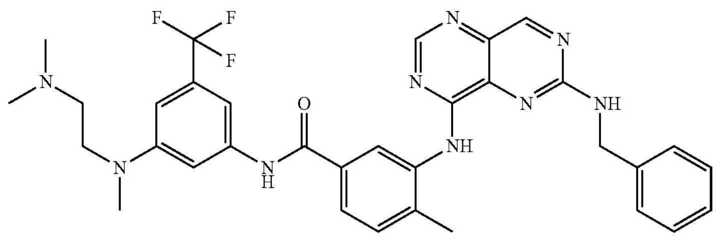 [SMILES: Cc1ccc(C(=O)Nc2cc(N(C)CCN(C)C)cc(C(F)(F)F)c2)cc1Nc1ncnc2cnc(NCc3ccccc3)nc12] | 1.67 | 315 (M + 2H)$^{2+}$ |
| III-167 | 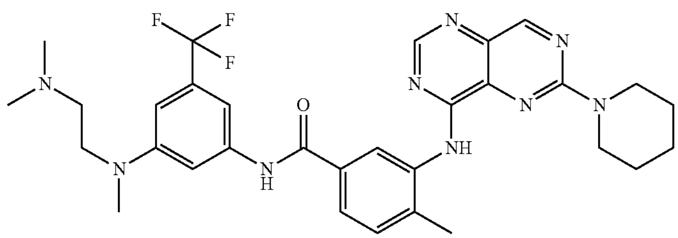 [SMILES: Cc1ccc(C(=O)Nc2cc(N(C)CCN(C)C)cc(C(F)(F)F)c2)cc1Nc1ncnc2cnc(N3CCCCC3)nc12] | 1.72 | 304 (M + 2H)$^{2+}$ |
| III-168 | 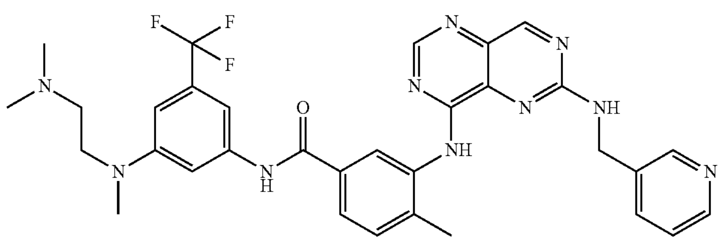 [SMILES: Cc1ccc(C(=O)Nc2cc(N(C)CCN(C)C)cc(C(F)(F)F)c2)cc1Nc1ncnc2cnc(NCc3cccnc3)nc12] | 1.34 | 316 (M + 2H)$^{2+}$ |
| III-169 | 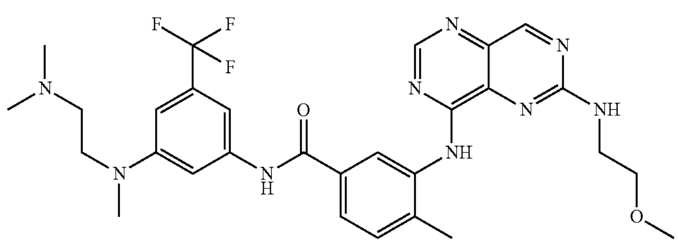 | 1.49 | 299 (M + 2H)$^{2+}$ |
| III-170 | 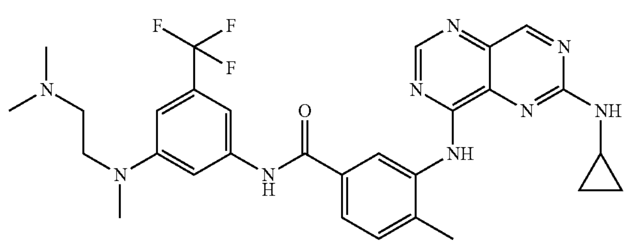 [SMILES: Cc1ccc(C(=O)Nc2cc(N(C)CCN(C)C)cc(C(F)(F)F)c2)cc1Nc1ncnc2cnc(NC3CC3)nc12] | 1.56 | 290 (M + 2H)$^{2+}$ |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-171 | 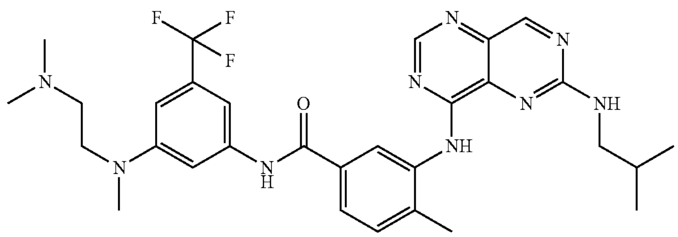 [SMILES: Cc1ccc(C(=O)Nc2cc(N(C)CCN(C)C)cc(C(F)(F)F)c2)cc1Nc1ncnc2cnc(NCC(C)C)nc12] | 1.66 | 298 (M + 2H)$^{2+}$ |
| III-172 | 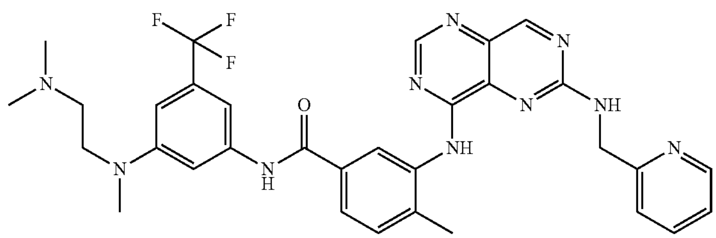 [SMILES: Cc1ccc(C(=O)Nc2cc(N(C)CCN(C)C)cc(C(F)(F)F)c2)cc1Nc1ncnc2cnc(NCc3ccccn3)nc12] | 1.36 | 316 (M + 2H)$^{2+}$ |
| III-173 | 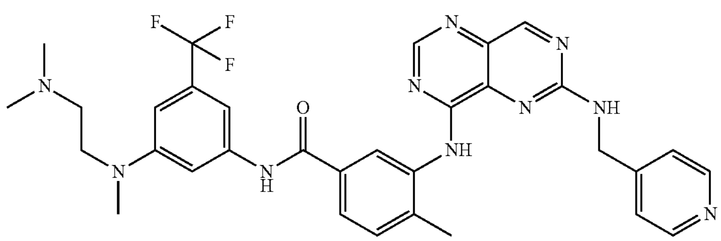 [SMILES: Cc1ccc(C(=O)Nc2cc(N(C)CCN(C)C)cc(C(F)(F)F)c2)cc1Nc1ncnc2cnc(NCc3ccncc3)nc12] | 1.34 | 316 (M + 2H)$^{2+}$ |
| III-174 | 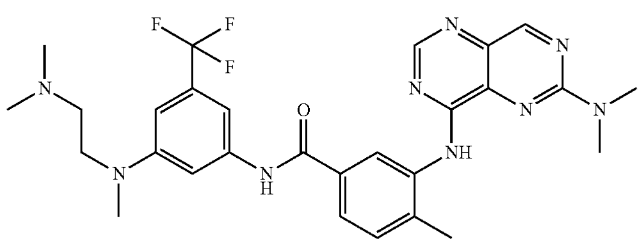 | 1.55 | 284 (M + 2H)$^{2+}$ |
| III-175 | 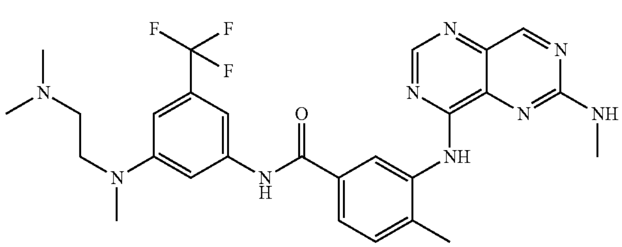 | 1.47 | 277 (M + 2H)$^{2+}$ |

TABLE 3-continued
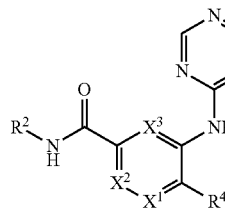 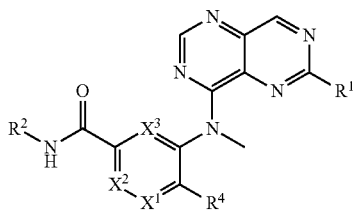 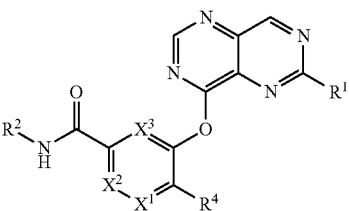
Example Compounds III-1 to III-579 and III-592 to III-608
Example Compounds III-580 to III-587
Example Compounds III-588 to III-591
| # | Structure | $t_{Ret.}$ (HPLC) [min] | MS $(M+H)^+$ |
|---|---|---|---|
| III-176 | 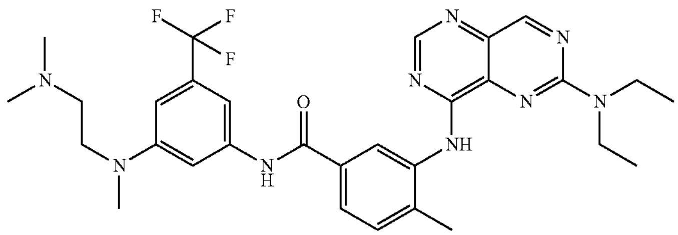 [SMILES: CCN(CC)c1ncc2ncnc(Nc3cc(C(=O)Nc4cc(N(C)CCN(C)C)cc(C(F)(F)F)c4)ccc3C)c2n1] | 1.69 | 298 $(M+2H)^{2+}$ |
| III-177 | 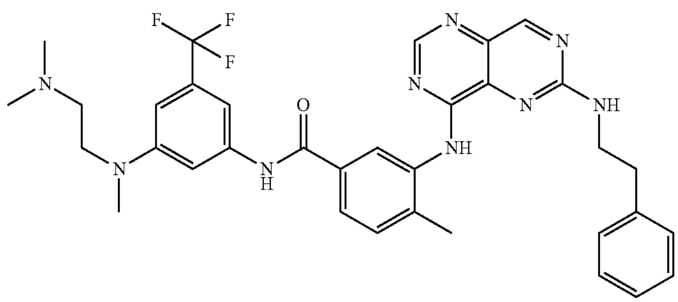 [SMILES: Cc1ccc(C(=O)Nc2cc(N(C)CCN(C)C)cc(C(F)(F)F)c2)cc1Nc1ncnc2cnc(NCCc3ccccc3)nc12] | 1.72 | 322 $(M+2H)^{2+}$ |
| III-178 | 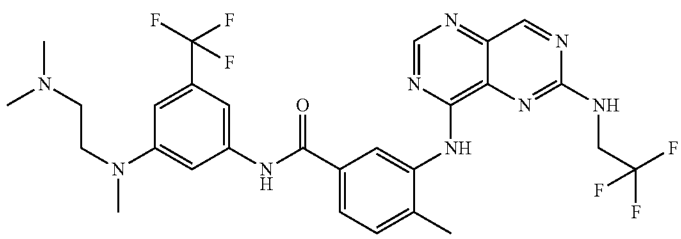 [SMILES: Cc1ccc(C(=O)Nc2cc(N(C)CCN(C)C)cc(C(F)(F)F)c2)cc1Nc1ncnc2cnc(NCC(F)(F)F)nc12] | 1.61 | 352 $(M+2H)^{2+}$ |
| III-179 | 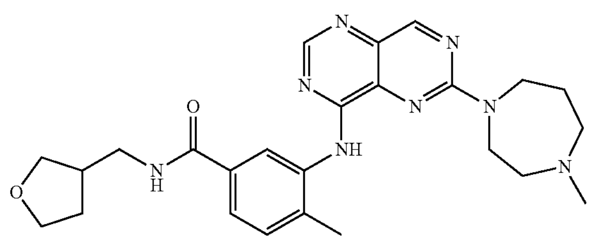 [SMILES: Cc1ccc(C(=O)NCC2CCOC2)cc1Nc1ncnc2cnc(N3CCCN(C)CC3)nc12] | 1.28 | 477 |
| III-180 | 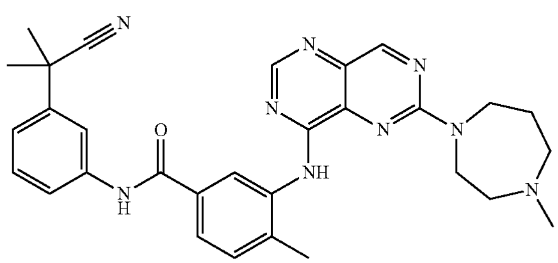 [SMILES: Cc1ccc(C(=O)Nc2cccc(C(C)(C)C#N)c2)cc1Nc1ncnc2cnc(N3CCCN(C)CC3)nc12] | 1.54 | 536 |

TABLE 3-continued
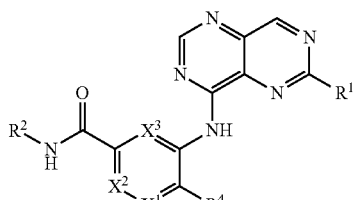
Example Compounds III-1 to III-579 and III-592 to III-608
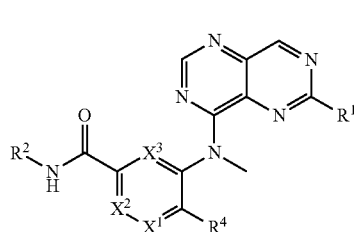
Example Compounds III-580 to III-587
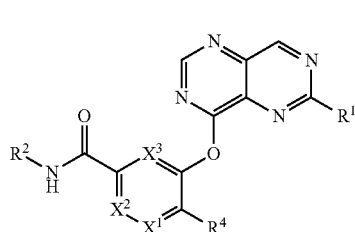
Example Compounds III-588 to III-591
| # | Structure | $t_{Ret.}$ (HPLC) [min] | MS (M + H)+ |
|---|---|---|---|
| III-181 | 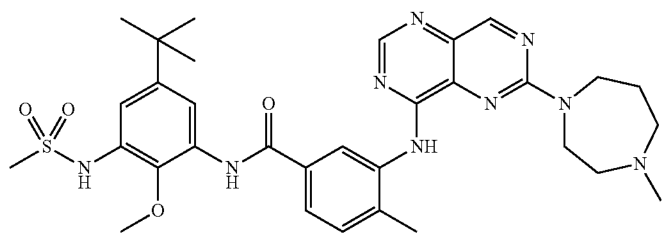 | 1.57 | 648 |
| III-182 | 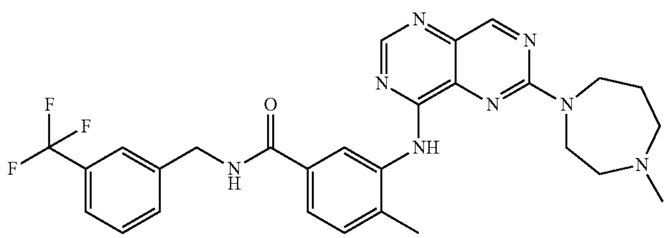 [SMILES: Cc1ccc(C(=O)NCc2cccc(C(F)(F)F)c2)cc1Nc1ncnc2cnc(N3CCCN(C)CC3)nc12] | 1.57 | 551 |
| III-183 | 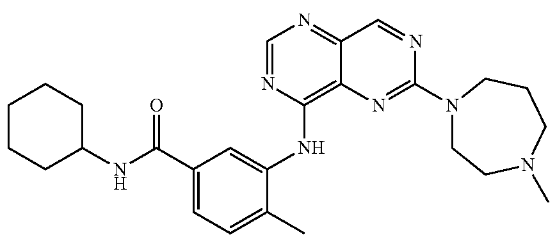 [SMILES: Cc1ccc(C(=O)NC2CCCCC2)cc1Nc1ncnc2cnc(N3CCCN(C)CC3)nc12] | 1.47 | 475 |
| III-184 | 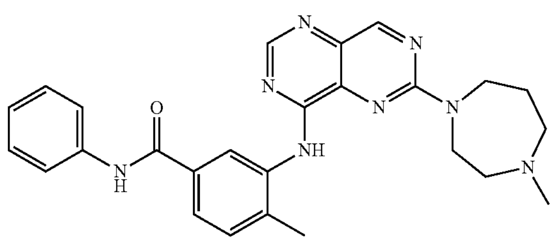 [SMILES: Cc1ccc(C(=O)Nc2ccccc2)cc1Nc1ncnc2cnc(N3CCCN(C)CC3)nc12] | 1.46 | 469 |
| III-185 | 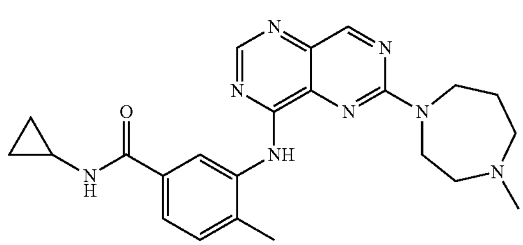 [SMILES: Cc1ccc(C(=O)NC2CC2)cc1Nc1ncnc2cnc(N3CCCN(C)CC3)nc12] | 1.28 | 433 |

TABLE 3-continued
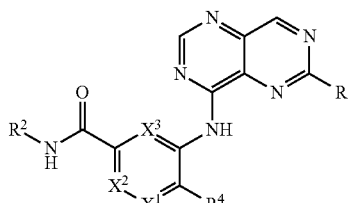
Example Compounds III-1 to III-579 and III-592 to III-608
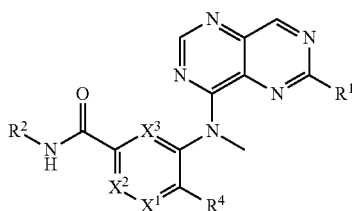
Example Compounds III-580 to III-587
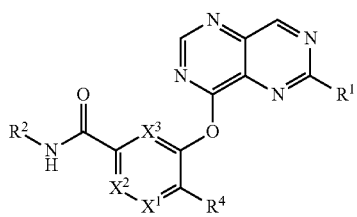
Example Compounds III-588 to III-591
| # | Structure | $t_{Ret.}$ (HPLC) [min] | MS (M + H)+ |
|---|---|---|---|
| III-186 | 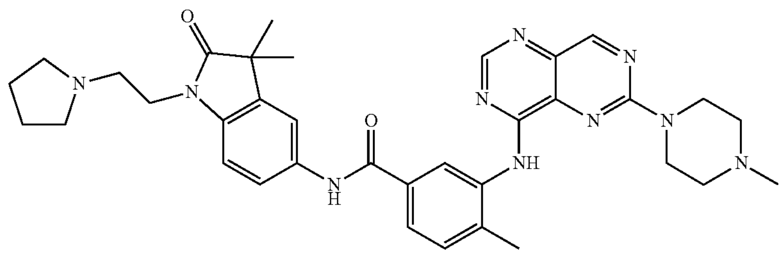 [SMILES: Cc1ccc(C(=O)Nc2ccc3c(c2)C(C)(C)C(=O)N3CCN2CCCC2)cc1Nc1ncnc2cnc(N3CCN(C)CC3)nc12] | 1.31 | 318 (M + 2H)$^{2+}$ |
| III-187 | 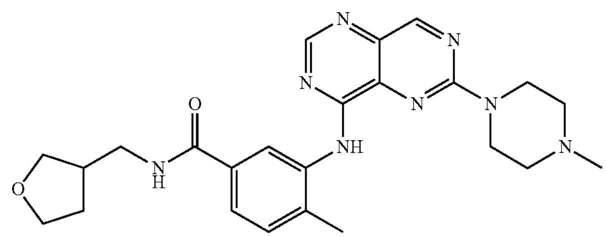 [SMILES: Cc1ccc(C(=O)NCC2CCOC2)cc1Nc1ncnc2cnc(N3CCN(C)CC3)nc12] | 1.26 | 463 |
| III-188 | 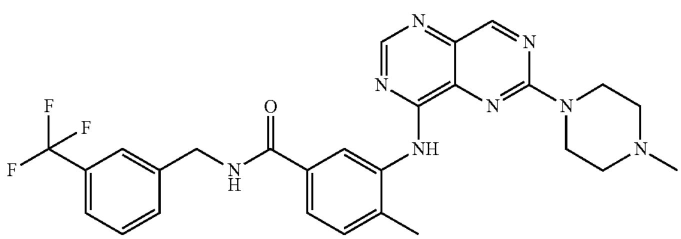 [SMILES: Cc1ccc(C(=O)NCc2cccc(C(F)(F)F)c2)cc1Nc1ncnc2cnc(N3CCN(C)CC3)nc12] | 1.57 | 537 |
| III-189 | 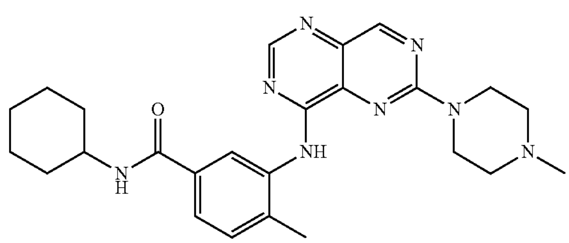 [SMILES: Cc1ccc(C(=O)NC2CCCCC2)cc1Nc1ncnc2cnc(N3CCN(C)CC3)nc12] | 1.46 | 461 |
| III-190 | 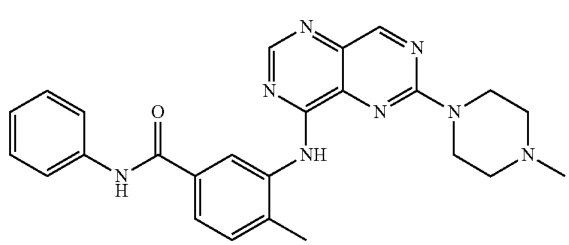 [SMILES: Cc1ccc(C(=O)Nc2ccccc2)cc1Nc1ncnc2cnc(N3CCN(C)CC3)nc12] | 1.46 | 455 |

TABLE 3-continued
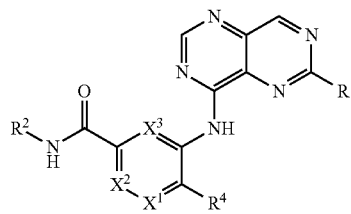
Example Compounds III-1 to III-579
and III-592 to III-608
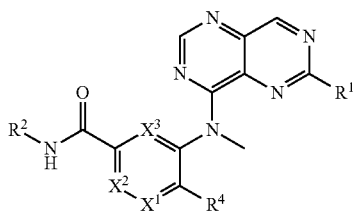
Example Compounds III-580 to III-587
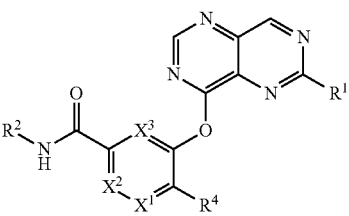
Example Compounds III-588 to III-591
| # | Structure | t$_{Ret.}$ (HPLC) [min] | MS (M + H)$^+$ |
|---|---|---|---|
| III-191 | 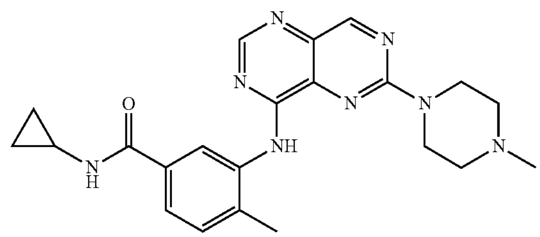 [SMILES: Cc1ccc(C(=O)NC2CC2)cc1Nc1ncnc2cnc(N3CCN(C)CC3)nc12] | 1.27 | 419 |
| III-192 | 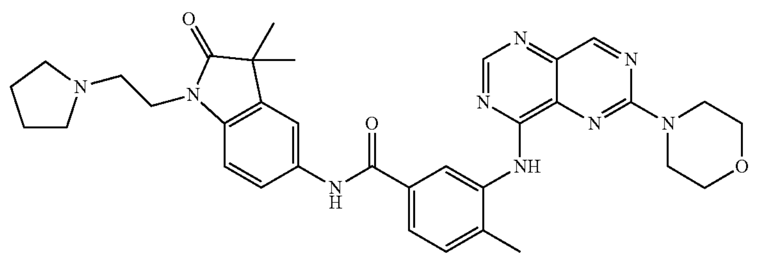 [SMILES: Cc1ccc(C(=O)Nc2ccc3c(c2)C(C)(C)C(=O)N3CCN2CCCC2)cc1Nc1ncnc2cnc(N3CCOCC3)nc12] | 1.48 | 311 (M + 2H)$^{2+}$ |
| III-193 | 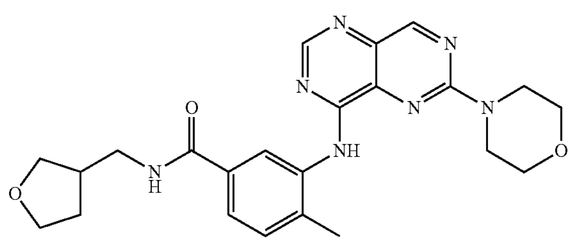 [SMILES: Cc1ccc(C(=O)NCC2CCOC2)cc1Nc1ncnc2cnc(N3CCOCC3)nc12] | 1.48 | 450 |
| III-194 | 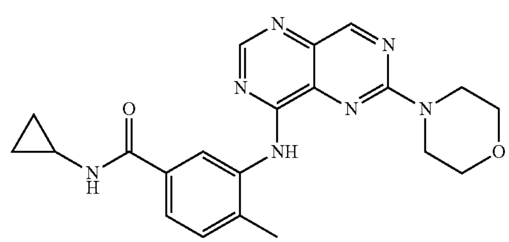 [SMILES: Cc1ccc(C(=O)NC2CC2)cc1Nc1ncnc2cnc(N3CCOCC3)nc12] | 1.51 | 406 |
| III-195 | 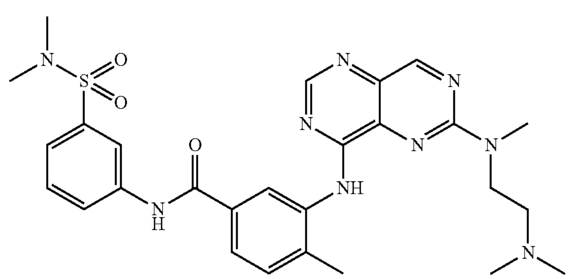 | 1.50 | 564 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-196 | 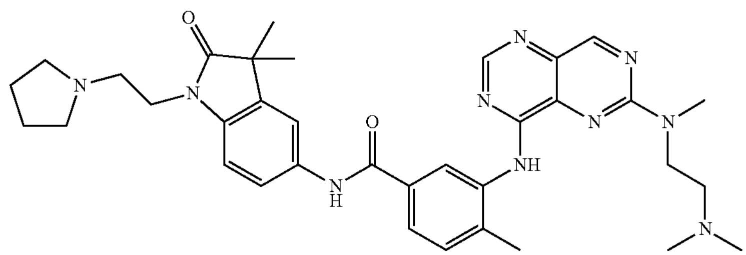 [SMILES: Cc1ccc(C(=O)Nc2ccc3c(c2)C(C)(C)C(=O)N3CCN2CCCC2)cc1Nc1ncnc2cnc(N(C)CCN(C)C)nc12] | 1.33 | 637 |
| III-197 | 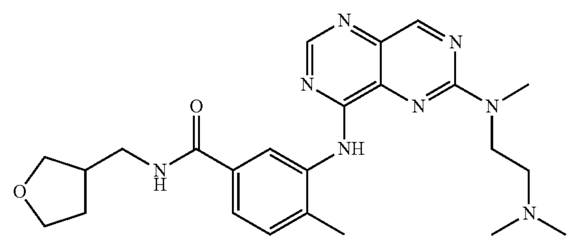 [SMILES: Cc1ccc(C(=O)NCC2CCOC2)cc1Nc1ncnc2cnc(N(C)CCN(C)C)nc12] | 1.28 | 465 |
| III-198 | 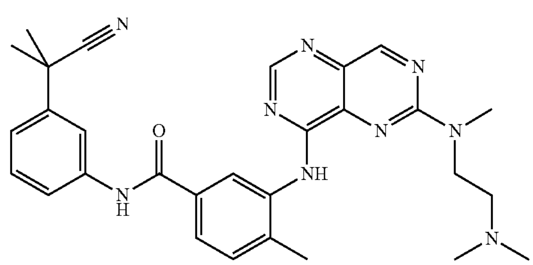 [SMILES: Cc1ccc(C(=O)Nc2cccc(C(C)(C)C#N)c2)cc1Nc1ncnc2cnc(N(C)CCN(C)C)nc12] | 1.55 | 524 |
| III-199 | 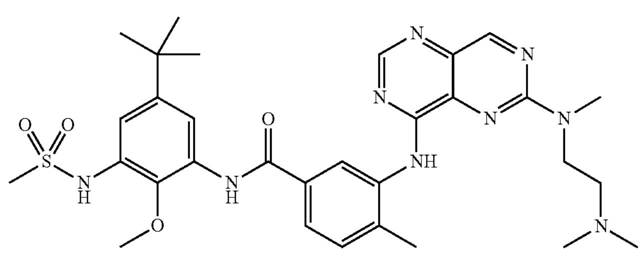 | 1.58 | 636 |
| III-200 | 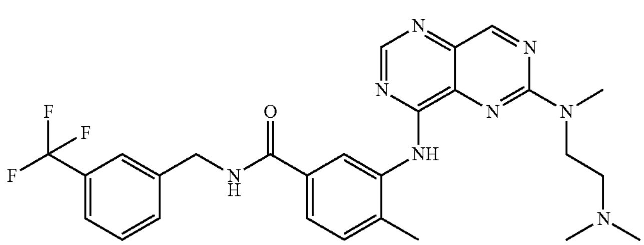 [SMILES: Cc1ccc(C(=O)NCc2cccc(C(F)(F)F)c2)cc1Nc1ncnc2cnc(N(C)CCN(C)C)nc12] | 1.57 | 539 |

TABLE 3-continued
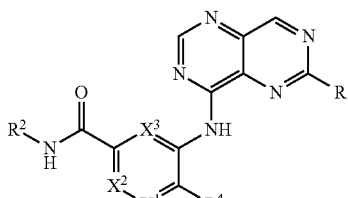
Example Compounds III-1 to III-579 and III-592 to III-608
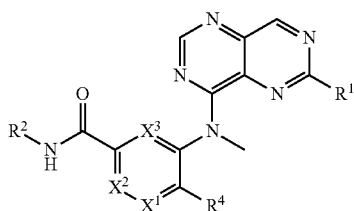
Example Compounds III-580 to III-587
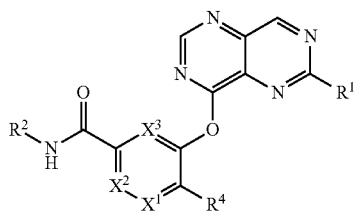
Example Compounds III-588 to III-591
| # | Structure | $t_{Ret.}$ (HPLC) [min] | MS (M + H)⁺ |
|---|---|---|---|
| III-201 | 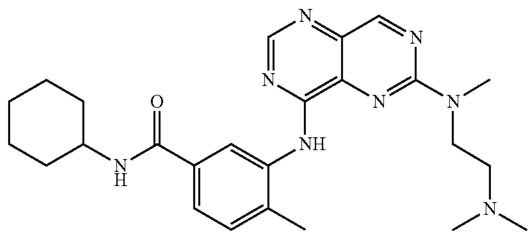 [SMILES: Cc1ccc(C(=O)NC2CCCCC2)cc1Nc1ncnc2cnc(N(C)CCN(C)C)nc12] | 1.48 | 463 |
| III-202 | 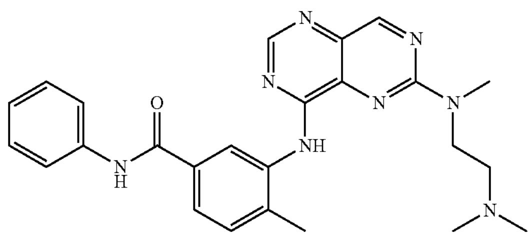 [SMILES: Cc1ccc(C(=O)Nc2ccccc2)cc1Nc1ncnc2cnc(N(C)CCN(C)C)nc12] | 1.47 | 457 |
| III-203 | 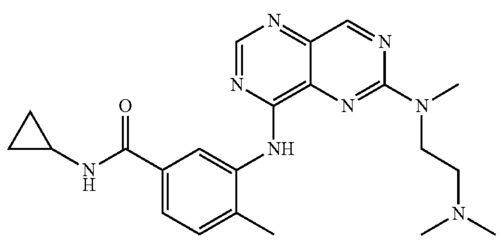 [SMILES: Cc1ccc(C(=O)NC2CC2)cc1Nc1ncnc2cnc(N(C)CCN(C)C)nc12] | 1.29 | 421 |
| III-204 | 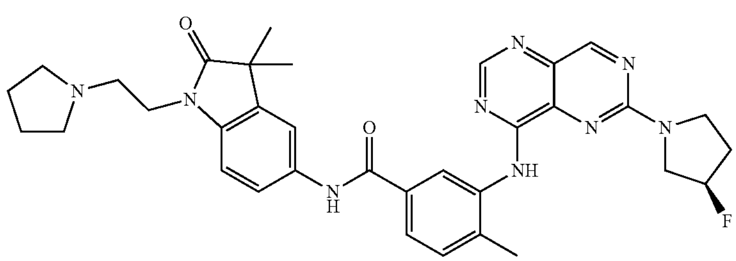 [SMILES: Cc1ccc(C(=O)Nc2ccc3c(c2)C(C)(C)C(=O)N3CCN2CCCC2)cc1Nc1ncnc2cnc(N3CC[C@@H](F)C3)nc12] | 1.52 | 312 (M + 2H)²⁺ |
| III-205 | 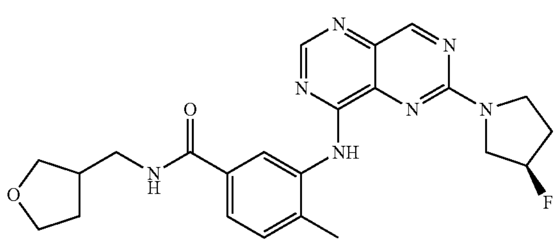 [SMILES: Cc1ccc(C(=O)NCC2CCOC2)cc1Nc1ncnc2cnc(N3CC[C@@H](F)C3)nc12] | 1.54 | 452 |

TABLE 3-continued
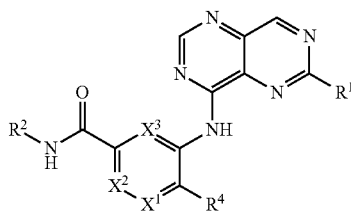
Example Compounds III-1 to III-579 and III-592 to III-608
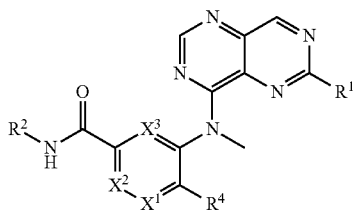
Example Compounds III-580 to III-587
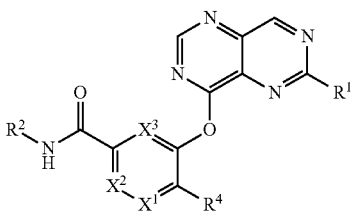
Example Compounds III-588 to III-591
| # | Structure | $t_{Ret.}$ (HPLC) [min] | MS (M + H)$^+$ |
|---|---|---|---|
| III-206 | 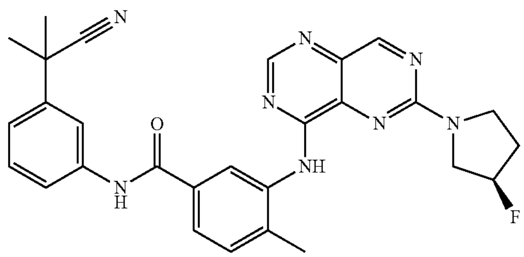 [SMILES: Cc1ccc(C(=O)Nc2cccc(C(C)(C)C#N)c2)cc1Nc1ncnc2cnc(N3CC[C@@H](F)C3)nc12] | 1.88 | 511 |
| III-207 | 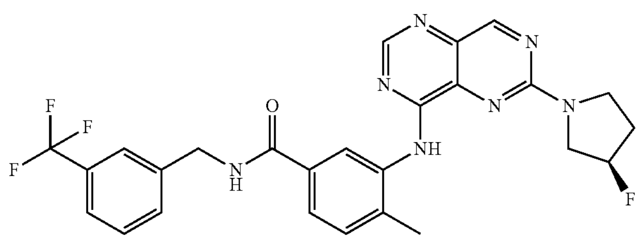 [SMILES: Cc1ccc(C(=O)NCc2cccc(C(F)(F)F)c2)cc1Nc1ncnc2cnc(N3CC[C@@H](F)C3)nc12] | 1.89 | 526 |
| III-208 | 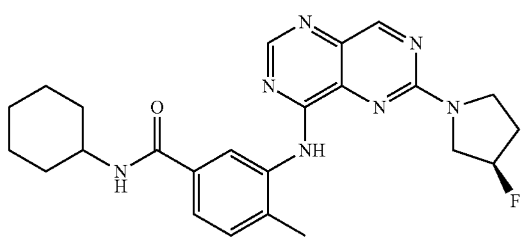 [SMILES: Cc1ccc(C(=O)NC2CCCCC2)cc1Nc1ncnc2cnc(N3CC[C@@H](F)C3)nc12] | 1.79 | 450 |
| III-209 | 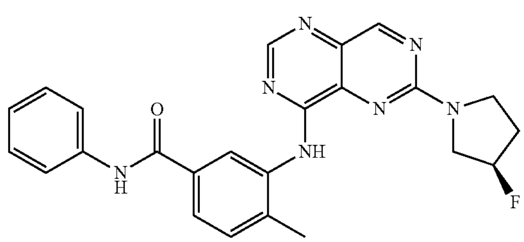 [SMILES: Cc1ccc(C(=O)Nc2ccccc2)cc1Nc1ncnc2cnc(N3CC[C@@H](F)C3)nc12] | 1.79 | 444 |
| III-210 | 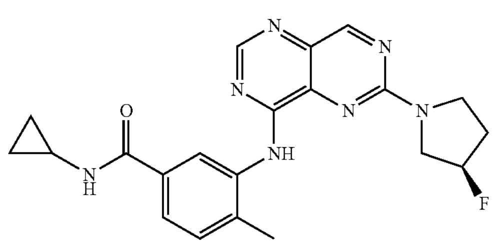 [SMILES: Cc1ccc(C(=O)NC2CC2)cc1Nc1ncnc2cnc(N3CC[C@@H](F)C3)nc12] | 1.57 | 408 |

TABLE 3-continued

Example Compounds III-1 to III-579 and III-592 to III-608

Example Compounds III-580 to III-587

Example Compounds III-588 to III-591

| # | Structure | t<sub>Ret.</sub> (HPLC) [min] | MS (M + H)⁺ |
|---|---|---|---|
| III-211 | 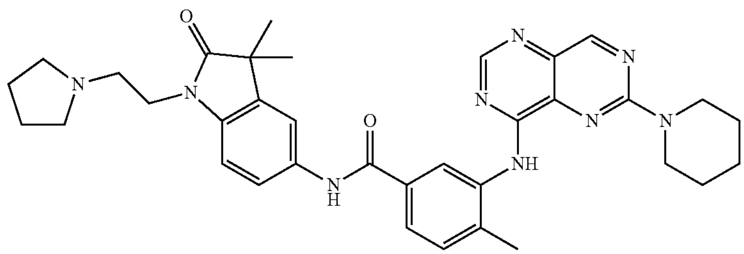 [SMILES: Cc1ccc(C(=O)Nc2ccc3c(c2)C(C)(C)C(=O)N3CCN2CCCC2)cc1Nc1ncnc2cnc(N3CCCCC3)nc12] | 1.61 | 310 (M + 2H)²⁺ |
| III-212 | 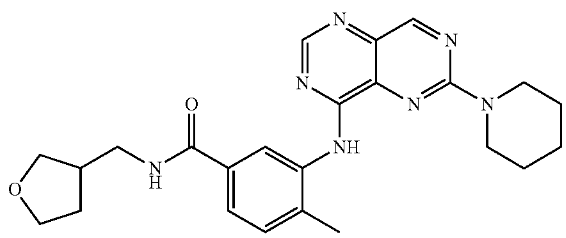 [SMILES: Cc1ccc(C(=O)NCC2CCOC2)cc1Nc1ncnc2cnc(N3CCCCC3)nc12] | 1.67 | 448 |
| III-213 | 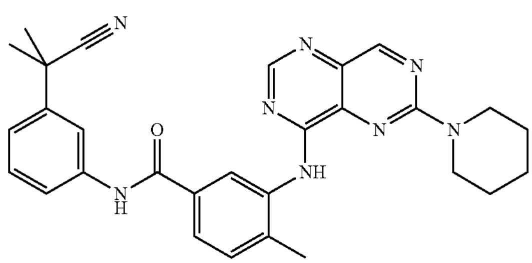 [SMILES: Cc1ccc(C(=O)Nc2cccc(C(C)(C)C#N)c2)cc1Nc1ncnc2cnc(N3CCCCC3)nc12] | 2.00 | 507 |
| III-214 | 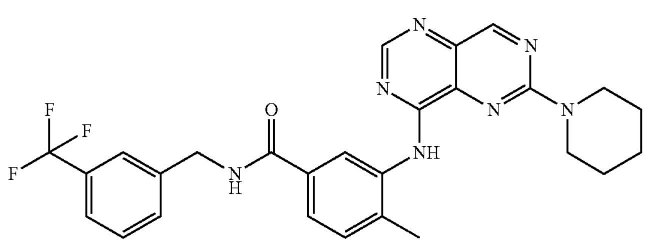 [SMILES: Cc1ccc(C(=O)NCc2cccc(C(F)(F)F)c2)cc1Nc1ncnc2cnc(N3CCCCC3)nc12] | 2.00 | 522 |
| III-215 | 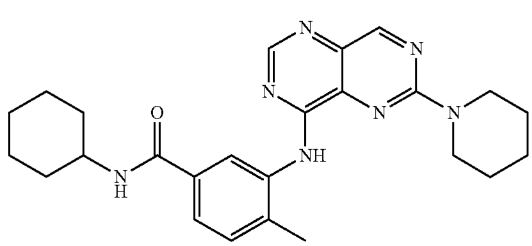 [SMILES: Cc1ccc(C(=O)NC2CCCCC2)cc1Nc1ncnc2cnc(N3CCCCC3)nc12] | 1.92 | 446 |

TABLE 3-continued
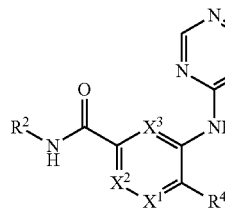
Example Compounds III-1 to III-579
and III-592 to III-608
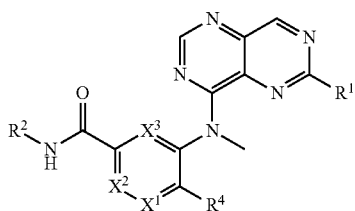
Example Compounds III-580 to III-587
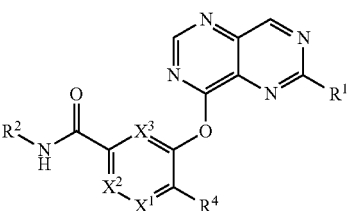
Example Compounds III-588 to III-591
| # | Structure | $t_{Ret.}$ (HPLC) [min] | MS (M + H)$^+$ |
|---|---|---|---|
| III-216 | 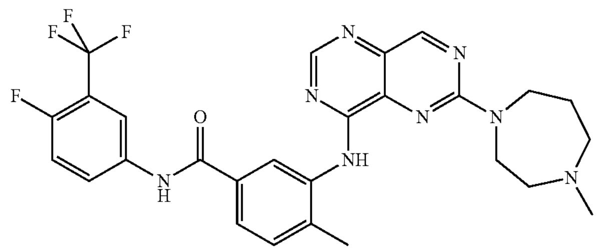 [SMILES: Cc1ccc(C(=O)Nc2ccc(F)c(C(F)(F)F)c2)cc1Nc1ncnc2cnc(N3CCCN(C)CC3)nc12] | 1.64 | 555 |
| III-217 | 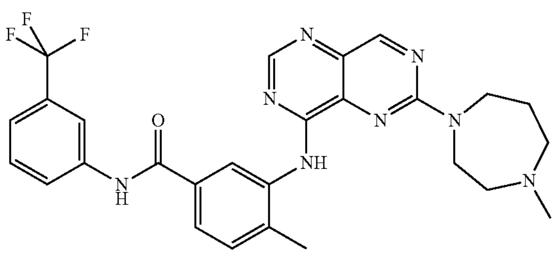 [SMILES: Cc1ccc(C(=O)Nc2cccc(C(F)(F)F)c2)cc1Nc1ncnc2cnc(N3CCCN(C)CC3)nc12] | 1.61 | 537 |
| III-218 | 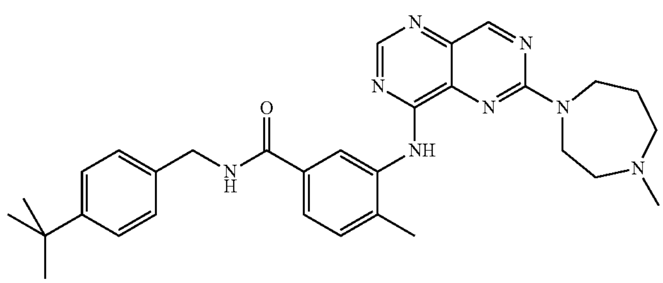 [SMILES: Cc1ccc(C(=O)NCc2ccc(C(C)(C)C)cc2)cc1Nc1ncnc2cnc(N3CCCN(C)CC3)nc12] | 1.65 | 539 |
| III-219 | 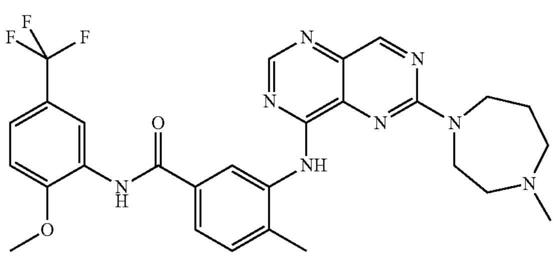 [SMILES: COc1ccc(C(F)(F)F)cc1NC(=O)c1ccc(C)c(Nc2ncnc3cnc(N4CCCN(C)CC4)nc23)c1] | 1.64 | 567 |
| III-220 | 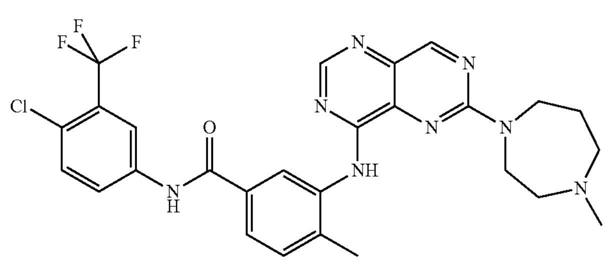 [SMILES: Cc1ccc(C(=O)Nc2ccc(Cl)c(C(F)(F)F)c2)cc1Nc1ncnc2cnc(N3CCCN(C)CC3)nc12] | 1.69 | 571 |

TABLE 3-continued
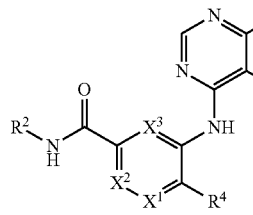
Example Compounds III-1 to III-579
and III-592 to III-608
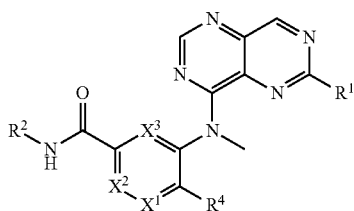
Example Compounds III-580 to III-587
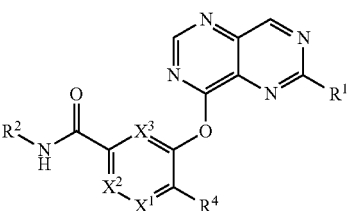
Example Compounds III-588 to III-591
| # | Structure | t$_{Ret.}$ (HPLC) [min] | MS (M + H)$^+$ |
|---|---|---|---|
| III-221 | 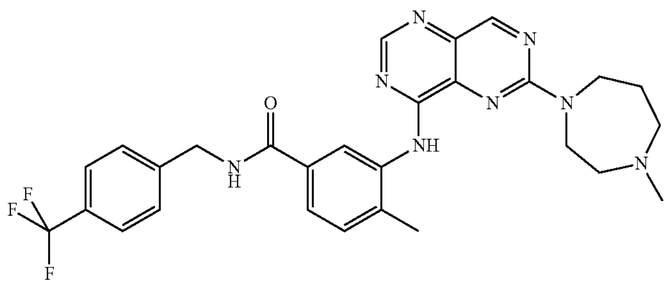 [SMILES: Cc1ccc(C(=O)NCc2ccc(C(F)(F)F)cc2)cc1Nc1ncnc2cnc(N3CCCN(C)CC3)nc12] | 1.57 | 551 |
| III-222 | 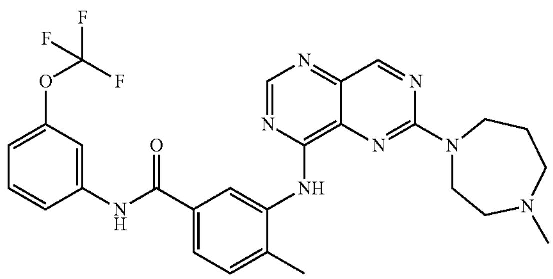 [SMILES: Cc1ccc(C(=O)Nc2cccc(OC(F)(F)F)c2)cc1Nc1ncnc2cnc(N3CCCN(C)CC3)nc12] | 1.64 | 553 |
| III-223 | 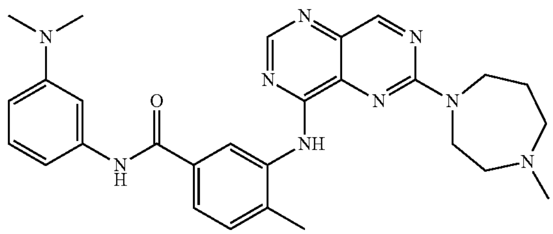 [SMILES: Cc1ccc(C(=O)Nc2cccc(N(C)C)c2)cc1Nc1ncnc2cnc(N3CCCN(C)CC3)nc12] | 1.26 | 256 (M + 2H)$^{2+}$ |
| III-224 | 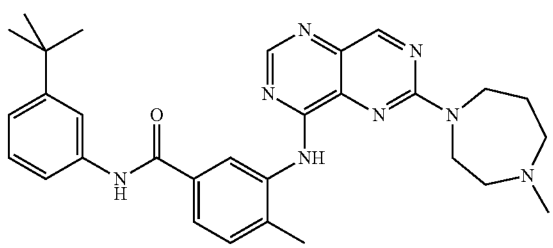 [SMILES: Cc1ccc(C(=O)Nc2cccc(C(C)(C)C)c2)cc1Nc1ncnc2cnc(N3CCCN(C)CC3)nc12] | 1.66 | 525 |
| III-225 | 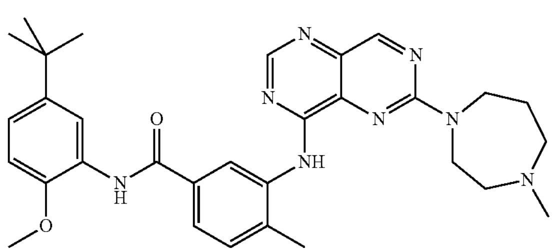 [SMILES: COc1ccc(C(C)(C)C)cc1NC(=O)c1ccc(C)c(Nc2ncnc3cnc(N4CCCN(C)CC4)nc23)c1] | 1.69 | 555 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-226 | 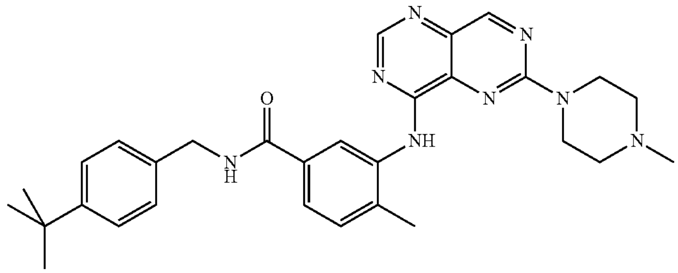 [SMILES: Cc1ccc(C(=O)NCc2ccc(C(C)(C)C)cc2)cc1Nc1ncnc2cnc(N3CCN(C)CC3)nc12] | 1.65 | 525 |
| III-227 | 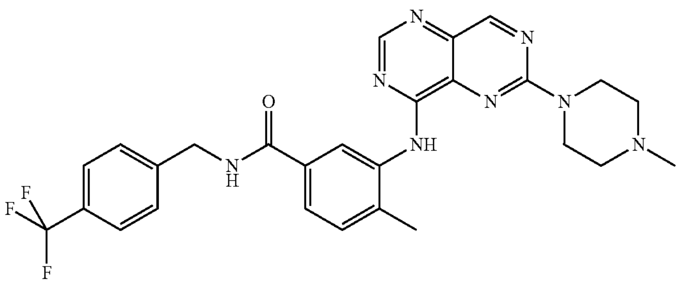 [SMILES: Cc1ccc(C(=O)NCc2ccc(C(F)(F)F)cc2)cc1Nc1ncnc2cnc(N3CCN(C)CC3)nc12] | 1.57 | 537 |
| III-228 | 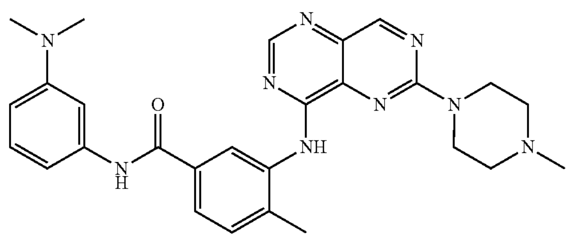 [SMILES: Cc1ccc(C(=O)Nc2cccc(N(C)C)c2)cc1Nc1ncnc2cnc(N3CCN(C)CC3)nc12] | 1.25 | 249 (M + 2H)$^{2+}$ |
| III-229 | 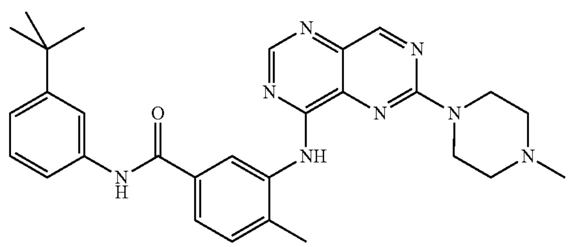 [SMILES: Cc1ccc(C(=O)Nc2cccc(C(C)(C)C)c2)cc1Nc1ncnc2cnc(N3CCN(C)CC3)nc12] | 1.67 | 511 |
| III-230 | 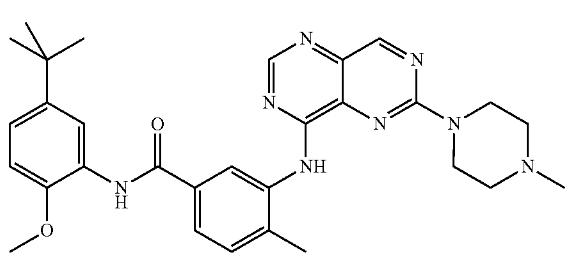 [SMILES: COc1ccc(C(C)(C)C)cc1NC(=O)c1ccc(C)c(Nc2ncnc3cnc(N4CCN(C)CC4)nc23)c1] | 1.69 | 541 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-231 | 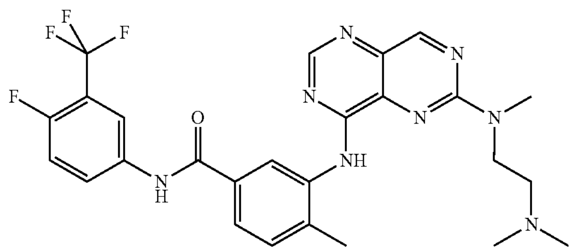 [SMILES: Cc1ccc(C(=O)Nc2ccc(F)c(C(F)(F)F)c2)cc1Nc1ncnc2cnc(N(C)CCN(C)C)nc12] | 1.65 | 543 |
| III-232 | 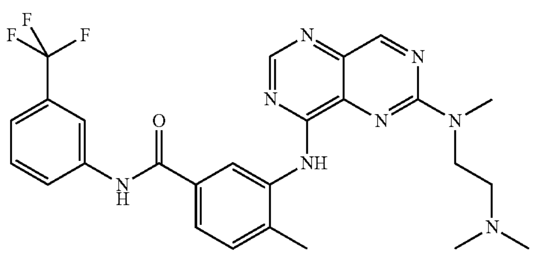 [SMILES: Cc1ccc(C(=O)Nc2cccc(C(F)(F)F)c2)cc1Nc1ncnc2cnc(N(C)CCN(C)C)nc12] | 1.62 | 525 |
| III-233 | 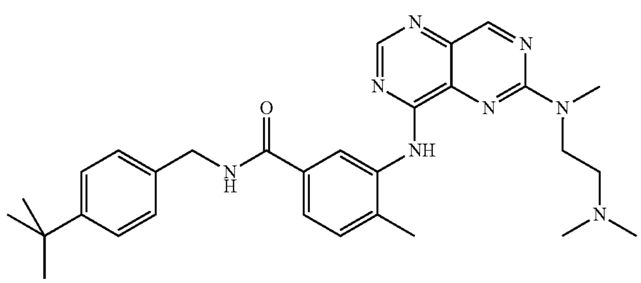 [SMILES: Cc1ccc(C(=O)NCc2ccc(C(C)(C)C)cc2)cc1Nc1ncnc2cnc(N(C)CCN(C)C)nc12] | 1.66 | 527 |
| III-234 | 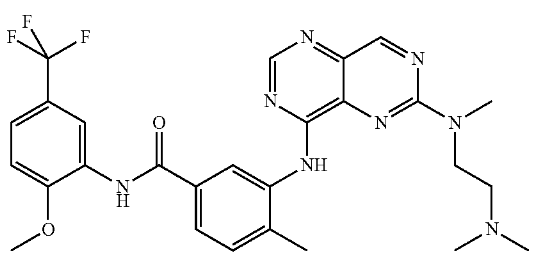 [SMILES: COc1ccc(C(F)(F)F)cc1NC(=O)c1ccc(C)c(Nc2ncnc3cnc(N(C)CCN(C)C)nc23)c1] | 1.65 | 555 |
| III-235 | 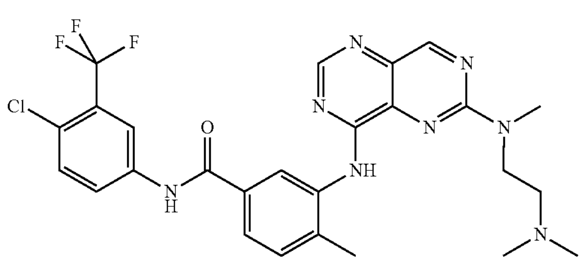 [SMILES: Cc1ccc(C(=O)Nc2ccc(Cl)c(C(F)(F)F)c2)cc1Nc1ncnc2cnc(N(C)CCN(C)C)nc12] | 1.71 | 559 |

TABLE 3-continued
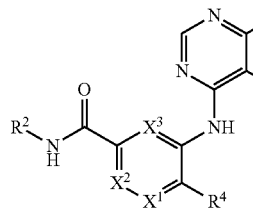
Example Compounds III-1 to III-579
and III-592 to III-608
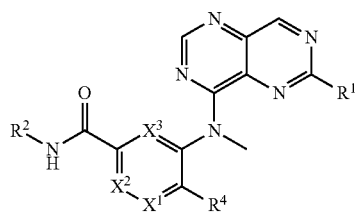
Example Compounds III-580 to III-587
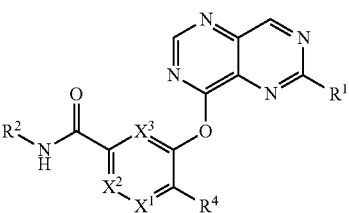
Example Compounds III-588 to III-591
| # | Structure | t$_{Ret.}$ (HPLC) [min] | MS (M + H)$^+$ |
|---|---|---|---|
| III-236 | 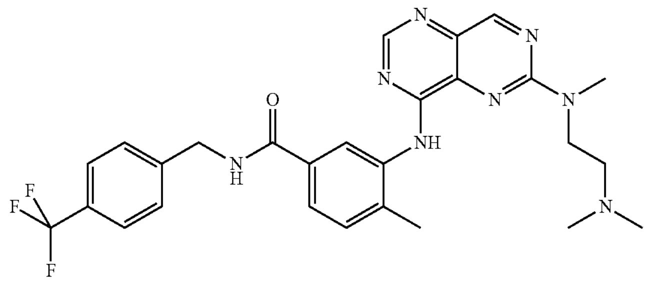 [SMILES: Cc1ccc(C(=O)NCc2ccc(C(F)(F)F)cc2)cc1Nc1ncnc2cnc(N(C)CCN(C)C)nc12] | 1.58 | 539 |
| III-237 | 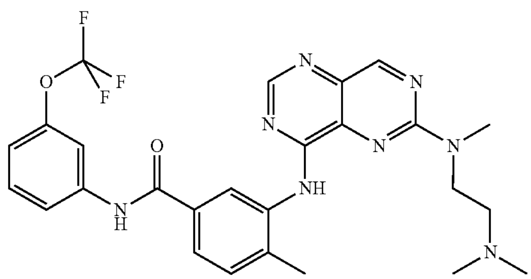 [SMILES: Cc1ccc(C(=O)Nc2cccc(OC(F)(F)F)c2)cc1Nc1ncnc2cnc(N(C)CCN(C)C)nc12] | 1.65 | 541 |
| III-238 | 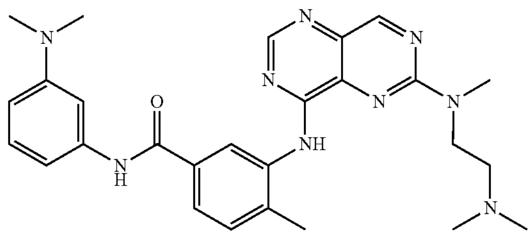 [SMILES: Cc1ccc(C(=O)Nc2cccc(N(C)C)c2)cc1Nc1ncnc2cnc(N(C)CCN(C)C)nc12] | 1.27 | 500 |
| III-239 | 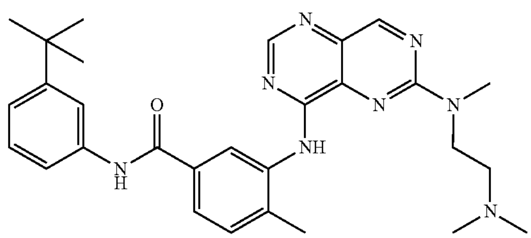 [SMILES: Cc1ccc(C(=O)Nc2cccc(C(C)(C)C)c2)cc1Nc1ncnc2cnc(N(C)CCN(C)C)nc12] | 1.68 | 513 |
| III-240 | 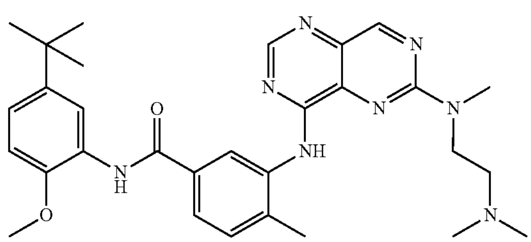 [SMILES: COc1ccc(C(C)(C)C)cc1NC(=O)c1ccc(C)c(Nc2ncnc3cnc(N(C)CCN(C)C)nc23)c1] | 1.70 | 543 |

US 8,653,087 B2
TABLE 3-continued
Example Compounds III-1 to III-579 and III-592 to III-608
Example Compounds III-580 to III-587
Example Compounds III-588 to III-591
| # | Structure | $t_{Ret.}$ (HPLC) [min] | MS (M + H)+ |
|---|---|---|---|
| III-241 | 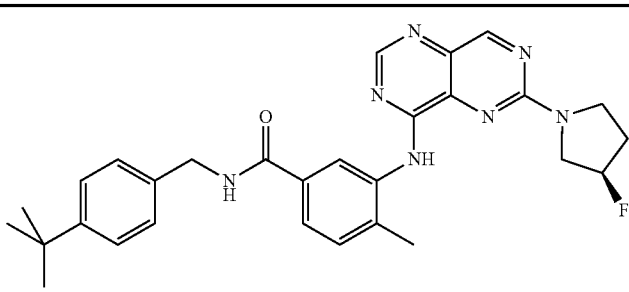 | 2.00 | 514 |
| III-242 | 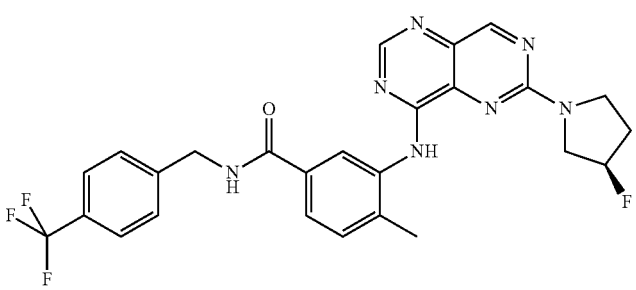 [SMILES: Cc1ccc(C(=O)NCc2ccc(C(F)(F)F)cc2)cc1Nc1ncnc2cnc(N3CC[C@@H](F)C3)nc12] | 1.90 | 526 |
| III-243 | 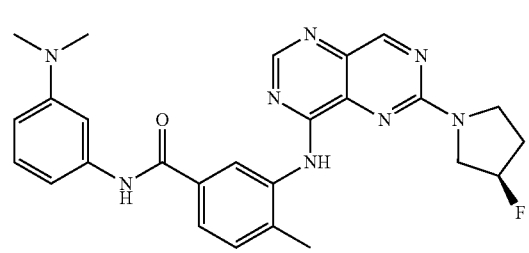 [SMILES: Cc1ccc(C(=O)Nc2cccc(N(C)C)c2)cc1Nc1ncnc2cnc(N3CC[C@@H](F)C3)nc12] | 1.47 | 244 (M + 2H)²⁺ |
| III-244 | 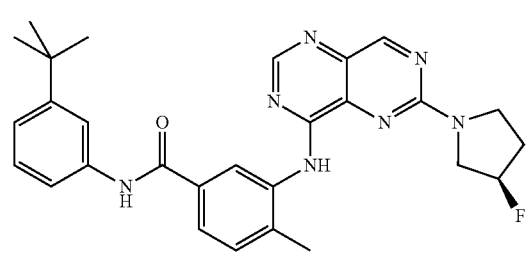 [SMILES: Cc1ccc(C(=O)Nc2cccc(C(C)(C)C)c2)cc1Nc1ncnc2cnc(N3CC[C@@H](F)C3)nc12] | 2.04 | 500 |

TABLE 3-continued
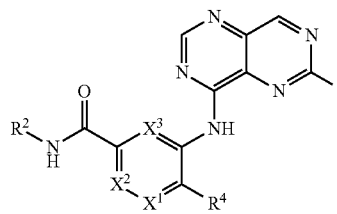
Example Compounds III-1 to III-579
and III-592 to III-608
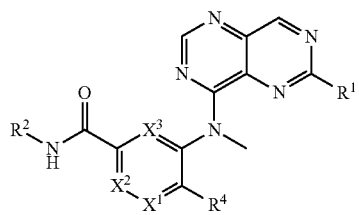
Example Compounds III-580 to III-587
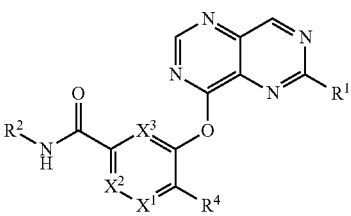
Example Compounds III-588 to III-591
| # | Structure | $t_{Ret.}$ (HPLC) [min] | MS (M + H)$^+$ |
|---|---|---|---|
| III-245 | 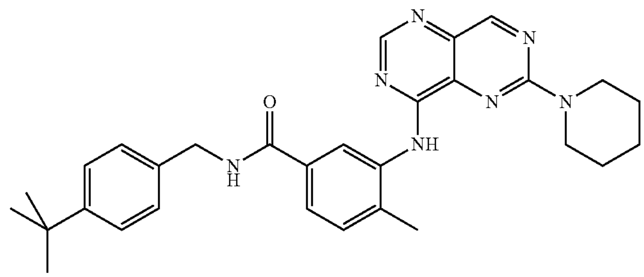 [SMILES: Cc1ccc(C(=O)NCc2ccc(C(C)(C)C)cc2)cc1Nc1ncnc2cnc(N3CCCCC3)nc12] | 2.12 | 510 |
| III-246 | 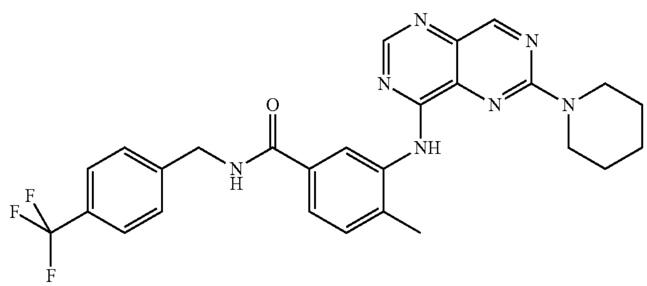 [SMILES: Cc1ccc(C(=O)NCc2ccc(C(F)(F)F)cc2)cc1Nc1ncnc2cnc(N3CCCCC3)nc12] | 2.01 | 522 |
| III-247 | 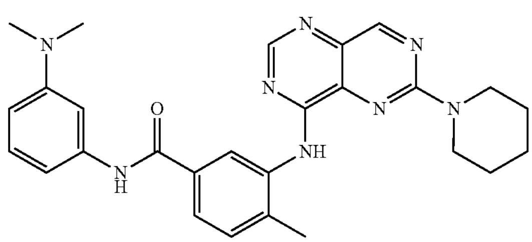 [SMILES: Cc1ccc(C(=O)Nc2cccc(N(C)C)c2)cc1Nc1ncnc2cnc(N3CCCCC3)nc12] | 1.58 | 242 (M + 2H)$^{2+}$ |
| III-248 | 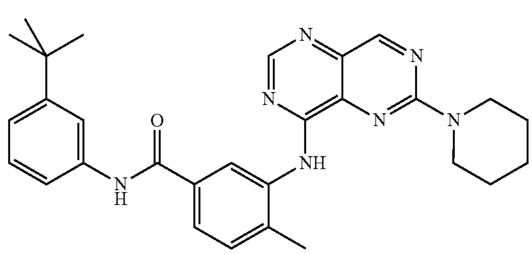 [SMILES: Cc1ccc(C(=O)Nc2cccc(C(C)(C)C)c2)cc1Nc1ncnc2cnc(N3CCCCC3)nc12] | 2.16 | 496 |
| III-249 | 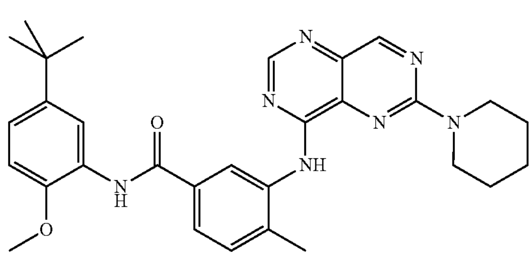 [SMILES: COc1ccc(C(C)(C)C)cc1NC(=O)c1ccc(C)c(Nc2ncnc3cnc(N4CCCCC4)nc23)c1] | 2.26 | 526 |

TABLE 3-continued
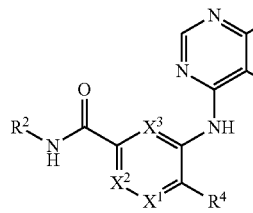
Example Compounds III-1 to III-579
and III-592 to III-608
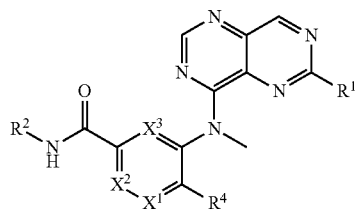
Example Compounds III-580 to III-587
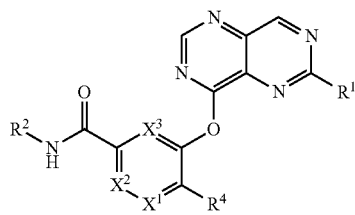
Example Compounds III-588 to III-591
| # | Structure | t$_{Ret.}$ (HPLC) [min] | MS (M + H)$^+$ |
|---|---|---|---|
| III-250 | 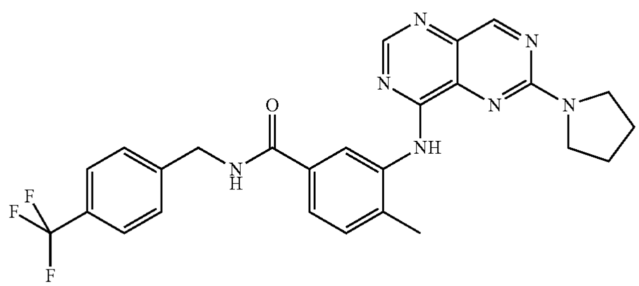 [SMILES: Cc1ccc(C(=O)NCc2ccc(C(F)(F)F)cc2)cc1Nc1ncnc2cnc(N3CCCC3)nc12] | 1.93 | 508 |
| III-251 | 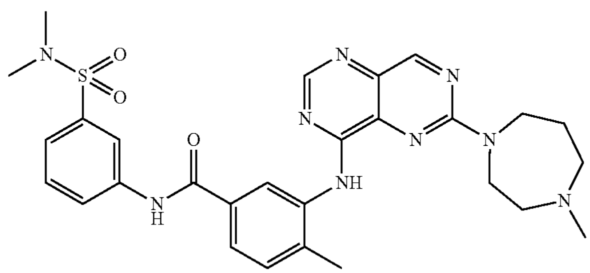 | 1.49 | 576 |
| III-252 | 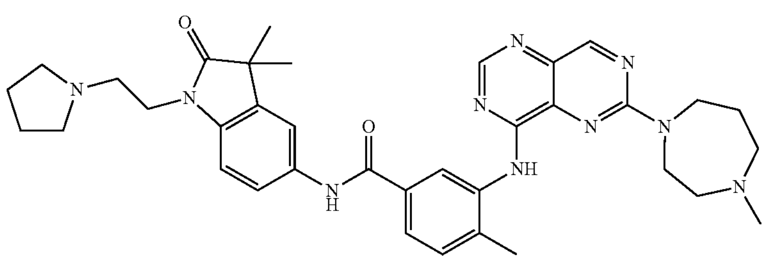 [SMILES: Cc1ccc(C(=O)Nc2ccc3c(c2)C(C)(C)C(=O)N3CCN2CCCC2)cc1Nc1ncnc2cnc(N3CCCN(C)CC3)nc12] | 1.32 | 325 (M + 2H)$^{2+}$ |
| III-253 | 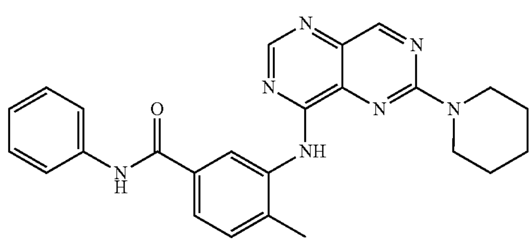 [SMILES: Cc1ccc(C(=O)Nc2ccccc2)cc1Nc1ncnc2cnc(N3CCCCC3)nc12] | 1.92 | 440 |
| III-254 | 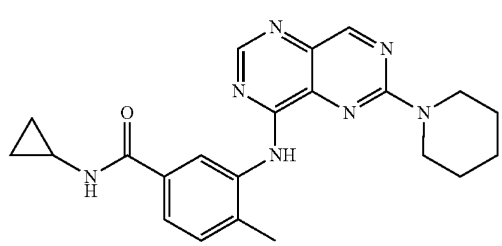 [SMILES: Cc1ccc(C(=O)NC2CC2)cc1Nc1ncnc2cnc(N3CCCCC3)nc12] | 1.71 | 404 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-255 | 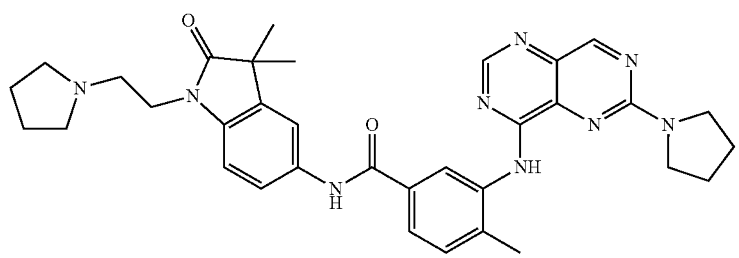 [SMILES: Cc1ccc(C(=O)Nc2ccc3c(c2)C(C)(C)C(=O)N3CCN2CCCC2)cc1Nc1ncnc2cnc(N3CCCC3)nc12] | 1.55 | 303 (M + 2H)2+ |
| III-256 | 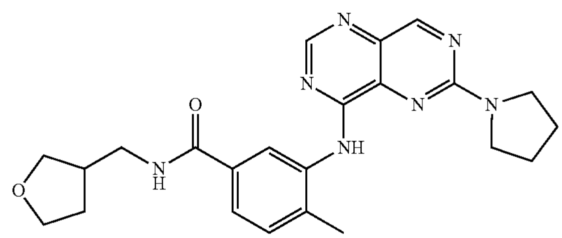 [SMILES: Cc1ccc(C(=O)NCC2CCOC2)cc1Nc1ncnc2cnc(N3CCCC3)nc12] | 1.58 | 434 |
| III-257 | 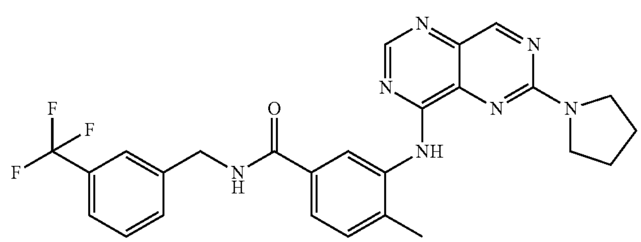 [SMILES: Cc1ccc(C(=O)NCc2cccc(C(F)(F)F)c2)cc1Nc1ncnc2cnc(N3CCCC3)nc12] | 2.04 | 508 |
| III-258 | 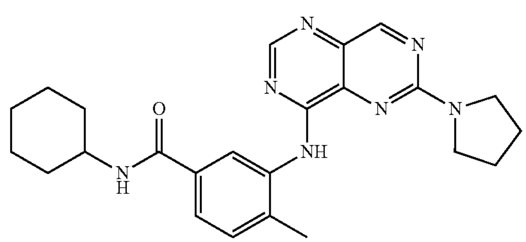 [SMILES: Cc1ccc(C(=O)NC2CCCCC2)cc1Nc1ncnc2cnc(N3CCCC3)nc12] | 1.94 | 432 |
| III-259 | 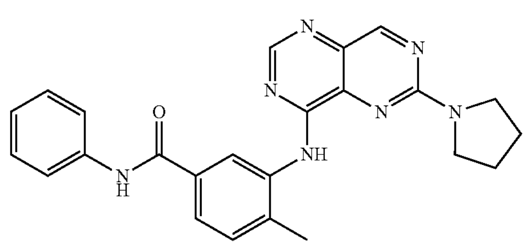 [SMILES: Cc1ccc(C(=O)Nc2ccccc2)cc1Nc1ncnc2cnc(N3CCCC3)nc12] | 1.95 | 426 |

TABLE 3-continued
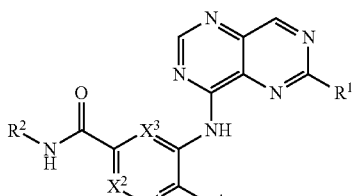
Example Compounds III-1 to III-579 and III-592 to III-608
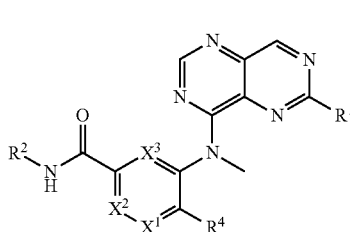
Example Compounds III-580 to III-587
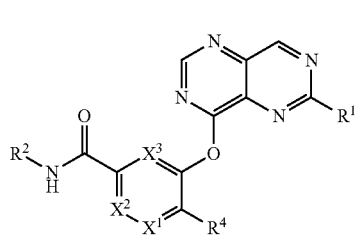
Example Compounds III-588 to III-591
| # | Structure | $t_{Ret.}$ (HPLC) [min] | MS (M + H)$^+$ |
|---|---|---|---|
| III-260 | 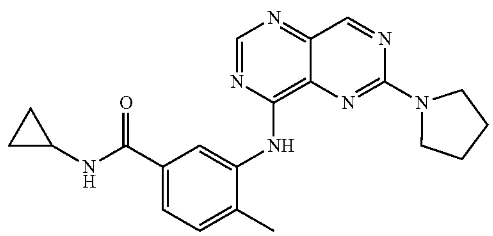 [SMILES: Cc1ccc(C(=O)NC2CC2)cc1Nc1ncnc2cnc(N3CCCC3)nc12] | 1.72 | 390 |
| III-261 | 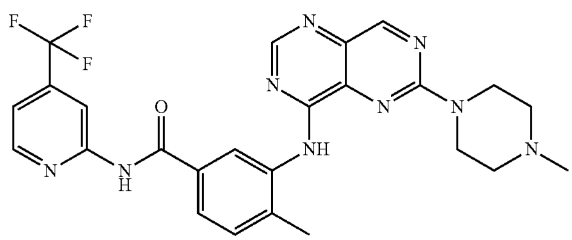 [SMILES: Cc1ccc(C(=O)Nc2cc(C(F)(F)F)ccn2)cc1Nc1ncnc2cnc(N3CCN(C)CC3)nc12] | 1.81 | 524 |
| III-262 | 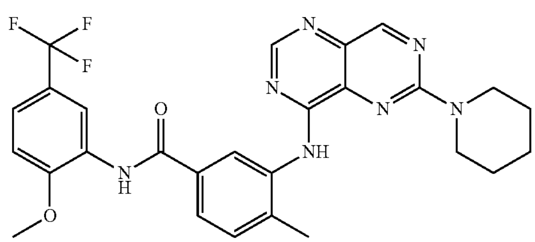 [SMILES: COc1ccc(C(F)(F)F)cc1NC(=O)c1ccc(C)c(Nc2ncnc3cnc(N4CCCCC4)nc23)c1] | 2.40 | 538 |
| III-263 | 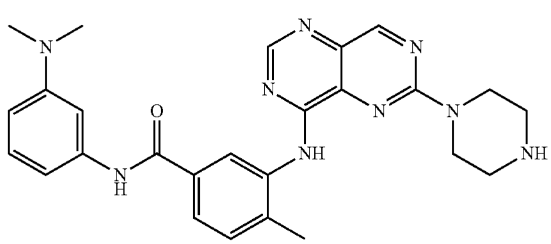 [SMILES: Cc1ccc(C(=O)Nc2cccc(N(C)C)c2)cc1Nc1ncnc2cnc(N3CCNCC3)nc12] | 1.12 | 484 |
| III-264 | 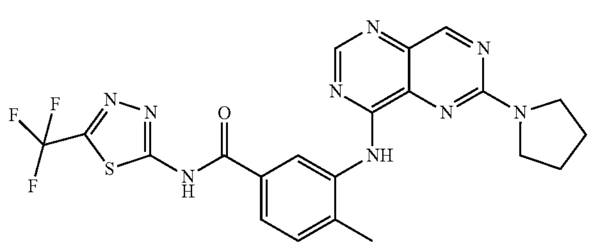 [SMILES: Cc1ccc(C(=O)Nc2nnc(C(F)(F)F)s2)cc1Nc1ncnc2cnc(N3CCCC3)nc12] | 2.13 | 502 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-265 | 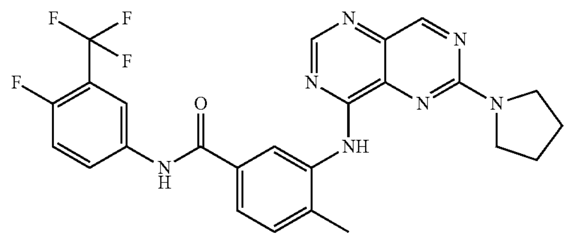 [SMILES: Cc1ccc(C(=O)Nc2ccc(F)c(C(F)(F)F)c2)cc1Nc1ncnc2cnc(N3CCCC3)nc12] | 2.17 | 512 |
| III-266 | 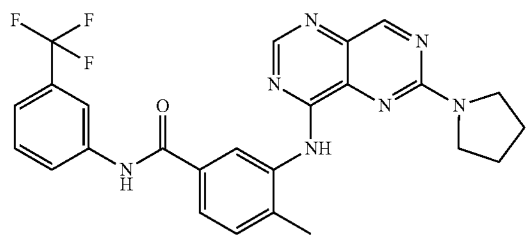 [SMILES: Cc1ccc(C(=O)Nc2cccc(C(F)(F)F)c2)cc1Nc1ncnc2cnc(N3CCCC3)nc12] | 2.14 | 494 |
| III-267 | 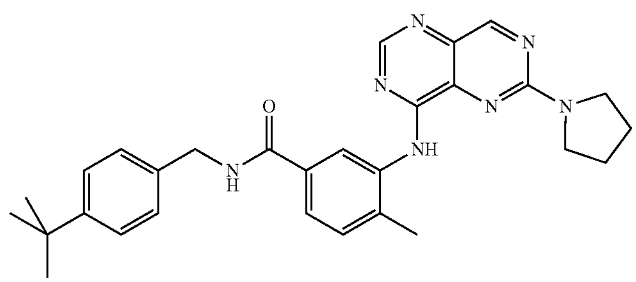 [SMILES: Cc1ccc(C(=O)NCc2ccc(C(C)(C)C)cc2)cc1Nc1ncnc2cnc(N3CCCC3)nc12] | 2.16 | 496 |
| III-268 | 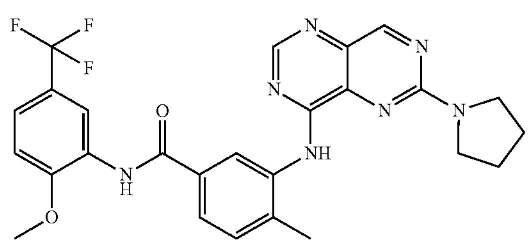 [SMILES: COc1ccc(C(F)(F)F)cc1NC(=O)c1ccc(C)c(Nc2ncnc3cnc(N4CCCC4)nc23)c1] | 2.22 | 524 |
| III-269 | 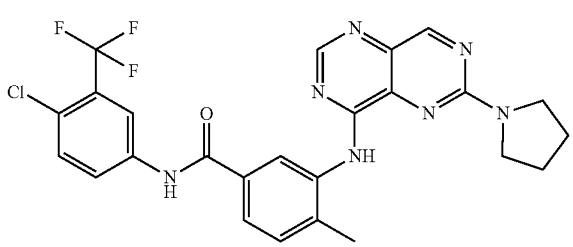 [SMILES: Cc1ccc(C(=O)Nc2ccc(Cl)c(C(F)(F)F)c2)cc1Nc1ncnc2cnc(N3CCCC3)nc12] | 2.24 | 528 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-270 | 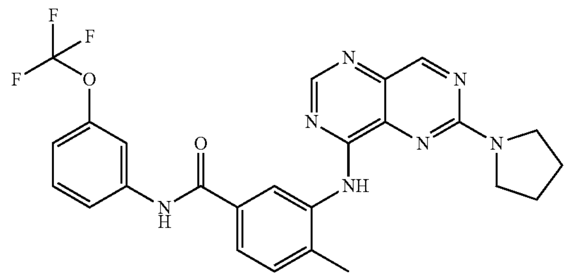 [SMILES: Cc1ccc(C(=O)Nc2cccc(OC(F)(F)F)c2)cc1Nc1ncnc2cnc(N3CCCC3)nc12] | 2.17 | 510 |
| III-271 | 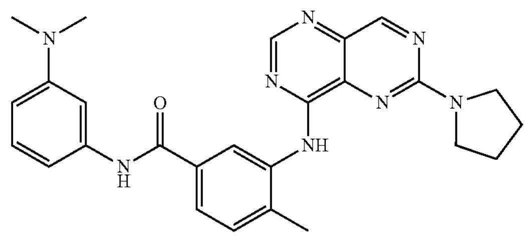 [SMILES: Cc1ccc(C(=O)Nc2cccc(N(C)C)c2)cc1Nc1ncnc2cnc(N3CCCC3)nc12] | 1.68 | 469 |
| III-272 | 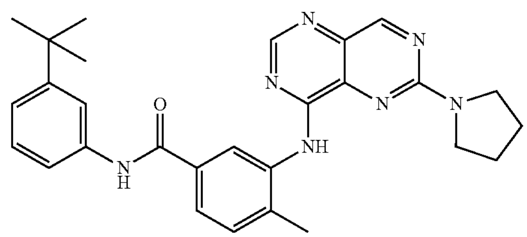 [SMILES: Cc1ccc(C(=O)Nc2cccc(C(C)(C)C)c2)cc1Nc1ncnc2cnc(N3CCCC3)nc12] | 2.20 | 482 |
| III-273 | 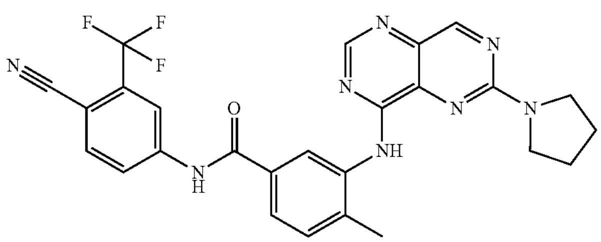 [SMILES: Cc1ccc(C(=O)Nc2ccc(C#N)c(C(F)(F)F)c2)cc1Nc1ncnc2cnc(N3CCCC3)nc12] | 2.16 | 519 |
| III-274 | 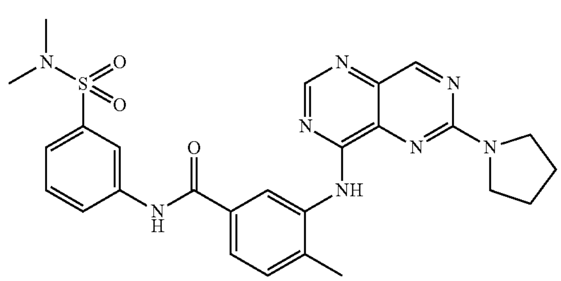 [SMILES: Cc1ccc(C(=O)Nc2cccc(S(=O)(=O)N(C)C)c2)cc1Nc1ncnc2cnc(N3CCCC3)nc12] | 1.95 | 533 |

TABLE 3-continued
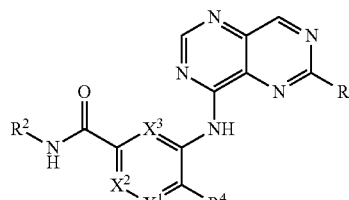
Example Compounds III-1 to III-579
and III-592 to III-608
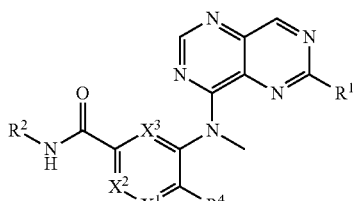
Example Compounds III-580 to III-587
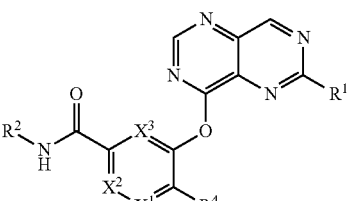
Example Compounds III-588 to III-591
| # | Structure | t_Ret. (HPLC) [min] | MS (M + H)+ |
|---|---|---|---|
| III-275 | 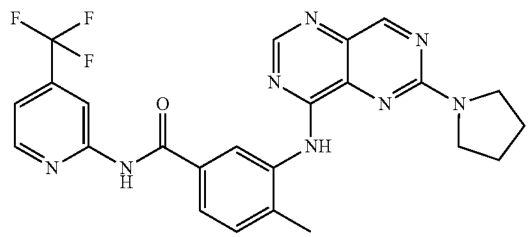 | 2.10 | 495 |
| III-276 | 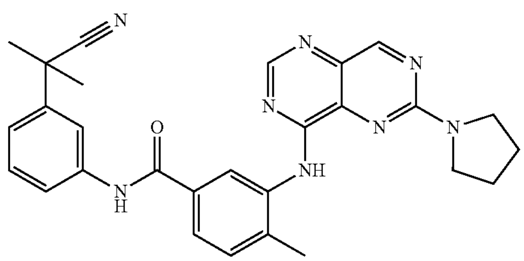 [SMILES: Cc1ccc(C(=O)Nc2cccc(C(C)(C)C#N)c2)cc1Nc1ncnc2cnc(N3CCCC3)nc12] | 2.03 | 493 |
| III-277 | 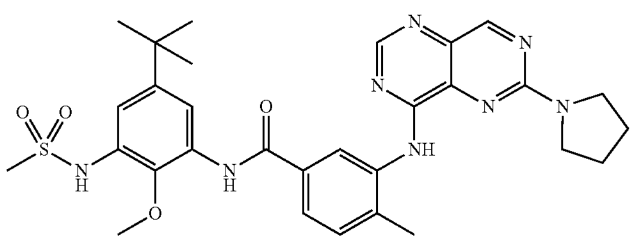 [SMILES: COc1c(NC(=O)c2ccc(C)c(Nc3ncnc4cnc(N5CCCC5)nc34)c2)cc(C(C)(C)C)cc1NS(C)(=O)=O] | 2.08 | 605 |
| III-278 | 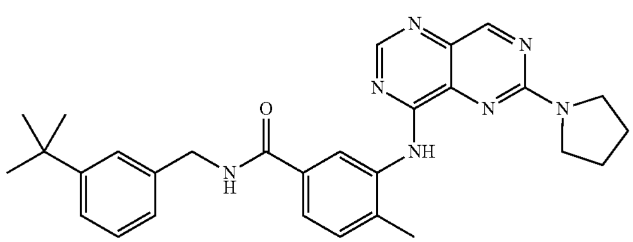 [SMILES: Cc1ccc(C(=O)NCc2cccc(C(C)(C)C)c2)cc1Nc1ncnc2cnc(N3CCCC3)nc12] | 2.15 | 496 |
| III-279 | 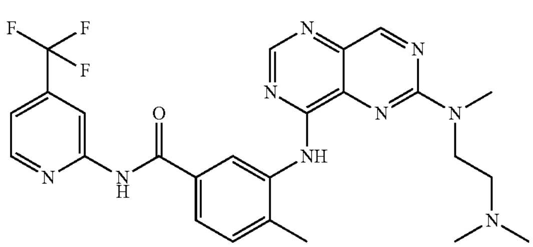 [SMILES: Cc1ccc(C(=O)Nc2cc(C(F)(F)F)ccn2)cc1Nc1ncnc2cnc(N(C)CCN(C)C)nc12] | 1.50 | 526 |

TABLE 3-continued
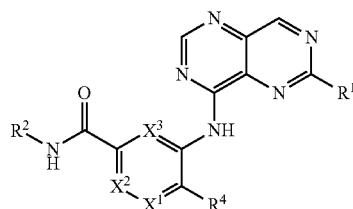
Example Compounds III-1 to III-579 and III-592 to III-608
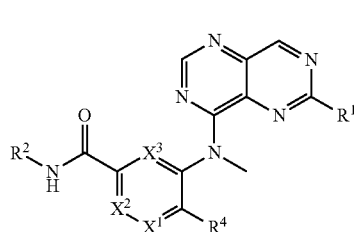
Example Compounds III-580 to III-587
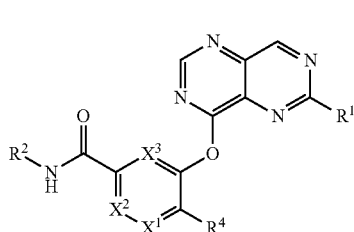
Example Compounds III-588 to III-591
| # | Structure | $t_{Ret.}$ (HPLC) [min] | MS (M + H)⁺ |
|---|---|---|---|
| III-280 | 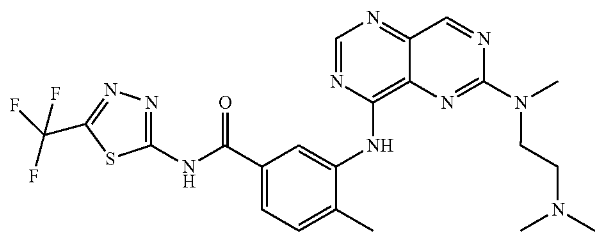 [SMILES: Cc1ccc(C(=O)Nc2nnc(C(F)(F)F)s2)cc1Nc1ncnc2cnc(N(C)CCN(C)C)nc12] | 1.79 | 533 |
| III-281 | 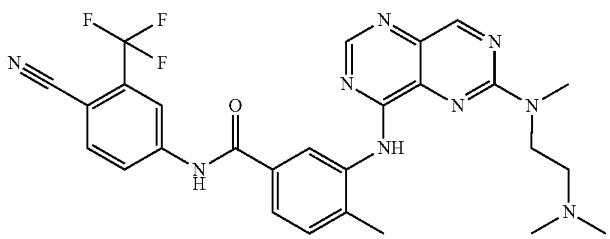 [SMILES: Cc1ccc(C(=O)Nc2ccc(C#N)c(C(F)(F)F)c2)cc1Nc1ncnc2cnc(N(C)CCN(C)C)nc12] | 1.76 | 550 |
| III-282 | 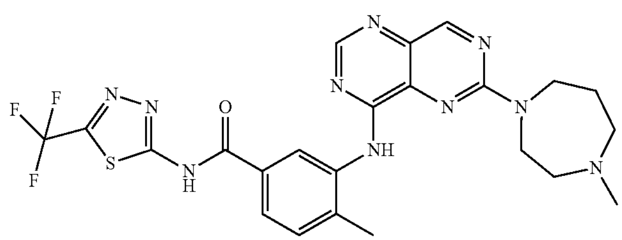 [SMILES: Cc1ccc(C(=O)Nc2nnc(C(F)(F)F)s2)cc1Nc1ncnc2cnc(N3CCCN(C)CC3)nc12] | 1.82 | 545 |
| III-283 | 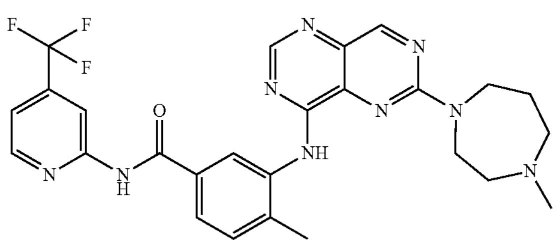 [SMILES: Cc1ccc(C(=O)Nc2cc(C(F)(F)F)ccn2)cc1Nc1ncnc2cnc(N3CCCN(C)CC3)nc12] | 1.75 | 538 |
| III-284 | 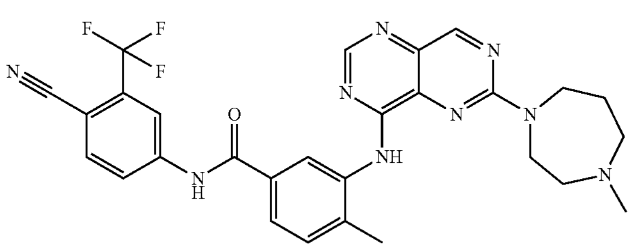 [SMILES: Cc1ccc(C(=O)Nc2ccc(C#N)c(C(F)(F)F)c2)cc1Nc1ncnc2cnc(N3CCCN(C)CC3)nc12] | 1.80 | 562 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-285 | 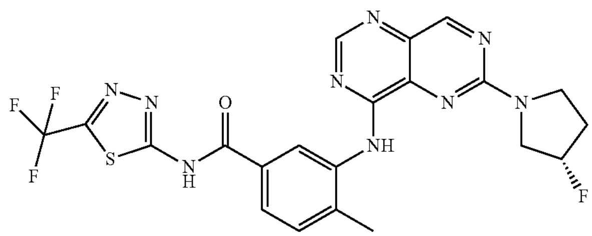 [SMILES: Cc1ccc(C(=O)Nc2nnc(C(F)(F)F)s2)cc1Nc1ncnc2cnc(N3CC[C@H](F)C3)nc12] | 1.80 | 520 |
| III-286 | 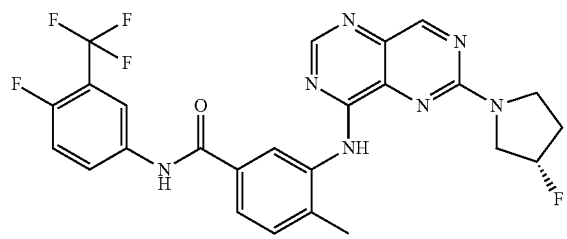 [SMILES: Cc1ccc(C(=O)Nc2ccc(F)c(C(F)(F)F)c2)cc1Nc1ncnc2cnc(N3CC[C@H](F)C3)nc12] | 1.87 | 530 |
| III-287 | 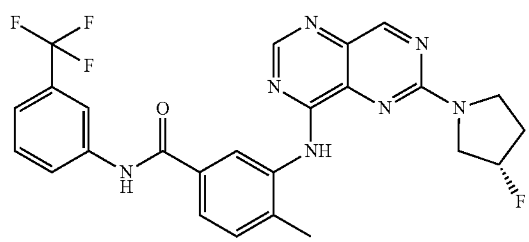 [SMILES: Cc1ccc(C(=O)Nc2cccc(C(F)(F)F)c2)cc1Nc1ncnc2cnc(N3CC[C@H](F)C3)nc12] | 1.82 | 512 |
| III-288 | 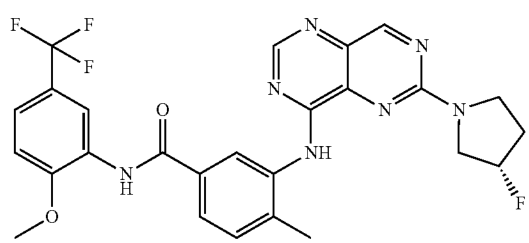 [SMILES: COc1ccc(C(F)(F)F)cc1NC(=O)c1ccc(C)c(Nc2ncnc3cnc(N4CC[C@H](F)C4)nc23)c1] | 1.92 | 542 |
| III-289 | 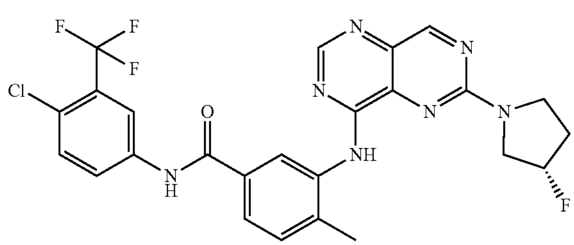 [SMILES: Cc1ccc(C(=O)Nc2ccc(Cl)c(C(F)(F)F)c2)cc1Nc1ncnc2cnc(N3CC[C@H](F)C3)nc12] | 1.95 | 546 |

US 8,653,087 B2

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-290 | 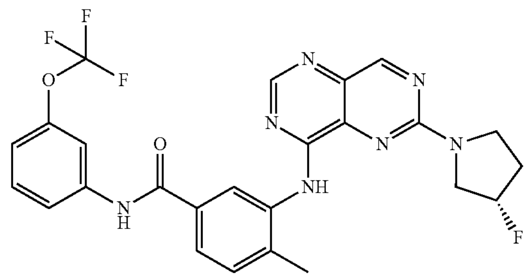 [SMILES: Cc1ccc(C(=O)Nc2cccc(OC(F)(F)F)c2)cc1Nc1ncnc2cnc(N3CC[C@H](F)C3)nc12] | 1.88 | 528 |
| III-291 | 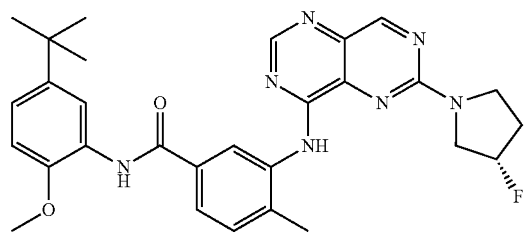 [SMILES: COc1ccc(C(C)(C)C)cc1NC(=O)c1ccc(C)c(Nc2ncnc3cnc(N4CC[C@H](F)C4)nc23)c1] | 2.02 | 530 |
| III-292 | 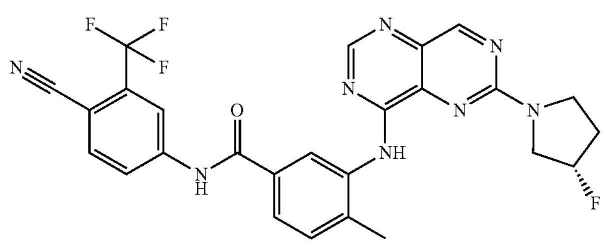 [SMILES: Cc1ccc(C(=O)Nc2ccc(C#N)c(C(F)(F)F)c2)cc1Nc1ncnc2cnc(N3CC[C@H](F)C3)nc12] | 1.85 | 537 |
| III-293 | 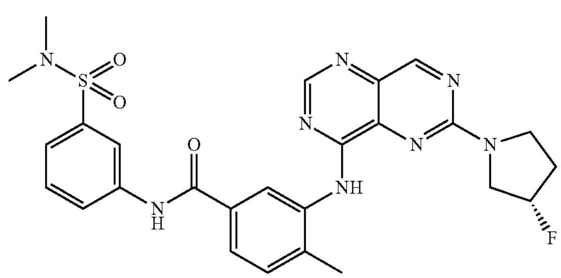 [SMILES: Cc1ccc(C(=O)Nc2cccc(S(=O)(=O)N(C)C)c2)cc1Nc1ncnc2cnc(N3CC[C@H](F)C3)nc12] | 1.67 | 551 |
| III-294 | 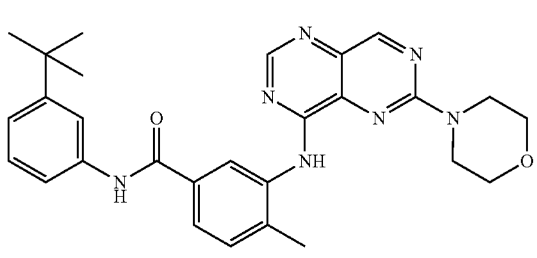 [SMILES: Cc1ccc(C(=O)Nc2cccc(C(C)(C)C)c2)cc1Nc1ncnc2cnc(N3CCOCC3)nc12] | 1.88 | 498 |

TABLE 3-continued
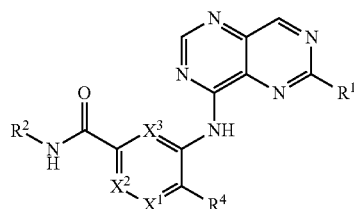
Example Compounds III-1 to III-579 and III-592 to III-608
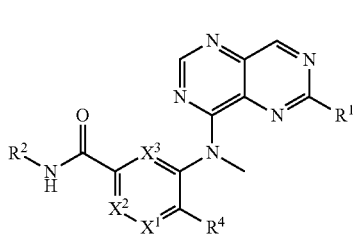
Example Compounds III-580 to III-587
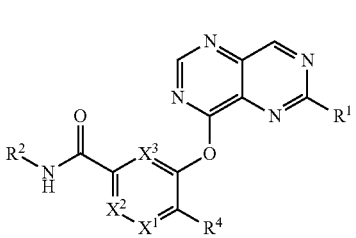
Example Compounds III-588 to III-591
| # | Structure | $t_{Ret.}$ (HPLC) [min] | MS (M + H)$^+$ |
|---|---|---|---|
| III-295 | 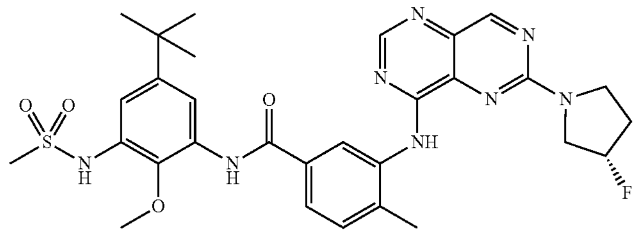 [SMILES: COc1c(NC(=O)c2ccc(C)c(Nc3ncnc4cnc(N5CC[C@H](F)C5)nc34)c2)cc(C(C)(C)C)cc1NS(C)(=O)=O] | 2.10 | 623 |
| III-296 | 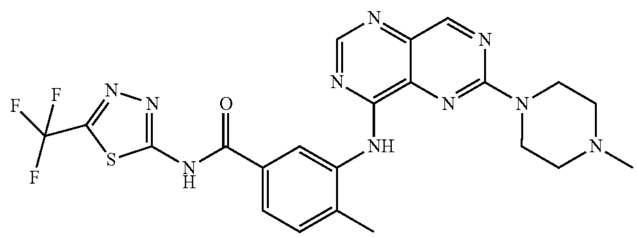 [SMILES: Cc1ccc(C(=O)Nc2nnc(C(F)(F)F)s2)cc1Nc1ncnc2cnc(N3CCN(C)CC3)nc12] | 1.46 | 531 |
| III-297 | 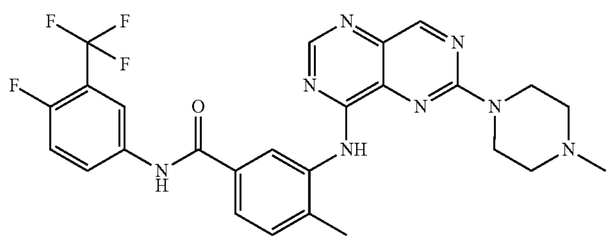 [SMILES: Cc1ccc(C(=O)Nc2ccc(F)c(C(F)(F)F)c2)cc1Nc1ncnc2cnc(N3CCN(C)CC3)nc12] | 1.55 | 541 |
| III-298 | 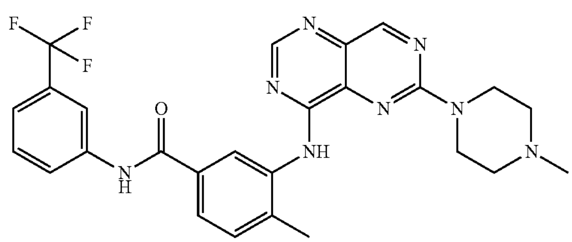 [SMILES: Cc1ccc(C(=O)Nc2cccc(C(F)(F)F)c2)cc1Nc1ncnc2cnc(N3CCN(C)CC3)nc12] | 1.53 | 523 |
| III-299 | 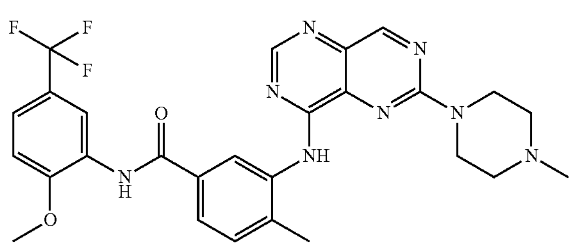 [SMILES: COc1ccc(C(F)(F)F)cc1NC(=O)c1ccc(C)c(Nc2ncnc3cnc(N4CCN(C)CC4)nc23)c1] | 1.56 | 553 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)⁺ |
|---|---|---|---|
| III-300 | 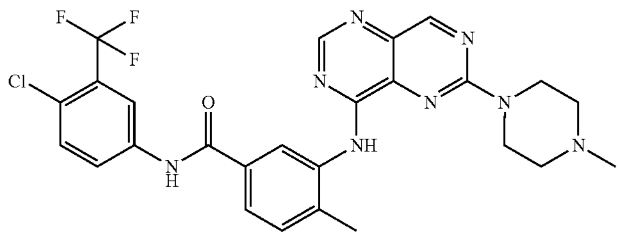 [SMILES: Cc1ccc(C(=O)Nc2ccc(Cl)c(C(F)(F)F)c2)cc1Nc1ncnc2cnc(N3CCN(C)CC3)nc12] | 1.62 | 557 |
| III-301 | 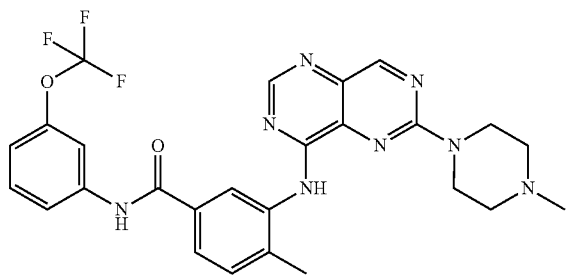 [SMILES: Cc1ccc(C(=O)Nc2cccc(OC(F)(F)F)c2)cc1Nc1ncnc2cnc(N3CCN(C)CC3)nc12] | 1.56 | 539 |
| III-302 | 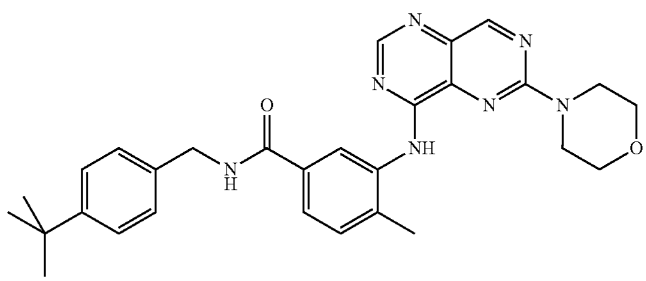 [SMILES: Cc1ccc(C(=O)NCc2ccc(C(C)(C)C)cc2)cc1Nc1ncnc2cnc(N3CCOCC3)nc12] | 1.85 | 512 |
| III-303 | 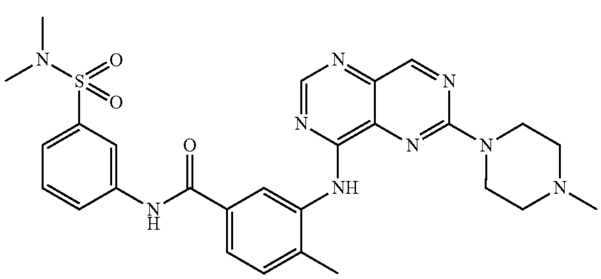 | 1.37 | 562 |
| III-304 | 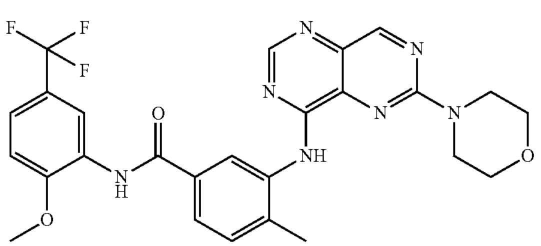 [SMILES: COc1ccc(C(F)(F)F)cc1NC(=O)c1ccc(C)c(Nc2ncnc3cnc(N4CCOCC4)nc23)c1] | 1.87 | 540 |

TABLE 3-continued
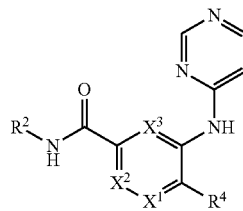
Example Compounds III-1 to III-579 and III-592 to III-608
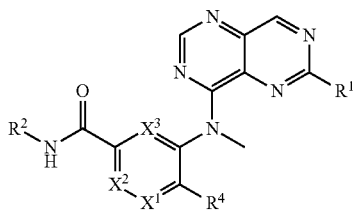
Example Compounds III-580 to III-587
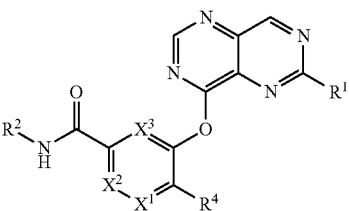
Example Compounds III-588 to III-591
| # | Structure | t$_{Ret.}$ (HPLC) [min] | MS (M + H)$^+$ |
|---|---|---|---|
| III-305 | 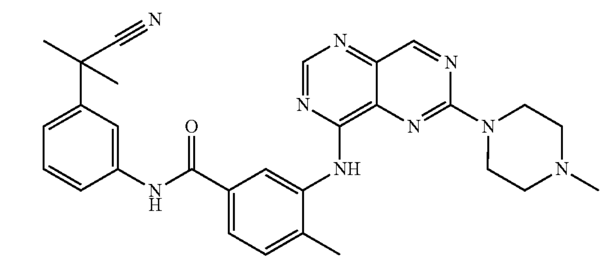 [SMILES: Cc1ccc(C(=O)Nc2cccc(C(C)(C)C#N)c2)cc1Nc1ncnc2cnc(N3CCN(C)CC3)nc12] | 1.45 | 522 |
| III-306 | 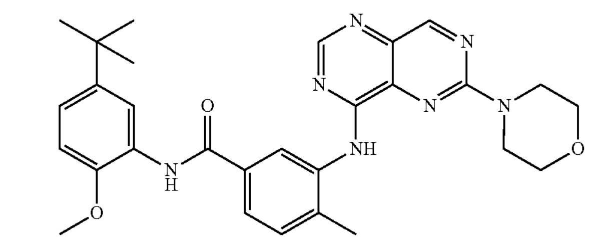 [SMILES: COc1ccc(C(C)(C)C)cc1NC(=O)c1ccc(C)c(Nc2ncnc3cnc(N4CCOCC4)nc23)c1] | 1.97 | 528 |
| III-307 | 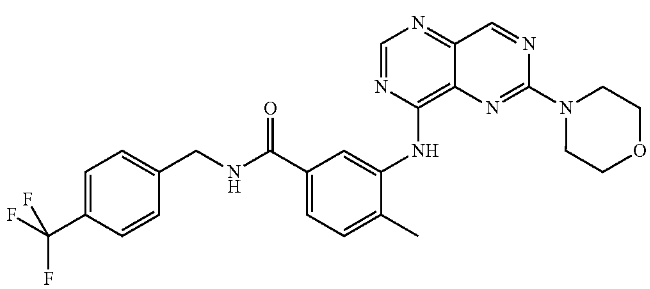 [SMILES: Cc1ccc(C(=O)NCc2ccc(C(F)(F)F)cc2)cc1Nc1ncnc2cnc(N3CCOCC3)nc12] | 1.72 | 524 |
| III-308 | 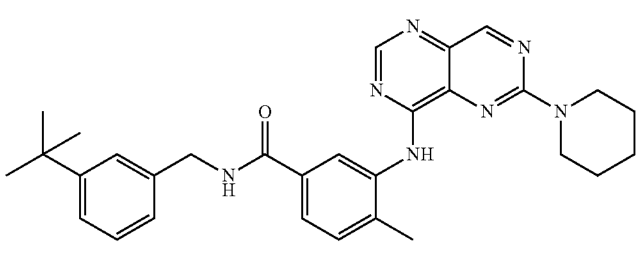 [SMILES: Cc1ccc(C(=O)NCc2cccc(C(C)(C)C)c2)cc1Nc1ncnc2cnc(N3CCCCC3)nc12] | 2.38 | 510 |
| III-309 | 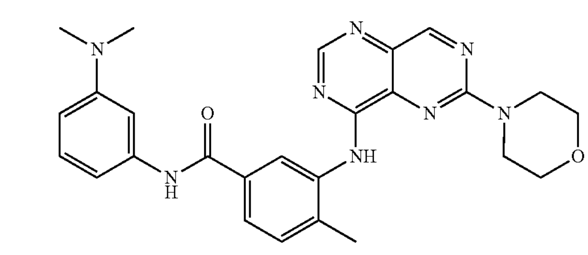 [SMILES: Cc1ccc(C(=O)Nc2cccc(N(C)C)c2)cc1Nc1ncnc2cnc(N3CCOCC3)nc12] | 1.32 | 485 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-310 | 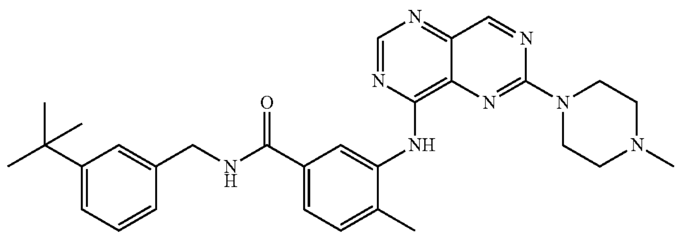 [SMILES: Cc1ccc(C(=O)NCc2cccc(C(C)(C)C)c2)cc1Nc1ncnc2cnc(N3CCN(C)CC3)nc12] | 1.82 | 525 |
| III-311 | 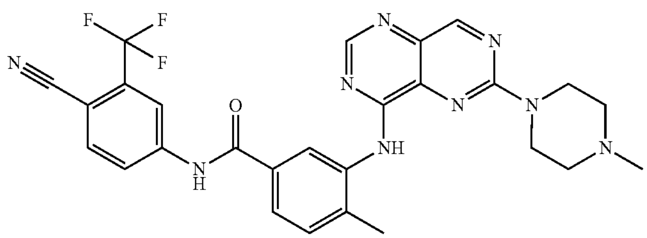 [SMILES: Cc1ccc(C(=O)Nc2ccc(C#N)c(C(F)(F)F)c2)cc1Nc1ncnc2cnc(N3CCN(C)CC3)nc12] | 1.53 | 548 |
| III-312 | 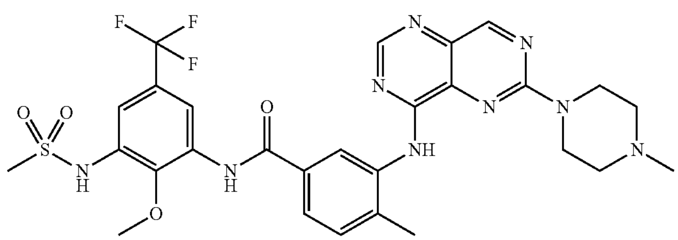 | 1.48 | 634 |
| III-313 | 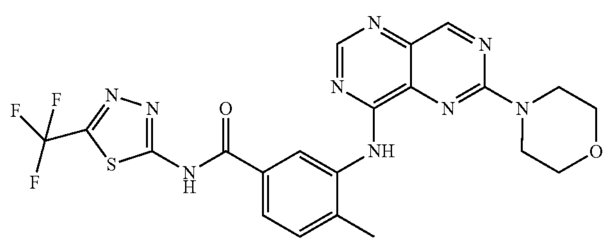 [SMILES: Cc1ccc(C(=O)Nc2nnc(C(F)(F)F)s2)cc1Nc1ncnc2cnc(N3CCOCC3)nc12] | 1.97 | 518 |
| III-314 | 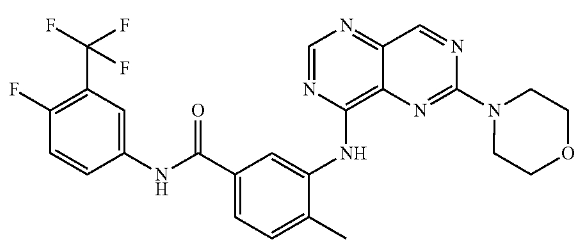 [SMILES: Cc1ccc(C(=O)Nc2ccc(F)c(C(F)(F)F)c2)cc1Nc1ncnc2cnc(N3CCOCC3)nc12] | 2.16 | 528 |

TABLE 3-continued
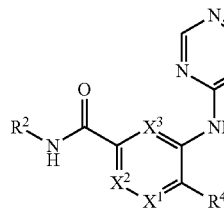
Example Compounds III-1 to III-579
and III-592 to III-608
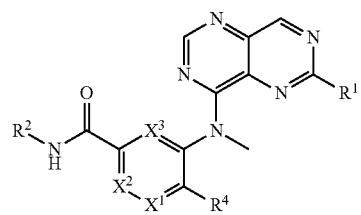
Example Compounds III-580 to III-587
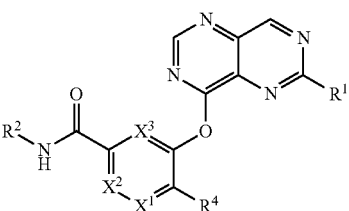
Example Compounds III-588 to III-591
| # | Structure | $t_{Ret.}$ (HPLC) [min] | MS (M + H)$^+$ |
|---|-----------|------------------------|----------------|
| III-315 | 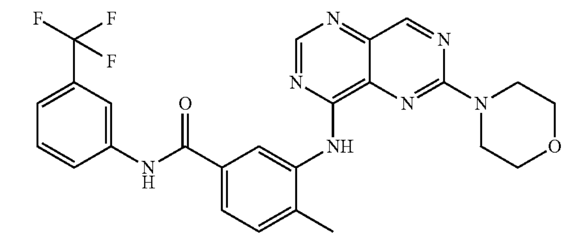 [SMILES: Cc1ccc(C(=O)Nc2cccc(C(F)(F)F)c2)cc1Nc1ncnc2cnc(N3CCOCC3)nc12] | 1.80 | 510 |
| III-316 | 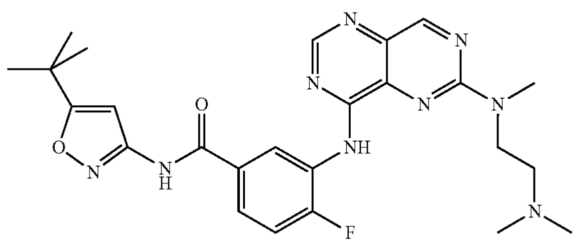 | 1.87 | 508 |
| III-317 | 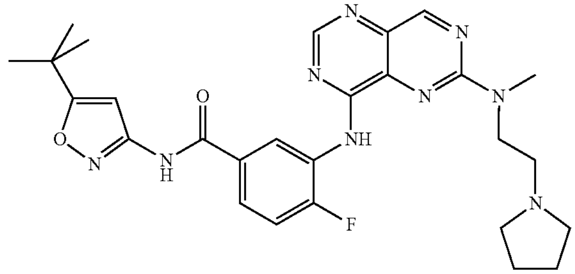 [SMILES: CN(CCN1CCCC1)c1ncc2ncnc(Nc3cc(C(=O)Nc4cc(C(C)(C)C)on4)ccc3F)c2n1] | 1.86 | 534 |
| III-318 | 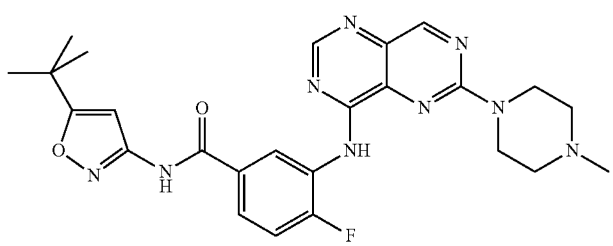 [SMILES: CN1CCN(c2ncc3ncnc(Nc4cc(C(=O)Nc5cc(C(C)(C)C)on5)ccc4F)c3n2)CC1] | 1.80 | 506 |
| III-319 | 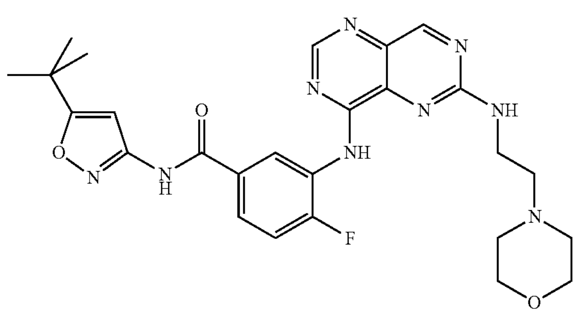 [SMILES: CC(C)(C)c1cc(NC(=O)c2ccc(F)c(Nc3ncnc4cnc(NCCN5CCOCC5)nc34)c2)no1] | 1.86 | 550 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-320 | 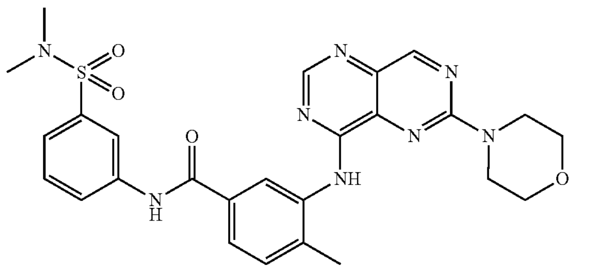 [SMILES: Cc1ccc(C(=O)Nc2cccc(S(=O)(=O)N(C)C)c2)cc1Nc1ncnc2cnc(N3CCOCC3)nc12] | 1.61 | 549 |
| III-321 | 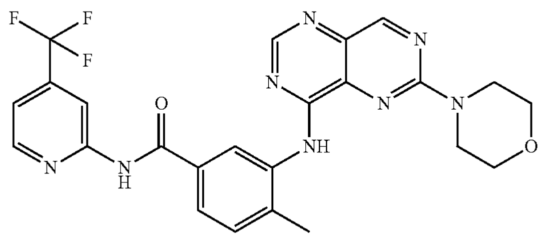 [SMILES: Cc1ccc(C(=O)Nc2cc(C(F)(F)F)ccn2)cc1Nc1ncnc2cnc(N3CCOCC3)nc12] | 1.75 | 511 |
| III-322 | 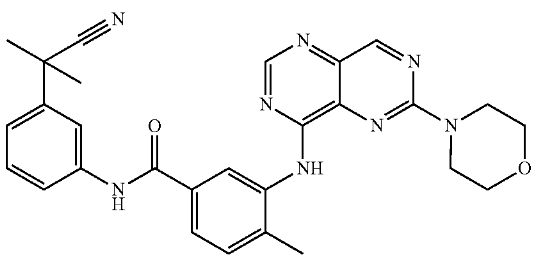 [SMILES: Cc1ccc(C(=O)Nc2cccc(C(C)(C)C#N)c2)cc1Nc1ncnc2cnc(N3CCOCC3)nc12] | 1.69 | 509 |
| III-323 | 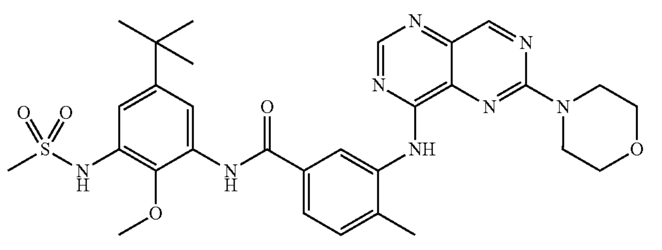 [SMILES: COc1c(NC(=O)c2ccc(C)c(Nc3ncnc4cnc(N5CCOCC5)nc34)c2)cc(C(C)(C)C)cc1NS(C)(=O)=O] | 1.86 | 621 |
| III-324 | 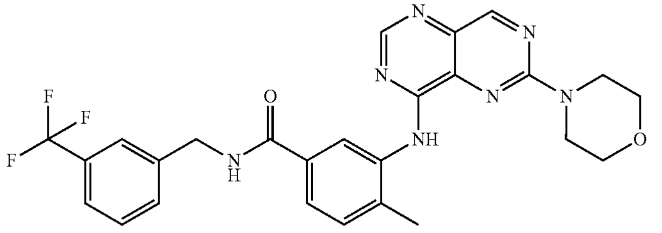 [SMILES: Cc1ccc(C(=O)NCc2cccc(C(F)(F)F)c2)cc1Nc1ncnc2cnc(N3CCOCC3)nc12] | 1.72 | 524 |

TABLE 3-continued
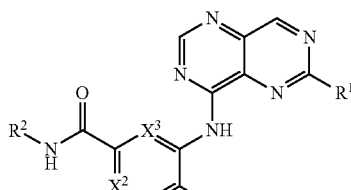
Example Compounds III-1 to III-579 and III-592 to III-608
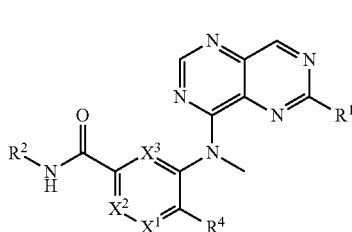
Example Compounds III-580 to III-587
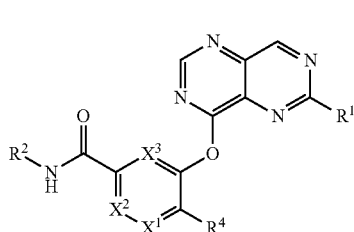
Example Compounds III-588 to III-591
| # | Structure | $t_{Ret.}$ (HPLC) [min] | MS (M + H)$^+$ |
|---|-----------|---|---|
| III-325 | 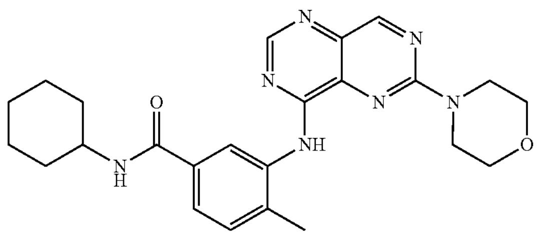 [SMILES: Cc1ccc(C(=O)NC2CCCCC2)cc1Nc1ncnc2cnc(N3CCOCC3)nc12] | 1.60 | 448 |
| III-326 | 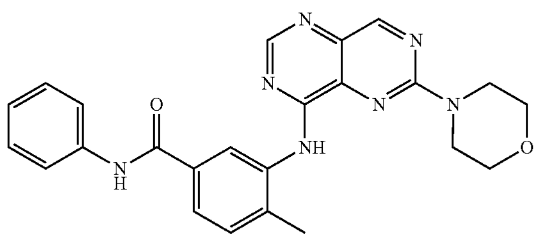 [SMILES: Cc1ccc(C(=O)Nc2ccccc2)cc1Nc1ncnc2cnc(N3CCOCC3)nc12] | 1.59 | 442 |
| III-327 | 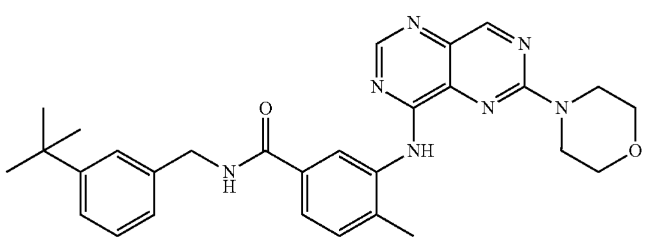 [SMILES: Cc1ccc(C(=O)NCc2cccc(C(C)(C)C)c2)cc1Nc1ncnc2cnc(N3CCOCC3)nc12] | 2.14 | 512/513 |
| III-328 | 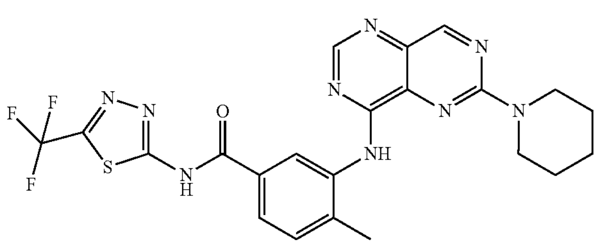 [SMILES: Cc1ccc(C(=O)Nc2nnc(C(F)(F)F)s2)cc1Nc1ncnc2cnc(N3CCCCC3)nc12] | 2.03 | 516 |
| III-329 | 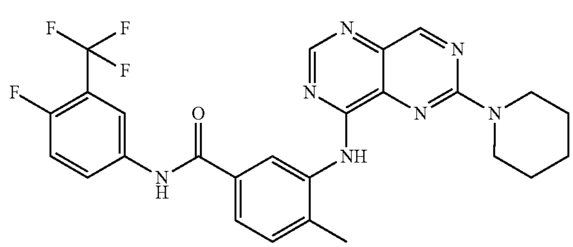 [SMILES: Cc1ccc(C(=O)Nc2ccc(F)c(C(F)(F)F)c2)cc1Nc1ncnc2cnc(N3CCCCC3)nc12] | 2.06 | 526 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-330 | 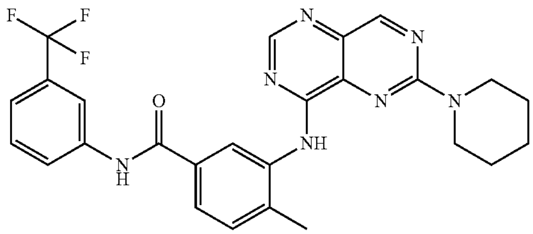 [SMILES: Cc1ccc(C(=O)Nc2cccc(C(F)(F)F)c2)cc1Nc1ncnc2cnc(N3CCCCC3)nc12] | 2.03 | 508 |
| III-331 | 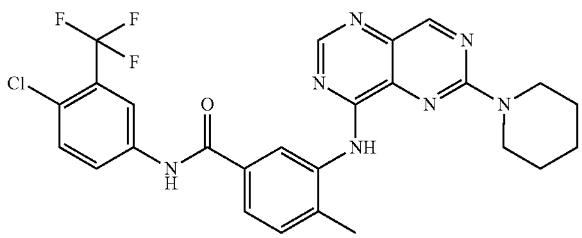 [SMILES: Cc1ccc(C(=O)Nc2ccc(Cl)c(C(F)(F)F)c2)cc1Nc1ncnc2cnc(N3CCCCC3)nc12] | 2.13 | 542 |
| III-332 | 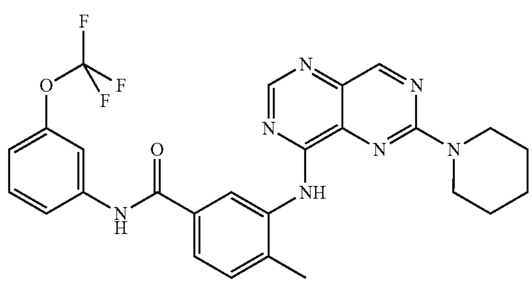 [SMILES: Cc1ccc(C(=O)Nc2cccc(OC(F)(F)F)c2)cc1Nc1ncnc2cnc(N3CCCCC3)nc12] | 2.06 | 524 |
| III-333 | 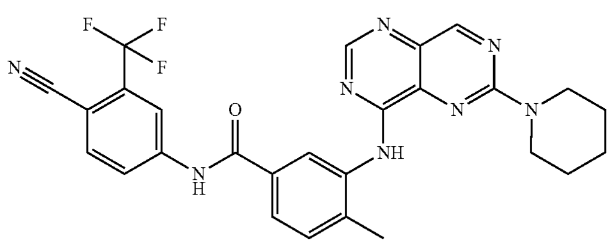 [SMILES: Cc1ccc(C(=O)Nc2ccc(C#N)c(C(F)(F)F)c2)cc1Nc1ncnc2cnc(N3CCCCC3)nc12] | 2.05 | 533 |
| III-334 | 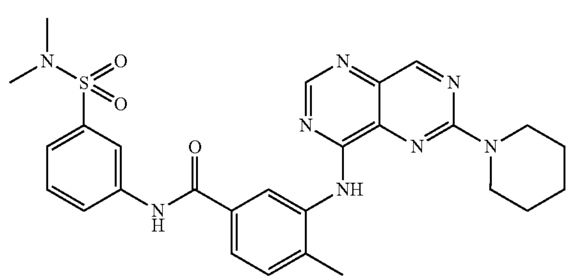 [SMILES: Cc1ccc(C(=O)Nc2cccc(S(=O)(=O)N(C)C)c2)cc1Nc1ncnc2cnc(N3CCCCC3)nc12] | 1.87 | 547 |

TABLE 3-continued
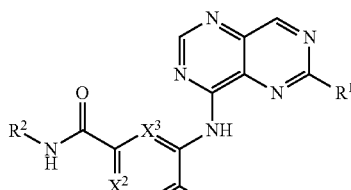
Example Compounds III-1 to III-579 and III-592 to III-608
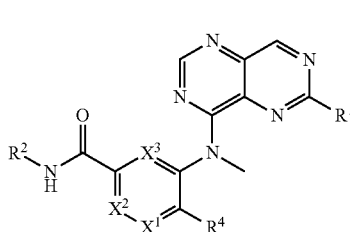
Example Compounds III-580 to III-587
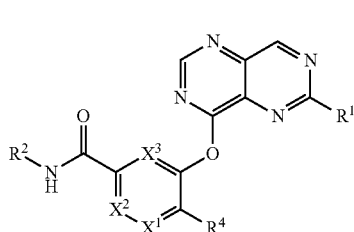
Example Compounds III-588 to III-591
| # | Structure | $t_{Ret.}$ (HPLC) [min] | MS (M + H)$^+$ |
|---|-----------|-------------------------|-----------------|
| III-335 | 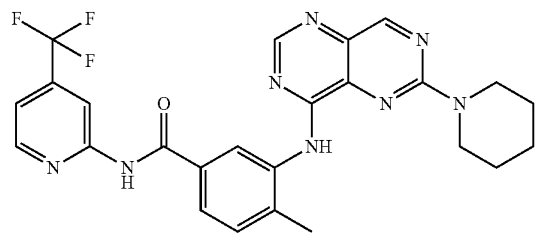 [SMILES: Cc1ccc(C(=O)Nc2cc(C(F)(F)F)ccn2)cc1Nc1ncnc2cnc(N3CCCCC3)nc12] | 2.00 | 509 |
| III-336 | 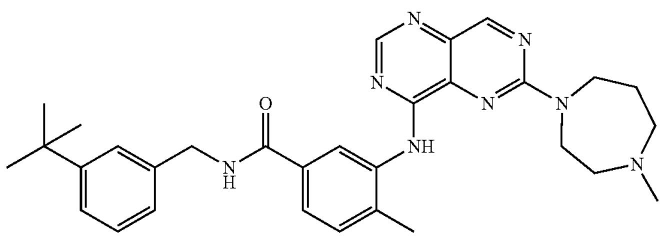 [SMILES: Cc1ccc(C(=O)NCc2cccc(C(C)(C)C)c2)cc1Nc1ncnc2cnc(N3CCCN(C)CC3)nc12] | 2.40 | 539 |
| III-337 | 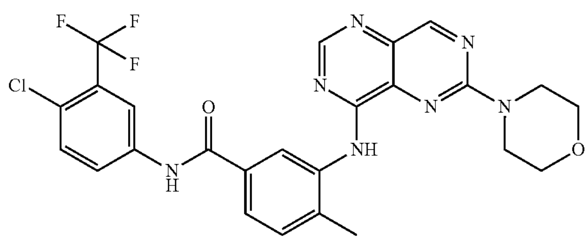 [SMILES: Cc1ccc(C(=O)Nc2ccc(Cl)c(C(F)(F)F)c2)cc1Nc1ncnc2cnc(N3CCOCC3)nc12] | 1.90 | 544 |
| III-338 | 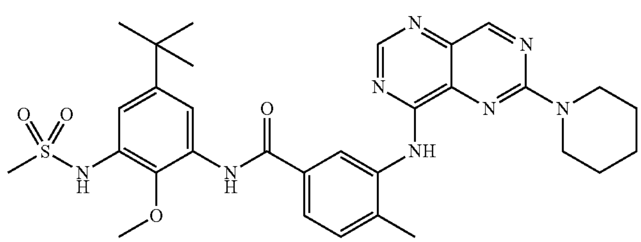 [SMILES: COc1c(NC(=O)c2ccc(C)c(Nc3ncnc4cnc(N5CCCCC5)nc34)c2)cc(C(C)(C)C)cc1NS(C)(=O)=O] | 1.97 | 619 |
| III-339 | 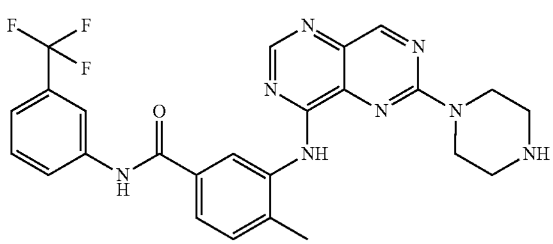 [SMILES: Cc1ccc(C(=O)Nc2cccc(C(F)(F)F)c2)cc1Nc1ncnc2cnc(N3CCNCC3)nc12] | 2.41 | 509 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-340 | 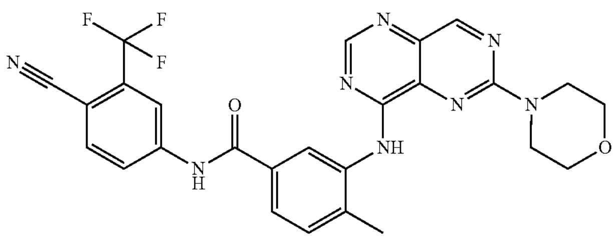 [SMILES: Cc1ccc(C(=O)Nc2ccc(C#N)c(C(F)(F)F)c2)cc1Nc1ncnc2cnc(N3CCOCC3)nc12] | 1.88 | 535 |
| III-341 | 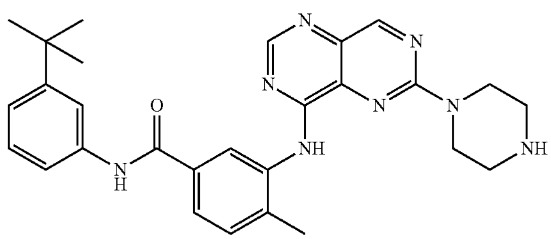 [SMILES: Cc1ccc(C(=O)Nc2cccc(C(C)(C)C)c2)cc1Nc1ncnc2cnc(N3CCNCC3)nc12] | 2.31 | 497 |
| III-342 | 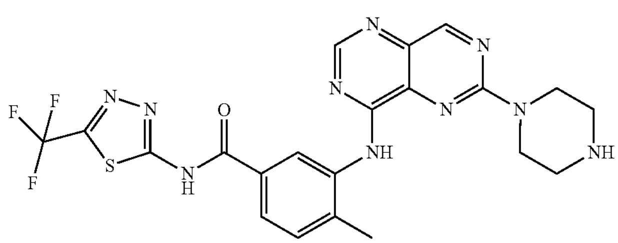 [SMILES: Cc1ccc(C(=O)Nc2nnc(C(F)(F)F)s2)cc1Nc1ncnc2cnc(N3CCNCC3)nc12] | 1.48 | 517 |
| III-343 | 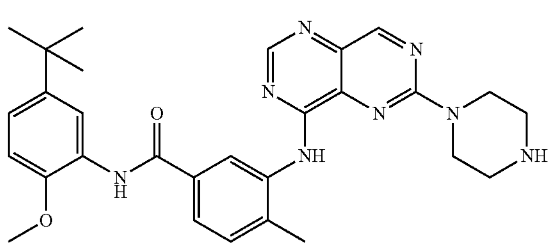 [SMILES: COc1ccc(C(C)(C)C)cc1NC(=O)c1ccc(C)c(Nc2ncnc3cnc(N4CCNCC4)nc23)c1] | 1.87 | 527 |
| III-344 | 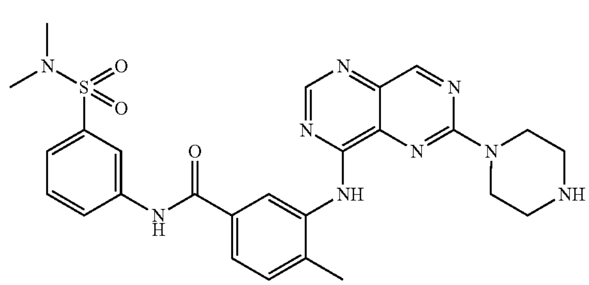 [SMILES: Cc1ccc(C(=O)Nc2cccc(S(=O)(=O)N(C)C)c2)cc1Nc1ncnc2cnc(N3CCNCC3)nc12] | 1.63 | 548 |

US 8,653,087 B2

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-345 | 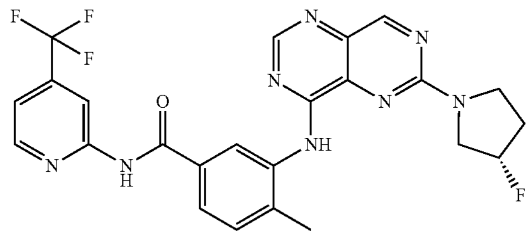 [SMILES: Cc1ccc(C(=O)Nc2cc(C(F)(F)F)ccn2)cc1Nc1ncnc2cnc(N3CC[C@H](F)C3)nc12] | 2.23 | 513 |
| III-346 | 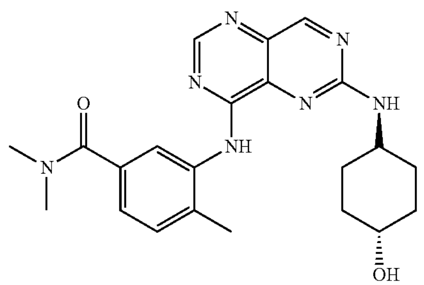 | 1.54 | 408 |
| III-347 | 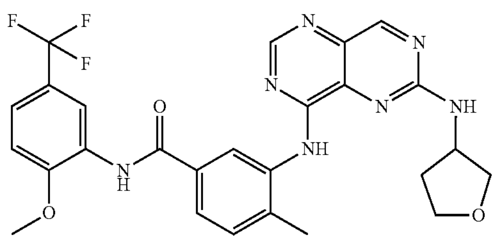 [SMILES: COc1ccc(C(F)(F)F)cc1NC(=O)c1ccc(C)c(Nc2ncnc3cnc(NC4CCOC4)nc23)c1] | 2.11 | 540 |
| III-348 | 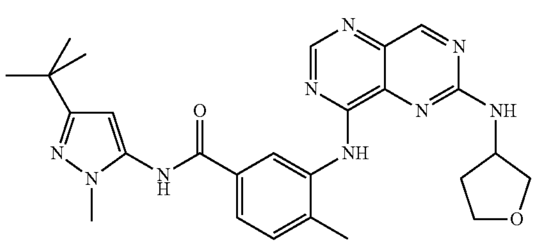 [SMILES: Cc1ccc(C(=O)Nc2cc(C(C)(C)C)nn2C)cc1Nc1ncnc2cnc(NC3CCOC3)nc12] | 1.91 | 502 |
| III-349 | 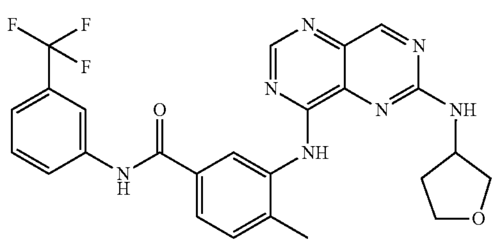 [SMILES: Cc1ccc(C(=O)Nc2cccc(C(F)(F)F)c2)cc1Nc1ncnc2cnc(NC3CCOC3)nc12] | 2.15 | 510 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-350 | 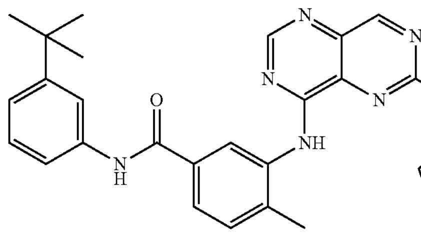 | 2.24 | 498 |
| III-351 | 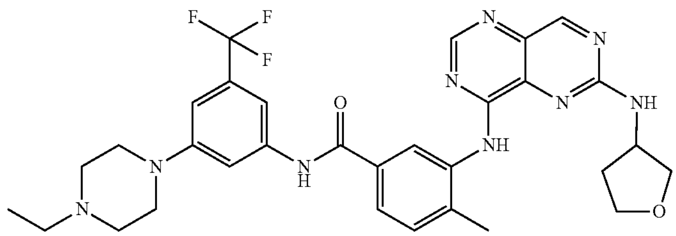 [SMILES: CCN1CCN(c2cc(NC(=O)c3ccc(C)c(Nc4ncnc5cnc(NC6CCOC6)nc45)c3)cc(C(F)(F)F)c2)CC1] | 2.20 | 622 |
| III-352 | 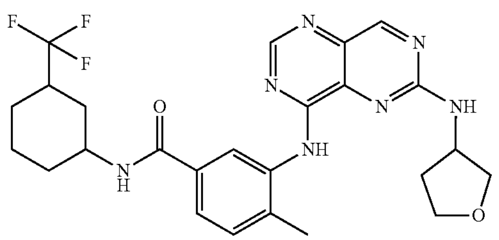 [SMILES: Cc1ccc(C(=O)NC2CCCC(C(F)(F)F)C2)cc1Nc1ncnc2cnc(NC3CCOC3)nc12] | 2.03 | 516 |
| III-353 | 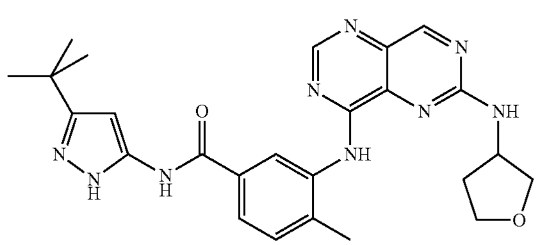 [SMILES: Cc1ccc(C(=O)Nc2cc(C(C)(C)C)n[nH]2)cc1Nc1ncnc2cnc(NC3CCOC3)nc12] | 1.86 | 488 |
| III-354 | 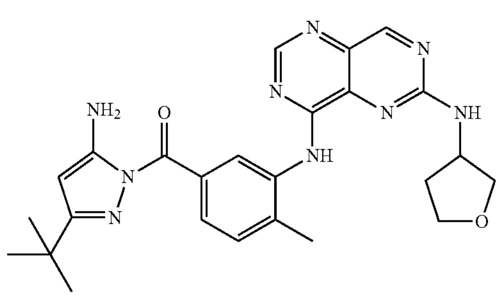 [SMILES: Cc1ccc(C(=O)n2nc(C(C)(C)C)cc2N)cc1Nc1ncnc2cnc(NC3CCOC3)nc12] | 2.14 | 488 |

TABLE 3-continued
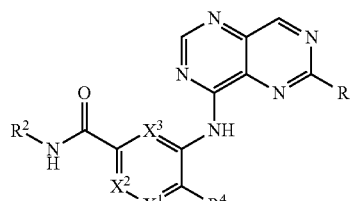
Example Compounds III-1 to III-579 and III-592 to III-608
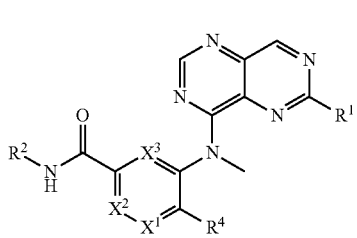
Example Compounds III-580 to III-587
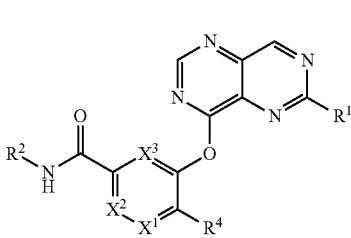
Example Compounds III-588 to III-591
| # | Structure | $t_{Ret.}$ (HPLC) [min] | MS (M + H)$^+$ |
|---|---|---|---|
| III-355 | 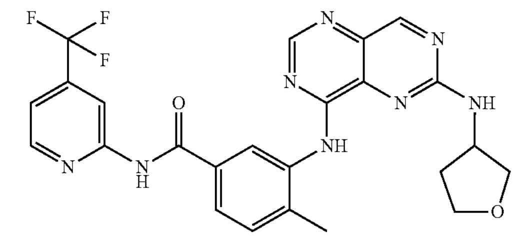 [SMILES: Cc1ccc(C(=O)Nc2cc(C(F)(F)F)ccn2)cc1Nc1ncnc2cnc(NC3CCOC3)nc12] | 2.09 | 511 |
| III-356 | 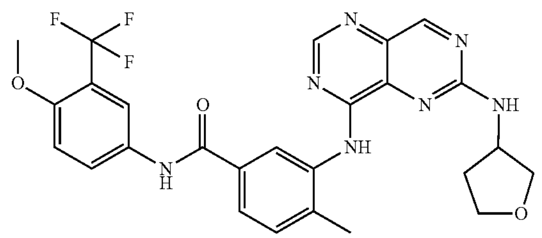 [SMILES: COc1ccc(NC(=O)c2ccc(C)c(Nc3ncnc4cnc(NC5CCOC5)nc34)c2)cc1C(F)(F)F] | 2.26 | 540 |
| III-357 | 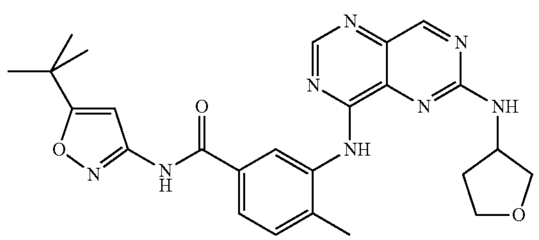 [SMILES: Cc1ccc(C(=O)Nc2cc(C(C)(C)C)on2)cc1Nc1ncnc2cnc(NC3CCOC3)nc12] | 2.08 | 489 |
| III-358 | 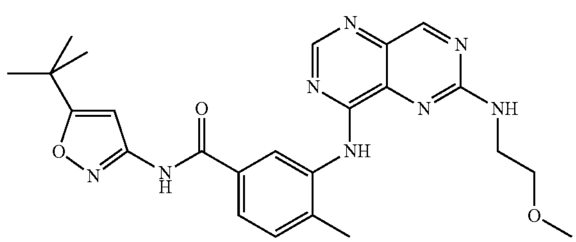 [SMILES: COCCNc1ncc2ncnc(Nc3cc(C(=O)Nc4cc(C(C)(C)C)on4)ccc3C)c2n1] | 2.09 | 477 |
| III-359 | 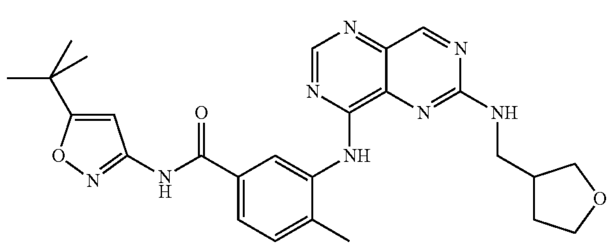 [SMILES: Cc1ccc(C(=O)Nc2cc(C(C)(C)C)on2)cc1Nc1ncnc2cnc(NCC3CCOC3)nc12] | 2.16 | 503 |

US 8,653,087 B2

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-360 | 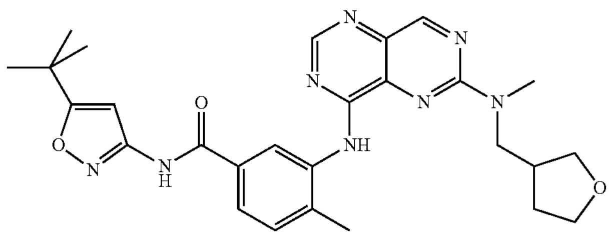 [SMILES: Cc1ccc(C(=O)Nc2cc(C(C)(C)C)on2)cc1Nc1ncnc2cnc(N(C)CC3CCOC3)nc12] | 2.35 | 517 |
| III-361 | 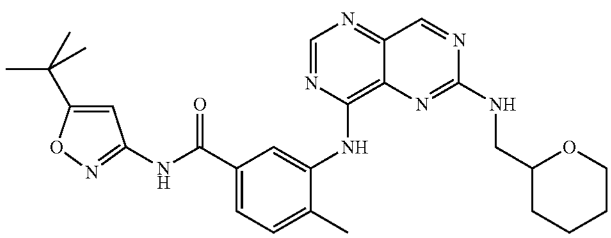 [SMILES: Cc1ccc(C(=O)Nc2cc(C(C)(C)C)on2)cc1Nc1ncnc2cnc(NCC3CCCCO3)nc12] | 2.16 | 517 |
| III-362 | 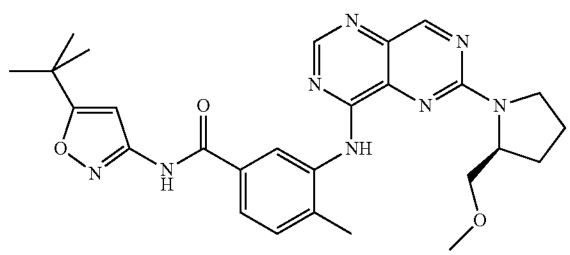 [SMILES: COC[C@@H]1CCCN1c1ncc2ncnc(Nc3cc(C(=O)Nc4cc(C(C)(C)C)on4)ccc3C)c2n1] | 2.42 | 517 |
| III-363 | 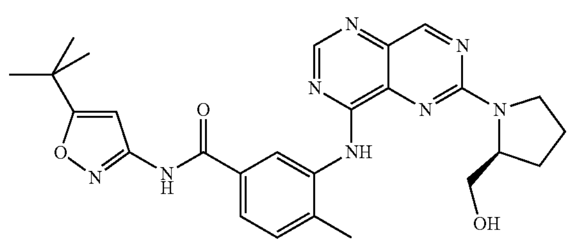 [SMILES: Cc1ccc(C(=O)Nc2cc(C(C)(C)C)on2)cc1Nc1ncnc2cnc(N3CCC[C@H]3CO)nc12] | 2.13 | 503 |
| III-364 | 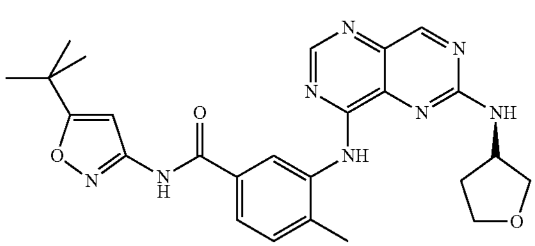 | 2.07 | 489 |

TABLE 3-continued
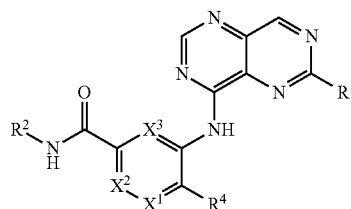 Example Compounds III-1 to III-579 and III-592 to III-608
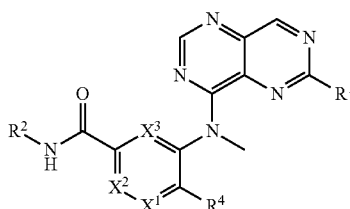 Example Compounds III-580 to III-587
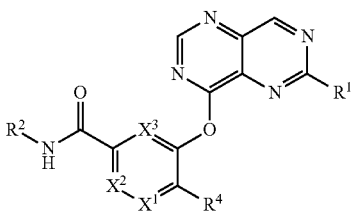 Example Compounds III-588 to III-591
| # | Structure | t_Ret. (HPLC) [min] | MS (M + H)+ |
|---|-----------|---------------------|-------------|
| III-365 | 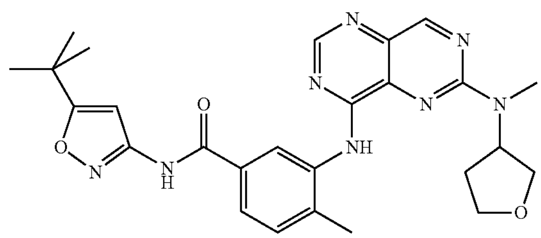 [SMILES: Cc1ccc(C(=O)Nc2cc(C(C)(C)C)on2)cc1Nc1ncnc2cnc(N(C)C3CCOC3)nc12] | 2.23 | 503 |
| III-366 | 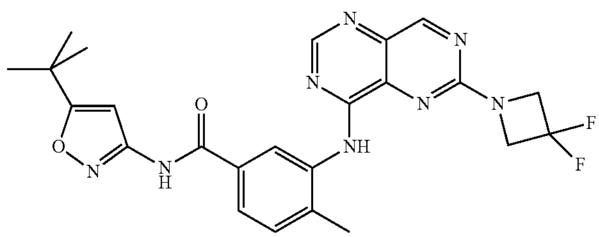 [SMILES: Cc1ccc(C(=O)Nc2cc(C(C)(C)C)on2)cc1Nc1ncnc2cnc(N3CC(F)(F)C3)nc12] | 2.27 | 495 |
| III-367 | 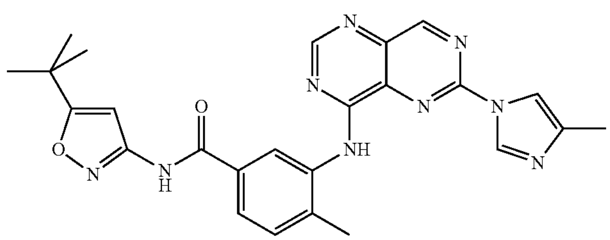 [SMILES: Cc1cn(-c2ncc3ncnc(Nc4cc(C(=O)Nc5cc(C(C)(C)C)on5)ccc4C)c3n2)cn1] | 2.07 | 484 |
| III-368 | 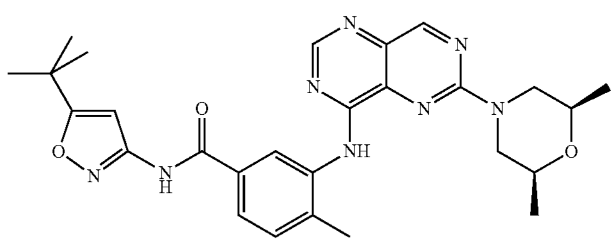 [SMILES: Cc1ccc(C(=O)Nc2cc(C(C)(C)C)on2)cc1Nc1ncnc2cnc(N3C[C@@H](C)O[C@@H](C)C3)nc12] | 2.37 | 517 |
| III-369 | 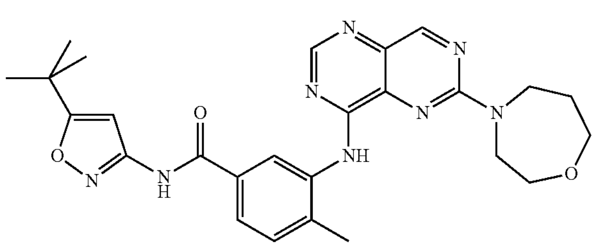 [SMILES: Cc1ccc(C(=O)Nc2cc(C(C)(C)C)on2)cc1Nc1ncnc2cnc(N3CCCOCC3)nc12] | 2.22 | 503 |

US 8,653,087 B2
TABLE 3-continued
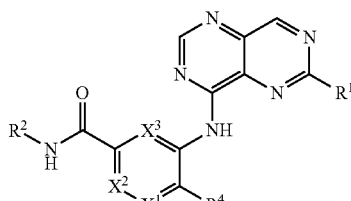
Example Compounds III-1 to III-579
and III-592 to III-608
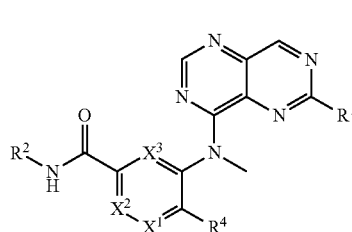
Example Compounds III-580 to III-587
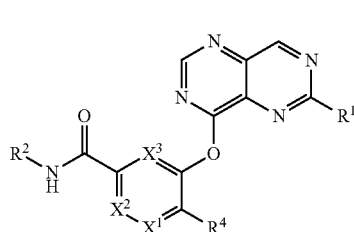
Example Compounds III-588 to III-591
| # | Structure | $t_{Ret.}$ (HPLC) [min] | MS (M + H)$^+$ |
|---|---|---|---|
| III-370 | 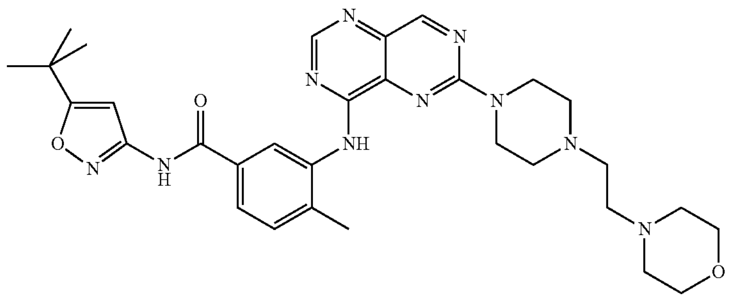 [SMILES: Cc1ccc(C(=O)Nc2cc(C(C)(C)C)on2)cc1Nc1ncnc2cnc(N3CCN(CCN4CCOCC4)CC3)nc12] | 2.08 | 601 |
| III-371 | 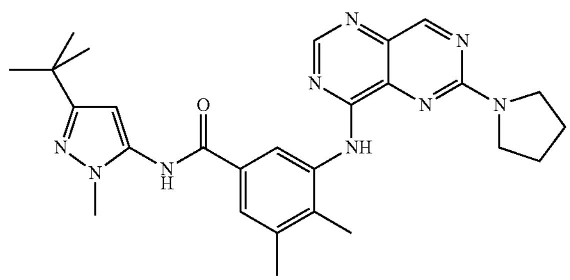 [SMILES: Cc1cc(C(=O)Nc2cc(C(C)(C)C)nn2C)cc(Nc2ncnc3cnc(N4CCCC4)nc23)c1C] | 2.24 | 500 |
| III-372 | 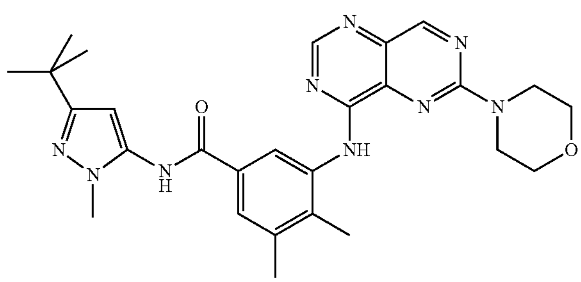 [SMILES: Cc1cc(C(=O)Nc2cc(C(C)(C)C)nn2C)cc(Nc2ncnc3cnc(N4CCOCC4)nc23)c1C] | 2.06 | 516 |
| III-373 | 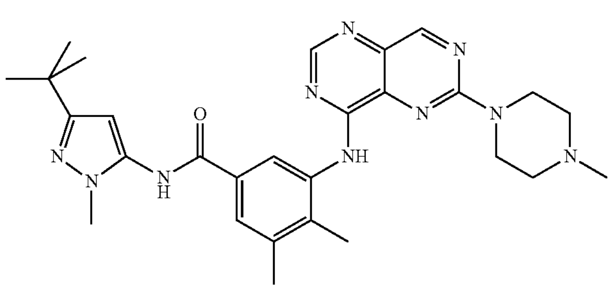 [SMILES: Cc1cc(C(=O)Nc2cc(C(C)(C)C)nn2C)cc(Nc2ncnc3cnc(N4CCN(C)CC4)nc23)c1C] | 2.00 | 529 |

TABLE 3-continued
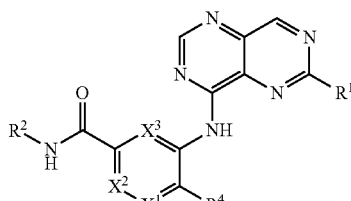
Example Compounds III-1 to III-579
and III-592 to III-608
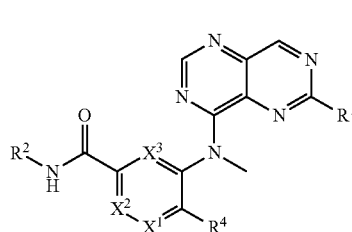
Example Compounds III-580 to III-587
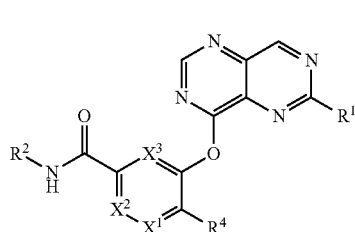
Example Compounds III-588 to III-591
| # | Structure | $t_{Ret.}$ (HPLC) [min] | MS (M + H)$^+$ |
|---|---|---|---|
| III-374 | 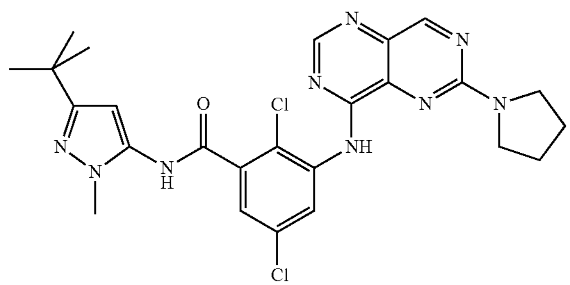 [SMILES: Cn1nc(C(C)(C)C)cc1NC(=O)c1cc(Cl)cc(Nc2ncnc3cnc(N4CCCC4)nc23)c1Cl] | 2.43 | 540/542 |
| III-375 | 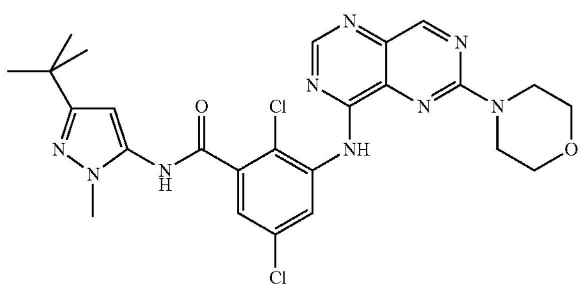 [SMILES: Cn1nc(C(C)(C)C)cc1NC(=O)c1cc(Cl)cc(Nc2ncnc3cnc(N4CCOCC4)nc23)c1Cl] | 2.21 | 556/558 |
| III-376 | 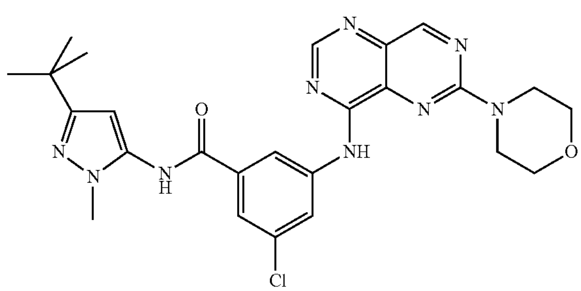 [SMILES: Cn1nc(C(C)(C)C)cc1NC(=O)c1cc(Cl)cc(Nc2ncnc3cnc(N4CCOCC4)nc23)c1] | 2.19 | 522 |
| III-377 | 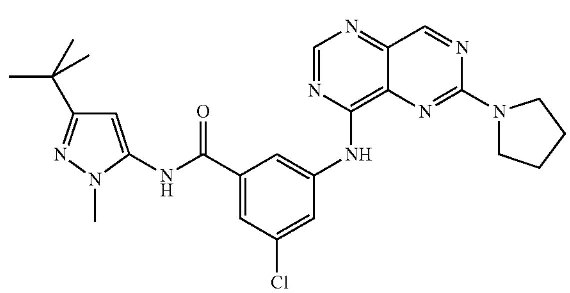 [SMILES: Cn1nc(C(C)(C)C)cc1NC(=O)c1cc(Cl)cc(Nc2ncnc3cnc(N4CCCC4)nc23)c1] | 2.36 | 506 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-378 | 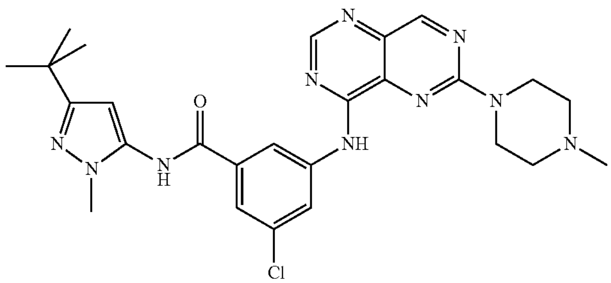 [SMILES: CN1CCN(c2ncc3ncnc(Nc4cc(Cl)cc(C(=O)Nc5cc(C(C)(C)C)nn5C)c4)c3n2)CC1] | 2.14 | 535 |
| III-379 | 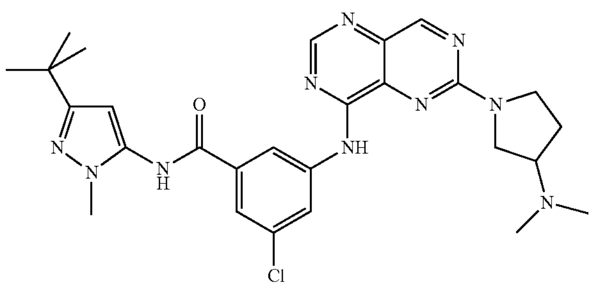 [SMILES: CN(C)C1CCN(c2ncc3ncnc(Nc4cc(Cl)cc(C(=O)Nc5cc(C(C)(C)C)nn5C)c4)c3n2)C1] | 2.17 | 549 |
| III-380 | 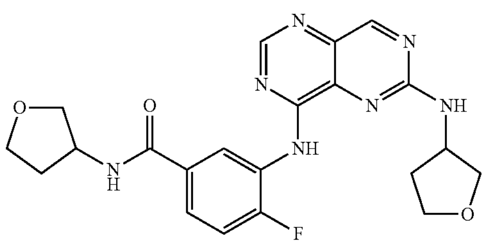 [SMILES: O=C(NC1CCOC1)c1ccc(F)c(Nc2ncnc3cnc(NC4CCOC4)nc23)c1] | 1.54 | 440 |
| III-381 | 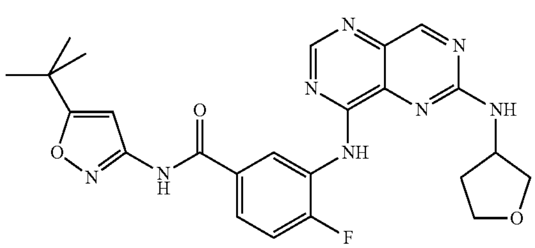 [SMILES: CC(C)(C)c1cc(NC(=O)c2ccc(F)c(Nc3ncnc4cnc(NC5CCOC5)nc34)c2)no1] | 2.02 | 493 |
| III-382 | 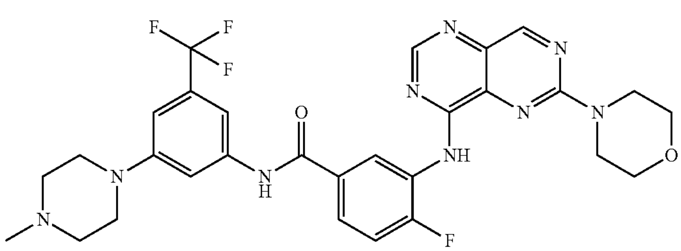 [SMILES: CN1CCN(c2cc(NC(=O)c3ccc(F)c(Nc4ncnc5cnc(N6CCOCC6)nc45)c3)cc(C(F)(F)F)c2)CC1] | 2.20 | 612 |

TABLE 3-continued
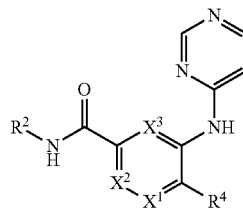
Example Compounds III-1 to III-579
and III-592 to III-608
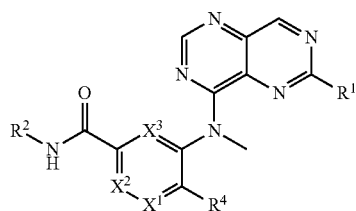
Example Compounds III-580 to III-587
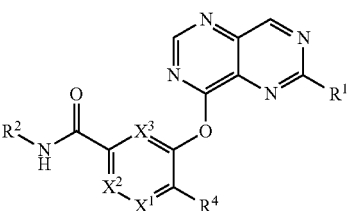
Example Compounds III-588 to III-591
| # | Structure | t_Ret. (HPLC) [min] | MS (M + H)+ |
|---|---|---|---|
| III-383 | 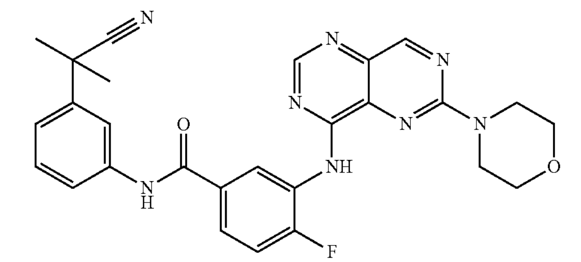 [SMILES: CC(C)(C#N)c1cccc(NC(=O)c2ccc(F)c(Nc3ncnc4cnc(N5CCOCC5)nc34)c2)c1] | 2.20 | 513 |
| III-384 | 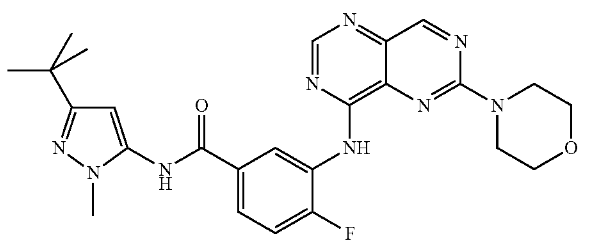 [SMILES: Cn1nc(C(C)(C)C)cc1NC(=O)c1ccc(F)c(Nc2ncnc3cnc(N4CCOCC4)nc23)c1] | 1.73 | 506 |
| III-385 | 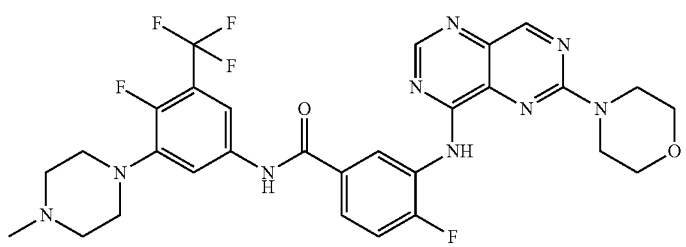 [SMILES: CN1CCN(c2cc(NC(=O)c3ccc(F)c(Nc4ncnc5cnc(N6CCOCC6)nc45)c3)cc(C(F)(F)F)c2F)CC1] | 2.04 | 630 |
| III-386 | 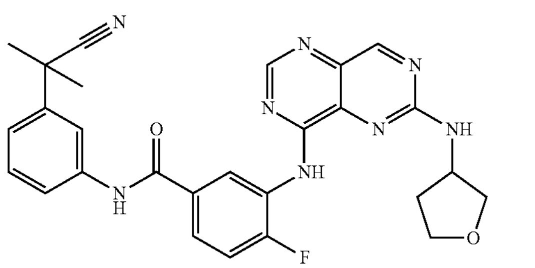 [SMILES: CC(C)(C#N)c1cccc(NC(=O)c2ccc(F)c(Nc3ncnc4cnc(NC5CCOC5)nc34)c2)c1] | 1.81 | 513 |
| III-387 | 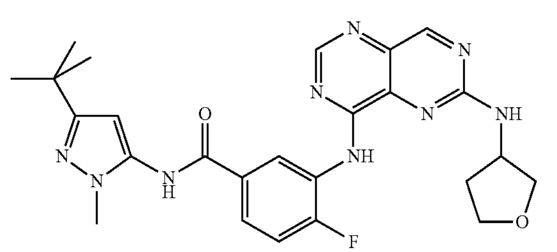 [SMILES: Cn1nc(C(C)(C)C)cc1NC(=O)c1ccc(F)c(Nc2ncnc3cnc(NC4CCOC4)nc23)c1] | 1.65 | 506 |

TABLE 3-continued
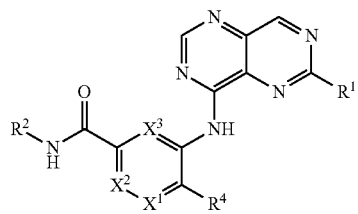
Example Compounds III-1 to III-579 and III-592 to III-608
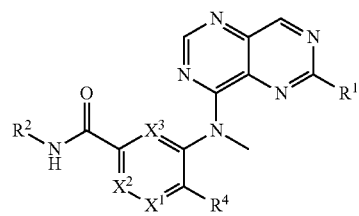
Example Compounds III-580 to III-587
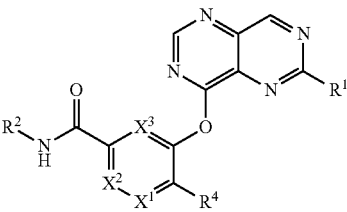
Example Compounds III-588 to III-591
| # | Structure | t$_{Ret.}$ (HPLC) [min] | MS (M + H)$^+$ |
|---|---|---|---|
| III-388 | 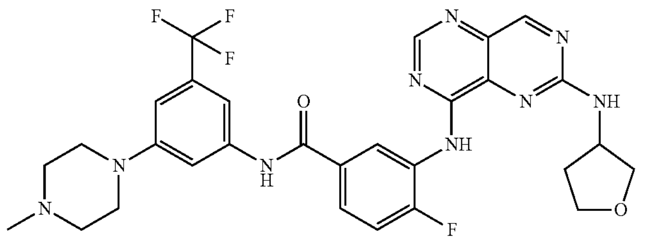 [SMILES: CN1CCN(c2cc(NC(=O)c3ccc(F)c(Nc4ncnc5cnc(NC6CCOC6)nc45)c3)cc(C(F)(F)F)c2)CC1] | 1.86 | 612 |
| III-389 | 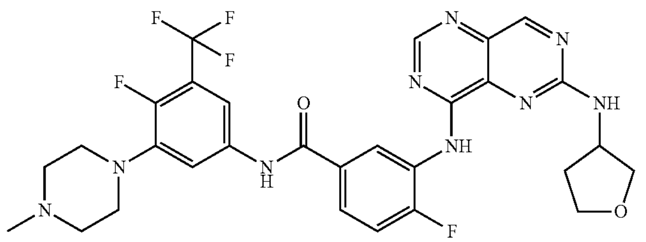 [SMILES: CN1CCN(c2cc(NC(=O)c3ccc(F)c(Nc4ncnc5cnc(NC6CCOC6)nc45)c3)cc(C(F)(F)F)c2F)CC1] | 1.93 | 630 |
| III-390 | 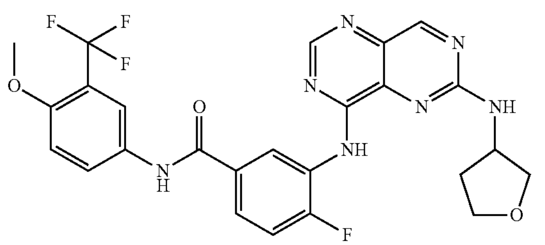 [SMILES: COc1ccc(NC(=O)c2ccc(F)c(Nc3ncnc4cnc(NC5CCOC5)nc34)c2)cc1C(F)(F)F] | 1.86 | 544 |
| III-391 | 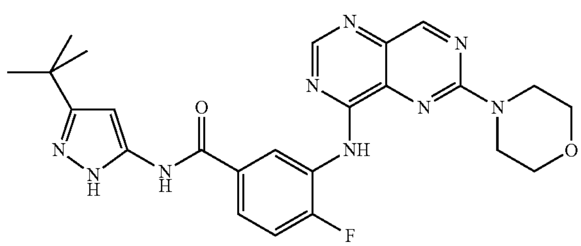 [SMILES: CC(C)(C)c1cc(NC(=O)c2ccc(F)c(Nc3ncnc4cnc(N5CCOCC5)nc34)c2)[nH]n1] | 1.73 | 492 |
| III-392 | 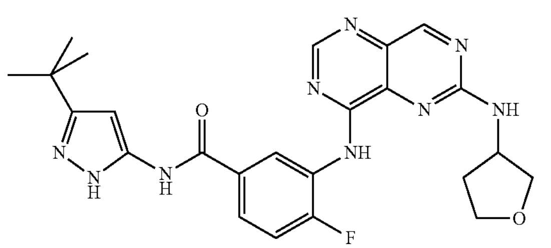 [SMILES: CC(C)(C)c1cc(NC(=O)c2ccc(F)c(Nc3ncnc4cnc(NC5CCOC5)nc34)c2)[nH]n1] | 1.63 | 492 |

TABLE 3-continued
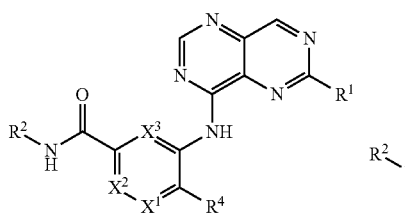 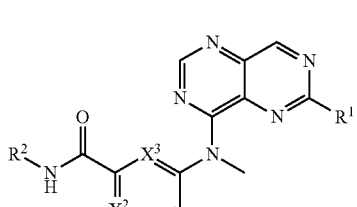 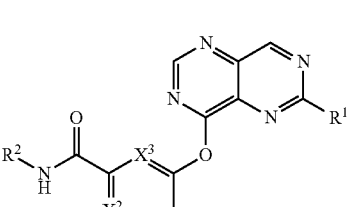
Example Compounds III-1 to III-579 and III-592 to III-608
Example Compounds III-580 to III-587
Example Compounds III-588 to III-591
| # | Structure | t_Ret. (HPLC) [min] | MS (M + H)+ |
|---|---|---|---|
| III-393 | 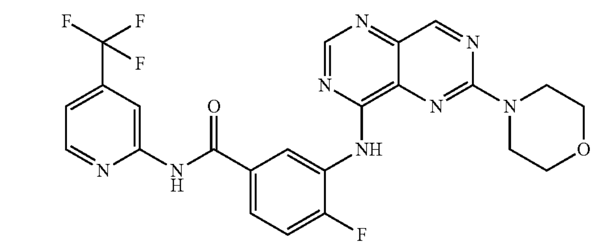 [SMILES: O=C(Nc1cc(C(F)(F)F)ccn1)c1ccc(F)c(Nc2ncnc3cnc(N4CCOCC4)nc23)c1] | 2.02 | 515 |
| III-394 | 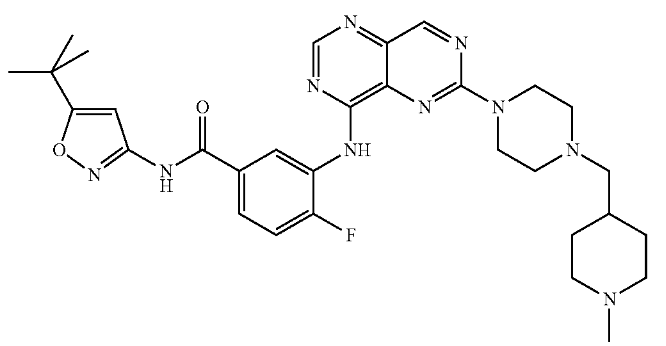 | 2.27 | 603 |
| III-395 | 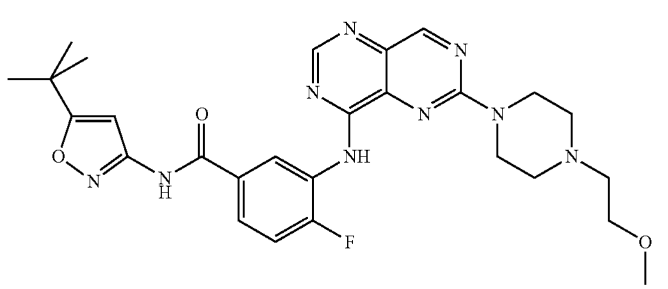 [SMILES: COCCN1CCN(c2ncc3ncnc(Nc4cc(C(=O)Nc5cc(C(C)(C)C)on5)ccc4F)c3n2)CC1] | 1.96 | 550 |
| III-396 | 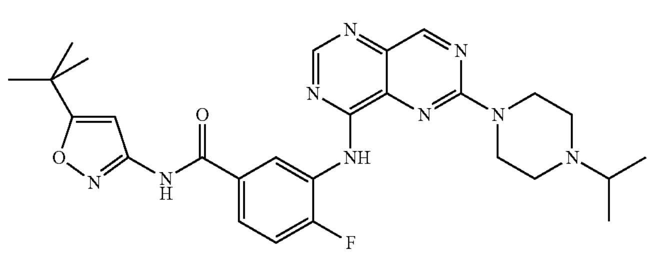 [SMILES: CC(C)N1CCN(c2ncc3ncnc(Nc4cc(C(=O)Nc5cc(C(C)(C)C)on5)ccc4F)c3n2)CC1] | 2.15 | 534 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-397 | 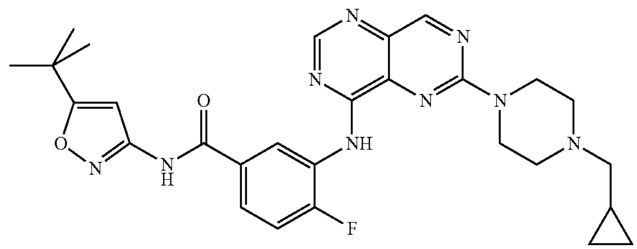 [SMILES: CC(C)(C)c1cc(NC(=O)c2ccc(F)c(Nc3ncnc4cnc(N5CCN(CC6CC6)CC5)nc34)c2)no1] | 2.18 | 546 |
| III-398 | 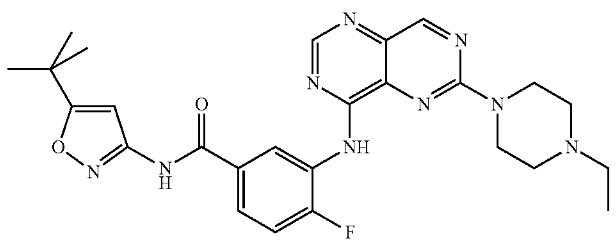 [SMILES: CCN1CCN(c2ncc3ncnc(Nc4cc(C(=O)Nc5cc(C(C)(C)C)on5)ccc4F)c3n2)CC1] | 2.03 | 520 |
| III-399 | 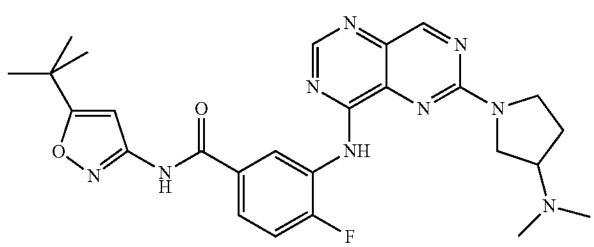 [SMILES: CN(C)C1CCN(c2ncc3ncnc(Nc4cc(C(=O)Nc5cc(C(C)(C)C)on5)ccc4F)c3n2)C1] | 1.96 | 520 |
| III-400 | 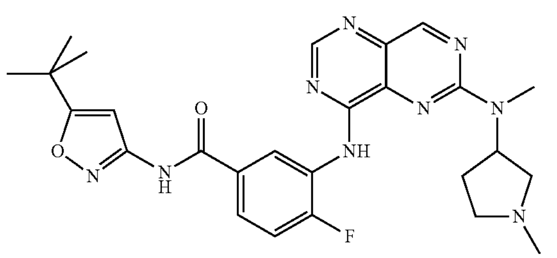 [SMILES: CN1CCC(N(C)c2ncc3ncnc(Nc4cc(C(=O)Nc5cc(C(C)(C)C)on5)ccc4F)c3n2)C1] | 2.15 | 520 |
| III-401 | 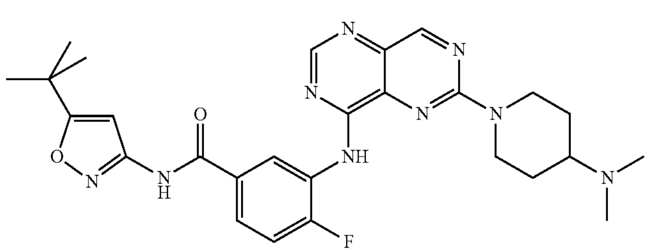 [SMILES: CN(C)C1CCN(c2ncc3ncnc(Nc4cc(C(=O)Nc5cc(C(C)(C)C)on5)ccc4F)c3n2)CC1] | 2.02 | 534 |

TABLE 3-continued
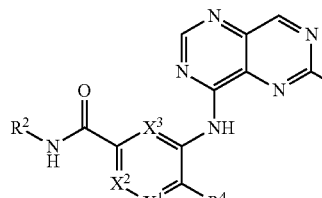
Example Compounds III-1 to III-579
and III-592 to III-608
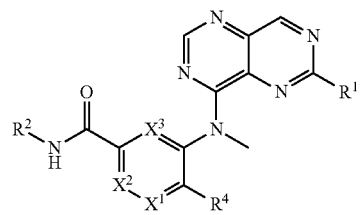
Example Compounds III-580 to III-587
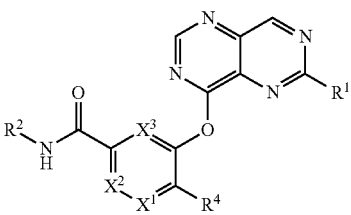
Example Compounds III-588 to III-591
| # | Structure | $t_{Ret.}$ (HPLC) [min] | MS (M + H)$^+$ |
|---|-----------|-------------------------|----------------|
| III-402 | 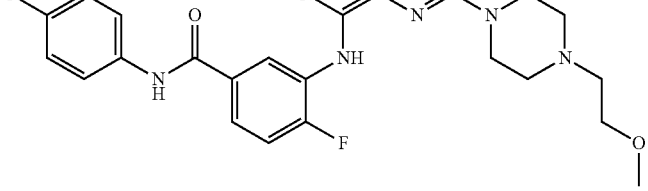 | 1.97 | 601 |
| III-403 | 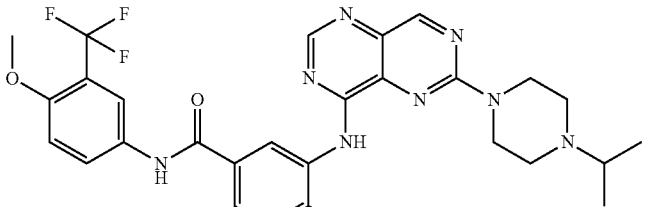 | 2.14 | 585 |
| III-404 | 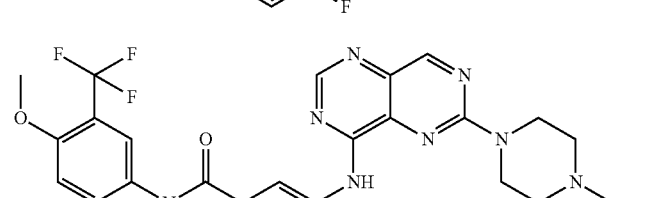 | 2.17 | 597 |
| III-405 | 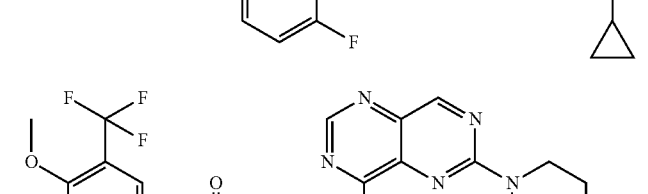 | 2.04 | 571 |
| III-406 | 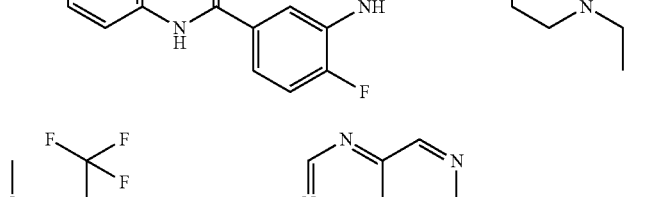 | 2.06 | 521 |

TABLE 3-continued
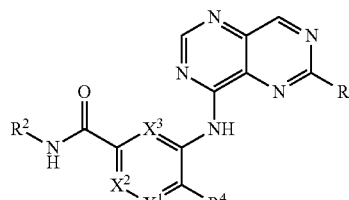
Example Compounds III-1 to III-579 and III-592 to III-608
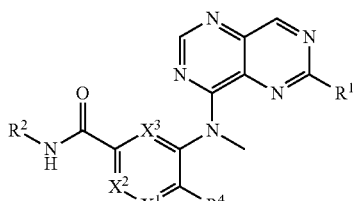
Example Compounds III-580 to III-587
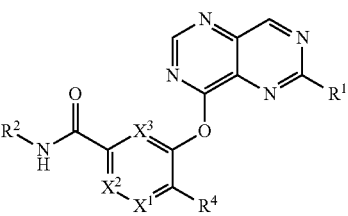
Example Compounds III-588 to III-591
| # | Structure | t_Ret. (HPLC) [min] | MS (M + H)+ |
|---|---|---|---|
| III-407 | 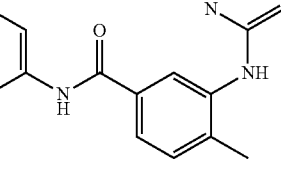 | 2.60 | 652 |
| III-408 | 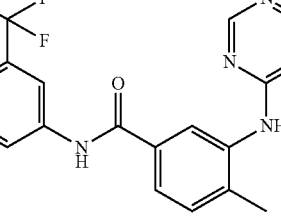 | 2.58 | 664 |
| III-409 | 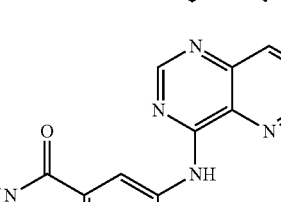 | 2.49 | 582 |
| III-410 | 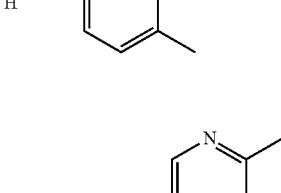 | 1.83 | 526 |
| III-411 | 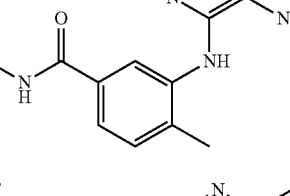 | 2.28 | 542 |

TABLE 3-continued
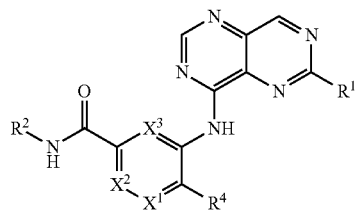
Example Compounds III-1 to III-579 and III-592 to III-608
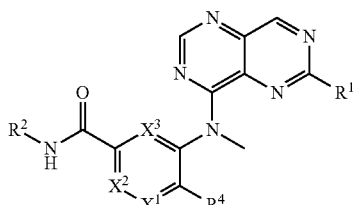
Example Compounds III-580 to III-587
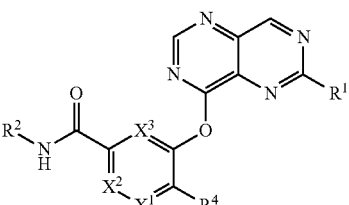
Example Compounds III-588 to III-591
| # | Structure | t_Ret. (HPLC) [min] | MS (M + H)+ |
|---|---|---|---|
| III-412 | 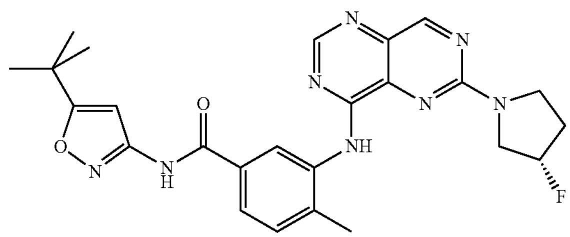 [SMILES: Cc1ccc(C(=O)Nc2cc(C(C)(C)C)on2)cc1Nc1ncnc2cnc(N3CC[C@H](F)C3)nc12] | 2.24 | 491 |
| III-413 | 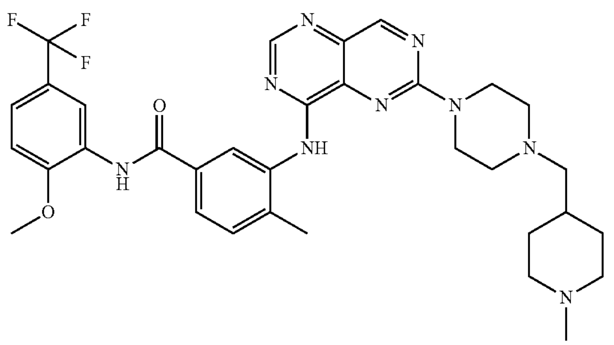 [SMILES: COc1ccc(C(F)(F)F)cc1NC(=O)c1ccc(C)c(Nc2ncnc3cnc(N4CCN(CC5CCN(C)CC5)CC4)nc23)c1] | 2.66 | 650 |
| III-414 | 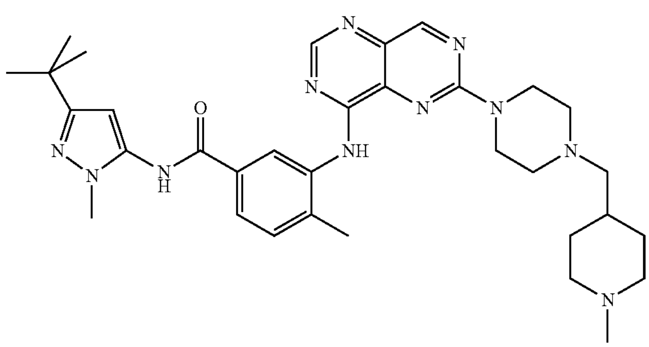 [SMILES: Cc1ccc(C(=O)Nc2cc(C(C)(C)C)nn2C)cc1Nc1ncnc2cnc(N3CCN(CC4CCN(C)CC4)CC3)nc12] | 2.26 | 612 |
| III-415 | 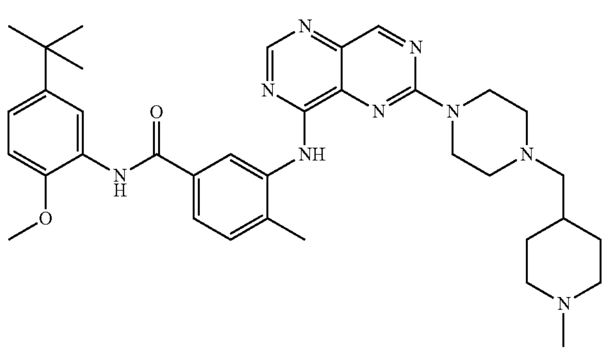 [SMILES: COc1ccc(C(C)(C)C)cc1NC(=O)c1ccc(C)c(Nc2ncnc3cnc(N4CCN(CC5CCN(C)CC5)CC4)nc23)c1] | 2.80 | 638 |

TABLE 3-continued
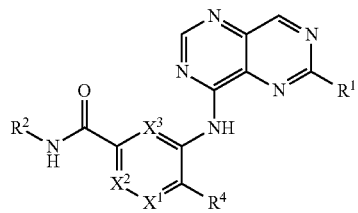
Example Compounds III-1 to III-579 and III-592 to III-608
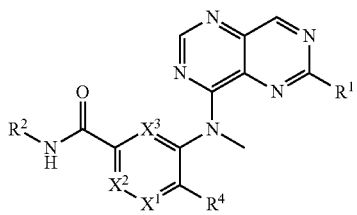
Example Compounds III-580 to III-587
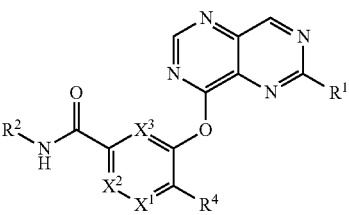
Example Compounds III-588 to III-591
| # | Structure | t$_{Ret.}$ (HPLC) [min] | MS (M + H)$^+$ |
|---|---|---|---|
| III-416 | 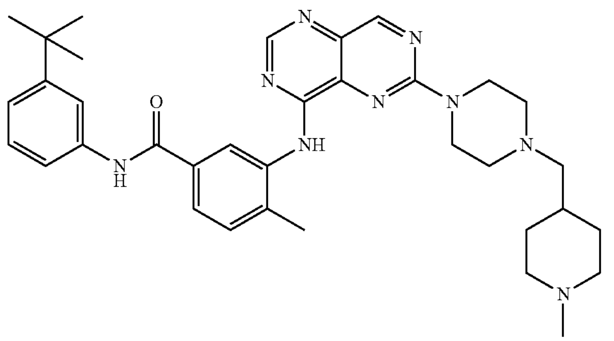 [SMILES: Cc1ccc(C(=O)Nc2cccc(C(C)(C)C)c2)cc1Nc1ncnc2cnc(N3CCN(CC4CCN(C)CC4)CC3)nc12] | 2.64 | 608 |
| III-417 | 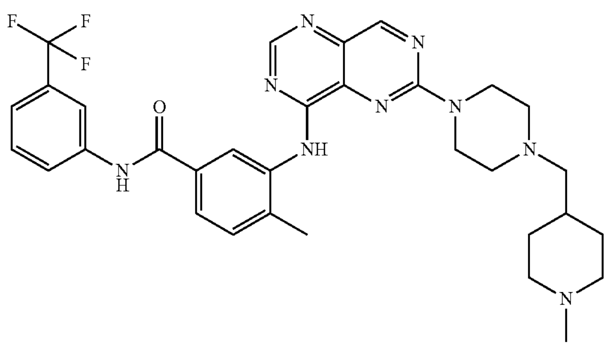 [SMILES: Cc1ccc(C(=O)Nc2cccc(C(F)(F)F)c2)cc1Nc1ncnc2cnc(N3CCN(CC4CCN(C)CC4)CC3)nc12] | 2.25 | 620 |
| III-418 | 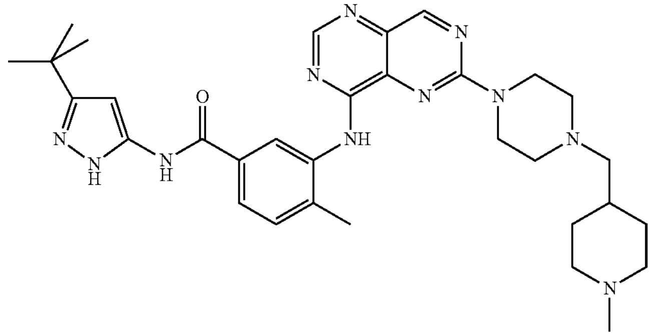 [SMILES: Cc1ccc(C(=O)Nc2cc(C(C)(C)C)n[nH]2)cc1Nc1ncnc2cnc(N3CCN(CC4CCN(C)CC4)CC3)nc12] | 2.20 | 598 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-419 | 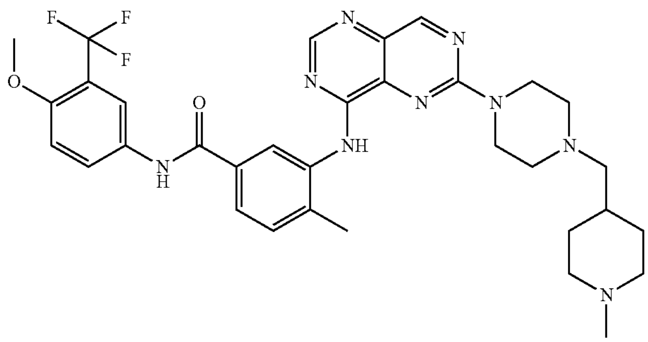 [SMILES: COc1ccc(NC(=O)c2ccc(C)c(Nc3ncnc4cnc(N5CCN(CC6CCN(C)CC6)CC5)nc34)c2)cc1C(F)(F)F] | 2.48 | 650 |
| III-420 | 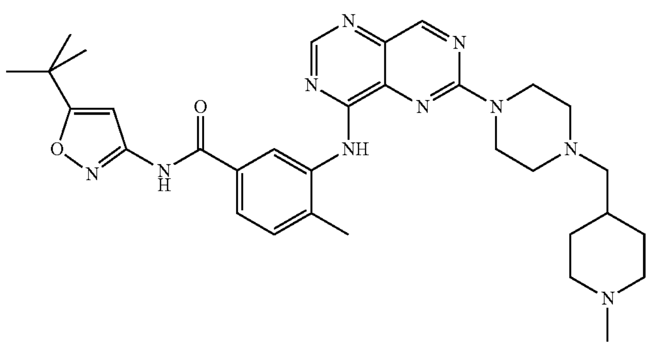 [SMILES: Cc1ccc(C(=O)Nc2cc(C(C)(C)C)on2)cc1Nc1ncnc2cnc(N3CCN(CC4CCN(C)CC4)CC3)nc12] | 2.45 | 599 |
| III-421 | 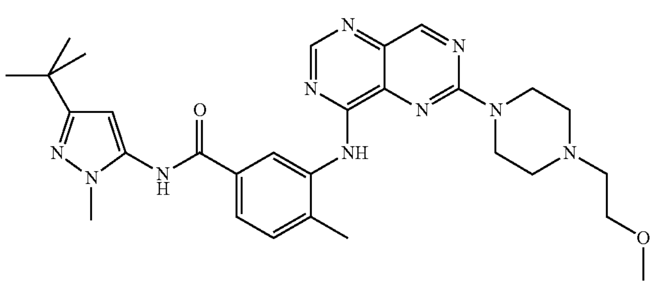 [SMILES: COCCN1CCN(c2ncc3ncnc(Nc4cc(C(=O)Nc5cc(C(C)(C)C)nn5C)ccc4C)c3n2)CC1] | 2.00 | 559 |
| III-422 | 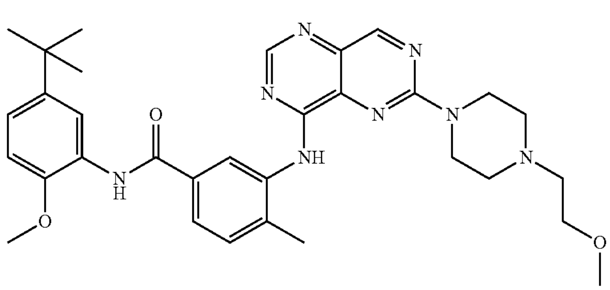 [SMILES: COCCN1CCN(c2ncc3ncnc(Nc4cc(C(=O)Nc5cc(C(C)(C)C)ccc5OC)ccc4C)c3n2)CC1] | 2.45 | 585 |

TABLE 3-continued
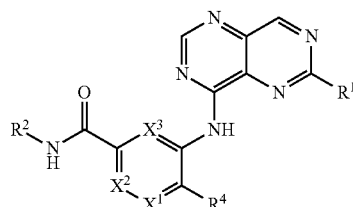
Example Compounds III-1 to III-579 and III-592 to III-608
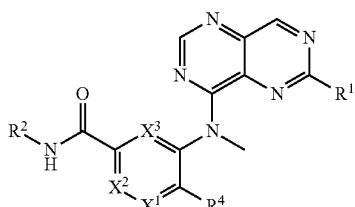
Example Compounds III-580 to III-587
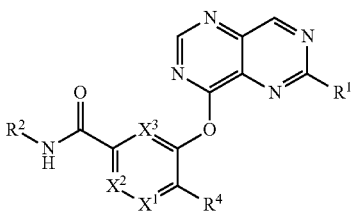
Example Compounds III-588 to III-591
| # | Structure | t_Ret. (HPLC) [min] | MS (M + H)+ |
|---|---|---|---|
| III-423 | 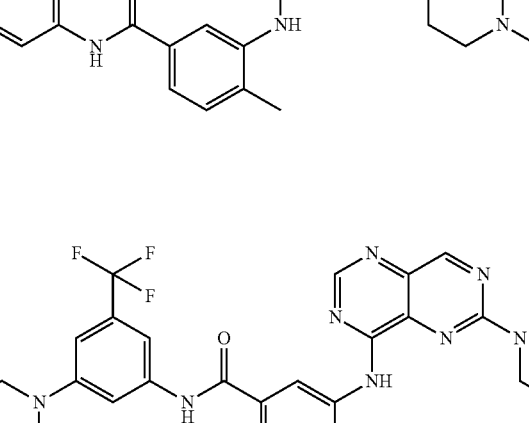 | 2.25 | 567 |
| III-424 | 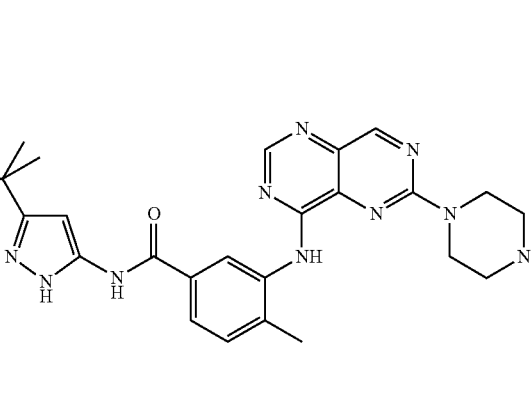 | 2.29 | 679 |
| III-425 | 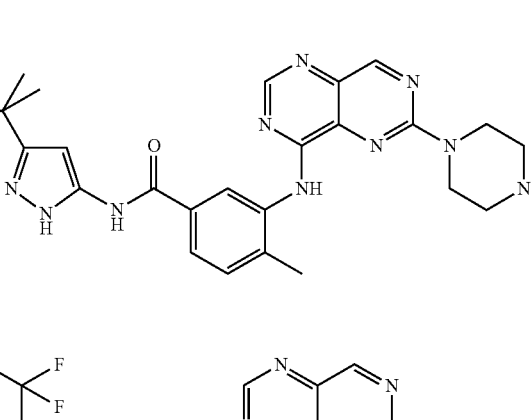 | 1.96 | 545 |
| III-426 | 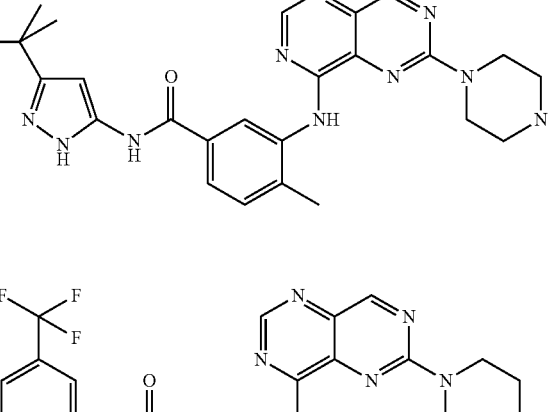 | 2.18 | 568 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-427 | 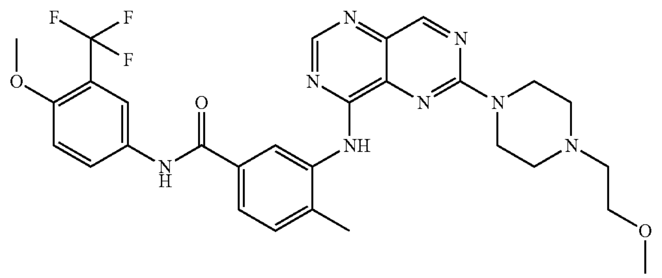 [SMILES: COCCN1CCN(c2ncc3ncnc(Nc4cc(C(=O)Nc5ccc(OC)c(C(F)(F)F)c5)ccc4C)c3n2)CC1] | 2.20 | 597 |
| III-428 | 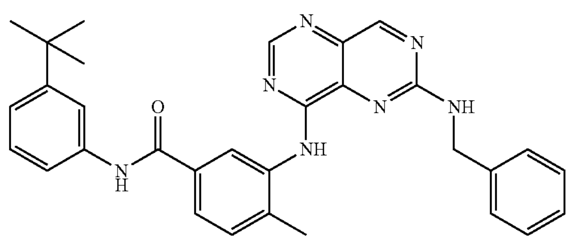 [SMILES: Cc1ccc(C(=O)Nc2cccc(C(C)(C)C)c2)cc1Nc1ncnc2cnc(NCc3ccccc3)nc12] | 2.50 | 518 |
| III-429 | 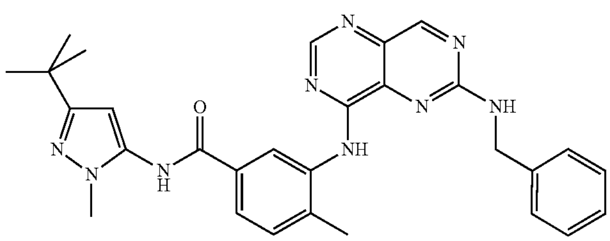 | 2.18 | 522 |
| III-430 | 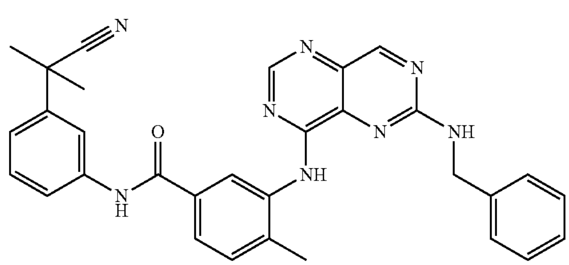 [SMILES: Cc1ccc(C(=O)Nc2cccc(C(C)(C)C#N)c2)cc1Nc1ncnc2cnc(NCc3ccccc3)nc12] | 2.28 | 529 |
| III-431 | 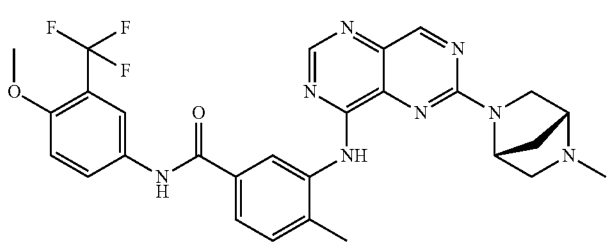 [SMILES: COc1ccc(NC(=O)c2ccc(C)c(Nc3ncnc4cnc(N5C[C@H]6C[C@@H]5CN6C)nc34)c2)cc1C(F)(F)F] | 1.85 | 565 |

TABLE 3-continued
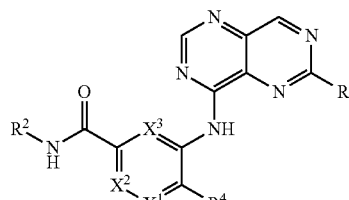
Example Compounds III-1 to III-579 and III-592 to III-608
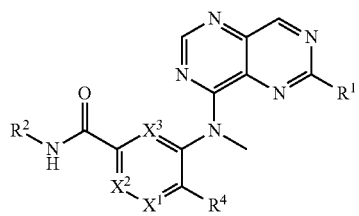
Example Compounds III-580 to III-587
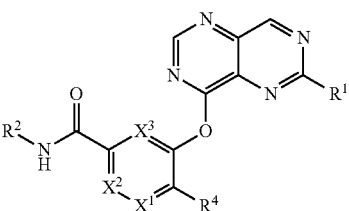
Example Compounds III-588 to III-591
| # | Structure | t$_{Ret.}$ (HPLC) [min] | MS (M + H)$^+$ |
|---|---|---|---|
| III-432 | 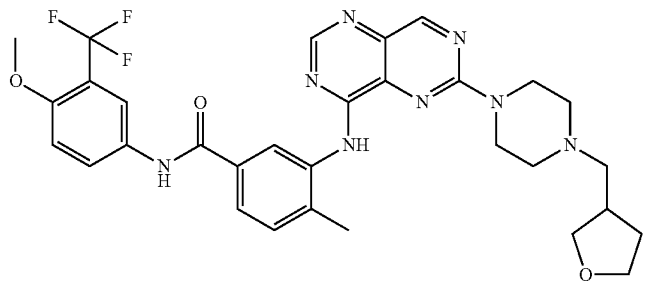 [SMILES: COc1ccc(NC(=O)c2ccc(C)c(Nc3ncnc4cnc(N5CCN(CC6CCOC6)CC5)nc34)c2)cc1C(F)(F)F] | 2.04 | 623 |
| III-433 | 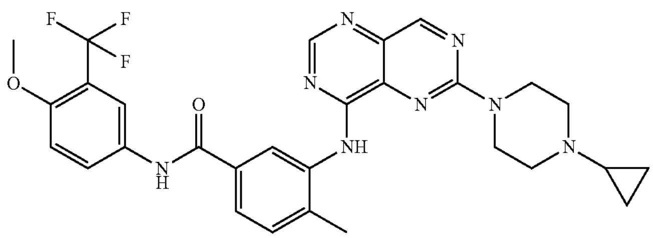 [SMILES: COc1ccc(NC(=O)c2ccc(C)c(Nc3ncnc4cnc(N5CCN(C6CC6)CC5)nc34)c2)cc1C(F)(F)F] | 2.13 | 579 |
| III-434 | 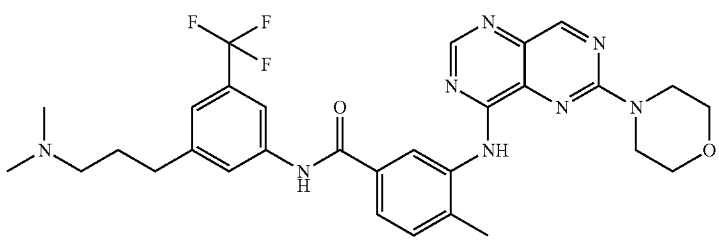 [SMILES: Cc1ccc(C(=O)Nc2cc(CCCN(C)C)cc(C(F)(F)F)c2)cc1Nc1ncnc2cnc(N3CCOCC3)nc12] | 2.03 | 595 |
| III-435 | 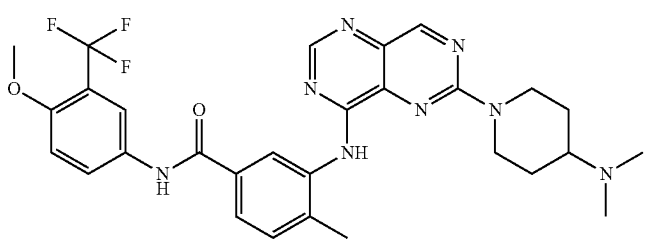 [SMILES: COc1ccc(NC(=O)c2ccc(C)c(Nc3ncnc4cnc(N5CCC(N(C)C)CC5)nc34)c2)cc1C(F)(F)F] | 2.01 | 581 |
| III-436 | 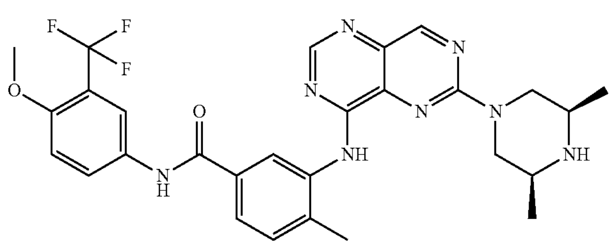 [SMILES: COc1ccc(NC(=O)c2ccc(C)c(Nc3ncnc4cnc(N5C[C@@H](C)N[C@@H](C)C5)nc34)c2)cc1C(F)(F)F] | 1.91 | 567 |

TABLE 3-continued
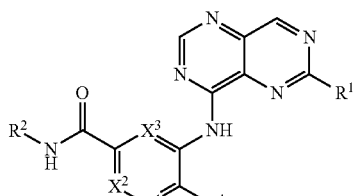
Example Compounds III-1 to III-579 and III-592 to III-608
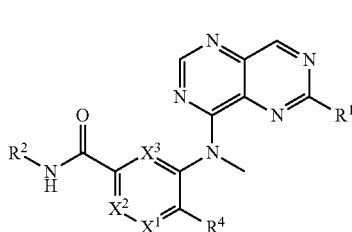
Example Compounds III-580 to III-587
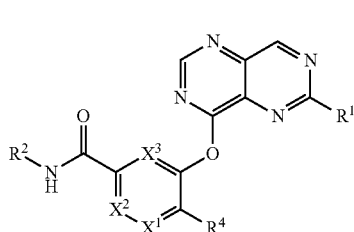
Example Compounds III-588 to III-591
| # | Structure | $t_{Ret.}$ (HPLC) [min] | MS (M + H)$^+$ |
|---|---|---|---|
| III-437 | 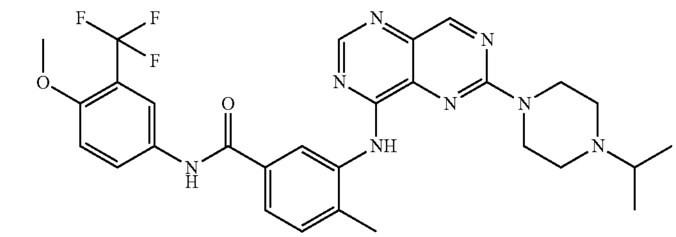 [SMILES: COc1ccc(NC(=O)c2ccc(C)c(Nc3ncnc4cnc(N5CCN(C(C)C)CC5)nc34)c2)cc1C(F)(F)F] | 2.10 | 581 |
| III-438 | 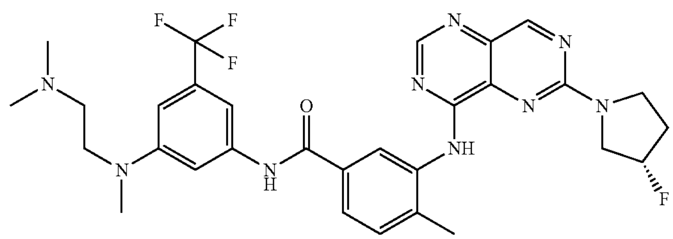 [SMILES: Cc1ccc(C(=O)Nc2cc(N(C)CCN(C)C)cc(C(F)(F)F)c2)cc1Nc1ncnc2cnc(N3CC[C@H](F)C3)nc12] | 2.38 | 612 |
| III-439 | 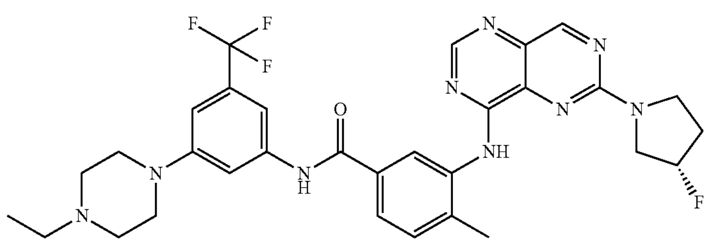 [SMILES: CCN1CCN(c2cc(NC(=O)c3ccc(C)c(Nc4ncnc5cnc(N6CC[C@H](F)C6)nc45)c3)cc(C(F)(F)F)c2)CC1] | 2.37 | 624 |
| III-440 | 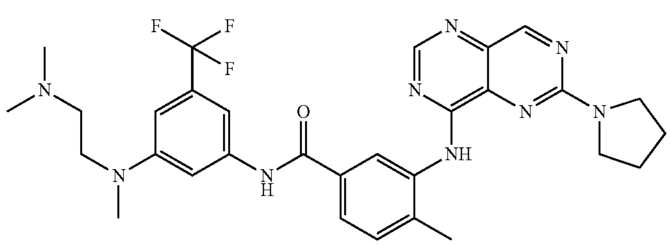 [SMILES: Cc1ccc(C(=O)Nc2cc(N(C)CCN(C)C)cc(C(F)(F)F)c2)cc1Nc1ncnc2cnc(N3CCCC3)nc12] | 2.49 | 594 |
| III-441 | 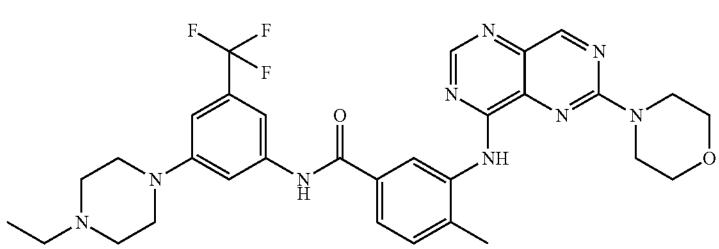 [SMILES: CCN1CCN(c2cc(NC(=O)c3ccc(C)c(Nc4ncnc5cnc(N6CCOCC6)nc45)c3)cc(C(F)(F)F)c2)CC1] | 2.29 | 622 |

TABLE 3-continued
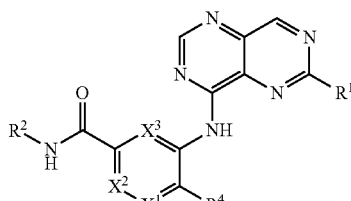
Example Compounds III-1 to III-579 and III-592 to III-608
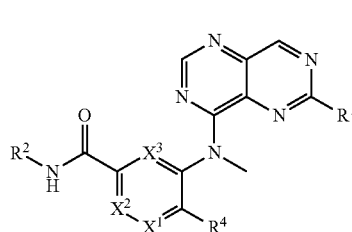
Example Compounds III-580 to III-587
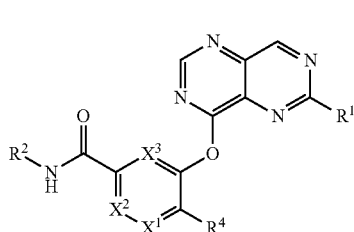
Example Compounds III-588 to III-591
| # | Structure | t$_{Ret.}$ (HPLC) [min] | MS (M + H)$^+$ |
|---|---|---|---|
| III-442 | 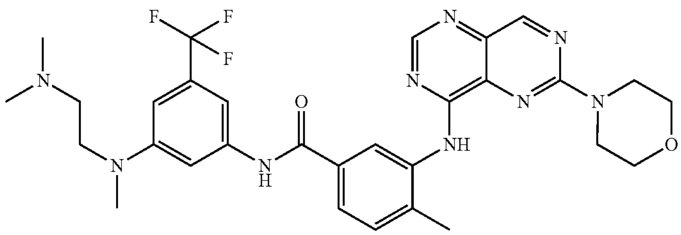 [SMILES: Cc1ccc(C(=O)Nc2cc(N(C)CCN(C)C)cc(C(F)(F)F)c2)cc1Nc1ncnc2cnc(N3CCOCC3)nc12] | 2.33 | 610 |
| III-443 | 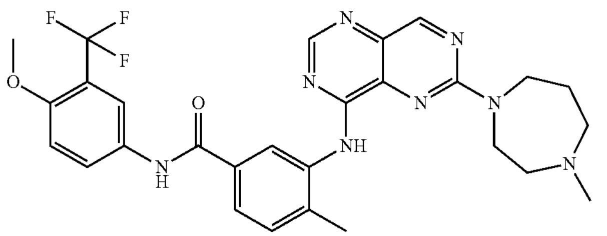 [SMILES: COc1ccc(NC(=O)c2ccc(C)c(Nc3ncnc4cnc(N5CCCN(C)CC5)nc34)c2)cc1C(F)(F)F] | 2.24 | 567 |
| III-444 | 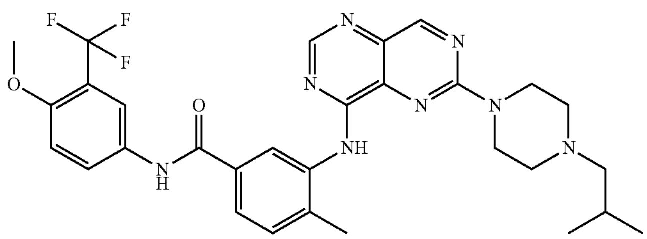 [SMILES: COc1ccc(NC(=O)c2ccc(C)c(Nc3ncnc4cnc(N5CCN(CC(C)C)CC5)nc34)c2)cc1C(F)(F)F] | 2.68 | 595 |
| III-445 | 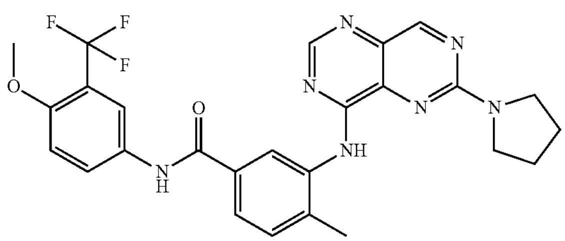 [SMILES: COc1ccc(NC(=O)c2ccc(C)c(Nc3ncnc4cnc(N5CCCC5)nc34)c2)cc1C(F)(F)F] | 2.38 | 524 |
| III-446 | 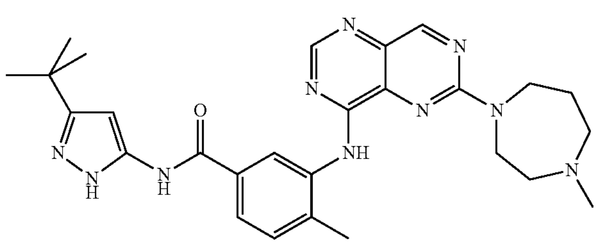 [SMILES: Cc1ccc(C(=O)Nc2cc(C(C)(C)C)n[nH]2)cc1Nc1ncnc2cnc(N3CCCN(C)CC3)nc12] | 1.98 | 515 |

TABLE 3-continued
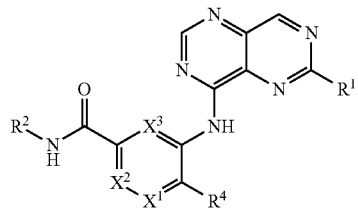 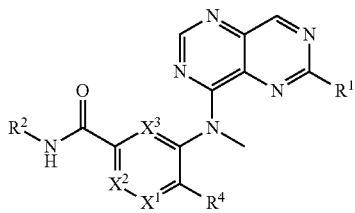 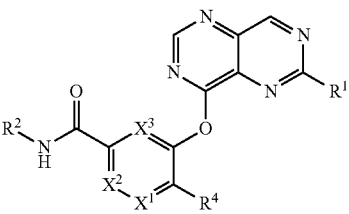
Example Compounds III-1 to III-579 and III-592 to III-608
Example Compounds III-580 to III-587
Example Compounds III-588 to III-591
| # | Structure | t_Ret. (HPLC) [min] | MS (M + H)+ |
|---|---|---|---|
| III-447 | 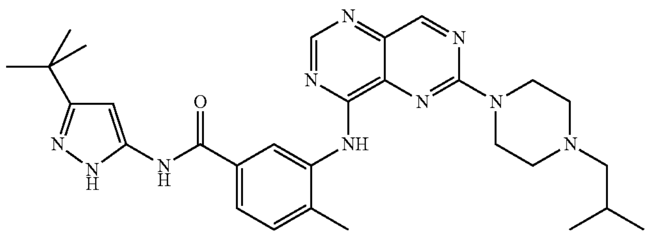 [SMILES: Cc1ccc(C(=O)Nc2cc(C(C)(C)C)n[nH]2)cc1Nc1ncnc2cnc(N3CCN(CC(C)C)CC3)nc12] | 2.42 | 543 |
| III-448 | 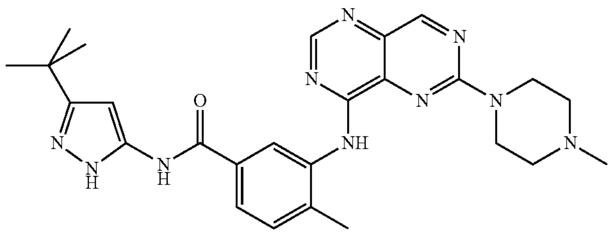 [SMILES: Cc1ccc(C(=O)Nc2cc(C(C)(C)C)n[nH]2)cc1Nc1ncnc2cnc(N3CCN(C)CC3)nc12] | 1.93 | 501 |
| III-449 | 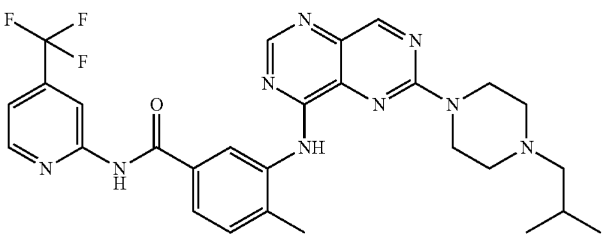 [SMILES: Cc1ccc(C(=O)Nc2cc(C(F)(F)F)ccn2)cc1Nc1ncnc2cnc(N3CCN(CC(C)C)CC3)nc12] | 2.72 | 566 |
| III-450 | 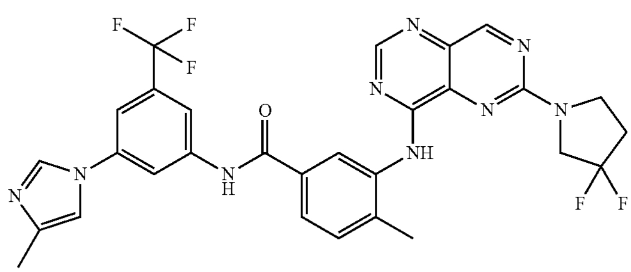 [SMILES: Cc1cn(-c2cc(NC(=O)c3ccc(C)c(Nc4ncnc5cnc(N6CCC(F)(F)C6)nc45)c3)cc(C(F)(F)F)c2)cn1] | 2.34 | 610 |
| III-451 | 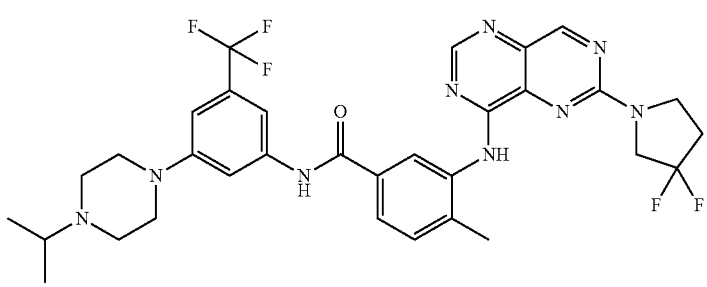 [SMILES: Cc1ccc(C(=O)Nc2cc(N3CCN(C(C)C)CC3)cc(C(F)(F)F)c2)cc1Nc1ncnc2cnc(N3CCC(F)(F)C3)nc12] | 2.54 | 656 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-452 | 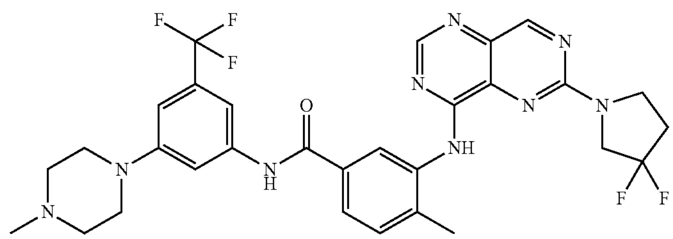 [SMILES: Cc1ccc(C(=O)Nc2cc(N3CCN(C)CC3)cc(C(F)(F)F)c2)cc1Nc1ncnc2cnc(N3CCC(F)(F)C3)nc12] | 2.36 | 628 |
| III-453 | 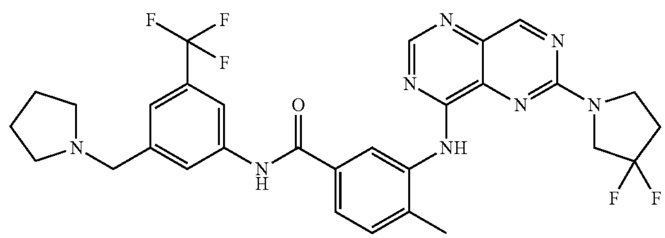 [SMILES: Cc1ccc(C(=O)Nc2cc(CN3CCCC3)cc(C(F)(F)F)c2)cc1Nc1ncnc2cnc(N3CCC(F)(F)C3)nc12] | 2.53 | 613 |
| III-454 | 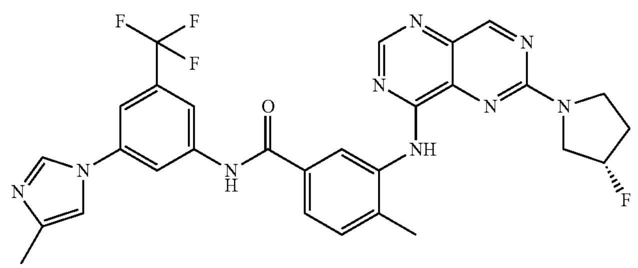 [SMILES: Cc1cn(-c2cc(NC(=O)c3ccc(C)c(Nc4ncnc5cnc(N6CC[C@H](F)C6)nc45)c3)cc(C(F)(F)F)c2)cn1] | 2.26 | 592 |
| III-455 | 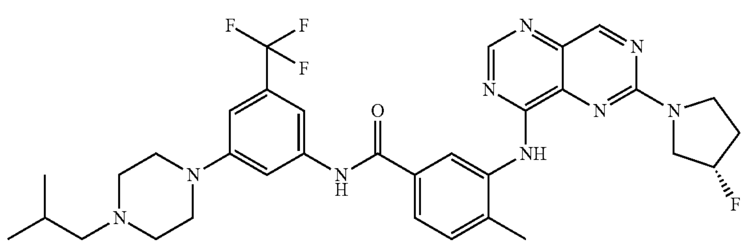 [SMILES: Cc1ccc(C(=O)Nc2cc(N3CCN(CC(C)C)CC3)cc(C(F)(F)F)c2)cc1Nc1ncnc2cnc(N3CC[C@H](F)C3)nc12] | 2.76 | 652 |
| III-456 | 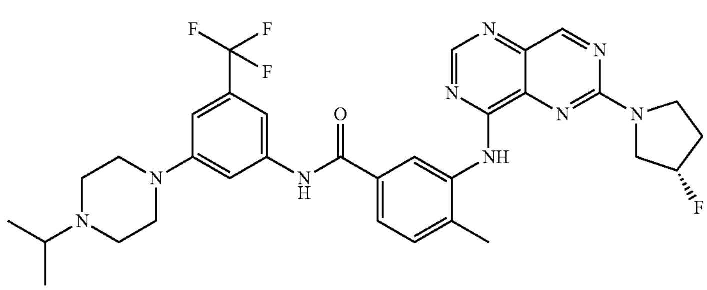 [SMILES: Cc1ccc(C(=O)Nc2cc(N3CCN(C(C)C)CC3)cc(C(F)(F)F)c2)cc1Nc1ncnc2cnc(N3CC[C@H](F)C3)nc12] | 2.40 | 638 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-457 | 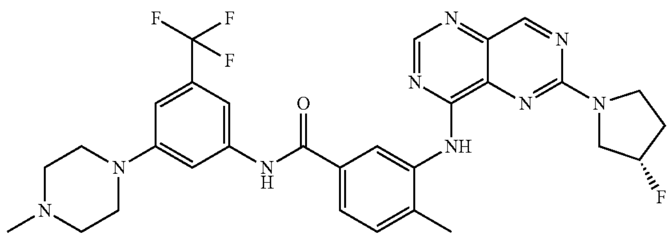 [SMILES: Cc1ccc(C(=O)Nc2cc(N3CCN(C)CC3)cc(C(F)(F)F)c2)cc1Nc1ncnc2cnc(N3CC[C@H](F)C3)nc12] | 2.30 | 610 |
| III-458 | 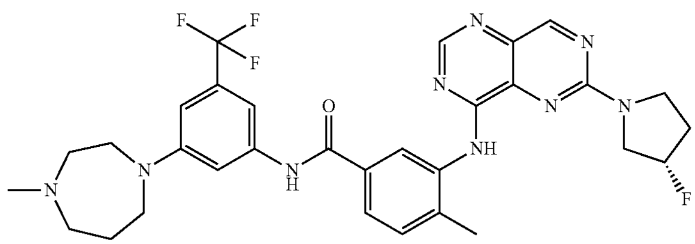 [SMILES: Cc1ccc(C(=O)Nc2cc(N3CCCN(C)CC3)cc(C(F)(F)F)c2)cc1Nc1ncnc2cnc(N3CC[C@H](F)C3)nc12] | 2.33 | 624 |
| III-459 | 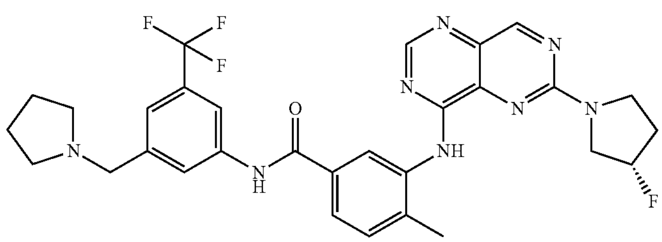 [SMILES: Cc1ccc(C(=O)Nc2cc(CN3CCCC3)cc(C(F)(F)F)c2)cc1Nc1ncnc2cnc(N3CC[C@H](F)C3)nc12] | 2.46 | 595 |
| III-460 | 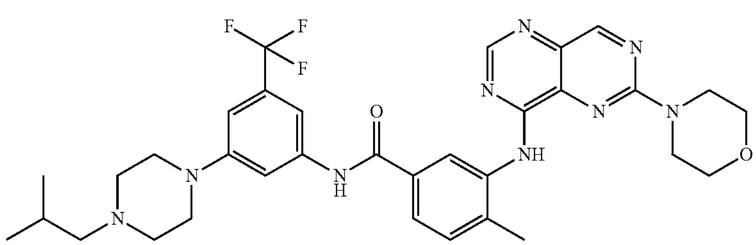 [SMILES: Cc1ccc(C(=O)Nc2cc(N3CCN(CC(C)C)CC3)cc(C(F)(F)F)c2)cc1Nc1ncnc2cnc(N3CCOCC3)nc12] | 2.69 | 650 |
| III-461 | 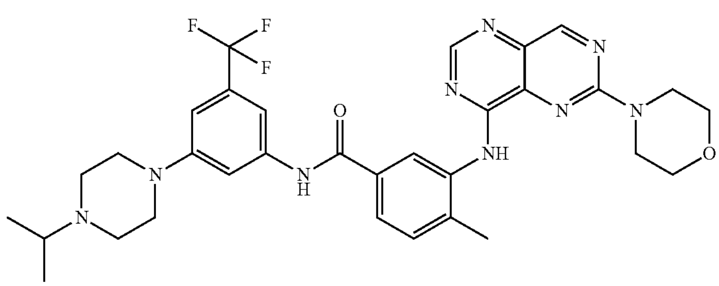 [SMILES: Cc1ccc(C(=O)Nc2cc(N3CCN(C(C)C)CC3)cc(C(F)(F)F)c2)cc1Nc1ncnc2cnc(N3CCOCC3)nc12] | 2.41 | 636 |

TABLE 3-continued
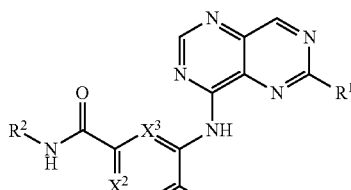
Example Compounds III-1 to III-579 and III-592 to III-608
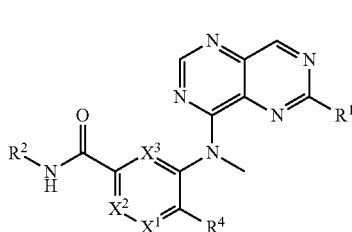
Example Compounds III-580 to III-587
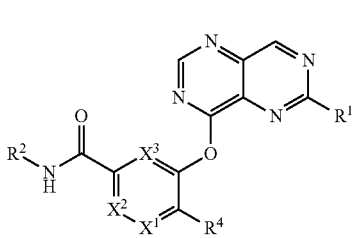
Example Compounds III-588 to III-591
| # | Structure | t_Ret. (HPLC) [min] | MS (M + H)+ |
|---|---|---|---|
| III-462 | 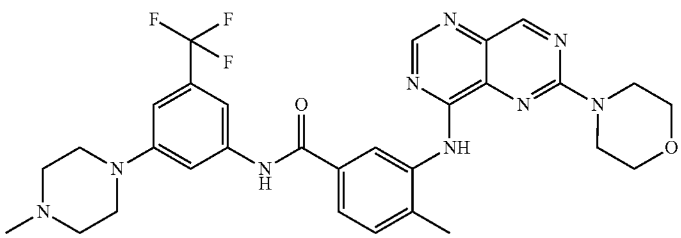 [SMILES: Cc1ccc(C(=O)Nc2cc(N3CCN(C)CC3)cc(C(F)(F)F)c2)cc1Nc1ncnc2cnc(N3CCOCC3)nc12] | 2.21 | 608 |
| III-463 | 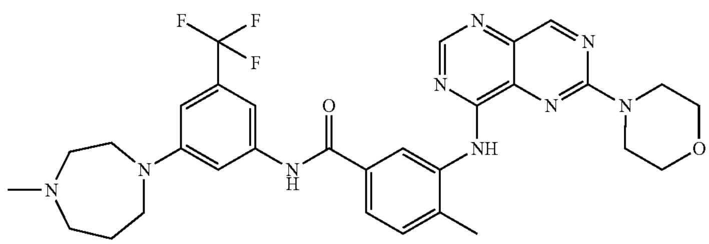 [SMILES: Cc1ccc(C(=O)Nc2cc(N3CCCN(C)CC3)cc(C(F)(F)F)c2)cc1Nc1ncnc2cnc(N3CCOCC3)nc12] | 2.25 | 622 |
| III-464 | 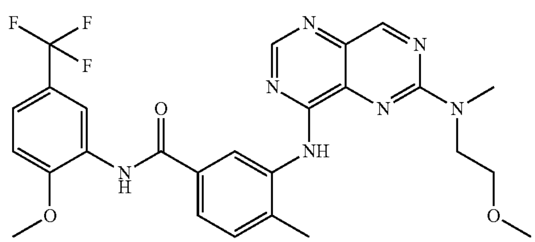 [SMILES: COCCN(C)c1ncc2ncnc(Nc3cc(C(=O)Nc4cc(C(F)(F)F)ccc4OC)ccc3C)c2n1] | 2.49 | 542 |
| III-465 | 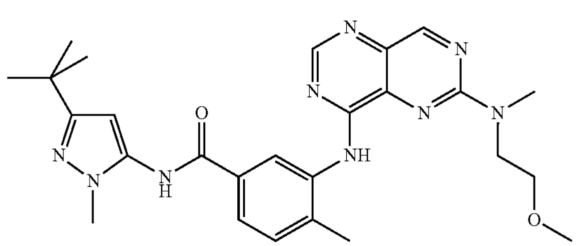 [SMILES: COCCN(C)c1ncc2ncnc(Nc3cc(C(=O)Nc4cc(C(C)(C)C)nn4C)ccc3C)c2n1] | 2.10 | 504 |
| III-466 | 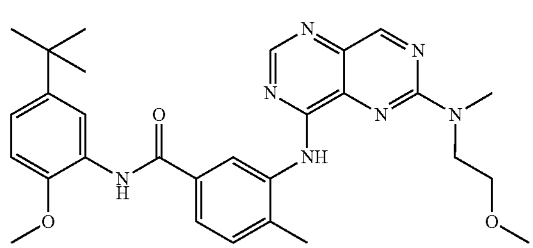 [SMILES: COCCN(C)c1ncc2ncnc(Nc3cc(C(=O)Nc4cc(C(C)(C)C)ccc4OC)ccc3C)c2n1] | 2.54 | 530 |

TABLE 3-continued
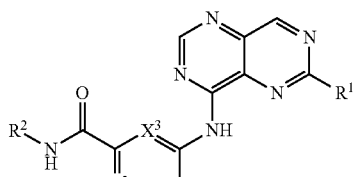
Example Compounds III-1 to III-579 and III-592 to III-608
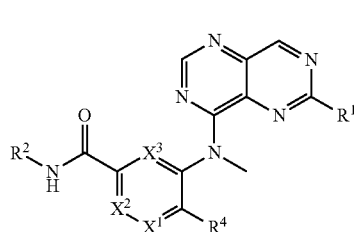
Example Compounds III-580 to III-587
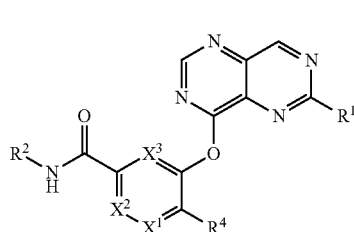
Example Compounds III-588 to III-591
| # | Structure | $t_{Ret.}$ (HPLC) [min] | MS (M + H)$^+$ |
|---|---|---|---|
| III-467 | 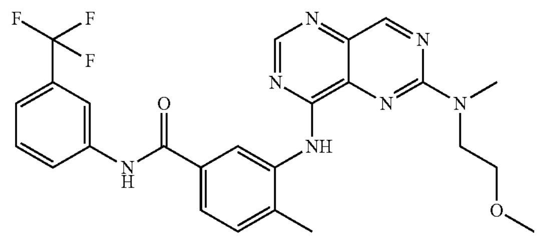 [SMILES: COCCN(C)c1ncc2ncnc(Nc3cc(C(=O)Nc4cccc(C(F)(F)F)c4)ccc3C)c2n1] | 2.35 | 512 |
| III-468 | 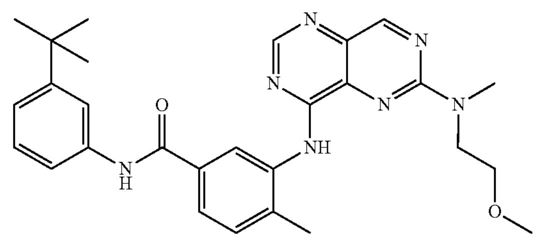 [SMILES: COCCN(C)c1ncc2ncnc(Nc3cc(C(=O)Nc4cccc(C(C)(C)C)c4)ccc3C)c2n1] | 2.39 | 500 |
| III-469 | 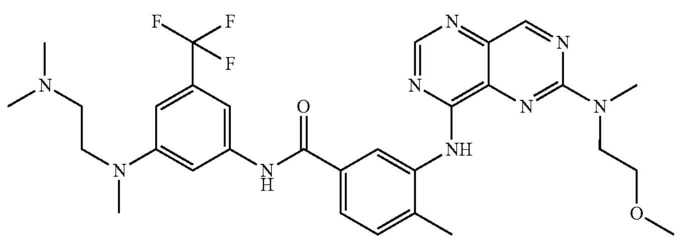 | 2.40 | 612 |
| III-470 | 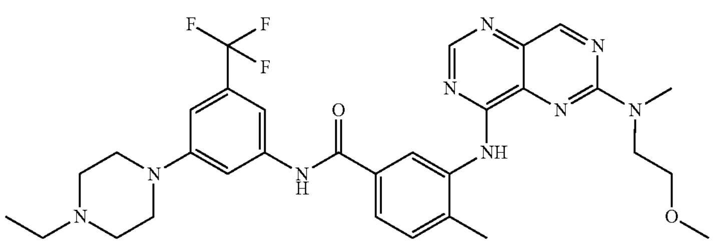 [SMILES: CCN1CCN(c2cc(NC(=O)c3ccc(C)c(Nc4ncnc5cnc(N(C)CCOC)nc45)c3)cc(C(F)(F)F)c2)CC1] | 2.37 | 624 |
| III-471 | 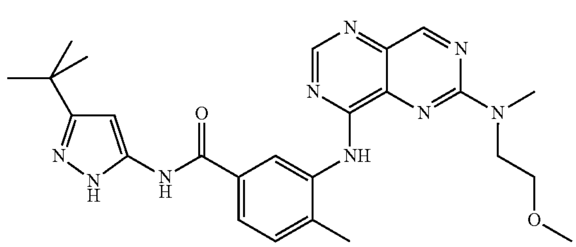 [SMILES: COCCN(C)c1ncc2ncnc(Nc3cc(C(=O)Nc4cc(C(C)(C)C)n[nH]4)ccc3C)c2n1] | 2.04 | 490 |

TABLE 3-continued
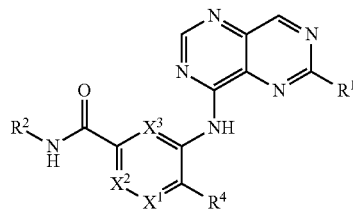
Example Compounds III-1 to III-579 and III-592 to III-608
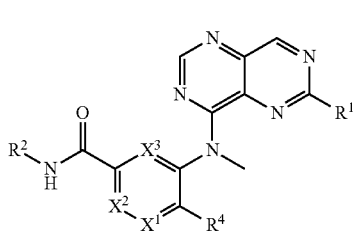
Example Compounds III-580 to III-587
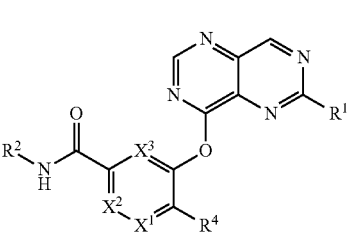
Example Compounds III-588 to III-591
| # | Structure | t_Ret. (HPLC) [min] | MS (M + H)+ |
|---|---|---|---|
| III-472 | 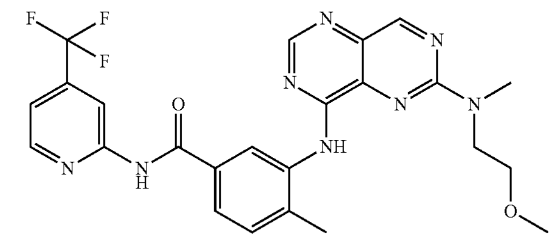 [SMILES: COCCN(C)c1ncc2ncnc(Nc3cc(C(=O)Nc4cc(C(F)(F)F)ccn4)ccc3C)c2n1] | 2.24 | 513 |
| III-473 | 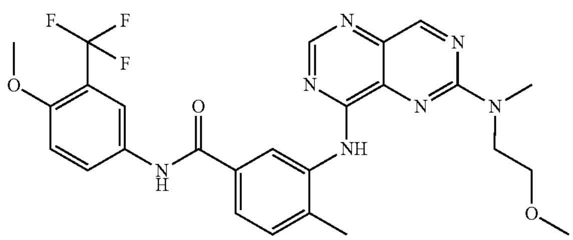 [SMILES: COCCN(C)c1ncc2ncnc(Nc3cc(C(=O)Nc4ccc(OC)c(C(F)(F)F)c4)ccc3C)c2n1] | 2.31 | 542 |
| III-474 | 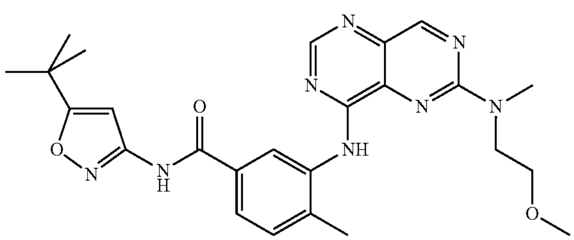 [SMILES: COCCN(C)c1ncc2ncnc(Nc3cc(C(=O)Nc4cc(C(C)(C)C)on4)ccc3C)c2n1] | 2.27 | 491 |
| III-475 | 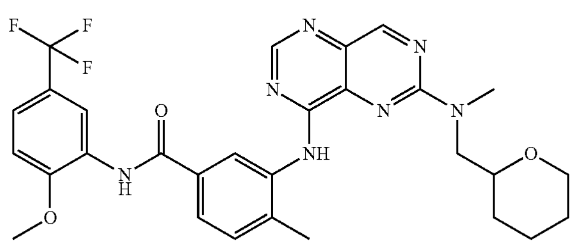 [SMILES: COc1ccc(C(F)(F)F)cc1NC(=O)c1ccc(C)c(Nc2ncnc3cnc(N(C)CC4CCCCO4)nc23)c1] | 2.70 | 582 |
| III-476 | 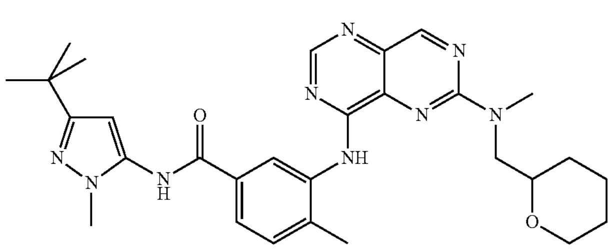 [SMILES: Cc1ccc(C(=O)Nc2cc(C(C)(C)C)nn2C)cc1Nc1ncnc2cnc(N(C)CC3CCCCO3)nc12] | 2.23 | 544 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-477 | 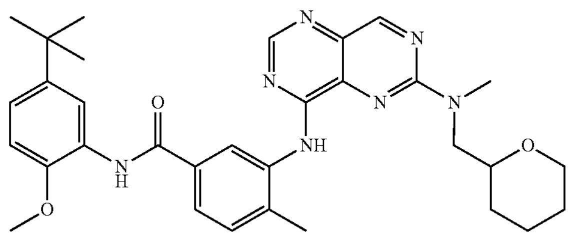 [SMILES: COc1ccc(C(C)(C)C)cc1NC(=O)c1ccc(C)c(Nc2ncnc3cnc(N(C)CC4CCCCO4)nc23)c1] | 2.83 | 570 |
| III-478 | 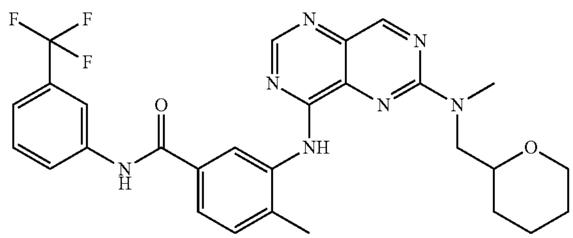 [SMILES: Cc1ccc(C(=O)Nc2cccc(C(F)(F)F)c2)cc1Nc1ncnc2cnc(N(C)CC3CCCCO3)nc12] | 2.48 | 552 |
| III-479 | 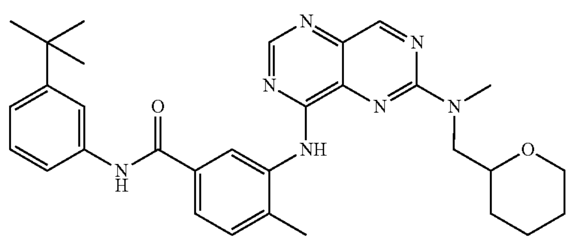 [SMILES: Cc1ccc(C(=O)Nc2cccc(C(C)(C)C)c2)cc1Nc1ncnc2cnc(N(C)CC3CCCCO3)nc12] | 2.65 | 540 |
| III-480 | 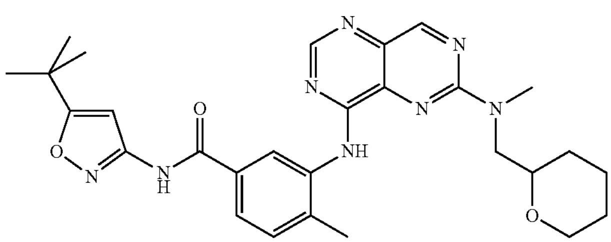 [SMILES: Cc1ccc(C(=O)Nc2cc(C(C)(C)C)on2)cc1Nc1ncnc2cnc(N(C)CC3CCCCO3)nc12] | 2.45 | 531 |
| III-481 | 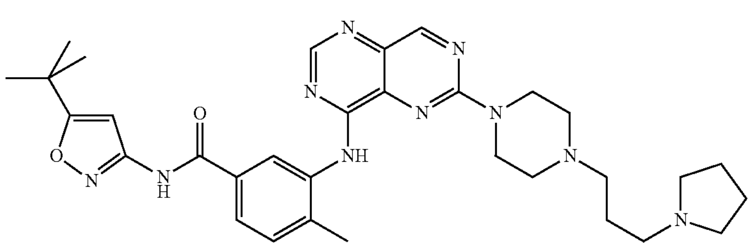 [SMILES: Cc1ccc(C(=O)Nc2cc(C(C)(C)C)on2)cc1Nc1ncnc2cnc(N3CCN(CCCN4CCCC4)CC3)nc12] | 2.38 | 599 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-482 | 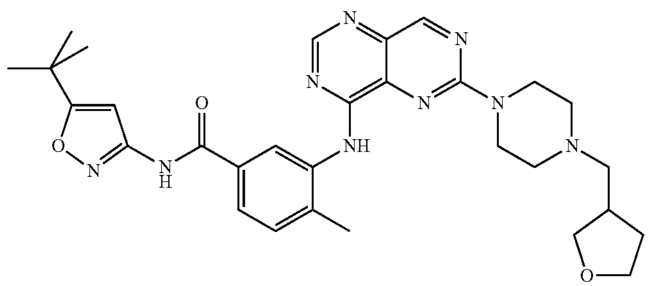 [SMILES: Cc1ccc(C(=O)Nc2cc(C(C)(C)C)on2)cc1Nc1ncnc2cnc(N3CCN(CC4CCOC4)CC3)nc12] | 2.28 | 572 |
| III-483 | 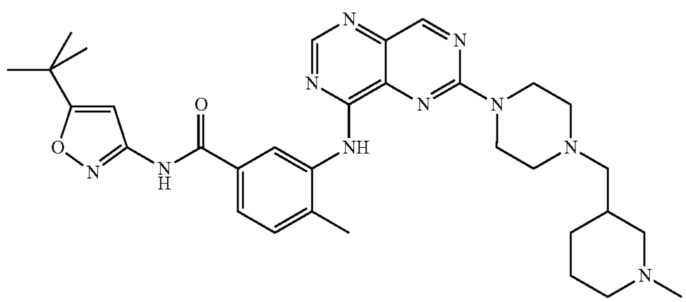 [SMILES: Cc1ccc(C(=O)Nc2cc(C(C)(C)C)on2)cc1Nc1ncnc2cnc(N3CCN(CC4CCCN(C)C4)CC3)nc12] | 2.39 | 599 |
| III-484 | 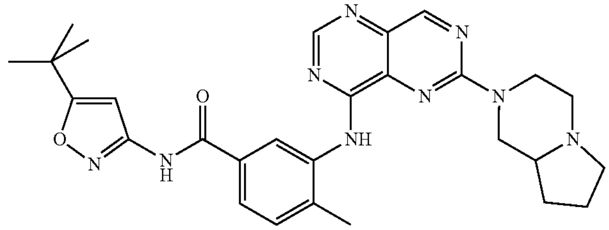 [SMILES: Cc1ccc(C(=O)Nc2cc(C(C)(C)C)on2)cc1Nc1ncnc2cnc(N3CCN4CCCC4C3)nc12] | 2.27 | 528 |
| III-485 | 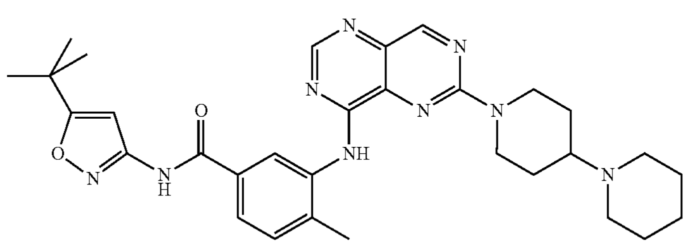 [SMILES: Cc1ccc(C(=O)Nc2cc(C(C)(C)C)on2)cc1Nc1ncnc2cnc(N3CCC(N4CCCCC4)CC3)nc12] | 2.49 | 570 |
| III-486 | 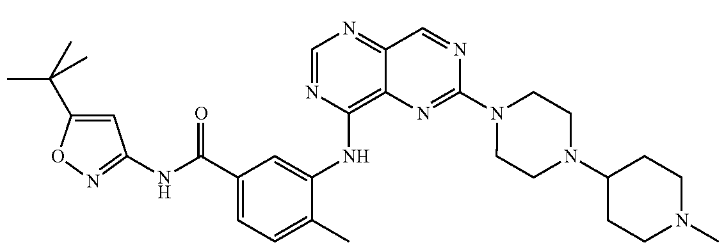 [SMILES: Cc1ccc(C(=O)Nc2cc(C(C)(C)C)on2)cc1Nc1ncnc2cnc(N3CCN(C4CCN(C)CC4)CC3)nc12] | 2.16 | 585 |

TABLE 3-continued
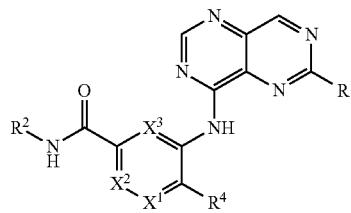
Example Compounds III-1 to III-579 and III-592 to III-608
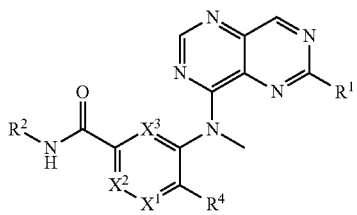
Example Compounds III-580 to III-587
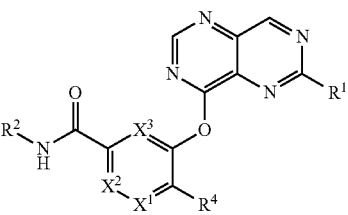
Example Compounds III-588 to III-591
| # | Structure | $t_{Ret.}$ (HPLC) [min] | MS (M + H)$^+$ |
|---|---|---|---|
| III-487 | 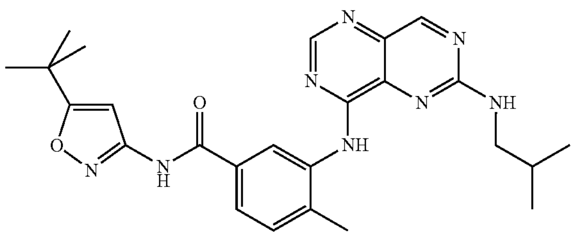 [SMILES: Cc1ccc(C(=O)Nc2cc(C(C)(C)C)on2)cc1Nc1ncnc2cnc(NCC(C)C)nc12] | 2.03 | 475 |
| III-488 | 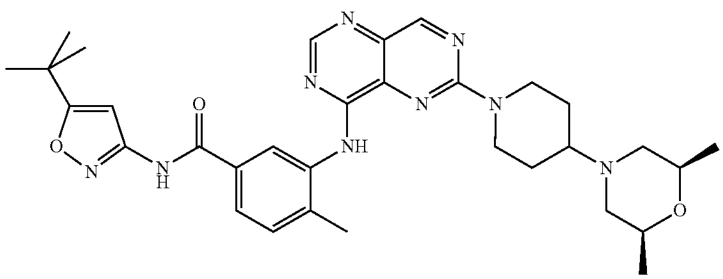 [SMILES: Cc1ccc(C(=O)Nc2cc(C(C)(C)C)on2)cc1Nc1ncnc2cnc(N3CCC(N4C[C@@H](C)O[C@@H](C)C4)CC3)nc12] | 1.99 | 600 |
| III-489 | 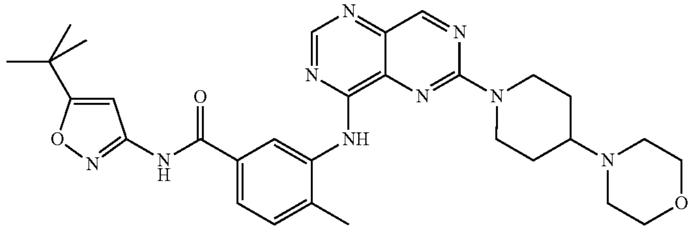 [SMILES: Cc1ccc(C(=O)Nc2cc(C(C)(C)C)on2)cc1Nc1ncnc2cnc(N3CCC(N4CCOCC4)CC3)nc12] | 1.80 | 572 |
| III-490 | 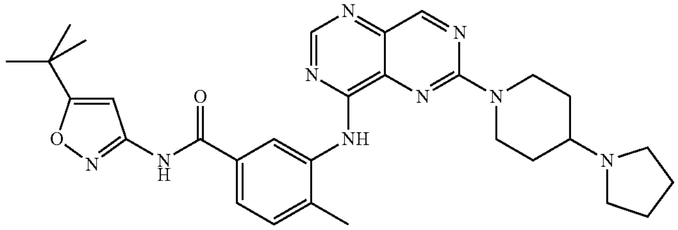 [SMILES: Cc1ccc(C(=O)Nc2cc(C(C)(C)C)on2)cc1Nc1ncnc2cnc(N3CCC(N4CCCC4)CC3)nc12] | 2.09 | 556 |
| III-491 | 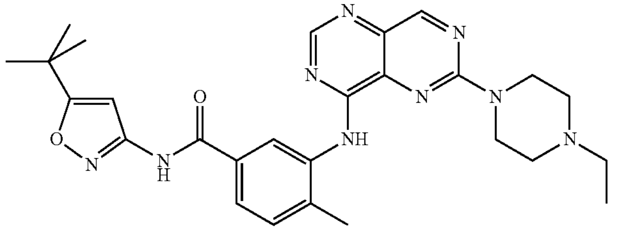 [SMILES: CCN1CCN(c2ncc3ncnc(Nc4cc(C(=O)Nc5cc(C(C)(C)C)on5)ccc4C)c3n2)CC1] | 1.92 | 516 |

TABLE 3-continued
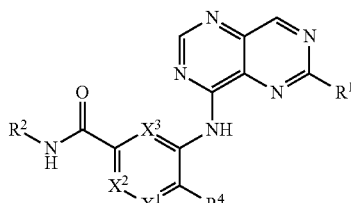
Example Compounds III-1 to III-579 and III-592 to III-608
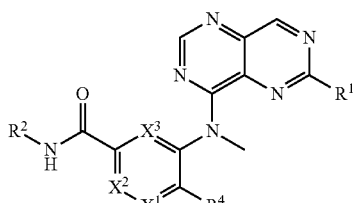
Example Compounds III-580 to III-587
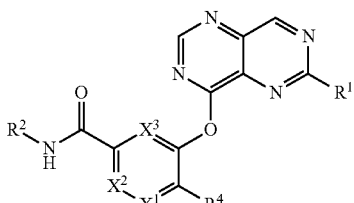
Example Compounds III-588 to III-591
| # | Structure | t_Ret. (HPLC) [min] | MS (M + H)+ |
|---|---|---|---|
| III-492 | 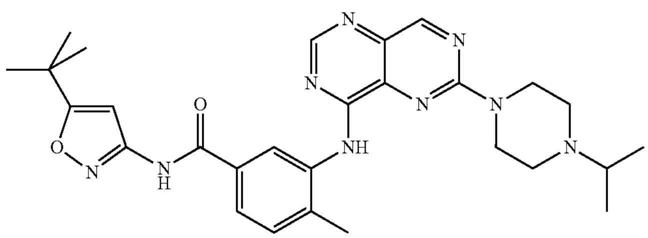 [SMILES: Cc1ccc(C(=O)Nc2cc(C(C)(C)C)on2)cc1Nc1ncnc2cnc(N3CCN(C(C)C)CC3)nc12] | 2.04 | 530 |
| III-493 | 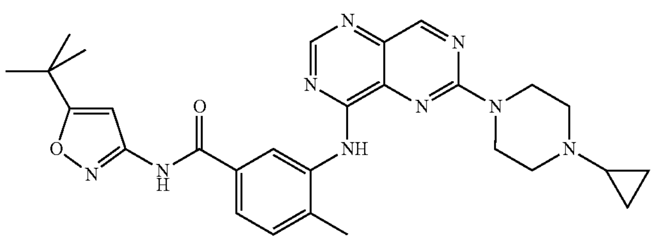 [SMILES: Cc1ccc(C(=O)Nc2cc(C(C)(C)C)on2)cc1Nc1ncnc2cnc(N3CCN(C4CC4)CC3)nc12] | 2.05 | 528 |
| III-494 | 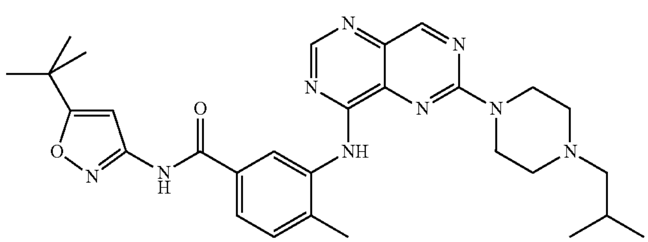 [SMILES: Cc1ccc(C(=O)Nc2cc(C(C)(C)C)on2)cc1Nc1ncnc2cnc(N3CCN(CC(C)C)CC3)nc12] | 2.34 | 544 |
| III-495 | 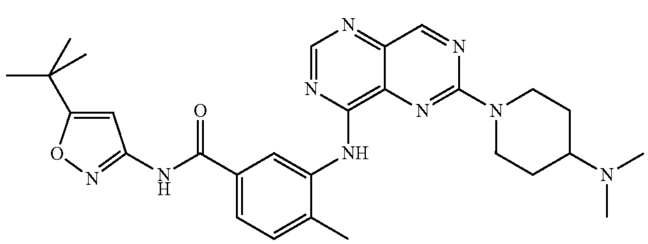 [SMILES: Cc1ccc(C(=O)Nc2cc(C(C)(C)C)on2)cc1Nc1ncnc2cnc(N3CCC(N(C)C)CC3)nc12] | 1.91 | 530 |
| III-496 | 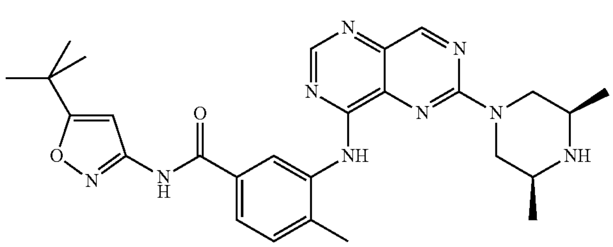 [SMILES: Cc1ccc(C(=O)Nc2cc(C(C)(C)C)on2)cc1Nc1ncnc2cnc(N3C[C@@H](C)N[C@@H](C)C3)nc12] | 1.85 | 516 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|-----------|---------------------|-------------|
| III-497 | 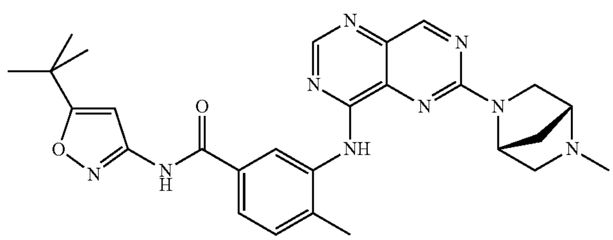 [SMILES: Cc1ccc(C(=O)Nc2cc(C(C)(C)C)on2)cc1Nc1ncnc2cnc(N3C[C@H]4C[C@@H]3CN4C)nc12] | 1.75 | 514 |
| III-498 | 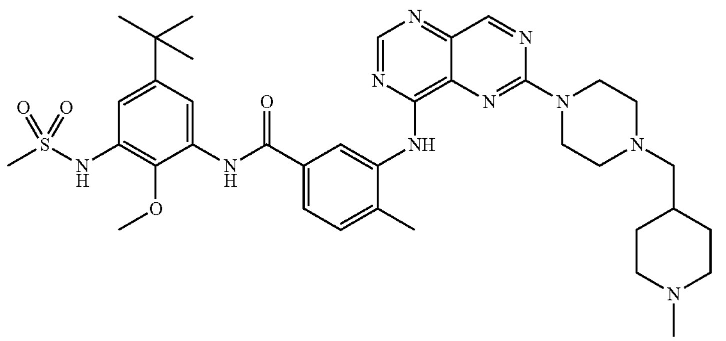 [SMILES: COc1c(NC(=O)c2ccc(C)c(Nc3ncnc4cnc(N5CCN(CC6CCN(C)CC6)CC5)nc34)c2)cc(C(C)(C)C)cc1NS(C)(=O)=O] | 2.04 | 732 |
| III-499 | 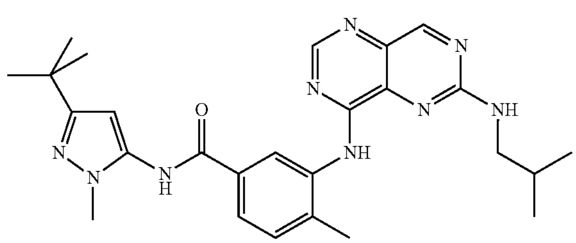 [SMILES: Cc1ccc(C(=O)Nc2cc(C(C)(C)C)nn2C)cc1Nc1ncnc2cnc(NCC(C)C)nc12] | 2.21 | 488 |
| III-500 | 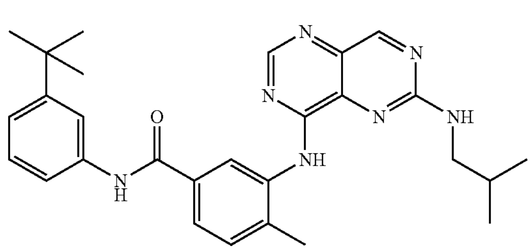 [SMILES: Cc1ccc(C(=O)Nc2cccc(C(C)(C)C)c2)cc1Nc1ncnc2cnc(NCC(C)C)nc12] | 2.54 | 484 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)⁺ |
|---|---|---|---|
| III-501 | 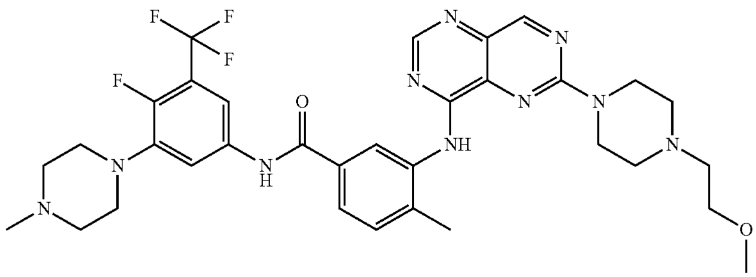 [SMILES: COCCN1CCN(c2ncc3ncnc(Nc4cc(C(=O)Nc5cc(N6CCN(C)CC6)c(F)c(C(F)(F)F)c5)ccc4C)c3n2)CC1] | 2.26 | 683 |
| III-502 | 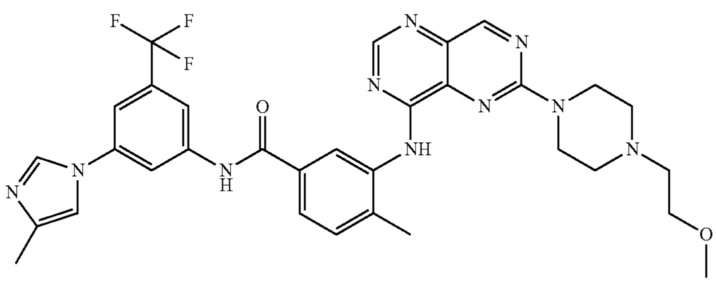 [SMILES: COCCN1CCN(c2ncc3ncnc(Nc4cc(C(=O)Nc5cc(-n6cnc(C)c6)cc(C(F)(F)F)c5)ccc4C)c3n2)CC1] | 2.16 | 647 |
| III-503 | 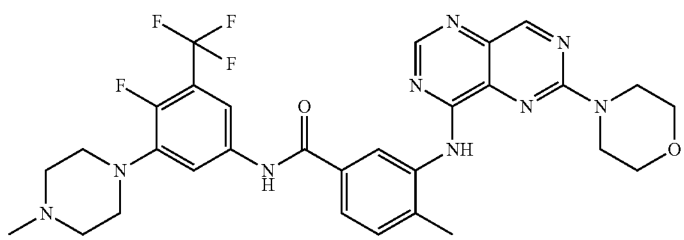 [SMILES: Cc1ccc(C(=O)Nc2cc(N3CCN(C)CC3)c(F)c(C(F)(F)F)c2)cc1Nc1ncnc2cnc(N3CCOCC3)nc12] | 2.28 | 626 |
| III-504 | 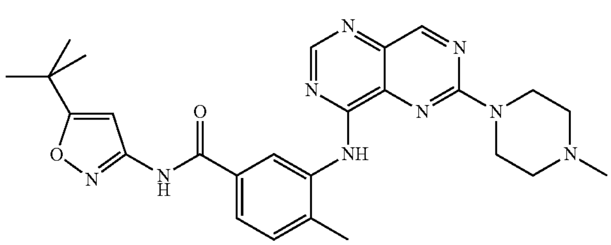 [SMILES: Cc1ccc(C(=O)Nc2cc(C(C)(C)C)on2)cc1Nc1ncnc2cnc(N3CCN(C)CC3)nc12] | 2.13 | 502 |
| III-505 | 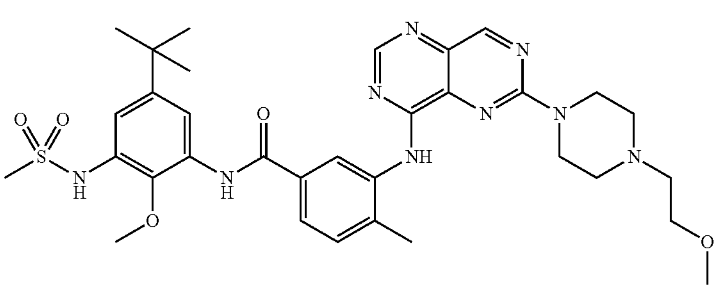 [SMILES: COCCN1CCN(c2ncc3ncnc(Nc4cc(C(=O)Nc5cc(C(C)(C)C)cc(NS(C)(=O)=O)c5OC)ccc4C)c3n2)CC1] | 1.87 | 678 |

TABLE 3-continued
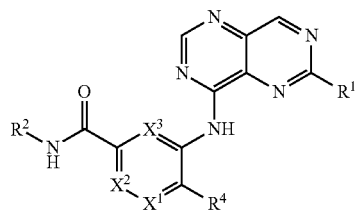
Example Compounds III-1 to III-579 and III-592 to III-608
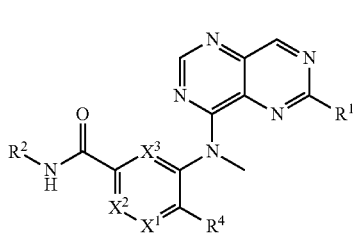
Example Compounds III-580 to III-587
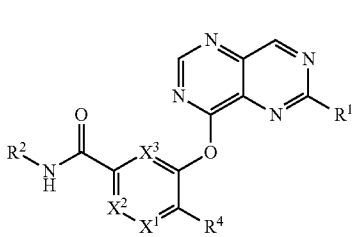
Example Compounds III-588 to III-591
| # | Structure | t_Ret. (HPLC) [min] | MS (M + H)+ |
|---|---|---|---|
| III-506 | 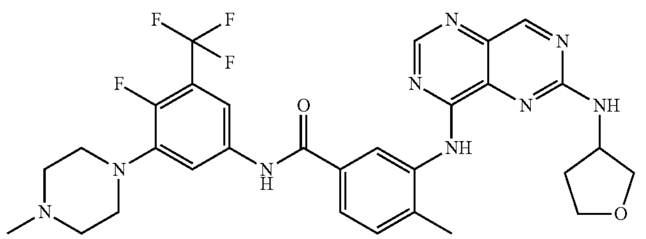 [SMILES: Cc1ccc(C(=O)Nc2cc(N3CCN(C)CC3)c(F)c(C(F)(F)F)c2)cc1Nc1ncnc2cnc(NC3CCOC3)nc12] | 2.17 | 626 |
| III-507 | 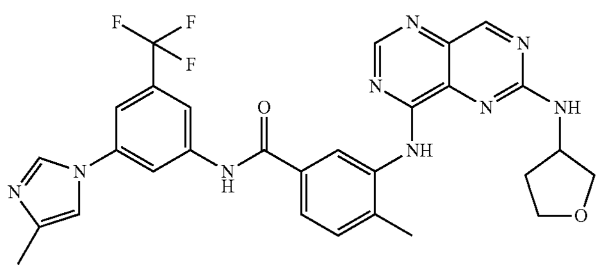 [SMILES: Cc1cn(-c2cc(NC(=O)c3ccc(C)c(Nc4ncnc5cnc(NC6CCOC6)nc45)c3)cc(C(F)(F)F)c2)cn1] | 2.07 | 590 |
| III-508 | 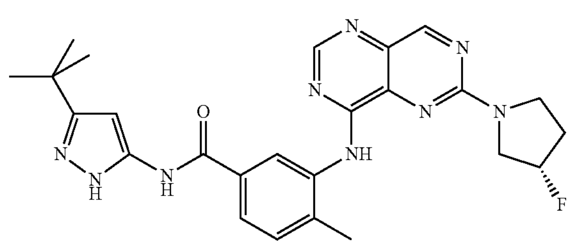 [SMILES: Cc1ccc(C(=O)Nc2cc(C(C)(C)C)n[nH]2)cc1Nc1ncnc2cnc(N3CC[C@H](F)C3)nc12] | 2.04 | 490 |
| III-509 | 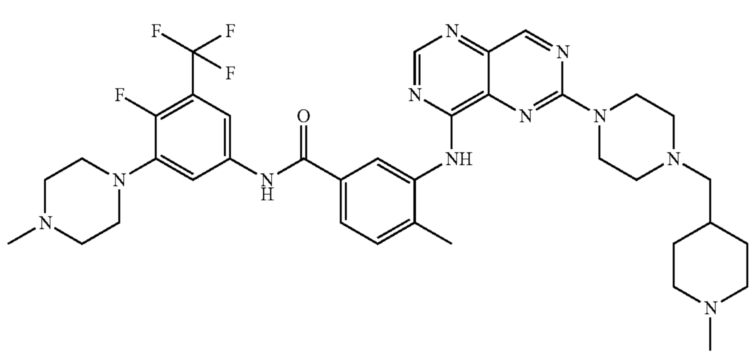 [SMILES: Cc1ccc(C(=O)Nc2cc(N3CCN(C)CC3)c(F)c(C(F)(F)F)c2)cc1Nc1ncnc2cnc(N3CCN(CC4CCN(C)CC4)CC3)nc12] | 2.47 | 736 |

TABLE 3-continued

Example Compounds III-1 to III-579 and III-592 to III-608

Example Compounds III-580 to III-587

Example Compounds III-588 to III-591

| # | Structure | t_{Ret.} (HPLC) [min] | MS (M + H)+ |
|---|---|---|---|
| III-510 | 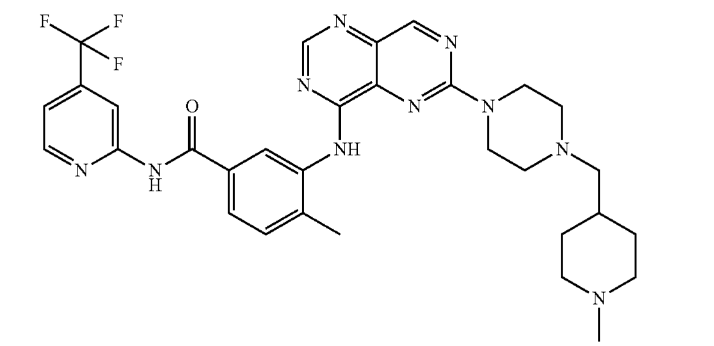 [SMILES: Cc1ccc(C(=O)Nc2cc(C(F)(F)F)ccn2)cc1Nc1ncnc2cnc(N3CCN(CC4CCN(C)CC4)CC3)nc12] | 2.41 | 621 |
| III-511 | 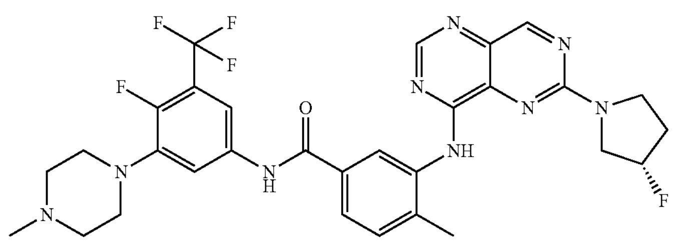 [SMILES: Cc1ccc(C(=O)Nc2cc(N3CCN(C)CC3)c(F)c(C(F)(F)F)c2)cc1Nc1ncnc2cnc(N3CC[C@H](F)C3)nc12] | 2.35 | 628 |
| III-512 | 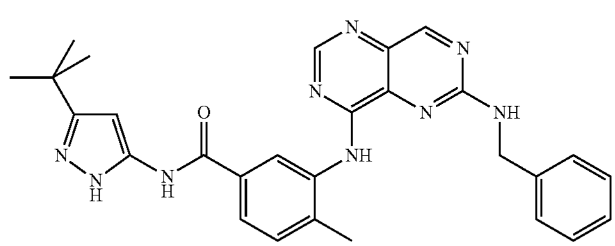 [SMILES: Cc1ccc(C(=O)Nc2cc(C(C)(C)C)n[nH]2)cc1Nc1ncnc2cnc(NCc3ccccc3)nc12] | 2.13 | 508 |
| III-513 | 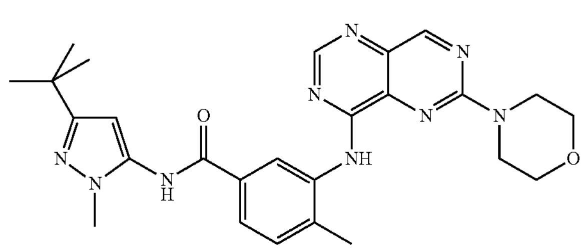 [SMILES: Cc1ccc(C(=O)Nc2cc(C(C)(C)C)nn2C)cc1Nc1ncnc2cnc(N3CCOCC3)nc12] | 1.99 | 502 |

TABLE 3-continued
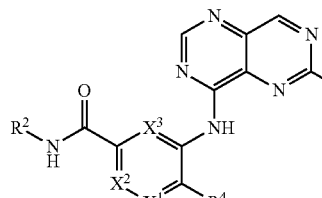
Example Compounds III-1 to III-579 and III-592 to III-608
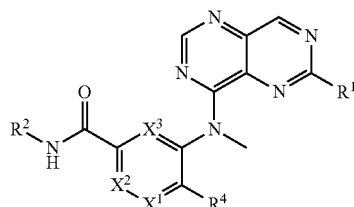
Example Compounds III-580 to III-587
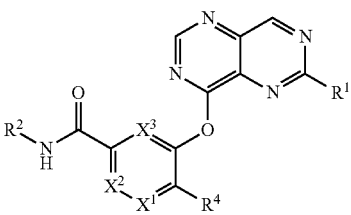
Example Compounds III-588 to III-591
| # | Structure | t$_{Ret.}$ (HPLC) [min] | MS (M + H)$^+$ |
|---|---|---|---|
| III-514 | 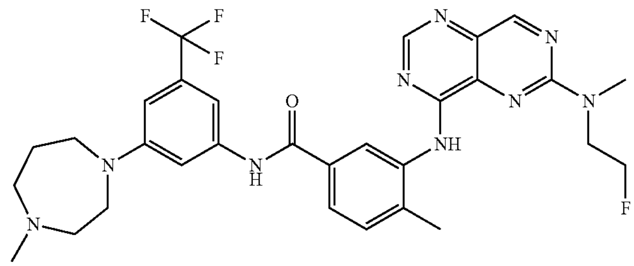 [SMILES: Cc1ccc(C(=O)Nc2cc(N3CCCN(C)CC3)cc(C(F)(F)F)c2)cc1Nc1ncnc2cnc(N(C)CCF)nc12] | 2.36 | 612 |
| III-515 | 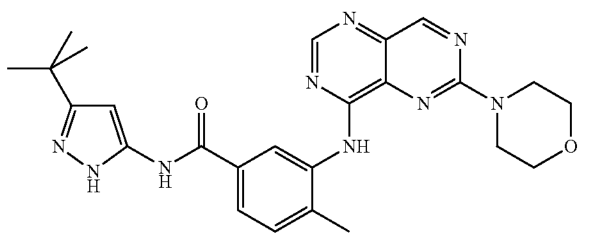 [SMILES: Cc1ccc(C(=O)Nc2cc(C(C)(C)C)n[nH]2)cc1Nc1ncnc2cnc(N3CCOCC3)nc12] | 1.95 | 488 |
| III-516 | 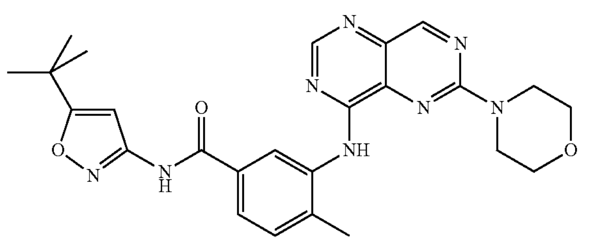 [SMILES: Cc1ccc(C(=O)Nc2cc(C(C)(C)C)on2)cc1Nc1ncnc2cnc(N3CCOCC3)nc12] | 2.18 | 489 |
| III-517 | 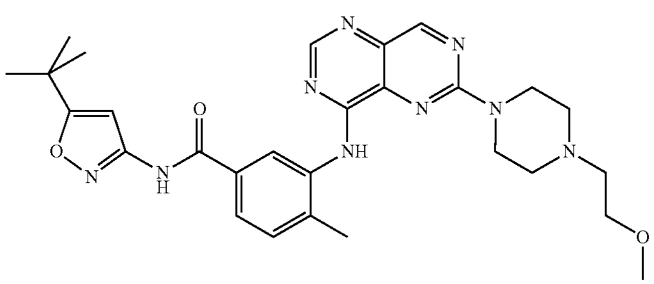 [SMILES: COCCN1CCN(c2ncc3ncnc(Nc4cc(C(=O)Nc5cc(C(C)(C)C)on5)ccc4C)c3n2)CC1] | 2.16 | 546 |
| III-518 | 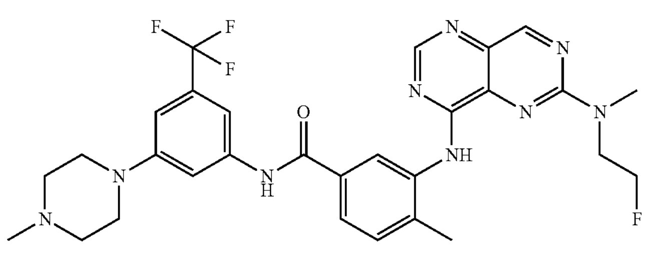 | 2.30 | 598 |

TABLE 3-continued
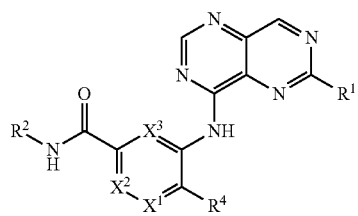
Example Compounds III-1 to III-579 and III-592 to III-608
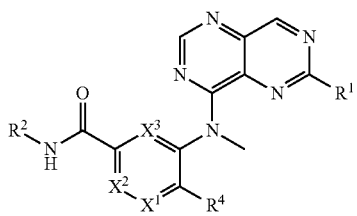
Example Compounds III-580 to III-587
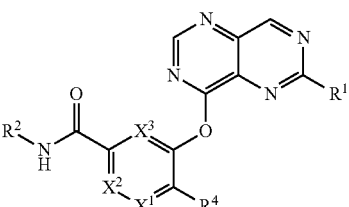
Example Compounds III-588 to III-591
| # | Structure | t_Ret. (HPLC) [min] | MS (M + H)+ |
|---|-----------|---------------------|-------------|
| III-519 | 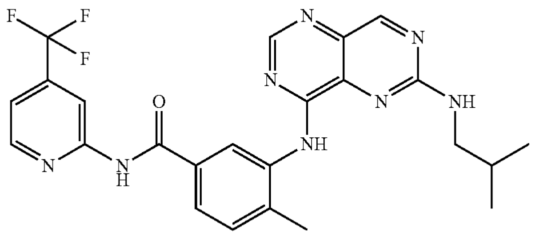 [SMILES: Cc1ccc(C(=O)Nc2cc(C(F)(F)F)ccn2)cc1Nc1ncnc2cnc(NCC(C)C)nc12] | 2.42 | 497 |
| III-520 | 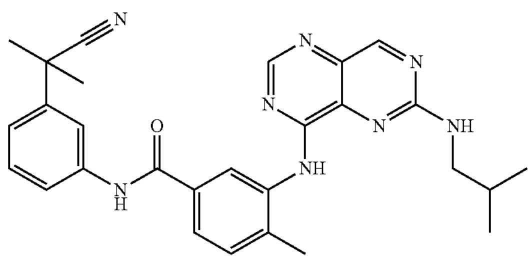 [SMILES: Cc1ccc(C(=O)Nc2cccc(C(C)(C)C#N)c2)cc1Nc1ncnc2cnc(NCC(C)C)nc12] | 2.32 | 495 |
| III-521 | 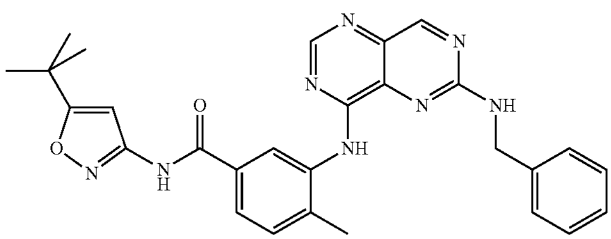 [SMILES: Cc1ccc(C(=O)Nc2cc(C(C)(C)C)on2)cc1Nc1ncnc2cnc(NCc3ccccc3)nc12] | 2.36 | 509 |
| III-522 | 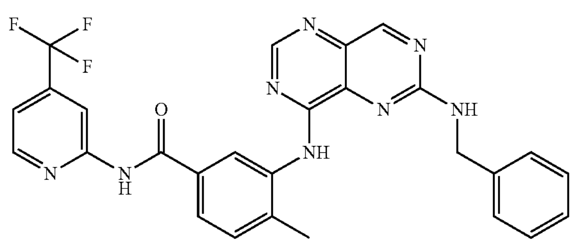 [SMILES: Cc1ccc(C(=O)Nc2cc(C(F)(F)F)ccn2)cc1Nc1ncnc2cnc(NCc3ccccc3)nc12] | 2.38 | 531 |
| III-523 | 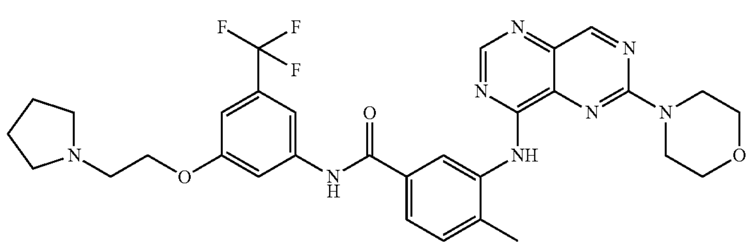 [SMILES: Cc1ccc(C(=O)Nc2cc(OCCN3CCCC3)cc(C(F)(F)F)c2)cc1Nc1ncnc2cnc(N3CCOCC3)nc12] | 2.09 | 623 |

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|---|---|---|
| III-524 | 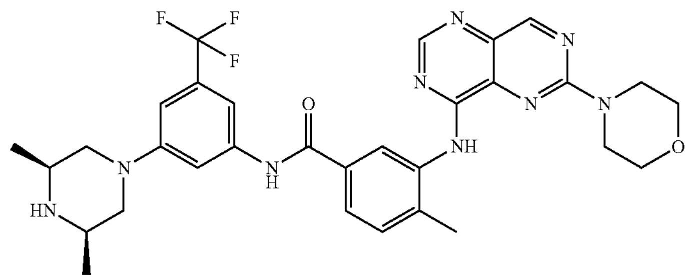 [SMILES: Cc1ccc(C(=O)Nc2cc(N3C[C@@H](C)N[C@@H](C)C3)cc(C(F)(F)F)c2)cc1Nc1ncnc2cnc(N3CCOCC3)nc12] | 1.99 | 622 |
| III-525 | 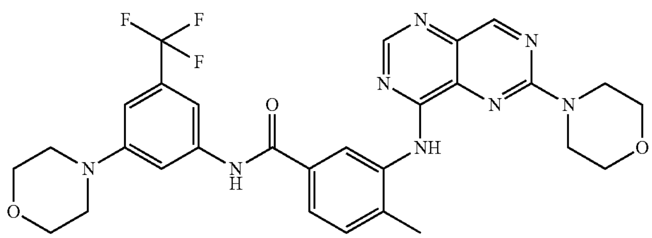 [SMILES: Cc1ccc(C(=O)Nc2cc(N3CCOCC3)cc(C(F)(F)F)c2)cc1Nc1ncnc2cnc(N3CCOCC3)nc12] | 1.97 | 595 |
| III-526 | 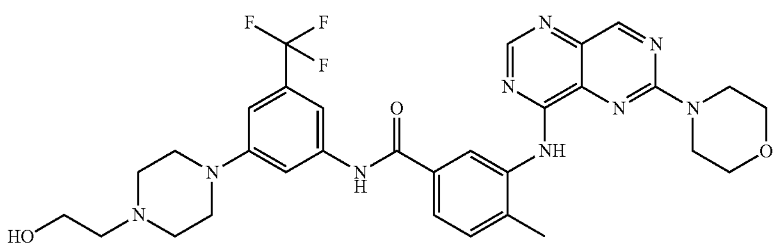 [SMILES: Cc1ccc(C(=O)Nc2cc(N3CCN(CCO)CC3)cc(C(F)(F)F)c2)cc1Nc1ncnc2cnc(N3CCOCC3)nc12] | 1.80 | 638 |
| III-527 | 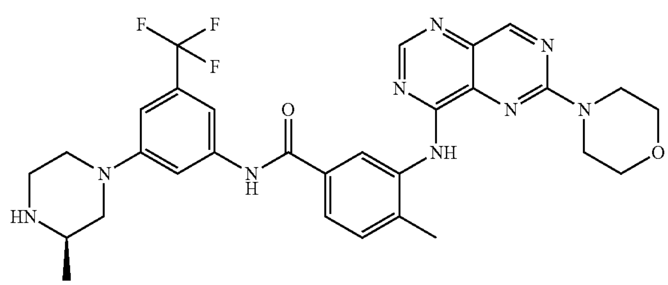 [SMILES: Cc1ccc(C(=O)Nc2cc(N3CCN[C@H](C)C3)cc(C(F)(F)F)c2)cc1Nc1ncnc2cnc(N3CCOCC3)nc12] | 1.86 | 608 |
| III-528 | 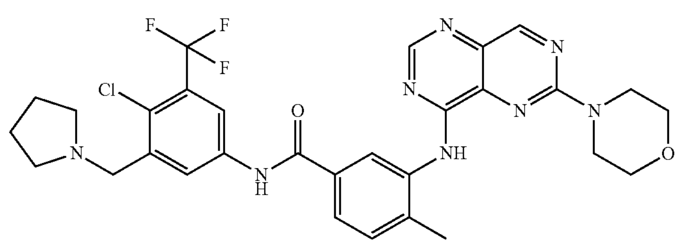 [SMILES: Cc1ccc(C(=O)Nc2cc(CN3CCCC3)c(Cl)c(C(F)(F)F)c2)cc1Nc1ncnc2cnc(N3CCOCC3)nc12] | 2.26 | 627/629 |

US 8,653,087 B2

359                                                                                  360

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)+ |
|---|-----------|-------------------------|-------------|
| III-529 | 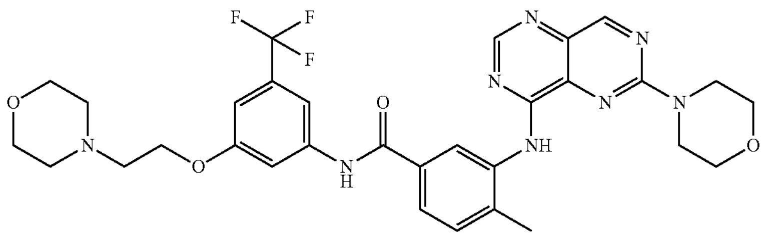 [SMILES: Cc1ccc(C(=O)Nc2cc(OCCN3CCOCC3)cc(C(F)(F)F)c2)cc1Nc1ncnc2cnc(N3CCOCC3)nc12] | 1.92 | 639 |
| III-530 | 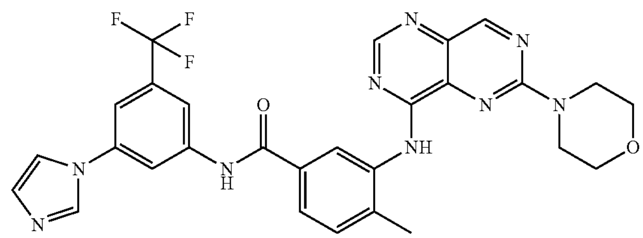 [SMILES: Cc1ccc(C(=O)Nc2cc(-n3ccnc3)cc(C(F)(F)F)c2)cc1Nc1ncnc2cnc(N3CCOCC3)nc12] | 1.86 | 576 |
| III-531 | 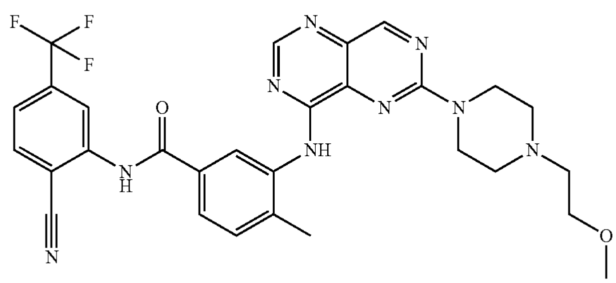 [SMILES: COCCN1CCN(c2ncc3ncnc(Nc4cc(C(=O)Nc5cc(C(F)(F)F)ccc5C#N)ccc4C)c3n2)CC1] | 1.89 | 592 |
| III-532 | 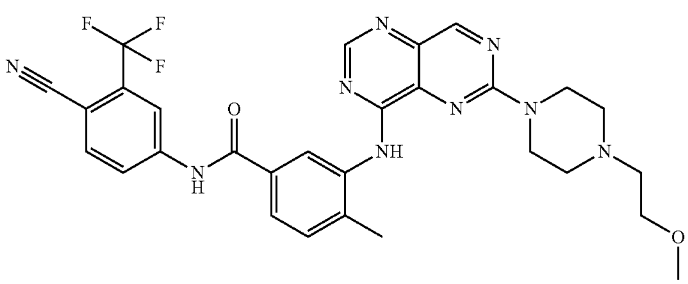 [SMILES: COCCN1CCN(c2ncc3ncnc(Nc4cc(C(=O)Nc5ccc(C#N)c(C(F)(F)F)c5)ccc4C)c3n2)CC1] | 1.96 | 592 |
| III-533 | 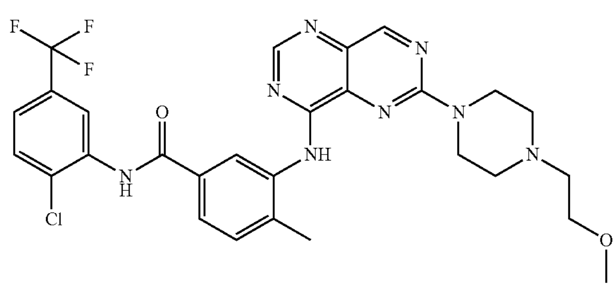 [SMILES: COCCN1CCN(c2ncc3ncnc(Nc4cc(C(=O)Nc5cc(C(F)(F)F)ccc5Cl)ccc4C)c3n2)CC1] | 2.11 | 601/603 |

TABLE 3-continued

Example Compounds III-1 to III-579 and III-592 to III-608

Example Compounds III-580 to III-587

Example Compounds III-588 to III-591

| # | Structure | t_Ret. (HPLC) [min] | MS (M + H)+ |
|---|---|---|---|
| III-534 | 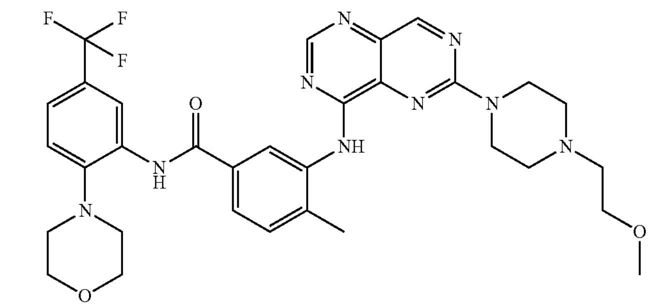 [SMILES: COCCN1CCN(c2ncc3ncnc(Nc4cc(C(=O)Nc5cc(C(F)(F)F)ccc5N5CCOCC5)ccc4C)c3n2)CC1] | 2.08 | 652 |
| III-535 | 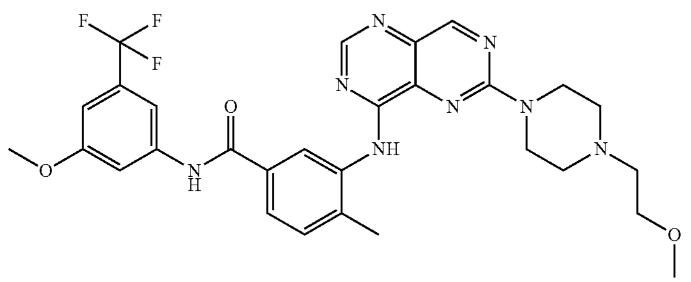 | 2.01 | 597 |
| III-536 | 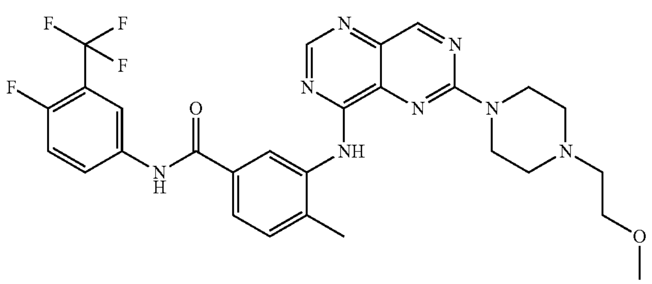 [SMILES: COCCN1CCN(c2ncc3ncnc(Nc4cc(C(=O)Nc5ccc(F)c(C(F)(F)F)c5)ccc4C)c3n2)CC1] | 1.99 | 585 |
| III-537 | 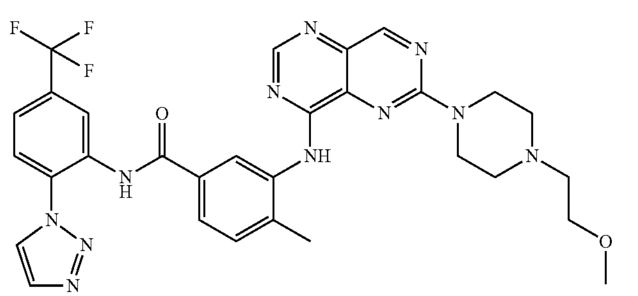 [SMILES: COCCN1CCN(c2ncc3ncnc(Nc4cc(C(=O)Nc5cc(C(F)(F)F)ccc5-n5ccnn5)ccc4C)c3n2)CC1] | 1.89 | 634 |

US 8,653,087 B2

TABLE 3-continued

Example Compounds III-1 to III-579 and III-592 to III-608

Example Compounds III-580 to III-587

Example Compounds III-588 to III-591

| # | Structure | $t_{Ret.}$ (HPLC) [min] | MS (M + H)$^+$ |
|---|---|---|---|
| III-538 | 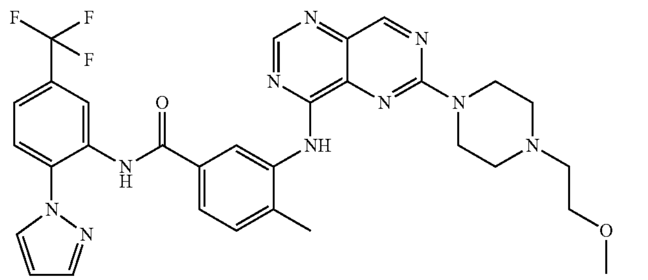 [SMILES: COCCN1CCN(c2ncc3ncnc(Nc4cc(C(=O)Nc5cc(C(F)(F)F)ccc5-n5cccn5)ccc4C)c3n2)CC1] | 2.18 | 633 |
| III-539 | 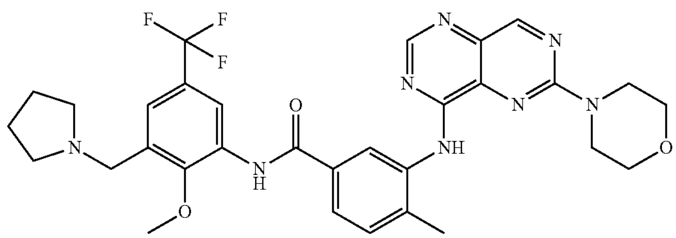 [SMILES: COc1c(CN2CCCC2)cc(C(F)(F)F)cc1NC(=O)c1ccc(C)c(Nc2ncnc3cnc(N4CCOCC4)nc23)c1] | 2.28 | 623 |
| III-540 | 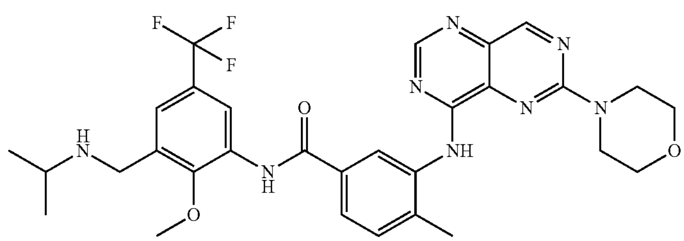 [SMILES: COc1c(CNC(C)C)cc(C(F)(F)F)cc1NC(=O)c1ccc(C)c(Nc2ncnc3cnc(N4CCOCC4)nc23)c1] | 2.13 | 611 |
| III-541 | 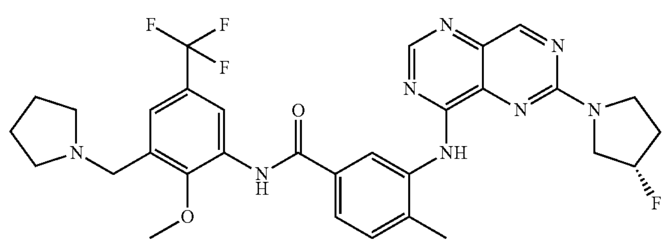 [SMILES: COc1c(CN2CCCC2)cc(C(F)(F)F)cc1NC(=O)c1ccc(C)c(Nc2ncnc3cnc(N4CC[C@H](F)C4)nc23)c1] | 2.38 | 625 |
| III-542 | 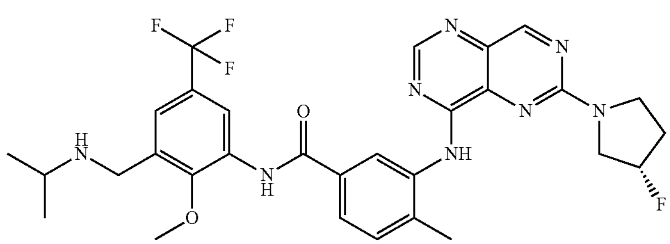 [SMILES: COc1c(CNC(C)C)cc(C(F)(F)F)cc1NC(=O)c1ccc(C)c(Nc2ncnc3cnc(N4CC[C@H](F)C4)nc23)c1] | 2.21 | 613 |

TABLE 3-continued
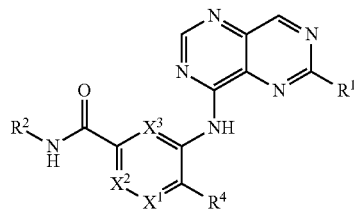
Example Compounds III-1 to III-579 and III-592 to III-608
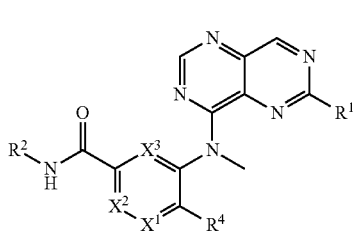
Example Compounds III-580 to III-587
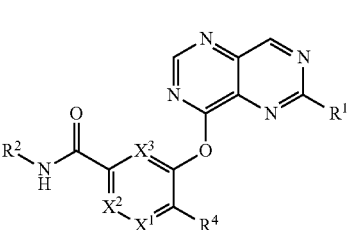
Example Compounds III-588 to III-591
| # | Structure | t_Ret. (HPLC) [min] | MS (M + H)+ |
|---|---|---|---|
| III-543 | 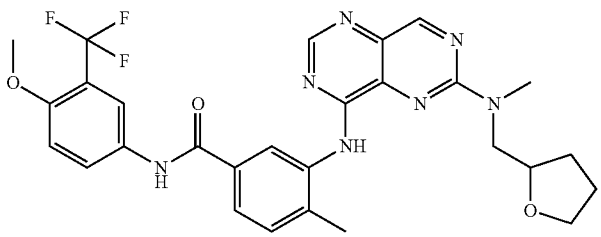 [SMILES: COc1ccc(NC(=O)c2ccc(C)c(Nc3ncnc4cnc(N(C)CC5CCCO5)nc34)c2)cc1C(F)(F)F] | 2.11 | 568 |
| III-544 | 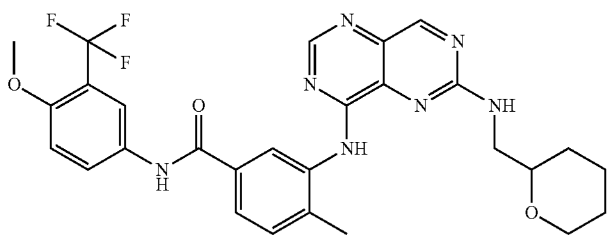 [SMILES: COc1ccc(NC(=O)c2ccc(C)c(Nc3ncnc4cnc(NCC5CCCCO5)nc34)c2)cc1C(F)(F)F] | 1.92 | 568 |
| III-545 | 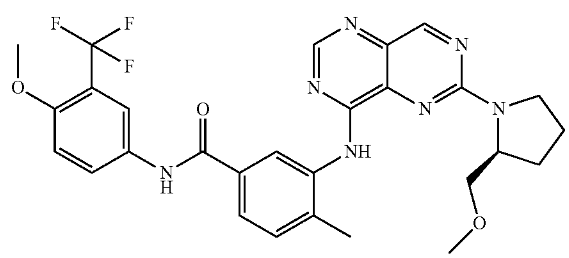 [SMILES: COC[C@@H]1CCCN1c1ncc2ncnc(Nc3cc(C(=O)Nc4ccc(OC)c(C(F)(F)F)c4)ccc3C)c2n1] | 2.17 | 568 |
| III-546 | 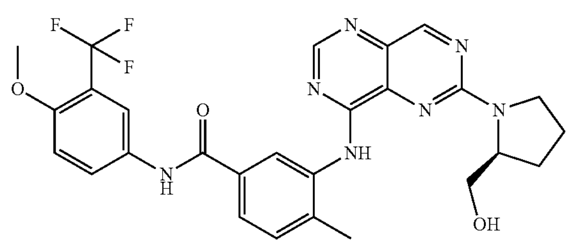 [SMILES: COc1ccc(NC(=O)c2ccc(C)c(Nc3ncnc4cnc(N5CCC[C@H]5CO)nc34)c2)cc1C(F)(F)F] | 1.91 | 554 |
| III-547 | 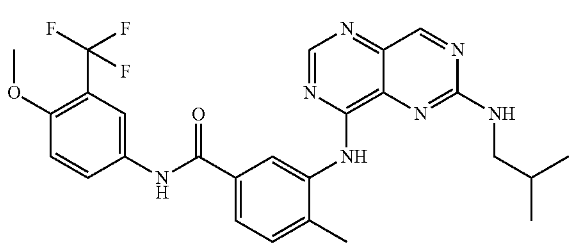 [SMILES: COc1ccc(NC(=O)c2ccc(C)c(Nc3ncnc4cnc(NCC(C)C)nc34)c2)cc1C(F)(F)F] | 2.15 | 526 |

TABLE 3-continued
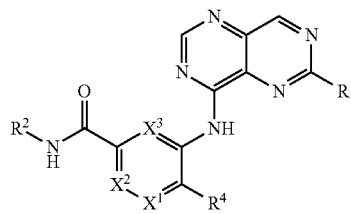
Example Compounds III-1 to III-579 and III-592 to III-608
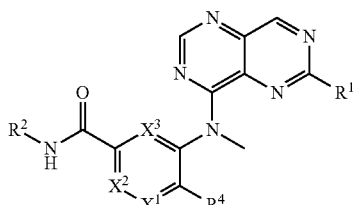
Example Compounds III-580 to III-587
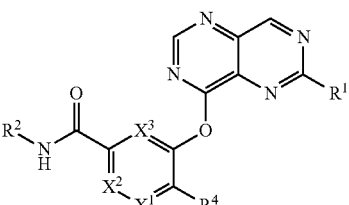
Example Compounds III-588 to III-591
| # | Structure | $t_{Ret.}$ (HPLC) [min] | MS (M + H)$^+$ |
|---|---|---|---|
| III-548 | 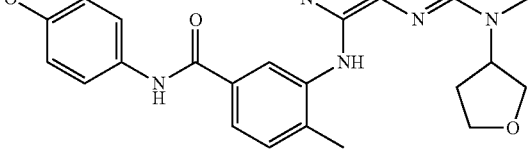 | 2.00 | 554 |
| III-549 | 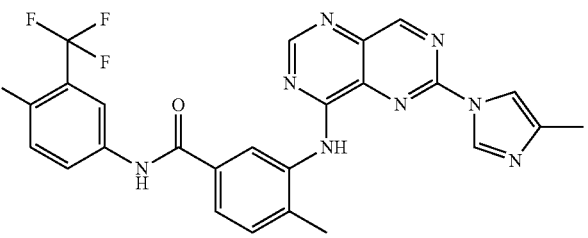 | 1.86 | 535 |
| III-550 | 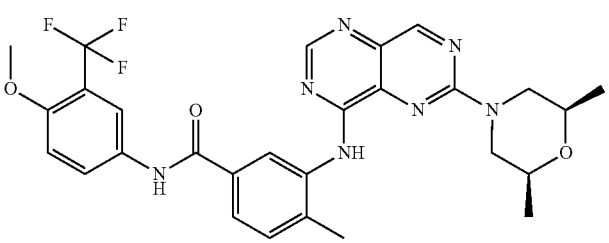 [SMILES: COc1ccc(NC(=O)c2ccc(C)c(Nc3ncnc4cnc(N5C[C@@H](C)O[C@@H](C)C5)nc34)c2)cc1C(F)(F)F] | 2.14 | 568 |
| III-551 | 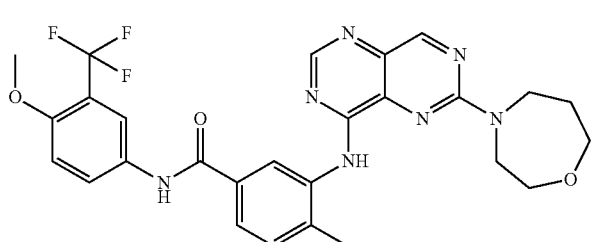 | 2.00 | 554 |
| III-552 | 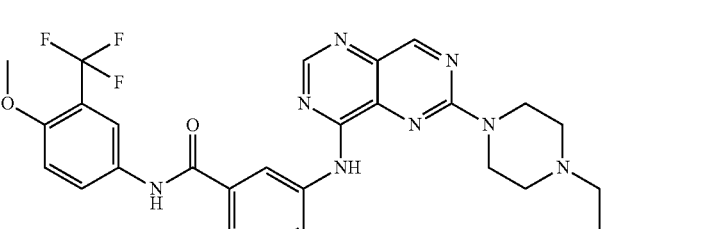 | 1.84 | 652 |

TABLE 3-continued
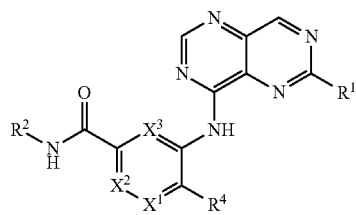
Example Compounds III-1 to III-579 and III-592 to III-608
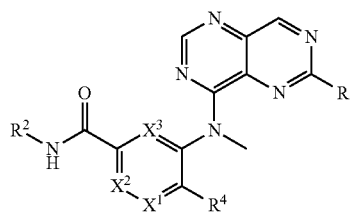
Example Compounds III-580 to III-587
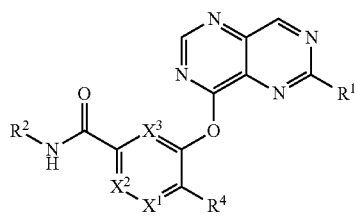
Example Compounds III-588 to III-591
| # | Structure | $t_{Ret.}$ (HPLC) [min] | MS (M + H)$^+$ |
|---|---|---|---|
| III-553 | 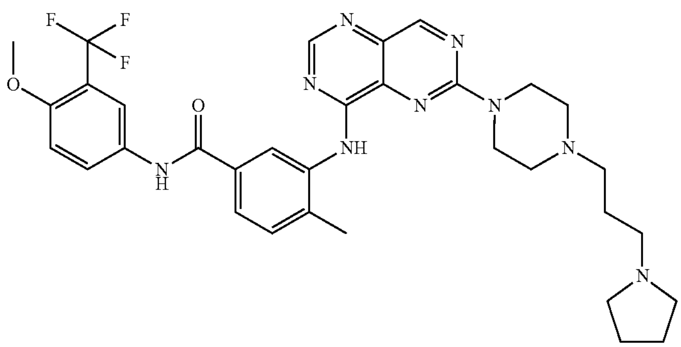 [SMILES: COc1ccc(NC(=O)c2ccc(C)c(Nc3ncnc4cnc(N5CCN(CCCN6CCCC6)CC5)nc34)c2)cc1C(F)(F)F] | 2.24 | 650 |
| III-554 | 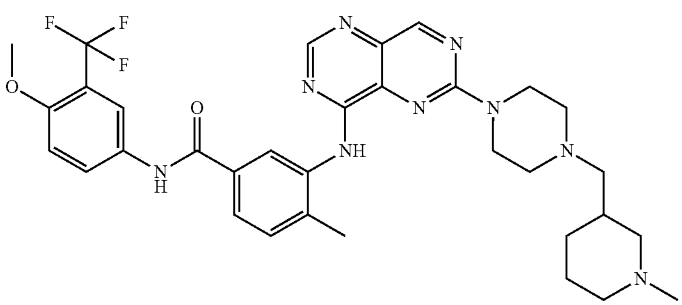 [SMILES: COc1ccc(NC(=O)c2ccc(C)c(Nc3ncnc4cnc(N5CCN(CC6CCCN(C)C6)CC5)nc34)c2)cc1C(F)(F)F] | 2.20 | 650 |
| III-555 | 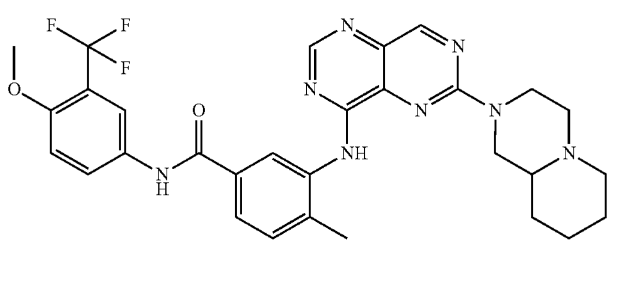 [SMILES: COc1ccc(NC(=O)c2ccc(C)c(Nc3ncnc4cnc(N5CCN6CCCCC6C5)nc34)c2)cc1C(F)(F)F] | 2.12 | 593 |
| III-556 | 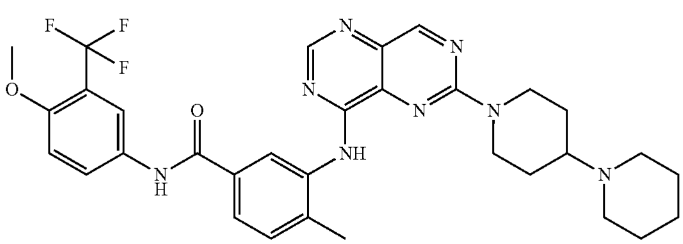 [SMILES: COc1ccc(NC(=O)c2ccc(C)c(Nc3ncnc4cnc(N5CCC(N6CCCCC6)CC5)nc34)c2)cc1C(F)(F)F] | 2.27 | 621 |

TABLE 3-continued
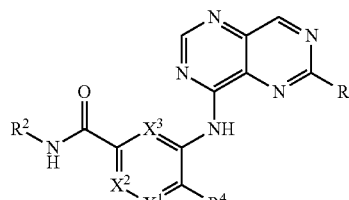 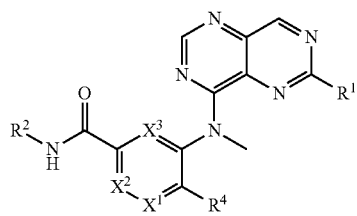 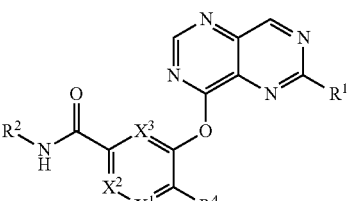
Example Compounds III-1 to III-579 and III-592 to III-608 | Example Compounds III-580 to III-587 | Example Compounds III-588 to III-591
| # | Structure | $t_{Ret.}$ (HPLC) [min] | MS (M + H)$^+$ |
|---|---|---|---|
| III-557 | 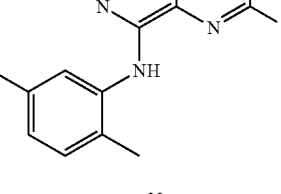 | 1.98 | 636 |
| III-558 | 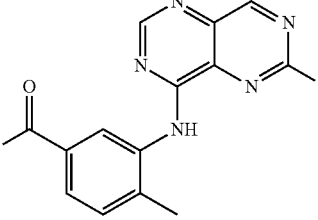 | 1.93 | 623 |
| III-559 | 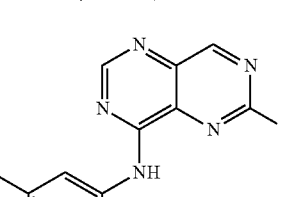 | 2.11 | 651 |
| III-560 | 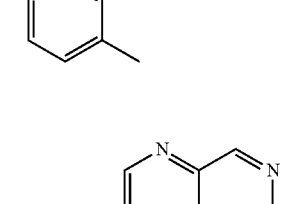 | 2.20 | 607 |
| III-561 | 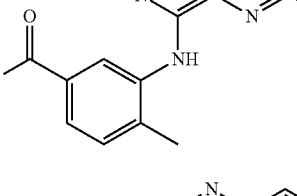 | 2.02 | 567 |

TABLE 3-continued
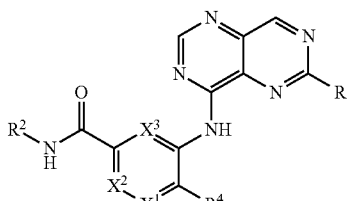
Example Compounds III-1 to III-579 and III-592 to III-608
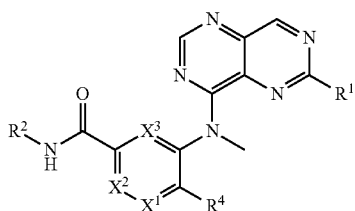
Example Compounds III-580 to III-587
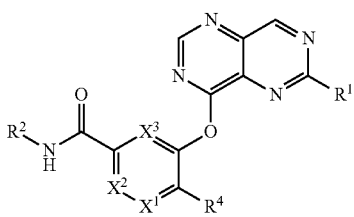
Example Compounds III-588 to III-591
| # | Structure | $t_{Ret.}$ (HPLC) [min] | MS (M + H)$^+$ |
|---|---|---|---|
| III-562 | 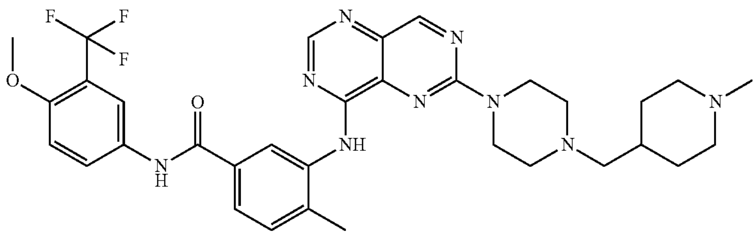 [SMILES: COc1ccc(NC(=O)c2ccc(C)c(Nc3ncnc4cnc(N5CCN(CC6CCN(C)CC6)CC5)nc34)c2)cc1C(F)(F)F] | 2.22 | 654 |
| III-563 | 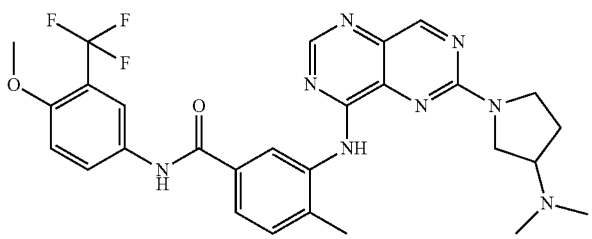 [SMILES: COc1ccc(NC(=O)c2ccc(C)c(Nc3ncnc4cnc(N5CCC(N(C)C)C5)nc34)c2)cc1C(F)(F)F] | 1.98 | 571 |
| III-564 | 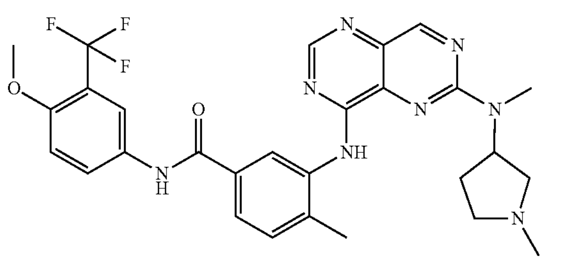 [SMILES: COc1ccc(NC(=O)c2ccc(C)c(Nc3ncnc4cnc(N(C)C5CCN(C)C5)nc34)c2)cc1C(F)(F)F] | 2.07 | 571 |
| III-565* | 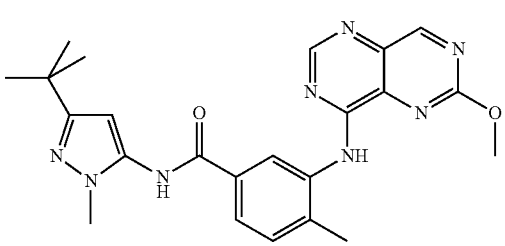 [SMILES: COc1ncc2ncnc(Nc3cc(C(=O)Nc4cc(C(C)(C)C)nn4C)ccc3C)c2n1] | 1.88 | 447 |
| III-566* | 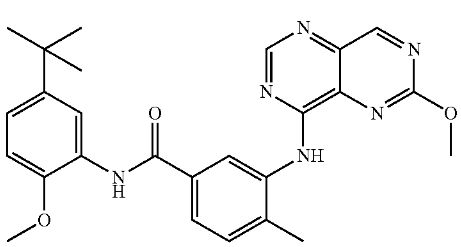 [SMILES: COc1ncc2ncnc(Nc3cc(C(=O)Nc4cc(C(C)(C)C)ccc4OC)ccc3C)c2n1] | 2.37 | 473 |

US 8,653,087 B2
TABLE 3-continued
Example Compounds III-1 to III-579 and III-592 to III-608
Example Compounds III-580 to III-587
Example Compounds III-588 to III-591
| # | Structure | t$_{Ret.}$ (HPLC) [min] | MS (M + H)$^+$ |
|---|-----------|-------------------------|-----------------|
| III-567* | 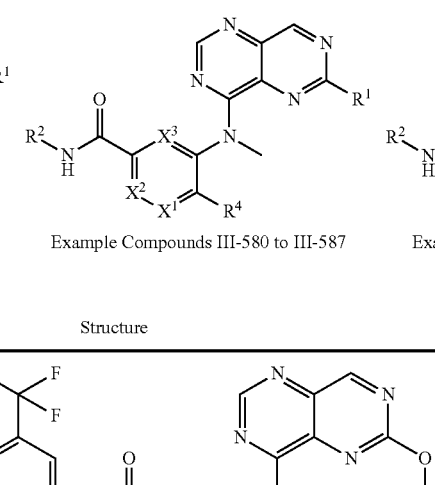 | 2.31 | 581 |
| III-568* | 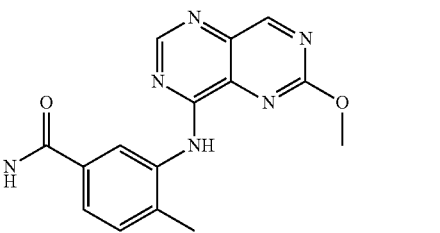 | 2.15 | 455 |
| III-569* | 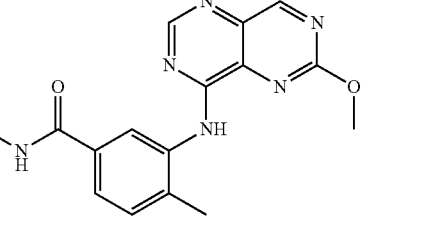 | 2.11 | 485 |
| III-570* | 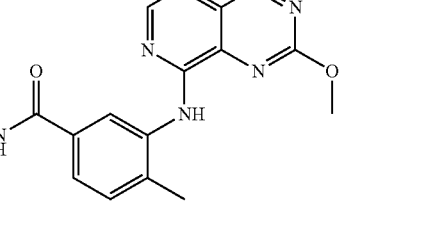 | 2.25 | 443 |
| III-571* | 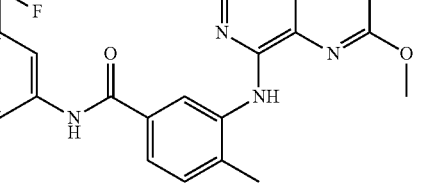 | 2.19 | 555 |

TABLE 3-continued
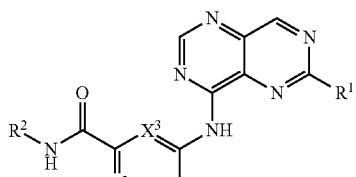
Example Compounds III-1 to III-579 and III-592 to III-608
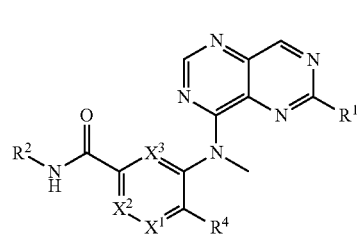
Example Compounds III-580 to III-587
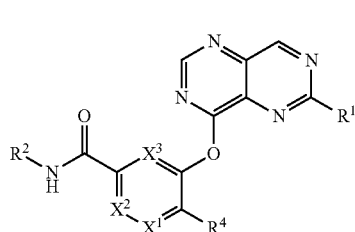
Example Compounds III-588 to III-591
| # | Structure | t$_{Ret.}$ (HPLC) [min] | MS (M + H)$^+$ |
|---|---|---|---|
| III-572* | 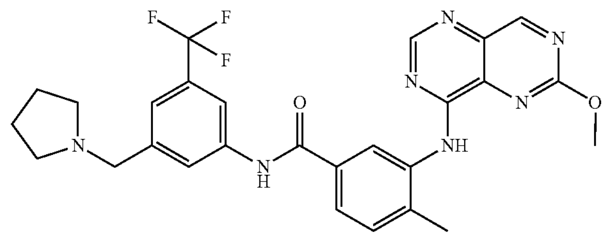 [SMILES: COc1ncc2ncnc(Nc3cc(C(=O)Nc4cc(CN5CCCC5)cc(C(F)(F)F)c4)ccc3C)c2n1] | 2.28 | 538 |
| III-573* | 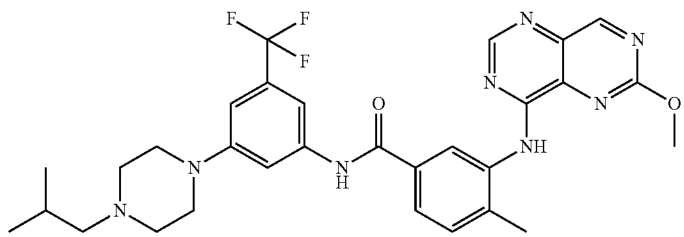 [SMILES: COc1ncc2ncnc(Nc3cc(C(=O)Nc4cc(N5CCN(CC(C)C)CC5)cc(C(F)(F)F)c4)ccc3C)c2n1] | 2.59 | 595 |
| III-574* | 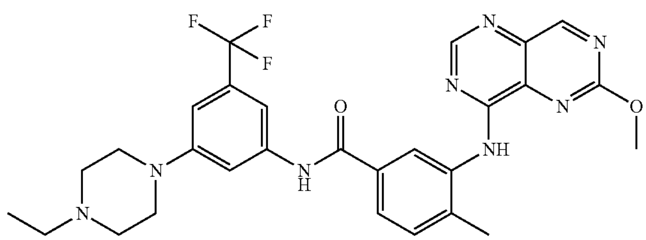 [SMILES: CCN1CCN(c2cc(NC(=O)c3ccc(C)c(Nc4ncnc5cnc(OC)nc45)c3)cc(C(F)(F)F)c2)CC1] | 2.21 | 567 |
| III-575* | 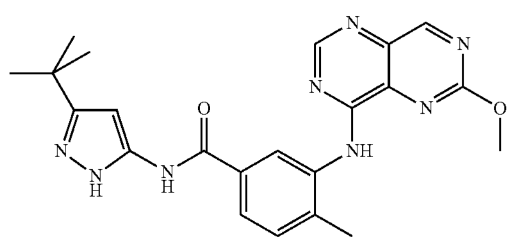 | 1.85 | 433 |
| III-576* | 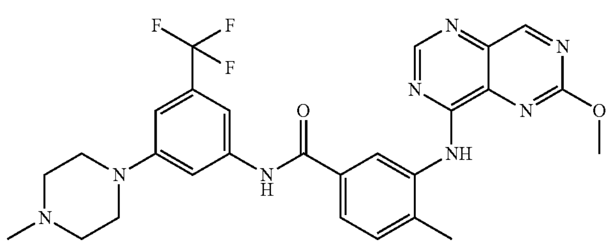 | 2.11 | 553 |

TABLE 3-continued
Example Compounds III-1 to III-579 and III-592 to III-608
Example Compounds III-580 to III-587
Example Compounds III-588 to III-591
| # | Structure | t$_{Ret.}$ (HPLC) [min] | MS (M + H)$^+$ |
|---|---|---|---|
| III-577* | 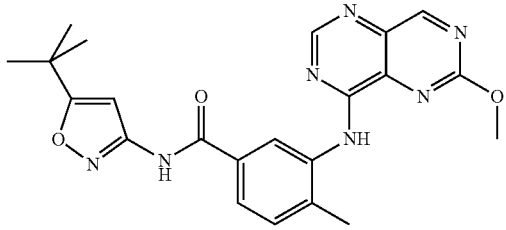 [SMILES: COc1ncc2ncnc(Nc3cc(C(=O)Nc4cc(C(C)(C)C)on4)ccc3C)c2n1] | 2.07 | 434 |
| III-578* | 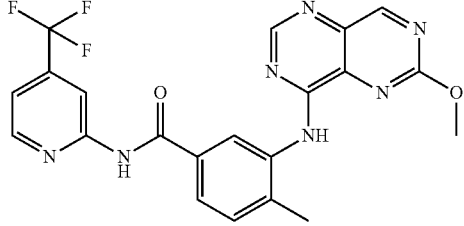 [SMILES: COc1ncc2ncnc(Nc3cc(C(=O)Nc4cc(C(F)(F)F)ccn4)ccc3C)c2n1] | 2.08 | 456 |
| III-579* | 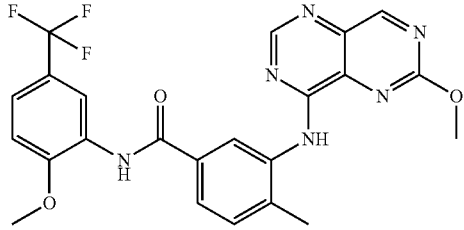 | 2.24 | 485 |
| III-580 | 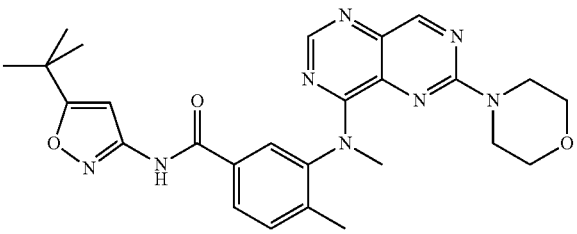 [SMILES: Cc1ccc(C(=O)Nc2cc(C(C)(C)C)on2)cc1N(C)c1ncnc2cnc(N3CCOCC3)nc12] | 2.21 | 503 |
| III-581 | 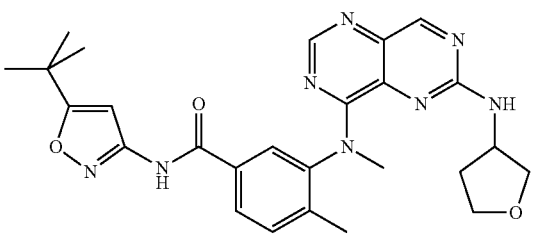 [SMILES: Cc1ccc(C(=O)Nc2cc(C(C)(C)C)on2)cc1N(C)c1ncnc2cnc(NC3CCOC3)nc12] | 2.08 | 503 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-582 | 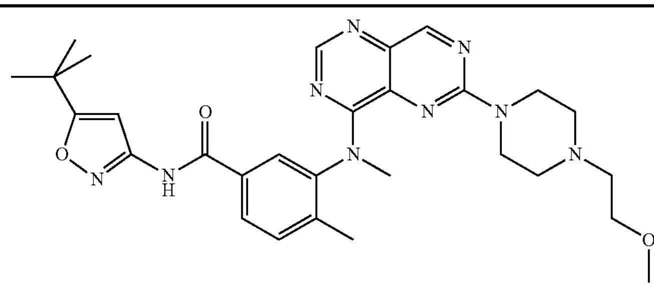 | 2.10 | 560 |
| III-583 | 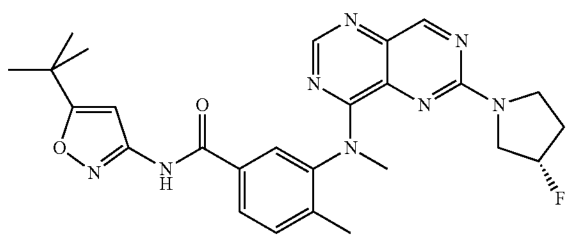 [SMILES: Cc1ccc(C(=O)Nc2cc(C(C)(C)C)on2)cc1N(C)c1ncnc2cnc(N3CC[C@H](F)C3)nc12] | 2.23 | 505 |
| III-584 | 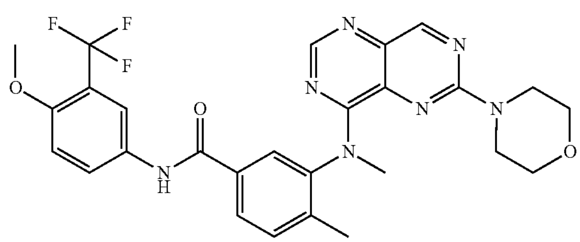 [SMILES: COc1ccc(NC(=O)c2ccc(C)c(N(C)c3ncnc4cnc(N5CCOCC5)nc34)c2)cc1C(F)(F)F] | 2.20 | 554 |
| III-585 | 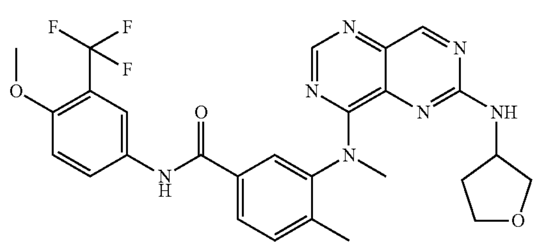 [SMILES: COc1ccc(NC(=O)c2ccc(C)c(N(C)c3ncnc4cnc(NC5CCOC5)nc34)c2)cc1C(F)(F)F] | 2.12 | 554 |
| III-586 | 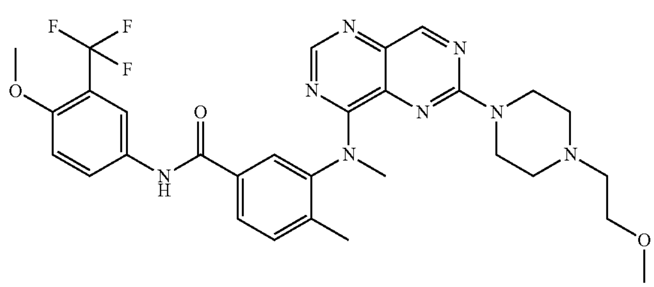 [SMILES: COCCN1CCN(c2ncc3ncnc(N(C)c4cc(C(=O)Nc5ccc(OC)c(C(F)(F)F)c5)ccc4C)c3n2)CC1] | 2.12 | 611 |

TABLE 3-continued
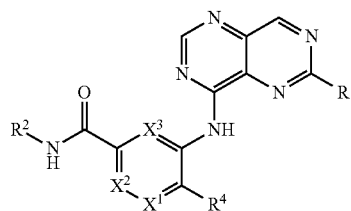
Example Compounds III-1 to III-579 and III-592 to III-608
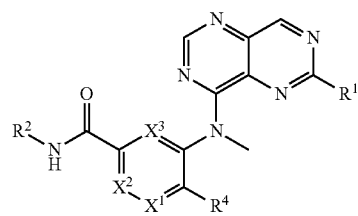
Example Compounds III-580 to III-587
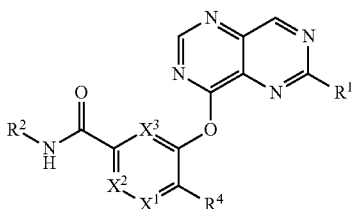
Example Compounds III-588 to III-591
| # | Structure | $t_{Ret.}$ (HPLC) [min] | MS (M + H)⁺ |
|---|---|---|---|
| III-587 | 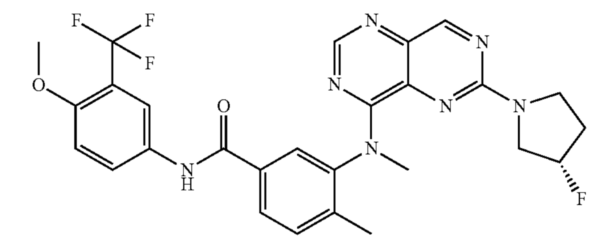 [SMILES: COc1ccc(NC(=O)c2ccc(C)c(N(C)c3ncnc4cnc(N5CC[C@H](F)C5)nc34)c2)cc1C(F)(F)F] | 2.29 | 556 |
| III-588** | 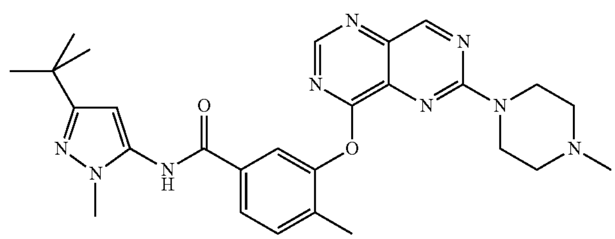 [SMILES: Cc1ccc(C(=O)Nc2cc(C(C)(C)C)nn2C)cc1Oc1ncnc2cnc(N3CCN(C)CC3)nc12] | 1.98 | 516 |
| III-589** | 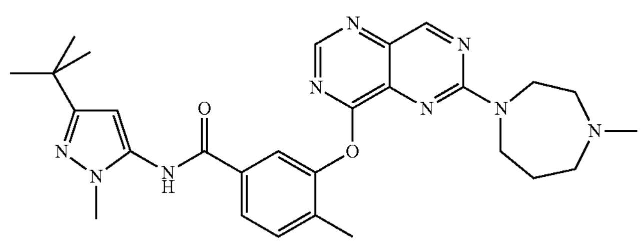 [SMILES: Cc1ccc(C(=O)Nc2cc(C(C)(C)C)nn2C)cc1Oc1ncnc2cnc(N3CCCN(C)CC3)nc12] | 2.01 | 530 |
| III-590** | 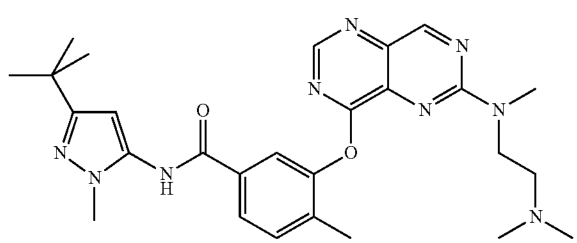 [SMILES: Cc1ccc(C(=O)Nc2cc(C(C)(C)C)nn2C)cc1Oc1ncnc2cnc(N(C)CCN(C)C)nc12] | 1.96 | 518 |
| III-591** | 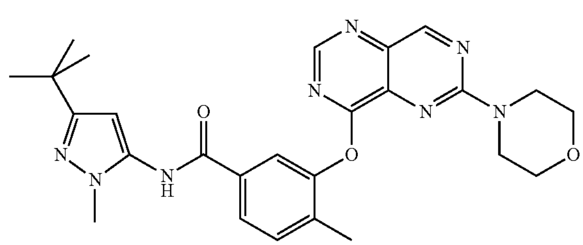 [SMILES: Cc1ccc(C(=O)Nc2cc(C(C)(C)C)nn2C)cc1Oc1ncnc2cnc(N3CCOCC3)nc12] | 2.02 | 503 |

TABLE 3-continued
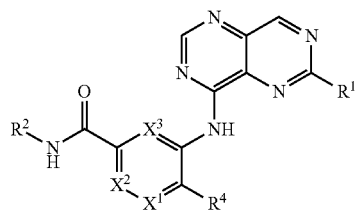
Example Compounds III-1 to III-579 and III-592 to III-608
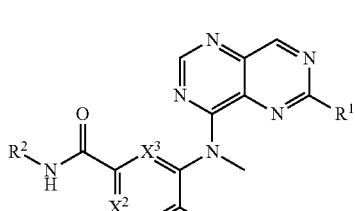
Example Compounds III-580 to III-587
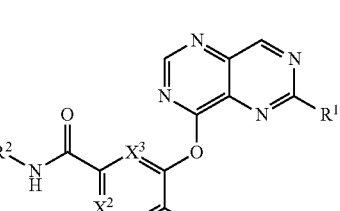
Example Compounds III-588 to III-591
| # | Structure | $t_{Ret.}$ (HPLC) [min] | MS (M + H)+ |
|---|---|---|---|
| III-592 | 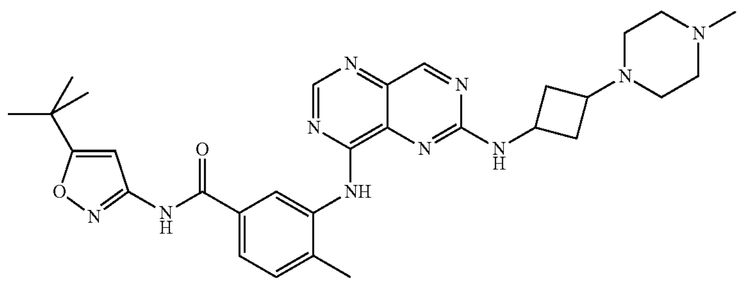 [SMILES: Cc1ccc(C(=O)Nc2cc(C(C)(C)C)on2)cc1Nc1ncnc2cnc(NC3CC(N4CCN(C)CC4)C3)nc12] | 1.81 | 571 |
| III-593 | 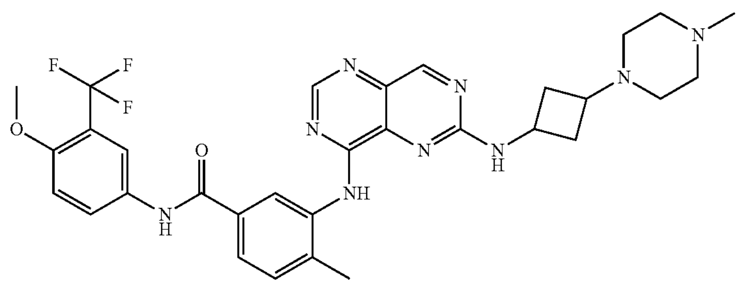 [SMILES: COc1ccc(NC(=O)c2ccc(C)c(Nc3ncnc4cnc(NC5CC(N6CCN(C)CC6)C5)nc34)c2)cc1C(F)(F)F] | 1.83 | 622 |
| III-594 | 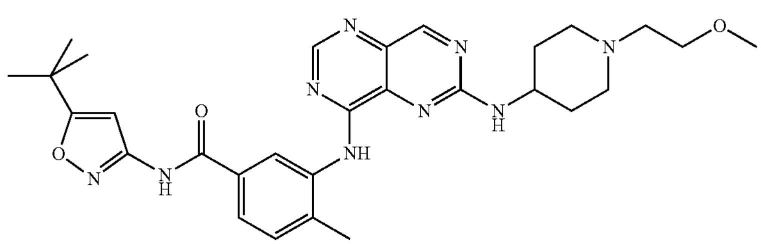 [SMILES: COCCN1CCC(Nc2ncc3ncnc(Nc4cc(C(=O)Nc5cc(C(C)(C)C)on5)ccc4C)c3n2)CC1] | 1.94 | 560 |
| III-595 | 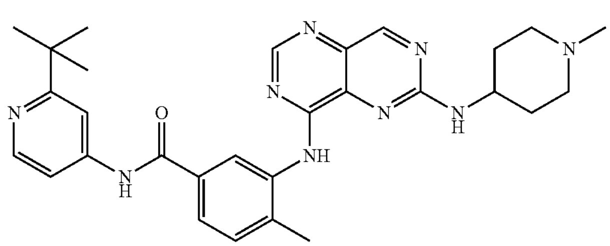 [SMILES: Cc1ccc(C(=O)Nc2ccnc(C(C)(C)C)c2)cc1Nc1ncnc2cnc(NC3CCN(C)CC3)nc12] | 1.66 | 526 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-596 | 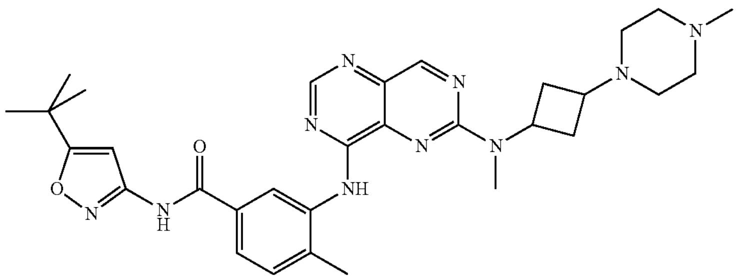 [SMILES: Cc1ccc(C(=O)Nc2cc(C(C)(C)C)on2)cc1Nc1ncnc2cnc(N(C)C3CC(N4CCN(C)CC4)C3)nc12] | 2.01 | 585 |
| III-597 | 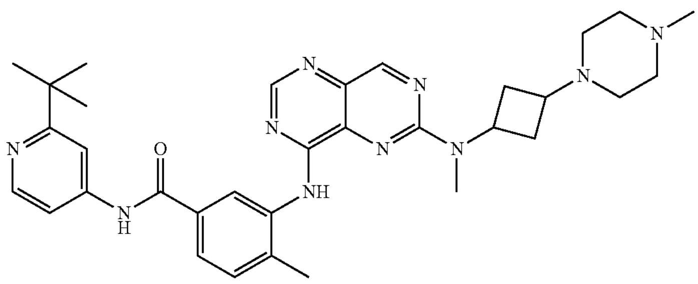 [SMILES: Cc1ccc(C(=O)Nc2ccnc(C(C)(C)C)c2)cc1Nc1ncnc2cnc(N(C)C3CC(N4CCN(C)CC4)C3)nc12] | 2.05 | 595 |
| III-598 | 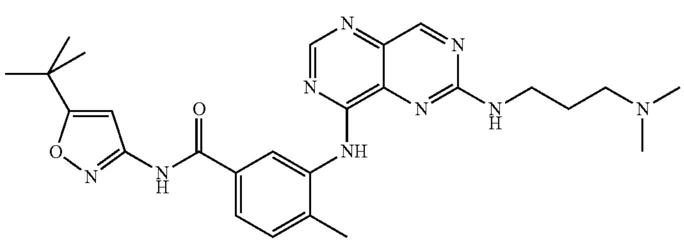 [SMILES: Cc1ccc(C(=O)Nc2cc(C(C)(C)C)on2)cc1Nc1ncnc2cnc(NCCCN(C)C)nc12] | 1.93 | 504 |
| III-599 | 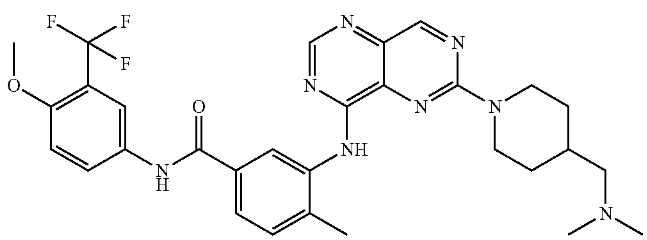 [SMILES: COc1ccc(NC(=O)c2ccc(C)c(Nc3ncnc4cnc(N5CCC(CN(C)C)CC5)nc34)c2)cc1C(F)(F)F] | 2.17 | 595 |

TABLE 3-continued

Example Compounds III-1 to III-579 and III-592 to III-608

Example Compounds III-580 to III-587

Example Compounds III-588 to III-591

| # | Structure | t$_{Ret.}$ (HPLC) [min] | MS (M + H)$^+$ |
|---|---|---|---|
| III-600 | 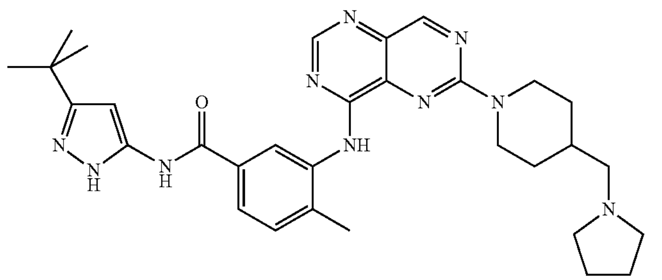 [SMILES: Cc1ccc(C(=O)Nc2cc(C(C)(C)C)n[nH]2)cc1Nc1ncnc2cnc(N3CCC(CN4CCCC4)CC3)nc12] | 2.18 | 569 |
| III-601 | 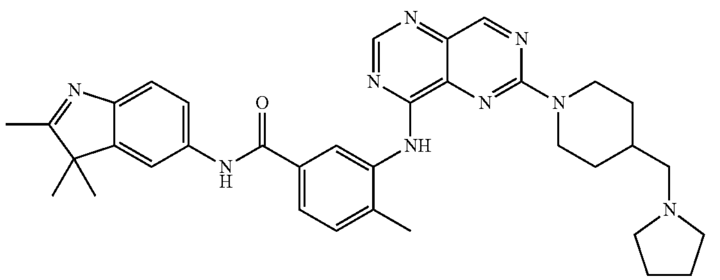 [SMILES: CC1=Nc2ccc(NC(=O)c3ccc(C)c(Nc4ncnc5cnc(N6CCC(CN7CCCC7)CC6)nc45)c3)cc2C1(C)C] | 2.14 | 604 |
| III-602 | 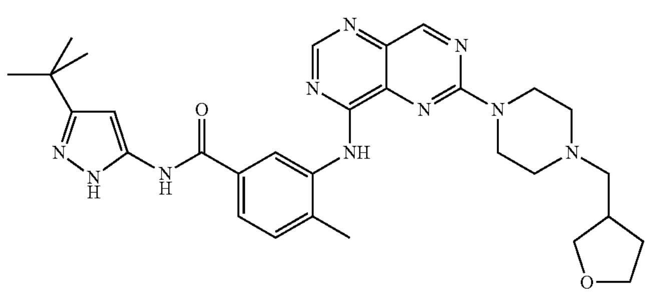 [SMILES: Cc1ccc(C(=O)Nc2cc(C(C)(C)C)n[nH]2)cc1Nc1ncnc2cnc(N3CCN(CC4CCOC4)CC3)nc12] | 1.86 | 571 |
| III-603 | 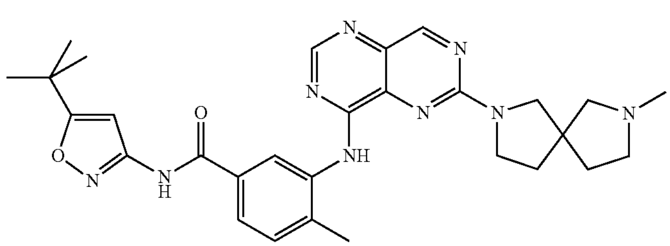 [SMILES: Cc1ccc(C(=O)Nc2cc(C(C)(C)C)on2)cc1Nc1ncnc2cnc(N3CCC4(CCN(C)C4)C3)nc12] | 2.04 | 542 |

TABLE 3-continued
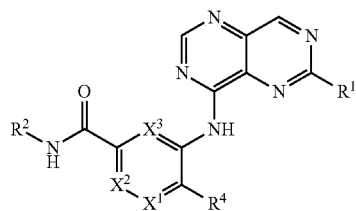
Example Compounds III-1 to III-579 and III-592 to III-608
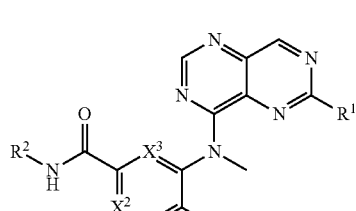
Example Compounds III-580 to III-587
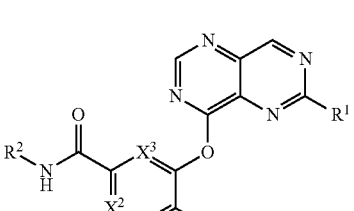
Example Compounds III-588 to III-591
| # | Structure | $t_{Ret.}$ (HPLC) [min] | MS (M + H)⁺ |
|---|---|---|---|
| III-604 | 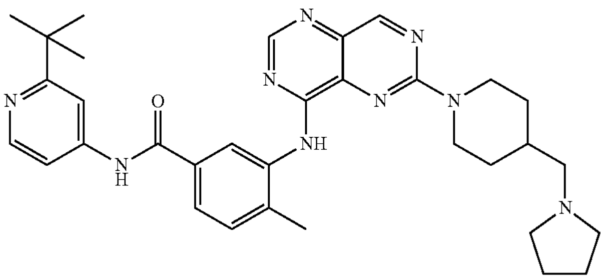 [SMILES: Cc1ccc(C(=O)Nc2ccnc(C(C)(C)C)c2)cc1Nc1ncnc2cnc(N3CCC(CN4CCCC4)CC3)nc12] | 2.10 | 580 |
| III-605 | 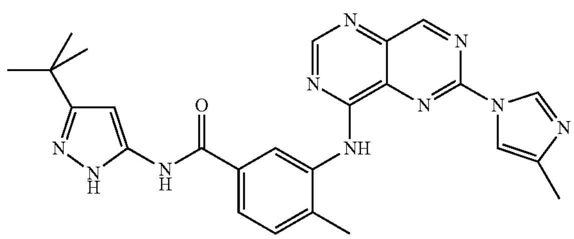 [SMILES: Cc1cn(-c2ncc3ncnc(Nc4cc(C(=O)Nc5cc(C(C)(C)C)n[nH]5)ccc4C)c3n2)cn1] | 1.66 | 483 |
| III-606 | 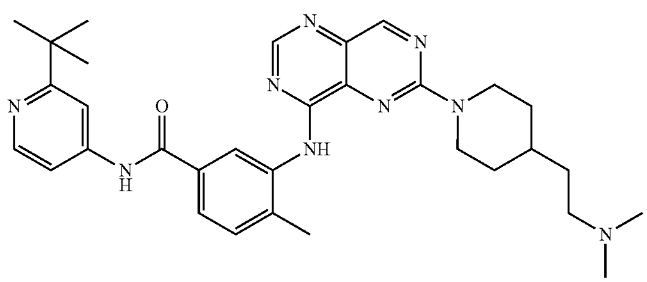 [SMILES: Cc1ccc(C(=O)Nc2ccnc(C(C)(C)C)c2)cc1Nc1ncnc2cnc(N3CCC(CCN(C)C)CC3)nc12] | 2.00 | 568 |
| III-607 | 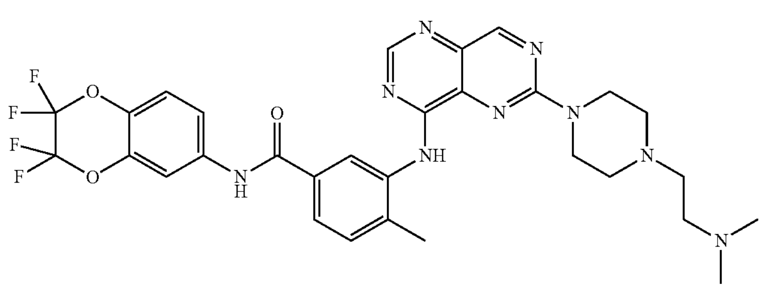 [SMILES: Cc1ccc(C(=O)Nc2ccc3c(c2)OC(F)(F)C(F)(F)O3)cc1Nc1ncnc2cnc(N3CCN(CCN(C)C)CC3)nc12] | 2.15 | 642 |

TABLE 3-continued
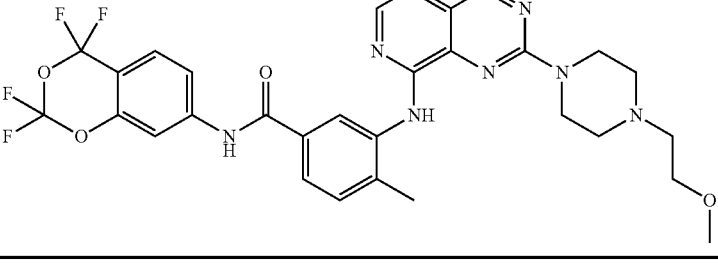
Example Compounds III-1 to III-579 and III-592 to III-608
Example Compounds III-580 to III-587
Example Compounds III-588 to III-591
| # | Structure | $t_{Ret.}$ (HPLC) [min] | MS (M + H)$^+$ |
|---|-----------|-------------------------|----------------|
| III-608 | 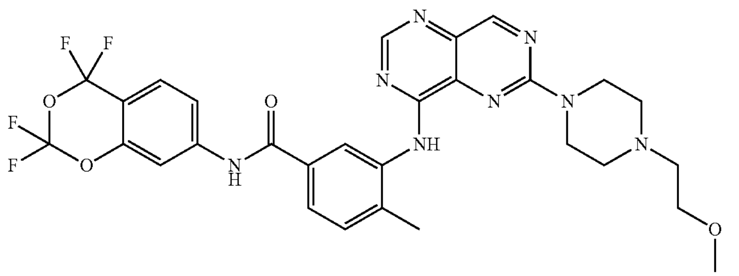 [SMILES: COCCN1CCN(c2ncc3ncnc(Nc4cc(C(=O)Nc5ccc6c(c5)OC(F)(F)OC6(F)F)ccc4C)c3n2)CC1] | 2.23 | 629 |
*using NaOMe instead of amines (E-3)
**using phenols instead of anilines A-1

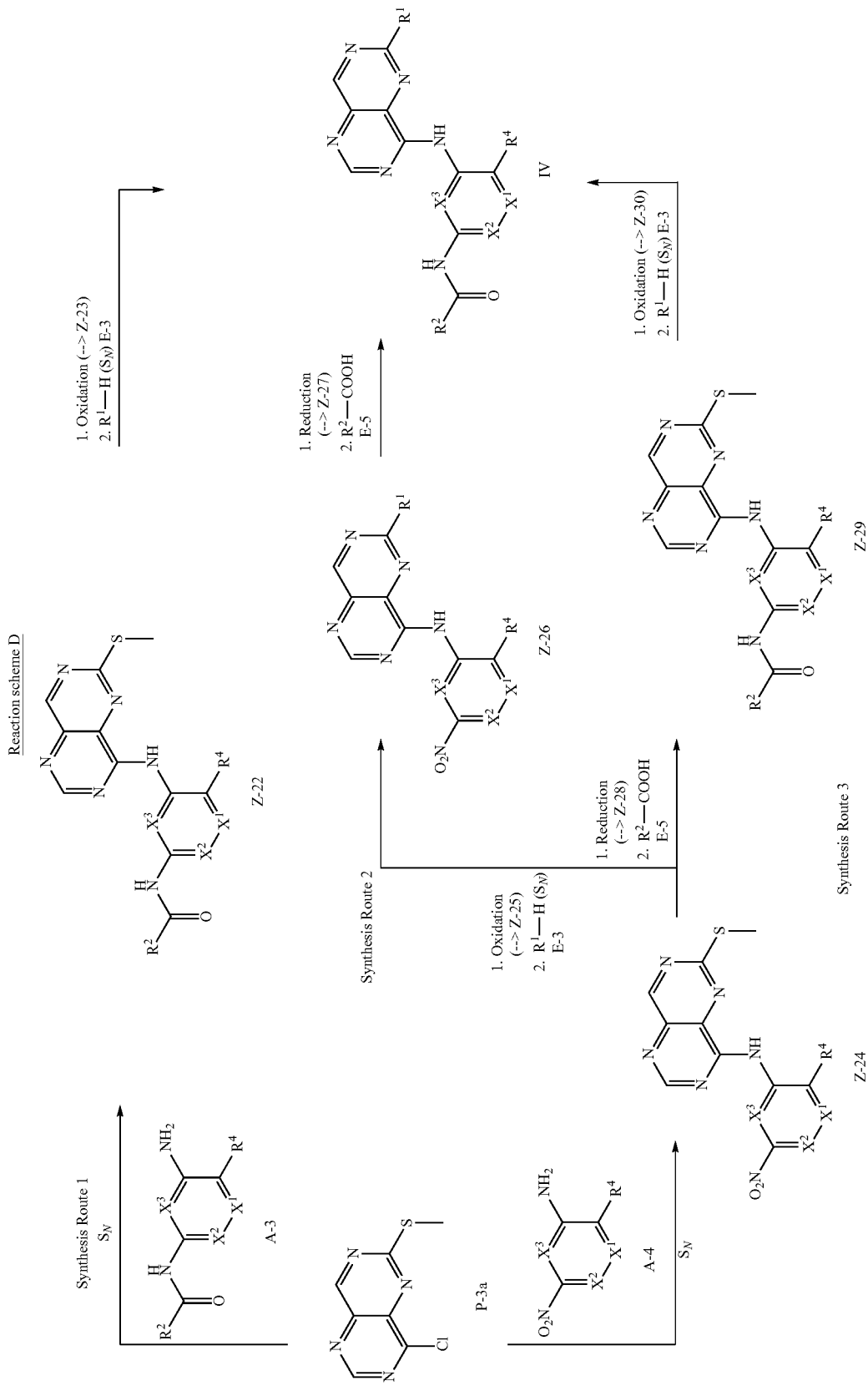

Example Compounds of Type IV:

Example compounds IV differ from those of type III by an inverted amide bond between the central (hetero-)aromatic six-membered ring and the group $R^2$ (Reaction scheme D). These compounds are obtained analogously to the compounds III in terms of the method used, except that the reactivities are inverted accordingly in the educt components E-4 and E-5 (for the synthesis of A-3, cf. Reaction scheme B) or A-4 (compared with E-1 and E-2 or A-2, cf. Reaction schemes A and C).

For the compound of type IV for example the following two synthesis routes are possible:

Starting from P-3a the 8-position is substituted by the aniline components A-3 or A-4, preferably under basically catalysed conditions at elevated temperature.

With regard to the use of A-3 (synthesis route 1) reference is made to the remarks relating to Reaction scheme C (synthesis route 1 via intermediate compound Z-12) (final substitution by E-3 after oxidative activation of the methylsulphanyl group; regarding the synthesis of components A-3 cf. the remarks under Reaction scheme B).

When A-4 is used (synthesis routes 2 and 3) first of all only the central phenyl or heteroaryl ring and the precursor of a linker fragment (nitro→amino) of the later linker $L^2$ is incorporated. With the intermediate compound Z-24 there are the alternative possibilities of either oxidising/activating the methylsulphanyl group, then substituting it with a component E-3 and lastly, after reduction, introducing the group $R^2$ (via the component E-5) (synthesis route 2) or first of all carrying out reduction and amide coupling with E-5 and then after oxidative activation carrying out the nucleophilic substitution by E-3 (synthesis route 3).

Both the group $R^1$ and the group $R^2$ of compounds IV according to the invention may be modified in other reaction steps (not shown), to obtain further compounds IV according to the invention. These reaction steps may be reactions of substitution, alkylation, acylation or addition.

a) Method for Synthesising Z-24a:

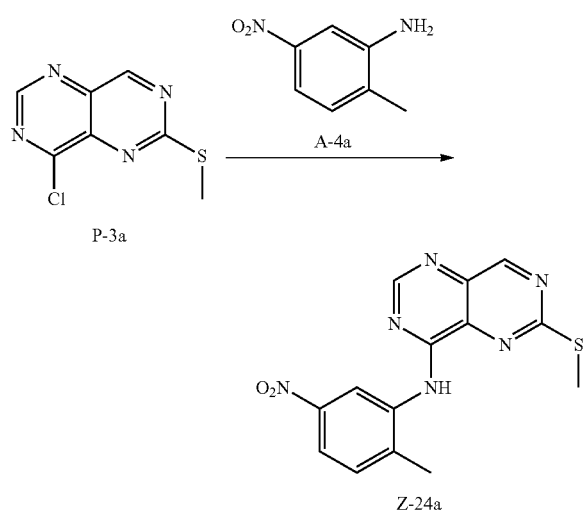

8-chloro-2-methylsulphanyl-pyrimido[5,4-d]pyrimidine P-3a (3 g, 14.11 mmol) and nitroaniline A-4-a (2.21 g, 14.53 mmol) are placed in dioxane (25 mL) and DIPEA (3.393 mL, 18.34 mmol) and refluxed overnight with stirring. For working up the reaction mixture is evaporated down, the residue is suspended in MeOH, the precipitate formed is filtered off, dried and Z-24a (HPLC-MS: $t_{Ret.}$=2.05 min; MS (M+H)$^+$= 329) is obtained.

Analogously to the method for synthesising Z-24a further intermediate compounds Z-24 are obtained by reacting components A-4 with P-3a.

b) Method for Synthesising Z-26a:

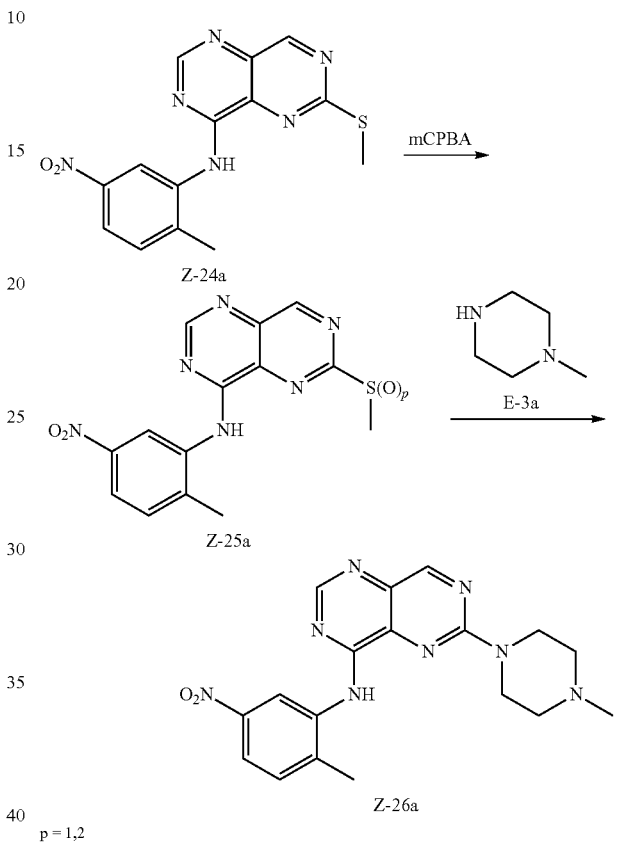

p = 1,2

Z-24a (5 g, 14.47 mmol) is taken up in DCM (50 mL), combined at RT with mCPBA (3.24 g, 14.47 mmol) and stirred for 2 h at RT. The reaction mixture is filtered off, the filtrate is diluted with DCM and washed 3× with saturated NaHCO$_3$ solution. The organic phase is dried on Na$_2$SO$_4$, filtered off, evaporated down and Z-25a is obtained. Z-25a is further reacted directly without any further purification (content of sulphoxide/sulphone approx. 85%).

Sulphoxide/sulphone Z-25a (85%, 1 g, 2.47 mmol) and N-methylpiperazine E-3a (4.381 mL, 3.95 mmol) are placed in dioxane (6 mL). TEA (718 µL, 4.94 mmol) is added dropwise to this suspension, then it is heated to 60° C. and stirred for 1 h. For working up the mixture is evaporated down, the residue is suspended with iPrOH/water, filtered and dried. The precipitate is purified by chromatography on NP with DCM/MeOH (9:1) and Z-26a (HPLC-MS: $t_{Ret.}$=1.96 min; MS (M+H)$^+$=381) is obtained.

Analogously to the method for synthesising Z-26a further intermediate compounds Z-26 are obtained by oxidation of components Z-24 and reaction with amines E-3. Further intermediate compounds Z-26 are obtained by reacting with alcohols E-3 (in the form of their alkoxides), e.g. with sodium methoxide.

c) Method for Synthesising Example Compound IV-1:

d) Method for Synthesising Z-29a:

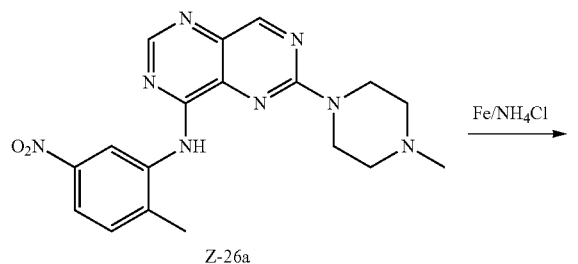
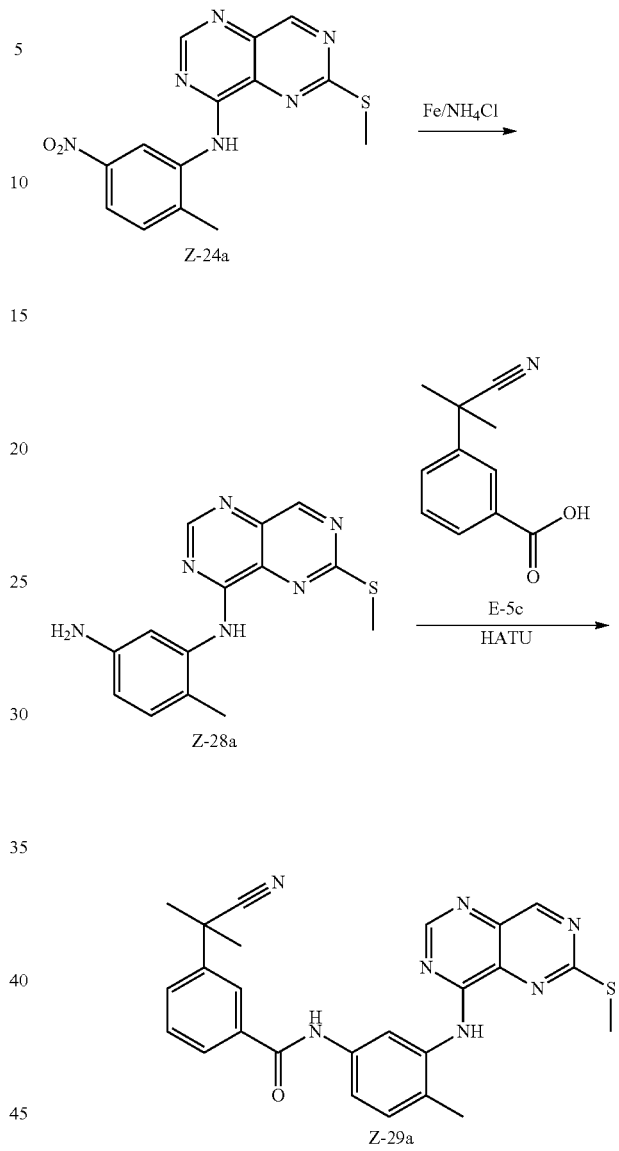

Nitro compound Z-26a (490 mg, 1.29 mmol) is taken up in EtOH (10 mL), combined with ammonium chloride (34 mg, 0.64 mmol) in water (10 mL) and heated to 60° C. At this temperature iron powder (719 mg, 12.88 mmol) is added batchwise and the mixture is stirred for a further 1.5 h at 60° C. After cooling it is filtered through silica gel, washed with DCM/MeOH, the filtrate obtained is dried using the rotary evaporator and Z-27a (HPLC-MS: $t_{Ret.}$=1.64 min; MS (M+H)$^+$=351) is obtained.

4-methoxy-3-trifluoromethylbenzoic acid E-5b (62 mg, 0.29 mmol) is taken up in NMP (750 μL) and combined with DIPEA (166 μL, 1.03 mmol) and HATU (147 mg, 0.39 mmol). After 1 h aniline Z-27a (90 mg, 0.26 mmol) is added and the mixture is stirred at RT. The reaction mixture is purified by preparative HPLC and Example compound IV-1 (HPLC-MS: $t_{Ret.}$=2.17 min; MS (M+H)$^+$=553) is obtained.

Nitro compound Z-24a (2.96 g, 9.02 mmol) is taken up in dioxane (100 mL), combined with ammonium chloride (241 mg, 4.51 mmol) in water (100 mL) and heated to 70° C. At this temperature iron powder (5.04 g, 90.2 mmol) is added batchwise and the mixture is stirred for a further 5 h at 70° C. After cooling it is filtered through silica gel, washed with DCM/MeOH, the filtrate obtained is dried using the rotary evaporator and Z-28a (HPLC-MS: $t_{Ret.}$=1.70 min; MS (M+H)$^+$=299) is obtained.

Benzoic acid E-5c (1 g, 5.29 mmol) is taken up in NMP (10 mL) and combined with DIPEA (3.415 mL, 21.14 mmol) and HATU (3.02 g, 7.93 mmol). After 1 h aniline Z-28a (1.58 g, 5.29 mmol) is added and the mixture is stirred at RT. The reaction mixture is mixed with water. The precipitate formed is filtered off, washed repeatedly with water, then dried and Z-29a (HPLC-MS: $t_{Ret.}$=2.16 min; MS (M+H)$^+$=470) is obtained.

Analogously to the method for synthesising Z-29a further intermediate compounds Z-29 are obtained by reduction of components Z-24 and reaction with acids E-5.

e) Method for Synthesising Example Compound IV-2:

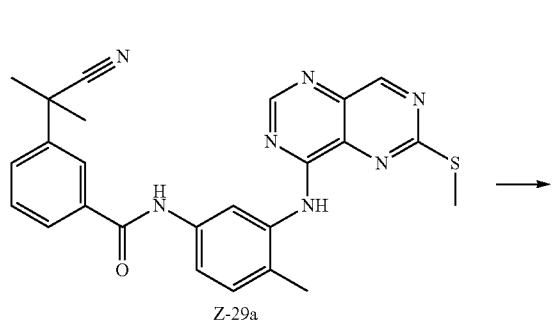

Z-29a

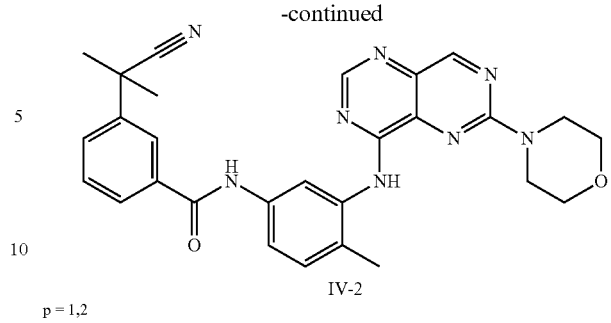

IV-2
p = 1,2

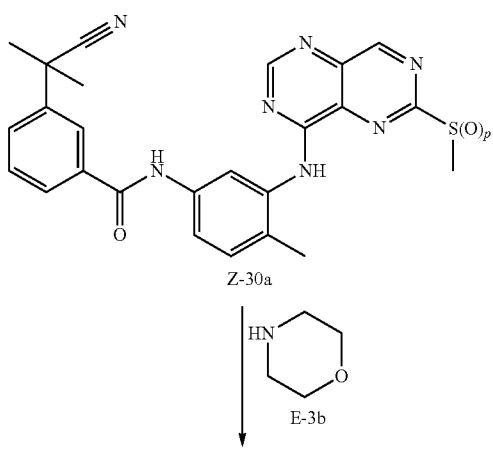

Z-30a

E-3b

Z-29a (1.91 g, 4.07 mmol) is suspended in DCM (40 mL), combined at 0° C. with mCPBA (950 mg, 4.23 mmol) and stirred for 2 h at RT. The reaction mixture is diluted with DCM and washed 2× with saturated NaHCO$_3$ solution. The organic phase is dried on Na$_2$SO$_4$, filtered off, evaporated down and Z-30a is obtained.

Sulphoxide/sulphone Z-30a (1.39 g, 2.86 mmol) is placed in dioxane (10 mL) and mixed with TEA (1.607 mL, 11.45 mmol). Morpholine E-3b (250 μL, 2.86 mmol) is added dropwise to this suspension, it is heated to 60° C. and stirred for 4 h. For working up the mixture is evaporated down, the residue is dissolved with DMF, purified by preparative HPLC and Example compound IV-2 (HPLC-MS: $t_{Ret.}$=2.09 min; MS (M+H)$^+$=509) is obtained.

Analogously to methods a) to c) (synthesis route 2) or a), d) and e) (synthesis route 3) as well as synthesis route 1 shown, besides IV-1 and IV-2 the following compounds IV-3 to IV-68 according to the invention are also prepared (Table 4).

TABLE 4

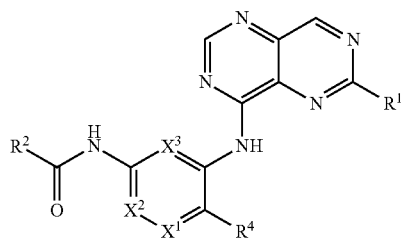

Example Compounds IV-1 to IV-52 and IV-67 and IV-68

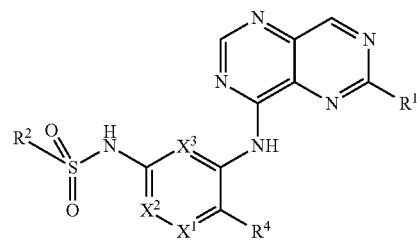

Example Compounds IV-53 to IV-66

| # | Structure | $t_{Ret.}$ (HPLC) [min] | MS (M + H)$^+$ |
|---|---|---|---|
| IV-1 | (structure shown) | 2.17 | 533 |

TABLE 4-continued
Example Compounds IV-1 to IV-52 and IV-67 and IV-68
Example Compounds IV-53 to IV-66
| # | Structure | $t_{Ret.}$ (HPLC) [min] | MS (M + H)⁺ |
|---|---|---|---|
| IV-2 | 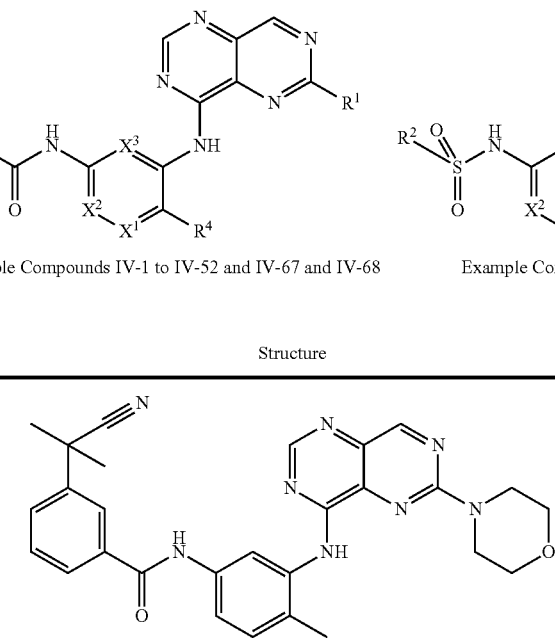 | 2.09 | 509 |
| IV-3 | 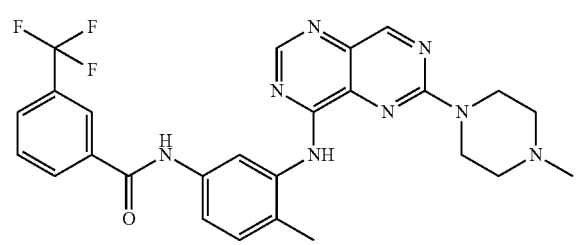 [SMILES: Cc1ccc(NC(=O)c2cccc(C(F)(F)F)c2)cc1Nc1ncnc2cnc(N3CCN(C)CC3)nc12] | 2.17 | 523 |
| IV-4 | 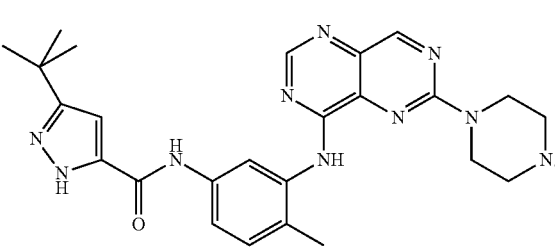 | 1.99 | 501 |
| IV-5 | 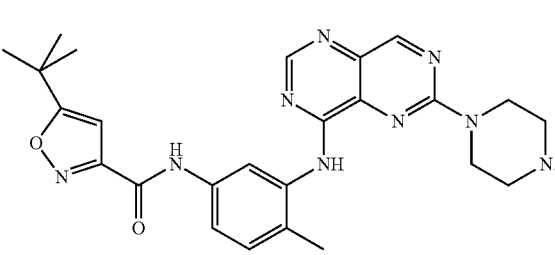 | 2.22 | 502 |
| IV-6 | 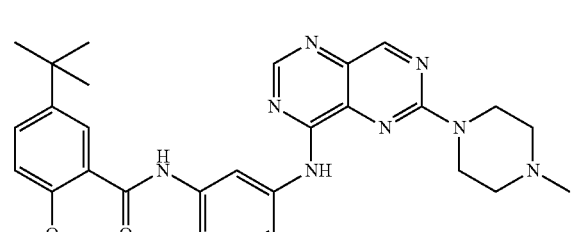 | 2.40 | 541 |

TABLE 4-continued

Example Compounds IV-1 to IV-52 and IV-67 and IV-68

Example Compounds IV-53 to IV-66

| # | Structure | $t_{Ret.}$ (HPLC) [min] | MS (M + H)⁺ |
|---|---|---|---|
| IV-7 | 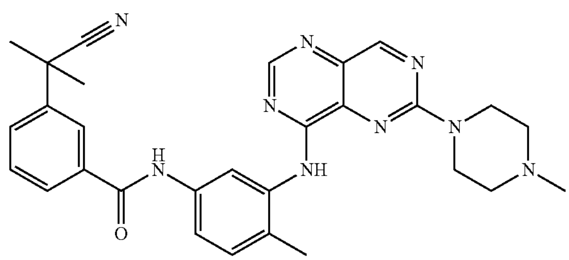 [SMILES: Cc1ccc(NC(=O)c2cccc(C(C)(C)C#N)c2)cc1Nc1ncnc2cnc(N3CCN(C)CC3)nc12] | 2.04 | 522 |
| IV-8 | 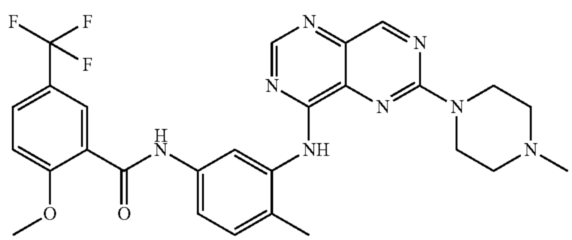 [SMILES: COc1ccc(C(F)(F)F)cc1C(=O)Nc1ccc(C)c(Nc2ncnc3cnc(N4CCN(C)CC4)nc23)c1] | 2.24 | 553 |
| IV-9 | 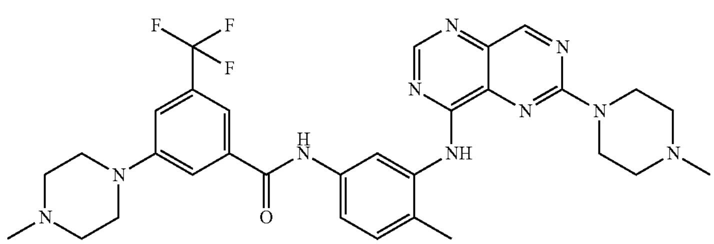 | 2.16 | 621 |
| IV-10 | 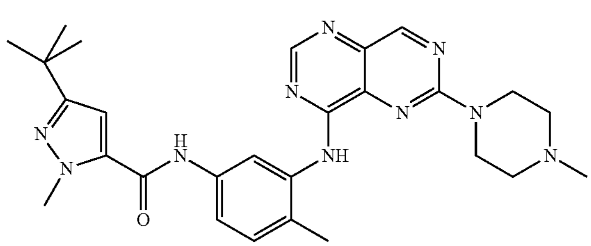 [SMILES: Cc1ccc(NC(=O)c2cc(C(C)(C)C)nn2C)cc1Nc1ncnc2cnc(N3CCN(C)CC3)nc12] | 2.13 | 515 |
| IV-11 | 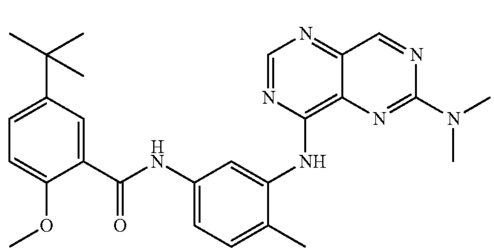 [SMILES: COc1ccc(C(C)(C)C)cc1C(=O)Nc1ccc(C)c(Nc2ncnc3cnc(N(C)C)nc23)c1] | 2.58 | 486 |

TABLE 4-continued
Example Compounds IV-1 to IV-52 and IV-67 and IV-68
Example Compounds IV-53 to IV-66
| # | Structure | $t_{Ret.}$ (HPLC) [min] | MS (M + H)+ |
|---|---|---|---|
| IV-12 | 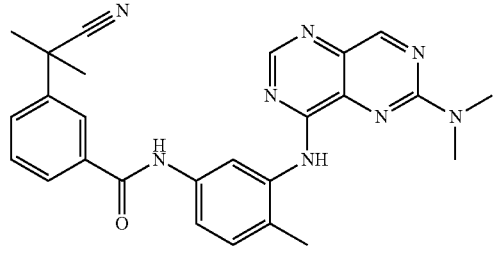 [SMILES: Cc1ccc(NC(=O)c2cccc(C(C)(C)C#N)c2)cc1Nc1ncnc2cnc(N(C)C)nc12] | 2.19 | 467 |
| IV-13 | 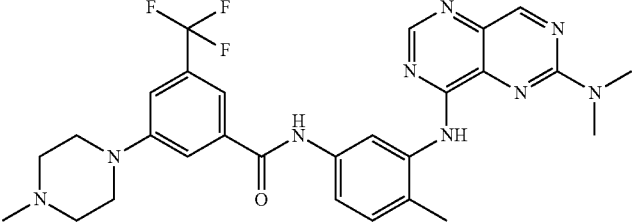 | 2.30 | 566 |
| IV-14 | 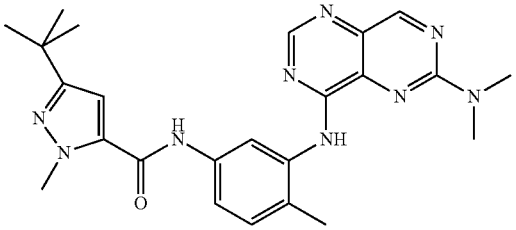 [SMILES: Cc1ccc(NC(=O)c2cc(C(C)(C)C)nn2C)cc1Nc1ncnc2cnc(N(C)C)nc12] | 2.30 | 460 |
| IV-15 | 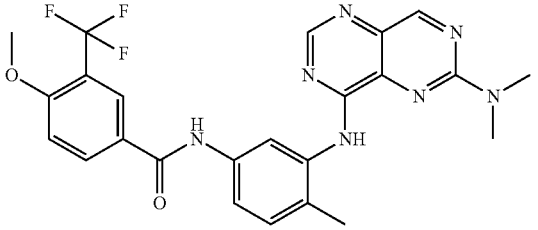 [SMILES: COc1ccc(C(=O)Nc2ccc(C)c(Nc3ncnc4cnc(N(C)C)nc34)c2)cc1C(F)(F)F] | 2.31 | 498 |
| IV-16 | 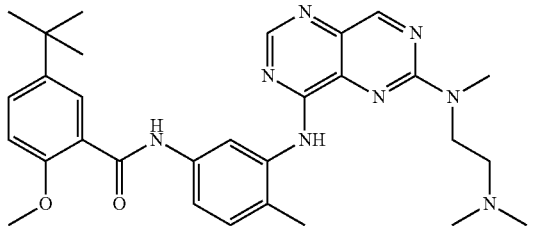 [SMILES: COc1ccc(C(C)(C)C)cc1C(=O)Nc1ccc(C)c(Nc2ncnc3cnc(N(C)CCN(C)C)nc23)c1] | 2.51 | 543 |

TABLE 4-continued

Example Compounds IV-1 to IV-52 and IV-67 and IV-68

Example Compounds IV-53 to IV-66

| # | Structure | t$_{Ret.}$ (HPLC) [min] | MS (M + H)$^+$ |
|---|---|---|---|
| IV-17 | 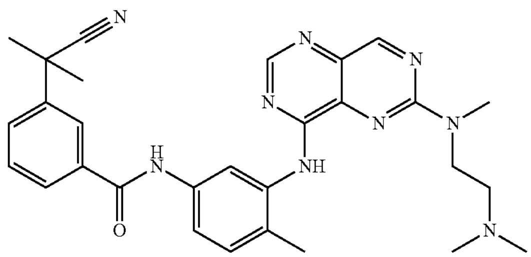 [SMILES: Cc1ccc(NC(=O)c2cccc(C(C)(C)C#N)c2)cc1Nc1ncnc2cnc(N(C)CCN(C)C)nc12] | 2.15 | 524 |
| IV-18 | 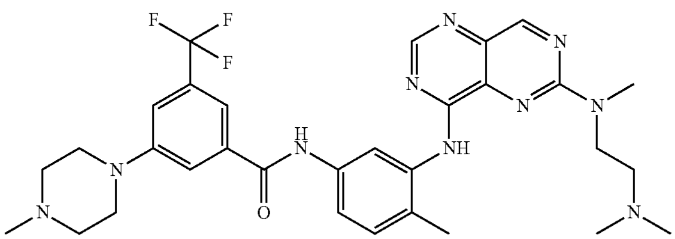 | 2.24 | 623 |
| IV-19 | 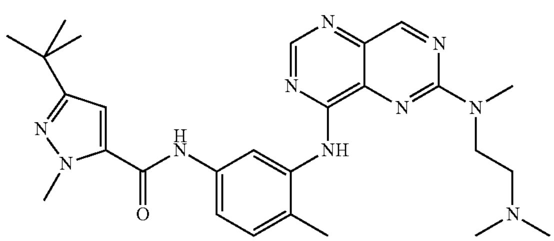 [SMILES: Cc1ccc(NC(=O)c2cc(C(C)(C)C)nn2C)cc1Nc1ncnc2cnc(N(C)CCN(C)C)nc12] | 2.23 | 517 |
| IV-20 | 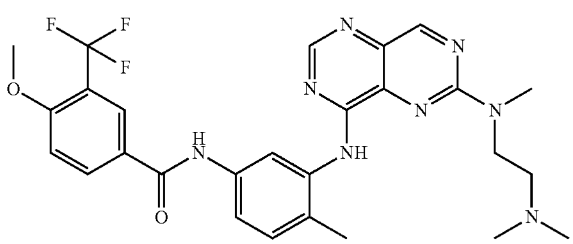 [SMILES: COc1ccc(C(=O)Nc2ccc(C)c(Nc3ncnc4cnc(N(C)CCN(C)C)nc34)c2)cc1C(F)(F)F] | 2.25 | 555 |
| IV-21 | 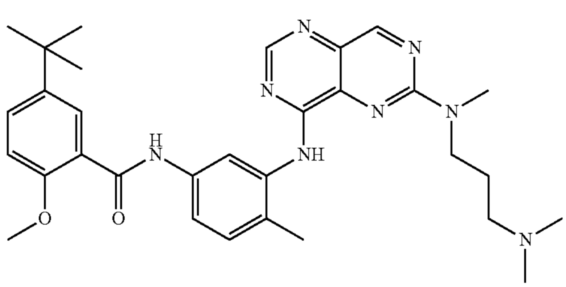 [SMILES: COc1ccc(C(C)(C)C)cc1C(=O)Nc1ccc(C)c(Nc2ncnc3cnc(N(C)CCCN(C)C)nc23)c1] | 2.54 | 557 |

TABLE 4-continued

Example Compounds IV-1 to IV-52 and IV-67 and IV-68

Example Compounds IV-53 to IV-66

| # | Structure | $t_{Ret.}$ (HPLC) [min] | MS (M + H)+ |
|---|---|---|---|
| IV-22 | 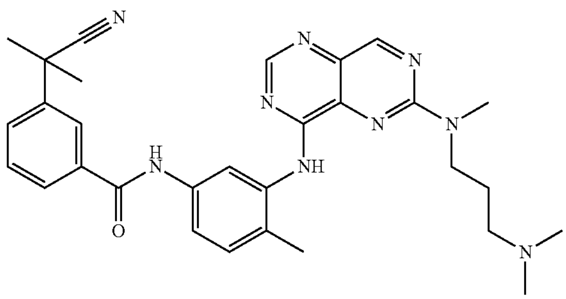 [SMILES: Cc1ccc(NC(=O)c2cccc(C(C)(C)C#N)c2)cc1Nc1ncnc2cnc(N(C)CCCN(C)C)nc12] | 2.16 | 538 |
| IV-23 | 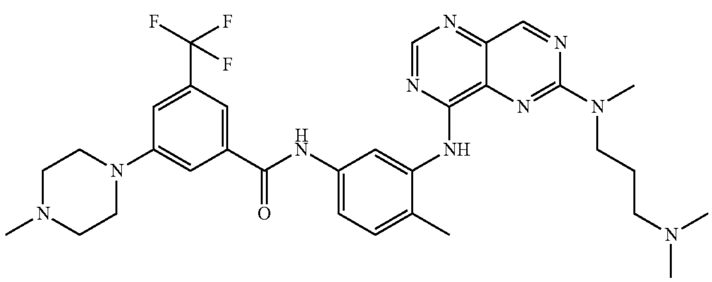 | 2.28 | 637 |
| IV-24 | 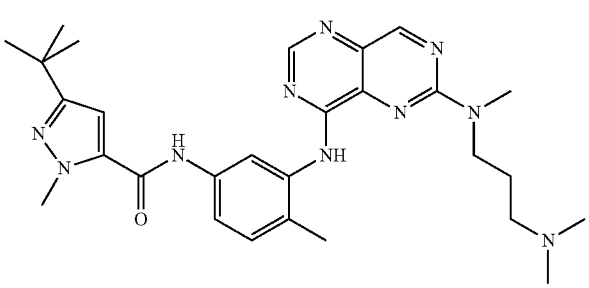 [SMILES: Cc1ccc(NC(=O)c2cc(C(C)(C)C)nn2C)cc1Nc1ncnc2cnc(N(C)CCCN(C)C)nc12] | 2.27 | 531 |
| IV-25 | 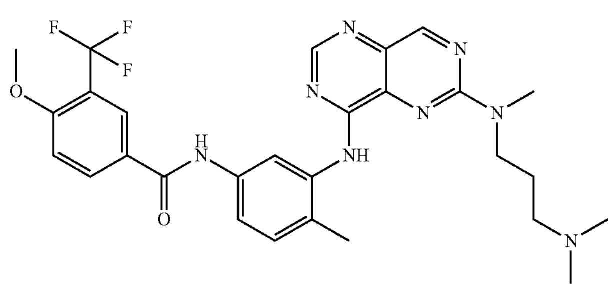 [SMILES: COc1ccc(C(=O)Nc2ccc(C)c(Nc3ncnc4cnc(N(C)CCCN(C)C)nc34)c2)cc1C(F)(F)F] | 2.28 | 569 |

TABLE 4-continued

Example Compounds IV-1 to IV-52 and IV-67 and IV-68

Example Compounds IV-53 to IV-66

| # | Structure | t_Ret. (HPLC) [min] | MS (M + H)+ |
|---|---|---|---|
| IV-26 | 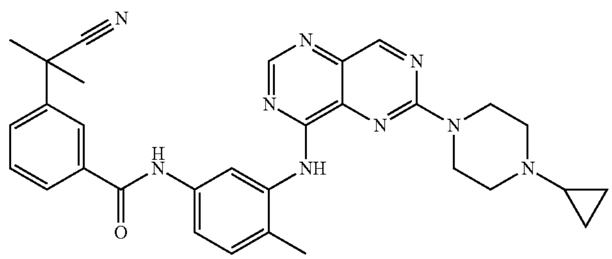 [SMILES: Cc1ccc(NC(=O)c2cccc(C(C)(C)C#N)c2)cc1Nc1ncnc2cnc(N3CCN(C4CC4)CC3)nc12] | 2.29 | 548 |
| IV-27 | 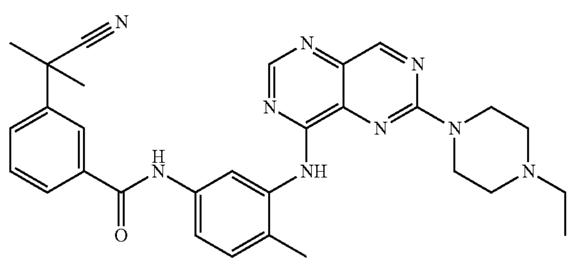 [SMILES: CCN1CCN(c2ncc3ncnc(Nc4cc(NC(=O)c5cccc(C(C)(C)C#N)c5)ccc4C)c3n2)CC1] | 2.14 | 536 |
| IV-28 | 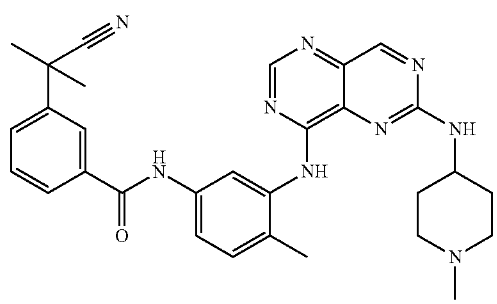 | 2.05 | 536 |
| IV-29 | 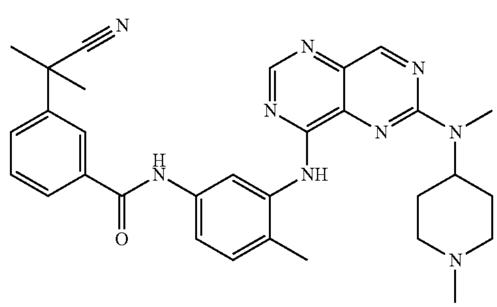 [SMILES: Cc1ccc(NC(=O)c2cccc(C(C)(C)C#N)c2)cc1Nc1ncnc2cnc(N(C)C3CCN(C)CC3)nc12] | 2.16 | 550 |

TABLE 4-continued

Example Compounds IV-1 to IV-52 and IV-67 and IV-68

Example Compounds IV-53 to IV-66

| # | Structure | t$_{Ret.}$ (HPLC) [min] | MS (M + H)$^+$ |
|---|---|---|---|
| IV-30 | 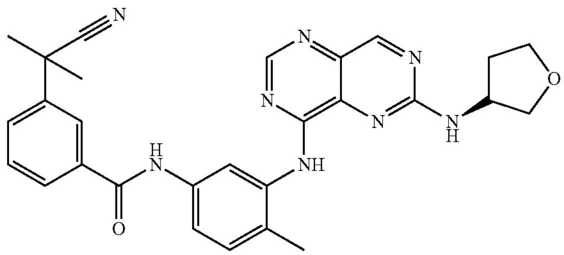 | 1.98 | 509 |
| IV-31 | 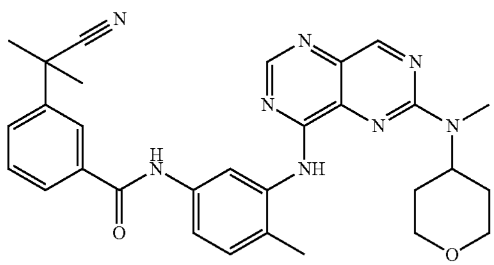 [SMILES: Cc1ccc(NC(=O)c2cccc(C(C)(C)C#N)c2)cc1Nc1ncnc2cnc(N(C)C3CCOCC3)nc12] | 2.20 | 537 |
| IV-32 | 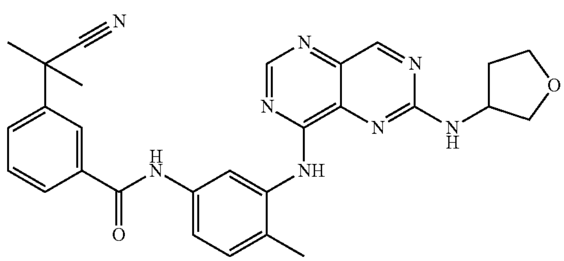 | 1.99 | 509 |
| IV-33 | 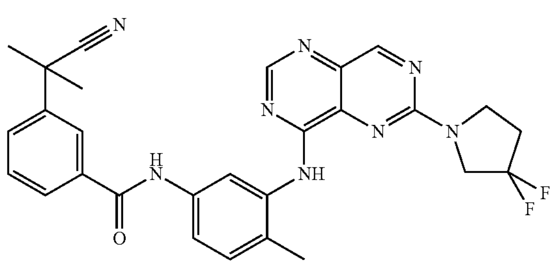 [SMILES: Cc1ccc(NC(=O)c2cccc(C(C)(C)C#N)c2)cc1Nc1ncnc2cnc(N3CCC(F)(F)C3)nc12] | 2.26 | 529 |
| IV-34 | 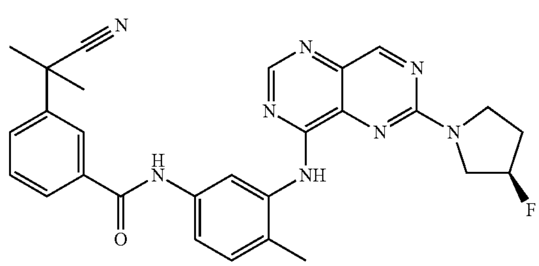 [SMILES: Cc1ccc(NC(=O)c2cccc(C(C)(C)C#N)c2)cc1Nc1ncnc2cnc(N3CC[C@@H](F)C3)nc12] | 2.18 | 511 |

TABLE 4-continued

Example Compounds IV-1 to IV-52 and IV-67 and IV-68

Example Compounds IV-53 to IV-66

| # | Structure | t$_{Ret.}$ (HPLC) [min] | MS (M + H)⁺ |
|---|---|---|---|
| IV-35 | 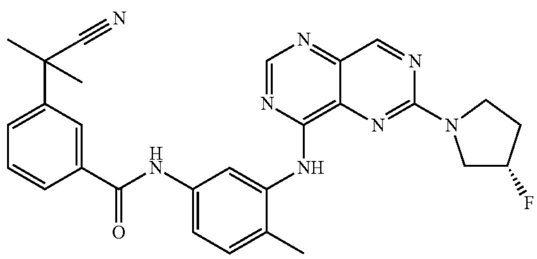 [SMILES: Cc1ccc(NC(=O)c2cccc(C(C)(C)C#N)c2)cc1Nc1ncnc2cnc(N3CC[C@H](F)C3)nc12] | 2.19 | 511 |
| IV-36 | 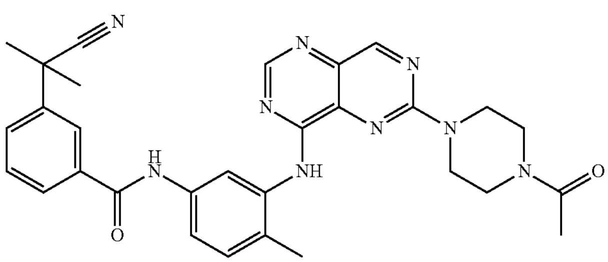 [SMILES: CC(=O)N1CCN(c2ncc3ncnc(Nc4cc(NC(=O)c5cccc(C(C)(C)C#N)c5)ccc4C)c3n2)CC1] | 1.93 | 550 |
| IV-37 | 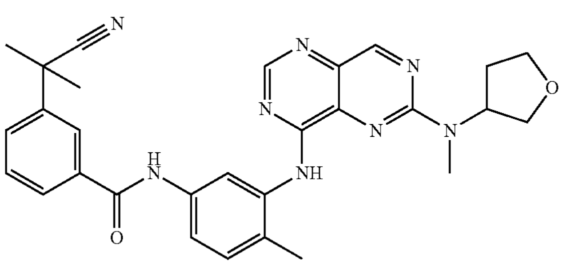 [SMILES: Cc1ccc(NC(=O)c2cccc(C(C)(C)C#N)c2)cc1Nc1ncnc2cnc(N(C)C3CCOC3)nc12] | 2.13 | 523 |
| IV-38 | 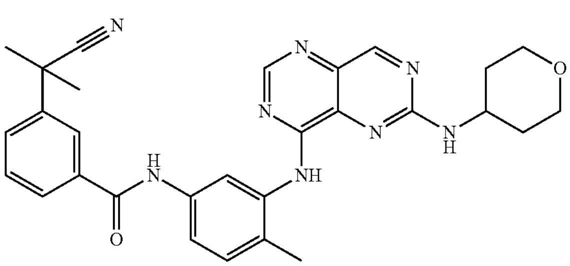 [SMILES: Cc1ccc(NC(=O)c2cccc(C(C)(C)C#N)c2)cc1Nc1ncnc2cnc(NC3CCOCC3)nc12] | 2.03 | 523 |

TABLE 4-continued
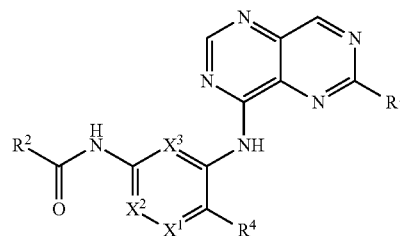
Example Compounds IV-1 to IV-52 and IV-67 and IV-68
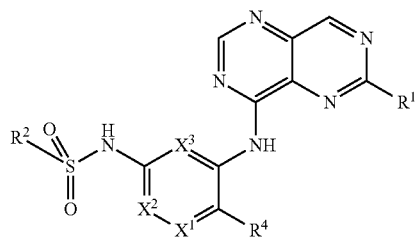
Example Compounds IV-53 to IV-66
| # | Structure | $t_{Ret.}$ (HPLC) [min] | MS (M + H)+ |
|---|---|---|---|
| IV-39 | 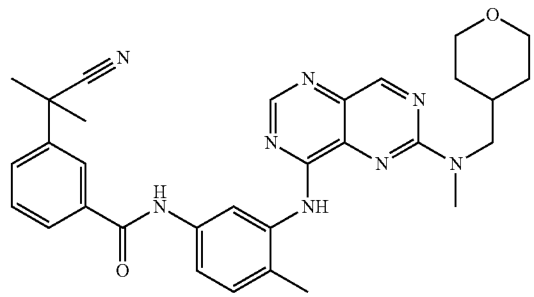 [SMILES: Cc1ccc(NC(=O)c2cccc(C(C)(C)C#N)c2)cc1Nc1ncnc2cnc(N(C)CC3CCOCC3)nc12] | 2.40 | 551 |
| IV-40* | 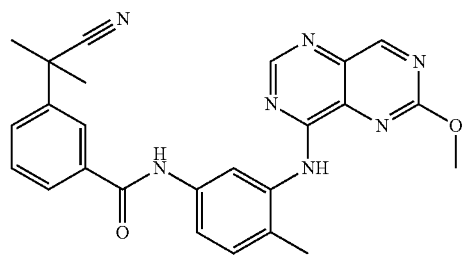 [SMILES: COc1ncc2ncnc(Nc3cc(NC(=O)c4cccc(C(C)(C)C#N)c4)ccc3C)c2n1] | 1.99 | 454 |
| IV-41* | 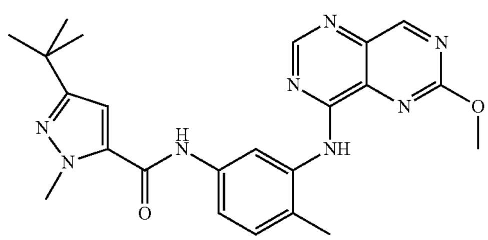 [SMILES: COc1ncc2ncnc(Nc3cc(NC(=O)c4cc(C(C)(C)C)nn4C)ccc3C)c2n1] | 2.08 | 447 |
| IV-42* | 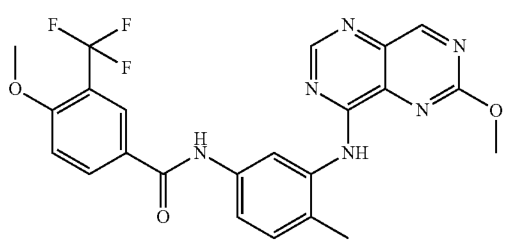 [SMILES: COc1ncc2ncnc(Nc3cc(NC(=O)c4ccc(OC)c(C(F)(F)F)c4)ccc3C)c2n1] | 2.12 | 485 |
| IV-43* | 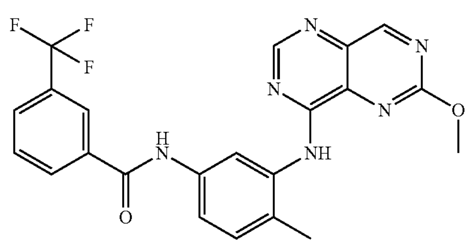 [SMILES: COc1ncc2ncnc(Nc3cc(NC(=O)c4cccc(C(F)(F)F)c4)ccc3C)c2n1] | 2.11 | 455 |

TABLE 4-continued
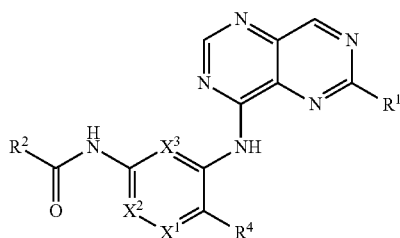
Example Compounds IV-1 to IV-52 and IV-67 and IV-68
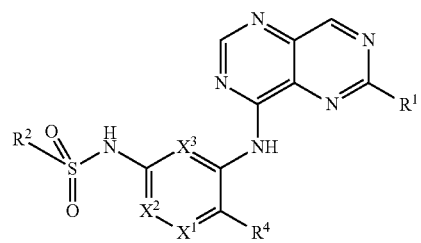
Example Compounds IV-53 to IV-66
| # | Structure | $t_{Ret.}$ (HPLC) [min] | MS $(M + H)^+$ |
|---|---|---|---|
| IV-44* | 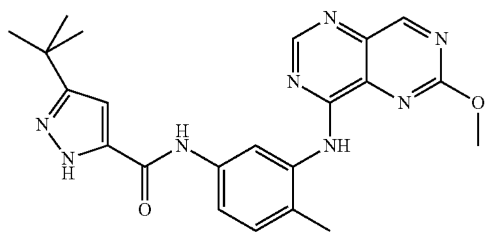 [SMILES: COc1ncc2ncnc(Nc3cc(NC(=O)c4cc(C(C)(C)C)n[nH]4)ccc3C)c2n1] | 1.92 | 433 |
| IV-45* | 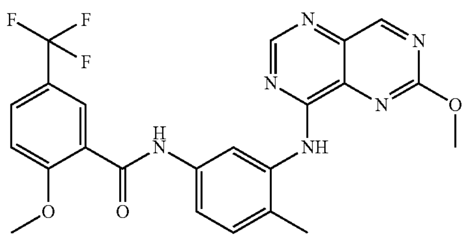 [SMILES: COc1ncc2ncnc(Nc3cc(NC(=O)c4cc(C(F)(F)F)ccc4OC)ccc3C)c2n1] | 2.18 | 485 |
| IV-46* | 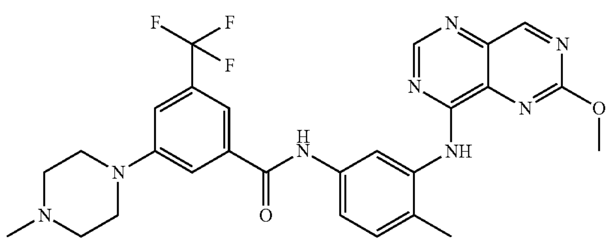 | 2.11 | 553 |
| IV-47* | 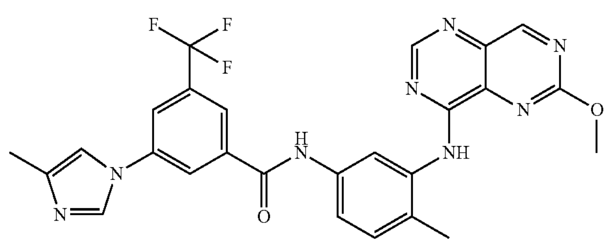 | 2.06 | 535 |
| IV-48* | 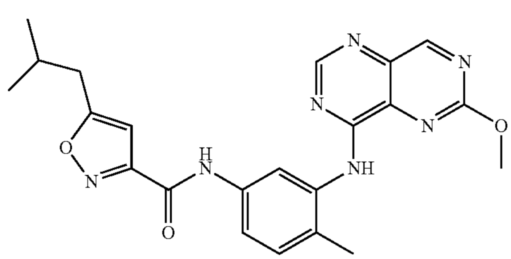 [SMILES: COc1ncc2ncnc(Nc3cc(NC(=O)c4cc(CC(C)C)on4)ccc3C)c2n1] | 2.17 | 434 |

TABLE 4-continued
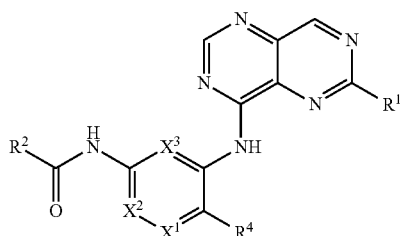
Example Compounds IV-1 to IV-52 and IV-67 and IV-68
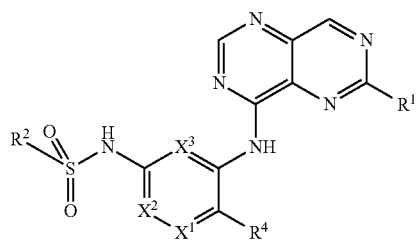
Example Compounds IV-53 to IV-66
| # | Structure | $t_{Ret.}$ (HPLC) [min] | MS (M + H)⁺ |
|---|---|---|---|
| IV-49* | 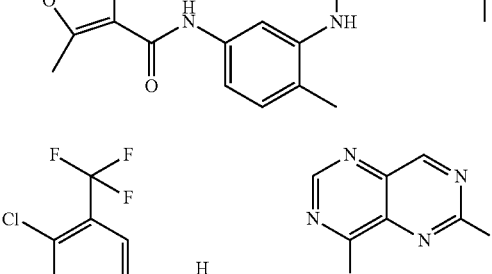 | 2.28 | 447 |
| IV-50* | 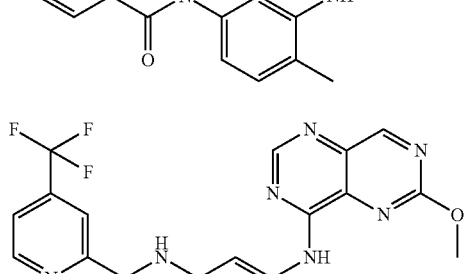 | 2.23 | 489 |
| IV-51* | 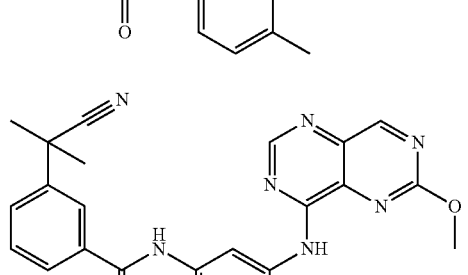 | 2.11 | 456 |
| IV-52* | 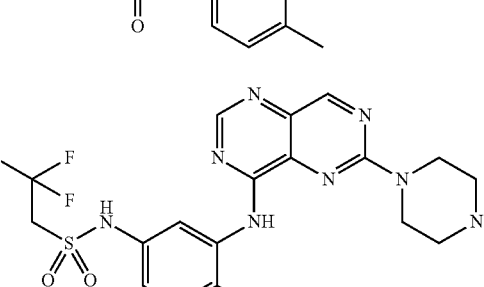 | 1.99 | 454 |
| IV-53** | 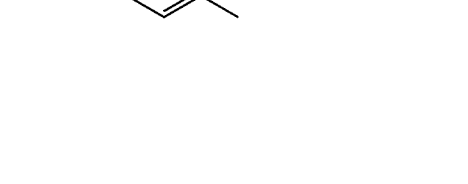 | 0.0 | 497 |

TABLE 4-continued
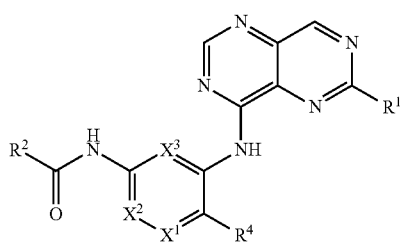
Example Compounds IV-1 to IV-52 and IV-67 and IV-68
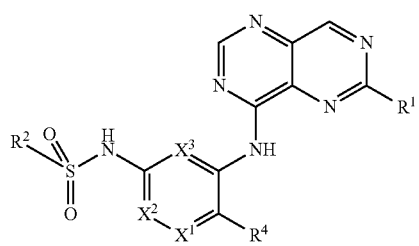
Example Compounds IV-53 to IV-66
| # | Structure | $t_{Ret.}$ (HPLC) [min] | MS (M + H)+ |
|---|---|---|---|
| IV-54** | 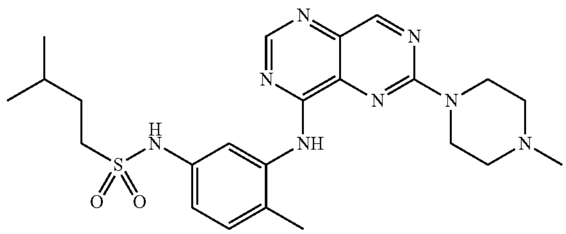 [SMILES: Cc1ccc(NS(=O)(=O)CCC(C)C)cc1Nc1ncnc2cnc(N3CCN(C)CC3)nc12] | 1.78 | 485 |
| IV-55** | 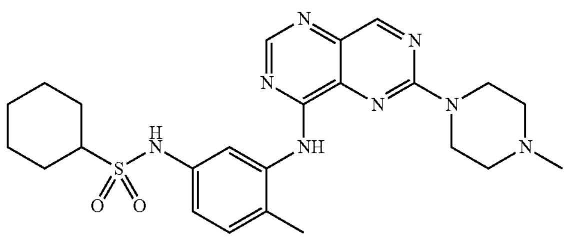 [SMILES: Cc1ccc(NS(=O)(=O)C2CCCCC2)cc1Nc1ncnc2cnc(N3CCN(C)CC3)nc12] | 1.86 | 497 |
| IV-56** | 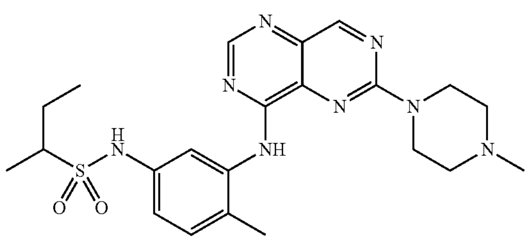 [SMILES: CCC(C)S(=O)(=O)Nc1ccc(C)c(Nc2ncnc3cnc(N4CCN(C)CC4)nc23)c1] | 1.72 | 471 |
| IV-57** | 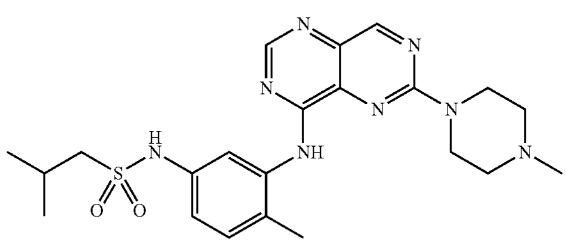 [SMILES: Cc1ccc(NS(=O)(=O)CC(C)C)cc1Nc1ncnc2cnc(N3CCN(C)CC3)nc12] | 1.59 | 471 |
| IV-58** | 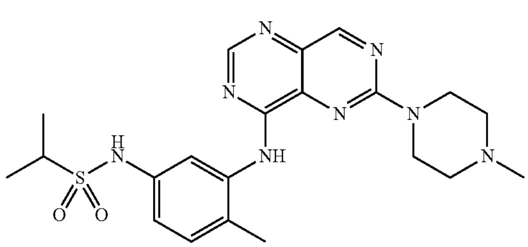 [SMILES: Cc1ccc(NS(=O)(=O)C(C)C)cc1Nc1ncnc2cnc(N3CCN(C)CC3)nc12] | 1.56 | 457 |

TABLE 4-continued

Example Compounds IV-1 to IV-52 and IV-67 and IV-68

Example Compounds IV-53 to IV-66

| # | Structure | t$_{Ret.}$ (HPLC) [min] | MS (M + H)$^+$ |
|---|---|---|---|
| IV-59** | 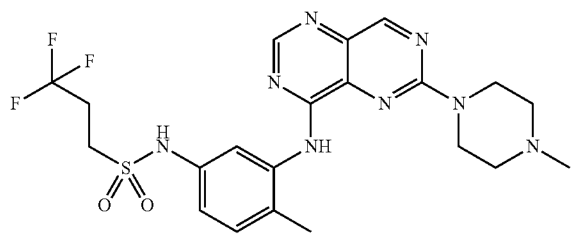 [SMILES: Cc1ccc(NS(=O)(=O)CCC(F)(F)F)cc1Nc1ncnc2cnc(N3CCN(C)CC3)nc12] | 1.43 | 511 |
| IV-60** | 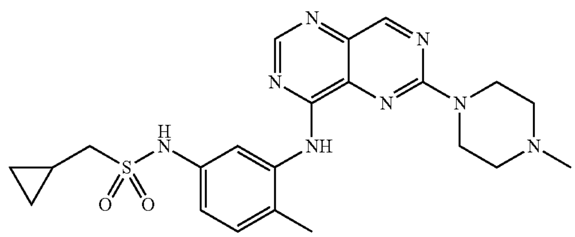 [SMILES: Cc1ccc(NS(=O)(=O)CC2CC2)cc1Nc1ncnc2cnc(N3CCN(C)CC3)nc12] | 1.60 | 469 |
| IV-61** | 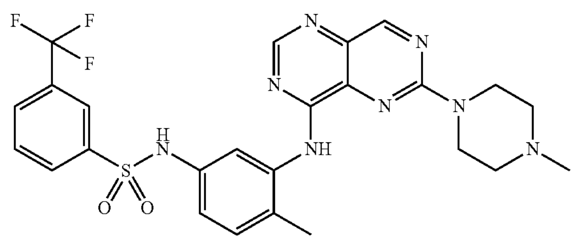 [SMILES: Cc1ccc(NS(=O)(=O)c2cccc(C(F)(F)F)c2)cc1Nc1ncnc2cnc(N3CCN(C)CC3)nc12] | 1.49 | 559 |
| IV-62** | 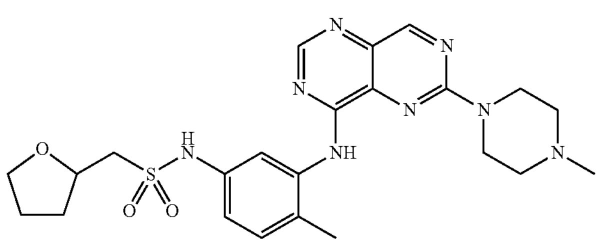 [SMILES: Cc1ccc(NS(=O)(=O)CC2CCCO2)cc1Nc1ncnc2cnc(N3CCN(C)CC3)nc12] | 1.39 | 499 |
| IV-63** | 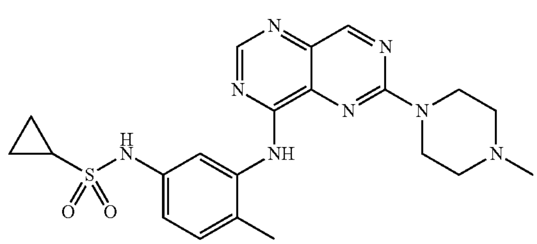 [SMILES: Cc1ccc(NS(=O)(=O)C2CC2)cc1Nc1ncnc2cnc(N3CCN(C)CC3)nc12] | 1.49 | 455 |

TABLE 4-continued
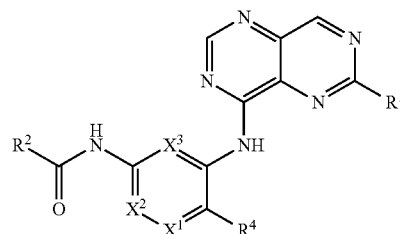
Example Compounds IV-1 to IV-52 and IV-67 and IV-68
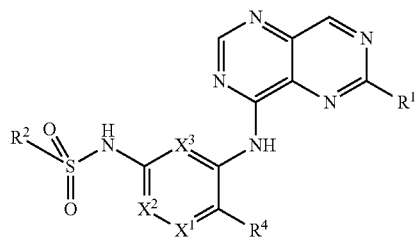
Example Compounds IV-53 to IV-66
| # | Structure | $t_{Ret.}$ (HPLC) [min] | MS (M + H)⁺ |
|---|---|---|---|
| IV-64** | 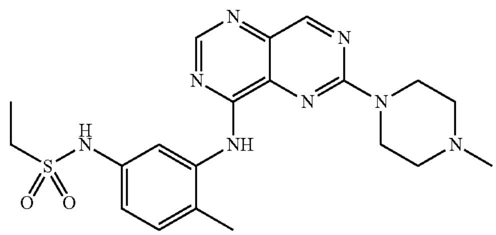 [SMILES: CCS(=O)(=O)Nc1ccc(C)c(Nc2ncnc3cnc(N4CCN(C)CC4)nc23)c1] | 1.44 | 443 |
| IV-65** | 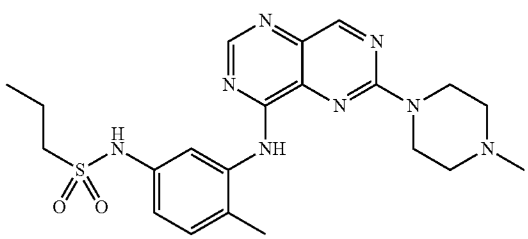 [SMILES: CCCS(=O)(=O)Nc1ccc(C)c(Nc2ncnc3cnc(N4CCN(C)CC4)nc23)c1] | 1.58 | 457 |
| IV-66** | 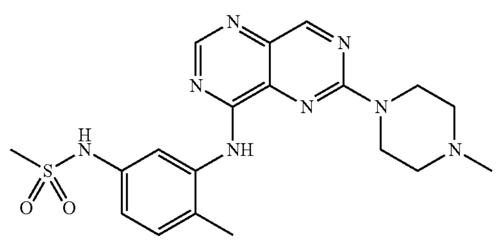 | 1.29 | 429 |
| IV-67 | 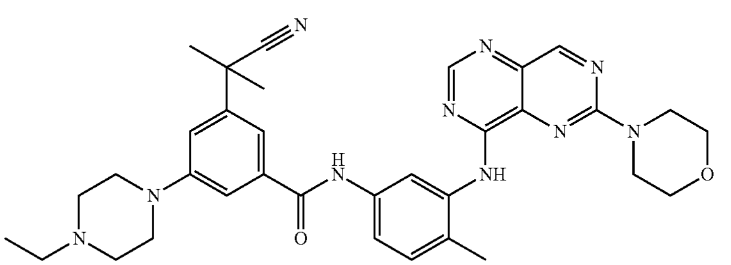 [SMILES: CCN1CCN(c2cc(C(=O)Nc3ccc(C)c(Nc4ncnc5cnc(N6CCOCC6)nc45)c3)cc(C(C)(C)C#N)c2)CC1] | 1.96 | 621 |
| IV-68 | 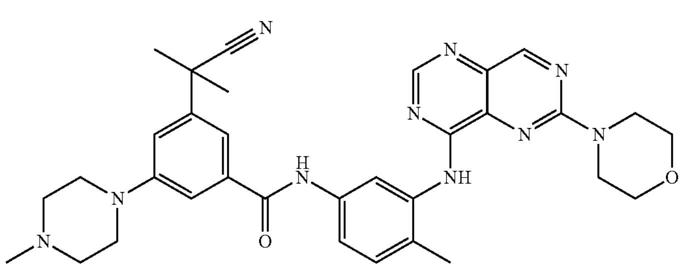 [SMILES: Cc1ccc(NC(=O)c2cc(N3CCN(C)CC3)cc(C(C)(C)C#N)c2)cc1Nc1ncnc2cnc(N3CCOCC3)nc12] | 1.87 | 607 |
*using NaOMe instead of amines (E-3)
**by coupling a sulphonic acid instead of carboxylic acid E-5 to the intermediate Z-27

Reaction scheme E

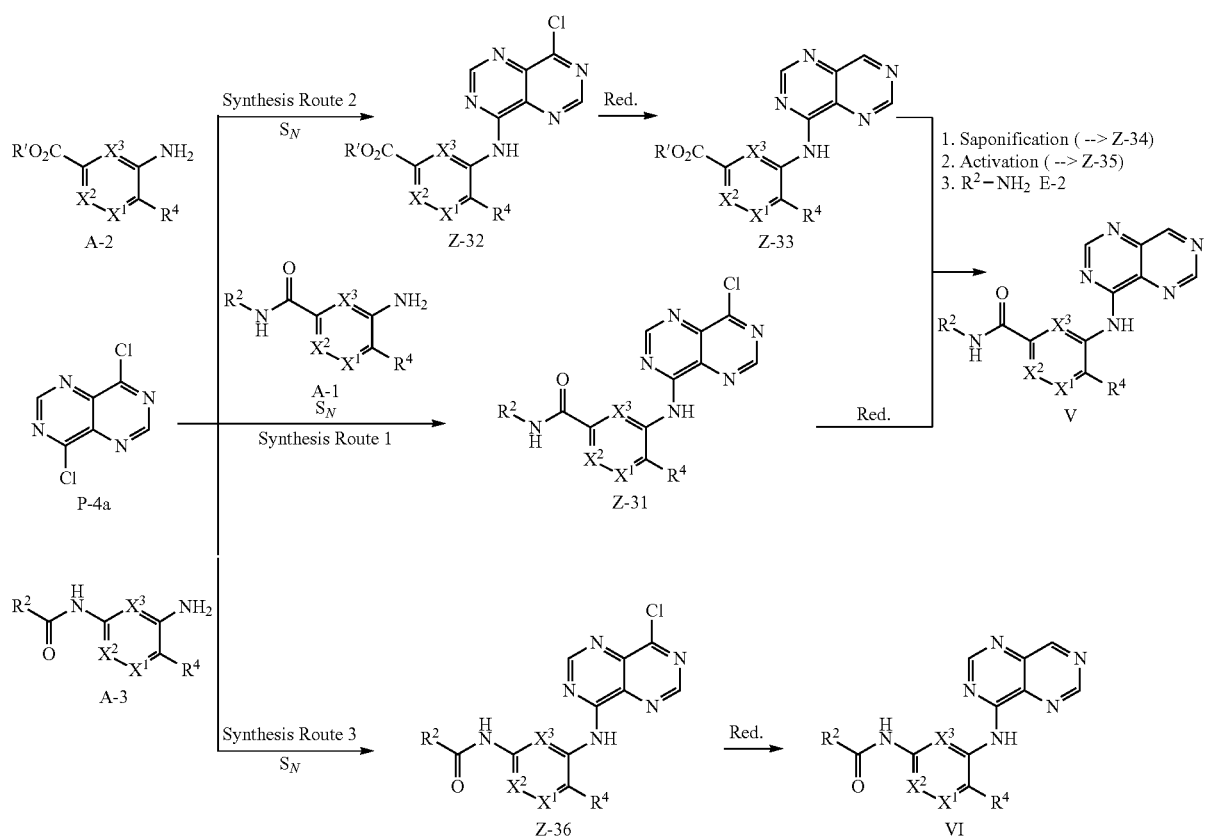

(R' = common carboxyl protecting group
e.g. $C_{1-6}$Alkyl, Benzyl)

Example Compounds of Type V and VI:

Compounds of type V and VI are pyrimidopyrimidines monosubstituted in the 8-position (Reaction scheme E).

Starting from 4,8-dichloro-pyrimido[5,4-d]pyrimidine P-4-a, one chlorine atom is substituted nucleophilically by the aniline components A-1 (synthesis route 1), A-2 (synthesis route 2) or A-3 (synthesis route 3) while the other chlorine atom is reductively removed.

The substitution by A-1 or A-2 to obtain the intermediate compounds Z-31 or Z-32 is carried out in comparable manner to the steps illustrated in Reaction scheme A or C (reactions to obtain intermediate compounds Z-2, Z-3, Z-12 or Z-14). Whereas example compounds V may be obtained directly from Z-31 (reduction), saponification and amide coupling with amines E-2 are also necessary in addition to the reduction for the synthesis starting from Z-32.

By using the anilines A-3, after reduction of the intermediate compound Z-36, example compounds VI with an inverted amide bond are obtained (regarding the synthesis of A-1 or A-3 cf. the remarks made on Reaction scheme A or B)

a) Method for Synthesising P-4-a:

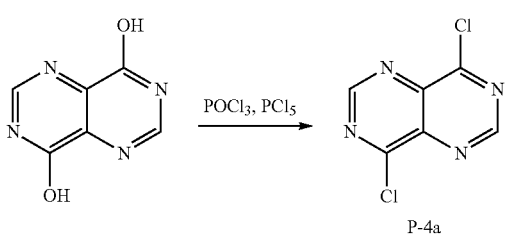 [SMILES: Oc1ncnc2c(O)ncnc12 ; Clc1ncnc2c(Cl)ncnc12]

4,8-dihydroxypyrimidopyrimidine (2.0 g, 12 mmol) is taken. Phosphorus oxychloride (7.0 mL, 76 mmol) and potassium chloride (2.6 g, 35 mmol) are added. Finally, phosphorus pentachloride (6.2 g, 30 mmol) is added batchwise. The reaction mixture is stirred for 1.5 d at 130° C. and 1.5 d at RT. The excess $POCl_3$ is distilled off, the residue is mixed with water and extracted several times with DCM. The combined organic phases are mixed with $MgSO_4$, filtered through silica gel and washed with DCM. The filtrate is slowly evaporated down to about 15 mL. The precipitate formed is suction filtered and P-4-a (HPLC-MS: MS $(M+H)^+$=200/202/204) is obtained.

b) Method for Synthesising Z-31a:

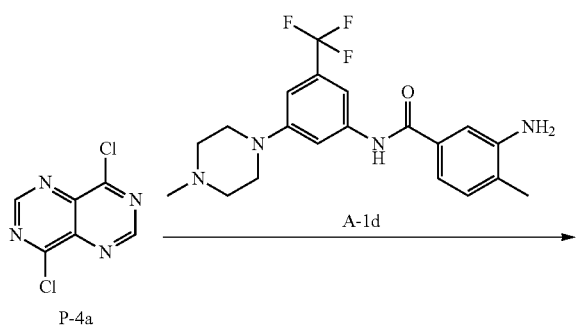

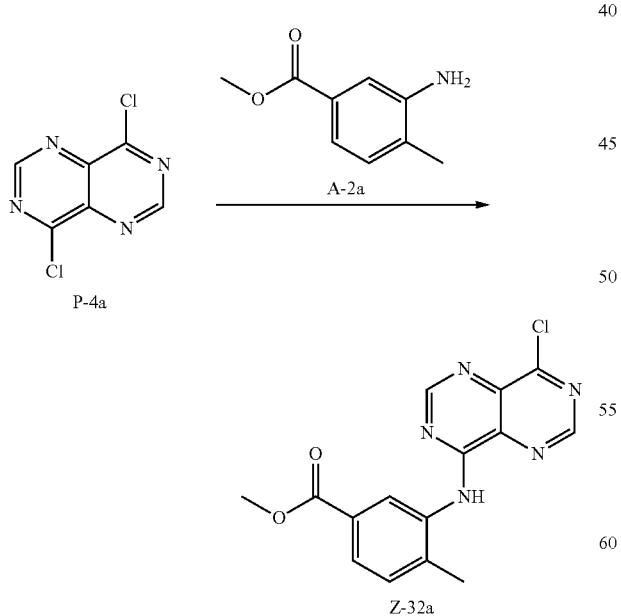

4,8-dichloropyrimidopyrimidine P-4-a (100 mg, 0.50 mmol) is placed in THF (2 mL) while cooling with ice. Aniline A-1d (195 mg, 0.50 mmol) and DIPEA (0.1 mL, 0.58 mmol) are added. The reaction mixture is thawed to RT overnight and stirred. For working up it is mixed with a little acetonitrile. The precipitate is filtered off, dried and Z-31a is obtained. Analogously to the method for synthesising Z-31a further intermediate compounds Z-31 are obtained by reacting components A-1 with P-4-a.

c) Method for Synthesising Z-32a:

4,8-dichloropyrimidopyrimidine P-4-a (1.0 g, 4.98 mmol) is placed in THF (20 mL) and cooled in the ice bath. Aniline A-2a (840 mg, 4.98 mmol) is added batchwise. The reaction mixture is combined with DIPEA (940 µL, 5.49 mmol) and thawed to RT overnight and stirred. For working up the mixture is evaporated to dryness, taken up in acetonitrile and treated for 5 min in the ultrasound bath. The precipitate is filtered off, washed with a mixture of water and acetonitrile (1:1), dried and Z-32a (HPLC-MS: $t_{Ret.}$=1.83 min; MS $(M+H)^+$=330) is obtained.

Analogously to the method for synthesising Z-32a further intermediate compounds Z-32 are obtained by reacting components A-2 with P-4-a.

d) Method for Synthesising Z-33a:

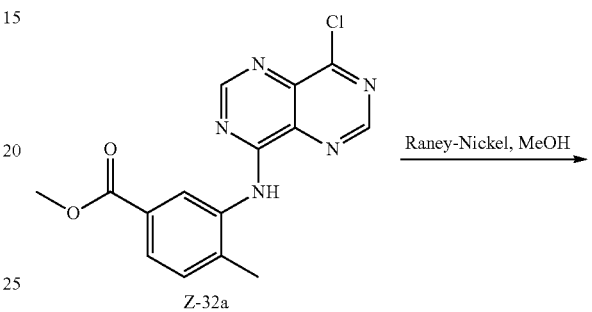

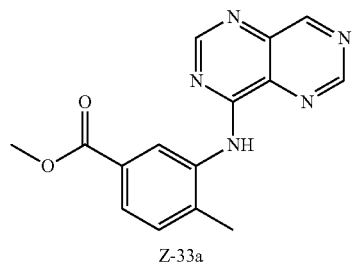

Z-32a (1.25 g, 3.79 mmol) is suspended in MeOH (130 mL), combined with Raney nickel and hydrogenated overnight at 2 bar. The reaction mixture is filtered off from the catalyst, evaporated to dryness and Z-33a (HPLC-MS: $t_{Ret.}$=1.58 min; MS $(M+H)^+$=296) is obtained, which is reacted further without any further working up (purity approx. 80%). Analogously to the method for synthesising Z-33a further intermediate compounds Z-33 are obtained by reduction of intermediate compounds Z-32.

e) Method for Synthesising Example Compound V-1:

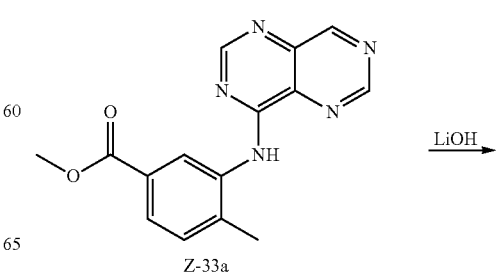

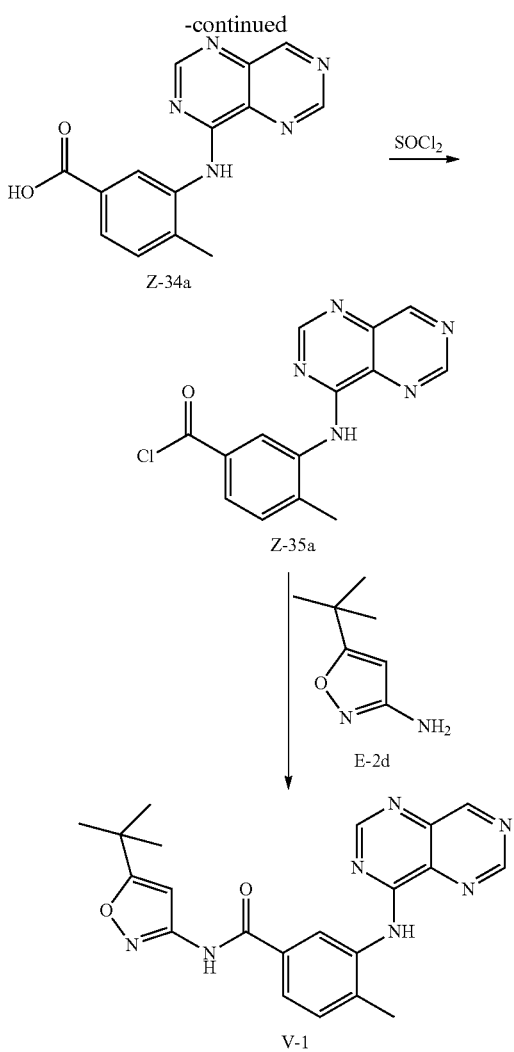

Ester Z-33a (80%, 817 mg, 2.21 mmol) is combined with a methanolic LiOH solution (270 mg, 11.05 mmol LiOH in 35 mL MeOH). The reaction mixture is stirred overnight at 60° C. For working up the mixture is diluted with 15 mL water and extracted 1× with DCM. The aqueous phase is adjusted to an acidic pH with 2N HCl solution and extracted 5× with EE. The combined organic phases are extracted 1× with saturated NaCl solution, dried on MgSO$_4$, filtered, evaporated down and Z-34a (HPLC-MS: t$_{Ret.}$=0.11 min; MS (M+H)$^+$=282) is obtained.

Benzoic acid Z-34a (462 mg, 1.64 mmol) is suspended in thionyl chloride (10 mL, 134 mmol). The reaction mixture is refluxed for 1 h and stirred overnight at 60° C. The excess thionyl chloride is spun off and the remainder is dried azeotropically 1× with toluene. The acid chloride Z-35a is used again directly.

3-amino-5-tert-butylisoxazole E-2d (58 mg, 0.40 mmol) is placed in DCM (4 mL), combined with pyridine (200 μL, 2.47 mmol) and cooled in the ice bath. Then a solution of the acid chloride Z-35a (120 mg, 0.40 mmol) in 3 mL DCM is added. The reaction mixture is stirred for 1 h at RT. For working up the mixture is diluted with water, the DCM is spun off, placed in solution with DMF and chromatographed by RP-MPLC (7% to 90% acetonitrile). The product-containing fractions of V-1 (HPLC-MS: t$_{Ret.}$=1.94 min; MS (M+H)$^+$=404) are mixed with 2N HCl solution and freeze-dried.

Analogously to the methods a) and c) to e) (synthesis route 2) or the synthesis route 1 shown, besides V-1 the following compounds V-2 to V-10 according to the invention are prepared (Table 5).

Compound of type VI is synthesised according to synthesis route 3 shown.

TABLE 5

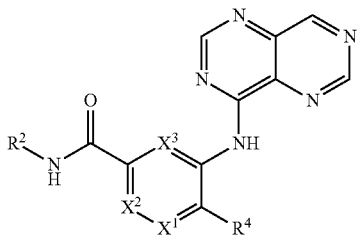

Example Compounds V-1 to V-10

| # | Structure | t$_{Ret.}$ (HPLC) [min] | MS (M + H)$^+$ |
|---|-----------|-------------------------|----------------|
| V-1 | 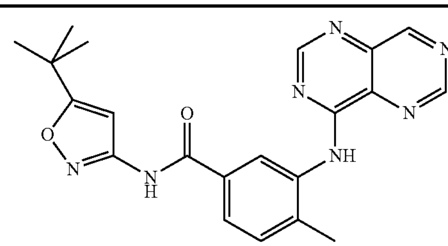 | 1.94 | 404 |

TABLE 5-continued

Example Compounds V-1 to V-10

| # | Structure | $t_{Ret.}$ (HPLC) [min] | MS (M + H)+ |
|---|---|---|---|
| V-2 | 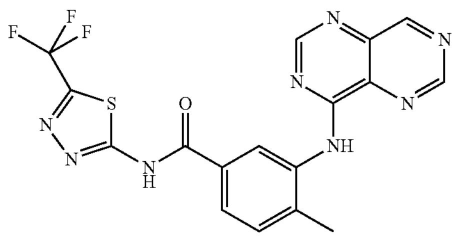 [SMILES: Cc1ccc(C(=O)Nc2nnc(C(F)(F)F)s2)cc1Nc1ncnc2cncnc12] | 1.37 | 433 |
| V-3 | 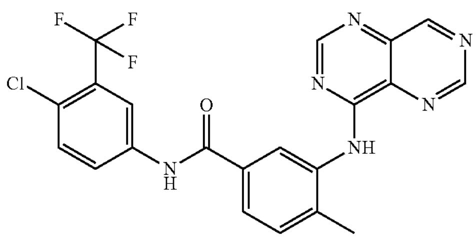 [SMILES: Cc1ccc(C(=O)Nc2ccc(Cl)c(C(F)(F)F)c2)cc1Nc1ncnc2cncnc12] | 2.17 | 459 |
| V-4 | 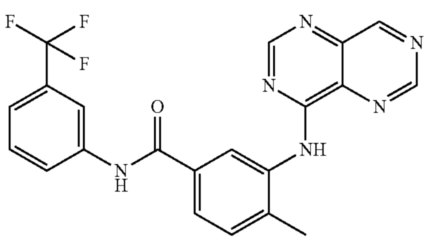 [SMILES: Cc1ccc(C(=O)Nc2cccc(C(F)(F)F)c2)cc1Nc1ncnc2cncnc12] | 2.04 | 425 |
| V-5 | 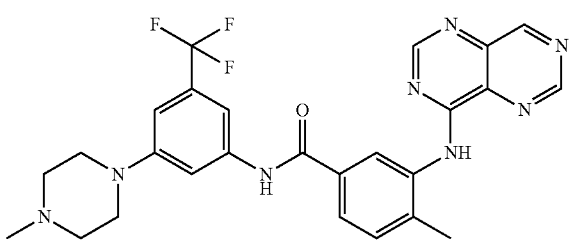 [SMILES: Cc1ccc(C(=O)Nc2cc(N3CCN(C)CC3)cc(C(F)(F)F)c2)cc1Nc1ncnc2cncnc12] | 2.01 | 523 |
| V-6 | 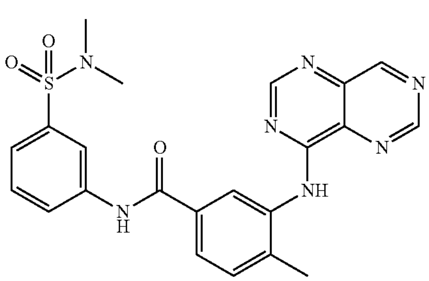 [SMILES: Cc1ccc(C(=O)Nc2cccc(S(=O)(=O)N(C)C)c2)cc1Nc1ncnc2cncnc12] | 1.78 | 464 |

TABLE 5-continued
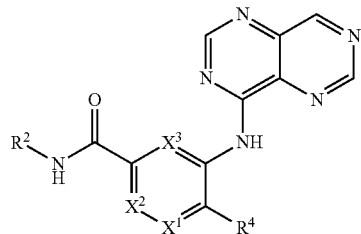
Example Compounds V-1 to V-10
| # | Structure | t_Ret. (HPLC) [min] | MS (M + H)+ |
|---|---|---|---|
| V-7 | 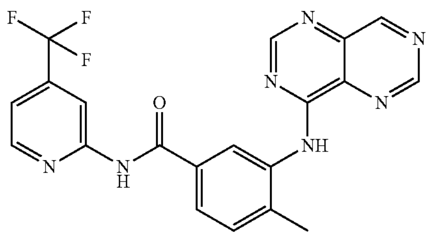 [SMILES: Cc1ccc(C(=O)Nc2cc(C(F)(F)F)ccn2)cc1Nc1ncnc2cncnc12] | 1.96 | 426 |
| V-8 | 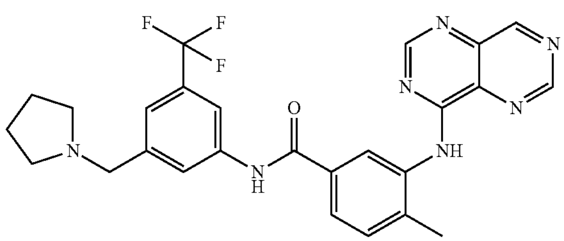 [SMILES: Cc1ccc(C(=O)Nc2cc(CN3CCCC3)cc(C(F)(F)F)c2)cc1Nc1ncnc2cncnc12] | 1.25 | 508 |
| V-9 | 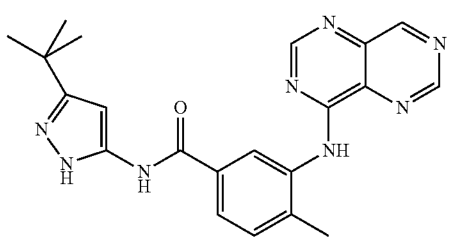 [SMILES: Cc1ccc(C(=O)Nc2cc(C(C)(C)C)n[nH]2)cc1Nc1ncnc2cncnc12] | 1.04 | 403 |
| V-10 | 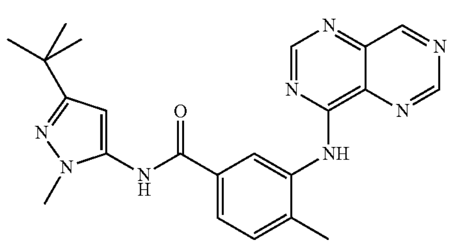 [SMILES: Cc1ccc(C(=O)Nc2cc(C(C)(C)C)nn2C)cc1Nc1ncnc2cncnc12] | 1.07 | 417 |

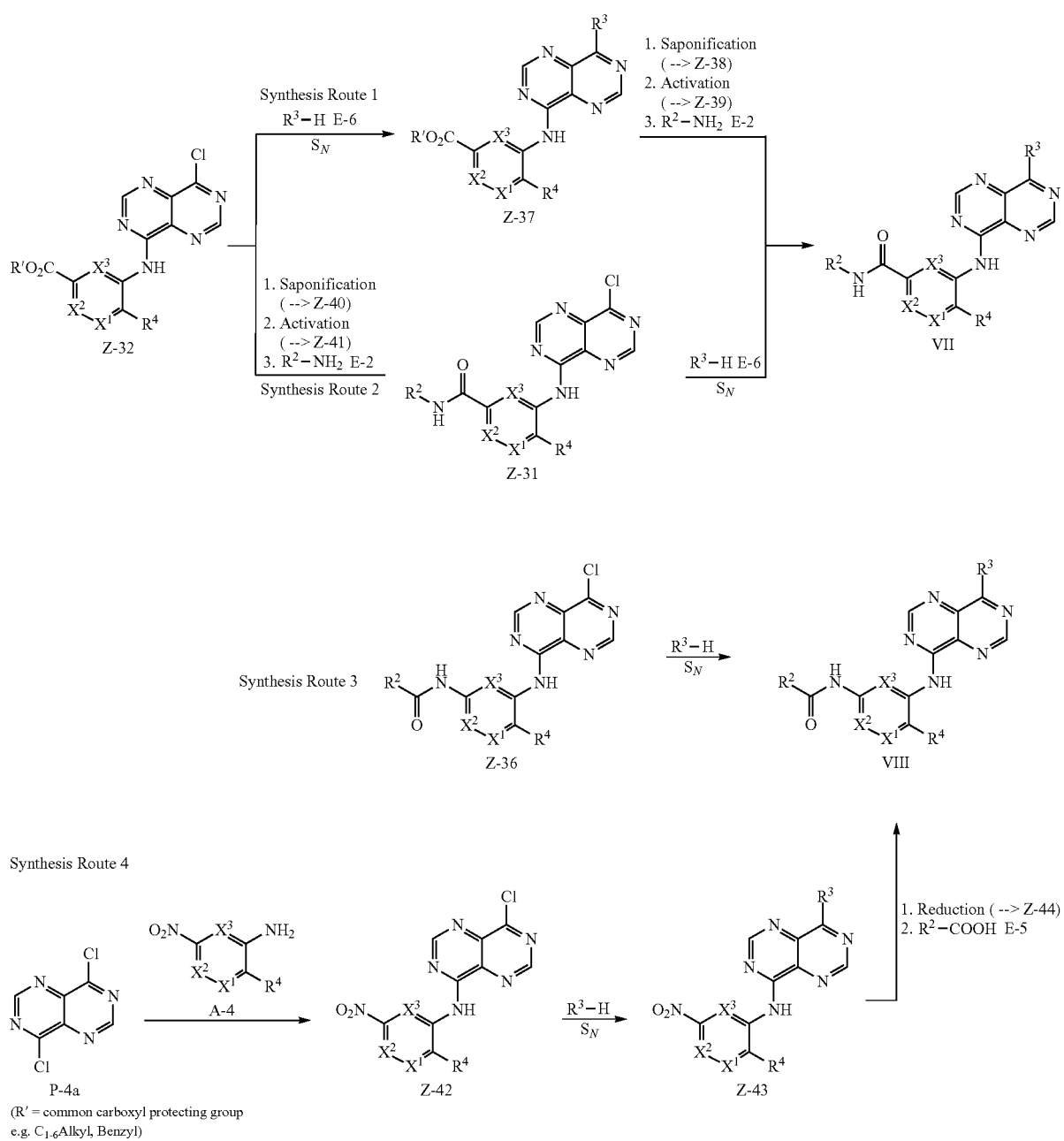

Reaction scheme F

Example Compounds of Type VII and VIII:

Compounds of type VII and VIII are pyrimidopyrimidines disubstituted in the 4- and 8-position (Reaction scheme F).

Starting from 4,8-dichloro-pyrimido[5,4-d]pyrimidine P-4-a (synthesis route 4→Z-37) or the intermediate compounds Z-31, Z-32 or Z-36 (cf. their synthesis from P-4-a according to Reaction scheme E) the chlorine atoms in the 4-position are substituted by $R^3$—H (ammonia, methylamine or water/hydroxide). The other reaction steps according to Reaction scheme F correspond to those already described.

a) Method for Synthesising VII-1:

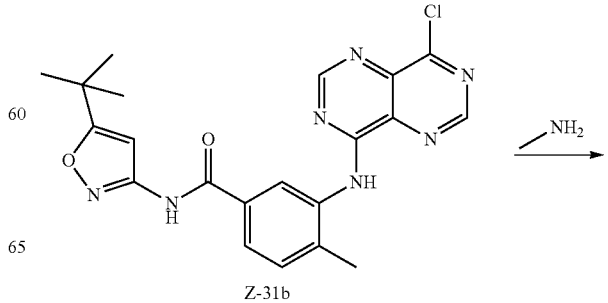

-continued

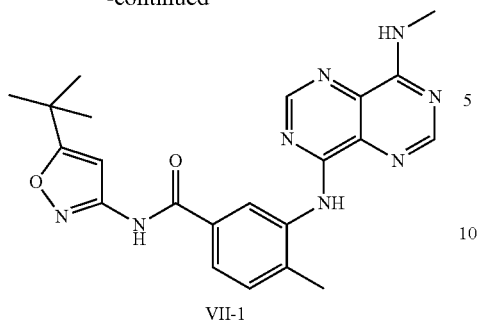

VII-1

Substance Z-31b (34%, 141.0 mg, 0.109 mmol) is mixed with methylamine (2M in THF, 1 mL). The reaction mixture is stirred for 20 min at RT. For working up it is evaporated down, the residue is dissolved with DMSO, purified by preparative HPLC and example compound VII-1 (HPLC-MS: $t_{Ret.}$=1.85 min; MS (M+H)$^+$=433) is obtained.

b) Method for Synthesising Z-42a:

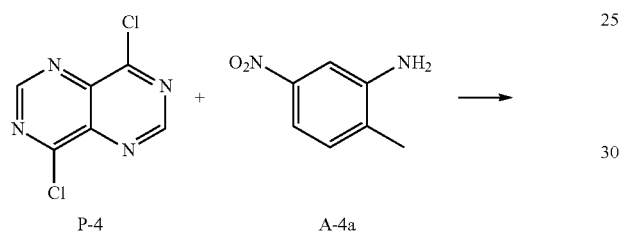

P-4   A-4a 4,8-dichloropyrimidopyrimidine P-4 (2.0 g, 9.95 mmol) is placed in dioxane (40 mL) and cooled in the ice bath. The aniline A-4-a (1.514 g, 9.95 mmol) is taken up in 20 mL dioxane and added dropwise to the 4,8-dichloropyrimidopyrimidine solution. Then dipotassium hydrogen phosphate trihydrate (3 M, 6.633 mL, 19.89 mmol) is added. The reaction mixture is heated to RT and stirred overnight at 65° C. For working up the mixture is cooled and evaporated down. The residue is dissolved in DCM and washed 3× with water. The organic phase is dried on Na$_2$SO$_4$, filtered off, evaporated down and Z-42a (HPLC-MS: $t_{Ret.}$=1.81 min; MS (M+H)$^+$= 317) is obtained.

c) Method for Synthesising Z-43a:

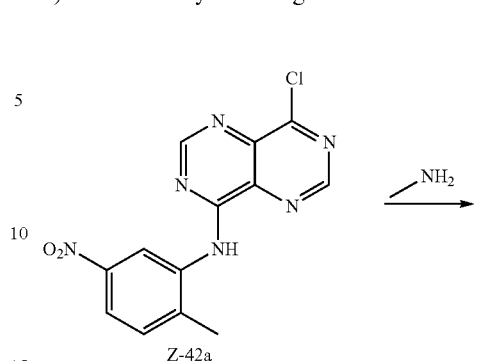

Z-42a

Z-43a

Substance Z-42a (100 mg, 0.32 mmol) is mixed with methylamine (2M in THF, 2 mL). The reaction mixture is stirred for 30 min at RT. The precipitate formed is filtered off, washed with a little THF, dried in vacuo and Z-43a (HPLC-MS: $t_{Ret.}$=1.68 min; MS (M+H)$^+$=312) is obtained.

d) Method for Synthesising VIII-1:

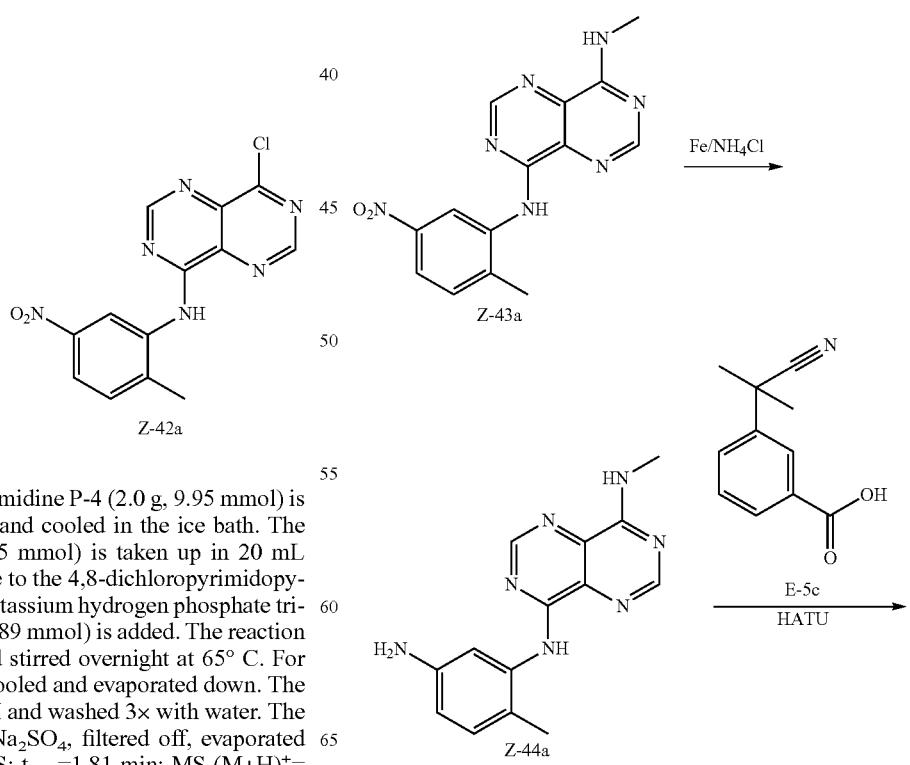

Z-43a

Z-44a

E-5c
HATU

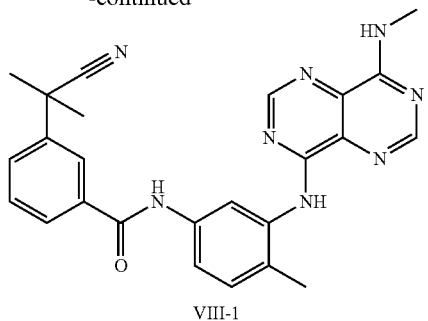

VIII-1

Nitro compound Z-43a (80 mg, 0.26 mmol) is taken up in EtOH (2 mL), mixed with ammonium chloride (7 mg, 0.13 mmol) in water (2 mL) and heated to 75° C. At this temperature iron powder (72 mg, 1.29 mmol) is added batchwise and the mixture is stirred for a further hour at 75° C. After cooling it is filtered through silica gel, washed with DCM/MeOH (9:1), the filtrate obtained is dried using the rotary evaporator and Z-44a (HPLC-MS: $t_{Ret.}$=1.25 min; MS (M+H)$^+$=282) is obtained.

Benzoic acid E-5c (40 mg, 0.21 mmol) is taken up in DCM (1 mL) and mixed with DIPEA (109 μL, 0.63 mmol) and HATU (88 mg, 0.23 mmol). After 15 min aniline Z-44a (60 mg, 0.21 mmol) is added and the mixture is stirred at RT. For working up the mixture is evaporated down, the residue is dissolved with DMSO, purified by preparative HPLC and example compound VIII-1 (HPLC-MS: $t_{Ret.}$=1.78 min; MS (M+H)$^+$=453) is obtained.

TABLE 6

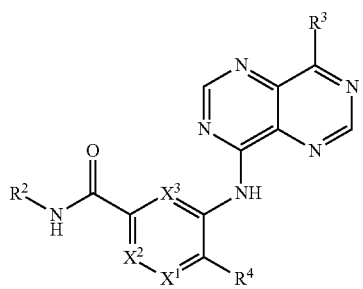

Example Compound VII-1

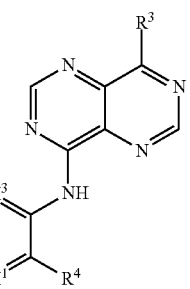

Example Compound VIII-1 to VIII-3

| # | Structure | $t_{Ret.}$ (HPLC) [min] | MS (M + H)$^+$ |
|---|---|---|---|
| VII-1 | 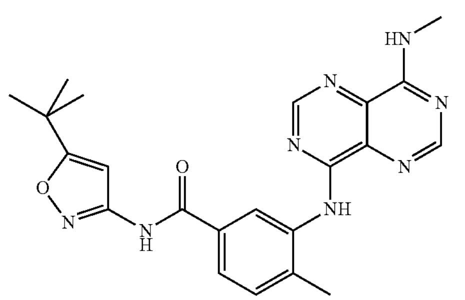 [SMILES: CNc1ncnc2c(Nc3cc(C(=O)Nc4cc(C(C)(C)C)on4)ccc3C)ncnc12] | 1.85 | 433 |
| VIII-1 | 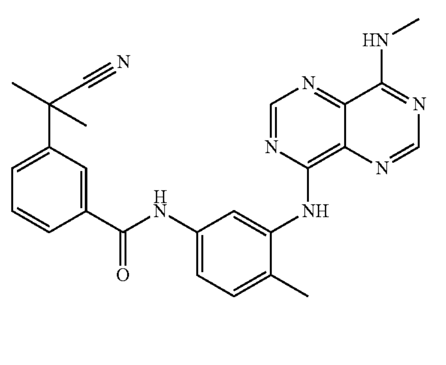 [SMILES: CNc1ncnc2c(Nc3cc(NC(=O)c4cccc(C(C)(C)C#N)c4)ccc3C)ncnc12] | 1.78 | 453 |

TABLE 6-continued

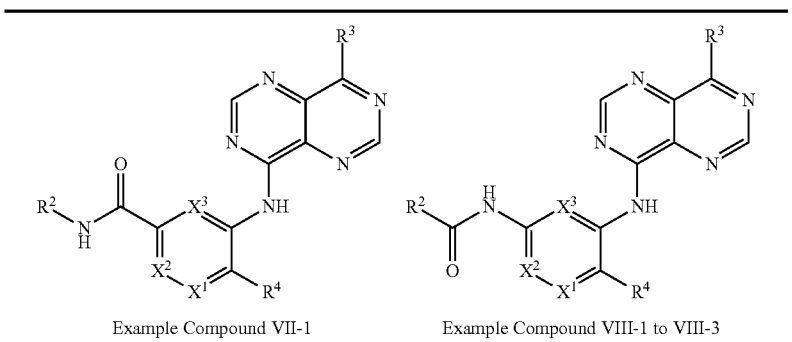

Example Compound VII-1                Example Compound VIII-1 to VIII-3

| # | Structure | $t_{Ret.}$ (HPLC) [min] | MS (M + H)+ |
|---|-----------|---|---|
| VIII-2 | 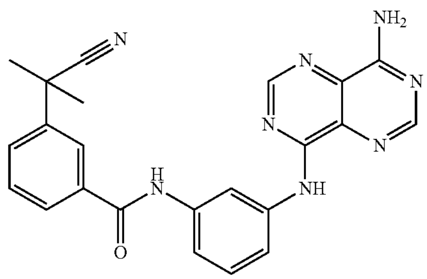 [SMILES: CC(C)(C#N)c1cccc(C(=O)Nc2cccc(Nc3ncnc4c(N)ncnc34)c2)c1] | 1.74 | 425 |
| VIII-3 | 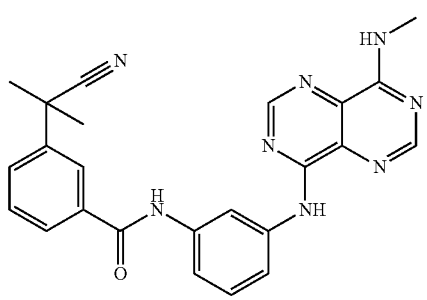 [SMILES: CNc1ncnc2c(Nc3cccc(NC(=O)c4cccc(C(C)(C)C#N)c4)c3)ncnc12] | 1.88 | 439 |

Further Information on Reaction Schemes A to F and all the Types of Example Compounds (I to VIII):

For synthesising compounds (1) according to the invention the key educts E-1, E-2, E-3, E-4, E-5, A-2 and A-4 are needed, in particular. These starting compounds may be obtained in numerous ways. A significant number of such synthesis components are commercially obtainable or may be prepared by the skilled man using routine methods. In addition, these components and their preparation are known from the prior art or may be carried out routinely analogously to methods known in the prior art or may be expanded into these. These include in particular methods published in the following publications: WO 2004/050642, WO 2005/056535, WO 2005/090333, WO 2005/115991, US 2006/100204, WO 2008/003770, WO 2005/023761, WO 2008/021388, WO 2007/075896, WO 2007/056016, WO 2008/089034, WO 2009/003999 and WO 2009/003998.

For educts A-4 there is also the alternative possibility of obtaining them from the aromatic nitro acids A-6 by CURTIUS degradation:

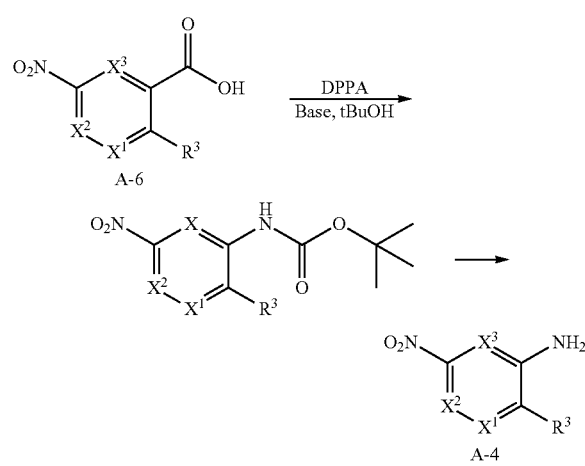

For incorporated linker units L² which are different from —C(O)NH— and —NHC(O)—, the synthesis components required may be converted routinely. Thus, for example, instead of carboxylic acids, sulphonic acids may be used to synthesise the corresponding sulphonamides. Urea linkers are obtained by reacting isocyanates with amines or the compound of two amines via a carbonylbiselectrophil (e.g. CDI, triphosgene).

The following Examples describe the biological activity of the compounds according to the invention, without restricting the invention to these Examples.

Compounds of general formula (1) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

Kinase Test B-RAF (V600E)

In a dilution series 10 µL of test substance solution are placed in a multiwell plate. The dilution series is selected so that generally a range of concentrations of 2 µM to 0.119 nM or 0.017 nM is covered. If necessary the initial concentration of 2 µM is changed to 50 µM, 10 µM or 0.4 µM or 0.2857 µM and further dilution is carried out accordingly. The final concentration of DMSO is 5%. 10 µL of the B-Raf (V600E)-kinase solution are pipetted in (containing 0.5 ng B-Raf (V600E)-kinase in 20 mM Tris-HCl pH 7.5, 0.1 mM EDTA, 0.1 mM EGTA, 0.286 mM sodium orthovanadate, 10% glycerol, 1 mg/mL bovine serum albumin, 1 mM dithiothreitol) and the mixture is incubated for 24 h at RT under with shaking. The kinase reaction is started by the addition of 20 µL ATP solution [final concentration: 250 µM ATP, 30 mM Tris-HCl pH 7.5, 0.02% Brij, 0.2 mM sodium orthovanadate, 10 mM magnesium acetate, 0.1 mM EGTA, phosphatase cocktail (Sigma, # P2850, dilution recommended by the manufacturer), 0.1 mM EGTA] and 10 µL MEK1 solution [containing 50 ng biotinylated MEK1 (prepared from purified MEK1 according to standard procedure, e.g. with EZ-Link Sulpho-NHS-LC-Biotin reagent, Pierce, #21335) and carried out for 60 min at RT with constant shaking. The reaction is stopped by the addition of 12 µL of a 100 mM EDTA solution and incubation is continued for a further 5 min. 55 µL of the reaction solution are transferred into a streptavidin-coated plate (e.g. Streptawell HighBond, Roche, #11989685001) and shaken gently for 1 h at RT, in order to bind biotinylated MEK1 to the plate. After elimination of the liquid the plate is washed five times with 200 µL of 1×PBS and 100 µL solution of primary antibody plus europium-labelled secondary antibody [Anti Phospho-MEK (Ser217/221), Cell Signaling, #9121 and Eu-N1 labeled goat-anti-rabbit antibody, Perkin Elmer, # AD0105], the primary antibody is diluted 1:2000 and the secondary antibody is diluted to 0.4-0.5 µg/mL in Delfia Assay Buffer (Perkin Elmer, #1244-111). After 1 h shaking at RT the solution is poured away and washed five times with 200 µL Delfia Wash Buffer (Perkin Elmer, #4010-0010/#1244-114). After the addition of 200 µL Enhancement Solution (Perkin Elmer, #4001-0010/#1244-105) the mixture is shaken for 10 min at RT and then measured in a Wallac Victor using the program "Delfia Time Resolved Fluorescence (Europium)". $IC_{50}$ values are obtained from these dosage-activity curves using a software program (GraphPad-Prizm).

Table 7 gives the $IC_{50}$ values determined for the compounds according to the invention using the above B-RAF-kinase test.

TABLE 7

| # | $IC_{50}$ [nM] |
|---|---|
| I-1 | 26 |
| I-2 | 9 |
| I-3 | 9 |
| I-4 | 7 |
| I-5 | 5 |
| I-6 | 68 |
| I-7 | 3 |
| I-8 | 2 |
| I-9 | 3 |
| I-10 | 1 |
| I-11 | 1 |
| I-12 | 2 |
| I-13 | 4 |
| I-14 | 3 |
| I-15 | 1 |
| I-16 | 1 |
| I-17 | 1 |
| I-18 | 3 |
| I-19 | 57 |
| I-20 | 50 |
| I-21 | 22 |
| I-22 | 13 |
| I-23 | 14 |
| I-24 | 9 |
| I-25 | 3 |
| I-26 | 70 |
| I-27 | 83 |
| I-28 | 13 |
| I-29 | 15 |
| I-30 | 35 |
| I-31 | 58 |
| I-32 | 14 |
| I-33 | 12 |
| I-34 | 2 |
| I-35 | 2 |
| I-36 | 4 |
| I-37 | 4 |
| I-38 | 6 |
| I-39 | 5 |
| I-40 | 3 |
| I-41 | 5 |
| I-42 | 9 |
| I-43 | 4 |
| I-52 | 55 |
| I-53 | 21 |
| I-54 | 5 |
| I-55 | <1 |
| I-56 | <1 |
| I-57 | <1 |
| I-58 | 1 |
| I-59 | 1 |
| I-60 | <1 |
| I-61 | <1 |
| I-62 | 2 |
| I-63 | 1 |
| I-64 | <1 |
| I-65 | <1 |
| I-66 | <1 |
| I-67 | 3 |
| I-68 | <1 |
| I-69 | 2 |
| I-70 | 3 |
| I-71 | 7 |
| I-72 | 12 |
| I-73 | 2 |
| I-74 | 3 |
| I-75 | 54 |
| I-76 | 1 |
| I-77 | 2 |
| I-78 | 8 |
| I-79 | 19 |
| I-80 | 2 |
| I-81 | 3 |
| I-82 | 676 |
| I-83 | 2203 |
| I-84 | 11 |
| I-85 | 7 |
| I-86 | 4 |

TABLE 7-continued

| # | IC$_{50}$ [nM] |
|---|---|
| I-87 | 9 |
| I-88 | 10 |
| II-1 | 26 |
| II-2 | 41 |
| II-3 | 50 |
| II-4 | 81 |
| II-5 | 50 |
| II-6 | 96 |
| II-7 | 15 |
| II-8 | 2 |
| II-9 | 24 |
| II-10 | 25 |
| II-11 | 20 |
| II-12 | 7 |
| II-13 | 7 |
| II-14 | 4 |
| II-15 | 40 |
| II-16 | 45 |
| II-17 | 13 |
| II-18 | 9 |
| II-19 | 9 |
| III-1 | 2 |
| III-2 | <1 |
| III-3 | 118 |
| III-4 | 2 |
| III-5 | 2 |
| III-6 | 7 |
| III-7 | 1 |
| III-8 | 3 |
| III-9 | 7 |
| III-10 | 6 |
| III-11 | 4 |
| III-12 | 2 |
| III-13 | 9 |
| III-14 | 3 |
| III-15 | 5 |
| III-16 | 2 |
| III-17 | 3 |
| III-18 | 4 |
| III-19 | 1 |
| III-20 | 3 |
| III-21 | 3 |
| III-22 | 6 |
| III-23 | 7 |
| III-24 | 5 |
| III-25 | 2 |
| III-26 | 24 |
| III-27 | 8 |
| III-28 | 3 |
| III-29 | 2 |
| III-30 | 2 |
| III-31 | <1 |
| III-32 | 1 |
| III-33 | 1 |
| III-34 | 2 |
| III-35 | 5 |
| III-36 | 3 |
| III-37 | 4 |
| III-38 | 5 |
| III-39 | 2 |
| III-40 | 2 |
| III-41 | 1 |
| III-42 | 64 |
| III-43 | 972 |
| III-44 | >2000 |
| III-45 | 283 |
| III-46 | 451 |
| III-47 | 95 |
| III-48 | >1000 |
| III-49 | 587 |
| III-50 | 5 |
| III-51 | 381 |
| III-52 | 2231 |
| III-53 | 318 |
| III-54 | 543 |
| III-55 | >150 |
| III-56 | 1989 |
| III-57 | 1827 |
| III-58 | 88 |
| III-59 | 835 |
| III-60 | 230 |
| III-61 | 2242 |
| III-62 | 546 |
| III-63 | 13 |
| III-64 | >1000 |
| III-65 | 4171 |
| III-66 | 1139 |
| III-67 | 5 |
| III-68 | 8 |
| III-69 | 6 |
| III-70 | 4 |
| III-71 | 3 |
| III-72 | 4 |
| III-73 | 4 |
| III-74 | 1 |
| III-75 | 1 |
| III-76 | 11 |
| III-77 | 2 |
| III-78 | 2 |
| III-79 | 1 |
| III-80 | 6 |
| III-81 | 2 |
| III-82 | 20 |
| III-83 | 8 |
| III-84 | 2 |
| III-85 | 7 |
| III-86 | <1 |
| III-87 | 3 |
| III-88 | 5 |
| III-89 | 4 |
| III-90 | 5 |
| III-91 | 1 |
| III-92 | 1 |
| III-93 | 1 |
| III-94 | 6 |
| III-95 | 2 |
| III-96 | 2 |
| III-97 | 4 |
| III-98 | 2 |
| III-99 | 5 |
| III-100 | 4 |
| III-101 | 1 |
| III-102 | 4 |
| III-103 | 2 |
| III-104 | 1 |
| III-105 | 3 |
| III-106 | 2 |
| III-107 | 1 |
| III-108 | <1 |
| III-109 | 2 |
| III-110 | 1 |
| III-111 | <1 |
| III-112 | 2 |
| III-113 | 2 |
| III-114 | 2 |
| III-115 | 2 |
| III-116 | <1 |
| III-117 | 2 |
| III-118 | 2 |
| III-119 | 3 |
| III-120 | 3 |
| III-121 | 2 |
| III-122 | 2 |
| III-123 | <1 |
| III-124 | 3 |
| III-125 | 4 |
| III-126 | <1 |
| III-127 | 3 |
| III-128 | 3 |
| III-129 | 2 |
| III-130 | 3 |
| III-131 | 2 |
| III-132 | <1 |
| III-133 | <1 |
| III-134 | 2 |
| III-135 | 4 |

TABLE 7-continued

| # | IC$_{50}$ [nM] |
|---|---|
| III-136 | 3 |
| III-137 | 3 |
| III-138 | <1 |
| III-139 | 3 |
| III-140 | 5 |
| III-141 | 2 |
| III-142 | 3 |
| III-143 | 2 |
| III-144 | <1 |
| III-145 | 2 |
| III-146 | <1 |
| III-147 | 1 |
| III-148 | 1 |
| III-149 | <1 |
| III-150 | 2 |
| III-151 | 1 |
| III-152 | <1 |
| III-153 | <1 |
| III-154 | 4 |
| III-155 | 2 |
| III-156 | <1 |
| III-157 | 3 |
| III-158 | 7 |
| III-159 | 5 |
| III-160 | 3 |
| III-161 | 6 |
| III-162 | <1 |
| III-163 | 9 |
| III-164 | 2 |
| III-165 | <1 |
| III-166 | 4 |
| III-167 | 5 |
| III-168 | <1 |
| III-169 | 1 |
| III-170 | <1 |
| III-171 | 3 |
| III-172 | 2 |
| III-173 | 1 |
| III-174 | 2 |
| III-175 | <1 |
| III-176 | 4 |
| III-177 | 4 |
| III-178 | 2 |
| III-179 | >7000 |
| III-180 | 3 |
| III-181 | 17 |
| III-182 | 245 |
| III-183 | >15000 |
| III-184 | 2880 |
| III-185 | >15000 |
| III-186 | 26 |
| III-187 | >2000 |
| III-188 | 104 |
| III-189 | >15000 |
| III-190 | 1535 |
| III-191 | >15000 |
| III-192 | 2 |
| III-193 | >15000 |
| III-194 | >2000 |
| III-195 | 59 |
| III-196 | 16 |
| III-197 | >15000 |
| III-198 | 11 |
| III-199 | 23 |
| III-200 | 971 |
| III-201 | >10000 |
| III-202 | >2000 |
| III-203 | >10000 |
| III-204 | 4 |
| III-205 | >2000 |
| III-206 | 2 |
| III-207 | 11 |
| III-208 | >2000 |
| III-209 | 162 |
| III-210 | >2000 |
| III-211 | 4 |
| III-212 | >15000 |
| III-213 | 3 |
| III-214 | 56 |
| III-215 | >10000 |
| III-216 | 3 |
| III-217 | 2 |
| III-218 | 293 |
| III-219 | 8 |
| III-220 | 5 |
| III-221 | 171 |
| III-222 | <1 |
| III-223 | 15 |
| III-224 | <1 |
| III-225 | 2 |
| III-226 | 101 |
| III-227 | 41 |
| III-228 | 5 |
| III-229 | 1 |
| III-230 | 6 |
| III-231 | 29 |
| III-232 | 4 |
| III-233 | 571 |
| III-234 | 15 |
| III-235 | 2 |
| III-236 | 1124 |
| III-237 | 2 |
| III-238 | 87 |
| III-239 | 6 |
| III-240 | 4 |
| III-241 | 48 |
| III-242 | 19 |
| III-243 | <1 |
| III-244 | <1 |
| III-245 | 460 |
| III-246 | 29 |
| III-247 | 1 |
| III-248 | 2 |
| III-249 | 10 |
| III-250 | 40 |
| III-251 | 19 |
| III-252 | 8 |
| III-253 | 269 |
| III-254 | 2000 |
| III-255 | 23 |
| III-256 | 15000 |
| III-257 | 61 |
| III-258 | 15000 |
| III-259 | 505 |
| III-260 | 2000 |
| III-261 | <1 |
| III-262 | 9 |
| III-263 | 15 |
| III-264 | 2600 |
| III-265 | 4 |
| III-266 | 1 |
| III-267 | 836 |
| III-268 | 120 |
| III-269 | 33 |
| III-270 | 20 |
| III-271 | 10 |
| III-272 | 2 |
| III-273 | 31 |
| III-274 | 3 |
| III-275 | 2 |
| III-276 | 6 |
| III-277 | 23 |
| III-278 | 88 |
| III-279 | 6 |
| III-280 | 10000 |
| III-281 | 5 |
| III-282 | 1400 |
| III-283 | 3 |
| III-284 | 3 |
| III-285 | 274 |
| III-286 | 3 |
| III-287 | 1 |
| III-288 | 2 |
| III-289 | 13 |
| III-290 | 1 |
| III-291 | 21 |

TABLE 7-continued

| # | IC$_{50}$ [nM] |
|---|---|
| III-292 | 36 |
| III-293 | 7 |
| III-294 | 1 |
| III-295 | 17 |
| III-296 | 198 |
| III-297 | 1 |
| III-298 | 1 |
| III-299 | 5 |
| III-300 | 4 |
| III-301 | <1 |
| III-302 | 115 |
| III-303 | 7 |
| III-304 | <1 |
| III-305 | 2 |
| III-306 | 4 |
| III-307 | 114 |
| III-308 | 47 |
| III-309 | 4 |
| III-310 | 50 |
| III-311 | 2 |
| III-312 | 27 |
| III-313 | 200 |
| III-314 | 9 |
| III-315 | <1 |
| III-316 | 3 |
| III-317 | 14 |
| III-318 | 2 |
| III-319 | 1 |
| III-320 | 2 |
| III-321 | <1 |
| III-322 | 1 |
| III-323 | 11 |
| III-324 | 55 |
| III-325 | 1400 |
| III-326 | 292 |
| III-327 | 56 |
| III-328 | 442 |
| III-329 | 17 |
| III-330 | 6 |
| III-331 | 10 |
| III-332 | 4 |
| III-333 | 56 |
| III-334 | 10 |
| III-335 | 8 |
| III-336 | 140 |
| III-337 | 2 |
| III-338 | 41 |
| III-339 | 1 |
| III-340 | 4 |
| III-341 | <1 |
| III-342 | 2121 |
| III-343 | 2 |
| III-344 | 7 |
| III-345 | 1 |
| III-346 | 7000 |
| III-347 | 1 |
| III-348 | <1 |
| III-349 | <1 |
| III-350 | <1 |
| III-351 | <1 |
| III-353 | <1 |
| III-354 | 20 |
| III-355 | <1 |
| III-356 | <1 |
| III-357 | <1 |
| III-358 | 1 |
| III-359 | 2 |
| III-360 | 3 |
| III-361 | 2 |
| III-362 | 3 |
| III-363 | <1 |
| III-364 | <1 |
| III-365 | 1 |
| III-366 | 6 |
| III-367 | 2 |
| III-368 | 14 |
| III-369 | 2 |
| III-370 | 1 |
| III-372 | 5 |
| III-373 | 8 |
| III-374 | 2000 |
| III-375 | 2000 |
| III-376 | 7 |
| III-377 | 4 |
| III-378 | 8 |
| III-379 | 6 |
| III-380 | 1400 |
| III-381 | 3 |
| III-382 | <1 |
| III-383 | 4 |
| III-384 | 2 |
| III-385 | 2 |
| III-386 | 1 |
| III-387 | 2 |
| III-388 | <1 |
| III-389 | <1 |
| III-390 | <1 |
| III-391 | 1 |
| III-392 | 3 |
| III-393 | 1 |
| III-394 | 1 |
| III-395 | 4 |
| III-396 | 3 |
| III-397 | 4 |
| III-398 | 1 |
| III-399 | 2 |
| III-400 | 4 |
| III-401 | 3 |
| III-402 | 2 |
| III-403 | 3 |
| III-404 | 6 |
| III-405 | 5 |
| III-406 | 3 |
| III-407 | 10 |
| III-408 | 25 |
| III-409 | 9 |
| III-410 | 1 |
| III-411 | 3 |
| III-412 | 5 |
| III-413 | <1 |
| III-414 | 7 |
| III-415 | 3 |
| III-416 | 1 |
| III-417 | <1 |
| III-418 | 2 |
| III-419 | 1 |
| III-420 | 1 |
| III-421 | 12 |
| III-422 | 5 |
| III-423 | <1 |
| III-424 | 6 |
| III-425 | 7 |
| III-426 | <1 |
| III-427 | 2 |
| III-428 | <1 |
| III-429 | 2 |
| III-430 | 7 |
| III-431 | 3 |
| III-432 | 6 |
| III-433 | 7 |
| III-435 | 1 |
| III-436 | 2 |
| III-437 | 2 |
| III-438 | 6 |
| III-439 | 4 |
| III-440 | 272 |
| III-441 | 2 |
| III-442 | 1 |
| III-443 | 1 |
| III-444 | 4 |
| III-445 | 2 |
| III-446 | 6 |
| III-447 | 13 |
| III-448 | 8 |
| III-449 | 3 |
| III-450 | 3 |

TABLE 7-continued

| # | IC$_{50}$ [nM] |
|---|---|
| III-454 | 4 |
| III-455 | 8 |
| III-456 | 3 |
| III-457 | 4 |
| III-458 | 1 |
| III-459 | 2 |
| III-460 | 4 |
| III-461 | 2 |
| III-462 | 1 |
| III-463 | 2 |
| III-465 | 2 |
| III-467 | 2 |
| III-468 | <1 |
| III-469 | <1 |
| III-470 | 2 |
| III-471 | 4 |
| III-472 | 2 |
| III-473 | 1 |
| III-474 | 1 |
| III-476 | 17 |
| III-480 | 4 |
| III-481 | 1 |
| III-482 | 4 |
| III-483 | 1 |
| III-484 | 3 |
| III-485 | 3 |
| III-486 | 4 |
| III-487 | 13 |
| III-488 | 6 |
| III-489 | 1 |
| III-490 | 2 |
| III-491 | 2 |
| III-492 | 2 |
| III-493 | 5 |
| III-494 | 4 |
| III-495 | 2 |
| III-496 | 2 |
| III-497 | 2 |
| III-499 | 3 |
| III-500 | <1 |
| III-501 | 25 |
| III-502 | 8 |
| III-503 | 1 |
| III-504 | 2 |
| III-505 | 49 |
| III-506 | 4 |
| III-507 | 1 |
| III-508 | 3 |
| III-509 | 5 |
| III-510 | <1 |
| III-511 | 4 |
| III-512 | 2 |
| III-513 | 1 |
| III-514 | 1 |
| III-515 | <1 |
| III-516 | <1 |
| III-517 | 3 |
| III-518 | 2 |
| III-519 | <1 |
| III-520 | 2 |
| III-521 | 2 |
| III-522 | 3 |
| III-523 | 1 |
| III-524 | 3 |
| III-525 | 3 |
| III-526 | 4 |
| III-527 | <1 |
| III-528 | 2 |
| III-529 | 3 |
| III-530 | 582 |
| III-531 | 13 |
| III-532 | 2 |
| III-533 | 6 |
| III-534 | 106 |
| III-535 | 4 |
| III-536 | 1 |
| III-537 | 12 |
| III-538 | 10 |
| III-539 | 2 |
| III-540 | 5 |
| III-541 | 15 |
| III-542 | 12 |
| III-543 | 3 |
| III-544 | 1 |
| III-545 | 2 |
| III-546 | 4 |
| III-547 | <1 |
| III-548 | 3 |
| III-549 | 8 |
| III-550 | 4 |
| III-551 | 1 |
| III-552 | 17 |
| III-553 | 2 |
| III-554 | 3 |
| III-555 | 18 |
| III-556 | 7 |
| III-557 | 4 |
| III-558 | 23 |
| III-559 | 14 |
| III-560 | 7 |
| III-561 | 9 |
| III-562 | 1 |
| III-563 | 2 |
| III-564 | 1 |
| III-565 | 11 |
| III-567 | 2 |
| III-568 | 1 |
| III-569 | 2 |
| III-570 | <1 |
| III-571 | 2 |
| III-572 | 1 |
| III-575 | 3 |
| III-577 | 2 |
| III-580 | 28 |
| III-581 | 33 |
| III-582 | 74 |
| III-583 | 32 |
| III-584 | 18 |
| III-585 | 27 |
| III-586 | 193 |
| III-587 | 65 |
| III-591 | 1 |
| III-592 | <1 |
| III-593 | 1 |
| III-594 | 1 |
| III-595 | 1 |
| III-596 | 2 |
| III-597 | 5 |
| III-598 | <1 |
| III-599 | 1 |
| III-600 | 3 |
| III-601 | 6 |
| III-602 | 9 |
| III-603 | 1 |
| III-604 | 3 |
| III-605 | 6 |
| III-606 | 3 |
| III-607 | 1 |
| III-608 | 7 |
| IV-1 | 13 |
| IV-2 | <1 |
| IV-3 | 12 |
| IV-4 | 44 |
| IV-5 | 129 |
| IV-7 | 1 |
| IV-10 | 221 |
| IV-12 | 1 |
| IV-13 | 3 |
| IV-15 | 3 |
| IV-18 | 9 |
| IV-22 | 2 |
| IV-23 | 4 |
| IV-24 | 72 |
| IV-26 | 2 |
| IV-27 | 1 |
| IV-28 | 1 |

TABLE 7-continued

| # | IC$_{50}$ [nM] |
|---|---|
| IV-29 | 1 |
| IV-30 | <1 |
| IV-31 | 5 |
| IV-32 | 1 |
| IV-33 | 2 |
| IV-34 | 2 |
| IV-35 | 2 |
| IV-36 | 4 |
| IV-37 | 1 |
| IV-38 | 2 |
| IV-39 | 4 |
| IV-40 | 2 |
| IV-42 | 13 |
| IV-46 | 3 |
| IV-50 | 59 |
| IV-53 | 10000 |
| IV-54 | 10000 |
| IV-55 | 10000 |
| IV-56 | 10000 |
| IV-57 | 10000 |
| IV-58 | 49 |
| IV-59 | 2000 |
| IV-60 | 2000 |
| IV-61 | 10000 |
| IV-62 | 2000 |
| IV-63 | 595 |
| IV-64 | 521 |
| IV-65 | 2000 |
| IV-66 | 10000 |
| IV-67 | 2 |
| IV-68 | 3 |
| V-1 | 2 |
| V-8 | 4 |
| V-9 | 5 |
| V-10 | 14 |
| VII-1 | 1 |
| VIII-1 | <1 |
| VIII-2 | 30 |
| VIII-3 | 13 |

Measurement of the Inhibition of the Proliferation of Cultivated Human Melanoma Cells (SK-MEL-28, B-RAF$^{V600E}$ Mutated)

For measuring the proliferation of cultivated human tumour cells, cells of the melanoma cell line SK-MEL-28 [American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, # BE13-114E) and 2 mM glutamine. SK-MEL28 cells are placed in 96-well flat bottomed dishes in a density of 2500 cells per well in supplemented MEM medium (see above) and incubated overnight in an incubator (at 37° C. and 5% CO$_2$). The active substances are added to the cells in different concentrations, so that a concentration range of 50 µM to 3.2 nM is covered. If necessary the initial concentration of 50 µM is changed to 10 µM or 2 µM and further dilution is carried out accordingly (to 0.6 nM or 0.12 nM). After an incubation period of a further 72 h 20 µL AlamarBlue reagent (Serotec Ltd., # BUF012B) are added to each well and the cells are incubated for a further 3-6 h. The colour change of the AlamarBlue reagent is determined in a fluorescence spectrophotometer (e.g. Gemini, Molecular Devices). EC$_{50}$ values are calculated using a software program (GraphPadPrizm).

Measurement of the Inhibition of the Proliferation of Cultivated Human Melanoma Cells (A375, B-RAF$^{V600E}$ Mutated)

For measuring the proliferation of cultivated human tumour cells, cells of the melanoma cell line A375 [American Type Culture Collection (ATCC)] are cultivated in DMEM medium, supplemented with 10% foetal calf serum and 2% sodium bicarbonate. Test substances are tested on A375 cells according to the procedure described for SK-MEL28 cells (see above), but seeding them at 5000 cells per well.

Most of the example compounds of types I to VIII (Tables 1 to 6) show good to very good activity in the cellular A375 and SK-MEL-28 proliferation test, i.e. an EC$_{50}$ value of less than 5 µM, generally less than 1 µM.

The active substances are characterised in that they have a significantly lower antiproliferative effect on cell lines that do not have a B-RAF mutation, i.e. the EC$_{50}$ value is generally higher, by a factor of 10, than the EC$_{50}$ value of B-RAF mutated cell lines.

The cellular selectivity of the active substances is demonstrated by the fact that the EC$_{50}$ value of the phospho-ERK reduction correlates with the EC$_{50}$ value of the antiproliferative activity in B-RAF mutated cell lines.

Measurement of the Reduction in the Phospho-Erk Signal in Cultivated Human Melanoma Cells (SK-MEL-28, B-RAF$^{V600E}$ Mutated)

In order to measure the reduction in the phospho-ERK signal of cultivated human tumour cells, cells of the melanoma cell line SK-MEL-28 [American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, # BE13-114E) and 2 mM glutamine. SK-MEL28 cells are placed in 96-well flat bottomed dishes at a density of 7500 cells per well in supplemented MEM medium (see above) and incubated overnight in an incubator (at 37° C. and 5% CO$_2$). The active substances are added to the cells in different concentrations, so that a concentration range of 10 µM to 2.4 nM is covered. If necessary the initial concentration of 10 µM is changed to 50 µM or 2.5 µM and further dilution is carried out accordingly (to 12.2 nM or 0.6 nM). After an incubation period of a further 2 h the cells are fixed with 4% formaldehyde and rendered permeable with 0.1% Triton X-100 in PBS. Non-specific antibody binding is reduced by incubation with 5% skimmed milk powder dissolved in TBS-T. Phosphorylated ERK is detected with a mouse monoclonal anti-diphosphorylated ERK1/2 antibody (from Sigma, #M8159). After washing steps with 0.1% Tween 20 in PBS the bound first antibody is detected by the second antibody (peroxidase coupled polyclonal rabbit anti mouse IgG from DAKO #P0161). After further washing steps, the substrate (TMB Peroxidase Substrate Solution from Bender MedSystems #BMS406) is added. The colour reaction is stopped after a few minutes with 1 M phosphoric acid. The colour is measured with a Spectra max Plus reader from Molecular Devices at 450 nm. EC$_{50}$ values are calculated using a software program (GraphPadPrizm).

The substances of the present invention are B-RAF-kinase inhibitors. As can be demonstrated by DNA staining followed by FACS or Cellomics Array Scan analysis, the inhibition of proliferation achieved by means of the compounds according to the invention is brought about above all by preventing entry into the DNA synthesis phase. The treated cells arrest in the G1 phase of the cell cycle.

Accordingly, the compounds according to the invention are also tested on other tumour cells. For example these compounds are effective on the colon carcinoma line, e.g. Colo205, and may be used in this and other indications. This demonstrates the usefulness of the compounds according to the invention for the treatment of different types of tumours.

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. Cisplatin, oxaliplatin, carboplatin); alkylation agents (e.g. Estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (1) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (1) | 80 mg |
| | lactose | 55 mg |
| | corn starch | 190 mg |
| | microcrystalline cellulose | 35 mg |
| | polyvinylpyrrolidone | 15 mg |

-continued

| B) | Tablets | per tablet |
|---|---|---|
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (1) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of formula (1)

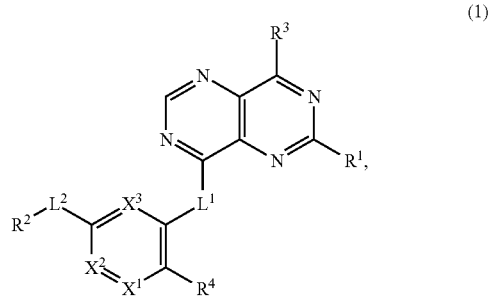

wherein
$R^1$ denotes hydrogen or a group optionally substituted by one or more identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl,
or
a suitable substituent, selected from among —$OR^c$, —$SR^c$, —$NR^cR^c$, —$NR^gNR^cR^c$ and —$S(O)R^c$;
$R^2$ denotes a group optionally substituted by one or more identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;
$R^3$ is selected from among hydrogen, $C_{1-4}$alkyl, halogen, —OH, —O($C_{1-4}$alkyl), —$NH_2$, —NH($C_{1-4}$alkyl) and —N($C_{1-4}$alkyl)$_2$;

$R^4$ is selected from among hydrogen, —CN, —$NO_2$, —$NH_2$, —NH($C_{1-4}$alkyl), —N($C_{1-4}$alkyl)$_2$, $C_{1-4}$alkyl, $C_{1-4}$haloalkyl, $C_{1-4}$alkoxy, $C_{1-5}$cycloalkyl and halogen;
$X^1$, $X^2$ and $X^3$ are each $CR^{4*}$,
wherein $R^{4*}$ are each selected independently of one another from among hydrogen, —CN, —$NO_2$, —$NH_2$, —NH($C_{1-4}$alkyl), —N($C_{1-4}$alkyl)$_2$, $C_{1-4}$alkyl, $C_{1-4}$haloalkyl, $C_{1-4}$alkoxy, $C_{1-5}$cycloalkyl and halogen;
$L^1$ is selected from among —$CH_2$—, —NH—, —NMe-, —O— and —S—;
$L^2$ is selected from among —C(O)NH—, —C(O)N($C_{1-4}$alkyl)-, —NHC(O)—, —N($C_{1-4}$alkyl)C(O)—, —$CH_2$—NHC(O)—, —C(O)—, —C(S)NH—, —NHC(S)—, —$NHCH_2$—, —$CH_2$NH—, —$S(O)_2$NH—, —$NHS(O)_2$—, —NHC(O)NH—, —OC(O)NH— and —NHC(O)O—;
each $R^b$ is a suitable substituent and is selected independently of one another from among —$OR^c$, —$SR^c$, —$NR^cR^c$, —$ONR^cR^c$, —$N(OR^c)R^c$, —$NR^gNR^cR^c$, halogen, —CN, —$NO_2$, —$N_3$, —$C(O)R^c$, —$C(O)OR^c$, —$C(O)NR^cR^c$, —$C(O)NR^gNR^cR^c$, —$C(O)NR^gOR^c$, —$C(NR^g)R^c$, —$N=CR^cR^c$, —$C(NR^g)OR^c$, —$C(NR^g)NR^cR^c$, —$C(NR^g)NR^gNR^cR^c$, —$C(NOR^g)R^c$, —$C(NOR^g)NR^cR^c$, —$C(NNR^gR^g)R^c$, —$OS(O)R^c$, —$OS(O)OR^c$, —$OS(O)NR^cR^c$, —$OS(O)_2R^c$, —$OS(O)_2OR^c$, —$OS(O)_2NR^cR^c$, —$OC(O)R^c$, —$OC(O)OR^c$, —$OC(O)NR^cR^c$, —$OC(NR^g)R^c$, —$OC(NR^g)NR^cR^c$, —$ONR^gC(O)R^c$, —$S(O)R^c$, —$S(O)OR^c$, —$S(O)NR^cR^c$, —$S(O)_2R^c$, —$S(O)_2OR^c$, —$S(O)_2NR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —$N=CR^cNR^cR^c$, —$NR^gC(NR^g)OR^c$, —$NR^gC(NR^g)NR^cR^c$, —$NR^gC(NOR^g)R^c$, —$NR^gS(O)R^c$, —$NR^gS(O)OR^c$, —$NR^gS(O)_2R^c$, —$NR^gS(O)_2OR^c$, —$NR^gS(O)_2NR^cR^c$, —$NR^gNR^gC(O)R^c$, —$NR^gNR^gC(O)NR^cR^c$, —$NR^gNR^gC(NR^g)R^c$ and —$N(OR^g)C(O)R^c$ and the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems;
each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;
each $R^d$ is a suitable substituent and is selected independently of one another from among —$OR^e$, —$SR^e$, —$NR^eR^e$, —$ONR^eR^e$, —$N(OR^e)R^e$, —$N(R^g)NR^eR^e$, halogen, —CN, —NO, —$NO_2$, —$N_3$, —$C(O)R^e$, —$C(O)OR^e$, —$C(O)NR^eR^e$, —$C(O)NR^gNR^eR^e$, —$C(O)NR^gOR^e$, —$C(NR^g)R^e$, —$N=CR^eR^e$, —$C(NR^g)OR^e$, —$C(NR^g)NR^eR^e$, —$C(NR^g)NR^gNR^e$ $R^e$, —$C(NOR^g)R^e$, —$C(NOR^g)NR^eR^e$, —$C(NNR^gR^g)R^e$, —$OS(O)R^e$, —$OS(O)OR^e$, —$OS(O)NR^eR^e$, —$OS(O)_2R^e$, —$OS(O)_2OR^e$, —$OS(O)_2NR^eR^e$, —$OC(O)R^e$, —$OC(O)OR^e$, —$OC(O)NR^eR^e$, —$OC(NR^g)R^e$, —$OC(NR^g)NR^eR^e$, —$ONR^gC(O)R^e$, —$S(O)R^e$, —$S(O)OR^e$, —$S(O)NR^eR^e$, —$S(O)_2R^e$, —$S(O)_2OR^e$, —$S(O)_2NR^e$ $R^e$, —$NR^gC(O)R^e$, —$NR^gC(O)OR^e$, —$NR^gC(O)NR^e$ $R^e$, —$NR^gC(O)NR^gNR^eR^e$, —$NR^gC(NR^g)R^e$, —$N=CR^eNR^eR^e$, —$NR^gC(NR^g)OR^e$, —$NR^gC(NR^g)$ $NR^eR^e$, —$NR^gC(NR^g)SR^e$, —$NR^gC(NOR^g)R^e$, —$NR^gS(O)R^e$, —$NR^gS(O)OR^e$, —$NR^gS(O)_2R^e$, —$NR^gS(O)_2OR^e$, —$NR^gS(O)_2NR^eR^e$, —$NR^gNR^gC(O)R^e$, —$NR^gNR^gC(O)NR^eR^e$, —$NR^gNR^gC(NR^g)R^e$ and —N(OR$^g$)C(O)R$^e$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^f$ is a suitable substituent and is selected independently of one another from among these bivalenten OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO$_2$, —N$_3$, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N=CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —NR$^h$C(O)R$^g$, —NR$^h$C(O)OR$^g$, —NR$^h$C(O)NR$^g$R$^g$, —NR$^h$C(O)NR$^h$NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^h$ is selected independently of one another from among hydrogen, C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

a tautomer, a racemate, an enantiomer, a diastereomer or a mixture thereof, or a pharmacologically acceptable salt thereof.

2. The compound according to claim 1, wherein R$^1$ is a group optionally substituted by one or more identical or different R$^b$ and/or R$^c$, selected from among 5-12 membered heteroaryl and 3-14 membered heterocycloalkyl.

3. The compound according to claim 2, wherein R$^1$ is a 3-7 membered, monocyclic and nitrogen-containing heterocycloalkyl or 6-10 membered, bicyclic and nitrogen-containing heterocycloalkyl optionally substituted by one or more identical or different R$^b$ and/or R$^c$, and R$^1$ is bound to the pyrimido[5,4-d]pyrimidine structure via a nitrogen atom.

4. The compound according to claim 2, wherein R$^1$ is heterocycloalkyl, which is bound to the pyrimido[5,4-d]pyrimidine structure via a nitrogen atom and is optionally substituted by one or more substituents, each independently selected from among R$^{b1}$ and R$^{c1}$;

each R$^{b1}$ is selected independently of one another from among —OR$^{c1}$, —NR$^{c1}$R$^{c1}$, halogen, —C(O)R$^{c1}$ and =O, wherein the latter substituent may only be a substituent in non-aromatic ring systems, each R$^{c1}$ independently of one another denotes hydrogen or a group optionally substituted by one or more identical or different R$^{d1}$ and/or R$^{e1}$, selected from among C$_{1-6}$alkyl, phenyl, C$_{3-10}$cycloalkyl, 5-12 membered heteroaryl and 3-14 membered heterocycloalkyl, each R$^{d1}$ is selected independently of one another from among —OR$^{e1}$ and —NR$^{e1}$R$^{e1}$, each R$^{e1}$ independently of one another denotes hydrogen or a group optionally substituted by one or more identical or different C$_{1-6}$alkyl, selected from among C$_{1-6}$alkyl, C$_{3-10}$cycloalkyl, 5-12 membered heteroaryl and 3-14 membered heterocycloalkyl.

5. The compound according to claim 1, wherein R$^1$ denotes —NR$^{c2}$R$^{c3}$.

6. The compound according to claim 5, wherein R$^1$ denotes —NR$^{c2}$R$^{c3}$ and R$^{c2}$ is selected from among hydrogen, C$_{1-6}$alkyl, C$_{3-6}$cycloalkyl, phenyl, 5-6 membered heteroaryl and 3-7 membered heterocycloalkyl, R$^{c3}$ is a group optionally substituted by one or more identical or different R$^{d3}$ and/or R$^{e3}$, selected from among C$_{1-6}$alkyl, C$_{1-6}$haloalkyl, C$_{3-10}$cycloalkyl and 3-14 membered heterocycloalkyl, each R$^{d3}$ is selected independently of one another from among halogen, —NR$^{e3}$R$^{e3}$ and —OR$^{e3}$, each R$^{e3}$ independently of one another denotes hydrogen or a group optionally substituted by one or more identical or different R$^{f3}$ and/or R$^{g3}$, selected from among C$_{1-6}$alkyl, C$_{6-10}$aryl, 5-12 membered heteroaryl and 3-14 membered heterocycloalkyl, each R$^{f3}$ denotes —OR$^{g3}$ and each R$^{g3}$ is selected independently of one another from among hydrogen and C$_{1-6}$alkyl.

7. The compound according to claim 1, wherein X$^1$ denotes CR$^{4*-1}$, X$^2$ denotes CR$^{4*-2}$ and X$^3$ denotes CR$^{4*-3}$ and R$^{4*-1}$, R$^{4*-2}$ and R$^{4*-3}$ are each selected from among hydrogen, fluorine, bromine, chlorine and methyl and at least two of the groups R$^{4*-1}$, R$^{4*-2}$ and R$^{4*-3}$ denote hydrogen.

8. The compound according to claim 1, wherein R$^2$ is a group optionally substituted by one or more identical or different R$^b$ and/or R$^c$, selected from among C$_{6-10}$aryl and 5-12 membered heteroaryl.

9. The compound according to claim 8, wherein R$^2$ is a group optionally substituted by one or more identical or different R$^b$ and/or R$^c$, selected from among phenyl and 5-6 membered heteroaryl.

10. The compound according to claim 9, wherein R$^2$ is a heteroaryl which is selected from among furyl, thienyl, pyrrolyl, oxazolyl, thiazolyl, triazolyl, isoxazolyl, isothiazolyl, pyrazolyl, imidazolyl, oxadiazolyl, thiadiazolyl, pyridyl and pyrimidyl, and is optionally substituted by one or two substituents, each independently selected from among C$_{3-7}$cycloalkyl, phenyl, 4-7 membered heterocycloalkyl, methyl, ethyl, n-propyl, isopropyl, n-butyl, 1-methylpropyl, isobutyl, sec.-butyl, tert.-butyl, n-pentyl, 1-methylbutyl, 1-ethylpropyl, isopentyl, Neopentyl, trifluoromethyl, difluoromethyl, fluoromethyl, tert.-butoxy, trifluoromethoxy,

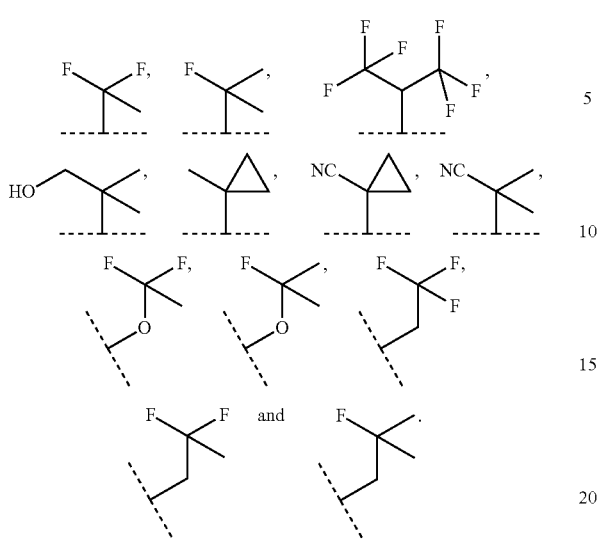

11. The compound according to claim 9, wherein $R^2$ denotes a phenyl

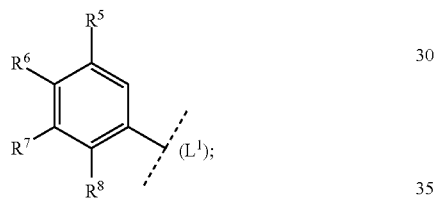

$R^5$ is selected from among hydrogen, $C_{1-6}$alkyl, $-OC_{1-6}$ alkyl, $C_{1-6}$haloalkyl, $-OC_{1-6}$haloalkyl, $C_{3-7}$cycloalkyl and 3-7 membered heterocycloalkyl, all the above-mentioned groups optionally being substituted by $C_{1-6}$alkyl, $-CN$ or $-OH$;

$R^6$ is selected from among hydrogen, $C_{1-6}$alkyl, $-OC_{1-6}$ alkyl, $C_{1-6}$haloalkyl, $-OC_{1-6}$haloalkyl, $-CN$, $-OH$, halogen, $-NHC_{1-6}$alkyl and $-N(C_{1-6}$alkyl$)_2$, the latter two optionally being substituted in the alkyl moiety by a substituent $-N(C_{1-6}$alkyl$)_2$;

$R^7$ is selected from among hydrogen, $-OC_{1-6}$alkyl, halogen, $-NHS(O)_2C_{1-6}$alkyl, $-S(O)_2NH_2$, $-S(O)_2 NHC_{1-6}$alkyl, $-S(O)_2N(C_{1-6}$alkyl$)_2$,

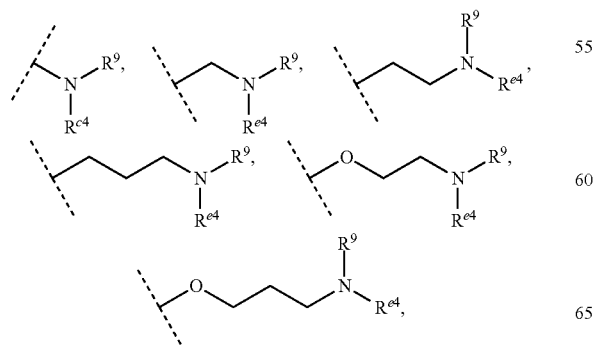

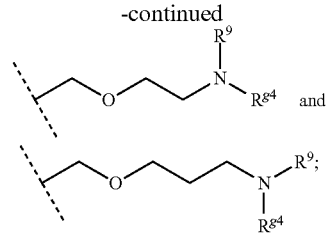

$R^9$ is selected from among hydrogen and $C_{1-6}$alkyl;

$R^{c4}$ denotes hydrogen or a group optionally substituted by one or more identical or different $R^{d4}$ and/or $R^{e4}$, selected from among $C_{1-6}$alkyl and 3-14 membered heterocycloalkyl;

each $R^{d4}$ is a suitable substituent and is selected independently of one another from among $-OR^{e4}$, $-NR^{e4}R^{e4}$ and halogen;

each $R^{e4}$ independently of one another denote hydrogen or a group optionally substituted by one or more identical or different $R^{f4}$ and/or $R^{g4}$, selected from among $C_{1-6}$alkyl, $C_{1-6}$haloalkyl, $C_{3-10}$cycloalkyl, $C_{6-10}$-aryl, 5-12 membered heteroaryl and 3-14 membered heterocycloalkyl;

each $R^{f4}$ is a suitable substituent and is selected independently of one another from among $-OR^{g4}$, $-NR^{g4}R^{g4}$ and halogen as well as the bivalent substituent $=O$, which may only be a substituent in non-aromatic ring systems;

each $R^{g4}$ independently of one another denote hydrogen or a group optionally substituted by one or more identical or different $R^{h4}$, selected from among $C_{1-6}$alkyl, $C_{3-10}$cycloalkyl, 5-12 membered heteroaryl and 3-14 membered heterocycloalkyl;

each $R^{h4}$ is selected independently of one another from among $C_{1-6}$alkyl and the bivalent substituent $=O$, which may only be a substituent in non-aromatic ring systems;

or the group $-NR^9R^{c4}$ denotes a nitrogen-containing, 3-14 membered heterocycloalkyl or 5-12 membered heteroaryl, optionally substituted by one or more identical or different group(s) selected from among $R^{d4}$ and $R^{e4}$;

the group $-NR^9R^{c4}$ denotes a nitrogen-containing, 3-14 membered heterocycloalkyl or 5-12 membered heteroaryl, optionally substituted by one or more identical or different group(s) selected from among $R^{f4}$ and $R^{g4}$;

the group $-NR^9R^{g4}$ denotes a nitrogen-containing, 3-14 membered heterocycloalkyl or 5-12 membered heteroaryl, optionally substituted by one or more identical or different group(s) $R^{h4}$; and $R^8$ is selected from among hydrogen, $C_{1-6}$alkyl, $-OC_{1-6}$ alkyl, $-CN$, halogen, 5-12 membered heteroaryl and 3-14 membered heterocycloalkyl.

12. The compound according to claim 11, wherein $R^5$ is selected from among

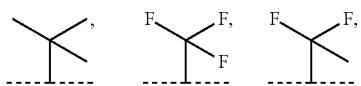

-continued
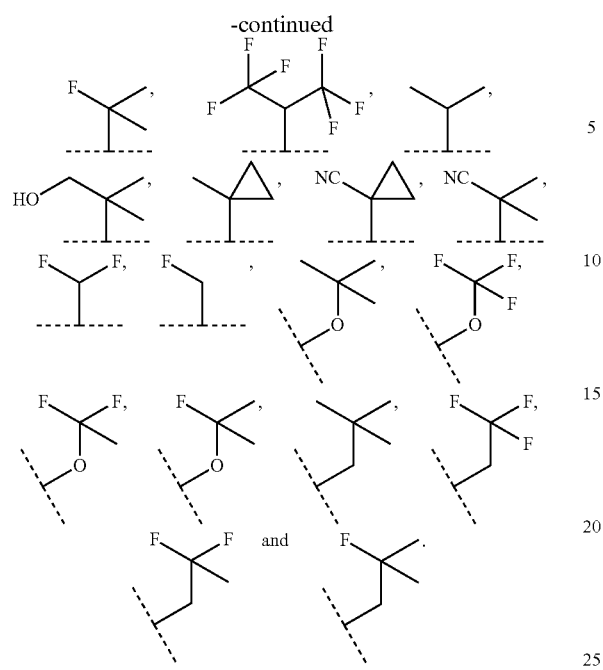
13. A pharmaceutical preparation, comprising as active substance one or more compound of formula (1) according to claim 1.
* * * * *

UNITED STATES PATENT AND TRADEMARK OFFICE
CERTIFICATE OF CORRECTION

PATENT NO. : 8,653,087 B2  
APPLICATION NO. : 13/062058  
DATED : February 18, 2014  
INVENTOR(S) : Mantoulidis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 70 days.

Signed and Sealed this
Twenty-ninth Day of September, 2015

Michelle K. Lee
*Director of the United States Patent and Trademark Office*